United States Patent
Shah et al.

(10) Patent No.: US 11,623,959 B2
(45) Date of Patent: *Apr. 11, 2023

(54) PD-1-BINDING MOLECULES AND METHODS OF USE THEREOF

(71) Applicant: MACROGENICS, INC., Rockville, MD (US)

(72) Inventors: Kalpana Shah, Boyds, MD (US); Douglas H. Smith, San Mateo, CA (US); Ross La Motte-Mohs, Boyds, MD (US); Leslie S. Johnson, Darnestown, MD (US); Paul A. Moore, North Potomac, MD (US); Ezio Bonvini, Potomac, MD (US); Scott Koenig, Rockville, MD (US)

(73) Assignee: MACROGENICS, INC., Rockville, MD (US)

(*) Notice: Subject to any disclaimer, the term of this patent is extended or adjusted under 35 U.S.C. 154(b) by 576 days.

This patent is subject to a terminal disclaimer.

(21) Appl. No.: 16/752,464

(22) Filed: Jan. 24, 2020

(65) Prior Publication Data

US 2020/0231675 A1 Jul. 23, 2020

Related U.S. Application Data

(63) Continuation of application No. 15/748,458, filed as application No. PCT/US2016/044430 on Jul. 28, 2016, now Pat. No. 10,577,422.

(60) Provisional application No. 62/322,974, filed on Apr. 15, 2016, provisional application No. 62/255,140, filed on Nov. 13, 2015, provisional application No. 62/239,559, filed on Oct. 9, 2015, provisional application No. 62/198,867, filed on Jul. 30, 2015.

(51) Int. Cl.
*A61K 39/00* (2006.01)
*C07K 16/28* (2006.01)

(52) U.S. Cl.
CPC ...... *C07K 16/2818* (2013.01); *C07K 16/2803* (2013.01); *C07K 2317/24* (2013.01); *C07K 2317/31* (2013.01); *C07K 2317/33* (2013.01); *C07K 2317/52* (2013.01); *C07K 2317/76* (2013.01); *C07K 2317/92* (2013.01)

(58) Field of Classification Search
CPC ............ C07K 16/2818; C07K 16/2803; C07K 2317/24; C07K 2317/31; A61P 35/00; G01N 33/574; A61K 2039/505
See application file for complete search history.

(56) References Cited

U.S. PATENT DOCUMENTS

| | | |
|---|---|---|
| 3,842,067 A | 10/1974 | Sarantakis |
| 3,862,925 A | 1/1975 | Sarantakis et al. |
| 3,972,859 A | 8/1976 | Fujino et al. |
| 4,105,603 A | 8/1978 | Vale, Jr. et al. |
| 4,526,938 A | 7/1985 | Churchill et al. |
| 4,816,567 A | 3/1989 | Cabilly et al. |
| 4,880,078 A | 11/1989 | Inque et al. |
| 4,980,286 A | 12/1990 | Morgan et al. |
| 5,128,326 A | 7/1992 | Balazs et al. |
| 5,290,540 A | 3/1994 | Prince et al. |
| 5,324,821 A | 6/1994 | Favre et al. |
| 5,565,332 A | 10/1996 | Baier et al. |
| 5,580,717 A | 12/1996 | Dower et al. |
| 5,624,821 A | 4/1997 | Winter et al. |
| 5,679,377 A | 10/1997 | Bernstein et al. |
| 5,733,743 A | 3/1998 | Johnson et al. |
| 5,773,578 A | 6/1998 | Hercend et al. |
| 5,807,715 A | 9/1998 | Morrison et al. |
| 5,811,097 A | 9/1998 | Allison et al. |

(Continued)

FOREIGN PATENT DOCUMENTS

| | | |
|---|---|---|
| CA | 2932966 | 6/2015 |
| EP | 0359096 | 11/1997 |

(Continued)

OTHER PUBLICATIONS

Wines, et al., "The IgG Fc Contains Distinct Fc Receptor (FcR) Binding Sites: The Leukocyte Receptors FcγRI and FcγRIIa Bind to a Region in the Fc Distinct from That Recognized by Neonatal FcR and Protein A," *Journal of Immunology*, vol. 164, p. 5313-5318 (2000).

Dall'Acqua et al., "Properties of Human IgG1s Engineered for Enhanced Binding to the Neonatal Fc Receptor (FCRn)," JBC, vol. 281, p. 23514-23524 (2006).

Notice of Reasons for Rejection issued in co-pending Japanese Patent Application No. 2018-504643, dated Jun. 23, 2020.

Matsuzaki, et al., "Tumor-Infiltrating NY-ESO-1-specific CD8+ T cells are Negatively Regulated by LAG-3 and PD-1 in Human Ovarian Cancer," PNAS, vol. 107, pp. 7875-7880 (2010).

(Continued)

*Primary Examiner* — Sheela J. Huff
(74) *Attorney, Agent, or Firm* — Foley & Lardner LLP

(57) ABSTRACT

The present invention is directed to selected anti-PD-1 antibodies capable of binding to both cynomolgus monkey PD-1 and to human PD-1: PD-1 mAb 1, PD-1 mAb 2, PD-1 mAb 3, PD-1 mAb 4, PD-1 mAb 5, PD-1 mAb 6, PD-1 mAb 7, PD-1 mAb 8, PD-1 mAb 9, PD-1 mAb 10, PD-1 mAb 11, PD-1 mAb 12, PD-1 mAb 13, PD-1 mAb 14, or PD-1 mAb 15, and to humanized and chimeric versions of such antibodies. The invention additionally pertains to PD-1-binding molecules that comprise PD-1 binding fragments of such anti-PD-1 antibodies, immunoconjugates, and to bispecific molecules, including diabodies, BiTEs, bispecific antibodies, etc., that comprise (i) such PD-1-binding fragments, and (ii) a domain capable of binding an epitope of a molecule involved in regulating an immune check point present on the surface of an immune cells. The present invention also pertains to methods of using molecules that bind PD-1 for stimulating immune responses, as well as methods of detecting PD-1.

23 Claims, 38 Drawing Sheets

Specification includes a Sequence Listing.

(56) References Cited

U.S. PATENT DOCUMENTS

| | | |
|---|---|---|
| 5,843,749 A | 12/1998 | Masiakowski et al. |
| 5,855,913 A | 1/1999 | Hanes et al. |
| 5,866,692 A | 2/1999 | Shitara et al. |
| 5,874,064 A | 2/1999 | Edwards et al. |
| 5,885,573 A | 3/1999 | Bluestone et al. |
| 5,888,533 A | 3/1999 | Dunn |
| 5,912,015 A | 6/1999 | Bernstein et al. |
| 5,916,597 A | 6/1999 | Lee et al. |
| 5,934,272 A | 8/1999 | Lloyd et al. |
| 5,945,155 A | 8/1999 | Grill et al. |
| 5,955,300 A | 9/1999 | Faure et al. |
| 5,985,309 A | 11/1999 | Edwards et al. |
| 5,985,320 A | 11/1999 | Edwards et al. |
| 5,989,463 A | 11/1999 | Tracy et al. |
| 5,997,867 A | 12/1999 | Waldmann et al. |
| 6,019,968 A | 2/2000 | Platz et al. |
| 6,054,297 A | 4/2000 | Carter et al. |
| 6,180,377 B1 | 1/2001 | Morgan et al. |
| 6,194,551 B1 | 2/2001 | Presta et al. |
| 6,218,149 B1 | 4/2001 | Morrison et al. |
| 6,265,150 B1 | 7/2001 | Logtenberg et al. |
| 6,277,375 B1 | 8/2001 | Ward |
| 6,331,415 B1 | 12/2001 | Cabilly et al. |
| 6,472,511 B1 | 10/2002 | Leung et al. |
| 6,482,925 B1 | 11/2002 | El Tayar et al. |
| 6,803,192 B1 | 10/2004 | Chen |
| 6,808,710 B1 | 10/2004 | Wood et al. |
| 7,083,784 B2 | 8/2006 | Johnson et al. |
| 7,101,550 B2 | 9/2006 | Wood et al. |
| 7,129,330 B1 | 10/2006 | Little et al. |
| 7,148,038 B2 | 12/2006 | Mather |
| 7,217,797 B2 | 5/2007 | Hinton et al. |
| 7,276,586 B2 | 10/2007 | Goddard et al. |
| 7,317,091 B2 | 1/2008 | Dang et al. |
| 7,405,061 B2 | 7/2008 | Mather et al. |
| 7,488,802 B2 | 2/2009 | Collins et al. |
| 7,521,051 B2 | 4/2009 | Collins et al. |
| 7,563,869 B2 | 7/2009 | Honjo et al. |
| 7,569,672 B2 | 8/2009 | Mather et al. |
| 7,572,896 B2 | 8/2009 | Mather et al. |
| 7,575,895 B2 | 8/2009 | Mather et al. |
| 7,565,048 B1 | 9/2009 | Honjo et al. |
| 7,595,048 B2 | 9/2009 | Honjo et al. |
| 7,635,757 B2 | 12/2009 | Freeman et al. |
| 7,722,868 B2 | 5/2010 | Freeman et al. |
| 7,794,710 B2 | 9/2010 | Chen et al. |
| 7,858,746 B2 | 12/2010 | Honjo et al. |
| 7,998,479 B2 | 8/2011 | Honjo et al. |
| 8,008,449 B2 | 8/2011 | Korman et al. |
| 8,088,376 B2 | 1/2012 | Chamberlain et al. |
| 8,354,509 B2 | 1/2013 | Carven et al. |
| 8,460,886 B2 | 6/2013 | Shibayama et al. |
| 8,552,154 B2 | 10/2013 | Freeman et al. |
| 8,728,474 B2 | 5/2014 | Honjo et al. |
| 8,735,553 B1 | 5/2014 | Li et al. |
| 8,779,105 B2 | 7/2014 | Korman et al. |
| 8,900,587 B2 | 12/2014 | Carven et al. |
| 8,952,136 B2 | 2/2015 | Carven et al. |
| 9,005,629 B2 | 4/2015 | Pardoll et al. |
| 9,067,999 B1 | 6/2015 | Honjo et al. |
| 9,073,994 B2 | 7/2015 | Honjo et al. |
| 9,084,776 B2 | 7/2015 | Korman et al. |
| 9,163,087 B2 | 10/2015 | Kuchroo et al. |
| 9,217,034 B2 | 12/2015 | Li et al. |
| 9,220,776 B2 | 12/2015 | Sharma et al. |
| 9,358,289 B2 | 6/2016 | Korman et al. |
| 9,387,247 B2 | 7/2016 | Korman et al. |
| 9,492,539 B2 | 11/2016 | Korman et al. |
| 9,492,540 B2 | 11/2016 | Qian et al. |
| 10,344,090 B2 | 7/2019 | Yuan et al. |
| 10,577,422 B2 * | 3/2020 | Shah .................. A61P 25/00 |
| 2002/0028486 A1 | 3/2002 | Morrison et al. |
| 2002/0147311 A1 | 10/2002 | Gillies et al. |
| 2003/0115614 A1 | 6/2003 | Kanda et al. |
| 2004/0058400 A1 | 3/2004 | Holliger et al. |
| 2004/0220388 A1 | 11/2004 | Mertens et al. |
| 2004/0241745 A1 | 12/2004 | Honjo et al. |
| 2005/0059051 A1 | 3/2005 | Chen |
| 2005/0079170 A1 | 4/2005 | Le Gall et al. |
| 2006/0166291 A1 | 7/2006 | Mather et al. |
| 2006/0172349 A1 | 8/2006 | Mather et al. |
| 2006/0172350 A1 | 8/2006 | Mather et al. |
| 2007/0031436 A1 | 2/2007 | Little et al. |
| 2007/0036783 A1 | 2/2007 | Humeau et al. |
| 2007/0087006 A1 | 4/2007 | Frantz et al. |
| 2007/0148164 A1 | 6/2007 | Farrington et al. |
| 2007/0166281 A1 | 7/2007 | Kosak |
| 2007/0202100 A1 | 8/2007 | Wood et al. |
| 2008/0311117 A1 | 12/2008 | Johnson et al. |
| 2009/0055944 A1 | 2/2009 | Korman et al. |
| 2009/0060910 A1 | 3/2009 | Johnson et al. |
| 2009/0110667 A1 | 4/2009 | Mozaffarian et al. |
| 2009/0217401 A1 | 8/2009 | Korman et al. |
| 2009/0274666 A1 | 11/2009 | Chen |
| 2009/0313687 A1 | 12/2009 | Popp et al. |
| 2010/0028330 A1 | 2/2010 | Collins et al. |
| 2010/0040614 A1 | 2/2010 | Ahmed et al. |
| 2010/0099853 A1 | 4/2010 | Little et al. |
| 2010/0174053 A1 | 7/2010 | Johnson et al. |
| 2011/0020667 A1 | 1/2011 | Deeman et al. |
| 2012/0114648 A1 | 5/2012 | Langermann et al. |
| 2012/0114649 A1 | 5/2012 | Langermann et al. |
| 2013/0017199 A1 | 1/2013 | Langermann |
| 2013/0109843 A1 | 5/2013 | Carven et al. |
| 2013/0189263 A1 | 7/2013 | Little et al. |
| 2013/0230514 A1 | 9/2013 | Langermann et al. |
| 2013/0295121 A1 | 11/2013 | Johnson et al. |
| 2014/0044738 A1 | 2/2014 | Langermann et al. |
| 2014/0093511 A1 | 4/2014 | Longerg et al. |
| 2014/0099318 A1 | 4/2014 | Huang et al. |
| 2014/0234296 A1 | 8/2014 | Sharma et al. |
| 2014/0255407 A1 | 9/2014 | Koenig |
| 2014/0348743 A1 | 11/2014 | Korman et al. |
| 2015/0079109 A1 | 3/2015 | Li et al. |
| 2015/0175697 A1 | 6/2015 | Bonvini et al. |
| 2015/0307620 A1 | 10/2015 | Vella et al. |
| 2017/0210806 A1 | 7/2017 | Liu |

FOREIGN PATENT DOCUMENTS

| | | |
|---|---|---|
| EP | 1078004 | 5/1999 |
| EP | 1293514 | 11/2006 |
| EP | 2371866 | 10/2011 |
| EP | 2 839 842 A1 | 2/2015 |
| EP | 2361936 | 4/2016 |
| EP | 2714079 | 9/2016 |
| EP | 2601216 | 1/2018 |
| EP | 2158221 | 8/2018 |
| WO | WO 1991/003493 | 3/1991 |
| WO | WO 1991/005548 | 5/1991 |
| WO | WO 1991/010682 | 7/1991 |
| WO | WO 1992/019244 | 11/1992 |
| WO | WO 1992/022583 | 12/1992 |
| WO | WO 1995/015171 | 6/1995 |
| WO | WO 1995/020605 | 8/1995 |
| WO | WO 1995/030750 | 11/1995 |
| WO | WO 1996/020698 | 7/1996 |
| WO | WO 1997/032572 | 9/1997 |
| WO | WO 1997/044013 | 11/1997 |
| WO | WO 1998/002463 | 1/1998 |
| WO | WO 1998/023289 | 6/1998 |
| WO | WO 1998/023741 | 6/1998 |
| WO | WO 1998/031346 | 7/1998 |
| WO | WO 1998/058059 | 12/1998 |
| WO | WO 1999/015154 | 4/1999 |
| WO | WO 1999/020253 | 4/1999 |
| WO | WO 1999/057150 | 11/1999 |
| WO | WO 1999/058572 | 11/1999 |
| WO | WO 1999/066903 | 12/1999 |
| WO | WO 2000/042072 | 7/2000 |
| WO | WO 2001/014557 | 3/2001 |
| WO | WO 2001/039722 | 6/2001 |
| WO | WO 2002/002781 | 1/2002 |
| WO | WO 2002/086083 | 10/2002 |

(56) References Cited

FOREIGN PATENT DOCUMENTS

| | | |
|---|---|---|
| WO | WO 2003/011911 | 2/2003 |
| WO | WO 2003/012069 | 2/2003 |
| WO | WO 2003/024191 | 3/2003 |
| WO | WO 2003/025018 | 3/2003 |
| WO | WO 2003/032814 | 4/2003 |
| WO | WO 2003/035835 | 5/2003 |
| WO | WO 2003/042402 | 5/2003 |
| WO | WO 2003/087340 | 10/2003 |
| WO | WO 2003/093443 | 11/2003 |
| WO | WO 2003/099196 | 12/2003 |
| WO | WO 2004/004771 | 1/2004 |
| WO | WO 2004/043239 | 5/2004 |
| WO | WO 2004/056875 | 7/2004 |
| WO | WO 2004/063351 | 7/2004 |
| WO | WO 2004/072286 | 8/2004 |
| WO | WO 2004/078928 | 9/2004 |
| WO | WO 2005/019258 | 3/2005 |
| WO | WO 2005/028498 | 3/2005 |
| WO | WO 2005/070966 | 8/2005 |
| WO | WO 2005/077415 | 8/2005 |
| WO | WO 2005/121179 | 12/2005 |
| WO | WO 2006/021955 | 3/2006 |
| WO | WO 2006/076584 | 7/2006 |
| WO | WO 2006/083852 | 8/2006 |
| WO | WO 2006/084075 | 8/2006 |
| WO | WO 2006/084078 | 8/2006 |
| WO | WO 2006/084092 | 8/2006 |
| WO | WO 2006/084226 | 8/2006 |
| WO | WO 2006/088494 | 8/2006 |
| WO | WO 2006/107617 | 10/2006 |
| WO | WO 2006/107786 | 10/2006 |
| WO | WO 2006/113665 | 10/2006 |
| WO | WO 2006/121168 | 11/2006 |
| WO | WO 2006/133396 | 12/2006 |
| WO | WO 2008/156712 | 12/2006 |
| WO | WO 2007/005874 | 1/2007 |
| WO | WO 2007/021841 | 2/2007 |
| WO | WO 2007/024249 | 3/2007 |
| WO | WO 2007/024715 | 3/2007 |
| WO | WO 2007/046893 | 4/2007 |
| WO | WO 2007/075270 | 7/2007 |
| WO | WO 2007/106707 | 9/2007 |
| WO | WO 2007/110205 | 10/2007 |
| WO | WO 2007/146968 | 12/2007 |
| WO | WO 2008/003103 | 1/2008 |
| WO | WO 2008/003116 | 1/2008 |
| WO | WO 2008/024188 | 2/2008 |
| WO | WO 2008/027236 | 3/2008 |
| WO | WO 2008/146911 | 4/2008 |
| WO | WO 2008/083174 | 7/2008 |
| WO | WO 2008/132601 | 11/2008 |
| WO | WO 2008/140603 | 11/2008 |
| WO | WO 2008/145142 | 12/2008 |
| WO | WO 2009/014708 | 1/2009 |
| WO | WO 2009/018386 | 2/2009 |
| WO | WO 2009/058492 | 5/2009 |
| WO | WO 2009/073533 | 6/2009 |
| WO | WO 2009/080251 | 7/2009 |
| WO | WO 2009/080254 | 7/2009 |
| WO | WO 2009/089004 | 7/2009 |
| WO | WO 2009/101611 | 8/2009 |
| WO | WO 2009/132876 | 11/2009 |
| WO | WO 2010/019570 | 2/2010 |
| WO | WO 2010/028795 | 3/2010 |
| WO | WO 2010/028796 | 3/2010 |
| WO | WO 2010/028797 | 3/2010 |
| WO | WO 2010/033279 | 3/2010 |
| WO | WO 2010/036959 | 4/2010 |
| WO | WO 2010/080538 | 7/2010 |
| WO | WO 2010/089411 | 8/2010 |
| WO | WO 2010/108127 | 9/2010 |
| WO | WO 2010/136172 | 12/2010 |
| WO | WO 2011/044368 | 4/2011 |
| WO | WO 2011/066342 | 6/2011 |
| WO | WO 2011/069104 | 6/2011 |
| WO | WO 2011/086091 | 7/2011 |
| WO | WO 2011/110604 | 9/2011 |
| WO | WO 2011/117329 | 9/2011 |
| WO | WO 2011/131746 | 10/2011 |
| WO | WO 2011/133886 | 10/2011 |
| WO | WO 2011/143545 | 11/2011 |
| WO | WO 2011/159877 | 12/2011 |
| WO | WO 2012/009544 | 1/2012 |
| WO | WO 2012/018687 | 2/2012 |
| WO | WO 2012/023053 | 2/2012 |
| WO | WO 2012/058768 | 5/2012 |
| WO | WO 2012/135408 | 10/2012 |
| WO | WO 2012/145493 | 10/2012 |
| WO | WO 2012/145549 | 10/2012 |
| WO | WO 2012/156430 | 11/2012 |
| WO | WO 2012/162068 | 11/2012 |
| WO | WO 2012/162583 | 11/2012 |
| WO | WO 2013/003652 | 1/2013 |
| WO | WO 2013/003761 | 1/2013 |
| WO | WO 2013/006544 | 1/2013 |
| WO | WO 2013/006867 | 1/2013 |
| WO | WO 2013/013700 | 1/2013 |
| WO | WO 2013/014668 | 1/2013 |
| WO | WO 2013/060867 | 5/2013 |
| WO | WO 2013/070565 | 5/2013 |
| WO | WO 2013/119903 | 8/2013 |
| WO | WO 2013/163427 | 10/2013 |
| WO | WO 2013/173223 | 11/2013 |
| WO | WO 2013/174873 | 11/2013 |
| WO | WO 2014/008218 | 1/2014 |
| WO | WO 2014/022540 | 2/2014 |
| WO | WO 2014/022758 | 2/2014 |
| WO | WO 2014/043708 | 3/2014 |
| WO | WO 2014/055648 | 4/2014 |
| WO | WO 2014/059251 | 4/2014 |
| WO | WO 2014/066532 | 5/2014 |
| WO | WO 2014/066834 | 5/2014 |
| WO | WO 2014/140180 | 9/2014 |
| WO | WO 2014/179664 | 11/2014 |
| WO | WO 2014/194302 | 12/2014 |
| WO | WO 2014/209804 | 12/2014 |
| WO | WO 2015/018420 | 2/2015 |
| WO | WO 2015/026684 | 2/2015 |
| WO | WO 2015/026894 | 2/2015 |
| WO | WO 2015/036394 | 3/2015 |
| WO | WO 2015/042246 | 3/2015 |
| WO | WO 2015/048312 | 4/2015 |
| WO | WO 2015/085847 A1 | 6/2015 |
| WO | WO 2015/103072 | 7/2015 |
| WO | WO 2015/112534 | 7/2015 |
| WO | WO 2015/112800 | 7/2015 |
| WO | WO 2015/112900 A1 | 7/2015 |
| WO | WO 2015/116539 | 8/2015 |
| WO | WO 2015/138920 | 9/2015 |
| WO | WO 2015/176033 | 11/2015 |
| WO | WO 2015/184203 | 12/2015 |
| WO | WO 2015/184207 | 12/2015 |
| WO | WO 2015/195163 | 12/2015 |
| WO | WO 2015/200119 | 12/2015 |
| WO | WO 2015/200828 | 12/2015 |
| WO | WO 2016/014688 | 1/2016 |
| WO | WO 2016/015685 | 2/2016 |
| WO | WO 2016/020856 | 2/2016 |
| WO | WO 2016/022630 | 2/2016 |
| WO | WO 2016/028672 | 2/2016 |
| WO | WO 2016/068801 | 5/2016 |
| WO | WO 2016/077397 | 5/2016 |
| WO | WO 2016/092419 | 6/2016 |
| WO | WO 2016/106159 | 6/2016 |
| WO | WO 2016/127179 | 8/2016 |
| WO | WO 2016/168716 | 10/2016 |
| WO | WO 2016/200782 | 12/2016 |
| WO | WO 2016/201051 A1 | 12/2016 |

(56) References Cited

FOREIGN PATENT DOCUMENTS

| | | |
|---|---|---|
| WO | WO 2017/062619 | 4/2017 |
| WO | WO 2017/079112 | 5/2017 |

OTHER PUBLICATIONS

Notice of Reasons for Rejection issued in co-pending Japanese Patent Application No. 2018-177320, dated Jun. 25, 2020.
Abdulghani, J. et al. (2010) "*TRAIL Receptor Signaling And Therapeutics*," Expert Opin. Ther. Targets 14(10):1091-1108.
Adenis, A. et al. (2003) "[*Inhibitors of Epidermal Growth Factor Receptor and Colorectal Cancer*]," Bull. Du Cancer 90 Spec No. S228-S232 (Abstract Only).
Agarwal, A. et al. (2008) "*The Role Of Positive Costimulatory Molecules In Transplantation And Tolerance*," Curr. Opin. Organ Transplant. 13:366-372.
Agata, T. et al. (1996) "*Expression Of The PD-1 Antigen On The Surface Of Stimulated Mouse T And B Lymphocytes*," Int. Immunol. 8(5):765-772.
Akcakanat, A. et al. (2006) "*Heterogeneous expression of GAGE, NY-ESO-1, MAGE-A and SSX proteins in esophageal cancer: Implications for immunotherapy*" Int J Cancer. 118(1):123-128.
Al Hussaini M. et al. (2015) "*Targeting CD123 In AML Using A T-Cell Directed Dual-Affinity Re-Targeting (DART®) Platform,* " Blood pii: blood-2014-05-575704.
Alegre, M.L. et al. (1994) "*A Non-Activating "Humanized" Anti-CD 3 Monoclonal Antibody Retains Immunosuppressive Properties In Vivo*," Transplantation 57:1537-1543.
Almqvist, Y. (2006) "*In vitro and in vivo characterization of 177Lu-huA33 A radioimmunoconjugate against colorectal cancer*" Nucl Med Biol. Nov.;33(8):991-998.
Alt, M. et al. (1999) "*Novel Tetravalent and Bispecific IgG-like Antibody Molecules Combining Single-Chain Diabodies with the Immunoglobulin γ1 Fc or CH3 Region*," FEBS Lett. 454(1-2):90-94.
Andera, L. (2009) "*Signaling Activated By The Death Receptors Of The TNFR Family*," Biomed. Pap. Med. Fac. Univ. Palacky Olomouc Czech. Repub. 153(3):173-180.
Apostolovic, B. et al. (2008) "*pH-Sensitivity of the E3/K3 Heterodimeric Coiled Coil*," Biomacromolecules 9:3173-3180.
Armour, K.L. et al. (1999) "*Recombinant human IgG Molecules Lacking Fcgamma Receptor I Binding And Monocyte Triggering Activities*," Eur. J. Immunol. 29:2613-24.
Arndt, K.M. et al. (2001) "*Helix-stabilized Fv (hsFv) Antibody Fragments: Substituting the Constant Domains of a Fab Fragment for a Heterodimeric Coiled-coil Domain*," J. Molec. Biol. 312:221-228.
Aruffo, A. et al. (1987) "*Molecular Cloning Of A CD28 cDNA By A High-Efficiency COS Cell Expression System*," Proc. Natl. Acad. Sci. (U.S.A.) 84:8573-8577.
Asano et al. (2004) "*A Diabody For Cancer Immunotherapy And Its Functional Enhancement By Fusion Of Human Fc Domain*," Abstract 3P-683, J. Biochem. 76(8):992.
Atwell et al. (1997) "*Stable Heterodimers From Remodeling The Domain Interface Of A Homodimer Using A Phage Display Library*," J. Mol. Biol. 270: 26-35.
Baeuerle, P.A. et al. (2009) "*Bispecific T-Cell Engaging Antibodies For Cancer Therapy*," Cancer Res. 69(12):4941-4944.
Barber, D. L. et al. (2006) "*Restoring function in exhausted CD8 T cells during chronic viral infection*," Nature 439, 682-687.
Barderas, R. et al. (2012) "*High Expression Of IL-13 Receptor A2 In Colorectal Cancer Is Associated With Invasion, Liver Metastasis, And Poor Prognosis*," Cancer Res. 72(11):2780-2790.
Bast, R.C. Jr. et al. (2005) "*New tumor markers: CA125 and beyond*" Int J Gynecol Cancer 15 Suppl 3:274-81.
Bataille, R. (2006) "*The phenotype of normal, reactive and malignant plasma cells. Identification of many and multiple myelomas*"and of new targets for myeloma therapy" " Haematologica 91(9):1234-40.

Bennett F, et al., (2003) "*Program Death-1 Engagement Upon TCR Activation Has Distinct Effects on Costimulation and Cytokine-Driven Proliferation: Attenuation of ICOS, IL-4, and IL-21, But Not CD28, IL-7, IL-15 Responses*" J Immunol 170:711-718.
Berger, R. et al. (2008) "*Phase I Safety And Pharmacokinetic Study Of CT-011, A Humanized Antibody Interacting With PD-1, In Patients With Advanced Hematologic Malignancies*," Clin. Cancer Res. 14(10):3044-3051.
Bhattacharya-Chatteijee et al. (1988) "*Idiotype Vaccines Against Human T Cell Leukemia. II. Generation And Characterization Of A Monoclonal Idiotype Cascade (Ab1, Ab2, and Ab 3)*," J. Immunol. 141:1398-1403.
Bird et al. (1988) "*Single-Chain Antigen-Binding Proteins*," Science 242:423-426.
Blank, C. et al. (2006) "*Contribution Of The PD-L1/PD-1 Pathway To T-Cell Exhaustion: An Update On Implications For Chronic Infections And Tumor Evasion Cancer*," Immunol. Immunother. 56(5):739-745.
Bodey, B. (2002) "*Cancer-testis antigens: promising targets for antigen directed antineoplastic immunotherapy*" Expert Opin Biol Ther. 2(6):577-584.
Boghaert, E.R. et al. (2007) "*The Oncofetal Protein, 5T4, Is A Suitable Target For Antibody-Guided Anti-Cancer Chemotherapy With Calicheamicin*," Int. J. Oncol. 32(1):221-234.
Boucher, C. et al. (2010) "*Protein Detection By Western Blot Via Coiled-Coil Interactions*," Analytical Biochemistry 399:138-140.
Bozinov, O. et al. (2010) "*Decreasing Expression Of The Interleukin-13 Receptor IL-13Ralpha2 In Treated Recurrent Malignant Gliomas*,"Neurol. Med. Chir. (Tokyo) 50(8):617-621.
Brahmer JR, et al., (2010) "*Phase I Study of Single-Agent Anti-Programmed Death-1 (MDX-1106) in Refractory Solid Tumors: Safety, Clinical Activity, Pharmacodynamics, and Immunologic Correlates*" J Clin Oncol 28:3167-75.
Brown et al. (1987) "*Tumor-Specific Genetically Engineered Murine/Human Chimeric Monoclonal Antibody*," Cancer Res. 47:3577-3583.
Brown, C.E. et al. (2013) "*Glioma IL13Ra2 Is Associated With Mesenchymal Signature Gene Expression And Poor Patient Prognosis*," PLoS One. 18;8(10):e77769.
Brown, J.A. et al. (2003) "*Blockade Of Programmed Death-1 Ligands On Dendritic Cells Enhances T-Cell Activation And Cytokine Production*," J. Immunol. 170:1257-1266.
Brüggemarm et al. (1987) "*Comparison of the effector functions of human immunoglobulins using a matched set of chimeric antibodies*" J. Exp. Med 166:1351-1361.
Buchwald et al. (1980) "*Long-Term, Continuous Intravenous Heparin Administration By An Implantable Infusion Pump In Ambulatory Patients With Recurrent Venous Thrombosis*," Surgery 88:507-516.
Cachia, P.J. et al. (2004) "*Synthetic Peptide Vaccine Development: Measurement Of Polyclonal Antibody Affinity And Cross-Reactivity Using A New Peptide Capture And Release System For Surface Plasmon Resonance Spectroscopy*," J. Mol. Recognit. 17:540-557.
Calin, G.A. et al. (2006) "*Genomics of chronic lymphocytic leukemia microRNAs as new players with clinical significance*" Semin Oncol. 33(2):167-173.
Carlo-Stella, C. et al. (2007) "*Targeting TRAIL Agonistic Receptors for Cancer Therapy*," Clin. Cancer 13(8):2313-2317.
Caron, P.C. et al. (1992) "*Engineered Humanized Dimeric Forms Of IgG Are More Effective Antibodies*," J. Exp. Med. 176:1191-1195.
Carter, L. et al. (2002) "*PD-1:PD-L Inhibitory Pathway Affects Both CD4(+) and CD8(+) T-cells And Is Overcome By IL-2*," Eur. J. Immunol. 32(3):634-643.
Carter, P. et al. (1992) "*Humanization Of An Anti-p185her2 Antibody For Human Cancer Therapy*," Proc. Natl. Acad. Sci. (U.S.A.) 89:4285-4289.
Castelli, C. et al. (2000) "*T-Cell recognition of melanoma-associated antigens*" J Cell Physiol. 182(3):323-331.
Chan, C.E. et al. (2009) "*The Use Of Antibodies In The Treatment Of Infectious Diseases*," Singapore Med. J. 50(7):663-666.
Chang K, and Pastan I. (1996) "*Molecular cloning of mesothelin, a differentiation antigen present on mesothelium, mesotheliomas, and ovarian cancers*," Proc Natl Acad Sci USA 93:136-140.

(56) References Cited

OTHER PUBLICATIONS

Chapoval, A. et al. (2001) "*B7-H3: A Costimulatory Molecule for T Cell Activation and IFN-γ Production*," Nature Immunol. 2:269-274.

Chappel et al. (1991) "*Identification of the Fcγ receptor class I binding site in human IgG through the use of recombinant IgG1/IgG2 hybrid and point-mutated antibodies*," Proc. Natl. Acad. Sci. (U.S.A.) 88:9036-9040.

Chappel et al. (1993) "*Identification of a Secondary FcRI Binding Site within a Genetically Engineered Human IgG Antibody*\**" J. Biol. Chem. 33:25124-25131.

Chaudhari, B.R. et al. (2006) "*Following the TRAIL to Apoptosis*," Immunologic Res. 35(3):249-262.

Chen, Y. et al. (2005) "*Expression of B7-H1 in Inflammatory Renal Tubular Epithelial Cells*," Nephron. Exp. Nephrol. 102:e81-e92.

Chichili, G.R. et al. (2015) "*A CD3xCD123 Bispecific DART For Redirecting Host T Cells To Myelogenous Leukemia: Preclinical Activity And Safety In Nonhuman Primates*," Sci. Transl. Med. 7(289):289ra82.

Chothia, C. & Lesk, A. M. (1987) "*Canonical structures for the hypervariable regions of immunoglobulins,*". J. Mol. Biol. 196:901-917.

Chu, P.G. et al. (2001) "*CD79: A Review*" Appl Immunohistochem Mol Morphol. 9(2):97-106.

Co, M. S. et al. (1991) "*Humanized Antibodies For Antiviral Therapy*," Proc. Natl. Acad. Sci. (U.S.A.) 88:2869-2873.

Collins, M. et al. (2005) "*The B7 Family Of Immune-Regulatory Ligands*," Genome Biol. 6:223.1-223.7.

Coyle, A.J. et al. (2001) "*The Expanding B7 Superfamily: Increasing Complexity In Costimulatory Signals Regulating T-Cell Function*," Nature Immunol. 2(3):203-209.

Cracco, C.M. et al. (2005) "*Immune Response in Prostate Cancer*" Minerva Urol Nefrol. 57(4):301-311.

Daugherty et al. (1991) "*Polymerase Chain Reaction Facilitates The Cloning, CDR-Grafting, And Rapid Expression Of A Murine Monoclonal Antibody Directed Against The CD 18 Component Of Leukocyte Integrins*," Nucl. Acids Res. 19:2471-2476.

De Crescenzo, G.D. et al. (2003) "*Real-Time Monitoring of the Interactions of Two-Stranded de novo Designed Coiled-Coils: Effect of Chain Length on the Kinetic and Thermodynamic Constants of Binding*," Biochemistry 42:1754-1763.

De Haij, S. et al. (2005) "*Renal Tubular Epithelial Cells Modulate T-Cell Responses Via ICOS-L And B7-H1*" Kidney Int. 68:2091-2102.

Del Rio, M-L. et al. (2005) "*Antibody-Mediated Signaling Through PD-1 Costimulates T Cells And Enhances CD28-Dependent Proliferation*," Eur. J. Immunol 35:3545-3560.

Dennis, J.W. et al. (1999) "*Glycoprotein Glycosylation and Cancer Progression*" Biochim Biophys Acta. 1473(1):21-34.

Di Bartolomeo, M. et al. (2015) "*Bevacizumab treatment in the elderly patient with metastatic colorectal cancer*," Clin. Interv. Aging 10:127-133.

Disis, M. L. et al. (2002) "*Generation of T-cell immunity to the HER-2/neu protein after active immunization with HER-2/neu peptide-based vaccines*," J. Clin. Oncol. 20, 2624-2632.

Dong, C. et al. (2003) "*Immune Regulation by Novel Costimulatory Molecules*," Immunolog. Res. 28(1):39-48.

Dong, H. (2003) "*B7-H1 Pathway And Its Role In The Evasion Of Tumor Immunity*," J. Mol. Med. 81:281-287.

Dorfman DM, et al., (2006) "*Programmed Death-1 (PD-1) is a Marker of Germinal Center-associated T Cells and Angioimmunoblastic T-Cell Lymphoma*" Am J Surg Pathol 30:802-10.

Duncan, A.R. et al. (1988) "*Localization Of The Binding Site For The Human High-Affinity Fc Receptor On IgG*," Nature 332:563-564.

During et al. (1989) "*Controlled Release Of Dopamine From A Polymeric Brain Implant: In Vivo Characterization*," Ann. Neurol. 25:351-356.

Edelson (1998) "*Cutaneous T-Cell Lymphoma: A Model For Selective Immunotherapy*," Cancer J Sci Am. 4:62-71.

Egloff, A.M. et al. (2006) "*Cyclin B1 and other cyclins as tumor antigens in immunosurveillance and immunotherapy of cancer*" Cancer Res. 66(1):6-9.

Eisen, T. et al. (2014) "*Naptumomab Estafenatox: Targeted Immunotherapy with a Novel Immunotoxin*," Curr. Oncol. Rep. 16:370, pp. 1-6.

Eppihimer MJ, et al., (2009) "*Expression and Regulation of the PD-L1 Immunoinhibitory Molecule on Microvascular Endothelial Cells*" Microcirculation 9: 133-145.

Estin et al. (1989) "*Transfected Mouse Melanoma Lines That Express Various Levels Of Human Melanoma-Associated Antigen p97*," J. Natl. Cancer Instit. 81(6):445-448.

Fedorov V.D. (2013) "*PD-1- and CTLA-4-Based Inhibitory Chimeric Antigen Receptors (iCARs) Divert Off-Target Immunotherapy Responses*," Sci. Tranl. Med. 5:215ra172 doi:10.1126/scitranslmed. 3006597.

Feizi (1985) "*Demonstration By Monoclonal Antibodies That Carbohydrate Structures Of Glycoproteins And Glycolipids Are Onco-Developmental Antigens*," Nature 314:53-57.

Fernandez-Rodriquez, J. et al. (2012) "*Induced Heterodimerization And Purification Of Two Target Proteins By A Synthetic Coiled-Coil Tag*," Protein Science 21:511-519.

Field, K.M. (2015) "*Bevacizumab And Glioblastoma: Scientific Review, Newly Reported Updates, And Ongoing Controversies*," Cancer 121(7):997-1007.

Fitzgerald et al. (1997) "*Improved Tumour Targeting By Disulphide Stabilized Diabodies Expressed In Pichia pastoris*," Protein Eng. 10:1221.

Flajnik, M.F. et al. (2012) "Evolution of The B7 Family: Co-Evolution of B7H6 And Nkp30, Identification of A New B7 Family Member, B7H7, And of B7's Historical Relationship with the MHC," Immunogenetics epub doi.org/10.1007/s00251-012-0616.

Flesch and Neppert (1999) "*Functions of the Fc regions for immunoglobulin G*" J. Clin Lab. Anal. 14:141-156.

Flies, D.B. et al. (2007) "*The New B7s: Playing a Pivotal Role in Tumor Immunity*," J. Immunother. 30(3):251-260.

Foon et al. (1995) "*Immune Response to The Carcinoembryonic Antigen in Patients Treated with An Anti-Idiotype Antibody Vaccine*," J. Clin. Invest. 96(1):334-42.

Freeman, G.J. et al. (2000) "*Engagement of the PD-1 Immunoinhibitory Receptor by A Novel B7 Family Member Leads to Negative Regulation of Lymphocyte Activation*," J. Exp. Med. 192:1-9.

Fujisawa, T. et al. (2009) "*A novel role of interleukin-13 receptor alpha2 in pancreatic cancer invasion and metastasis*," Cancer Res. 69(22):8678-8685.

Ganesan, A. (2006) "*Solid-Phase Synthesis in The Twenty-First Century*," Mini Rev. Med. Chem. 6(1):3-10.

Gardnerova, M. et al. (2000) "*The Use of TNF Family Ligands and Receptors and Agents which Modify Their Interaction as Therapeutic Agents*" Curr Drug Targets. 1(4):327-364.

Ge, Y. (2005) "*CD36: A Multiligand Molecule*" Lab Hematol. 11(1):31-37 (Abstract Only).

Ghetie et al. (1994) "*Anti-CD19 Inhibits the Growth of Human B-Cell Tumor Lines In Vitro And Of Daudi Cells In SCID Mice By Inducing Cell Cycle Arrest*," Blood 83:1329-1336.

Ghosh, T.S. et al. (2009) "*End-To-End and End-To-Middle Interhelical Interactions: New Classes Of Interacting Helix Pairs In Protein Structures*," Acta Crystallographica D65:1032-1041.

Gil, J. et al. (2006) "*Regulation of the INK4b-ARF-INK4a tumour suppressor locus: all for one or one for all*" Nat Rev Mol Cell Biol. 7(9):667-77.

Gill, S. et al. (2014) "*Efficacy Against Human Acute Myeloid Leukemia and Myeloablation Of Normal Hematopoiesis in A Mouse Model Using Chimeric Antigen Receptor-Modified T Cells*," Blood 123(15): 2343-2354.

Gorman, S. D. et al. (1991) "*Reshaping A Therapeutic CD4 Antibody*,"Proc. Natl. Acad. Sci. (U.S.A.) 88:4181-4185.

Greenwald, R.J. et al. (2005) "*The B7 Family Revisited*," Ann. Rev. Immunol. 23:515-548.

Grigoryan, G. et al. (2008) "*Structural Specificity In Coiled-Coil Interactions*," Curr. Opin. Struc. Biol. 18:477-483.

(56) References Cited

OTHER PUBLICATIONS

Gross, J., et al. (1992) "Identification And Distribution Of The Costimulatory Receptor CD28 In The Mouse," J. Immunol. 149:380-388.

Hamid O, et al., (2013) "Safety and tumor responses with lambrolizumab (anti-PD-1) in melanoma" N Engl J Med 369:134-44.

Hardy B, et al., (1994) "A Monoclonal Antibody against a Human B Lymphoblastoid Cell Line Induces Tumor Regression in Mice" Cancer Res 54:5793-5796.

Hardy B, et al., (1997) "A lymphocyte-activating monoclonal antibody induces regression of human tumors in severe combined immunodeficient mice" PNAS 94:5756-5760.

Heath, J.K. et al. (1997) "The Human A33 Antigen Is A Transmembrane Glycoprotein And A Novel Member Of The Immunoglobulin Superfamily," Proc. Natl. Acad. Sci. (U.S.A.) 94(2):469-474.

Hellström et al. (1985) "Monoclonal Antibodies To Cell Surface Antigens Shared By Chemically Induced Mouse Bladder Carcinomas," Cancer. Res. 45:2210-2188.

Henttu et al. (1989) "cDNA Coding For The Entire Human Prostate Specific Antigen Shows High Homologies To The Human Tissue Kallikrein Genes," Biochem. Biophys. Res. Comm. 160(2):903-910.

Herlyn et al. (1982) "Monoclonal Antibody Detection Of A Circulating Tumor-Associated Antigen. I. Presence Of Antigen In Sera Of Patients With Colorectal, Gastric, And Pancreatic Carcinoma," J. Clin. Immunol. 2(2):135-140.

Hilkens et al. (1992) "Cell Membrane-Associated Mucins And Their Adhesion-Modulating Property," Trends in Biochem. Sci. 17:359-363.

Hoelzer, D. (2013) "Targeted Therapy With Monoclonal Antibodies In Acute Lymphoblastic Leukemia," Curr. Opin. Oncol. 25(6):701-706.

Holliger et al. (1993) "'Diabodies': Small Bivalent And Bispecific Antibody Fragments," Proc. Natl. Acad. Sci. (U.S.A.) 90:6444-6448.

Holliger et al. (1996) "Specific Killing Of Lymphoma Cells By Cytotoxic T-Cells Mediated By A Bispecific Diabody," Protein Eng. 9:299-305.

Holmberg, L.A. et al. (2001) "Theratope® vaccine (STn-KLH)" Expert Opin Biol Ther. 1(5):881-91.

Hoon et al. (1993) "Molecular Cloning Of A Human Monoclonal Antibody Reactive To Ganglioside GM3 Antigen On Human Cancers," Cancer Res. 53:5244-5250.

Houghten, R.A. (1985) "General Method For The Rapid Solid-Phase Synthesis Of Large Numbers Of Peptides: Specificity Of Antigen-Antibody Interaction At The Level Of Individual Amino Acids," Proc. Natl. Acad. Sci. (U.S.A.) 82(15):5131-5135.

Howard et al. (1989) "Intracerebral Drug Delivery In Rats With Lesion-Induced Memory Deficits," J. Neurosurg. 7(1):105-112.

Hutchins et al. (1995) "Improved Biodistribution, Tumor Targeting, And Reduced Immunogenicity In Mice With A Gamma 4 Variant Of Campath-1H," Proc. Natl. Acad. Sci. (U.S.A.) 92:11980-84.

Hutloff et al. (1999) "ICOS Is An Inducible T-Cell Co-Stimulator Structurally And Functionally Related To CD28," Nature 397:263-266.

Idusogie, E.E. et al. (2000) "Mapping Of The C1q Binding Site On Rituxan, A Chimeric Antibody With A Human IgG Fc," J. Immunol. 164:4178-84.

Idusogie, E.E. et al. (2001) "Engineered Antibodies With Increased Activity To Recruit Complement," J. Immunol. 166:2571-75.

Ishida, Y. et al. (1992) "Induced Expression Of PD-1, A Novel Member Of The Immunoglobulin Gene Superfamily, Upon Programmed Cell Death," EMBO J. 11:3887-3895.

Israeli et al. (1993) "Molecular Cloning Of A Complementary DNA Encoding A Prostate-Specific Membrane Antigen," Cancer Res. 53:227-230.

Ito et al. (2000) "Effective Priming Of Cytotoxic T Lymphocyte Precursors By Subcutaneous Administration Of Peptide Antigens In Liposomes Accompanied By Anti-CD40 And Anti-CTLA-4 Antibodies,"Immunobiology 201:527-40.

Iwai, Y. et al. (2002) "Involvement Of PD-L1 On Tumor Cells In The Escape From Host Immune System And Tumor Immunotherapy By PD-L1 Blockade, " Proc. Natl Acad. Sci. USA 99, 12293-12297.

Jefferis, B.J. et al. (2002) "Interaction Sites On Human IgG-Fc For FcgammaR: Current Models, " Immunol. Lett. 82:57-65.

Jefferis, R. et al. (1995) "Recognition Sites On Human IgG For Fc Gamma Receptors: The Role Of Glycosylation, " Immunol. Lett. 44:111-17.

Jefferis, R. et al. (1996) "Modulation Of Fc(Gamma)R And Human Complement Activation By IgG3-Core Oligosaccharide Interactions, " Immunol. Lett. 54:101-04.

Jennings, V.M. (1995) "Review of Selected Adjuvants Used in Antibody Production," ILAR J. 37(3):119-125.

Johansson, M.U. et al. (2002) "Structure, Specificity, And Mode Of Interaction For Bacterial Albumin-Binding Modules," J. Biol. Chem. 277(10):8114-8120.

Johnson, S. et al. (2010) "Effector Cell Recruitment With Novel Fv-Based Dual-Affinity Re-Targeting Protein Leads To Potent Tumor Cytolysis And in vivo B-Cell Depletion," J. Mol. Biol. 399(3):436-449.

Joliot et al. (1991) "Antennapedia Homeobox Peptide Regulates Neural Morphogenesis," Proc. Natl. Acad. Sci. (U.S.A.) 88:1864-1868.

Jones et al. (1986) "Replacing The Complementarity-Determining Regions In A Human Antibody With Those From A Mouse," Nature 321:522-525.

Jurcic, J.G. (2005) "Immunotherapy for Acute Myeloid Leukemia" Curr Oncol Rep. 7(5):339-346).

Kasaian, M.T. et al. (2011) "IL-13 Antibodies Influence IL-13 Clearance In Humans By Modulating Scavenger Activity Of IL-13Ra2," J. Immunol. 187(1):561-569.

Kawai, S. et al. (2008) "Interferon-A Enhances CD317 Expression And The Antitumor Activity Of Anti-CD317 Monoclonal Antibody In Renal Cell Carcinoma Xenograft Models," Cancer Science 99(12):2461-2466.

Kettleborough, C. A. et al. (1991) "Humanization Of A Mouse Monoclonal Antibody By CDR-Grafting: The Importance Of Framework Residues On Loop Conformation," Protein Engineering 4:773-3783.

Kohler, G. et al. (1975) "Continuous Cultures Of Fused Cells Secreting Antibody Of Predefined Specificity," Nature 256:495-497.

Korman, A.J. et al. (2007) "Checkpoint Blockade in Cancer Immunotherapy," Adv. Immunol. 90:297-339.

Kounalakis, N. et al. (2005) "Tumor Cell and Circulating Markers in Melanoma Diagnosis, Prognosis, and Management" Curr Oncol Rep. 7(5):377-382.

Kreitman, R.J. (2006) "Immunotoxins for Targeted Cancer Therapy" AAPS J. 18;8(3):E532-E551.

Kumar, Pal S et al. (2006) "Human Papilloma Virus in Oral Cavity Cancer and Relation to Change in Quality of Life Following Treatment—a Pilot Study from Northern India," Indian J. Surg. Oncol. 7(4):386-391.

La Motte-Mohs, R. ""MGD013, a Bispecific PD-1 x LAGS Dual-Affinity Re-Targeting (DART®) Protein with T-cell Immunomodulatory Activity for Cancer Treatment"" American Association for Cancer Research Annual Meeting (AACR) Apr. 16-20, 2016, New Orleans, LA.

Langer (1990) "New Methods Of Drug Delivery," Science 249:1527-1533.

Latchman, Y. et al. (2001) "PD-L2 Is A Second Ligand For PD-1 And Inhibits T-Cell Activation," Nat. Immunol 2:261-268.

Leach, D. R., et al., (1996) "Enhancement Of Antitumor Immunity By CTLA-4 Blockade," Science 271, 1734-1736.

Lee, Y.M. et al. (2006) "Targeting Cyclins and Clyclin-Dependent Kinases in Cancer" Cell Cycle 5(18):2110-2114.

Lefranc, G. et al., (1979) "Gm, Am and Km Immunoglobulin Allotypes of Two Populations in Tunisia" Hum. Genet.: 50, 199-211.

Lenschow, D.J. et al. (1996) "CD28/B7 System of T-Cell Costimulation," Ann. Rev. Immunol. 14:233-258.

Lepenies, B. et al. (2008) "The Role Of Negative Costimulators During Parasitic Infections," Endocrine, Metabolic & Immune Disorders—Drug Targets 8:279-288.

(56) References Cited

OTHER PUBLICATIONS

Levy et al. (1985) "*Inhibition Of Calcification Of Bioprosthetic Heart Valves By Local Controlled-Release Diphosphonate*," Science 228:190-192.

Lindley, P.S. et al. (2009) "*The Clinical Utility Of Inhibiting CD28-Mediated Costimulation*," Immunol. Rev. 229:307-321.

Linsley, P. et al. (1996) "*Intracellular Trafficking Of CTLA4 And Focal Localization Towards Sites Of TCR Engagement*," Immunity 4:535-543.

Litowski, J.R. et al. (2002) "*Designing Heterodimeric Two-Stranded α-Helical Coiled-Coils: The Effects Of Hydrophobicity And α-Helical Propensity On Protein Folding, Stability, And Specificity*," J. Biol. Chem. 277:37272-37279.

Livingston et al. (1994) "*Improved Survival In Stage III Melanoma Patients With GM2 Antibodies: A Randomized Trial Of Acljuvant Vaccination With GM2 Ganglioside*," J. Clin. Oncol. 12:1036-1044.

Livingston, P.O. et al. (2005) "*Selection of GM2 fucosyl GM1, globo H and polysialic acid as targets on small cell lung cancers for antibody mediated immunotherapy*" Cancer Immunol Immunother. 54(10):1018-1025.

Lobuglio et al. (1989) "*Mouse/Human Chimeric Monoclonal Antibody In Man: Kinetics And Immune Response*," Proc. Natl. Acad. Sci. (U.S.A.) 86:4220-4224.

Loke, P. et al. (2004) "*Emerging Mechanisms Of Immune Regulation: The Extended B7 Family And Regulatory T-Cells.*" Arthritis Res. Ther. 6:208-214.

Lonberg, N. et al. (1995) "*Human Antibodies From Transgenic Mice*," Int. Rev. Immunol 13:65-93.

Lotem, M. et al. (2006) "*Presentation of Tumor Antigens by Dendritic Cells Genetically Modified with Viral and Nonviral Vectors*," J Immunother. 29(6):616-627.

Lu et al., (2008) "*The Effect Of A Point Mutation On The Stability Of IgG4 As Monitored By Analytical Ultracentrifugation*," J. Pharmaceutical Sciences 97:960-969.

Lu, D. et al. (2005) "*A Fully Human Recombinant IgG-Like Bispecific Antibody To Both The Epidermal Growth Factor Receptor And The Insulin-Like Growth Factor Receptor For Enhanced Antitumor Activity*," J. Biol. Chem. 280(20):19665-19672.

Lund et al. (1991) "*Human Fc Gamma RI And Fc Gamma RII Interact With Distinct But Overlapping Sites On Human IgG*," J. Immunol. 147:2657-2662.

Lund et al. (1992) "*Multiple Binding Sites On The CH2 Domain Of IgG For Mouse Fc Gamma R11*," Mol. Immunol. 29:53-59.

Lund, J. et al. (1995) "*Oligosaccharide-Protein Interactions In IgG Can Modulate Recognition By Fc Gamma Receptors*," FASEB J. 9:115-19.

Lund, J. et al. (1996) "*Multiple Interactions Of IgG With Its Core Oligosaccharide Can Modulate Recognition By Complement And Human Fc Gamma Receptor I And Influence The Synthesis Of Its Oligosaccharide Chains*," J. Immunol. 157:4963-4969.

MacroGenics Research Day Oct. 13, 2015.

Maeda, H. et al. (1991) "*Construction Of Reshaped Human Antibodies With HIV-Neutralizing Activity*," Human Antibodies Hybridoma 2:124-134.

Mardiros, A. et al. (2013) "*T Cells Expressing CD123-Specific Chimeric Antigen Receptors Exhibit Specific Cytolytic Effector Functions And Antitumor Effects Against Human Acute Myeloid Leukemia*," Blood 122:3138-3148.

Martin-Orozco, N. et al. (2007) "*Inhibitory Costimulation And Anti-Tumor Immunity*," Semin. Cancer Biol. 17(4):288-298.

Marvin et al. (2005) "*Recombinant Approaches To IgG-Like Bispecific Antibodies*," Acta Pharmacol. Sin. 26:649-658.

Mathelin, C. (2006) "*Marqueurs Proteiques circulants et cancer du sein*" Gynecol Obstet Fertil. 34(7-8):638-646.

Mazanet, M.M. et al. (2002) "*B7-H1 Is Expressed By Human Endothelial Cells And Suppresses T-Cell Cytokine Synthesis*," J. Immunol. 169:3581-3588.

Melero et al. (1997) "*Monoclonal Antibodies Against The 4-1BB T-Cell Activation Molecule Eradicate Established Tumors*," Nature Medicine 3: 682-685.

Mellman, I. et al. (2011) "*Cancer immunotherapy comes of age*," Nature 480, 480-489.

Merrifield, B. et al. (1986) "*Solid Phase Synthesis*," Science 232(4748):341-347.

Messmer, D. et al. (2005) "*CD 154 Therapy for Human B-Cell Malignancies*" Ann NY Acad Sci. 1062:51-60.

Mittelman et al. (1990) "*Active Specific Immunotherapy In Patients With Melanoma: A Clinical Trial With Mouse Antiidiotypic Monoclonal Antibodies Elicited With Syngeneic Anti-High-Molecular-Weight-Melanoma-AssociatedAntigen Monoclonal Antibodies*," J. Clin. Invest. 86:2136-2144.

Mokyr et al. (1998) "*Realization of the Therapeutic Potential of CTLA-4 Blockade in Low-Dose Chemotherapy-treated Tumor-bearing Mice*" Cancer Research 58: 5301-5304.

Möller et al. (1991) "*Bi-specific-Monoclonal-Antibody-Directed Lysis Of Ovarian Carcinoma Cells By Activated Human T Lymphocytes*," Cancer Immunol. Immunother. 33(4):210-216.

Moore, P. "*Dart Molecules for Immunomodulatory Therapeutic Strategies*" 8th GTC Immunotherapeutics and Immunomonitoring Conference, Jan. 25, 2016, San Diego, CA.

Moore, P.A. et al. (2011) "*Application Of Dual Affinity Retargeting Molecules To Achieve Optimal Redirected T-Cell Killing Of B-Cell Lymphoma*," Blood 117(17):4542-4551.

Moran, A.E. et al. (2013) "*The TNFRs OX40, 4-1BB, and CD40As Targets For Cancer Immunotherapy*," Curr Opin Immunol. Apr. 2013; 25(2):10.1016/j.coi.2013.01.004.

Natali et al. (1987) "*Immunohistochemical Detection Of Antigen In Human Primary And Metastatic Melanomas By The Monoclonal Antibody 140.240 And Its Possible Prognostic Significance*," Cancer 59:55-63.

Ning et al. (1996) "*Intratumoral Radioimmunotherapy Of A Human Colon Cancer Xenograft Using A Sustained Release Gel*," Radiotherapy & Oncology 39:179 189.

Nishimura, H. et al. (2000) "*Facilitation Of Beta Selection And Modification Of Positive Selection In The Thymus Of PD-1-Deficient Mice*," J. Exp. Med. 191:891-898.

O'Dwyer. P.J. (2006) "*The Present and Future of Angiogenesis-Directed Treatments of Colorectal Cancer*" Oncologist. 11(9):992-998.

Olafsen et al. (2004) "*Covalent Disulfide-Linked Anti-CEA Diabody Allows Site-Specific Conjugation And Radiolabeling For Tumor Targeting Applications*," Prot. Engr. Des. Sel. 17:21-27.

Palena, C., et al. (2006) "*Cancer vaccines: preclinical studies and novel strategies*," Adv. Cancer Res. 95, 115-145.

Peeters et al. (2001) "*Production Of Antibodies And Antibody Fragments In Plants*," Vaccine 19:2756.

Peggs, K.S. et al. (2006) "*Principles and use of anti-CTLA4 antibody in human cancer immunotherapy*" Curr Opin Immunol. 18(2):206-213.

Perez et al. (1989) "*Isolation And Characterization Of A cDNA Encoding The KS1/4 Epithelial Carcinoma Marker,* " J. Immunol. 142:3662 3667.

Peters, P et al. (2012) "*Engineering an Improved IgG4 Molecule with Reduced Disulfide Bond Heterogeneity and Increased Fab Domain Thermal Stability*," J. Biol. Chem., 287:24525-24533.

Petroff, M.G. et al. (2002) "*B7 Family Molecules: Novel Immunomodulators At The Maternal-Fetal Interface*," Placenta 23:S95-S101.

Pietrantonio, F. et al. (2015) "*Bevacizumab-Based Neoadjuvant Chemotherapy For Colorectal Cancer Liver Metastases: Pitfalls And Helpful Tricks In A Review For Clinicians*," Crit. Rev. Oncol. Hematol. 95(3):272-281.

Pizzitola, I. et al. (2014) "*Chimeric Antigen Receptors Against CD33/CD123 Antigens Efficiently Target Primary Acute Myeloid Leukemia Cells in vivo*," Leukemia doi:10.1038/leu.2014.62.

Pollock et al. (1999) "*Transgenic Milk As A Method For The Production Of Recombinant Antibodies*," J. Immunol Methods 231:147-157.

Prange W. et al. (2003) "*Beta-catenin accumulation in the progression of human hepatocarcinogenesis correlates with loss of E-cadherin and accumulation of p53, but not with expression of conventional WNT-target genes*" J Pathol. 201(2):250-259.

(56) References Cited

OTHER PUBLICATIONS

Presta, L.G. et al. (2002) "*Engineering Therapeutic Antibodies For Improved Function*," Biochem. Soc. Trans. 30:487-90.

Ragupathi, G. (2005) "*Antibody Inducing Polyvalent Cancer Vaccines*" Cancer Treat Res. 123:157-180.

Reddy, M.P. et al. (2000) "*Elimination Of Fc Receptor-Dependent Effector Functions Of A Modified IgG4 Monoclonal Antibody To Human CD4*," J. Immunol. 164:1925-1933.

Reff et al. (1994) "*Depletion Of B Cells In Vivo By A Chimeric Mouse Human Monoclonal Antibody To CD20*," Blood 83:435-445.

Ridgway et al. (1996) "*Knobs-Into-Holes' Engineering Of Antibody CHS Domains For Heavy Chain Heterodimerization*," Protein Engr. 9:617-621.

Riechmann, L. et al. (1988) "*Reshaping Human Antibodies for Therapy*," Nature 332:323-327.

Rimon, E. et al. (2004) "*Gonadotropin-induced Gene Regulation in Human Granulosa Cells Obtained from IVF Patients: Modulation of Genes Coding for Growth Factors and Their Receptors and Genes Involved in Cancer and Other Diseases*," Int J Oncol. 24(5): 1325-1338.

Ritter, G. et al. (1997) "*Characterization Of Posttranslational Modifications Of Human A33 Antigen, A Novel Palmitoylated Surface Glycoprotein Of Human Gastrointestinal Epithelium,*" Biochem. Biophys. Res. Commun, 236(3):682-686.

Rosati, S. et al. (2005) "*Chronic Lymphocytic Leukaemia: A Review of the Immuno-architecture*," Curr Top Microbiol Immunol. 294:91-107.

Saleh et al. (1993) "*Generation Of A Human Anti-Idiotypic Antibody That Mimics The GD2 Antigen*," J.Immunol., 151, 3390-3398.

Sato, K. et al. (1993) "*Reshaping a Human Antibody to Inhibit the Interleukin 6-dependent Tumor Cell Growth1*" Cancer Res 53:851-856.

Saudek et al. (1989) "*A Preliminary Trial Of The Programmable Implantable Medication System For Insulin Delivery*," N. Engl. J. Med. 321:574-579.

Sayeed, A. et al. (2013) "*Aberrant Regulation Of The BST2 (Tetherin) Promoter Enhances Cell Proliferation And Apoptosis Evasion In High Grade Breast Cancer Cells*," PLoS One 8(6)e67191, pp. 1-10.

Sefton, (1987) "*Implantable Pumps*," CRC Crit. Rev. Biomed. Eng. 14:201-240 (Abstract Only).

Sgouros et al. (1993) "*Modeling And Dosimetry Of Monoclonal Antibody M195 (Anti-CD 33) In Acute Myelogenous Leukemia*," J. Nucl. Med. 34:422-430.

Sharpe, A.H. et al. (2002) "*The B7-CD28 Superfamily*," Nature Rev. Immunol. 2:116-126.

Shaw et al. (1987) "*Characterization Of A Mouse/Human Chimeric Monoclonal Antibody (17-1A) To A Colon Cancer Tumor-Associated Antigen*," J. Immunol. 138:4534-4538.

Shields, R.L. et al. (2001) "*High Resolution Mapping Of The Binding Site On Human IgG1 For Fc Gamma RI, Fc Gamma RII, Fc Gamma RIII, And FcRn And Design Of IgG1 Variants With Improved Binding To The Fc gamma R*," J. Biol. Chem. 276:6591-6604.

Shitara et al. (1993) "*A Mouse/Human Chimeric Anti-(Ganglioside GD3) Antibody With Enhanced Antitumor Activities*," Cancer Immunol. Immunother. 36:373-380.

Shopes, B. (1992) "*A Genetically Engineered Human IgG Mutant With Enhanced Cytolytic Activity*," J. Immunol. 148(9):2918-2922.

Sloan, D.D. et al. (2015) "*Targeting HIV Reservoir in Infected CD4 T Cells by Dual-Affinity Retargeting Molecules (DARTs) that Bind HIV Envelope and Recruit Cytotoxic T Cells*," PLoS Pathog. 11(11):e1005233. doi: 10.1371/journal.ppat.1005233.

Song et al. (1995) "*Antibody Mediated Lung Targeting Of Long Circulating Emulsions*," PDA Journal of Pharmaceutical Science & Technology 50:372 397.

Staerz et al. (1985) "*Hybrid Antibodies Can Target Sites For Attack By T Cells*," Nature 314:628-631.

Stavenhagen, J.B. et al. (2007) "*Fc Optimization Of Therapeutic Antibodies Enhances Their Ability To Kill Tumor Cells In Vitro And Controls Tumor Expansion In Vivo Via Low-Affinity Activating Fcgamma Receptors*," Cancer Res. 57(18):8882-8890.

Steinkruger, J.D. et al. (2012) "*The d'-d-d' Vertical Triad is Less Discriminating Than the a'-a-a' Vertical Triad in the Antiparallel Coiled-coil Dimer Motif*" J. Amer. Chem. Soc. 134(5):2626-2633.

Stephan, J. et al. (1999) "*Selective Cloning Of Cell Surface Proteins Involved In Organ Development: Epithelial Glycoprotein Is Involved In Normal Epithelial Differentiation*," Endocrinol. 140:5841-5854.

Stevenson, G.T. et al. (1989) "*A Chimeric Antibody With Dual Fc Regions (bisFabFc) Prepared By Manipulations At The IgG Hinge*," Anti-Cancer Drug Design 3:219-230 (Abstract Only).

Straussman, R. et al. (2007) "*Kinking the Coiled Coil—Negatively Charged Residues at the Coiled-coil Interface*," J. Molec. Biol. 366:1232-1242.

Subudhi, S.K. et al. (2005) "*The Balance Of Immune Responses: Costimulation Verse Coinhibition,*" J. Molec. Med. 83:193-202.

Suh, D.H. et al. (2015) "*Major Clinical Research Advances In Gynecologic Cancer In 2014*," J. Gynecol. Oncol. 26(2):156-167.

Sun, M. et al. (2002) "*Characterization of Mouse and Human B7-H3 Genes*," J. Immunol. 168:6294-6297.

Suresh, T. et al. (2014) "*New Antibody Approaches To Lymphoma Therapy*," J. Hematol. Oncol. 7:58.

Tailor et al. (1990) "*Nucleotide Sequence Of Human Prostatic Acid Phosphatase Determined From A Full-Length cDNA Clone,*" Nucl. Acids Res. 18(16):4928.

Takemura, S. et al. (2000) "*Construction Of A Diabody (Small Recombinant Bispecific Antibody) Using A Refolding System*," Protein Eng. 13(8):583-588.

Tellez-Avila, F.I. et al. (2005) "*The Carcinoembryonic Antigen: Apropos of an Old Friend*," Rev Invest Clin. 57(6):814-819 (Abstract Only).

Tempest, P.R. et al. (1991) "*Reshaping A Human Monoclonal Antibody To Inhibit Human Respiratory Syncytial Virus Infection in vivo*," Bio/Technology 9:266-271.

Tettamanti, S. et al. (2013) "*Targeting Of Acute Myeloid Leukaemia By Cytokine-Induced Killer Cells Redirected With A Novel CD123-Specific Chimeric Antigen Receptor*," Br. J. Haematol. 161:389-401.

Thomas, D.A. et al. (2006) "*Monoclonal Antibody Therapy for Hairy Cell Leukemia*," Hematol Oncol Clin North Am. 20(5):1125-1136.

Topalian SL, et al. (2012) "*Safety, activity, and immune correlates of anti-PD-1 antibody in cancer*" N Engl J Med 366:2443-54.

Trauth et al. (1989) "*Monoclonal Antibody-Mediated Tumor Regression By Induction Of Apoptosis*," Science 245:301-304.

Tripet, B. et al. (2002) "*Kinetic Analysis of the Interactions between Troponin C and the C-terminal Troponin I Regulatory Region and Validation of a New Peptide Delivery/Capture System used for Surface Plasmon Resonance*," J. Molec. Biol. 323:345-362.

Troussard, X. et al. (1998) "*Hairy Cell Leukemia. What is New Forty Years After the First Description?*" Hematol Cell Ther. 40(4):139-148 (Abstract Only).

Tumis M, et al., (2012) "*Combinatorial immunotherapy PD-1 may not be LAG-ing behind any more*" OncoImmunology 1:7, 1172-1174.

Van Horssen, R. et al. (2006) "*TNF-α in Cancer Treatment: Molecular Insights, Antitumor Effects, and Clinical Utility*," Oncologist. 11(4):397-408.

Verhoeyen, M. et al. (1988) "*Reshaping Human Antibodies: Grafting An Antilysozyme Activity*," Science 239:1534-1536.

Veri, M.C. et al. (2010) "*Therapeutic Control Of B Cell Activation Via Recruitment Of Fcgamma Receptor IIb (CD32B) Inhibitory Function With A Novel Bispecific Antibody Scaffold*," Arthritis Rheum. 62(7):1933-1943.

Vermeij, R. et al. (2012) "*Potentiation of a p53-SLP vaccine by cyclophosphamide in ovarian cancer: a single-arm phase II study.*" Int. J. Cancer 131, E670-E680.

Viglietta, V. et al. (2007) "*Modulating Co-Stimulation*," Neurotherapeutics 4:666-675.

Vijayasardahl et al. (1990) "*The Melanoma Antigen Gp75 Is The Human Homologue Of The Mouse B (Brown) Locus Gene Product*," J. Exp. Med. 171(4):1375-1380.

(56) References Cited

OTHER PUBLICATIONS

Wang, L. et al. (2011) "*Vista, A Novel Mouse Ig Superfamily Ligand That Negatively Regulates T-Cell Responses*," J. Exp. Med. 10.1084/jem.20100619:1-16.
Wang, S. et al. (2004) "*Co-Signaling Molecules Of The B7-CD28 Family In Positive And Negative Regulation Of T Lymphocyte Responses*," Microbes Infect. 6:759-766.
Wang, W. et al. (2009) "*Chimeric And Humanized Anti-HM1.24 Antibodies Mediate Antibody-Dependent Cellular Cytotoxicity Against Lung Cancer Cells. Lung Cancer*," 63(1):23-31.
Weinberg et al. (2000) "*Engagement of the OX-40 Receptor In Vivo Enhances Antitumor Immunity*," Immunol 164:2160-2169.
Winter et al. (1991) "*Man-made Antibodies*,"Nature 349:293-299.
Winter, G. et al. (1994) "*Making Antibodies By Phage Display Technology*," Annu. Rev. Immunol. 12.433-455.
Wolff, E.A. et al. (1993) "*Monoclonal Antibody Homodimers: Enhanced Antitumor Activity In Nude Mice*," Cancer Research 53:2560-2565.
Wong, N.A. et al. (2006) "*EpCAM and gpA33 Are Markers Of Barrett's Metaplasia*," J. Clin Pathol. 59(3):260-263.
Woo S-R, et al., (2012) "*Immune inhibitory molecules LAG-3 and PD-1 synergistically regulate T cell function to promote tumoral immune escape*," Cancer Res. 72:917-927.
Woolfson, D.N. (2005) "*The Design Of Coiled-Coil Structures And Assemblies*," Adv. Prot. Chem. 70:79-112.
Wu et al. (1987) "*Receptor-Mediated In Vitro Gene Transformation By A Soluble DNA Carrier System*," J. Biol. Chem. 262:4429-4432.
Wu, A. et al. (2001) "*Multimerization Of A Chimeric Anti-CD20 Single Chain Fv-Fv Fusion Protein Is Mediated Through Variable Domain Exchange*," Protein Engineering 14(2):1025-1033.
Xie et al. (2005) "*A New Format Of Bispecific Antibody: Highly Efficient Heterodimerization, Expression And Tumor Cell Lysis*," J. Immunol. Methods 296:95-101.
Xu, D. et al. (2000) "*In Vitro Characterization of Five Humanized OKT3 Effector Function Variant Antibodies*," Cell. Immunol. 200:16-26.
Yamazaki, T. et al. (2002) "*Expression Of Programmed Death 1 Ligands By Murine T-Cells And APC*," J. Immunol. 169:5538-5545.
Yokota et al. (1992) "*Rapid Tumor Penetration Of A Single-Chain Fv And Comparison With Other Immunoglobulin Forms*," Cancer Res. 52:3402-3408.
Yu et al. (1991) "*Coexpression Of Different Antigenic Markers On Moieties That Bear CA 125 Determinants*," Cancer Res. 51(2):468 475.
Zeng, Y. et al. (2008) "*A Ligand-Pseudoreceptor System Based On de novo Designed Peptides For The Generation Of Adenoviral Vectors With Altered Tropism.*," J. Gene Med. 10:355-367.
Zhang, X. M. et al. (2008) "*The anti-tumor immune response induced by a combination of MAGE-3/MAGE-n-derived peptides*," Oncol. Rep. 20, 245-252.
Zheng, C. et al. (2011) "*A Novel Anti-CEACAM5 Monoclonal Antibody, CC4, Suppresses Colorectal Tumor Growth and Enhances NK Celis-Mediated Tumor Immunity*," PLoS One 6(6):e21146, pp. 1-11.
Zhou, H. et al. (2002) "*Lung Tumorigenesis Associated with erb-B-2 and erb-B-3 Over expression in Human erb-B-3 Transgenic Mice is Enhanced by Methylnitrosourea*," Oncogene 21(57):8732-8740.
International Search Report PCT/US2016/044430 (WO 2017/019846) (dated 2016) (4 pages).

Written Opinion of the International Searching Authority PCT/US2016/044430 (WO 2017/019846) (dated 2016) (6 pages).
Jing, et al., "Combined Immune Checkpoint Protein Blockade and Low Dose Whole Body Irradiation as Immunotherapy for Myeloma," J. Immunother. Cancer, vol. 3, No. 2, pp. 1-5 (2015).
Matsuzaki, et al., "Tumor-Infiltrating NY-ESO-1-Specific CD8+ T Cells are Negatively Regulated by LAG-3 and PD-1 Human Ovarian Cancer," Proc. Natl. Acad. Sci., vol. 107, No. 17, pp. 7875-7880 (2010).
Extended European Search Report EP 16831339 (dated Nov. 27, 2018), 8 pages.
Dimaio, D. et al. (2006) "*Human Papillomaviruses and Cervical Cancer*," Adv. Vims Res. 66:125-159.
Grabowski, J.P. et al. (2015) "*Current Management of Ovarian Cancer*," Minerva Med. 106(3):151-156 (Abstract Only).
Liu, K.J. et al. (2015) "*Bevacizumab In Combination With Anticancer Drugs For Previously Treated Advanced Non-Small Cell Lunz Cancer*," Tumour Biol. 36(3):1323-1327.
Ragnhammar et al. (1993) "*Effect Of Monoclonal Antibody 17-JA And GM-CSF In Patients With Advanced Colorectal Carcinoma—Long-Lasting, Complete Remissions Can Be Induced*," Int. J. Cancer 53:751-758.
Sylvan, S.E. et al. (2014) "*Alemtuzumab (Anti-CD52 Monoclonal Antibody) As Single-Agent Therapy In Patients With Relapsed/Refractory Chronic Lymphocytic Leukaemia (CLL)—A Single Region Exverience On Consecutive Patients*,"Ann Hematol. 93(10):1725-1733.
Wang, W. et al. (2009) "*HMJ.24 (CD317) Is A Novel Target Against Lung Cancer For Immunotheravv Usinz Anti-HMJ.24 Antibody*," Cancer Immunology, Immunotherapy 58(6):967-976.
Oganesyan, V. et al. (2009) "*Structural Characterization of a Human Fe Fragment Engineered for Extended Serum Half-Life*," Molecular Inununology 46:1750-1755.
Antonia et al., "Immuno-oncology Combinations: A Review of Clinical Experience and Future Prospects," *Clin Cancer Res* 20(24):6258-6258 (2014).
Butler et al., "Therapeutic PD-L1 and LAG-3 blockade rapidly clears established blood-stage Plasmodium infection," Nat Immunol 13(2):188-195 (2012).
Chan & Carter, "Therapeutic antibodies for autoimmunity and inflammation," *Nat Rev Immunol* 10:301-306 (2010).
Kulpa et al., "PD-1 Coinhibitory Signals: The Link Between Pathogenesis and Protection," Semin Immunol 25(3), pp. 1-20 (2013).
Mahoney et al., "The Next Immune-Checkpoint Inhibitors: PD-1/PD-L1 Blockade in Melanoma," Clin Therapeutics 37(4):764-782 (2015).
Okazaki et al., "PD-1 and LAG-3 Inhibitory Co-Receptors Act Synergistically to Prevent Autoimmunity in Mice", The Journal of Experimental Medicine, 208(2): 395-407 (2011).
Poirier, N. et al., "*Antibody-Mediated Depletion Of Lymphocyte-Activation Gene-3 (LAG-3+ )-Activated T Lymphocytes Prevents Delayed-Type Hypersensitivity In Non-Human Primates*," Clin Exper. Immunol. 164:265-274 (2011).
Search Report and official action issued in co-pending Chinese Patent Application No. 2016800443929, dated Dec. 9, 2020.
Ryoyo Ikebuchi, "Influence of cross-linking on cell death in PD-L1 expressing cell lines and bovine lymphocytes," Immunology, vol. 4, pp. 551-561 (2014).
Official Action issued in Colombia Patent Application No. NC2020/0007460, dated Nov. 19, 2021.

\* cited by examiner

PD-1-BINDING MOLECULES AND METHODS OF USE THEREOF

CROSS-REFERENCE TO RELATED APPLICATIONS

This application is a continuation of U.S. patent application Ser. No. 15/748,458, filed Jan. 29, 2018, which is the U.S. National Stage of International Patent Application No. PCT/US2016/044430, filed Jul. 28, 2016, which claims priority from U.S. Provisional Patent Application Nos. 62/322,974, filed Apr. 15, 2016, 62/255,140, filed Nov. 13, 2015, 62/239,559, filed Oct. 9, 2015, and 62/198,867, filed Jul. 30, 2015. The contents of these applications are incorporated herein by reference in their entirety.

REFERENCE TO SEQUENCE LISTING

This application includes one or more Sequence Listings pursuant to 37 C.F.R. 1.821 et seq., which are disclosed in computer-readable media (file name: 1301_0122PCT_Sequence_Listing_ST25.txt, created on Jul. 1, 2016, and having a size of 282,789 bytes), which file is herein incorporated by reference in its entirety.

FIELD OF THE INVENTION

The present invention is directed to PD-1 binding molecules that comprise the PD-1-binding domain of selected anti-PD-1 antibodies capable of binding to both cynomolgus monkey PD-1 and to human PD-1: PD-1 mAb 1, PD-1 mAb 2, PD-1 mAb 3, PD-1 mAb 4, PD-1 mAb 5, PD-1 mAb 6, PD-1 mAb 7, PD-1 mAb 8, PD-1 mAb 9, PD-1 mAb 10, PD-1 mAb 11, PD-1 mAb 12, PD-1 mAb 13, PD-1 mAb 14, or PD-1 mAb 15. The invention particularly concerns PD-1 binding molecules that are humanized or chimeric versions of such antibodies, or that comprise PD-1 binding-fragments of such anti-PD-1 antibodies (especially immunoconjugates, diabodies, BiTEs, bispecific antibodies, etc.). The invention particularly concerns such PD-1-binding molecules that are additionally capable of binding an epitope of a molecule involved in regulating an immune check point that is present on the surface of an immune cell. The present invention also pertains to methods of using such PD-1-binding molecules to detect PD-1 or to stimulate an immune response. The present invention also pertains to methods of combination therapy in which a PD-1-binding molecule that comprises one or more PD-1-binding domain(s) of such selected anti-PD-1 antibodies is administered in combination with one or more additional molecules that are effective in stimulating an immune 4847-6634-0280.1 response and/or in combination with one or more additional molecules that specifically bind a cancer antigen.

BACKGROUND OF THE INVENTION

I. Cell Mediated Immune Responses

The immune system of humans and other mammals is responsible for providing protection against infection and disease. Such protection is provided both by a humoral immune response and by a cell-mediated immune response. The humoral response results in the production of antibodies and other biomolecules that are capable of recognizing and neutralizing foreign targets (antigens). In contrast, the cell-mediated immune response involves the activation of macrophages, Natural Killer cells (NK), and antigen specific cytotoxic T-lymphocytes by T-cells, and the release of various cytokines in response to the recognition of an antigen (Dong, C. et al. (2003) "*Immune Regulation by Novel Costimulatory Molecules*," Immunolog. Res. 28(1): 39-48).

The ability of T-cells to optimally mediate an immune response against an antigen requires two distinct signaling interactions (Viglietta, V. et al. (2007) "*Modulating Co-Stimulation*," Neurotherapeutics 4:666-675; Korman, A. J. et al. (2007) "*Checkpoint Blockade in Cancer Immunotherapy*," Adv. Immunol. 90:297-339). First, antigen that has been arrayed on the surface of Antigen-Presenting Cells (APC) must be presented to an antigen-specific naive CD4$^+$ T-cell. Such presentation delivers a signal via the T-Cell Receptor (TCR) that directs the T-cell to initiate an immune response that will be specific to the presented antigen. Second, a series of costimulatory and inhibitory signals, mediated through interactions between the APC and distinct T-cell surface molecules, triggers first the activation and proliferation of the T-cells and ultimately their inhibition. Thus, the first signal confers specificity to the immune response whereas the second signal serves to determine the nature, magnitude and duration of the response.

The immune system is tightly controlled by costimulatory and co-inhibitory ligands and receptors. These molecules provide the second signal for T-cell activation and provide a balanced network of positive and negative signals to maximize immune responses against infection while limiting immunity to self (Wang, L. et al. (Mar. 7, 2011) "*VISTA, A Novel Mouse Ig Superfamily Ligand That Negatively Regulates T-Cell Responses*," J. Exp. Med. 10.1084/jem.20100619:1-16; Lepenies, B. et al. (2008) "*The Role Of Negative Costimulators During Parasitic Infections*," Endocrine, Metabolic & Immune Disorders—Drug Targets 8:279-288). Of particular importance is binding between the B7.1 (CD80) and B7.2 (CD86) ligands of the Antigen-Presenting Cell and the CD28 and CTLA-4 receptors of the CD4+T lymphocyte (Sharpe, A. H. et al. (2002) "*The B7-CD28 Superfamily*," Nature Rev. Immunol. 2:116-126; Dong, C. et al. (2003) "*Immune Regulation by Novel Costimulatory Molecules*," Immunolog. Res. 28(1):39-48; Lindley, P. S. et al. (2009) "*The Clinical Utility Of Inhibiting CD28 Mediated Costimulation*," Immunol. Rev. 229:307-321). Binding of B7.1 or of B7.2 to CD28 stimulates T-cell activation; binding of B7.1 or B7.2 to CTLA-4 inhibits such activation (Dong, C. et al. (2003) "*Immune Regulation by Novel Costimulatory Molecules*," Immunolog. Res. 28(1): 39-48; Lindley, P. S. et al. (2009) "*The Clinical Utility Of InhibitingCD28Mediated Costimulation*," Immunol. Rev. 229:307-321; Greenwald, R. J. et al. (2005) "*The B7 Family Revisited*," Ann. Rev. Immunol. 23:515-548). CD28 is constitutively expressed on the surface of T-cells (Gross, J., et al. (1992) "*Identification And Distribution Of The Costimulatory Receptor CD28 In The Mouse*," J. Immunol. 149: 380-388), whereas CTLA-4 expression is rapidly upregulated following T-cell activation (Linsley, P. et al. (1996) "*Intracellular Trafficking Of CTLA4 And Focal Localization Towards Sites Of TCR Engagement*," Immunity 4:535-543). Since CTLA-4 is the higher affinity receptor (Sharpe, A. H. et al. (2002) "*The B7-CD28 Superfamily*," Nature Rev. Immunol. 2:116-126), binding first initiates T-cell proliferation (via CD28) and then inhibits it (via nascent expression of CTLA-4), thereby dampening the effect when proliferation is no longer needed.

Further investigations into the ligands of the CD28 receptor have led to the identification and characterization of a set of related B7 molecules (the "B7 Superfamily") (Coyle, A. J. et al. (2001) "*The Expanding B7 Superfamily: Increasing*

*Complexity In Costimulatory Signals Regulating T-Cell Function*," Nature Immunol. 2(3):203-209; Sharpe, A. H. et al. (2002) "*The B7-CD28 Superfamily*," Nature Rev. Immunol. 2:116-126; Greenwald, R. J. et al. (2005) "*The B7 Family Revisited*," Ann. Rev. Immunol. 23:515-548; Collins, M. et al. (2005) "*The B7 Family Of Immune-Regulatory Ligands*," Genome Biol. 6:223.1-223.7; Loke, P. et al. (2004) "*Emerging Mechanisms Of Immune Regulation: The Extended B7 Family And Regulatory T-Cells*." Arthritis Res. Ther. 6:208-214; Korman, A. J. et al. (2007) "*Checkpoint Blockade in Cancer Immunotherapy*," Adv. Immunol. 90:297-339; Flies, D. B. et al. (2007) "*The New B7s: Playing a Pivotal Role in Tumor Immunity*," J. Immunother. 30(3): 251-260; Agarwal, A. et al. (2008) "*The Role Of Positive Costimulatory Molecules In Transplantation And Tolerance*," Curr. Opin. Organ Transplant. 13:366-372; Lenschow, D. J. et al. (1996) "*CD28/B7 System of T-Cell Costimulation*," Ann. Rev. Immunol. 14:233-258; Wang, S. et al. (2004) "*Co-Signaling Molecules Of The B7-CD28 Family In Positive And Negative Regulation Of T Lymphocyte Responses*," Microbes Infect. 6:759-766). There are currently several known members of the family: B7.1 (CD80), B7.2 (CD86), the inducible co-stimulator ligand (ICOS-L), the programmed death-1 ligand (PD-L1; B7-H1), the programmed death-2 ligand (PD-L2; B7-DC), B7-H3, B7-H4 and B7-H6 (Collins, M. et al. (2005) "The B7 *Family Of Immune-Regulatory Ligands*," Genome Biol. 6:223.1-223.7; Flajnik, M. F. et al. (2012) "*Evolution Of The B7 Family: Co-Evolution Of B7H6 And Nkp30, Identification Of A New B7 Family Member, B7H7, And Of B7's Historical Relationship With The MHC*," Immunogenetics epub doi.org/10.1007/s00251-012-0616-2).

II. Programmed Death-1 ("PD-1")

Programmed Death-1 ("PD-1," also known as "CD279") is an approximately 31 kD type I membrane protein member of the extended CD28/CTLA-4 family of T-cell regulators that broadly negatively regulates immune responses (Ishida, Y. et al. (1992) "*Induced Expression Of PD-1, A Novel Member Of The Immunoglobulin Gene Superfamily, Upon Programmed Cell Death*," EMBO J. 11:3887-3895; United States Patent Application Publication No. 2007/0202100; 2008/0311117; 2009/00110667; U.S. Pat. Nos. 6,808,710; 7,101,550; 7,488,802; 7,635,757; 7,722,868; PCT Publication No. WO 01/14557).

PD-1 is expressed on activated T-cells, B-cells, and monocytes (Agata, Y. et al. (1996) "*Expression Of The PD-1 Antigen On The Surface Of Stimulated Mouse T And B Lymphocytes*," Int. Immunol. 8(5):765-772; Yamazaki, T. et al. (2002) "*Expression Of Programmed Death 1 Ligands By Murine T-Cells And APC*," J. Immunol. 169:5538-5545) and at low levels in natural killer (NK) T-cells (Nishimura, H. et al. (2000) "*Facilitation Of Beta Selection And Modification Of Positive Selection In The Thymus Of PD-1-Deficient Mice*," J. Exp. Med. 191:891-898; Martin-Orozco, N. et al. (2007) "*Inhibitory Costimulation And Anti-Tumor Immunity*," Semin. Cancer Biol. 17(4):288-298).

The extracellular region of PD-1 consists of a single immunoglobulin (Ig)V domain with 23% identity to the equivalent domain in CTLA-4 (Martin-Orozco, N. et al. (2007) "*Inhibitory Costimulation And Anti-Tumor Immunity*," Semin. Cancer Biol. 17(4):288-298). The extracellular IgV domain is followed by a transmembrane region and an intracellular tail. The intracellular tail contains two phosphorylation sites located in an immunoreceptor tyrosine-based inhibitory motif and an immunoreceptor tyrosine-based switch motif, which suggests that PD-1 negatively regulates TCR signals (Ishida, Y. et al. (1992) "*Induced Expression Of PD-1, A Novel Member Of The Immunoglobulin Gene Superfamily, Upon Programmed Cell Death*," EMBO J. 11:3887-3895; Blank, C. et al. (2006) "*Contribution Of The PD-L1/PD-1 Pathway To T-Cell Exhaustion: An Update On Implications For Chronic Infections And Tumor Evasion Cancer*," Immunol. Immunother. 56(5):739-745).

PD-1 mediates its inhibition of the immune system by binding to B7-H1 and B7-DC (Flies, D. B. et al. (2007) "*The New B7s: Playing a Pivotal Role in Tumor Immunity*," J. Immunother. 30(3):251-260; U.S. Pat. Nos. 6,803,192; 7,794,710; United States Patent Application Publication Nos. 2005/0059051; 2009/0055944; 2009/0274666; 2009/0313687; PCT Publication Nos. WO 01/39722; WO 02/086083).

B7-H1 and B7-DC are broadly expressed on the surfaces of human and murine tissues, such as heart, placenta, muscle, fetal liver, spleen, lymph nodes, and thymus as well as murine liver, lung, kidney, islets cells of the pancreas and small intestine (Martin-Orozco, N. et al. (2007) "*Inhibitory Costimulation And Anti-Tumor Immunity*," Semin. Cancer Biol. 17(4):288-298). In humans, B7-H1 protein expression has been found in human endothelial cells (Chen, Y. et al. (2005) "*Expression of B7-H1 in Inflammatory Renal Tubular Epithelial Cells*," Nephron. Exp. Nephrol. 102:e81-e92; de Haij, S. et al. (2005) "*Renal Tubular Epithelial Cells Modulate T-Cell Responses Via ICOS-L And B7-H1*" Kidney Int. 68:2091-2102; Mazanet, M. M. et al. (2002) "*B7-H1 Is Expressed By Human Endothelial Cells And Suppresses T-Cell Cytokine Synthesis*," J. Immunol. 169:3581-3588), myocardium (Brown, J. A. et al. (2003) "*Blockade Of Programmed Death-1 Ligands On Dendritic Cells Enhances T-Cell Activation And Cytokine Production*," J. Immunol. 170:1257-1266), syncyciotrophoblasts (Petroff, M. G. et al. (2002) "*B7 Family Molecules: Novel Immunomodulators At The Maternal-Fetal Interface*," Placenta 23:S95-S101). The molecules are also expressed by resident macrophages of some tissues, by macrophages that have been activated with interferon (IFN)-γ or tumor necrosis factor (TNF)-α (Latchman, Y. et al. (2001) "*PD-L2 Is A Second Ligand For PD-1 And Inhibits T-Cell Activation*," Nat. Immunol 2:261-268), and in tumors (Dong, H. (2003) "*B7-H1 Pathway And Its Role In The Evasion Of Tumor Immunity*," J. Mol. Med. 81:281-287).

The interaction between B7-H1 and PD-1 has been found to provide a crucial negative costimulatory signal to T and B-cells (Martin-Orozco, N. et al. (2007) "*Inhibitory Costimulation And Anti-Tumor Immunity*," Semin. Cancer Biol. 17(4):288-298) and functions as a cell death inducer (Ishida, Y. et al. (1992) "*Induced Expression Of PD-1, A Novel Member Of The Immunoglobulin Gene Superfamily, Upon Programmed Cell Death*," EMBO J. 11:3887-3895; Subudhi, S. K. et al. (2005) "*The Balance Of Immune Responses: Costimulation Verse Coinhibition*," J. Molec. Med. 83:193-202). More specifically, interaction between low concentrations of the PD-1 receptor and the B7-H1 ligand has been found to result in the transmission of an inhibitory signal that strongly inhibits the proliferation of antigen-specific $CD8^+$ T-cells; at higher concentrations the interactions with PD-1 do not inhibit T-cell proliferation but markedly reduce the production of multiple cytokines (Sharpe, A. H. et al. (2002) "*The B7-CD28 Superfamily*," Nature Rev. Immunol. 2:116-126). T-cell proliferation and cytokine production by both resting and previously activated CD4 and CD8 T-cells, and even naive T-cells from umbilical-cord blood, have been found to be inhibited by soluble B7-H1-Fc fusion proteins (Freeman, G. J. et al. (2000) "*Engagement Of The PD-1 Immunoinhibitory Receptor By A

*Novel B7 Family Member Leads To Negative Regulation Of Lymphocyte Activation,*" J. Exp. Med. 192:1-9; Latchman, Y. et al. (2001) "*PD-L2 Is A Second Ligand For PD-1 And Inhibits T-Cell Activation,*" Nature Immunol. 2:261-268; Carter, L. et al. (2002) "*PD-1:PD-L Inhibitory Pathway Affects Both CD4(+) and CD8(+) T-cells And Is Overcome By IL-2,*" Eur. J. Immunol. 32(3):634-643; Sharpe, A. H. et al. (2002) "*The B7-CD28 Superfamily,*" Nature Rev. Immunol. 2:116-126).

The role of B7-H1 and PD-1 in inhibiting T-cell activation and proliferation has suggested that these biomolecules might serve as therapeutic targets for treatments of inflammation and cancer. Thus, the use of anti-PD-1 antibodies to treat infections and tumors and up-modulate an adaptive immune response has been proposed (see, United States Patent Application Publication Nos. 2010/0040614; 2010/0028330; 2004/0241745; 2008/0311117; 2009/0217401; U.S. Pat. Nos. 7,521,051; 7,563,869; 7,595,048; PCT Publications Nos. WO 2004/056875; WO 2008/083174). Antibodies capable of specifically binding to PD-1 have been reported by Agata, T. et al. (1996) "*Expression Of The PD-1 Antigen On The Surface Of Stimulated Mouse T And B Lymphocytes,*" Int. Immunol. 8(5):765-772; and Berger, R. et al. (2008) "*Phase I Safety And Pharmacokinetic Study Of CT-011, A Humanized Antibody Interacting With PD-1, In Patients With Advanced Hematologic Malignancies,*" Clin. Cancer Res. 14(10):3044-3051 (see, also, U.S. Pat. Nos. 8,008,449 and 8,552,154; US Patent Publication Nos. 2007/0166281; 2012/0114648; 2012/0114649; 2013/0017199; 2013/0230514 and 2014/0044738; and PCT Patent Publication Nos. WO 2003/099196; WO 2004/004771; WO 2004/056875; WO 2004/072286; WO 2006/121168; WO 2007/005874; WO 2008/083174; WO 2009/014708; WO 2009/073533; WO 2012/135408, WO 2012/145549; and WO 2013/014668).

However, despite all such prior advances, a need remains for improved compositions capable of more vigorously directing the body's immune system to attack cancer cells or pathogen-infected cells, especially at lower therapeutic concentrations. For although the adaptive immune system can be a potent defense mechanism against cancer and disease, it is often hampered by immune suppressive mechanisms in the tumor microenvironment, such as the expression of PD-1. Furthermore, co-inhibitory molecules expressed by tumor cells, immune cells, and stromal cells in the tumor milieu can dominantly attenuate T-cell responses against cancer cells. Thus, a need remains for potent PD-1-binding molecules. In particular, a need exists for potent PD-1-binding molecules having a desirable binding kinetic profile and that antagonize the PD-1/PD-L1 axis by blocking the PD-1/PD-L1 interaction, which could provide improved therapeutic value to patients suffering from cancer or other diseases and conditions. The present invention is directed to these and other goals.

SUMMARY OF THE INVENTION

The present invention is directed to PD-1 binding molecules that comprise the PD-1-binding domain of selected anti-PD-1 antibodies capable of binding to both cynomolgus monkey PD-1 and to human PD-1: PD-1 mAb 1, PD-1 mAb 2, PD-1 mAb 3, PD-1 mAb 4, PD-1 mAb 5, PD-1 mAb 6, PD-1 mAb 7, PD-1 mAb 8, PD-1 mAb 9, PD-1 mAb 10, PD-1 mAb 11, PD-1 mAb 12, PD-1 mAb 13, PD-1 mAb 14, or PD-1 mAb 15. The invention particularly concerns PD-1 binding molecules that are humanized or chimeric versions of such antibodies, or that comprise PD-1 binding-fragments of such anti-PD-1 antibodies (especially immunoconjugates, diabodies, BiTEs, bispecific antibodies, etc.). The invention particularly concerns such PD-1-binding molecules that are additionally capable of binding an epitope of a molecule involved in regulating an immune check point that is present on the surface of an immune cell. The present invention also pertains to methods of using such PD-1-binding molecules to detect PD-1 or to stimulate an immune response. The present invention also pertains to methods of combination therapy in which a PD-1-binding molecule that comprises one or more PD-1-binding domain(s) of such selected anti-PD-1 antibodies is administered in combination with one or more additional molecules that are effective in stimulating an immune response and/or in combination with one or more additional molecules that specifically bind a cancer antigen.

In detail, the invention provides an anti-human PD-1-binding molecule that comprises the three Heavy Chain CDR Domains, $CDR_H1$, $CDR_H2$ and $CDR_H3$ and the three Light Chain CDR Domains, $CDR_L1$, $CDR_L2$, and $CDR_L3$, wherein:

(A) (1) the $CDR_H1$ Domain, $CDR_H2$ Domain, and $CDR_H3$ Domain are the Heavy Chain CDRs of PD-1 mAb 1, and respectively have the amino acid sequences: SEQ ID NO:71, SEQ ID NO:72, and SEQ ID NO:73; and
  (2) the $CDR_L1$ Domain, $CDR_L2$ Domain, and $CDR_L3$ Domain are the Light Chain CDRs of PD-1 mAb 1, and respectively have the amino acid sequences: SEQ ID NO:76, SEQ ID NO:77, and SEQ ID NO:78;

or (B) (1) the $CDR_H1$ Domain, $CDR_H2$ Domain, and $CDR_H3$ Domain are the Heavy Chain CDRs of PD-1 mAb 2, and respectively have the amino acid sequences: SEQ ID NO:85, SEQ ID NO:86, and SEQ ID NO:87; and
  (2) the $CDR_L1$ Domain, $CDR_L2$ Domain, and $CDR_L3$ Domain are the Light Chain CDRs of PD-1 mAb 2, and, respectively have the amino acid sequences: SEQ ID NO:90, SEQ ID NO:91, and SEQ ID NO:92;

or (C) (1) the $CDR_H1$ Domain, $CDR_H2$ Domain, and $CDR_H3$ Domain are the Heavy Chain CDRs of PD-1 mAb 3, and respectively have the amino acid sequences: SEQ ID NO:99, SEQ ID NO:100, and SEQ ID NO:101; and
  (2) the $CDR_L1$ Domain, $CDR_L2$ Domain, and $CDR_L3$ Domain are the Light Chain CDRs of PD-1 mAb 3, and, respectively have the amino acid sequences: SEQ ID NO:104, SEQ ID NO:105, and SEQ ID NO:106;

or (D) (1) the $CDR_H1$ Domain, $CDR_H2$ Domain, and $CDR_H3$ Domain are the Heavy Chain CDRs of PD-1 mAb 4, and respectively have the amino acid sequences: SEQ ID NO:109, SEQ ID NO:110, and SEQ ID NO:111; and
  (2) the $CDR_L1$ Domain, $CDR_L2$ Domain, and $CDR_L3$ Domain are the Light Chain CDRs of PD-1 mAb 4, and, respectively have the amino acid sequences: SEQ ID NO:114, SEQ ID NO:115, and SEQ ID NO:116;

or (E) (1) the $CDR_H1$ Domain, $CDR_H2$ Domain, and $CDR_H3$ Domain are the Heavy Chain CDRs of PD-1 mAb 5, and respectively have the amino acid sequences: SEQ ID NO:119, SEQ ID NO:120, and SEQ ID NO:121; and
(2) the $CDR_L1$ Domain, $CDR_L2$ Domain, and $CDR_L3$ Domain are the Light Chain CDRs of PD-1 mAb 5, and, respectively have the amino acid sequences: SEQ ID NO:124, SEQ ID NO:125, and SEQ ID NO:126;

or (F) (1) the $CDR_H1$ Domain, $CDR_H2$ Domain, and $CDR_H3$ Domain are the Heavy Chain CDRs of PD-1 mAb 6, and respectively have the amino acid sequences: SEQ ID NO:129, SEQ ID NO:130, and SEQ ID NO:131; and
(2) the $CDR_L1$ Domain, $CDR_L2$ Domain, and $CDR_L3$ Domain are the Light Chain CDRs of PD-1 mAb 6, and, respectively have the amino acid sequences: SEQ ID NO:134, SEQ ID NO:135, and SEQ ID NO:136;

or (G) (1) the $CDR_H1$ Domain, $CDR_H2$ Domain, and $CDR_H3$ Domain are the Heavy Chain CDRs of PD-1 mAb 7, and respectively have the amino acid sequences: SEQ ID NO:139, SEQ ID NO:140, and SEQ ID NO:141; and
(2) the $CDR_L1$ Domain, $CDR_L2$ Domain, and $CDR_L3$ Domain are the Light Chain CDRs of PD-1 mAb 7, and, respectively have the amino acid sequences: SEQ ID NO:144, SEQ ID NO:145, and SEQ ID NO:146;

or (H) (1) the $CDR_H1$ Domain, $CDR_H2$ Domain, and $CDR_H3$ Domain are the Heavy Chain CDRs of PD-1 mAb 8, and respectively have the amino acid sequences: SEQ ID NO:161, SEQ ID NO:162, and SEQ ID NO:163; and
(2) the $CDR_L1$ Domain, $CDR_L2$ Domain, and $CDR_L3$ Domain are the Light Chain CDRs of PD-1 mAb 8, and, respectively have the amino acid sequences: SEQ ID NO:166, SEQ ID NO:167, and SEQ ID NO:168;

or (I) (1) the $CDR_H1$ Domain, $CDR_H2$ Domain, and $CDR_H3$ Domain are the Heavy Chain CDRs of PD-1 mAb 9, and respectively have the amino acid sequences: SEQ ID NO:171, SEQ ID NO:172, and SEQ ID NO:173; and
(2) the $CDR_L1$ Domain, $CDR_L2$ Domain, and $CDR_L3$ Domain are the Light Chain CDRs of PD-1 mAb 9, and, respectively have the amino acid sequences: SEQ ID NO:176, SEQ ID NO:177, and SEQ ID NO:178;

or (J) (1) the $CDR_H1$ Domain, $CDR_H2$ Domain, and $CDR_H3$ Domain are the Heavy Chain CDRs of PD-1 mAb 10, and respectively have the amino acid sequences: SEQ ID NO:192, SEQ ID NO:193, and SEQ ID NO:194; and
(2) the $CDR_L1$ Domain, $CDR_L2$ Domain, and $CDR_L3$ Domain are the Light Chain CDRs of PD-1 mAb 10, and, respectively have the amino acid sequences: SEQ ID NO:197, SEQ ID NO:198, and SEQ ID NO:199;

or (K) (1) the $CDR_H1$ Domain, $CDR_H2$ Domain, and $CDR_H3$ Domain are the Heavy Chain CDRs of PD-1 mAb 11, and respectively have the amino acid sequences: SEQ ID NO:202, SEQ ID NO:203, and SEQ ID NO:204; and
(2) the $CDR_L1$ Domain, $CDR_L2$ Domain, and $CDR_L3$ Domain are the Light Chain CDRs of PD-1 mAb 11, and, respectively have the amino acid sequences: SEQ ID NO:207, SEQ ID NO:208, and SEQ ID NO:209;

or (L) (1) the $CDR_H1$ Domain, $CDR_H2$ Domain, and $CDR_H3$ Domain are the Heavy Chain CDRs of PD-1 mAb 12, and respectively have the amino acid sequences: SEQ ID NO:212, SEQ ID NO:213, and SEQ ID NO:214; and
(2) the $CDR_L1$ Domain, $CDR_L2$ Domain, and $CDR_L3$ Domain are the Light Chain CDRs of PD-1 mAb 12, and, respectively have the amino acid sequences: SEQ ID NO:217, SEQ ID NO:218, and SEQ ID NO:219 or (M) (1) the $CDR_H1$ Domain, $CDR_H2$ Domain, and $CDR_H3$ Domain are the Heavy Chain CDRs of PD-1 mAb 13, and respectively have the amino acid sequences: SEQ ID NO:222, SEQ ID NO:223, and SEQ ID NO:224; and
(2) the $CDR_L1$ Domain, $CDR_L2$ Domain, and $CDR_L3$ Domain are the Light Chain CDRs of PD-1 mAb 13, and, respectively have the amino acid sequences: SEQ ID NO:227, SEQ ID NO:228, and SEQ ID NO:229;

or (N) (1) the $CDR_H1$ Domain, $CDR_H2$ Domain, and $CDR_H3$ Domain are the Heavy Chain CDRs of PD-1 mAb 14, and respectively have the amino acid sequences: SEQ ID NO:232, SEQ ID NO:233, and SEQ ID NO:234; and
(2) the $CDR_L1$ Domain, $CDR_L2$ Domain, and $CDR_L3$ Domain are the Light Chain CDRs of PD-1 mAb 14, and, respectively have the amino acid sequences: SEQ ID NO:237, SEQ ID NO:238, and SEQ ID NO:239;

or (O) (1) the $CDR_H1$ Domain, $CDR_H2$ Domain, and $CDR_H3$ Domain are the Heavy Chain CDRs of PD-1 mAb 15, and respectively have the amino acid sequences: SEQ ID NO:242, SEQ ID NO:243, and SEQ ID NO:244; and
(2) the $CDR_L1$ Domain, $CDR_L2$ Domain, and $CDR_L3$ Domain are the Light Chain CDRs of PD-1 mAb 15, and, respectively have the amino acid sequences: SEQ ID NO:247, SEQ ID NO:248, and SEQ ID NO:249;

or (P) (1) the $CDR_H1$ Domain, $CDR_H2$ Domain, and $CDR_H3$ Domain are the Heavy Chain CDRs of hPD-1 mAb 7(1.2), and respectively have the amino acid sequences: SEQ ID NO:139, SEQ ID NO:140, and SEQ ID NO:141; and
(2) the $CDR_L1$ Domain, $CDR_L2$ Domain, and $CDR_L3$ Domain are the Light Chain CDRs of hPD-1 mAb 7(1.2), and, respectively have the amino acid sequences: SEQ ID NO:157, SEQ ID NO:145, and SEQ ID NO:146;

or (Q) (1) the $CDR_H1$ Domain, $CDR_H2$ Domain, and $CDR_H3$ Domain are the Heavy Chain CDRs of hPD-1 mAb 7(1.3), and respectively have the amino acid sequences: SEQ ID NO:139, SEQ ID NO:140, and SEQ ID NO:141; and
(2) the CDR$_L$1 Domain, CDR$_L$2 Domain, and CDR$_L$3 Domain are the Light Chain CDRs of hPD-1 mAb 7(1.3), and, respectively have the amino acid sequences: SEQ ID NO:157, SEQ ID NO:158, and SEQ ID NO:145;

or (R) (1) the CDR$_H$1 Domain, CDR$_H$2 Domain, and CDR$_H$3 Domain are the Heavy Chain CDRs of hPD-1 mAb 9(2.2), and respectively have the amino acid sequences: SEQ ID NO:183, SEQ ID NO:172, and SEQ ID NO:173; and
(2) the CDR$_L$1 Domain, CDR$_L$2 Domain, and CDR$_L$3 Domain are the Light Chain CDRs of hPD-1 mAb 9(2.2), and, respectively have the amino acid sequences: SEQ ID NO:188, SEQ ID NO:189, and SEQ ID NO:178.

The invention further concerns the embodiments of all such anti-human PD-1-binding molecules wherein the molecule is an antibody, and especially wherein the molecule is a chimeric antibody or a humanized antibody.

The invention further concerns the embodiments of such anti-human PD-1-binding molecules wherein the Heavy Chain Variable Domain has the amino acid sequence of SEQ ID NO:79, SEQ ID NO:93, SEQ ID NO:147, SEQ ID NO:149, SEQ ID NO:179, SEQ ID NO:181, or SEQ ID NO:250.

The invention further concerns the embodiments of such anti-human PD-1-binding molecules wherein the Light Chain Variable Domain has the amino acid sequence of SEQ ID NO:81, SEQ ID NO:95, SEQ ID NO:151, SEQ ID NO:153, SEQ ID NO:155, SEQ ID NO:184, SEQ ID NO:186, or SEQ ID NO:251.

The invention further concerns the embodiment wherein the anti-human PD-1-binding molecule is a bispecific binding molecule, capable of simultaneously binding to human PD-1 and to a second epitope, and particularly concerns the embodiment wherein the second epitope is an epitope of a molecule involved in regulating an immune check point present on the surface of an immune cell (especially wherein the second epitope is an epitope of B7-H3, B7-H4, BTLA, CD40, CD40L, CD47, CD70, CD80, CD86, CD94, CD137, CD137L, CD226, CTLA-4, Galectin-9, GITR, GITRL, HHLA2, ICOS, ICOSL, KIR, LAG-3, LIGHT, MHC class I or II, NKG2a, NKG2d, OX40, OX40L, PD1H, PD-1, PD-L1, PD-L2, PVR, SIRPa, TCR, TIGIT, TIM-3 or VISTA, and most particularly wherein the second epitope is an epitope of CD137, CTLA-4, LAG-3, OX40, TIGIT, or TIM-3).

The invention further concerns the embodiments wherein the anti-human PD-1-binding molecule is a bispecific molecule comprising a LAG-3 epitope-binding site, particularly wherein the LAG-3 epitope-binding site comprises:

(A) (1) the CDR$_H$1 Domain, CDR$_H$2 Domain, and CDR$_H$3 Domain of the Variable Heavy Chain of LAG-3 mAb 1, having the amino acid sequences: SEQ ID NO:42, SEQ ID NO:43, and SEQ ID NO:44, respectively; and
(2) the CDR$_L$1 Domain, CDR$_L$2 Domain, and CDR$_L$3 Domain of the Variable Light Chain of LAG-3 mAb 1, having the amino acid sequences: SEQ ID NO:46, SEQ ID NO:47, and SEQ ID NO:48, respectively;

or (B) (1) the CDR$_H$1 Domain, CDR$_H$2 Domain, and CDR$_H$3 Domain of the Variable Heavy Chain of hLAG-3 mAb 1 VH1, having the amino acid sequences: SEQ ID NO:42, SEQ ID NO:43, and SEQ ID NO:44, respectively; and
(2) the CDR$_L$1 Domain, CDR$_L$2 Domain, and CDR$_L$3 Domain of the Variable Light Chain of hLAG-3 mAb 1 VL4, having the amino acid sequences: SEQ ID NO:55, SEQ ID NO:47, and SEQ ID NO:48, respectively;

or (C) (1) the CDR$_H$1 Domain, CDR$_H$2 Domain, and CDR$_H$3 Domain of the Variable Heavy Chain of LAG-3 mAb 6, having the amino acid sequences: SEQ ID NO:57, SEQ ID NO:58, and SEQ ID NO:59, respectively; and
(2) the CDR$_L$1 Domain, CDR$_L$2 Domain, and CDR$_L$3 Domain of the Variable Light Chain of LAG-3 mAb 6, having the amino acid sequences: SEQ ID NO:61, SEQ ID NO:62, and SEQ ID NO:63, respectively;

or (D) (1) the CDR$_H$1 Domain, CDR$_H$2 Domain, and CDR$_H$3 Domain of the Variable Heavy Chain of hLAG-3 mAb 6 VH1, having the amino acid sequences: SEQ ID NO:57, SEQ ID NO:58, and SEQ ID NO:59, respectively; and
(2) the CDR$_L$1 Domain, CDR$_L$2 Domain, and CDR$_L$3 Domain of the Variable Light Chain of LAG-3 mAb 6, having the amino acid sequences: SEQ ID NO:298, SEQ ID NO:62, and SEQ ID NO:63, respectively.

The invention further concerns the embodiment of such anti-human PD-1-binding molecules wherein the molecule is a diabody, and especially, wherein the diabody is a covalently bonded complex that comprises two, or three, or four, or five polypeptide chains. The invention further concerns the embodiment of such anti-human PD-1-binding molecules wherein the molecule is a trivalent binding molecule, and especially wherein the trivalent binding molecule is a covalently bonded complex that comprises three, four, five or more than five polypeptide chains. The invention additionally concerns the embodiment of such anti-human PD-1-binding molecules in which the molecule comprises an Fc Region. The invention additionally concerns the embodiment of such anti-human PD-1-binding molecules in which the molecule comprises an Albumin-Binding Domain, and especially a deimmunized Albumin-Binding Domain.

The invention further concerns the embodiments of all such anti-human PD-1-binding molecules wherein the molecule comprises an Fc Region, and wherein the Fc Region is a variant Fc Region that comprises one or more amino acid modifications that reduces the affinity of the variant Fc Region for an FcγR and/or enhances the serum half-life, and more particularly, wherein the modifications comprise at least one amino acid substitution selected from the group consisting of:

(1) L234A; L235A;
(2) L234A and L235A;
(3) M252Y; M252Y and S254T;
(4) M252Y and T256E;
(5) M252Y, S254T and T256E; or
(6) K288D and H435K;

wherein the numbering is that of the EU index as in Kabat.

The invention further concerns the embodiments in which any of the above-described PD-1-binding molecules is used to stimulate a T-cell mediate immune response. The invention additionally concerns the embodiments in which any of the above-described PD-1-binding molecules is used in the treatment of a disease or condition associated with a suppressed immune system, especially cancer or an infection.

The invention particularly concerns such use in the treatment or diagnosis or prognosis of cancer, wherein the cancer is characterized by the presence of a cancer cell selected from the group consisting of a cell of: an adrenal gland tumor, an AIDS-associated cancer, an alveolar soft part sarcoma, an astrocytic tumor, bladder cancer, bone cancer, a brain and spinal cord cancer, a metastatic brain tumor, a breast cancer, a carotid body tumors, a cervical cancer, a chondrosarcoma, a chordoma, a chromophobe renal cell carcinoma, a clear cell carcinoma, a colon cancer, a colorectal cancer, a cutaneous benign fibrous histiocytoma, a desmoplastic small round cell tumor, an ependymoma, a Ewing's tumor, an extraskeletal myxoid chondrosarcoma, a fibrogenesis imperfecta ossium, a fibrous dysplasia of the bone, a gallbladder or bile duct cancer, gastric cancer, a gestational trophoblastic disease, a germ cell tumor, a head and neck cancer, hepatocellular carcinoma, an islet cell tumor, a Kaposi's Sarcoma, a kidney cancer, a leukemia, a lipoma/benign lipomatous tumor, a liposarcoma/malignant lipomatous tumor, a liver cancer, a lymphoma, a lung cancer, a medulloblastoma, a melanoma, a meningioma, a multiple endocrine neoplasia, a multiple myeloma, a myelodysplastic syndrome, a neuroblastoma, a neuroendocrine tumors, an ovarian cancer, a pancreatic cancer, a papillary thyroid carcinoma, a parathyroid tumor, a pediatric cancer, a peripheral nerve sheath tumor, a phaeochromocytoma, a pituitary tumor, a prostate cancer, a posterious uveal melanoma, a rare hematologic disorder, a renal metastatic cancer, a rhabdoid tumor, a rhabdomysarcoma, a sarcoma, a skin cancer, a soft-tissue sarcoma, a squamous cell cancer, a stomach cancer, a synovial sarcoma, a testicular cancer, a thymic carcinoma, a thymoma, a thyroid metastatic cancer, and a uterine cancer.

The invention particularly concerns such use in the treatment or diagnosis or prognosis of cancer, wherein the cancer is colorectal cancer, hepatocellular carcinoma, glioma, kidney cancer, breast cancer, multiple myeloma, bladder cancer, neuroblastoma; sarcoma, non-Hodgkin's lymphoma, non-small cell lung cancer, ovarian cancer, pancreatic cancer, a rectal cancer, acute myeloid leukemia (AML), chronic myelogenous leukemia (CML), acute B lymphoblastic leukemia (B-ALL), chronic lymphocytic leukemia (CLL), hairy cell leukemia (HCL), blastic plasmacytoid dendritic cell neoplasm (BPDCN), non-Hodgkin's lymphomas (NHL), including mantel cell leukemia (MCL), and small lymphocytic lymphoma (SLL), Hodgkin's lymphoma, systemic mastocytosis, or Burkitt's lymphoma.

The invention further concerns the embodiments in which any of the above-described PD-1-binding molecules is detectably labeled and is used in the detection of PD-1.

BRIEF DESCRIPTION OF THE DRAWINGS

FIG. 3A shows an Fc diabody which contains a peptide Heterodimer-Promoting Domain comprising a cysteine residue. FIG. 3B shows an Fc Region-containing diabody, which contains E-coil and K-coil Heterodimer-Promoting Domains comprising a cysteine residue and a linker (with an optional cysteine residue). FIG. 3C, shows an Fc-Region-Containing diabody, which contains antibody CH1 and CL domains.

FIGS. 6A and 6B, respectively, illustrate schematically the domains of trivalent binding molecules comprising two diabody-type binding domains and a Fab-type binding domain having different domain orientations in which the diabody-type binding domains are N-terminal or C-terminal to an Fc Region. The molecules in FIGS. 6A and 6B comprise four chains. FIGS. 6C and 6D, respectively, illustrate schematically the domains of trivalent binding molecules comprising two diabody-type binding domains N-terminal to an Fc Region, and a Fab-type binding domain in which the light chain and heavy chain are inked via a polypeptide spacer, or an scFv-type binding domain.

Figure 6A:
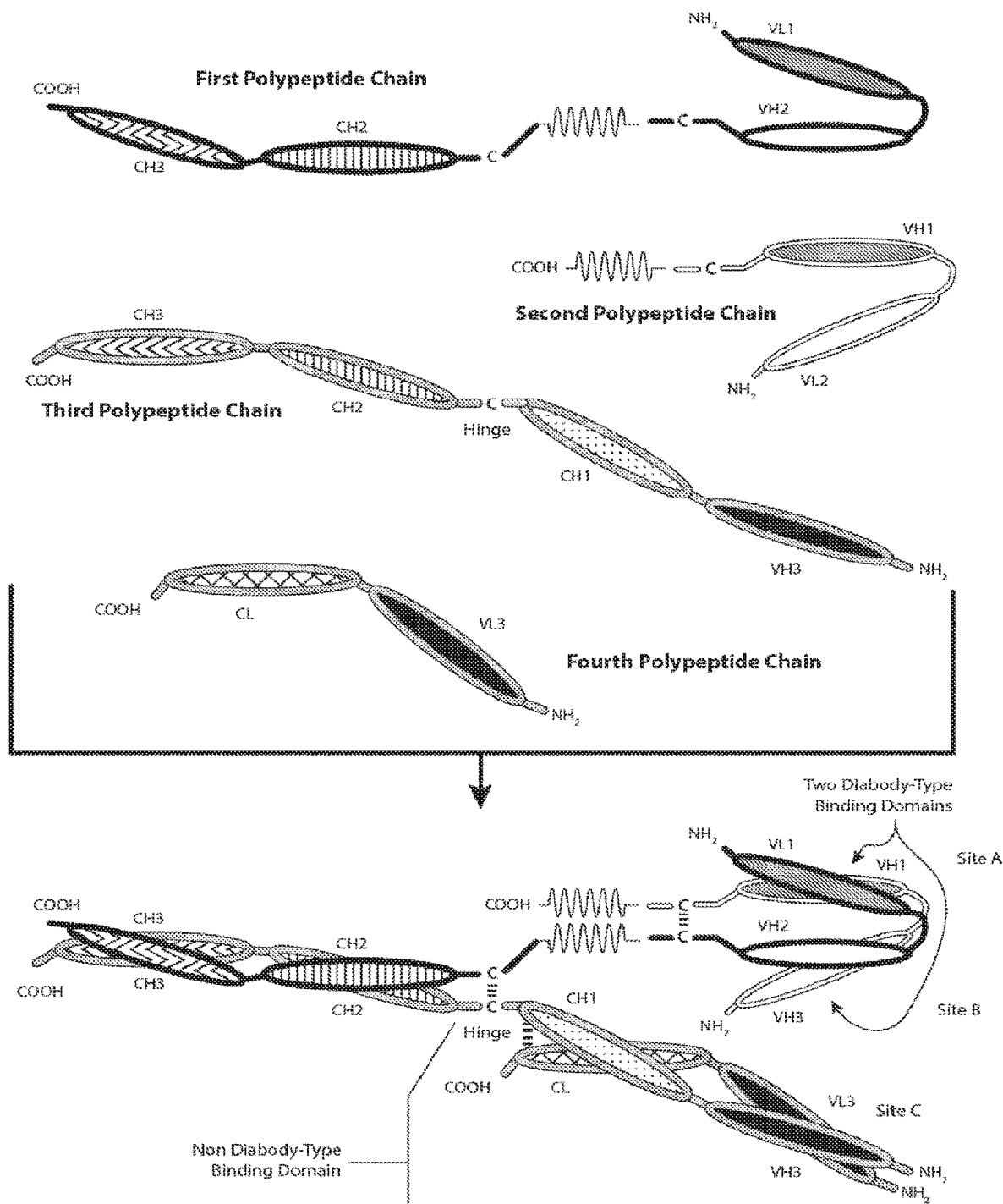
FIGS. 6A-6F provide schematics of representative Fc Region-containing trivalent binding molecules having three epitope-binding sites.
Figure 6B:
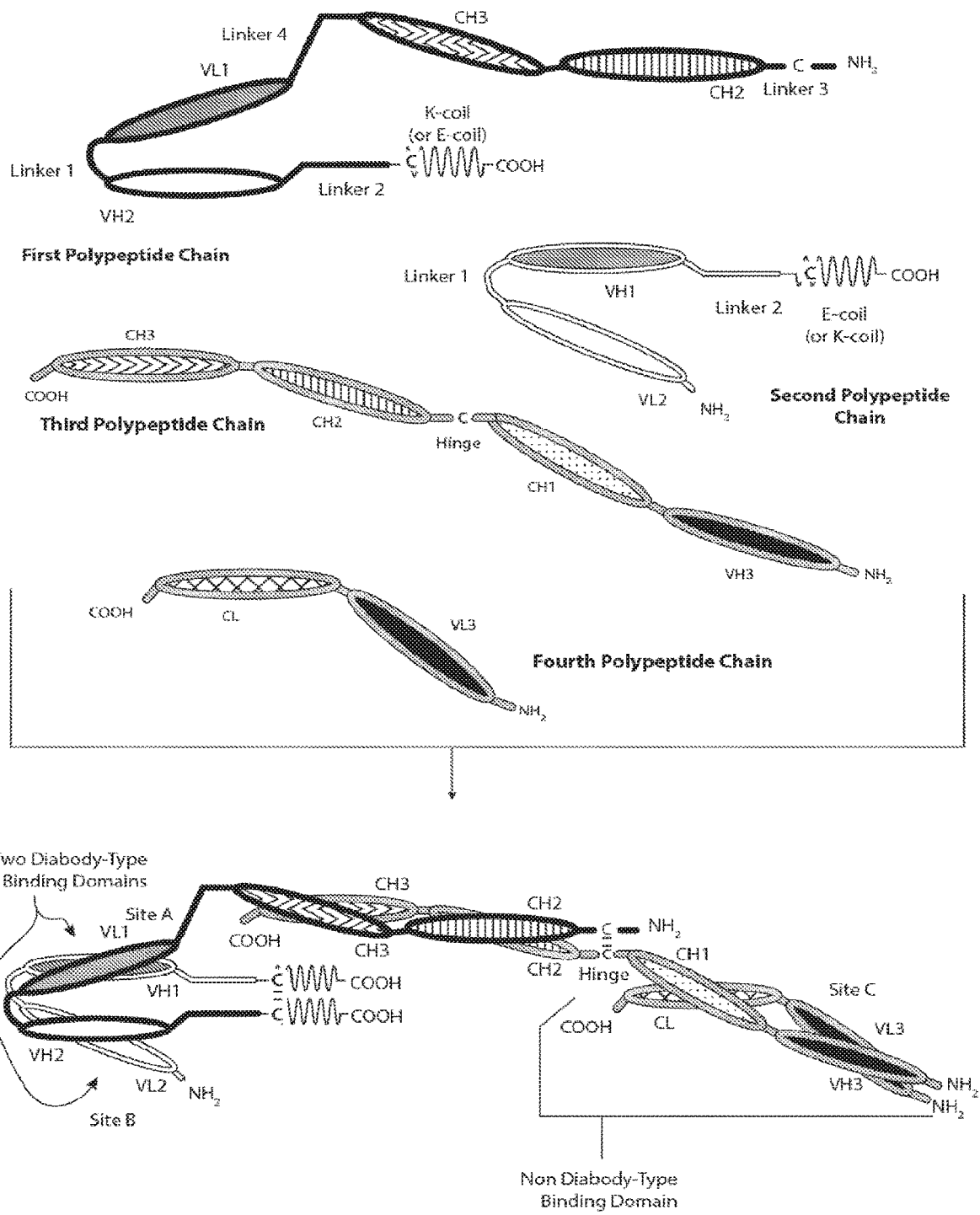
Figure 6C:
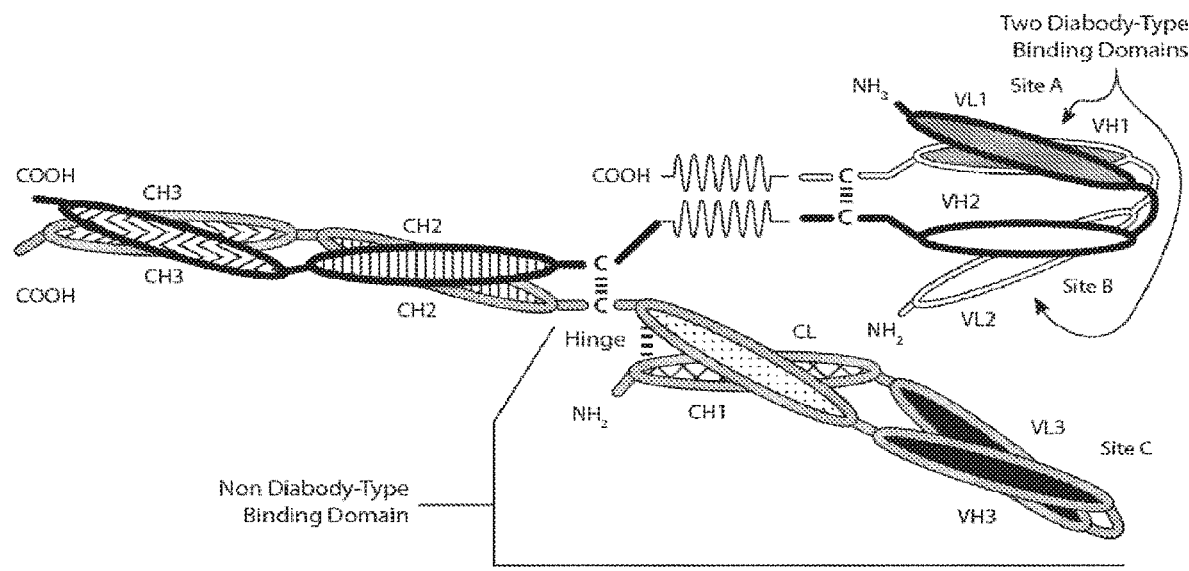
Figure 6D:
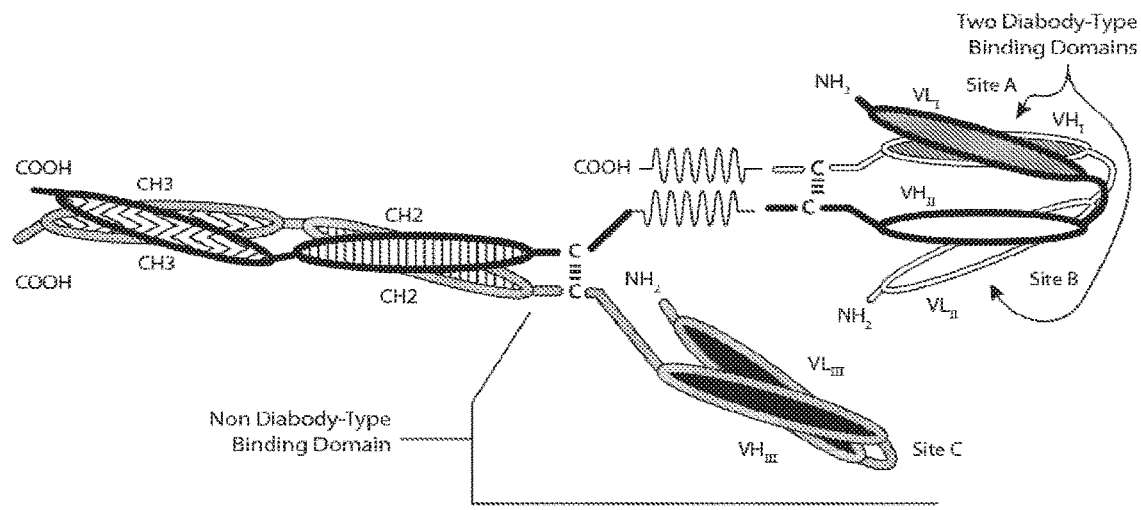
Figure 6E:
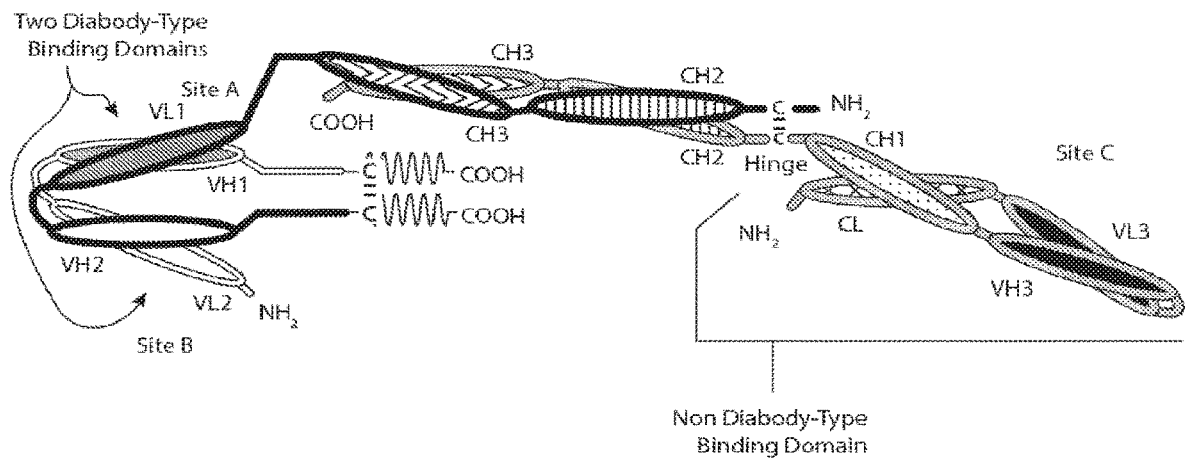
Figure 6F:
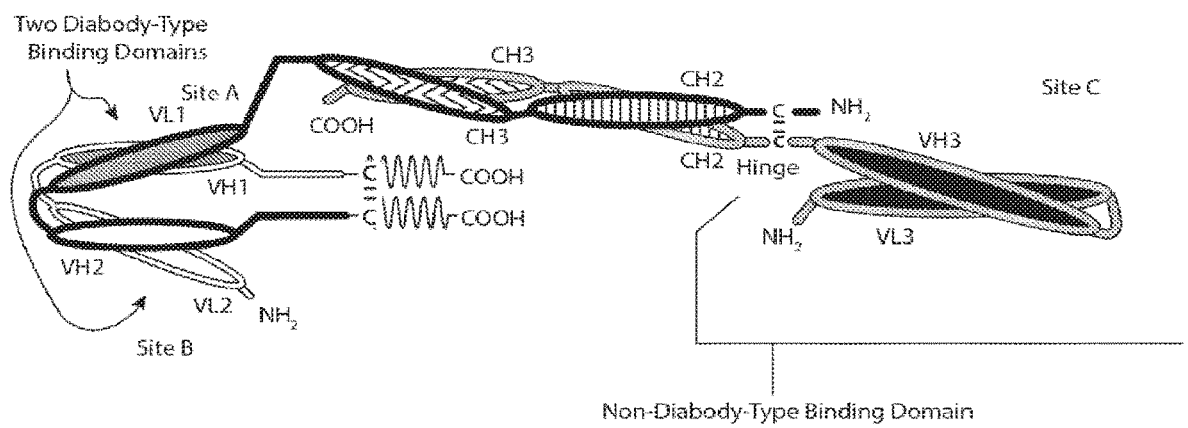

The trivalent binding molecules in FIGS. 6E and 6F, respectively illustrate schematically the domains of trivalent binding molecules comprising two diabody-type binding domains C-terminal to an Fc Region, and a linked Fab-type binding domain, or an scFv-type binding domain in which the diabody-type binding domains are. The trivalent binding molecules in FIGS. 6C-6F comprise three chains. VL and VH Domains that recognize the same epitope are shown using the same shading or fill pattern.

Figure 7A:
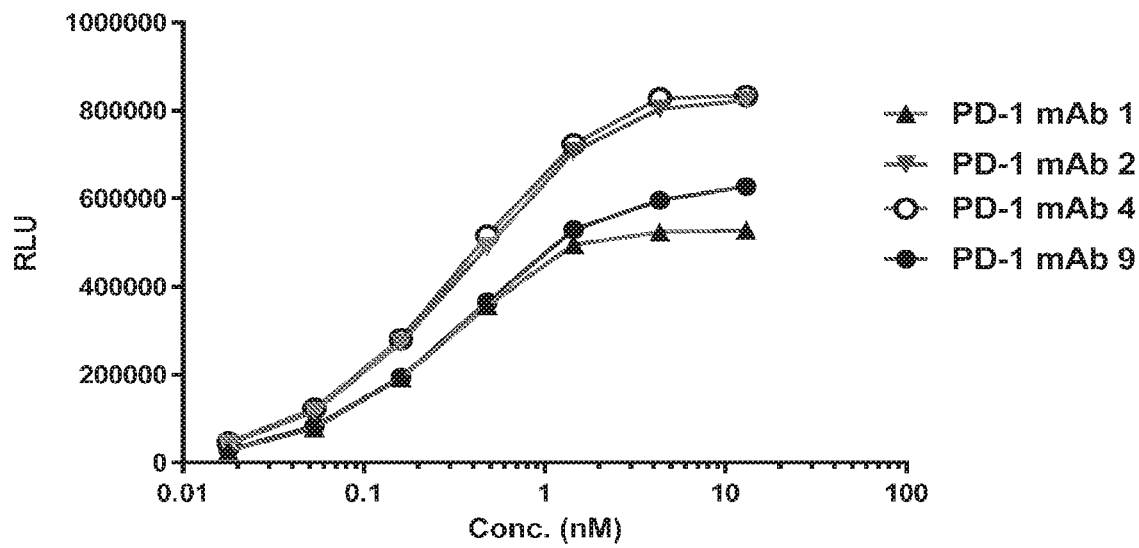
Figure 7B:
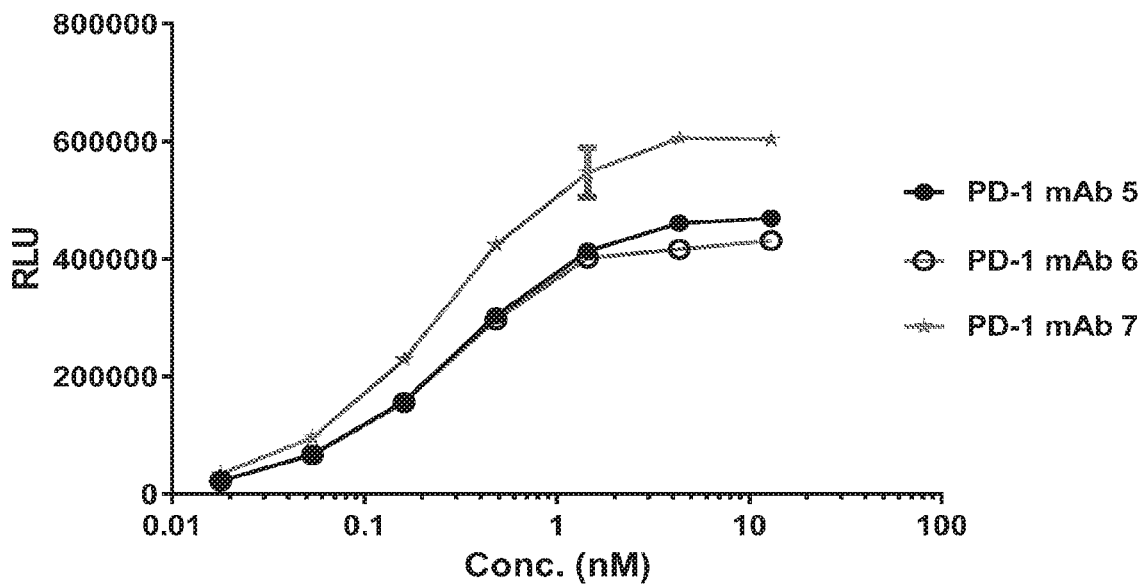
Figure 7C:
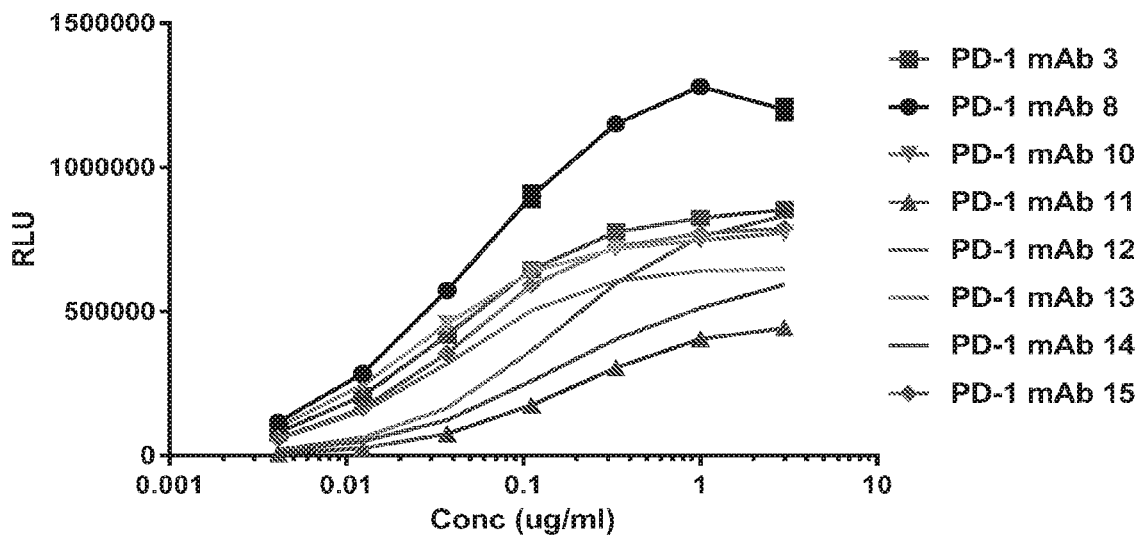
Figure 7D:
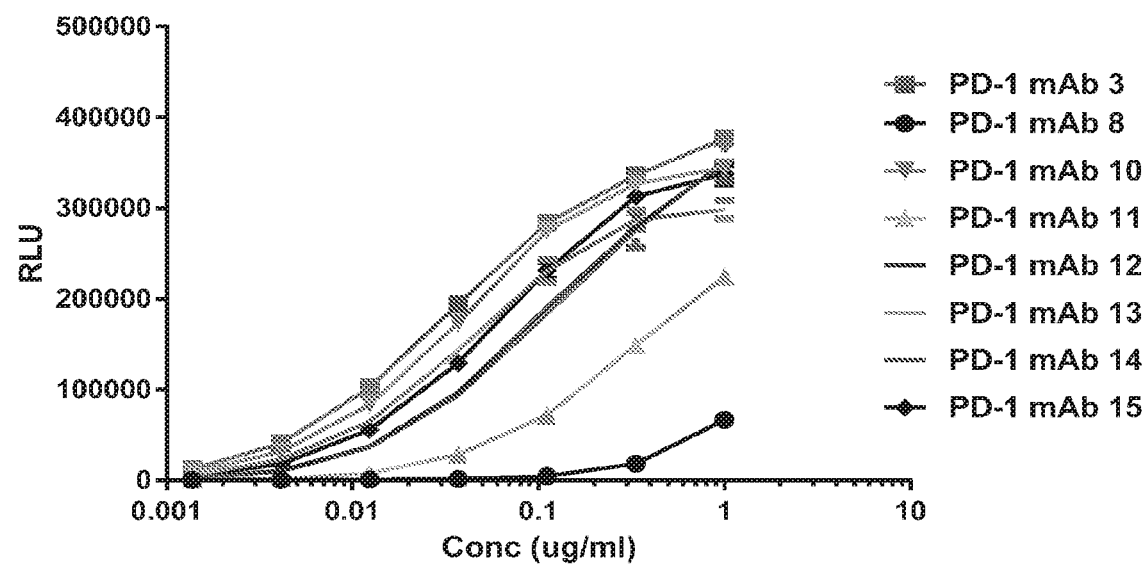

FIGS. 7A-7D shows that the anti-PD-1 antibodies PD-1 mAb 1-15 bind to human PD-1. Binding curves for binding to shPD-1-His are shown in FIG. 7A (PD-1 mAb 1, PD-1 mAb 2, PD-1 mAb 4 and PD-1 mAb 9), FIG. 7B (PD-1 mAb 5, PD-1 mAb 6, and PD-1 mAb 7), and FIG. 7C (PD-1 mAb 3, PD-1 mAb 8, PD-1 mAb 10, PD-1 mAb 11, PD-1 mAb 12, PD-1 mAb 13, PD-1 mAb 14, and PD-1 mAb 15). Binding curves for binding to shPD-1-human Fc are shown in FIG. 7D (PD-1 mAb 3, PD-1 mAb 8, PD-1 mAb 10, PD-1 mAb 11, PD-1 mAb 12, PD-1 mAb 13, PD-1 mAb 14, and PD-1 mAb 15).

Figure 8A:
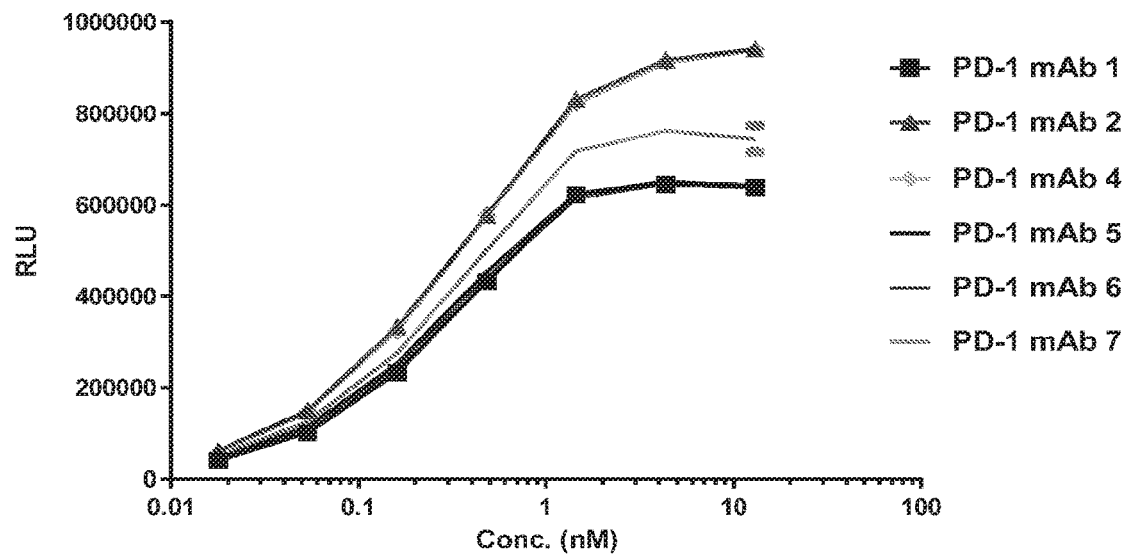
Figure 8B:
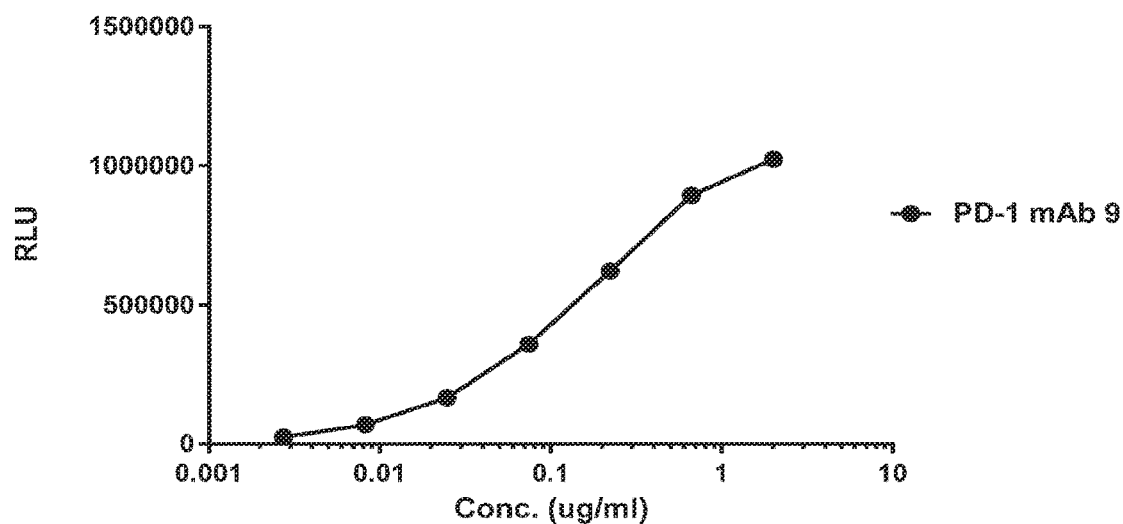
Figure 8C:
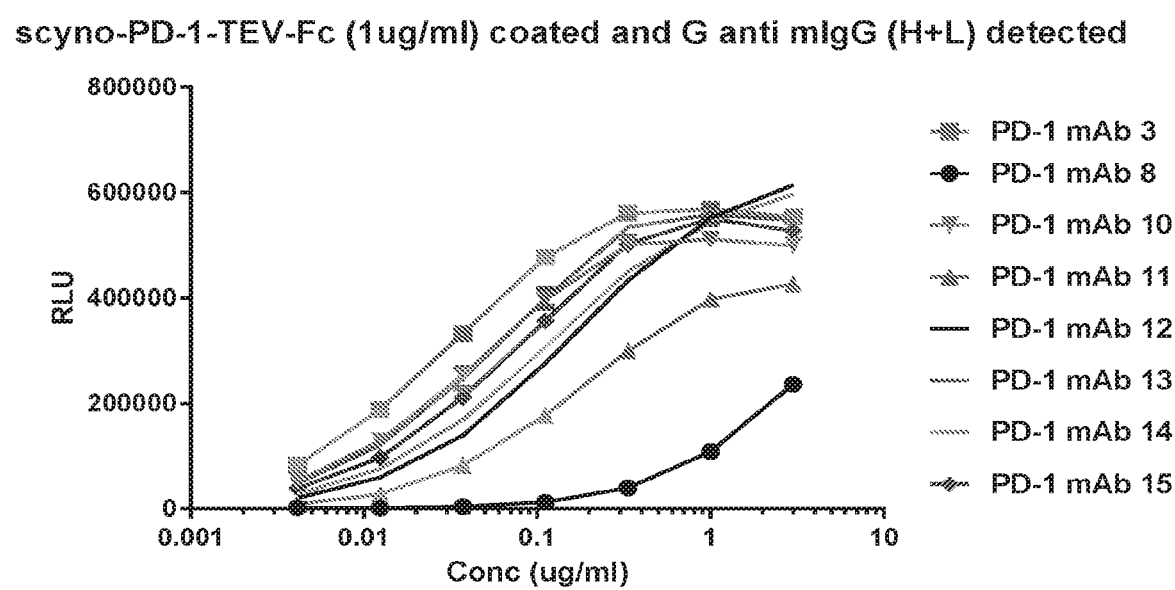

FIGS. 8A-8C shows that the anti-PD-1 antibodies PD-1 mAb 1-15 bind to cynomolgus monkey PD-1. Binding curves for binding to scynoPD-1-hFc are shown in FIG. 8A (PD-1 mAb 1, PD-1 mAb 2, PD-1 mAb 4, PD-1 mAb 5, PD-1 mAb 6, PD-1 mAb 7), FIG. 8B (PD-1 mAb 9), and FIG. 8C (PD-1 mAb 3, PD-1 mAb 8, PD-1 mAb 10, PD-1 mAb 11, PD-1 mAb 12, PD-1 mAb 13, PD-1 mAb 14, and PD-1 mAb 15).

Figure 9A:
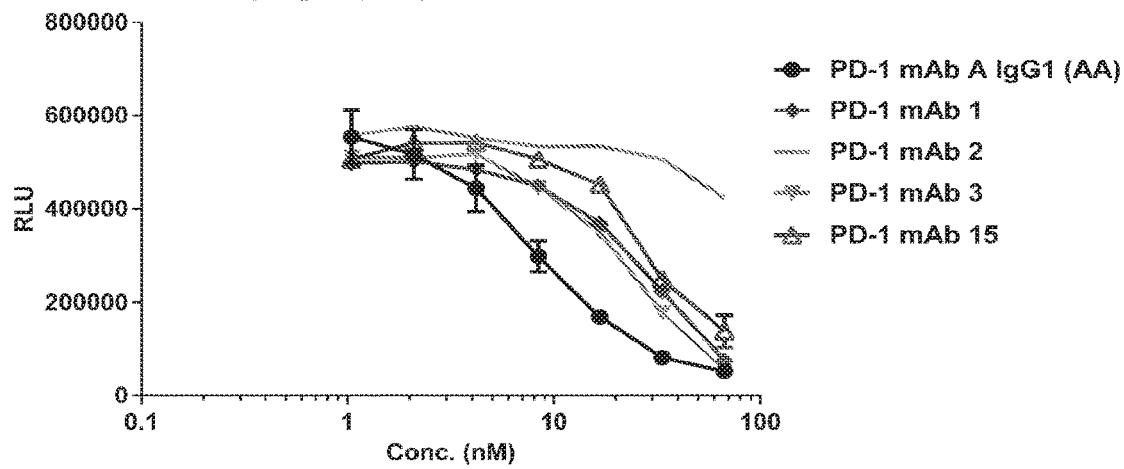
Figure 9B:
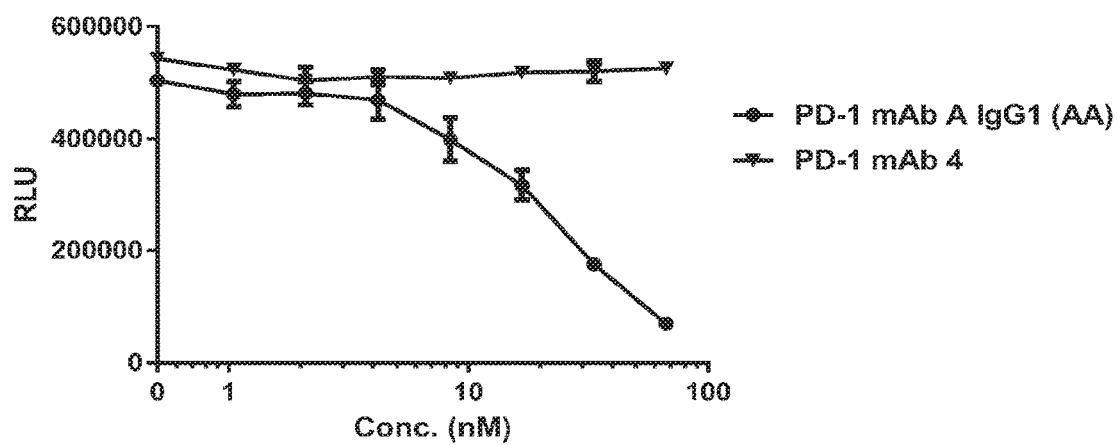
Figure 9C:
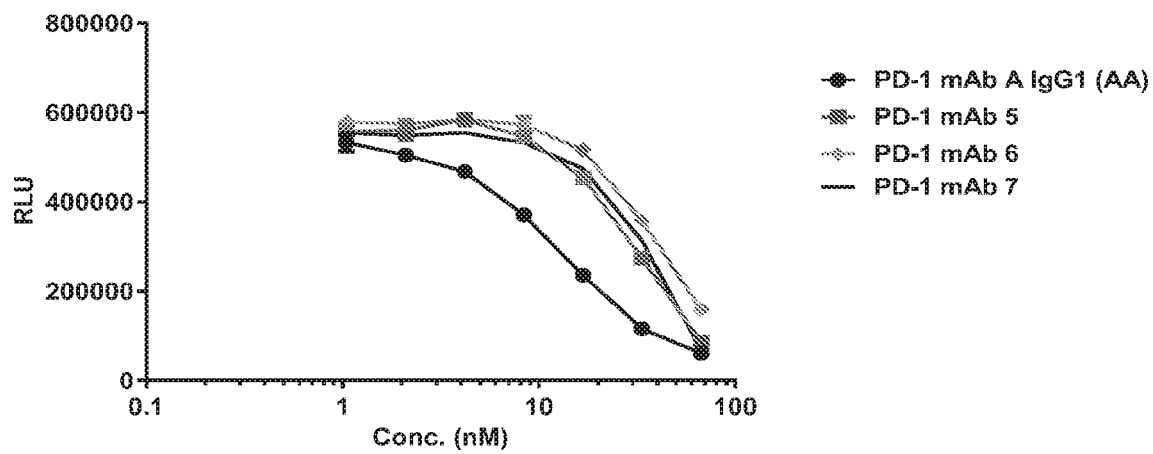
Figure 9D:
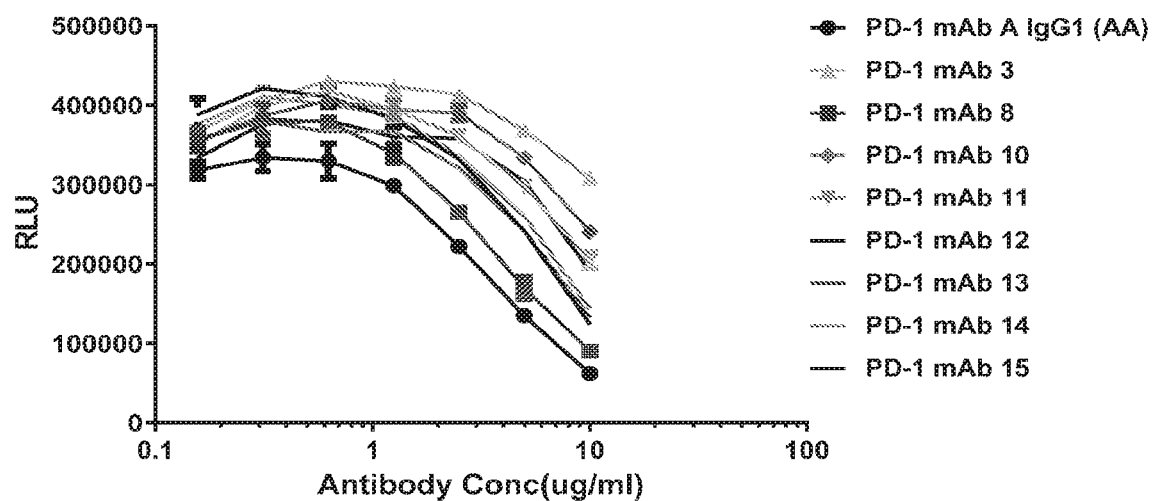

FIGS. 9A-9D show the ability of the anti-PD-1 antibodies PD-1 mAb 1-15 to block the binding of human PD-L1 to human PD-1. Inhibition curves are shown in FIG. 9A (PD-1 mAb 1, PD-1 mAb 2, PD-1 mAb 3, PD-1 mAb 15, and PD-1 mAb A), FIG. 9B (PD-1 mAb 4), FIG. 9C (PD-1 mAb 5, PD-1 mAb 6, PD-1 mAb 7, and PD-1 mAb A), and FIG. 9D (PD-1 mAb 3, PD-1 mAb 8, PD-1 mAb 10, PD-1 mAb 11, PD-1 mAb 12, PD-1 mAb 13, PD-1 mAb 14, PD-1 mAb 15, and PD-1 mAb A).

Figure 10A:
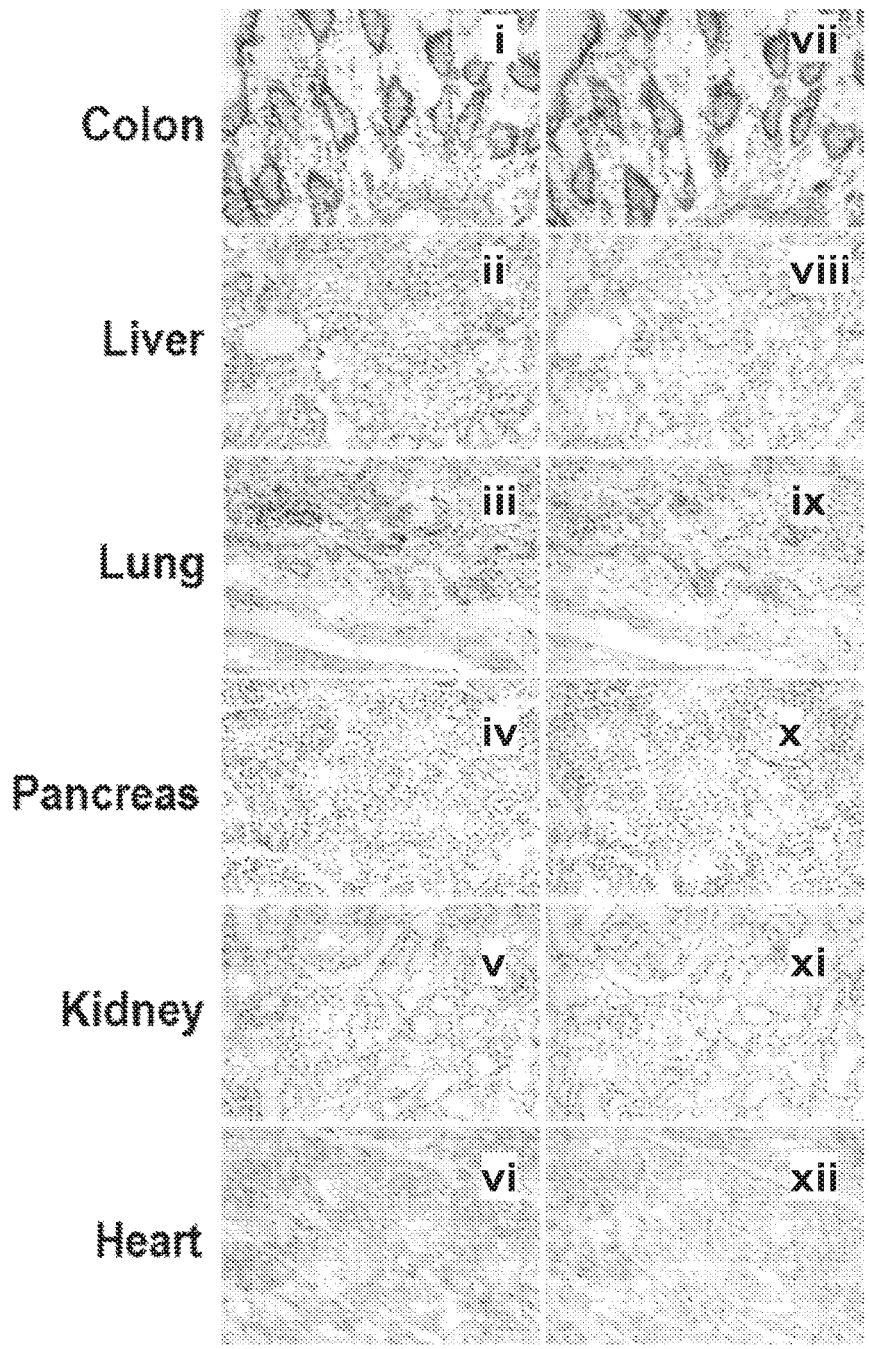
Figure 10B:
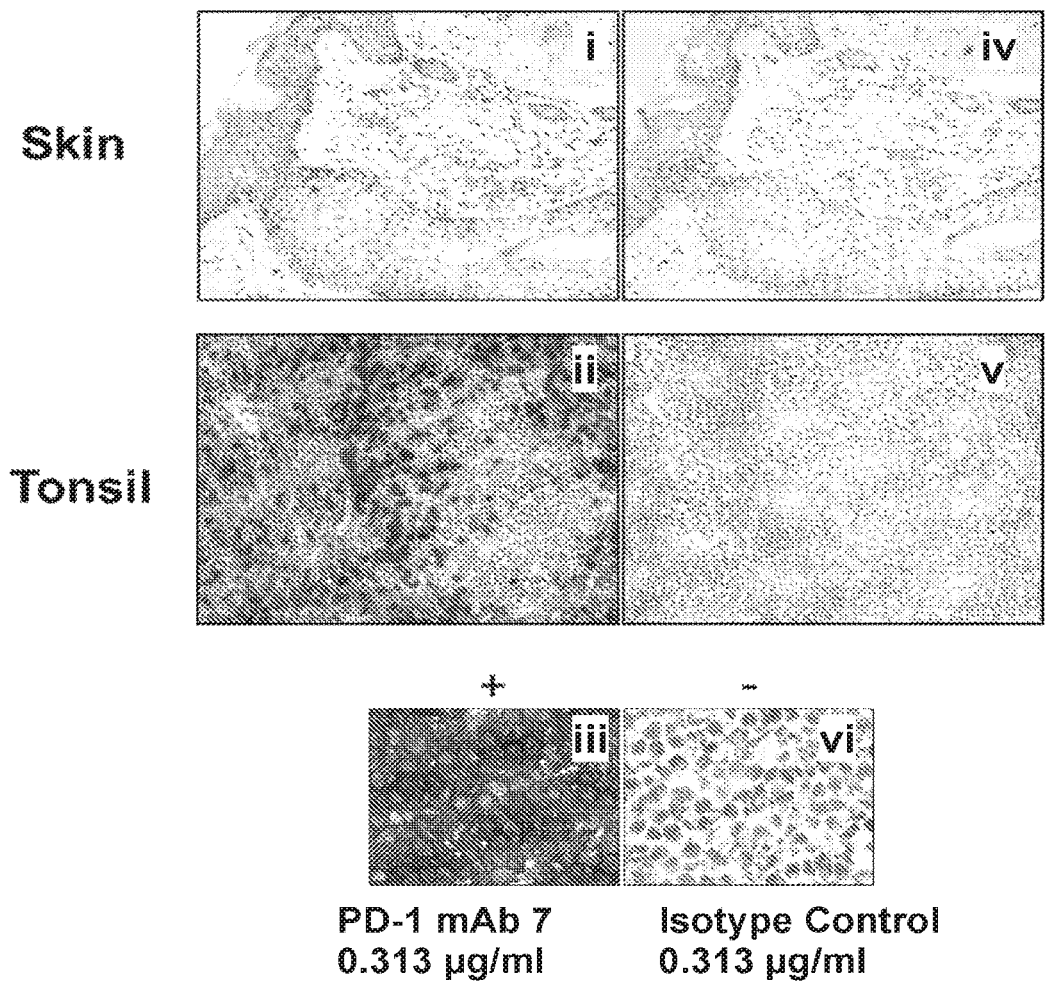

FIGS. 10A-10B show the tissue specificity of the anti-human PD-1 antibody PD-1 mAb 7. FIG. 10A shows histological stains of normal colon (Panels i and vii), liver (Panels ii and viii), lung (Panels iii and ix), pancreas (Panels iv and x), kidney (Panels v and xi) and heart (Panels vi and xii) tissue. FIG. 10A, Panels i-vi show the results of tissue incubated with labeled PD-1 mAb 7 (0.313 µg/mL). FIG. 10A, Panels vii-xii show the results of tissue incubated with labeled isotype control mAb (0.314 µg/mL). FIG. 10B shows histological stains of skin (Panels i and iv), tonsils (Panels ii and v), and NSO cells expressing PD-1 (Panels iii and vi). FIG. 10B, Panels i-iii show the results of tissue incubated with labeled PD-1 mAb 7 (0.313 µg/mL).

Figure 11:
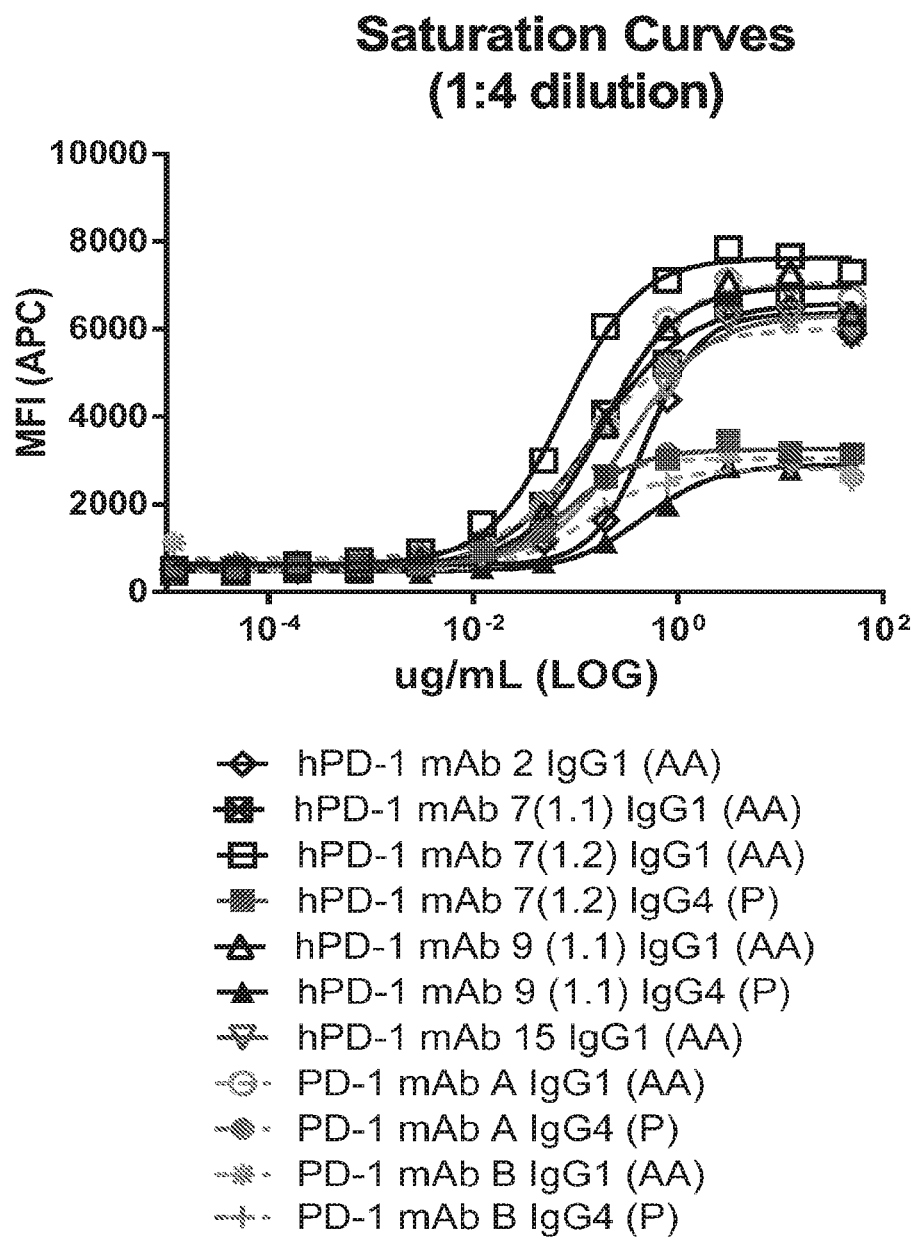

FIG. 11 shows the binding profiles of humanized anti-human PD-1 antibodies hPD-1 mAb 2, hPD-1 mAb 7(1.1), hPD-1 mAb 7(1.2), hPD-1 mAb 9(1.1), and the reference anti-PD-1 antibodies PD-1 mAb A and PD-1 mAb B having IgG1 (AA) or IgG4 (P) for binding to cell surface PD-1.

Figure 12A:
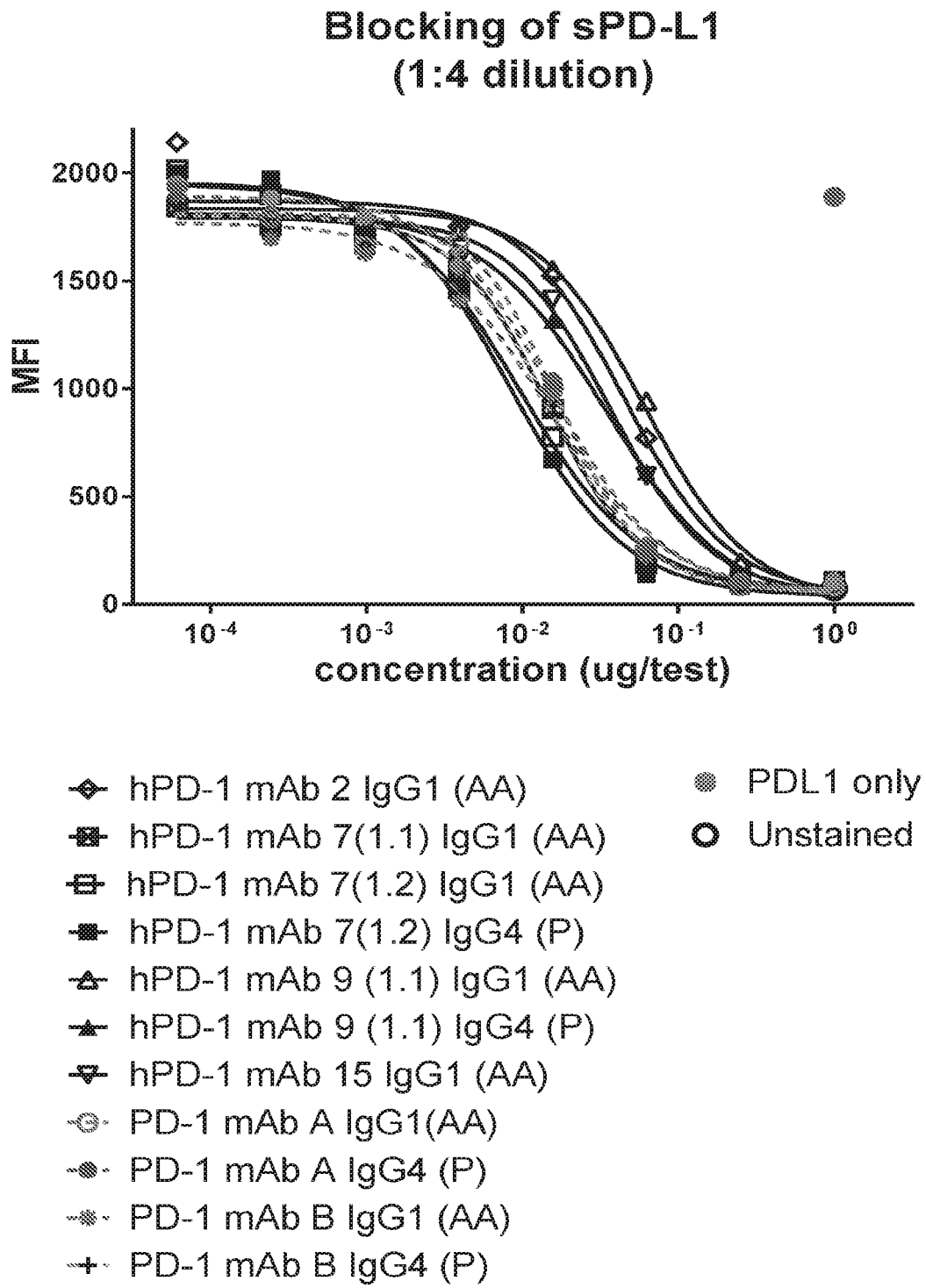
Figure 12B:
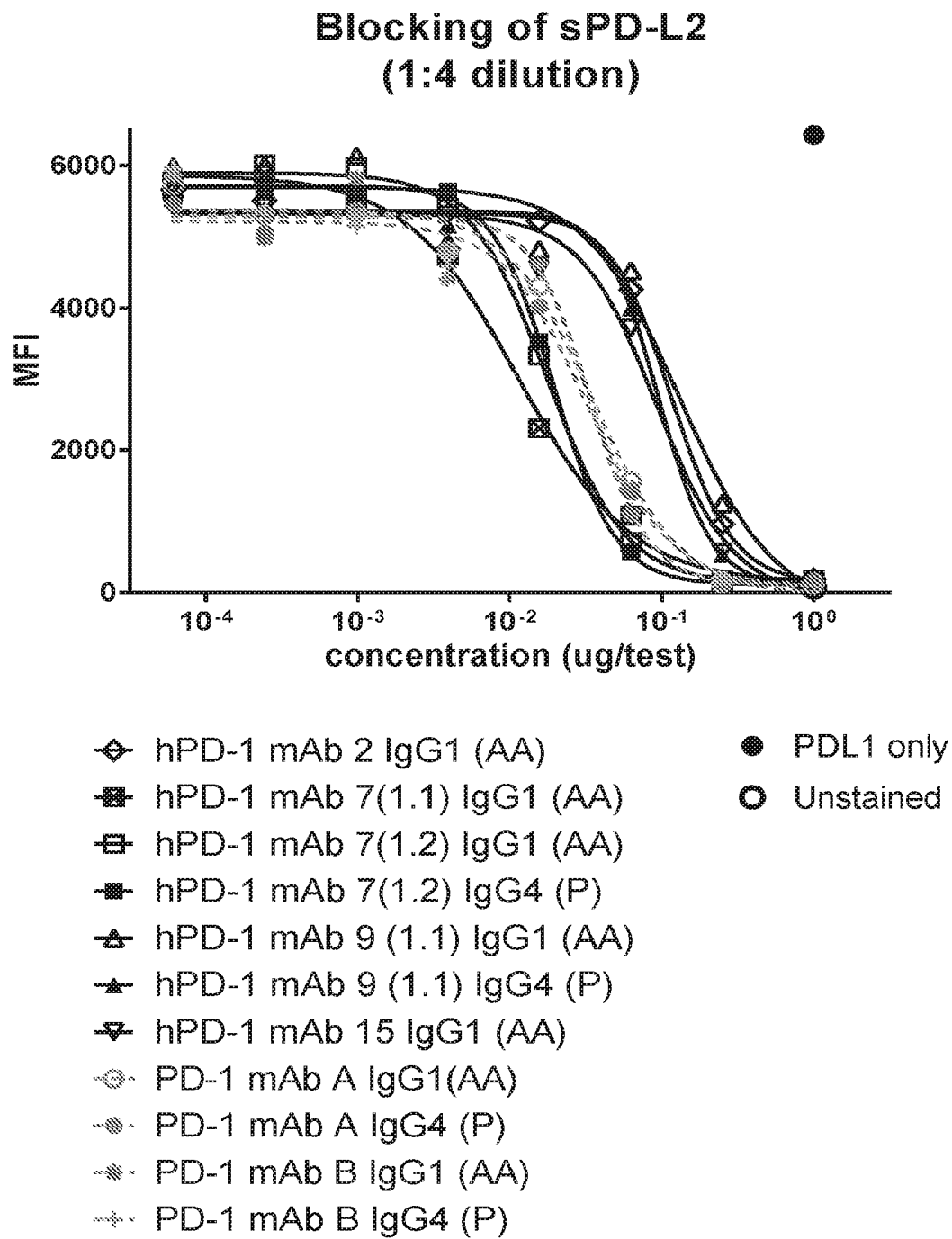

FIGS. 12A-12B show the ability of humanized anti-PD antibodies hPD-1 mAb 2, hPD-1 mAb 7(1.1), hPD-1 mAb 7(1.2), hPD-1 mAb 9(1.1), and the reference anti-PD-1 antibodies PD-1 mAb A and PD-1 mAb B, having IgG1 (AA) or IgG4 (P) to block the binding of soluble human PD-L1 (FIG. 12A) and soluble human PD-L2 (FIG. 12B) to cell surface human PD-1.

Figure 13:
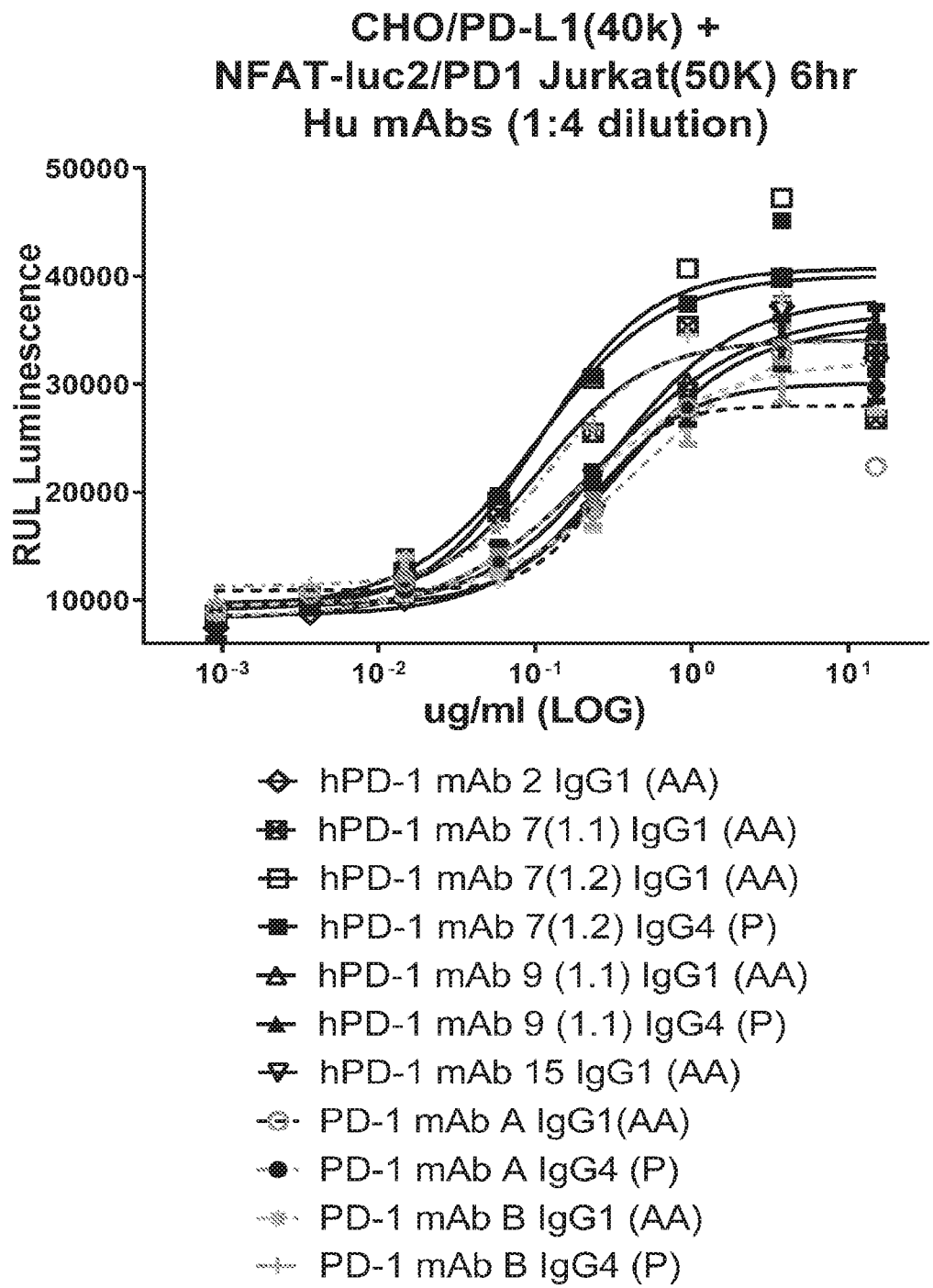

FIG. 13 shows the ability of humanized anti-PD antibodies hPD-1 mAb 2, hPD-1 mAb 7(1.1), hPD-1 mAb 7(1.2), hPD-1 mAb 9(1.1), and the reference anti-PD-1 antibodies PD-1 mAb A and PD-1 mAb B, having IgG1 (AA) or IgG4 (P) to antagonize the PD-1/PD-L1 axis by blocking the PD-1/PD-L1 interaction and preventing down-regulation of T-cell responses in a Jurkat-luc-NFAT/CHO-PD-L1 luciferase reporter assay.

Figure 14:
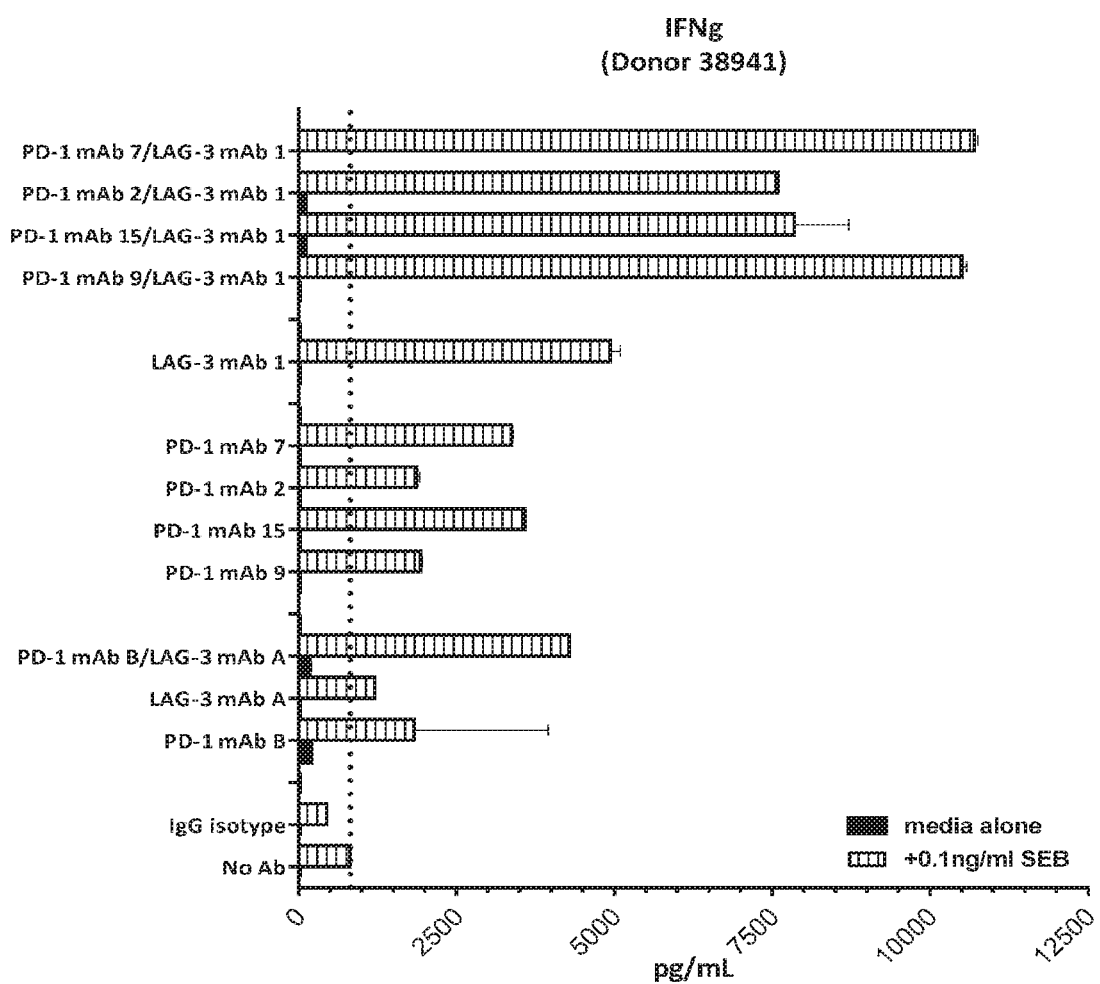

FIG. 14 shows that PD-1 mAb 2, PD-1 mAb 7, PD-1 mAb 9 and PD-1 mAb 15 are able to stimulate cytokine production to levels comparable or higher than the referenced anti-PD-1 antibodies (PD-1 mAb A and PD-1 mAb B) and that treatment with PD-1 mAb 2, PD-1 mAb 7, PD-1 mAb 9 and PD-1 mAb 15 in combination with LAG-3 mAb 1 provided the largest enhancement of cytokine release. IFNγ secretion profiles from Staphylococcal enterotoxin B (SEB)-stimulated PBMCs treated with anti-PD-1 and anti-LAG-3 antibodies alone and in combination.

Figure 15A:
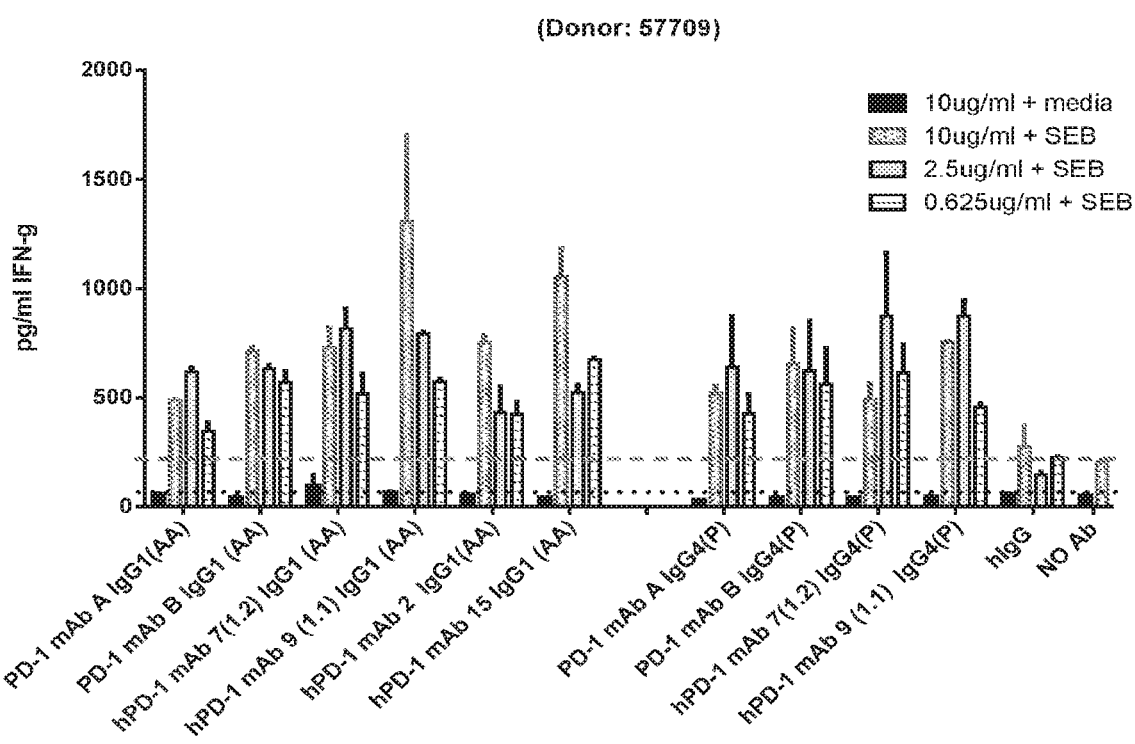
Figure 15B:
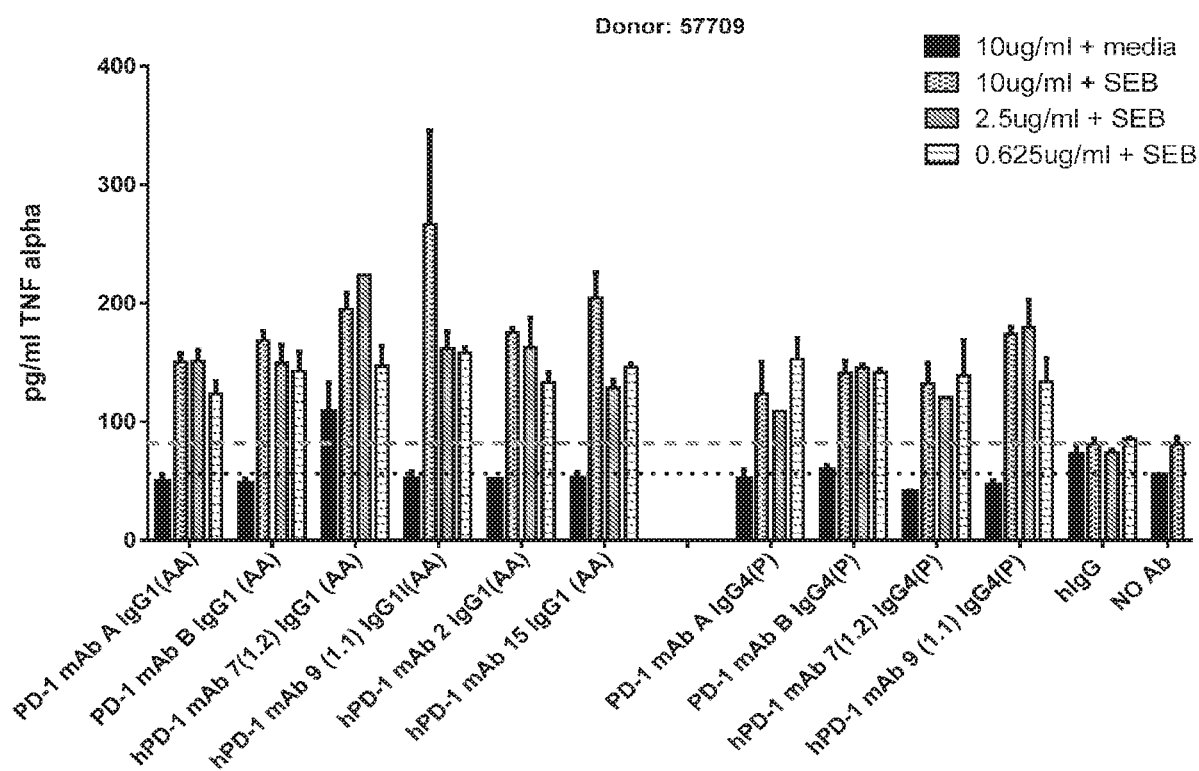

FIGS. 15A-15B show the ability of humanized anti-PD antibodies hPD-1 mAb 2, hPD-1 mAb 7(1.2), hPD-1 mAb 9(1.1), and the reference anti-PD-1 antibodies PD-1 mAb A and PD-1 mAb B, having IgG1 (AA) or IgG4 (P) to stimulate cytokine production. IFNγ (FIG. 15A) and TNFα (FIG. 15B), secretion profiles from SEB-stimulated PBMCs treated with anti-PD-1 antibodies.

Figure 16A:
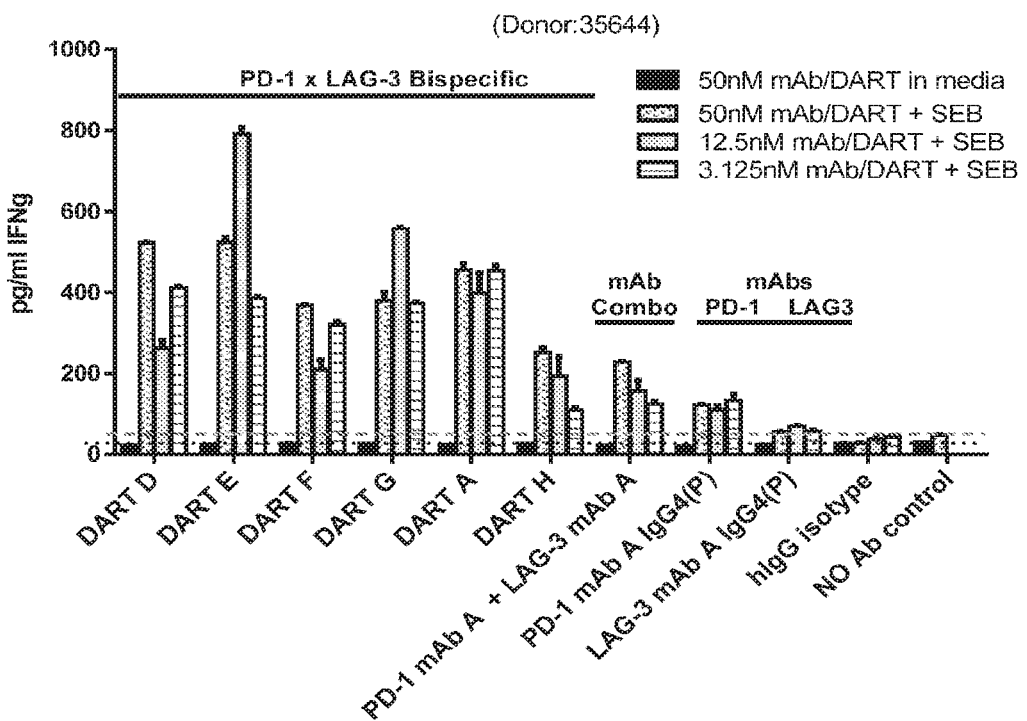
Figure 16B:
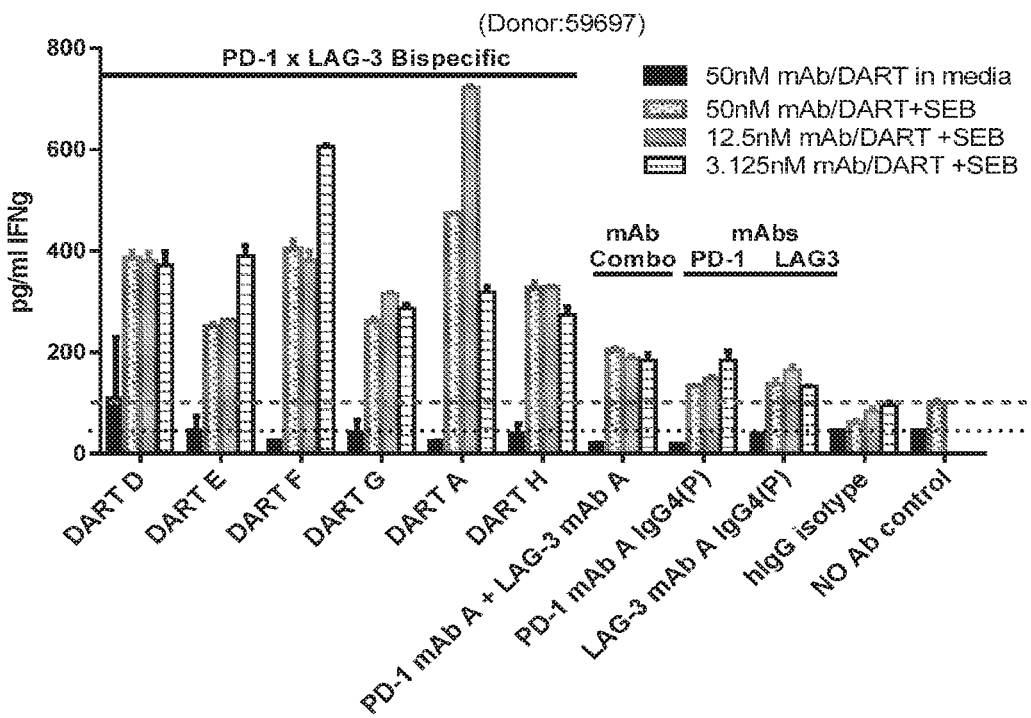

FIGS. 16A-16B show that the PD-1×LAG-3 bispecific diabody constructs DART A, DART D, DART E, DART F, DART G and DART H, are able to stimulate cytokine production to levels comparable or higher than that observed upon the administration of the combination of an anti-PD-1 mAb+an anti-LAG-3 mAb (PD-1 mAb A+LAG-3 mAb A), and that the PD-1×LAG-3 bispecific diabody constructs DART A, DART D, DART E, DART F and DART G provided the largest enhancement of cytokine release. IFNγ secretion profiles of PBMCs stimulated with a low concentration of SEB (0.2 ng/mL treated with PD-1×LAG-3 bispecific diabodies, or anti-PD-1 and anti-LAG-3 antibodies alone and in combination are plotted. The results using PBMCs from two representative donors are shown in FIG. 16A and FIG. 16B.

Figure 17A:
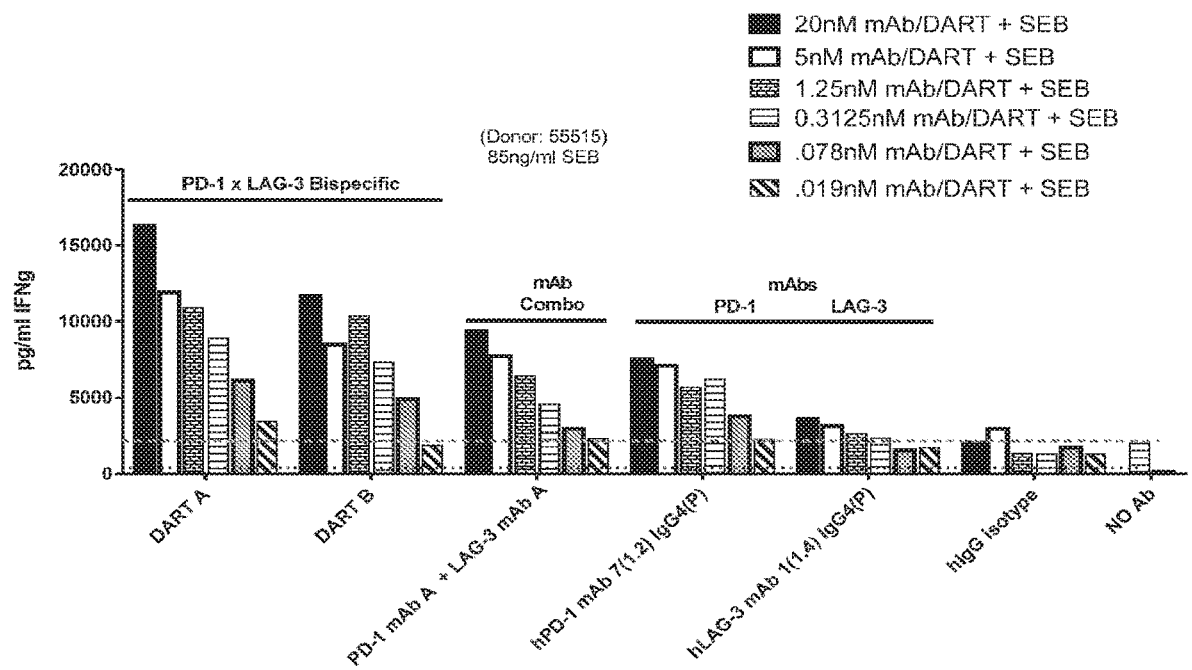
Figure 17B:
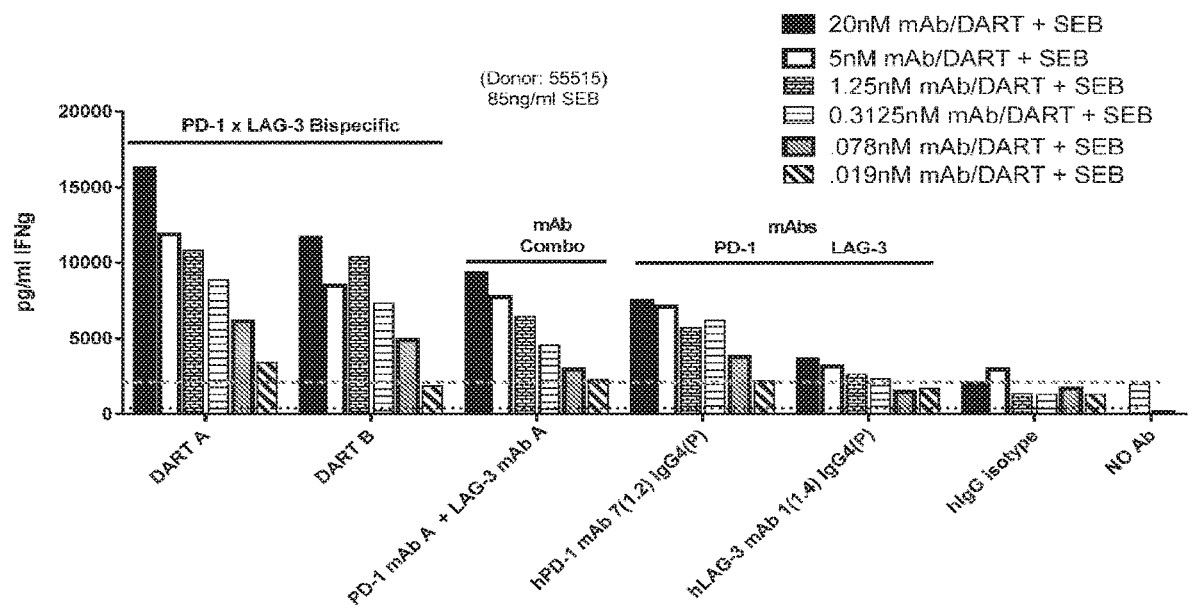

FIGS. 17A-17B show that the PD-1×LAG-3 bispecific diabody constructs DART A, DART B and DART C are able to stimulate cytokine production to levels higher than that observed upon the administration of the combination of an anti-PD-1 mAb+an anti-LAG-3 mAb (PD-1 mAb A+LAG-3 mAb A). IFNγ secretion profiles of PBMCs from two representative donors, stimulated with a high concentration of SEB (85 ng/mL) treated with PD-1×LAG-3 bispecific diabodies, or anti-PD-1 and anti-LAG-3 antibodies alone and in combination are plotted. The results using PBMCs from two representative donors are shown in FIG. 17A and FIG. 17B.

Figure 18A:
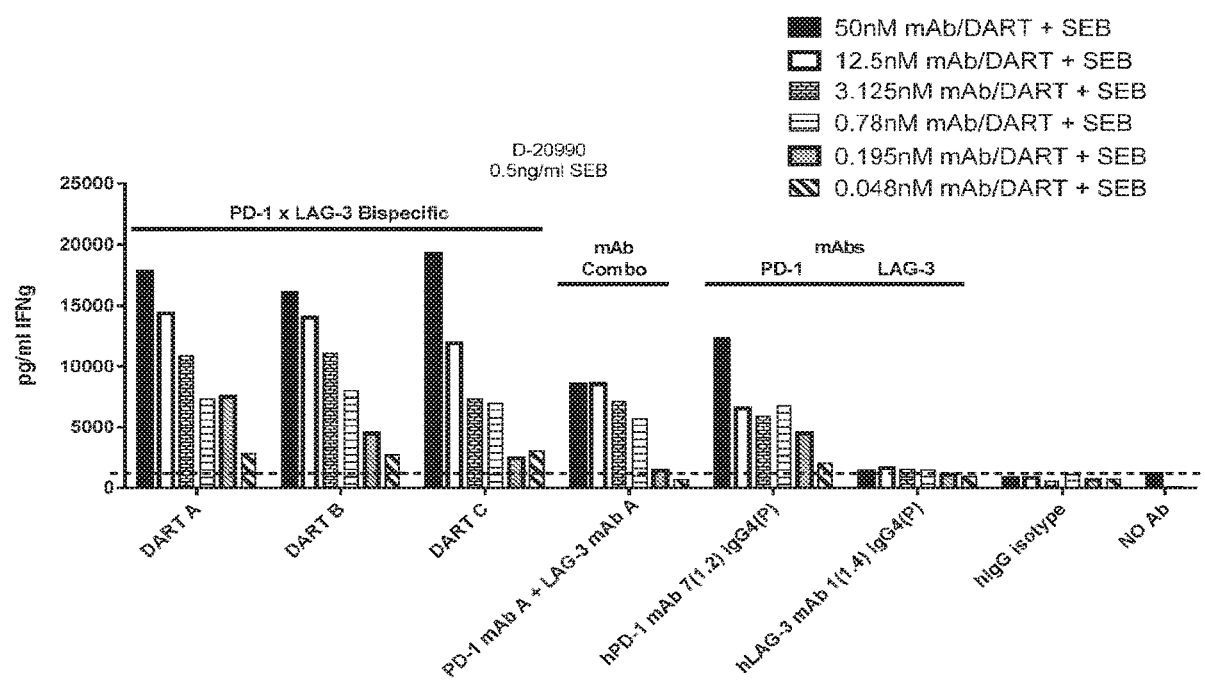
Figure 18B:
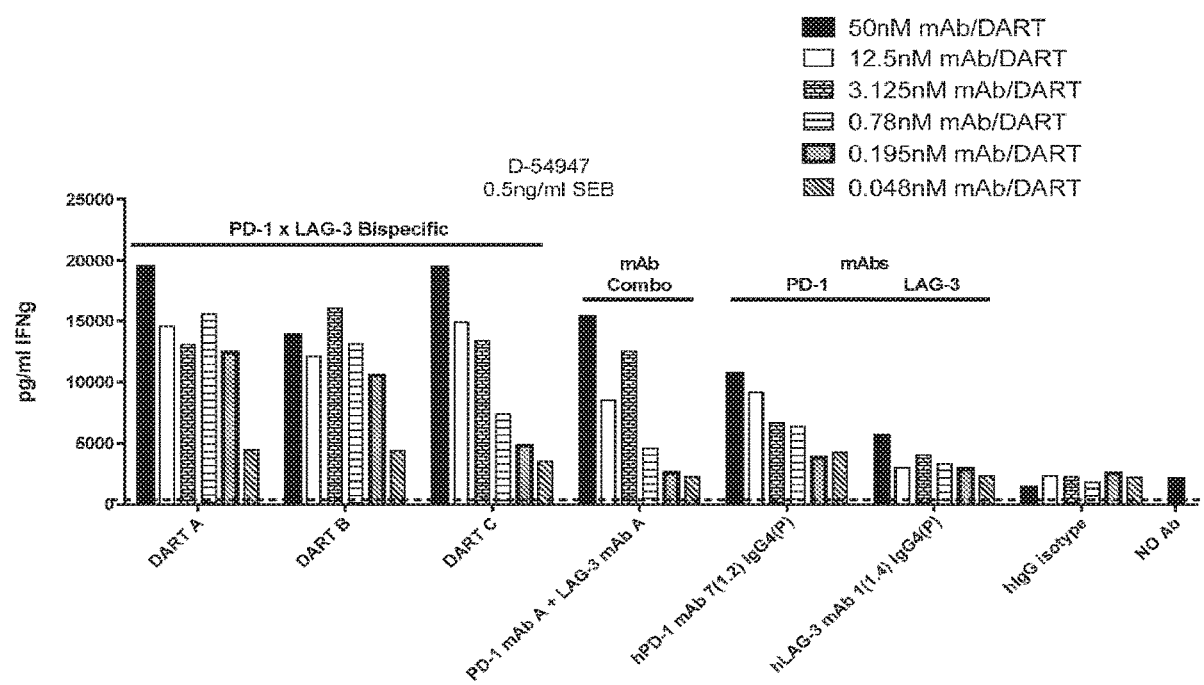

FIGS. 18A-18B show that the PD-1×LAG-3 bispecific diabody constructs DART A, DART B and DART C are able to stimulate cytokine production to levels higher than that observed upon the administration of the combination of an anti-PD-1 mAb+an anti-LAG-3 mAb (PD-1 mAb A+LAG-3 mAb A). IFNγ secretion profiles of PBMCs from two representative donors, stimulated with a middle concentration of SEB (0.5 ng/mL) treated with PD-1×LAG-3 bispecific diabodies, or anti-PD-1 and anti-LAG-3 antibodies alone and in combination are plotted. The results using PBMCs from two representative donors are shown in FIG. 18A and FIG. 18B.

Figure 19:
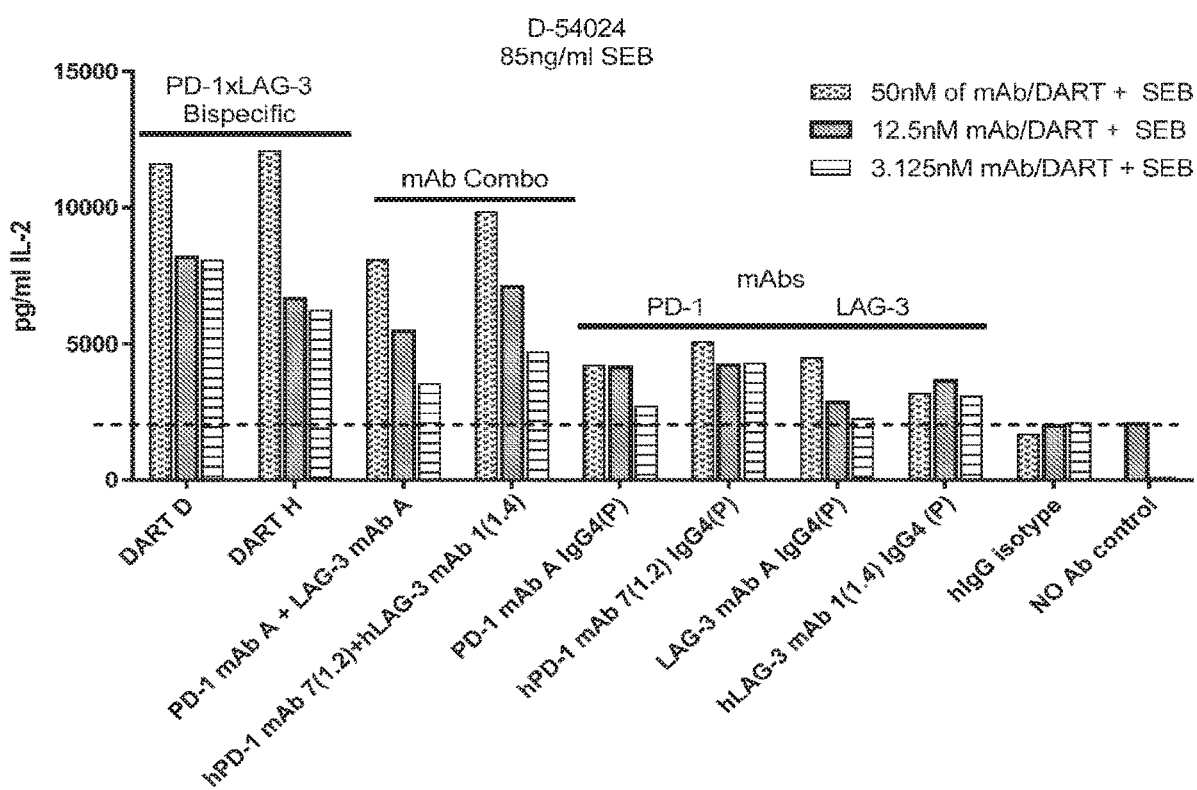

FIG. 19 shows that the PD-1×LAG-3 bispecific diabody constructs DART D and DART H are able to stimulate cytokine production to levels comparable or higher than that observed upon the administration of the combination of an anti-PD-1 mAb+an anti-LAG-3 mAb (PD-1 mAb A+LAG-3 mAb A), and that DART D provided the largest enhancement of cytokine release. IL-2 secretion profiles of PBMCs from a representative donor stimulated with a high concentration of SEB (85 ng/mL) treated with PD-1×LAG-3 bispecific diabodies, or anti-PD-1 and anti-LAG-3 antibodies alone and in combination are plotted.

Figure 20:
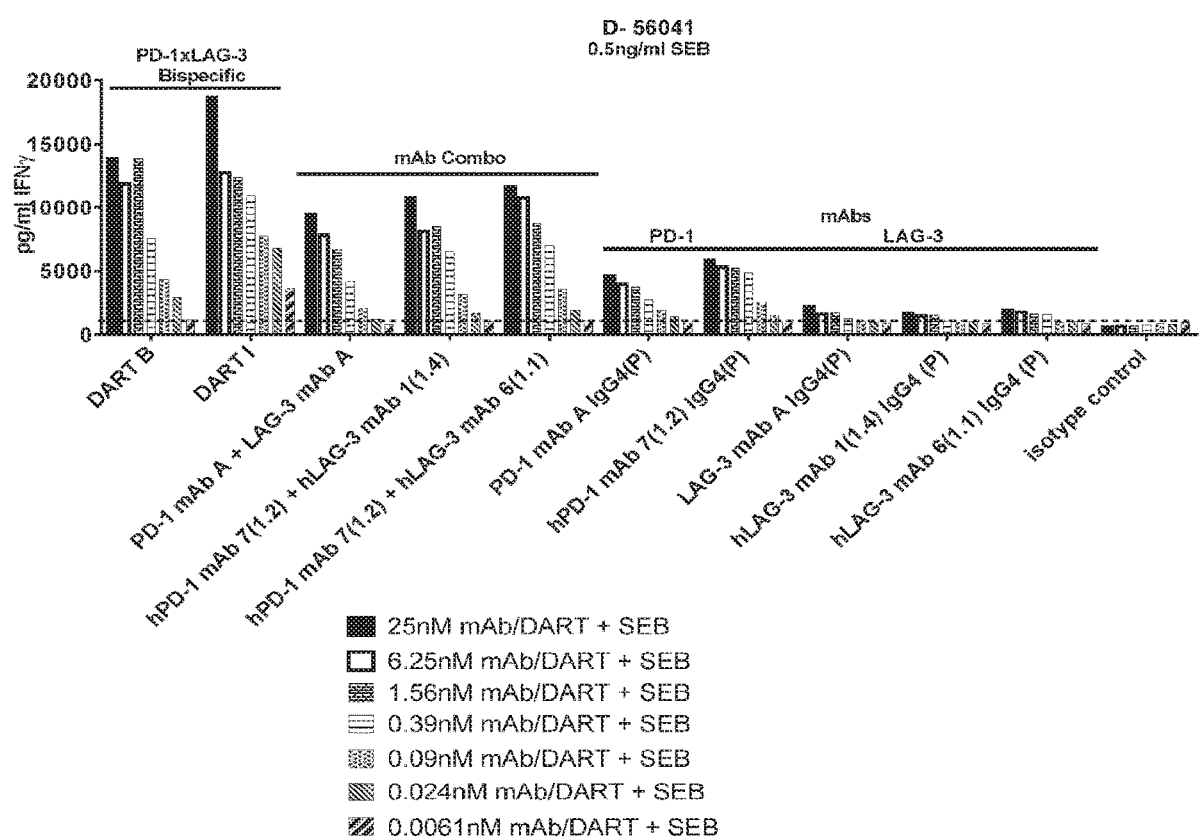
Figure 21A:
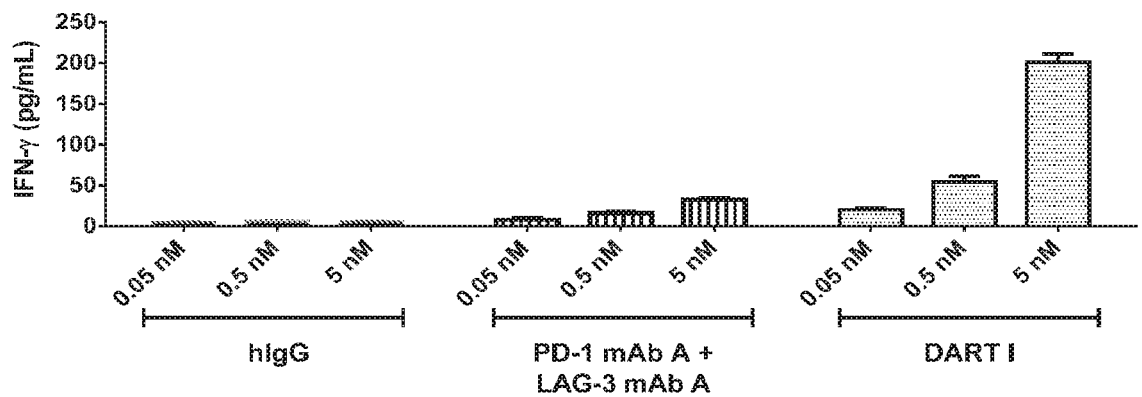
Figure 21B:
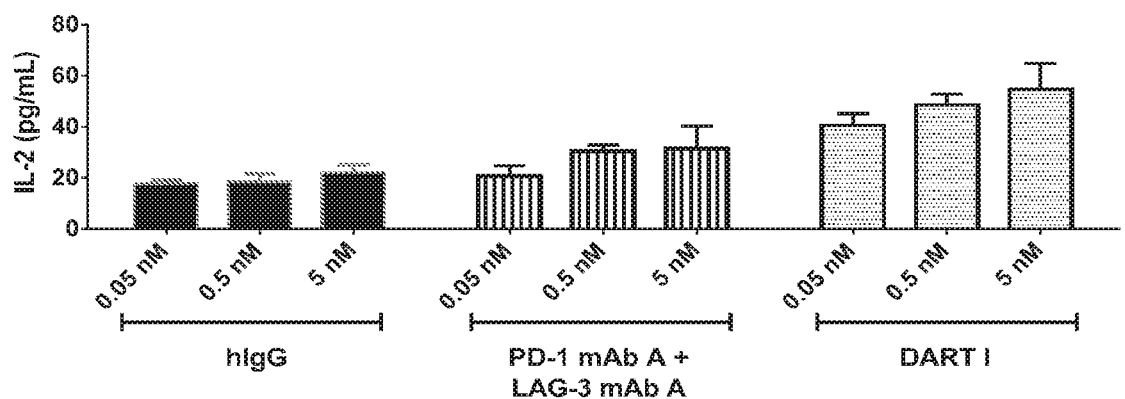
Figure 21C:
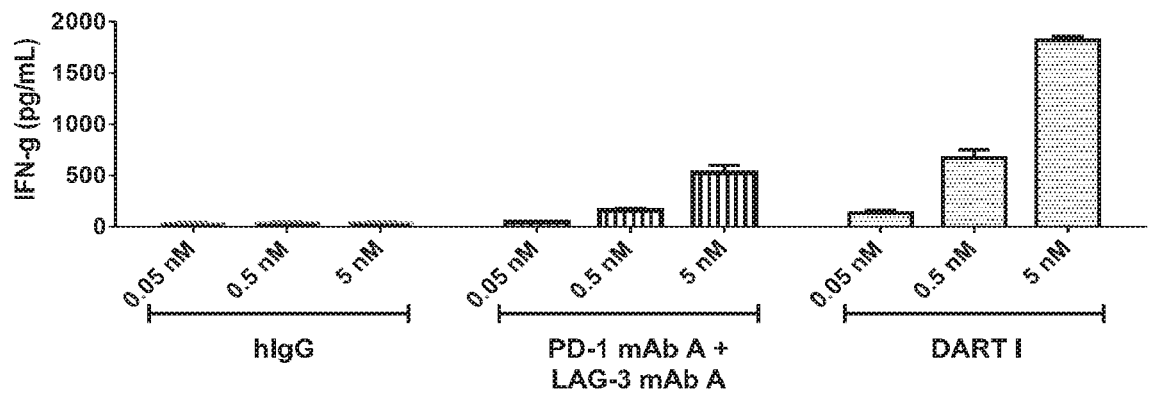
Figure 21D:
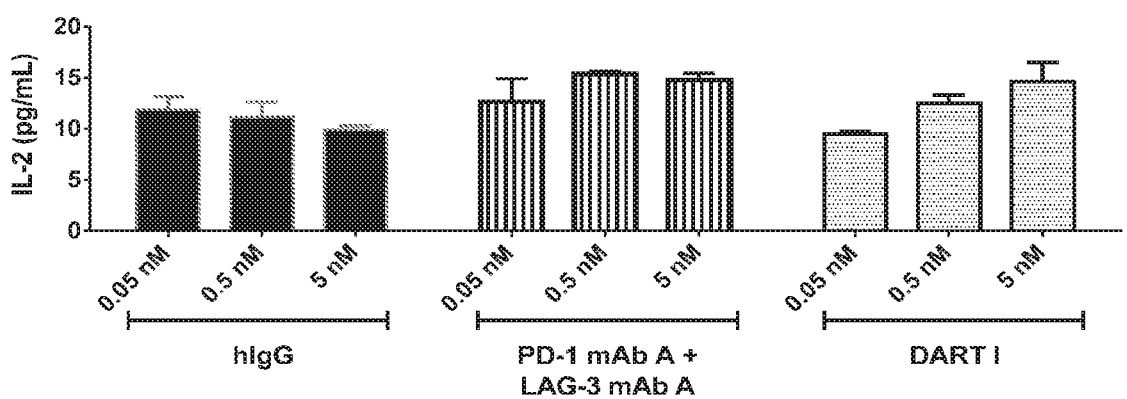

FIG. 20 shows that the PD-1×LAG-3 bispecific diabody constructs DART B and DART I are able to stimulate cytokine production to levels higher than that observed upon the administration of the combination of an anti-PD-1 mAb+ an anti-LAG-3 mAb (PD-1 mAb A+LAG-3 mAb A, hPD-1 mAb 7(1.2)+hLAG-3 mAb 1(1.4), hPD-1 mAb 7(1.2)+ hLAG-3 mAb 6(1.1)). IFNγ secretion profiles of PBMCs from a representative donor, stimulated with a middle concentration of SEB (0.5 ng/mL) treated with PD-1×LAG-3 bispecific diabodies, or anti-PD-1 and anti-LAG-3 antibodies alone and in combination are plotted.

FIGS. 21A-21D show that the that the PD-1×LAG-3 bispecific diabody DART I is able to stimulate cytokine production to levels higher than that observed upon the administration of the combination of an anti-PD-1 mAb+an anti-LAG-3 mAb (PD-1 mAb A+LAG-3 mAb A). IFNγ (FIGS. 21A and 21C) and IL-2 (FIGS. 21B and 21D) secretion profiles of CD4 memory cells from two representative donors, stimulated with tetanus toxoid (5 µg/mL) treated with the PD-1×LAG-3 bispecific diabody DART-I, anti-PD-1 and anti-LAG-3 antibodies in combination, or an isotype control are plotted. The results at day 7 using CD4 memory T cells from two representative donors are shown in FIGS. 21A-B and FIGS. 21C-D.

Figure 22:
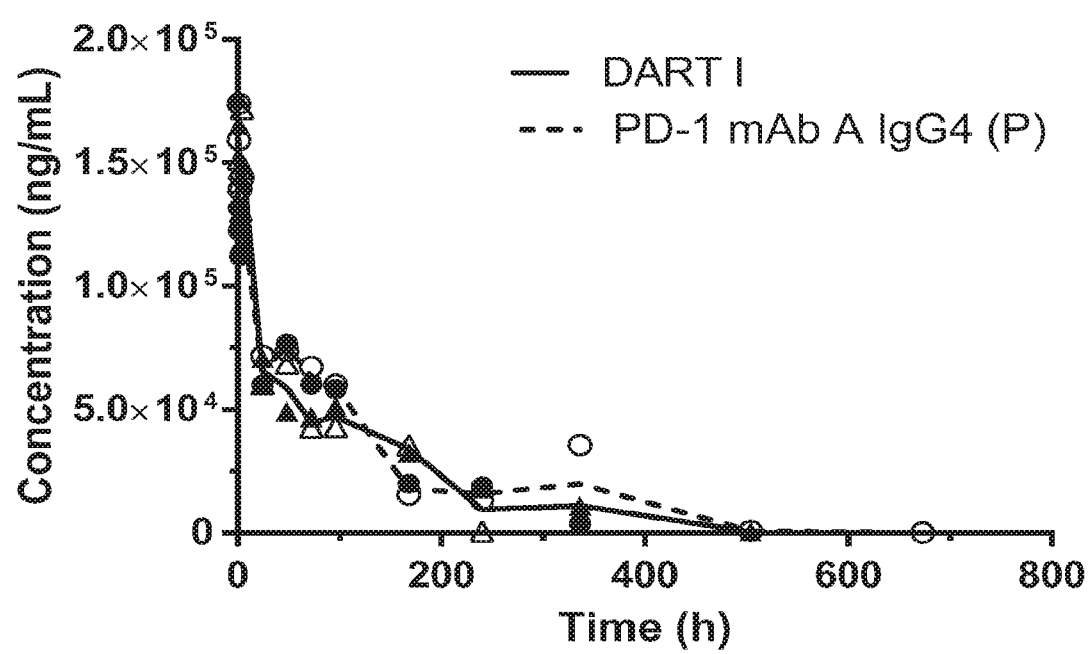

FIG. 22 shows that the the pharmacokinetics of the PD-1×LAG-3 bispecific molecule, DART I are comparable to those of the anti-PD-1 antibody, PD-1 mAb A IgG4 (P) in cynomolgus monkey. The lines indicate the mean serum concentration of DART I (solid) and PD-1 mAb A (dashed). The individual values for the male (filled) and female (open) monkeys are plotted for DART I (triangles) and PD-1 mAb A (circles).

Figure 23A:
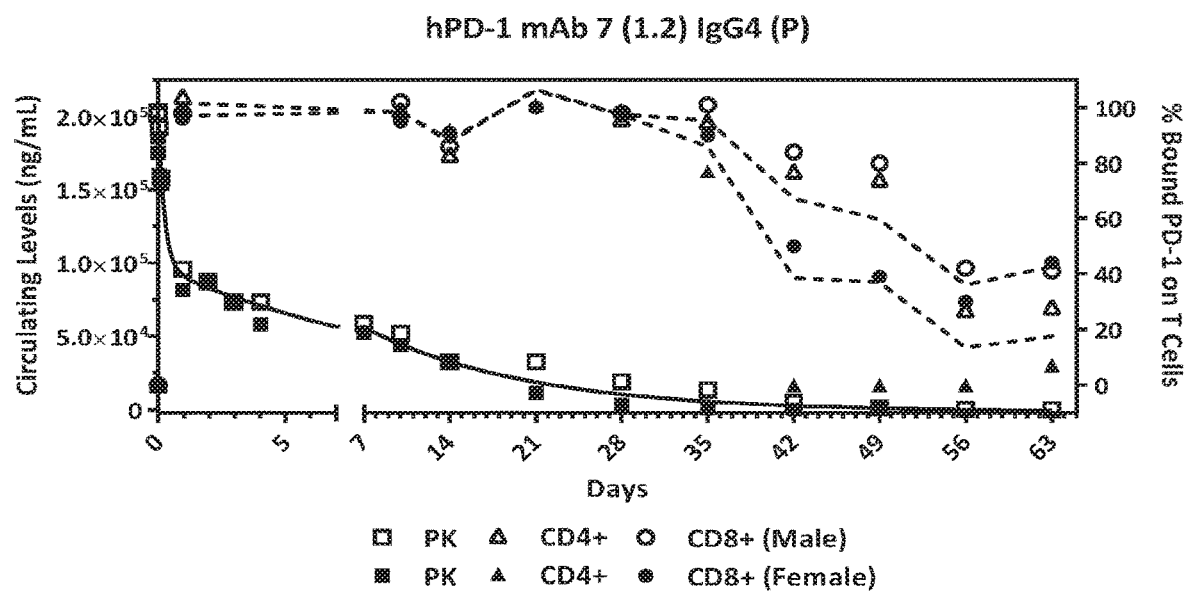
Figure 23B:
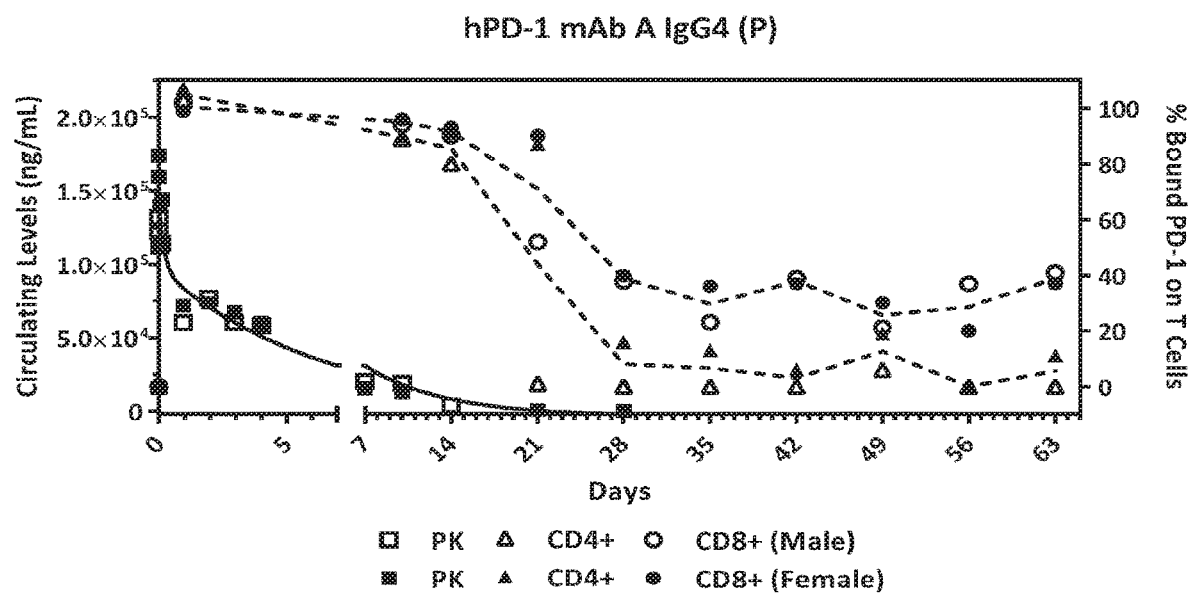
Figure 23C:
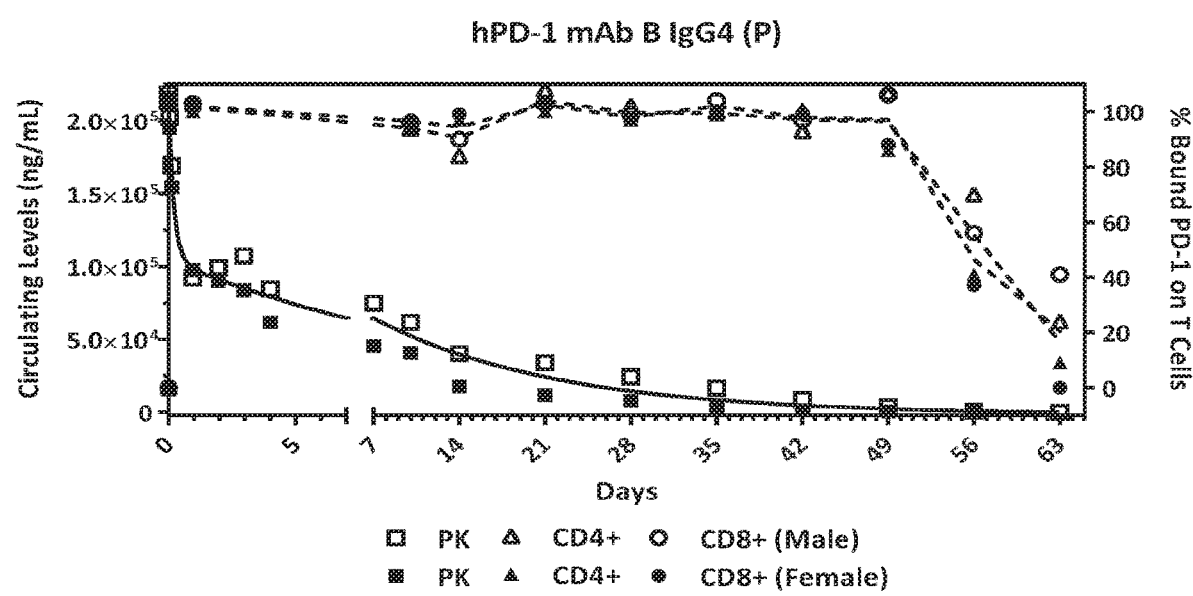

FIGS. 23A-23C show serum antibody concentrations and percentage of bound PD-1 on the surface of CD4+ or CD8+ T cells over time in animals following treatment with different anti-PD-1 antibodies. The percentage of bound PD 1 on the surface of CD4+ or CD8+ T cells following anti-PD 1 mAb treatment is plotted on the right y-axes; symbols represent % bound PD 1 on T cells for each individual animal and dashed lines represent the mean values. Serum mAb concentrations are plotted on the left y-axes; symbols represent serum levels for each individual animal and solid lines represent nonlinear fits of the data. Each panel presents data for animals (n=1/sex/group) administered 10 mg/kg hPD-1 mAb 7 (1.2) IgG4 (P) (FIG. 23A), PD-1 mAb A IgG4 (P) (FIG. 23B), or PD-1 mAb B IgG4 (P) (FIG. 23B) by IV infusion on Day 1.

DETAILED DESCRIPTION OF THE INVENTION

The present invention is directed to PD-1-binding molecules that comprise the PD-1-binding domain of selected anti-PD-1 antibodies capable of binding to both cynomolgus monkey PD-1 and to human PD-1: PD-1 mAb 1, PD-1 mAb 2, PD-1 mAb 3, PD-1 mAb 4, PD-1 mAb 5, PD-1 mAb 6, PD-1 mAb 7, PD-1 mAb 8, PD-1 mAb 9, PD-1 mAb 10, PD-1 mAb 11, PD-1 mAb 12, PD-1 mAb 13, PD-1 mAb 14, or PD-1 mAb 15. The invention particularly concerns PD-1-binding molecules that are humanized or chimeric versions of such antibodies, or that comprise PD-1-binding fragments of such anti-PD-1 antibodies (especially immunocongugates, diabodies (including but not limited to DART-A, DART-B, DART-C, DART-D, DART-E, DART-F, DART-G, DART-H, DART-I, and DART-J), BiTEs, bispecific antibodies, etc.). The invention particularly concerns such PD-1-binding molecules that are additionally capable of binding an epitope of a molecule involved in regulating an immune check point that is present on the surface of an immune cell. The present invention also pertains to methods of using such PD-1-binding molecules to detect PD-1 or to stimulate an immune response. The present invention also pertains to methods of combination therapy in which a PD-1-binding molecule that comprises one or more PD-1-binding domain(s) of such selected anti-PD-1 antibodies is administered in combination with one or more additional molecules that are effective in stimulating an immune response and/or in combination with one or more additional molecules that specifically bind a cancer antigen.

I. Antibodies and their Binding Domains

The antibodies of the present invention are immunoglobulin molecules capable of specific binding to a target, such as a carbohydrate, polynucleotide, lipid, polypeptide, etc., through at least one antigen recognition site, located in the Variable Domain of the immunoglobulin molecule. As used herein, the terms "antibody" and "antibodies" refer to monoclonal antibodies, multispecific antibodies, human antibodies, humanized antibodies, synthetic antibodies, chimeric antibodies, polyclonal antibodies, camelized antibodies, single-chain Fvs (scFv), single-chain antibodies, Fab fragments, F(ab') fragments, disulfide-linked bispecific Fvs (sdFv), intrabodies, and epitope-binding fragments of any of the above. In particular, antibodies include immunoglobulin molecules and immunologically active fragments of immunoglobulin molecules, i.e., molecules that contain an antigen-binding site. Immunoglobulin molecules can be of any type (e.g., IgG, IgE, IgM, IgD, IgA and IgY), class (e.g., $IgG_1$, $IgG_2$, $IgG_3$, $IgG_4$, $IgA_1$ and $IgA_2$) or subclass. In addition to their known uses in diagnostics, antibodies have been shown to be useful as therapeutic agents. Antibodies are capable of immunospecifically binding to a polypeptide or protein or a non-protein molecule due to the presence on such molecule of a particular domain or moiety or conformation (an "epitope"). An epitope-containing molecule may have immunogenic activity, such that it elicits an antibody production response in an animal; such molecules are termed "antigens"). The last few decades have seen a revival of interest in the therapeutic potential of antibodies, and antibodies have become one of the leading classes of biotechnology-derived drugs (Chan, C. E. et al. (2009) "*The Use Of Antibodies In The Treatment Of Infectious Diseases,*" Singapore Med. J. 50(7):663-666). Over 200 antibody-based drugs have been approved for use or are under development.

The term "monoclonal antibody" refers to a homogeneous antibody population wherein the monoclonal antibody is comprised of amino acids (naturally occurring and non-naturally occurring) that are involved in the selective binding of an antigen. Monoclonal antibodies are highly specific, being directed against a single epitope (or antigenic site). The term "monoclonal antibody" encompasses not only intact monoclonal antibodies and full-length monoclonal antibodies, but also fragments thereof (such as Fab, Fab', $F(ab')_2$ Fv), single-chain (scFv), mutants thereof, fusion proteins comprising an antibody portion, humanized monoclonal antibodies, chimeric monoclonal antibodies, and any other modified configuration of the immunoglobulin molecule that comprises an antigen recognition site of the required specificity and the ability to bind to an antigen. It is not intended to be limited as regards to the source of the antibody or the manner in which it is made (e.g., by hybridoma, phage selection, recombinant expression, transgenic animals, etc.). The term includes whole immunoglobulins as well as the fragments etc. described above under the definition of "antibody." Methods of making monoclonal antibodies are known in the art. One method which may be employed is the method of Kohler, G. et al. (1975) "*Continuous Cultures Of Fused Cells Secreting Antibody Of Predefined Specificity*," Nature 256:495-497 or a modification thereof. Typically, monoclonal antibodies are developed in mice, rats or rabbits. The antibodies are produced by immunizing an animal with an immunogenic amount of cells, cell extracts, or protein preparations that contain the desired epitope. The immunogen can be, but is not limited to, primary cells, cultured cell lines, cancerous cells, proteins, peptides, nucleic acids, or tissue. Cells used for immunization may be cultured for a period of time (e.g., at least 24 hours) prior to their use as an immunogen. Cells may be used as immunogens by themselves or in combination with a non-denaturing adjuvant, such as Ribi (see, e.g., Jennings, V. M. (1995) "*Review of Selected Adjuvants Used in Antibody Production*," ILAR J. 37(3): 119-125). In general, cells should be kept intact and preferably viable when used as immunogens. Intact cells may allow antigens to be better detected than ruptured cells by the immunized animal. Use of denaturing or harsh adjuvants, e.g., Freud's adjuvant, may rupture cells and therefore is discouraged. The immunogen may be administered multiple times at periodic intervals such as, bi-weekly, or weekly, or may be administered in such a way as to maintain viability in the animal (e.g., in a tissue recombinant). Alternatively, existing monoclonal antibodies and any other equivalent antibodies that are immunospecific for a desired pathogenic epitope can be sequenced and produced recombinantly by any means known in the art. In one embodiment, such an antibody is sequenced and the polynucleotide sequence is then cloned into a vector for expression or propagation. The sequence encoding the antibody of interest may be maintained in a vector in a host cell and the host cell can then be expanded and frozen for future use. The polynucleotide sequence of such antibodies may be used for genetic manipulation to generate the monospecific or multispecific (e.g., bispecific, trispecific and tetraspecific) molecules of the invention as well as an affinity optimized, a chimeric antibody, a humanized antibody, and/or a caninized antibody, to improve the affinity, or other characteristics of the antibody. The general principle in humanizing an antibody involves retaining the basic sequence of the antigen-binding portion of the antibody, while swapping the non-human remainder of the antibody with human antibody sequences.

Natural antibodies (such as IgG antibodies) are composed of two Light Chains complexed with two Heavy Chains. Each light chain contains a Variable Domain (VL) and a Constant Domain (CL). Each heavy chain contains a Variable Domain (VH), three Constant Domains (CH1, CH2 and CH3), and a hinge domain located between the CH1 and CH2 Domains. The basic structural unit of naturally occurring immunoglobulins (e.g., IgG) is thus a tetramer having two light chains and two heavy chains, usually expressed as a glycoprotein of about 150,000 Da. The amino-terminal ("N-terminal") portion of each chain includes a Variable Domain of about 100 to 110 or more amino acids primarily responsible for antigen recognition. The carboxy-terminal ("C-terminal") portion of each chain defines a constant region, with light chains having a single Constant Domain and heavy chains usually having three Constant Domains and a Hinge Domain. Thus, the structure of the light chains of an IgG molecule is n-VL-CL-c and the structure of the IgG heavy chains is n-VH—CH1-H—CH2-CH3-c (where H is the hinge domain, and n and c represent, respectively, the N-terminus and the C-terminus of the polypeptide). The Variable Domains of an IgG molecule consist of the complementarity determining regions (CDR), which contain the residues in contact with epitope, and non-CDR segments, referred to as framework segments (FR), which in general maintain the structure and determine the positioning of the CDR loops so as to permit such contacting (although certain framework residues may also contact antigen). Thus, the VL and VH Domains have the structure n-FR1-CDR1-FR2-CDR2-FR3-CDR3-FR4-c. Polypeptides that are (or may serve as) the first, second and third CDR of an antibody Light Chain are herein respectively designated $CDR_L1$ Domain, $CDR_L2$ Domain, and $CDR_L3$ Domain. Similarly, polypeptides that are (or may serve as) the first, second and third CDR of an antibody heavy chain are herein respectively designated $CDR_H1$ Domain, $CDR_H2$ Domain, and $CDR_H3$ Domain. Thus, the terms $CDR_L1$ Domain, $CDR_L2$ Domain, $CDR_L3$ Domain, $CDR_H1$ Domain, $CDR_H2$ Domain, and $CDR_H3$ Domain are directed to polypeptides that when incorporated into a protein cause that protein to be able to bind to a specific epitope regardless of whether such protein is an antibody having light and heavy chains or a diabody or a single-chain binding molecule (e.g., an scFv, a BiTe, etc.), or is another type of protein. Accordingly, as used herein, the term "epitope-binding fragment" means a fragment of an antibody capable of immunospecifically binding to an epitope, and the term "epitope-binding site" refers to that portion of a molecule comprising an epitope-binding fragment that is responsible for epitope binding. An epitope-binding site may contain 1, 2, 3, 4, 5 or all 6 of the CDR Domains of such antibody and, although capable of immunospecifically binding to such epitope, may exhibit an immunospecificity, affinity or selectivity toward such epitope that differs from that of such antibody. Preferably, however, an epitope-binding fragment will contain all 6 of the CDR Domains of such antibody. An epitope-binding fragment of an antibody may be a single polypeptide chain (e.g., an scFv), or may comprise two or more polypeptide chains, each having an amino terminus and a carboxy terminus (e.g., a diabody, a Fab fragment, an $F(ab')_2$ fragment, etc.).

The invention particularly encompasses single-chain Variable Domain fragments ("scFv") of the anti-PD-1 antibodies of this invention and multispecific binding molecules comprising the same. Single-chain Variable Domain fragments are made by linking Light and/or Heavy chain Variable Domain by using a short linking peptide. Bird et al. (1988) ("*Single-Chain Antigen-Binding Proteins*," Science 242:423-426) describes example of linking peptides which bridge approximately 3.5 nm between the carboxy terminus of one Variable Domain and the amino terminus of the other Variable Domain. Linkers of other sequences have been designed and used (Bird et al. (1988) "*Single-Chain Antigen-Binding Proteins*," Science 242:423-426). Linkers can in turn be modified for additional functions, such as attachment of drugs or attachment to solid supports. The single-chain variants can be produced either recombinantly or synthetically. For synthetic production of scFv, an automated synthesizer can be used. For recombinant production of scFv, a suitable plasmid containing polynucleotide that encodes the scFv can be introduced into a suitable host cell, either eukaryotic, such as yeast, plant, insect or mammalian cells, or prokaryotic, such as *E. coli*. Polynucleotides encoding the scFv of interest can be made by routine manipulations such as ligation of polynucleotides. The resultant scFv can be isolated using standard protein purification techniques known in the art.

The invention also particularly encompasses humanized variants of the anti-PD-1 antibodies of the invention and multispecific binding molecules comprising the same. The term "humanized" antibody refers to a chimeric molecule, generally prepared using recombinant techniques, having an antigen-binding site of an immunoglobulin from a non-human species and a remaining immunoglobulin structure of the molecule that is based upon the structure and/or sequence of a human immunoglobulin. The anti-human PD-1 antibodies of the present invention include humanized, chimeric or caninized variants of antibodies PD-1 mAb 1, PD-1 mAb 2, PD-1 mAb 3, PD-1 mAb 4, PD-1 mAb 5, PD-1 mAb 6, PD-1 mAb 7, PD-1 mAb 8, PD-1 mAb 9, PD-1 mAb 10, PD-1 mAb 11, PD-1 mAb 12, PD-1 mAb 13, PD-1 mAb 14, or PD-1 mAb 15. The polynucleotide sequence of the variable domains of such antibodies may be used for genetic manipulation to generate such derivatives and to improve the affinity, or other characteristics of such antibodies. The general principle in humanizing an antibody involves retaining the basic sequence of the antigen-binding portion of the antibody, while swapping the non-human remainder of the antibody with human antibody sequences. There are four general steps to humanize a monoclonal antibody. These are: (1) determining the nucleotide and predicted amino acid sequence of the starting antibody light and heavy variable domains (2) designing the humanized antibody or caninized antibody, i.e., deciding which antibody framework region to use during the humanizing or canonizing process (3) the actual humanizing or caninizing methodologies/techniques and (4) the transfection and expression of the humanized antibody. See, for example, U.S. Pat. Nos. 4,816,567; 5,807,715; 5,866,692; and 6,331,415.

The antigen-binding site may comprise either a complete Variable Domain fused to a Constant Domain or only the complementarity determining regions (CDRs) of such Variable Domain grafted to appropriate framework regions. Antigen-binding sites may be wild-type or modified by one or more amino acid substitutions. This eliminates the constant region as an immunogen in human individuals, but the possibility of an immune response to the foreign variable domain remains (LoBuglio, A. F. et al. (1989) "*Mouse/Human Chimeric Monoclonal Antibody In Man: Kinetics And Immune Response*," Proc. Natl. Acad. Sci. (U.S.A.) 86:4220-4224). Another approach focuses not only on providing human-derived constant regions, but modifying the variable domains as well so as to reshape them as closely as possible to human form. It is known that the variable domains of both heavy and light chains contain three complementarity determining regions (CDRs) which vary in response to the antigens in question and determine binding capability, flanked by four framework regions (FRs) which are relatively conserved in a given species and which putatively provide a scaffolding for the CDRs. When non-human antibodies are prepared with respect to a particular antigen, the variable domains can be "reshaped" or "humanized" by grafting CDRs derived from non-human antibody on the FRs present in the human antibody to be modified. Application of this approach to various antibodies has been reported by Sato, K. et al. (1993) Cancer Res 53:851-856. Riechmann, L. et al. (1988) "*Reshaping Human Antibodies for Therapy*," Nature 332:323-327; Verhoeyen, M. et al. (1988) "*Reshaping Human Antibodies: Grafting An Antilysozyme Activity*," Science 239:1534-1536; Kettleborough, C. A. et al. (1991) "*Humanization Of A Mouse Monoclonal Antibody By CDR-Grafting: The Importance Of Framework Residues On Loop Conformation*," Protein Engineering 4:773-3783; Maeda, H. et al. (1991) "*Construction Of Reshaped Human Antibodies With HIV-Neutralizing Activity*," Human Antibodies Hybridoma 2:124-134; Gorman, S. D. et al. (1991) "*Reshaping A Therapeutic CD4 Antibody*," Proc. Natl. Acad. Sci. (U.S.A.) 88:4181-4185; Tempest, P. R. et al. (1991) "*Reshaping A Human Monoclonal Antibody To Inhibit Human Respiratory Syncytial Virus Infection in vivo*," Bio/Technology 9:266-271; Co, M. S. et al. (1991) "*Humanized Antibodies For Antiviral Therapy*," Proc. Natl. Acad. Sci. (U.S.A.) 88:2869-2873; Carter, P. et al. (1992) "*Humanization Of An Anti-p185her2 Antibody For Human Cancer Therapy*," Proc. Natl. Acad. Sci. (U.S.A.) 89:4285-4289; and Co, M. S. et al. (1992) "*Chimeric And Humanized Antibodies With Specificity For The CD33 Antigen*," J. Immunol. 148:1149-1154. In some embodiments, humanized antibodies preserve all CDR sequences (for example, a humanized mouse antibody which contains all six CDRs from the mouse antibodies). In other embodiments, humanized antibodies have one or more CDRs (one, two, three, four, five, or six) which differ in sequence relative to the original antibody.

A number of "humanized" antibody molecules comprising an antigen-binding site derived from a non-human immunoglobulin have been described, including chimeric antibodies having rodent or modified rodent Variable Domain and their associated complementarity determining regions (CDRs) fused to human Constant Domains (see, for example, Winter et al. (1991) "*Man-made Antibodies*," Nature 349:293-299; Lobuglio et al. (1989) "*Mouse/Human Chimeric Monoclonal Antibody In Man: Kinetics And Immune Response*," Proc. Natl. Acad. Sci. (U.S.A.) 86:4220-4224 (1989), Shaw et al. (1987) "*Characterization Of A Mouse/Human Chimeric Monoclonal Antibody (17-1A) To A Colon Cancer Tumor Associated Antigen*," J. Immunol. 138:4534-4538, and Brown et al. (1987) "*Tumor-Specific Genetically Engineered Murine/Human Chimeric Monoclonal Antibody*," Cancer Res. 47:3577-3583). Other references describe rodent CDRs grafted into a human supporting framework region (FR) prior to fusion with an appropriate human antibody Constant Domain (see, for example, Riechmann, L. et al. (1988) "*Reshaping Human Antibodies for Therapy*," Nature 332:323-327; Verhoeyen, M. et al. (1988) "*Reshaping Human Antibodies: Grafting An Antilysozyme Activity*," Science 239:1534-1536; and Jones et al. (1986) "*Replacing The Complementarity-Determining Regions In A Human Antibody With Those From A Mouse*," Nature 321:522-525). Another reference describes rodent CDRs supported by recombinantly veneered rodent framework regions. See, for example, European Patent Publication No. 519,596. These "humanized" molecules are designed to minimize unwanted immunological response towards rodent anti-human antibody molecules, which limits the duration and effectiveness of therapeutic applications of those moieties in human recipients. Other methods of humanizing antibodies that may also be utilized are disclosed by Daugherty et al. (1991) "*Polymerase Chain Reaction Facilitates The Cloning, CDR-Grafting, And Rapid Expression Of A Murine Monoclonal Antibody Directed Against The CD18 Component Of Leukocyte Integrins*," Nucl. Acids Res. 19:2471-2476 and in U.S. Pat. Nos. 6,180,377; 6,054,297; 5,997,867; and 5,866,692.

II. Fcγ Receptors (FcγRs)

The CH2 and CH3 Domains of the two heavy chains interact to form the Fc Region, which is a domain that is recognized by cellular Fc Receptors, including but not limited to Fc gamma Receptors (FcγRs). As used herein, the term "Fc Region" is used to define a C-terminal region of an IgG heavy chain. The amino acid sequence of the CH2-CH3 Domain of an exemplary human IgG1 is (SEQ ID NO:1):

```
    231       240         250         260         270
    APELLGGPSV FLFPPKPKDT LMISRTPEVT CVVVDVSHED 280         290         300         310
    PEVKFNWYVD GVEVHNAKTK PREEQYNSTY RVVSVLTVLH 320         330         340         350
    QDWLNGKEYK CKVSNKALPA PIEKTISKAK GQPREPQVYT 360         370         380         390
    LPPSREEMTK NQVSLTCLVK GFYPSDIAVE WESNGQPENN 400         410         420         430
    YKTTPPVLDS DGSFFLYSKL TVDKSRWQQG NVFSCSVMHE 440         447
    ALHNHYTQKS LSLSPGX
``` as numbered by the EU index as set forth in Kabat, wherein, X is a lysine (K) or is absent.

The amino acid sequence of the CH2-CH3 Domain of an exemplary human IgG2 is (SEQ ID NO:2):

```
    231       240         250         260         270
    APPVA-GPSV FLFPPKPKDT LMISRTPEVT CVVVDVSHED 280         290         300         310
    PEVQFNWYVD GVEVHNAKTK PREEQFNSTF RVVSVLTVVH 320         330         340         350
    QDWLNGKEYK CKVSNKGLPA PIEKTISKTK GQPREPQVYT 360         370         380         390
    LPPSREEMTK NQVSLTCLVK GFYPSDISVE WESNGQPENN 400         410         420         430
    YKTTPPMLDS DGSFFLYSKL TVDKSRWQQG NVFSCSVMHE 440         447
    ALHNHYTQKS LSLSPGX
``` as numbered by the EU index as set forth in Kabat, wherein, X is a lysine (K) or is absent.

The amino acid sequence of the CH2-CH3 Domain of an exemplary human IgG3 is (SEQ ID NO:3):

```
    231       240         250         260         270
    APELLGGPSV FLFPPKPKDT LMISRTPEVT CVVVDVSHED 280         290         300         310
    PEVQFKWYVD GVEVHNAKTK PREEQYNSTF RVVSVLTVLH 320         330         340         350
    QDWLNGKEYK CKVSNKALPA PIEKTISKTK GQPREPQVYT 360         370         380         390
    LPPSREEMTK NQVSLTCLVK GFYPSDIAVE WESSGQPENN 400         410         420         430
    YNTTPPMLDS DGSFFLYSKL TVDKSRWQQG NIFSCSVMHE 440         447
    ALHNRFTQKS LSLSPGX
``` as numbered by the EU index as set forth in Kabat, wherein, X is a lysine (K) or is absent. The amino acid sequence of the CH2-CH3 Domain of an exemplary human IgG4 is (SEQ ID NO:4):

```
    231       240         250         260         270
    APEFLGGPSV FLFPPKPKDT LMISRTPEVT CVVVDVSQED 280         290         300         310
    PEVQFNWYVD GVEVHNAKTK PREEQFNSTY RVVSVLTVLH 320         330         340         350
    QDWLNGKEYK CKVSNKGLPS SIEKTISKAK GQPREPQVYT 360         370         380         390
    LPPSQEEMTK NQVSLTCLVK GFYPSDIAVE WESNGQPENN 400         410         420         430
    YKTTPPVLDS DGSFFLYSRL TVDKSRWQEG NVFSCSVMHE 440         447
    ALHNHYTQKS LSLSLGX
``` as numbered by the EU index as set forth in Kabat, wherein, X is a lysine (K) or is absent.

Throughout the present specification, the numbering of the residues in the constant region of an IgG heavy chain is that of the EU index as in Kabat et al., *Sequences of Proteins of Immunological Interest*, 5$^{th}$ Ed. Public Health Service, NH1, MD (1991) ("Kabat"), expressly incorporated herein by references. The term "EU index as in Kabat" refers to the numbering of the human IgG1 EU antibody. Amino acids from the Variable Domains of the mature heavy and light chains of immunoglobulins are designated by the position of an amino acid in the chain. Kabat described numerous amino acid sequences for antibodies, identified an amino acid consensus sequence for each subgroup, and assigned a residue number to each amino acid, and the CDRs are identified as defined by Kabat (it will be understood that CDR$_H$1 as defined by Chothia, C. & Lesk, A. M. ((1987) "Canonical structures for the hypervariable regions of immunoglobulins,". J. Mol. Biol. 196:901-917) begins five residues earlier). Kabat's numbering scheme is extendible to antibodies not included in his compendium by aligning the antibody in question with one of the consensus sequences in Kabat by reference to conserved amino acids. This method for assigning residue numbers has become standard in the field and readily identifies amino acids at equivalent positions in different antibodies, including chimeric or humanized variants. For example, an amino acid at position 50 of a human antibody light chain occupies the equivalent position to an amino acid at position 50 of a mouse antibody light chain.

Polymorphisms have been observed at a number of different positions within antibody constant regions (e.g., CH1 positions, including but not limited to positions 192, 193, and 214; Fc positions, including but not limited to positions 270, 272, 312, 315, 356, and 358 as numbered by the EU index as set forth in Kabat), and thus slight differences between the presented sequence and sequences in the prior art can exist. Polymorphic forms of human immunoglobulins have been well-characterized. At present, 18 Gm allotypes are known: G1m (1, 2, 3, 17) or G1m (a, x, f, z), G2m (23) or G2m (n), G3m (5, 6, 10, 11, 13, 14, 15, 16, 21, 24, 26, 27, 28) or G3m (b1, c3, b3, b0, b3, b4, s, t, g1, c5, u, v, g5) (Lefranc, et al., "*The Human IgG Subclasses: Molecular Analysis Of Structure, Function And Regulation*." Pergamon, Oxford, pp. 43-78 (1990); Lefranc, G. et al., 1979, Hum. Genet.: 50, 199-211). It is specifically contemplated that the antibodies of the present invention may be incorporate any allotype, isoallotype, or haplotype of any immunoglobulin gene, and are not limited to the allotype, isoallotype or haplotype of the sequences provided herein. Furthermore, in some expression systems the C-terminal amino acid residue (bolded above) of the CH3 Domain may be post-translationally removed. Accordingly, the C-terminal residue of the CH3 Domain is an optional amino acid residue in the PD-1-binding molecules of the invention. Specifically encompassed by the instant invention are PD-1-binding molecules lacking the C-terminal residue of the CH3 Domain. Also specifically encompassed by the instant invention are such constructs comprising the C-terminal lysine residue of the CH3 Domain.

Activating and inhibitory signals are transduced through the ligation of an Fc region to a cellular Fc gamma Receptor (FcγR). The ability of such ligation to result in diametrically opposing functions results from structural differences among the different FcγRs. Two distinct domains within the cytoplasmic signaling domains of the receptor called immunoreceptor tyrosine-based activation motifs (ITAMs) and immunoreceptor tyrosine-based inhibitory motifs (ITIMS) account for the different responses. The recruitment of different cytoplasmic enzymes to these structures dictates the outcome of the FcγR-mediated cellular responses. ITAM-containing FcγR complexes include FcγRI, FcγRIIA, FcγRIIIA, whereas ITIM-containing complexes only include FcγRIIB Human neutrophils express the FcγRIIA gene. FcγRIIA clustering via immune complexes or specific antibody cross-linking serves to aggregate ITAMs along with receptor-associated kinases which facilitate ITAM phosphorylation. ITAM phosphorylation serves as a docking site for Syk kinase, activation of which results in activation of downstream substrates (e.g., $PI_3K$). Cellular activation leads to release of proinflammatory mediators. The FcγRIIB gene is expressed on B lymphocytes; its extracellular domain is 96% identical to FcγRIIA and binds IgG complexes in an indistinguishable manner. The presence of an ITIM in the cytoplasmic domain of FcγRIIB defines this inhibitory subclass of FcγR. Recently the molecular basis of this inhibition was established. When co-ligated along with an activating FcγR, the ITIM in FcγRIIB becomes phosphorylated and attracts the SH2 domain of the inositol polyphosphate 5'-phosphatase (SHIP), which hydrolyzes phosphoinositol messengers released as a consequence of ITAM-containing FcγR-mediated tyrosine kinase activation, consequently preventing the influx of intracellular $Ca^{++}$. Thus cross-linking of FcγRIIB dampens the activating response to FcγR ligation and inhibits cellular responsiveness. B-cell activation, B-cell proliferation and antibody secretion is thus aborted.

III. Bispecific Antibodies, Multispecific Diabodies and DART® Diabodies

The ability of an antibody to bind an epitope of an antigen depends upon the presence and amino acid sequence of the antibody's VL and VH Domains. Interaction of an antibody light chain and an antibody heavy chain and, in particular, interaction of its VL and VH Domains forms one of the two epitope-binding sites of a natural antibody. Natural antibodies are capable of binding to only one epitope species (i.e., they are monospecific), although they can bind multiple copies of that species (i.e., exhibiting bivalency or multivalency).

The binding domains of the present invention bind to epitopes in an "immunospecific" manner. As used herein, an antibody, diabody or other epitope-binding molecule is said to "immunospecifically" bind a region of another molecule (i.e., an epitope) if it reacts or associates more frequently, more rapidly, with greater duration and/or with greater affinity with that epitope relative to alternative epitopes. For example, an antibody that immunospecifically binds to a viral epitope is an antibody that binds this viral epitope with greater affinity, avidity, more readily, and/or with greater duration than it immunospecifically binds to other viral epitopes or non-viral epitopes. It is also understood by reading this definition that, for example, an antibody (or moiety or epitope) that immunospecifically binds to a first target may or may not specifically or preferentially bind to a second target. As such, "immunospecific binding" does not necessarily require (although it can include) exclusive binding. Generally, but not necessarily, reference to binding means "specific" binding. Two molecules are said to be capable of binding to one another in a "physiospecific" manner, if such binding exhibits the specificity with which receptors bind to their respective ligands.

The functionality of antibodies can be enhanced by generating multispecific antibody-based molecules that can simultaneously bind two separate and distinct antigens (or different epitopes of the same antigen) and/or by generating antibody-based molecule having higher valency (i.e., more than two binding sites) for the same epitope and/or antigen.

In order to provide molecules having greater capability than natural antibodies, a wide variety of recombinant bispecific antibody formats have been developed (see, e.g., PCT Publication Nos. WO 2008/003116, WO 2009/132876, WO 2008/003103, WO 2007/146968, WO 2009/018386, WO 2012/009544, WO 2013/070565), most of which use linker peptides either to fuse a further epitope-binding fragment (e.g., an scFv, VL, VH, etc.) to, or within the antibody core (IgA, IgD, IgE, IgG or IgM), or to fuse multiple epitope-binding fragments (e.g., two Fab fragments or scFvs). Alternative formats use linker peptides to fuse an epitope-binding fragment (e.g., an scFv, VL, VH, etc.) to an a dimerization domain such as the CH2-CH3 Domain or alternative polypeptides (WO 2005/070966, WO 2006/107786A WO 2006/107617A, WO 2007/046893). Typically, such approaches involve compromises and trade-offs. For example, PCT Publications Nos. WO 2013/174873, WO 2011/133886 and WO 2010/136172 disclose that the use of linkers may cause problems in therapeutic settings, and teaches a trispecific antibody in which the CL and CH1 Domains are switched from their respective natural positions and the VL and VH Domains have been diversified (WO 2008/027236; WO 2010/108127) to allow them to bind to more than one antigen. Thus, the molecules disclosed in these documents trade binding specificity for the ability to bind additional antigen species. PCT Publications Nos. WO 2013/163427 and WO 2013/119903 disclose modifying the CH2 Domain to contain a fusion protein adduct comprising a binding domain. The document notes that the CH2 Domain likely plays only a minimal role in mediating effector function. PCT Publications Nos. WO 2010/028797, WO2010028796 and WO 2010/028795 disclose recombinant antibodies whose Fc Regions have been replaced with additional VL and VH Domains, so as to form trivalent binding molecules. PCT Publications Nos. WO 2003/025018 and WO2003012069 disclose recombinant diabodies whose individual chains contain scFv Domains. PCT Publications No. WO 2013/006544 discloses multivalent Fab molecules that are synthesized as a single polypeptide chain and then subjected to proteolysis to yield heterodimeric structures. Thus, the molecules disclosed in these documents trade all or some of the capability of mediating effector function for the ability to bind additional antigen species. PCT Publications Nos. WO 2014/022540, WO 2013/003652, WO 2012/162583, WO 2012/156430, WO 2011/086091, WO 2008/024188, WO 2007/024715, WO 2007/075270, WO 1998/002463, WO 1992/022583 and WO 1991/003493 disclose adding additional binding domains or functional groups to an antibody or an antibody portion (e.g., adding a diabody to the antibody's light chain, or adding additional VL and VH Domains to the antibody's light and heavy chains, or adding a heterologous fusion protein or chaining multiple Fab Domains to one another). Thus, the molecules disclosed in these documents trade native antibody structure for the ability to bind additional antigen species.

The art has additionally noted the capability to produce diabodies that differ from such natural antibodies in being capable of binding two or more different epitope species (i.e., exhibiting bispecificity or multispecificity in addition to bivalency or multivalency) (see, e.g., Holliger et al. (1993) "'Diabodies': Small Bivalent And Bispecific Antibody Fragments," Proc. Natl. Acad. Sci. (U.S.A.) 90:6444-6448; US 2004/0058400 (Hollinger et al.); US 2004/0220388/WO 02/02781 (Mertens et al.); Alt et al. (1999) FEBS Lett. 454(1-2):90-94; Lu, D. et al. (2005) "A Fully Human Recombinant IgG-Like Bispecific Antibody To Both The Epidermal Growth Factor Receptor And The Insulin-Like Growth Factor Receptor For Enhanced Antitumor Activity," J. Biol. Chem. 280(20):19665-19672; WO 02/02781 (Mertens et al.); Olafsen, T. et al. (2004) "Covalent Disulfide-Linked Anti-CEA Diabody Allows Site-Specific Conjugation And Radiolabeling For Tumor Targeting Applications," Protein Eng. Des. Sel. 17(1):21-27; Wu, A. et al. (2001) "Multimerization Of A Chimeric Anti-CD20 Single Chain Fv-Fv Fusion Protein Is Mediated Through Variable Domain Exchange," Protein Engineering 14(2): 1025-1033; Asano et al. (2004) "A Diabody For Cancer Immunotherapy And Its Functional Enhancement By Fusion Of Human Fc Domain," Abstract 3P-683, J. Biochem. 76(8):992; Takemura, S. et al. (2000) "Construction Of A Diabody (Small Recombinant Bispecific Antibody) Using A Refolding System," Protein Eng. 13(8):583-588; Baeuerle, P. A. et al. (2009) "Bispecific T-Cell Engaging Antibodies For Cancer Therapy," Cancer Res. 69(12):4941-4944).

The design of a diabody is based on the antibody derivative known as a single-chain Variable Domain fragment (scFv). Such molecules are made by linking Light and/or Heavy chain Variable Domains by using a short linking peptide. Bird et al. (1988) ("Single-Chain Antigen-Binding Proteins," Science 242:423-426) describes example of linking peptides which bridge approximately 3.5 nm between the carboxy terminus of one Variable Domain and the amino terminus of the other Variable Domain. Linkers of other sequences have been designed and used (Bird et al. (1988) "Single-Chain Antigen-Binding Proteins," Science 242:423-426). Linkers can in turn be modified for additional functions, such as attachment of drugs or attachment to solid supports. The single-chain variants can be produced either recombinantly or synthetically. For synthetic production of scFv, an automated synthesizer can be used. For recombinant production of scFv, a suitable plasmid containing polynucleotide that encodes the scFv can be introduced into a suitable host cell, either eukaryotic, such as yeast, plant, insect or mammalian cells, or prokaryotic, such as *E. coli*. Polynucleotides encoding the scFv of interest can be obtained by routine manipulations such as ligation of polynucleotides. The resultant scFv can be isolated using standard protein purification techniques known in the art.

The provision of non-monospecific diabodies provides a significant advantage over antibodies, including but not limited to, the capacity to co-ligate and co-localize cells that express different epitopes. Bispecific diabodies thus have wide-ranging applications including therapy and immunodiagnosis. Bispecificity allows for great flexibility in the design and engineering of the diabody in various applications, providing enhanced avidity to multimeric antigens, the cross-linking of differing antigens, and directed targeting to specific cell types relying on the presence of both target antigens. Due to their increased valency, low dissociation rates and rapid clearance from the circulation (for diabodies of small size, at or below ~50 kDa), diabody molecules known in the art have also shown particular use in the field of tumor imaging (Fitzgerald et al. (1997) "*Improved Tumour Targeting By Disulphide Stabilized Diabodies Expressed In Pichia pastoris*," Protein Eng. 10:1221).

The bispecificity of diabodies has led to their use for co-ligating differing cells, for example, the cross-linking of cytotoxic T-cells to tumor cells (Staerz et al. (1985) "*Hybrid Antibodies Can Target Sites For Attack By T Cells*," Nature 314:628-631, and Holliger et al. (1996) "*Specific Killing Of Lymphoma Cells By Cytotoxic T-Cells Mediated By A Bispecific Diabody*," Protein Eng. 9:299-305; Marvin et al. (2005) "*Recombinant Approaches To IgG-Like Bispecific Antibodies*," Acta Pharmacol. Sin. 26:649-658). Alternatively, or additionally, bispecific diabodies can be used to co-ligate receptors on the surface of different cells or on a single cell. Co-ligation of different cells and/or receptors is useful to modulation effector functions and/or immune cell signaling. Multispecific molecules (e.g., bispecific diabodies) comprising epitope-binding sites may be directed to a surface determinant of any immune cell such as B7-H3 (CD276), B7-H4 (VTCN1), BTLA (CD272), CD3, CD8, CD16, CD27, CD32, CD40, CD40L, CD47, CD64, CD70 (CD27L), CD80 (B7-1), CD86 (B7-2), CD94 (KLRD1), CD137 (4-1BB), CD137L (4-1BBL), CD226, CTLA-4 (CD152), Galectin-9, GITR, GITRL, HHLA2, ICOS (CD278), ICOSL (CD275), Killer Activation Receptor (KIR), LAG-3 (CD223), LIGHT (TNFSF14, CD258), WIC class I or II, NKG2a, NKG2d, OX40 (CD134), OX40L (CD134L), PD1H, PD-1 (CD279), PD-L1 (B7-H1, CD274), PD-L2 (B7-CD, CD273), PVR (NECLS, CD155), SIRPa, TCR, TIGIT, TIM-3 (HAVCR2), and/or VISTA (PD-1H), which are expressed on T lymphocytes, Natural Killer (NK) cells, Antigen-presenting cells or other mononuclear cell. In particular, epitope-binding sites directed to a cell surface receptor that is involved in regulating an immune checkpoint (or the ligand thereof) are useful in the generation of bispecific or multispecific binding molecules which antagonize or block the inhibitory signaling of immune checkpoint molecules and thereby stimulate, upregulate or enhance, immune responses in a subject. Molecules involved in regulating immune checkpoints include, but are not limited to B7-H3, B7-H4, BTLA, CD40, CD40L, CD47, CD70, CD80, CD86, CD94, CD137, CD137L, CD226, CTLA-4, Galectin-9, GITR, GITRL, HHLA2, ICOS, ICOSL, KIR, LAG-3, LIGHT, MHC class I or II, NKG2a, NKG2d, OX40, OX40L, PD1H, PD-1, PD-L1, PD-L2, PVR, SIRPa, TCR, TIGIT, TIM-3 and/or VISTA.

However, the above advantages come at a salient cost. The formation of such non-monospecific diabodies requires the successful assembly of two or more distinct and different polypeptides (i.e., such formation requires that the diabodies be formed through the heterodimerization of different polypeptide chain species). This fact is in contrast to monospecific diabodies, which are formed through the homodimerization of identical polypeptide chains. Because at least two dissimilar polypeptides (i.e., two polypeptide species) must be provided in order to form a non-monospecific diabody, and because homodimerization of such polypeptides leads to inactive molecules (Takemura, S. et al. (2000) "*Construction Of A Diabody (Small Recombinant Bispecific Antibody) Using A Refolding System*," Protein Eng. 13(8): 583-588), the production of such polypeptides must be accomplished in such a way as to prevent covalent bonding between polypeptides of the same species (i.e., so as to prevent homodimerization) (Takemura, S. et al. (2000) "*Construction Of A Diabody (Small Recombinant Bispecific Antibody) Using A Refolding System*," Protein Eng. 13(8): 583-588). The art has therefore taught the non-covalent association of such polypeptides (see, e.g., Olafsen et al. (2004) "*Covalent Disulfide-Linked Anti-CEA Diabody Allows Site-Specific Conjugation And Radiolabeling For Tumor Targeting Applications*," Prot. Engr. Des. Sel. 17:21-27; Asano et al. (2004) "*A Diabody For Cancer Immunotherapy And Its Functional Enhancement By Fusion Of Human Fc Domain*," Abstract 3P-683, J. Biochem. 76(8): 992; Takemura, S. et al. (2000) "*Construction Of A Diabody (Small Recombinant Bispecific Antibody) Using A Refolding System*," Protein Eng. 13(8):583-588; Lu, D. et al. (2005) "*A Fully Human Recombinant IgG-Like Bispecific Antibody To Both The Epidermal Growth Factor Receptor And The Insulin-Like Growth Factor Receptor For Enhanced Antitumor Activity*," J. Biol. Chem. 280(20):19665-19672).

However, the art has recognized that bispecific diabodies composed of non-covalently associated polypeptides are unstable and readily dissociate into non-functional monomers (see, e.g., Lu, D. et al. (2005) "*A Fully Human Recombinant IgG-Like Bispecific Antibody To Both The Epidermal Growth Factor Receptor And The Insulin-Like Growth Factor Receptor For Enhanced Antitumor Activity*," J. Biol. Chem. 280(20):19665-19672).

In the face of this challenge, the art has succeeded in developing stable, covalently bonded heterodimeric non-monospecific diabodies, termed DART® (Dual Affinity Re-Targeting Reagents) diabodies; see, e.g., United States Patent Publications No. 2013-0295121; 2010-0174053 and 2009-0060910; European Patent Publication No. EP 2714079; EP 2601216; EP 2376109; EP 2158221 and PCT Publications No. WO 2012/162068; WO 2012/018687; WO 2010/080538; and Sloan, D. D. et al. (2015) "*Targeting HIV Reservoir in Infected CD4 T Cells by Dual-Affinity Retargeting Molecules (DARTs) that Bind HIV Envelope and Recruit Cytotoxic T Cells*," PLoS Pathog. 11(11):e1005233. doi: 10.1371/journal.ppat.1005233; Al Hussaini, M. et al. (2015) "*Targeting CD123 In AML Using A T-Cell Directed Dual-Affinity Re-Targeting (DART®) Platform*," Blood pii: blood-2014-05-575704; Chichili, G. R. et al. (2015) "*A CD3×CD123 Bispecific DART For Redirecting Host T Cells To Myelogenous Leukemia: Preclinical Activity And Safety In Nonhuman Primates*," Sci. Transl. Med. 7(289):289ra82; Moore, P. A. et al. (2011) "*Application Of Dual Affinity Retargeting Molecules To Achieve Optimal Redirected T-Cell Killing Of B-Cell Lymphoma*," Blood 117(17):4542-4551; Veri, M. C. et al. (2010) "*Therapeutic Control Of B Cell Activation Via Recruitment Of Fcgamma Receptor IIb (CD32B) Inhibitory Function With A Novel Bispecific Antibody Scaffold*," Arthritis Rheum. 62(7):1933-1943; Johnson, S. et al. (2010) "*Effector Cell Recruitment With Novel Fv-Based Dual-Affinity Re-Targeting Protein Leads To Potent Tumor Cytolysis And in vivo B-Cell Depletion*," J. Mol. Biol. 399(3):436-449). Such diabodies comprise two or more covalently complexed polypeptides and involve engineering one or more cysteine residues into each of the employed polypeptide species that permit disulfide bonds to form and thereby covalently bond two polypeptide chains. For example, the addition of a cysteine residue to the C-terminus of such constructs has been shown to allow disulfide bonding between the polypeptide chains, stabilizing the resulting heterodimer without interfering with the binding characteristics of the bivalent molecule.

Figure 1:
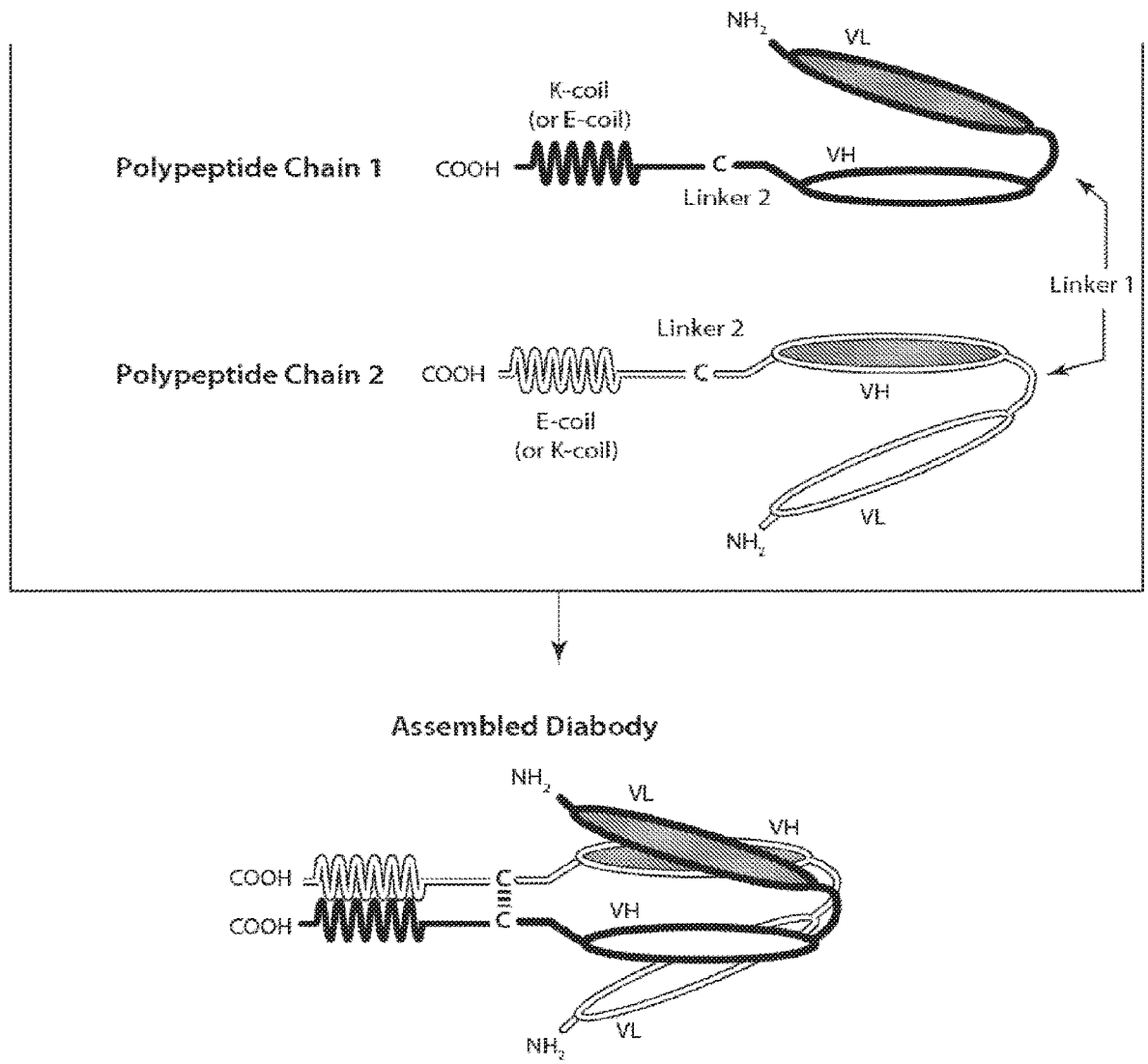
FIG. 1 provides a schematic of a representative covalently bonded diabody having two epitope-binding sites composed of two polypeptide chains, each having an E-coil or K-coil Heterodimer-Promoting Domain. A cysteine residue may be present in a linker and/or in the Heterodimer-Promoting Domain as shown in FIG. 3B. VL and VH Domains that recognize the same epitope are shown using the same shading or fill pattern.

Each of the two polypeptides of the simplest bispecific DART® diabody comprises three domains. The first polypeptide comprises (in the N-terminal to C-terminal direction): (i) a First Domain that comprises a binding region of a Light Chain Variable Domain of a first immunoglobulin (VL1), (ii) a Second Domain that comprises a binding region of a Heavy Chain Variable Domain of a second immunoglobulin (VH2), and (iii) a Third Domain that contains a cysteine residue (or a cysteine-containing domain) and a Heterodimer-Promoting Domain that serves to promote heterodimerization with the second polypeptide of the diabody and to covalently bond the diabody's first and second polypeptides to one another. The second polypeptide contains (in the N-terminal to C-terminal direction): (i) a First Domain that comprises a binding region of a Light Chain Variable Domain of the second immunoglobulin (VL2), (ii) a Second Domain that comprises a binding region of a Heavy Chain Variable Domain of the first immunoglobulin (VH1), and (iii) a Third Domain that contains a cysteine residue (or a cysteine-containing domain) and a complementary Heterodimer-Promoting Domain that complexes with the Heterodimer-Promoting Domain of the first polypeptide chain in order to promote heterodimerization with the first polypeptide chain. The cysteine residue (or a cysteine-containing domain) of the third domain of the second polypeptide chain serves to promote the covalent bonding of the second polypeptide chain to the first polypeptide chain of the diabody. Such molecules are stable, potent and have the ability to simultaneously bind two or more antigens. In one embodiment, the Third Domains of the first and second polypeptides each contain a cysteine residue, which serves to bind the polypeptides together via a disulfide bond. FIG. 1 provides a schematic of such a diabody, which utilizes E-coil/K-coil Heterodimer-Promoting domains and a cysteine containing linker for covalent bonding. As provided in FIG. 2 and FIGS. 3A-3C, one or both of the polypeptides may additionally possesses the sequence of a CH2-CH3 Domain, such that complexing between the two diabody polypeptides forms an Fc Region that is capable of binding to the Fc receptor of cells (such as B lymphocytes, dendritic cells, natural killer cells, macrophages, neutrophils, eosinophils, basophils and mast cells). As provided in more detail below, the CH2 and/or CH3 Domains of such polypeptide chains need not be identical in sequence, and advantageously are modified to foster complexing between the two polypeptide chains.

Figure 3A:
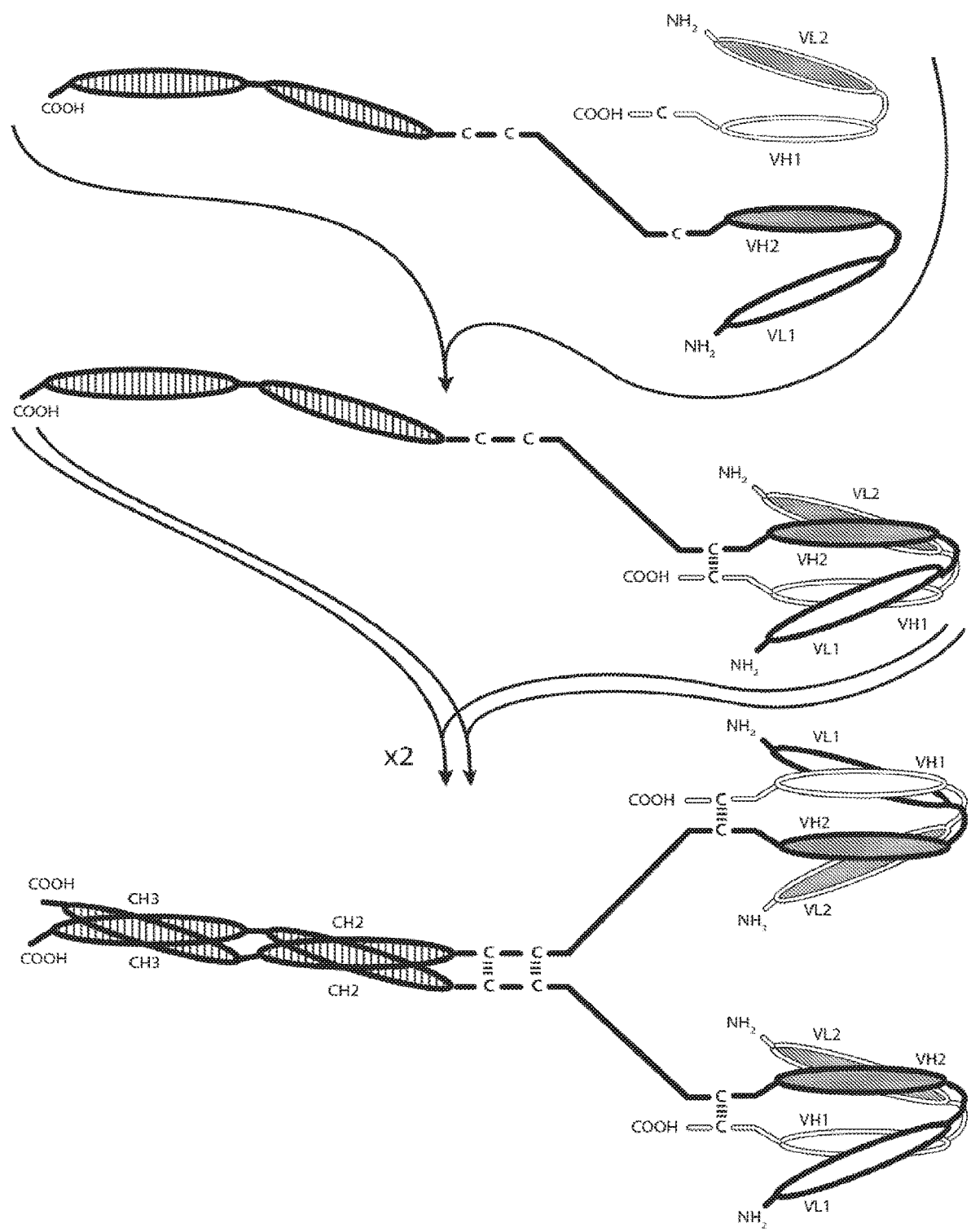
FIGS. 3A-3C provide schematics showing representative tetravalent diabodies having four epitope-binding sites composed of two pairs of polypeptide chains (i.e., four polypeptide chains in all). One polypeptide of each pair possesses a CH2 and CH3 Domain, such that the associated chains form all or part of an Fc Region. VL and VH Domains that recognize the same epitope are shown using the same shading or fill pattern. The two pairs of polypeptide chains may be same. In such embodiments wherein the VL and VH Domains recognize different epitopes (as shown in FIGS. 3A-3C), the resulting molecule possesses four epitope-binding sites and is bispecific and bivalent with respect to each bound epitope. In such embodiments wherein the VL and VH Domains recognize the same epitope (e.g., the same VL Domain CDRs and the same VH Domain CDRs are used on both chains), the resulting molecule possesses four epitope-binding sites and is monospecific and tetravalent with respect to a single epitope. Alternatively, the two pairs of polypeptides may be different. In such embodiments wherein the VL and VH Domains of each pair of polypeptides recognize different epitopes (as shown in FIGS. 3A-3C), the resulting molecule possesses four epitope-binding sites and is tetraspecific and monovalent with respect to each bound epitope.
Figure 3B:
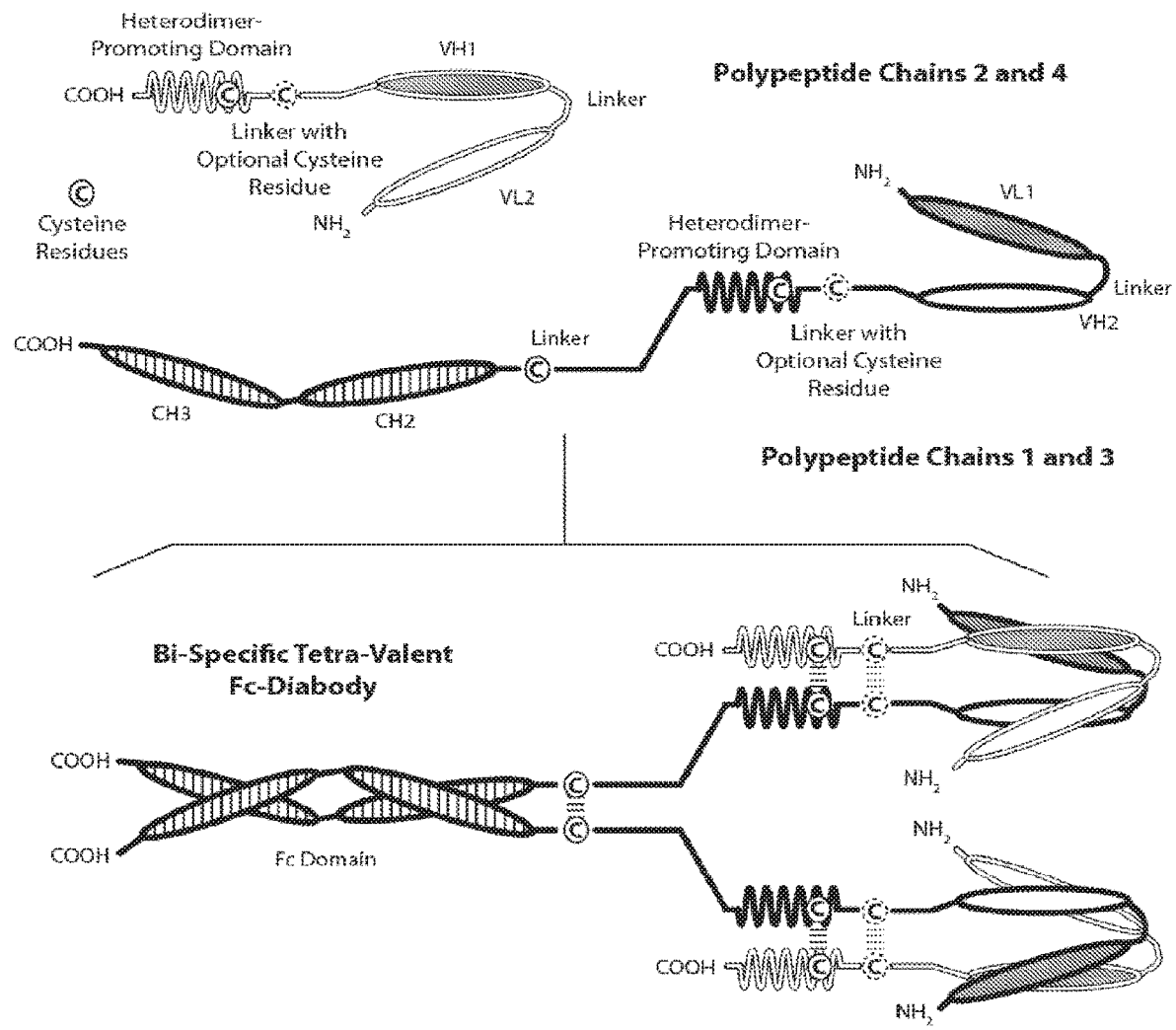
Figure 3C:
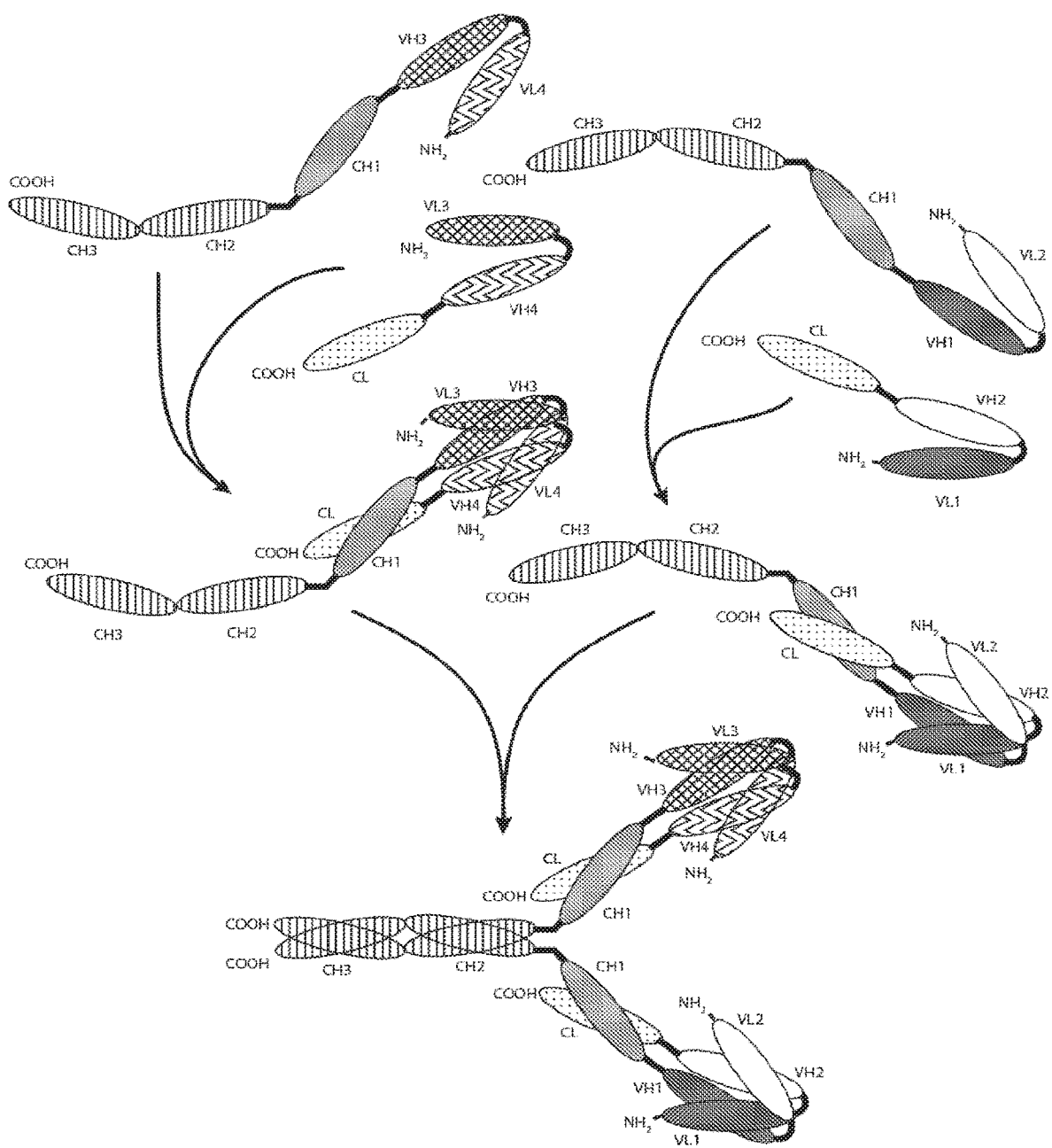

Many variations of such molecules have been described (see, e.g., United States Patent Publications No. 2015/0175697; 2014/0255407; 2014/0099318; 2013/0295121; 2010/0174053 and 2009/0060910; European Patent Publication No. EP 2714079; EP 2601216; EP 2376109; EP 2158221 and PCT Publications No. WO 2012/162068; WO 2012/018687; WO 2010/080538). These Fc Region-containing DART® diabodies may comprise two pairs of polypeptide chains. The first polypeptide chain comprises (in the N-terminal to C-terminal direction): (i) a First Domain that comprises a binding region of a Light Chain Variable Domain of a first immunoglobulin (VL1), (ii) a Second Domain that comprises a binding region of a Heavy Chain Variable Domain of a second immunoglobulin (VH2), (iii) a Third Domain that contains a cysteine residue (or a cysteine-containing domain) and a serves to promote heterodimerization with the second polypeptide of the diabody and to covalently bond the diabody's first and second polypeptides to one another, and (iv) a CH2-CH3 Domain. The second polypeptide contains (in the N-terminal to C-terminal direction): (i) a First Domain that comprises a binding region of a Light Chain Variable Domain of the second immunoglobulin (VL2), (ii) a Second Domain that comprises a binding region of a Heavy Chain Variable Domain of the first immunoglobulin (VH1), and (iii)) a Third Domain that contains a cysteine residue (or a cysteine-containing domain) and a Heterodimer-Promoting Domain that promotes heterodimerization with the first polypeptide chain. Here two first polypeptides complex with each other to form an Fc Region. FIGS. 3A-3C provide schematics of three variations of such diabodies utilizing different Heterodimer-Promoting Domains.

Figure 4A:
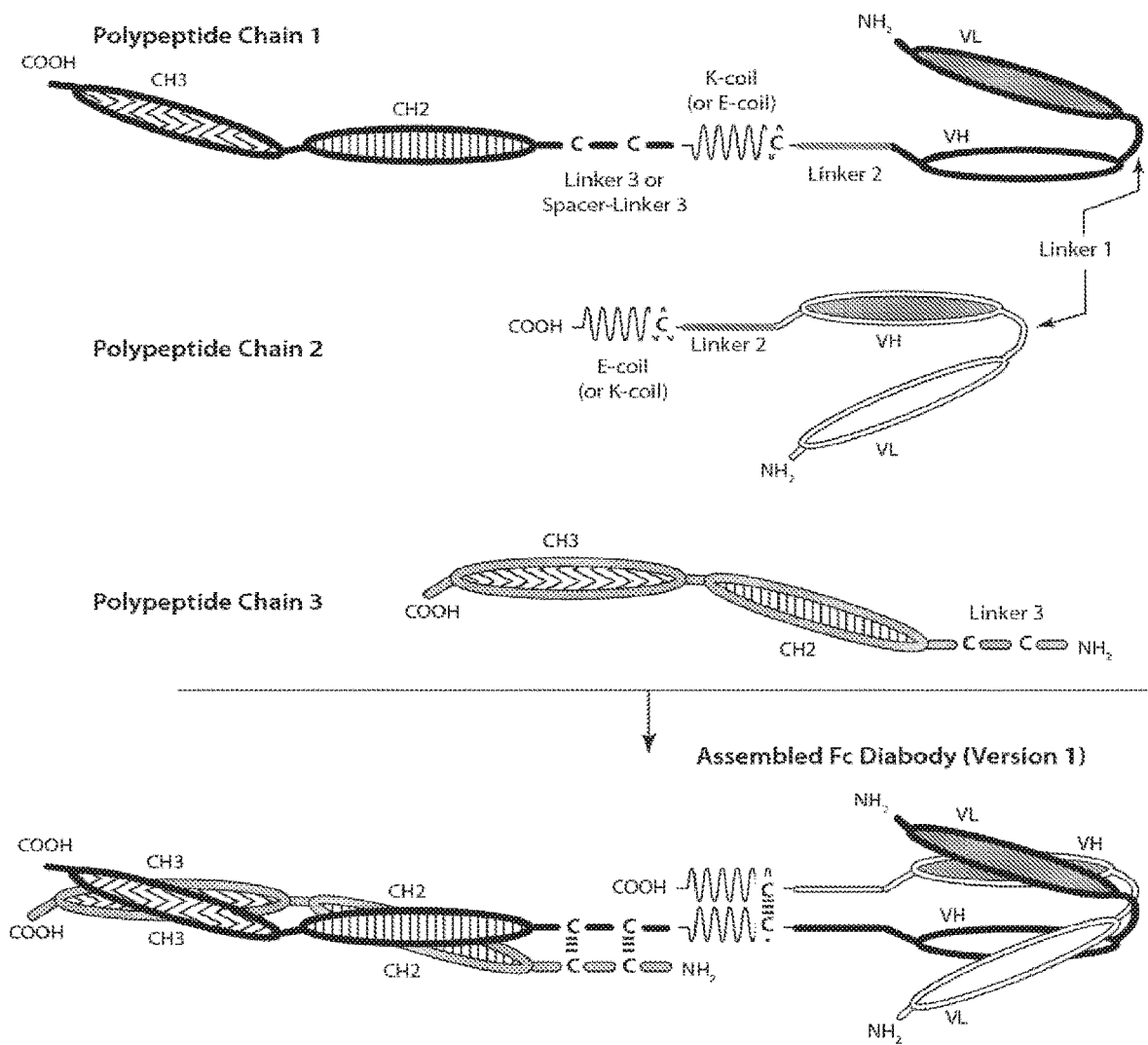
FIGS. 4A and 4B provide schematics of a representative covalently bonded diabody molecule having two epitope-binding sites composed of three polypeptide chains. Two of the polypeptide chains possess a CH2 and CH3 Domain, such that the associated chains form all or part of an Fc Region. The polypeptide chains comprising the VL and VH Domain further comprise a Heterodimer-Promoting Domain. VL and VH Domains that recognize the same epitope are shown using the same shading or fill pattern.
Figure 4B:
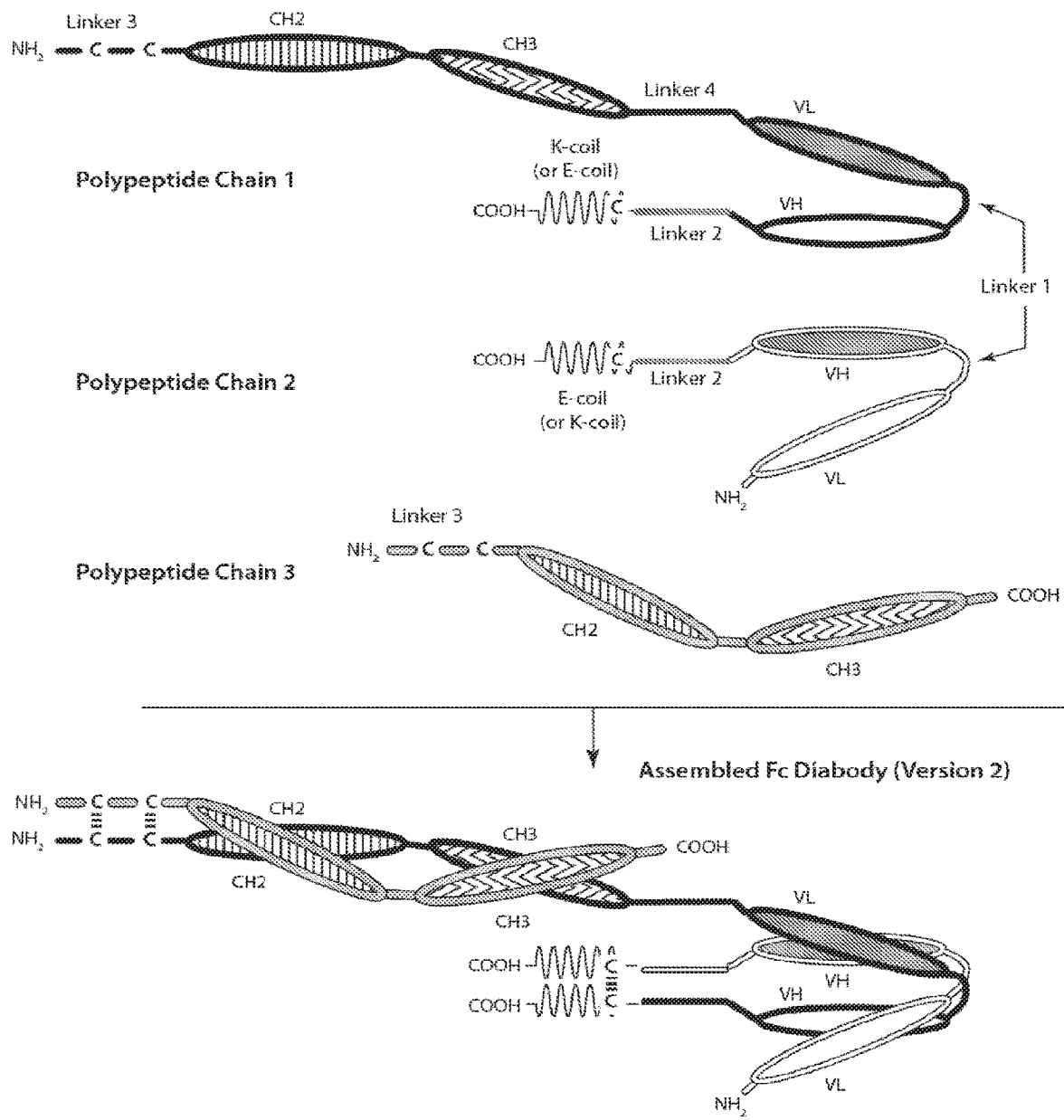

Other Fc-Region-containing DART® diabodies may comprise three polypeptide chains. The first polypeptide of such DART® diabodies contains three domains: (i) a VL1-containing Domain, (ii) a VH2-containing Domain and (iii) a Domain containing a CH2-CH3 sequence. The second polypeptide of such DART® diabodies contains: (i) a VL2-containing Domain, (ii) a VH1-containing Domain and (iii) a Domain that promotes heterodimerization and covalent bonding with the diabody's first polypeptide chain. The third polypeptide of such DART® diabodies comprises a CH2-CH3 sequence. Thus, the first and second polypeptide chains of such DART® diabodies associate together to form a VL1/VH1 binding site that is capable of binding to the epitope, as well as a VL2/VH2 binding site that is capable of binding to the second epitope. Such more complex DART® molecules also possess cysteine-containing domains which function to form a covalently bonded complex. Thus, the first and second polypeptides are bonded to one another through a disulfide bond involving cysteine residues in their respective Third Domains. Notably, the first and third polypeptide chains complex with one another to form an Fc Region that is stabilized via a disulfide bond. FIGS. 4A-4B provide schematics of such diabodies comprising three polypeptide chains.

Figure 5:
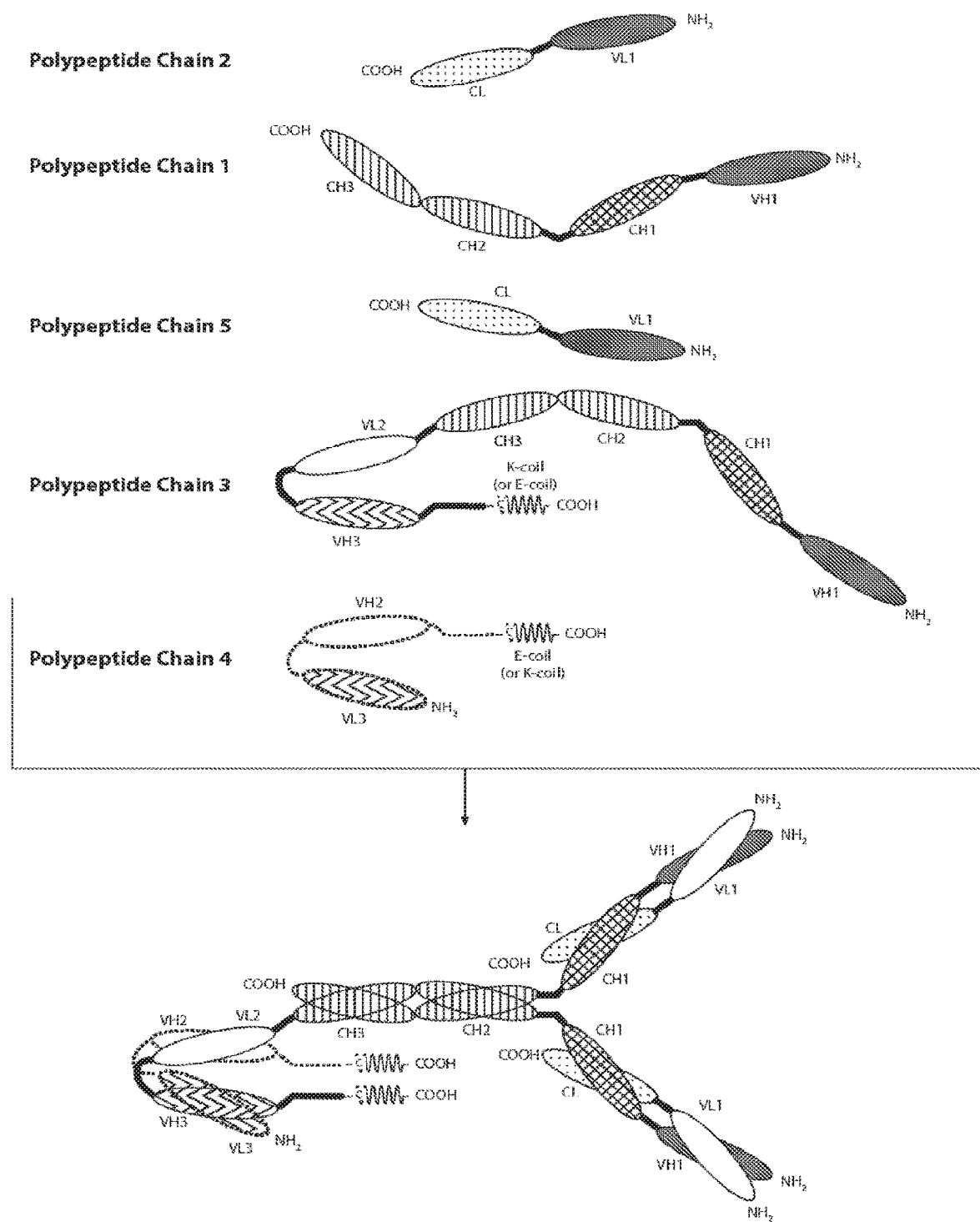
FIG. 5 provides the schematics of a representative covalently bonded diabody molecule having four epitope-binding sites composed of five polypeptide chains. Two of the polypeptide chains possess a CH2 and CH3 Domain, such that the associated chains form an Fc Region that comprises all or part of an Fc Region. The polypeptide chains comprising the linked VL and VH Domains further comprise a Heterodimer-Promoting Domain. VL and VH Domains that recognize the same epitope are shown using the same shading or fill pattern.

Still other Fc-Region-containing DART® diabodies may comprise five polypeptide chains which may comprise the binding regions from the Light and Heavy Chain Variable Domains of up to three different immunoglobulins (referred to as VL1/VH1, VL2/VH2 and VL3/VH3). For example, the first polypeptide chain of such diabodies may contain: (i) a VH1-containing domain, (ii) a CH1-containing domain, and (iii) a Domain containing a CH2-CH3 sequence. The second and fifth polypeptide chains of such diabodies may contain: (i) a VL1-containing domain, and (ii) a CL-containing domain. The third polypeptide chain of such diabodies may contain: (i) a VH1-containing domain, (ii) a CH1-containing domain, (iii) a Domain containing a CH2-CH3 sequence, (iv) a VL2-containing Domain, (v) a VH3-containing Domain and (vi) a Heterodimer-Promoting Domain, where the Heterodimer-Promoting Domains promote the dimerization of the third chain with the fourth chain. The fourth polypeptide of such diabodies may contain: (i) a VL3-containing Domain, (ii) a VH2-containing Domain and (iii) a Domain that promotes heterodimerization and covalent bonding with the diabody's third polypeptide chain. Here the first and third polypeptides complex with each other to form an Fc Region. Such more complex DART® molecules also possess cysteine-containing domains which function to form a covalently bonded complex, such that each polypeptide chain is bonded to at least one addition polypeptide chain through a disulfide bond involving cysteine residues. Preferably, such domains are ordered in the N-terminal to C-terminal direction. FIG. 5 provides schematics of such diabodies comprising five polypeptide chains.

Alternative constructs are known in the art for applications where a tetravalent molecule is desirable but an Fc is not required including, but not limited to, tetravalent tandem antibodies, also referred to as "TandAbs" (see, e.g. United States Patent Publications Nos. 2005-0079170, 2007-0031436, 2010-0099853, 2011-020667 2013-0189263; European Patent Publication Nos. EP 1078004, EP 2371866, EP 2361936 and EP 1293514; PCT Publications Nos. WO 1999/057150, WO 2003/025018, and WO 2013/013700) which are formed by the homo-dimerization of two identical chains each possessing a VH1, VL2, VH2, and VL2 Domain.

Recently, trivalent structures incorporating two diabody-type binding domains and one non-diabody-type domain and an Fc Region have been described (see, e.g., PCT Application No: PCT/US15/33076, titled "Tri-Specific Binding Molecules and Methods of Use Thereof," filed May 29, 2015; and PCT/US15/33081, titled "Tri-Specific Binding Molecules That Specifically Bind to Multiple Cancer Antigens and Methods of Use Thereof," filed May 29, 2015). Such trivalent molecules may be utilized to generate monospecific, bispecific or trispecific molecules. FIGS. 6A-6F provide schematics of such trivalent molecules comprising 3 or 4 polypeptide chains.

IV. The Anti-Human PD-1-Binding Molecules of the Present Invention

The preferred PD-1-binding molecules of the present invention include antibodies, diabodies, BiTEs, etc. and are capable of binding to a continuous or discontinuous (e.g., conformational) portion (epitope) of human PD-1 (CD279). The PD-1-binding molecules of the present invention will preferably also exhibit the ability to bind to PD-1 molecules of one or more non-human species, in particular, primate species (and especially a primate species, such as cynomolgus monkey). A representative human PD-1 polypeptide (NCBI Sequence NP 005009.2; including a 20 amino acid residue signal sequence (shown underlined) and the 268 amino acid residue mature protein) has the amino acid sequence (SEQ ID NO:68):

```
MQIPQAPWPV VWAVLQLGWR PGWFLDSPDR PWNPPTFSPA

LLVVTEGDNA TFTCSFSNTS ESFVLNWYRM SPSNQTDKLA

AFPEDRSQPG QDCRFRVTQL PNGRDFHMSV VRARRNDSGT

YLCGAISLAP KAQIKESLRA ELRVTERRAE VPTAHPSPSP

RPAGQFQTLV VGVVGGLLGS LVLLVWVLAV ICSRAARGTI

GARRTGQPLK EDPSAVPVFS VDYGELDFQW REKTPEPPVP

CVPEQTEYAT IVFPSGMGTS SPARRGSADG PRSAQPLRPE

DGHCSWPL
```

In certain embodiments the anti-human PD-1-binding molecules of the invention are characterized by any (one or more) of the following criteria:
  (1) specifically binds human PD-1 as endogenously expressed on the surface of a stimulated human T-cell;
  (2) specifically binds human PD-1 with an equilibrium binding constant ($K_D$) of 40 nM or less;

(3) specifically binds human PD-1 with an equilibrium binding constant ($K_D$) of 5 nM or less;
(4) specifically binds human PD-1 with an on rate ($k_a$) of $1.5 \times 10^4$ M$^{-1}$ min$^{-1}$ or more;
(5) specifically binds human PD-1 with an on rate ($k_a$) of $90.0 \times 10^4$ M$^{-1}$ min$^{-1}$ or more;
(6) specifically binds human PD-1 with an off rate ($k_d$) of $7 \times 10^{-4}$ min$^{-1}$ or less;
(7) specifically binds human PD-1 with an off rate ($k_d$) of $2 \times 10^{-4}$ min$^{-1}$ or less;
(8) specifically binds non-human primate PD-1 (e.g., PD-1 of cynomolgus monkey);
(9) inhibits (i.e., blocks or interferes with) the binding/the inhibitory activity) of PD-1 ligand (PD-L1/PD-L2) to PD-1;
(10) stimulates an immune response; and/or
(11) synergizes with an anti-human LAG-3 antibody to stimulate an antigen specific T-cell response.

As used here the term "antigen specific T-cell response" refers to responses by a T-cell that result from stimulation of the T-cell with the antigen for which the T-cell is specific. Non-limiting examples of responses by a T-cell upon antigen specific stimulation include proliferation and cytokine production (e.g., TNF-α, IFN-γ production). The ability of a molecule to stimulate an antigen specific T-cell response may be determined, for example, using the *Staphylococcus aureus* Enterotoxin type B antigen ("SEB")-stimulated PBMC assay described herein.

The preferred anti-human PD-1-binding molecules of the present invention possess the VH and/or VL Domains of murine anti-human PD-1 monoclonal antibodies "PD-1 mAb 1," "PD-1 mAb 2," "PD-1 mAb 3," "PD-1 mAb 4," "PD-1 mAb 5," "PD-1 mAb 6," "PD-1 mAb 7," "PD-1 mAb 8," "PD-1 mAb 9," "PD-1 mAb 10," "PD-1 mAb 11," "PD-1 mAb 12," "PD-1 mAb 13," "PD-1 mAb 14," or "PD-1 mAb 15," and more preferably possess 1, 2 or all 3 of the $CDR_H$s of the VH Domain and/or 1, 2 or all 3 of the $CDR_L$s of the VL Domain of such anti-human PD-1 monoclonal antibodies. Such preferred anti-human PD-1-binding molecules include bispecific (or multispecific) antibodies, chimeric or humanized antibodies, BiTes, diabodies, etc, and such binding molecules having variant Fc Regions.

The invention particularly relates to PD-1-binding molecules comprising a PD-1 binding domain that possess:
(A) (1) the three $CDR_H$s of the VH Domain of PD-1mAb 1;
    (2) the three $CDR_L$s of the VL Domain of PD-1 mAb 1;
    (3) the three $CDR_H$s of the VH Domain of PD-1 mAb 1 and the three $CDR_L$s of the VL Domain of PD-1 mAb 1;
    (4) the VH Domain of hPD-1 mAb 1 VH1;
    (5) the VL Domain of hPD-1 mAb 1 VL1;
    (6) the VH and VL Domains of hPD-1 mAb 1;
(B) (1) the three $CDR_H$s of the VH Domain of PD-1 mAb 2;
    (2) the three $CDR_L$s of the VL Domain of the PD-1 mAb 2;
    (3) the three $CDR_H$s of the VH Domain of PD-1 mAb 2 and the three $CDR_L$s of the VL Domain of PD-1 mAb 2;
    (4) the VH Domain of hPD-1 mAb 2 VH1;
    (5) the VL Domain of hPD-1 mAb 2 VL1;
    (6) the VH and VL Domains of hPD-1 mAb 2;
(C) (1) the three $CDR_H$s of the VH Domain of PD-1 mAb 3;
    (2) the three $CDR_L$s of the VL Domain of PD-1 mAb 3;
    (3) the three $CDR_H$s of the VH Domain of PD-1 mAb 3 and the three $CDR_L$s of the VL Domain of PD-1 mAb 3;
(D) (1) the three $CDR_H$s of the VH Domain of PD-1 mAb 4;
    (2) the three $CDR_L$s of the VL Domain of PD-1 mAb 4;
    (3) the three $CDR_H$s of the VH Domain of PD-1 mAb 4 and the three $CDR_L$s of the VL Domain of PD-1 mAb 4;
(E) (1) the three $CDR_H$s of the VH Domain of PD-1 mAb 5;
    (2) the three $CDR_L$s of the VL Domain of PD-1 mAb 5;
    (3) the three $CDR_H$s of the VH Domain of PD-1 mAb 5 and the three $CDR_L$s of the VL Domain of PD-1 mAb 5;
(F) (1) the three $CDR_H$s of the VH Domain of PD-1 mAb 6;
    (2) the three $CDR_L$s of the VL Domain of PD-1 mAb 6;
    (3) the three $CDR_H$s of the VH Domain of PD-1 mAb 6 and the three $CDR_L$s of the VL Domain of PD-1 mAb 6;
(G) (1) the three $CDR_H$s of the VH Domain of PD-1 mAb 7;
    (2) the three $CDR_L$s of the VL Domain of PD-1 mAb 7, or hPD-1 mAb 7 VL2, or hPD-1 mAb 7 VL3;
    (3) the three $CDR_H$s of the VH Domain of PD-1 mAb 7 and the three $CDR_L$s of the VL Domain of PD-1 mAb 7, or hPD-1 mAb 7 VL2, hPD-1 mAb 7 VL3;
    (4) the VH Domain of hPD-1 mAb 7 VH1, or hPD-1 mAb 7 VH2;
    (5) the VL Domain of hPD-1 mAb 7 VL1, or hPD-1 mAb 7 VL2, or hPD-1 mAb 7 VL 3;
    (6) the VH and VL Domains of the hPD-1 mAb 7(1.1), or hPD-1 mAb 7(1.2), or hPD-1 mAb 7(1.3), or hPD-1 mAb 7(2.1), or hPD-1 mAb 7(2.2), or hPD-1 mAb 7(2.3);
(H) (1) the three $CDR_H$s of the VH Domain of PD-1 mAb 8;
    (2) the three $CDR_L$s of the VL Domain of PD-1 mAb 8;
    (3) the three $CDR_H$s of the VH Domain of PD-1 mAb 8 and the three $CDR_L$s of the VL Domain of PD-1 mAb 8;
(I) (1) the three $CDR_H$s of the VH Domain of PD-1 mAb 9, or hPD-1 mAb 9 VH2;
    (2) the three $CDR_L$s of the VL Domain of PD-1 mAb 9, or hPD-1 mAb 9 VL2;
    (3) the three $CDR_H$s of the VH Domain of PD-1 mAb 9, or hPD-1 mAb 9 VH2 and the three $CDR_L$s of the VL Domain of PD-1 mAb 9, or hPD-1 mAb 9 VL2;
    (4) the VH Domain of hPD-1 mAb 9 VH1, or hPD-1 mAb 9 VH2;
    (5) the VL Domain of hPD-1 mAb 9 VL1, or hPD-1 mAb 9 VL2;
    (6) the VH and VL Domains of the hPD-1 mAb 9(1.1), or hPD-1 mAb 9(1.2), or hPD-1 mAb 9(2.1), or hPD-1 mAb 9(2.2);

(J) (1) the three CDR$_H$s of the VH Domain of PD-1 mAb 10;
(2) the three CDR$_L$s of the VL Domain of PD-1 mAb 10;
(3) the three CDR$_H$s of the VH Domain of PD-1 mAb 10 and the three CDR$_L$s of the VL Domain of PD-1 mAb 10;
(K) (1) the three CDR$_H$s of the VH Domain of PD-1 mAb 11;
(2) the three CDR$_L$s of the VL Domain of PD-1 mAb 11;
(3) the three CDR$_H$s of the VH Domain of PD-1 mAb 11 and the three CDR$_L$s of the VL Domain of PD-1 mAb 11;
(L) (1) the three CDR$_H$s of the VH Domain of PD-1 mAb 12;
(2) the three CDR$_L$s of the VL Domain of the PD-1 mAb 12;
(3) the three CDR$_H$s of the VH Domain of the PD-1 mAb 12 and the three CDR$_L$s of the VL Domain of PD-1 mAb 12;
(M) (1) the three CDR$_H$s of the VH Domain of PD-1 mAb 13;
(2) the three CDR$_L$s of the VL Domain of PD-1 mAb 13;
(3) the three CDR$_H$s of the VH Domain of PD-1 mAb 13 and the three CDR$_L$s of the VL Domain of PD-1 mAb 13;
(N) (1) the three CDR$_H$s of the VH Domain of PD-1 mAb 14;
(2) the three CDR$_L$s of the VL Domain of the PD-1 mAb 14;
(3) the three CDR$_H$s of the VH Domain of the PD-1 mAb 14 and the three CDR$_L$s of the VL Domain of PD-1 mAb 14;
(O) (1) the three CDR$_H$s of the VH Domain of PD-1 mAb 15;
(2) the three CDR$_L$s of the VL Domain of PD-1 mAb 15;
(3) the three CDR$_H$s of the VH Domain of PD-1 mAb 15 and the three CDR$_L$s of the VL Domain of PD-1 mAb 15;
(4) the VH Domain of hPD-1 mAb 15 VH1;
(5) the VL Domain of hPD-1 mAb 15 VL1;
(6) the VH and VL Domains of hPD-1 mAb 15;
or
that binds, or competes for binding with, the same epitope as PD-1 mAb 1, PD-1 mAb 2, PD-1 mAb 3, PD-1 mAb 4, PD-1 mAb 5, PD-1 mAb 6, PD-1 mAb 7, PD-1 mAb 8, PD-1 mAb 9, PD-1 mAb 10, PD-1 mAb 11, PD-1 mAb 12, PD-1 mAb 13, PD-1 mAb 14, or PD-1 mAb 15.

A. The Anti-Human PD-1 Antibody PD-1 mAb 1

1. Murine Anti-Human PD-1 Antibody PD-1 mAb 1

The amino acid sequence of the VH Domain of PD-1 mAb 1 (SEQ ID NO:69) is shown below (CDR$_H$ residues are shown underlined).

```
DVQLQESGPG RVKPSQSLSL TCTVTGFSIT NDYAWNWIRQ

FPGNKLEWMG HITYSGSTSY NPSLKSRISI TRDTSKNHFF

LQLSSVTPED TATYYCARDY GSGYPYTLDY WGQGTSVTVS S

CDRH1 of PD-1 mAb 1 (SEQ ID NO: 71):
NDYAWN

CDRH2 of PD-1 mAb 1 (SEQ ID NO: 72):
HITYSGSTSYNPSLKS

CDRH3 of PD-1 mAb 1 (SEQ ID NO: 73):
DYGSGYPYTLDY
```

An exemplary polynucleotide that encodes the VH Domain of PD-1 mAb 1 is SEQ ID NO:70 (nucleotides encoding the CDR$_H$ residues are shown underlined):

```
cagatccagt gatgtgcagc ttcaggagtc gggacctggc cgggtgaaac cttctcagtc tctgtccctc acctgcactg tcactggctt ctcaatcacc aatgattatg cctggaactg gatccgacag tttccaggaa acaaactgga gtggatgggc cacataacct acagtggcag cactagctac aacccatctc tcaaaagtcg aatctctatc actcgggaca catccaagaa ccacttcttc ctgcagttga gttctgtgac tcctgaggac acagccacat attactgtgc aagagattac ggtagtggct acccctatac tttggactac tggggtcaag gtacctcagt caccgtctcc tcc
```

The amino acid sequence of the VL Domain of PD-1 mAb 1 (SEQ ID NO:74) is shown below (CDR$_L$ residues are shown underlined):

```
QIVLTQSPAL MSASPGEKVT MTCSATSIVS YVYWYQQKPG

SSPQPWIYLT SNLASGVPAR FSGSGSGTSY SLTISSMEAE

DAATYYCQQW SDNPYTFGGG TKLEIK

CDRL1 of PD-1 mAb 1 (SEQ ID NO: 76):
SATSIVSYVY

CDRL2 of PD-1 mAb 1 (SEQ ID NO: 77):
LTSNLAS

CDRL3 of PD-1 mAb 1 (SEQ ID NO: 78):
QQWSDNPYT
```

An exemplary polynucleotide that encodes the VL Domain of PD-1 mAb 1 is SEQ ID NO:75 (nucleotides encoding the CDR$_L$ residues are shown underlined):

```
caaattgttc tcacccagtc tccagcactc atgtctgcat ctccagggga gaaggtcacc atgacctgca gtgccacctc aattgtaagt tacgtttact ggtaccagca gaagcctgga tcctcccccc aaccctggat ttatctcaca tccaacctgg cttctggagt ccctgctcgc ttcagtggca gtgggtctgg gacctcttac tctctcacaa tcagcagcat ggaggctgaa gatgctgcca cttattactg ccagcagtgg agtgataacc cgtacacgtt cggaggggggg accaagctgg aaataaaa
```

2. Humanization of the Anti-Human PD-1 Antibody PD-1 mAb 1 to Form "hPD-1 mAb 1"

The above-described murine anti-human PD-1 antibody PD-1 mAb 1 was humanized and further deimmunized when antigenic epitopes were identified in order to demonstrate the capability of humanizing an anti-human PD-1 antibody so as to decrease its antigenicity upon administration to a human recipient. The humanization yielded one humanized VH Domain, designated herein as "hPD-1 mAb 1 VH1," and one humanized VL Domain designated herein as "hPD-1 mAb 1 VL1." Accordingly, an antibody comprising the humanized VL Domains paired with the humanized VH Domain is referred to as "hPD-1 mAb 1."

The amino acid sequence of the VH Domain of hPD-1 mAb 1 VH1 (SEQ ID NO:79) is shown below (CDR$_H$ residues are shown underlined):

DVQLQESGPG LVKPSQTLSL TCTVSGFSIS NDYAWNWIRQ

PPGKGLEWIG HITYSGSTSY NPSLKSRLTI TRDTSKNQFV

LTMTNMDPVD TATYYCARDY GSGYPYTLDY WGQGTTVTVS S

An exemplary polynucleotide that encodes hPD-1 mAb 1 VH1 is SEQ ID NO:80 (nucleotides encoding the CDR$_H$ residues are shown underlined):

```
gacgtacagc tccaggaaag tggcccaggt ctggtgaagc catcccagac actgagcctg acttgcaccg tgagtggctt ctccatctca aatgactacg cctggaattg gattaggcag cctccggta aagggctgga gtggatcggc cacatcacat acagcggctc cacatcatat aatcccagtc tgaagagccg tcttaccatt actcgcgaca ctagtaagaa ccagtttgtt ctgaccatga ccaacatgga ccctgtggat actgcaacat actattgtgc tcgagattat ggttctggtt acccttatac actcgactac tggggacagg gaaccactgt gaccgtgagc tcc
```

The amino acid sequence of the VL Domain of hPD-1 mAb 1 VL1 (SEQ ID NO:81) is shown below (CDR$_H$ residues are shown underlined):

EIVLTQSPAT LSVSPGEKVT ITCSATSIVS YVYWYQQKPG

QAPQPLIYLT SNLASGIPAR FSGSGSGTDF TLTISSLEAE

DAATYYCQQW SDNPYTFGGG TKVEIK

An exemplary polynucleotide that encodes hPD-1 mAb 1 VL1 is SEQ ID NO:82 (nucleotides encoding the CDR$_H$ residues are shown underlined):

```
gaaatcgttc tgacccagag cccagcaacc ctgtctgtct ccccggaga aaaggtcacc attacttgct ctgctacttc tatcgtgtcc tacgtgtact ggtatcagca gaagcccggt caggctcccc agccattgat atatctgacc agcaacctgg cttctggtat cccagctcgt ttttccggta gcgggtccgg gactgatttc actttgacta tcagctctct ggaggcagaa gacgccgcca cctattattg tcaacagtgg tcagacaatc catacacttt tggcggtggc accaaagtcg aaataaag
```

B. The Anti-Human PD-1 Antibody PD-1 mAb 2
1. Murine Anti-Human PD-1 Antibody PD-1 mAb 2

The amino acid sequence of the VH Domain of PD-1 mAb 2 (SEQ ID NO:83) is shown below (CDR$_H$ residues are shown underlined).

DVQLVESGGG LVQPGGSRKL SCAASGFVFS SFGMHWVRQA

PEKGLEWVAY ISSGSMSISY ADTVKGRFTV TRDNAKNTLF

LQMTSLRSED TAIYYCASLS DYFDYWGQGT TLTVSS

CDR$_H$1 of PD-1 mAb 2 (SEQ ID NO: 85):
SFGMH

CDR$_H$2 of PD-1 mAb 2 (SEQ ID NO: 86):
YISSGSMSISYADTVKG

CDR$_H$3 of PD-1 mAb 2 (SEQ ID NO: 87):
LSDYFDY

An exemplary polynucleotide that encodes the VH Domain of PD-1 mAb 2 is SEQ ID NO:84 (nucleotides encoding the CDR$_H$ residues are shown underlined):

```
gatgtgcagc tcgtggagtc tgggggaggc ttagtgcagc ctggagggtc ccggaaactc tcctgtgcag cctctggatt cgttttcagt agctttggaa tgcactgggt tcgtcaggct ccagagaagg ggctggagtg ggtcgcatac atcagtagtg gcagtatgag catttcctat gcagacacag tgaagggccg attcaccgtc accagagaca tgccaagaa caccctgttc ctgcaaatga ccagtctaag gtctgaggac acggccattt attactgtgc atccctgagt gactactttg actactgggg ccaaggcacc actctcacag tctcctcc
```

The amino acid sequence of the VL Domain of PD-1 mAb 2 (SEQ ID NO:88) is shown below (CDR$_L$ residues are shown underlined):

DVVMSQTPLS LPVSLGDQAS ISCRSSQSLV HSTGNTYLHW

YLQKPGQSPK LLIYRVSNRF SGVPDRFSGS GSGTDFTLKI

SRVEAEDLGV FFCSQTTHVP WTFGGGTKLE IK

CDR$_L$1 of PD-1 mAb 2 (SEQ ID NO: 90):
RSSQSLVHSTGNTYLH

CDR$_L$2 of PD-1 mAb 2 (SEQ ID NO: 91):
RVSNRFS

CDR$_L$3 of PD-1 mAb 2 (SEQ ID NO: 92):
SQTTHVPWT

An exemplary polynucleotide that encodes the VL Domain of PD-1 mAb 2 is SEQ ID NO:89 (nucleotides encoding the CDR$_L$ residues are shown underlined):

```
gatgttgtga tgtcccaaac tccactctcc ctgcctgtca gtcttggaga tcaagcctcc atctcttgca gatctagtca gagccttgtt cacagtactg gaaacaccta tttacattgg tacctgcaga agccaggcca gtctccaaag ctcctgatct
```

```
ac agggtttc taaccgattt tctggggtcc ccgacaggtt cagtggcagt ggatcaggga cagatttcac actcaagatc agtagagtgg aggctgagga tctgggagtt ttttctgct ctcaaactac acatgttccg tggacgttcg gtggaggcac caagctggaa atcaaa
```

2. Humanization of the Anti-Human PD-1 Antibody PD-1 mAb 2 to Form "hPD-1 mAb 2"

The above-described murine anti-human PD-1 antibody PD-1 mAb 2 was humanized and further deimmunized when antigenic epitopes were identified in order to demonstrate the capability of humanizing an anti-human PD-1 antibody so as to decrease its antigenicity upon administration to a human recipient. The humanization yielded one humanized VH Domain, designated herein as "hPD-1 mAb 2 VH1," and one humanized VL Domains designated herein as "hPD-1 mAb 1 VL1." Accordingly, any antibody comprising the humanized VL Domains paired with the humanized VH Domain is referred to as "hPD-1 mAb 2."

The amino acid sequence of the VH Domain of hPD-1 mAb 2 VH1 (SEQ ID NO:93 is shown below (CDR$_H$ residues are shown underlined):

```
EVQLVESGGG LVQPGGSLRL SCAASGFVFS SFGMHWVRQA

PGKGLEWVAY ISSGSMSISY ADTVKGRFTI SRDNAKNTLY

LQMNSLRTED TALYYCASLS DYFDYWGQGT TVTVSS
```

An exemplary polynucleotide that encodes hPD-1 mAb 2 VH1 is SEQ ID NO:94 (nucleotides encoding the CDR$_H$ residues are shown underlined):

```
gaagtgcaat tggttgagag tggtggtggc ctggtgcagc caggtggaag tctgcggttg tcctgtgcag caagcggatt tgtgttcagc tcttttggga tgcattgggt gcgccaggct cccggcaagg gtctcgagtg ggtagcatac atctccagcg ggtccatgtc tattagttat gccgacacag tgaaaggcag gtttactatc tcccgtgaca atgcaaaaaa cacactgtac ctgcaaatga atagcctgcg caccgaggac accgccttgt actactgcgc ttccctgtct gattacttcg actactgggg tcagggcaca actgtgacag tttcttcc
```

The amino acid sequence of the VL Domain of hPD-1 mAb 2 VL1 (SEQ ID NO:95 is shown below (CDR$_H$ residues are shown underlined):

```
DVVMTQSPLS LPVTLGQPAS ISCRSSQSLV HSTGNTYLHW

YLQKPGQSPQ LLIYRVSNRF SGVPDRFSGS GSGTDFTLKI

SRVEAEDVGV YYCSQTTHVP WTFGQGTKLE IK
```

An exemplary polynucleotide that encodes hPD-1 mAb 2 VL1 is SEQ ID NO:96 (nucleotides encoding the CDR$_H$ residues are shown underlined):

```
gacgttgtga tgacacagtc accactgagt ctgccagtta ccctgggcca gccagccagt atttcttgtc ggagttcaca gagtctggta cattccacag gaaatacata tctccattgg tacctgcaaa aaccagggca gagcccccag ctgctgattt at agagtgtc taatcgattt tctggcgtgc cagatcggtt cagcggcagc gggtctggca ctgatttcac actgaaaatc tctagggtgg aggcagagga cgtaggcgtt tactactgta gtcagaccac ccatgtaccc tggactttg gccaaggtac taagctggaa atcaag
```

C. Murine Anti-Human PD-1 Antibody PD-1 mAb 3

The amino acid sequence of the VH Domain of PD-1 mAb 3 (SEQ ID NO:97) is shown below (CDR$_H$ residues are shown underlined).

```
QVQLQQSGAE LVRPGASVTL SCKASGYTFT DYVMHWVKQT

PVHGLEWIGT IDPETGGTAY NQKFKGKAIL TADKSSNTAY

MELRSLTSED SAVYYFTREK ITTIVEGTYW YFDVWGTGTT

VTVSS
```

CDR$_H$1 of PD-1 mAb 3 (SEQ ID NO: 99):
DYVMH

CDR$_H$2 of PD-1 mAb 3 (SEQ ID NO: 100):
TIDPETGGTAYNQKFKG

CDR$_H$3 of PD-1 mAb 3 (SEQ ID NO: 101):
EKITTIVEGTYWYFDV

An exemplary polynucleotide that encodes the VH Domain of PD-1 mAb 3 is SEQ ID NO:98 (nucleotides encoding the CDR$_H$ residues are shown underlined):

```
caggttcaac tgcaacagtc tggggctgag ctggtgaggc ctggggcttc agtgacgctg tcctgcaagg cttcgggcta cacatttact gactatgtaa tgcactgggt gaagcagaca cctgtgcatg gcctggaatg gattggaact attgatcctg aaactggtgg tactgcctac aatcagaagt tcaagggcaa ggccatactg actgcagaca gtcctccaa cacagcctac atggagctcc gcagcctgac atctgaggac tctgccgtct attactttac aagagagaag attactacga tagtagaggg gacatactgg tacttcgatg tctggggcac agggaccacg gtcaccgtct cctca
```

The amino acid sequence of the VL Domain of PD-1 mAb 3 (SEQ ID NO:102) is shown below (CDR$_L$ residues are shown underlined):

```
DVLLTQTPLS LPVSLGDQAS ISCRSSQNIV HSNGDTYLEW

YLQKPGQSPK LLIYKVSNRF SGVPDRFSGS GSGTDFTLKI

SRVEAEDLGV YYCFQGSHLP YTFGGGTKLE IK

CDR_L1 of PD-1 mAb 3 (SEQ ID NO: 104):
RSSQNIVHSNGDTYLE

CDR_L2 of PD-1 mAb 3 (SEQ ID NO: 105):
KVSNRFS

CDR_L3 of PD-1 mAb 3 (SEQ ID NO: 106):
FQGSHLPYT
```

An exemplary polynucleotide that encodes the VL Domain of PD-1 mAb 3 is SEQ ID NO:103 (nucleotides encoding the CDR$_L$ residues are shown underlined):

```
gatgttttgc tgacccaaac tccactctcc ctgcctgtca gtcttggaga tcaagcctcc atctcttgca gatctagtca gaacattgta catagtaatg gagacaccta tttggaatgg tacctgcaga accaggcca gtctccaaag ctcctgatct ataaagtttc caaccgattt tctggggtcc cagacaggtt cagtggcagt gggtcaggga cagatttac actcaaaatc agcagagtgg aggctgagga tctgggagtt tattactgct ttcaaggttc acatcttccg tacacgttcg gaggggggac caagctggaa ataaaa
```

D. Murine Anti-Human PD-1 Antibody PD-1 mAb 4

The amino acid sequence of the VH Domain of PD-1 mAb 4 (SEQ ID NO:107) is shown below (CDR$_H$ residues are shown underlined).

```
DVQLVESGGG LVQPGGSRKL SCAASGFVFS SFGMHWVRQA

PEKGLEWVAY ISSGSMSISY ADTVKGRFTV TRDNAKNTLF

LQMTSLRSED TAIYYCASLT DYFDYWGQGT TLTVSS

CDR_H1 of PD-1 mAb 4 (SEQ ID NO: 109):
SFGMH

CDR_H2 of PD-1 mAb 4 (SEQ ID NO: 110):
YISSGSMSISYADTVKG

CDR_H3 of PD-1 mAb 4 (SEQ ID NO: 111):
LTDYFDY
```

An exemplary polynucleotide that encodes the VH Domain of PD-1 mAb 4 is SEQ ID NO:108 (nucleotides encoding the CDR$_H$ residues are shown underlined):

```
gatgtgcagc tcgtggagtc tgggggaggc ttagtgcagc ctggagggtc ccggaaactc tcctgtgcag cctctggatt cgttttcagt agctttggaa tgcactgggt tcgtcaggct ccagagaagg ggctggagtg ggtcgcatat attagtagtg gcagtatgag tatttcctat gcagacacag tgaagggccg attcaccgtc accagagaca tgccaagaa caccctgttc ctgcaaatga ccagtctaag gtctgaggac acggccattt attactgtgc atccctgact gactactttg actactgggg ccaaggcacc actctcacag tctcctca
```

The amino acid sequence of the VL Domain of PD-1 mAb 4 (SEQ ID NO:112) is shown below (CDR$_L$ residues are shown underlined):

```
DVVMSQTPLS LPVSLGDQAS ISCRSSQSLV HSTGNTYFHW

YLQKPGQSPK LLIYRVSNRF SGVPDRFSGS GSGTDFTLKI

SRVEAEDLGV YFCSQTTHVP WTFGGGTKLE IK

CDR_L1 of PD-1 mAb 4 (SEQ ID NO: 114):
RSSQSLVHSTGNTYFH

CDR_L2 of PD-1 mAb 4 (SEQ ID NO: 115):
RVSNRFS

CDR_L3 of PD-1 mAb 4 (SEQ ID NO: 116):
SQTTHVPWT
```

An exemplary polynucleotide that encodes the VL Domain of PD-1 mAb 4 is SEQ ID NO:113 (nucleotides encoding the CDR$_L$ residues are shown underlined):

```
gatgttgtga tgtcccaaac tccactctcc ctgcctgtca gtcttggaga tcaagcctcc atctcctgca gatctagtca gagccttgtt cacagtactg gaaacaccta tttccattgg tacctgcaga agccaggcca gtctccaaag ctcctgatct acagggtttc taaccgattt tctggggtcc ccgacaggtt cagtggcagt ggatcaggga cagatttcac actcaagatc agcagagtgg aggctgagga tctgggagtt tatttctgct ctcaaactac acatgttccg tggacgttcg gtggaggcac caagctggaa atcaaa
```

E. Murine Anti-Human PD-1 Antibody PD-1 mAb 5

The amino acid sequence of the VH Domain of PD-1 mAb 5 (SEQ ID NO:117) is shown below (CDR$_H$ residues are shown underlined).

```
QVQLQQPGVE LVRPGASVKL SCKASGYSFT AYWMNWMKQR

PGQGLEWIGV IHPSDSETWL NQKFKDKATL TVDKSSSTAY

MQLISPTSED SAVYYCAREH YGSSPFAYWG QGTLVTVSA

CDR_H1 of PD-1 mAb 5 (SEQ ID NO: 119):
AYWMN

CDR_H2 of PD-1 mAb 5 (SEQ ID NO: 120):
VIHPSDSETWLNQKFED

CDR_H3 of PD-1 mAb 5 (SEQ ID NO: 121):
EHYGSSPFAY
```

An exemplary polynucleotide that encodes the VH Domain of PD-1 mAb 5 is SEQ ID NO:118 (nucleotides encoding the CDR$_H$ residues are shown underlined):

```
caggtccaac tgcagcagcc tggggttgaa ctggtgaggc ctggagcttc agtgaagctg tcctgcaagg cttctggcta ctccttcacc gcctactgga tgaactggat gaaacagagg cctggacaag gccttgagtg gattggcgtg attcatcctt ccgatagtga aacttggtta aatcagaagt tcaaggacaa ggccacattg actgtagaca atcctccag cacagcctac atgcaactca tcagcccgac atctgaggac tctgcggtct attactgtgc aagagagcac tacggtagta gcccgtttgc ttactggggc caagggactc tggtcactgt ctctgca
```

The amino acid sequence of the VL Domain of PD-1 mAb 5 (SEQ ID NO:122) is shown below (CDR$_L$ residues are shown underlined):

```
DIVLTQSPAS LAVSLGQRAT ISCRANESVD NYGMSFMNWF

QQKPGQPPKL LIYAASNQGS GVPARFSGSG SGTDFSLNIH

PMEEDDTAMY FCQQSKEVPY TFGGGTKLEI K
```

CDR$_L$1 of PD-1 mAb 5 (SEQ ID NO: 124):
RANESVDNYGMSFMN

CDR$_L$2 of PD-1 mAb 5 (SEQ ID NO: 125):
AASNQGS

CDR$_L$3 of PD-1 mAb 5 (SEQ ID NO: 126):
QQSKEVPYT

An exemplary polynucleotide that encodes the VL Domain of PD-1 mAb 5 is SEQ ID NO:123 (nucleotides encoding the CDR$_L$ residues are shown underlined):

```
gacattgtgc tgacccaatc tccagcttct ttggctgtgt ctctagggca gagggccacc atctcctgca gagccaacga aagtgttgat aattatggca tgagtttat gaactggttc caacagaaac caggacagcc acccaaactc ctcatctatg ctgcatccaa ccaaggatcc ggggtccctg ccaggtttag tggcagtggg tctgggacag atttcagcct caacatccat cctatggagg aggatgatac tgcaatgtat ttctgtcagc aaagtaagga ggttccgtac acgttcggag ggggaccaa gctggaaata aaa
```

F. Murine Anti-Human PD-1 Antibody PD-1 mAb 6

The amino acid sequence of the VH Domain of PD-1 mAb 6 (SEQ ID NO:127) is shown below (CDR$_H$ residues are shown underlined).

```
EVKLVESGGG LVNPGGSLKL SCAASGFTFS SYGMSWVRQT

PEKRLEWVAT ISGGGSDTYY PDSVKGRFTI SRDNAKNNLY

LQMSSLRSED TALYYCARQK ATTWFAYWGQ GTLVTVST
```

CDR$_H$1 of PD-1 mAb 6 (SEQ ID NO: 129):
SYGMS

CDR$_H$2 of PD-1 mAb 6 (SEQ ID NO: 130):
TISGGGSDTYYPDSVKG

CDR$_H$3 of PD-1 mAb 6 (SEQ ID NO: 131):
QKATTWFAY

An exemplary polynucleotide that encodes the VH Domain of PD-1 mAb 6 is SEQ ID NO:128 (nucleotides encoding the CDR$_H$ residues are shown underlined):

```
gaaatcgtac tcacccagtc acctgcaacc ctttctctga gccccggtga acgtgccact ctcagctgca gagcaagtga gagtgtggac aattacggca tgtccttcat gaactggttt cagcagaagc ctgggcagcc acctaagctg ctcatccacg ccgcctctaa ccgcggatct ggggtgcctt cacgtttttc tggatcagga agtggcactg acttcaccct tacaatcagc tctctggagc cagaggactt tgccgtctat ttctgccagc aatctaaaga ggtgccctat actttggtg gcgggaccaa ggttgagatc aaa
```

The amino acid sequence of the VL Domain of PD-1 mAb 6 (SEQ ID NO:132) is shown below (CDR$_L$ residues are shown underlined):

```
DIVLTQSPAS LAVSLGQRAT ISCRASESVD NYGISFMNWF

QQKPGQPPKL LIYPASNQGS GVPARFSGSG SGTDFSLNIH

PMEEDDAAMY FCQQSKEVPW TFGGGTKLEI K
```

CDR$_L$1 of PD-1 mAb 6 (SEQ ID NO: 134):
RASESVDNYGISFMN

CDR$_L$2 of PD-1 mAb 6 (SEQ ID NO: 135):
PASNQGS

CDR$_L$3 of PD-1 mAb 6 (SEQ ID NO: 136):
QQSKEVPWT

An exemplary polynucleotide that encodes the VL Domain of PD-1 mAb 6 is SEQ ID NO:133 (nucleotides encoding the CDR$_L$ residues are shown underlined):

```
gacattgtgc tgacccaatc tccagcttct ttggctgtgt ctctagggca gagggccacc atctcctgca gagccagcga aagtgttgat aattatggca ttagtttat gaactggttc caacagaaac caggacagcc acccaaactc ctcatctatc ctgcatccaa ccaaggatcc ggggtccctg ccaggtttag tggcagtggg tctgggacag acttcagcct caacatccat cctatggagg aggatgatgc tgcaatgtat ttctgtcagc aaagtaagga ggttccgtgg acgttcggtg gaggcaccaa gctggaaatc aaa
```

G. The Anti-Human PD-1 Antibody PD-1 mAb 7

1. Murine Anti-Human PD-1 Antibody PD-1 mAb 7

The amino acid sequence of the VH Domain of PD-1 mAb 7 (SEQ ID NO:137) is shown below (CDR$_H$ residues are shown underlined).

```
QVQLQQPGAE LVRPGASVKL SCKASGYSFT SYWMNWVKQR

PGQGLEWIGV IHPSDSETWL DQKFKDKATL TVDKSSTTAY

MQLISPTSED SAVYYCAREH YGTSPFAYWG QGTLVTVSS
```

CDR$_H$1 of PD-1 mAb 7 (SEQ ID NO: 139):
SYWMN

CDR$_H$2 of PD-1 mAb 7 (SEQ ID NO: 140):
VIHPSDSETWLDQKFED

CDR$_H$3 of PD-1 mAb 7 (SEQ ID NO: 141):
EHYGTSPFAY

An exemplary polynucleotide that encodes the VH Domain of PD-1 mAb 7 is SEQ ID NO:138 (nucleotides encoding the CDR$_H$ residues are shown underlined):

```
gaggtccaac tgcagcagcc tggggctgaa ctggtgaggc ctggagcttc agtgaagctg tcctgcaagg cttctggcta ctccttcacc agctactgga tgaactgggt gaagcagagg cctggacaag gccttgagtg gattggcgtg attcatcctt ccgatagtga aacttggtta gatcagaagt tcaaggacaa ggccacattg actgtagaca aatcctccac cacagcctac atgcaactca tcagcccgac atctgaggac tctgcggtct attactgtgc aagggagcac tacggtacta gcccgtttgc ttactggggc caaggactc tggtcactgt gtcttcc
```

The amino acid sequence of the VL Domain of PD-1 mAb 7 (SEQ ID NO:142) is shown below (CDR$_L$ residues are shown underlined):

```
DIVLTQSPAS LAVSLGQRAT ISCRANESVD NYGMSFMNWF

QQKPGQPPKL LIHAASNQGS GVPARFSGSG FGTDFSLNIH

PMEEDDAAMY FCQQSKEVPY TFGGGTKLEI K
```

CDR$_L$1 of PD-1 mAb 7 (SEQ ID NO: 144):
RANESVDNYGMSFMN

CDR$_L$2 of PD-1 mAb 7 (SEQ ID NO: 145):
AASNQGS

CDR$_L$3 of PD-1 mAb 7 (SEQ ID NO: 146):
QQSKEVPYT

An exemplary polynucleotide that encodes the VL Domain of PD-1 mAb 7 is SEQ ID NO:143 (nucleotides encoding the CDR$_L$ residues are shown underlined):

```
gacattgtgc tgacccaatc tccagcttct ttggctgtgt ctctagggca gagggccacc atctcctgca gagccaacga aagtgttgat aattatggca tgagttttat gaactggttc caacagaaac caggacagcc acccaaactc ctcatccatg ctgcatccaa ccaaggatcc ggggtccctg ccaggtttag tggcagtggg tttgggacag acttcagcct caacatccat cctatggagg aggatgatgc tgcaatgtat ttctgtcagc aaagtaagga ggttccgtac acgttcggag ggggaccaa gctggaaata aaa
```

2. Humanization of the Anti-Human PD-1 Antibody PD-1 mAb 7 to Form "hPD-1 mAb 7"

The above-described murine anti-human PD-1 antibody PD-1 mAb 7 was humanized and further deimmunized when antigenic epitopes were identified in order to demonstrate the capability of humanizing an anti-human PD-1 antibody so as to decrease its antigenicity upon administration to a human recipient. The humanization yielded two humanized VH Domains, designated herein as "hPD-1 mAb 7 VH1," and "hPD-1 mAb 7 VH2," and three humanized VL Domains designated herein as "hPD-1 mAb 7 VL1," "hPD-1 mAb 7 VL2," and "hPD-1 mAb 7 VL3." Any of the humanized VL Domains may be paired with either of the humanized VH Domains. Accordingly, any antibody comprising one of the humanized VL Domains paired with the humanized VH Domain is referred to generically as "hPD-1 mAb 7," and particular combinations of humanized VH/VL Domains are referred to by reference to the specific VH/VL Domains, for example a humanized antibody comprising hPD-1 mAb 7 VH1 and hPD-1 mAb 1 VL2 is specifically referred to as "hPD-1 mAb 7(1.2)."

The amino acid sequence of the VH Domain of hPD-1 mAb 7 VH1 (SEQ ID NO:147) is shown below (CDR$_H$ residues are shown underlined):

```
QVQLVQSGAE VKKPGASVKV SCKASGYSFT SYWMNWVRQA

PGQGLEWIGV IHPSDSETWL DQKFKDRVTI TVDKSTSTAY

MELSSLRSED TAVYYCAREH YGTSPFAYWG QGTLVTVSS
```

An exemplary polynucleotide that encodes hPD-1 mAb 7 VH1 is SEQ ID NO:148 (nucleotides encoding the CDR$_H$ residues are shown underlined):

```
caagttcaat tggtacagag cggggcagag gtgaagaaac ccggcgccag tgttaaggtg tcctgcaaag ccagcggtta cagctttaca agctattgga tgaattgggt gcgtcaagca ccagggcagg gtctggaatg gattgggtg atacatcctt ctgacagcga aacatggttg gaccagaaat ttaaagatcg tgtgacaatt acagtcgata agtccacaag cactgcttac atggaactct ccagcttgcg gtccgaggac accgctgtgt attattgcgc cagagagcac tacggcacat cacctttgc atactggggc cagggaactc tcgtaaccgt atcctcc
```

The amino acid sequence of the VH Domain of hPD-1 mAb 7 VH2 (SEQ ID NO:149) is shown below (CDR$_H$ residues are shown underlined):

```
QVQLVQSGAE VKKPGASVKV SCKASGYSFT SYWMNWVRQA

PGQGLEWAGV IHPSDSETWL DQKFKDRVTI TVDKSTSTAY

MELSSLRSED TAVYYCAREH YGTSPFAYWG QGTLVTVSS
```

An exemplary polynucleotide that encodes hPD-1 mAb 7 VH2 is SEQ ID NO:150 (nucleotides encoding the CDR$_H$ residues are shown underlined):

```
caagttcaat tggtacagag cggggcagag gtgaagaaac ccggcgccag tgttaaggtg tcctgcaaag ccagcggtta cagctttaca agctattgga tgaattgggt cgtcaagca ccagggcagg gtctggaatg ggctgggtg atacatcctt ctgacagcga aacatggttg gaccagaaat ttaaagatcg tgtgacaatt acagtcgata agtccacaag cactgcttac atggaactct ccagcttgcg gtccgaggac accgctgtgt attattgcgc cagagagcac tacggcacat caccttttgc atactggggc cagggaactc tcgtaaccgt atcctcc
```

The amino acid sequence of the VL Domain of hPD-1 mAb 7 VL1 (SEQ ID NO:151) is shown below (CDR$_H$ residues are shown underlined):

```
EIVLTQSPAT LSLSPGERAT LSCRANESVD NYGMSFMNWF

QQKPGQPPKL LIHAASNQGS GVPSRFSGSG SGTDFTLTIS

SLEPEDFAVY FCQQSKEVPY TFGGGTKVEI K
```

An exemplary polynucleotide that encodes hPD-1 mAb 7 VL1 is SEQ ID NO:152 (nucleotides encoding the CDR$_H$ residues are shown underlined):

```
gaaatcgtac tcacccagtc acctgcaacc ctttctctga gccccggtga acgtgccact ctcagctgca gagcaaatga gagtgtggac aattacggca tgtccttcat gaactggttt cagcagaagc ctgggcagcc acctaagctg ctcatccacg ccgcctctaa ccagggatct ggggtgcctt cacgttttc tggatcagga agtggcactg acttcaccct tacaatcagc tctctggagc cagaggactt tgccgtctat ttctgccagc aatctaaaga ggtgccctat acttttggtg cgggaccaa ggttgagatc aaa
```

The amino acid sequence of the VL Domain of hPD-1 mAb 7 VL2 (SEQ ID NO:153) is shown below (CDR$_H$ residues are shown underlined):

```
EIVLTQSPAT LSLSPGERAT LSCRASESVD NYGMSFMNWF

QQKPGQPPKL LIHAASNQGS GVPSRFSGSG SGTDFTLTIS

SLEPEDFAVY FCQQSKEVPY TFGGGTKVEI K
```

An exemplary polynucleotide that encodes hPD-1 mAb 7 VL2 is SEQ ID NO:154 (nucleotides encoding the CDR$_H$ residues are shown underlined):

```
gaaatcgtac tcacccagtc acctgcaacc ctttctctga gccccggtga acgtgccact ctcagctgca gagcaagtga gagtgtggac aattacggca tgtccttcat gaactggttt cagcagaagc ctgggcagcc acctaagctg ctcatccacg ccgcctctaa ccagggatct ggggtgcctt cacgttttc tggatcagga agtggcactg acttcaccct tacaatcagc tctctggagc cagaggactt tgccgtctat ttctgccagc aatctaaaga ggtgccctat acttttggtg cgggaccaa ggttgagatc aaa
```

The amino acid sequence of the VL Domain of hPD-1 mAb 7 VL3 (SEQ ID NO:155) is shown below (CDR$_H$ residues are shown underlined):

```
EIVLTQSPAT LSLSPGERAT LSCRASESVD NYGMSFMNWF

QQKPGQPPKL LIHAASNRGS GVPSRFSGSG SGTDFTLTIS

SLEPEDFAVY FCQQSKEVPY TFGGGTKVEI K
```

An exemplary polynucleotide that encodes hPD-1 mAb 7 VL3 is SEQ ID NO:156 (nucleotides encoding the CDR$_H$ residues are shown underlined):

```
gaaatcgtac tcacccagtc acctgcaacc ctttctctga gccccggtga acgtgccact ctcagctgca gagcaagtga gagtgtggac aattacggca tgtccttcat gaactggttt cagcagaagc ctgggcagcc acctaagctg ctcatccacg ccgcctctaa ccgcggatct ggggtgcctt cacgttttc tggatcagga agtggcactg acttcaccct tacaatcagc tctctggagc cagaggactt tgccgtctat ttctgccagc aatctaaaga ggtgccctat acttttggtg cgggaccaa ggttgagatc aaa
```

The CDR$_L$1 of the VL Domain of both hPD-1 mAb 7 VL2 and hPD-1 mAb 7 VL3 comprises an asparagine to serine amino acid substitution and has the amino acid sequence: RASESVDNYGMSFMN ((SEQ ID NO:157), the substituted serine is shown underlined). It is contemplated that a similar substitution may be incorporated into any of the PD-1 mAb 7 CDR$_L$1 Domains described above.

In addition, the CDR$_L$2 of the VL Domain of hPD-1 mAb 7 VL3 comprises a glutamine to arginine amino acid substitution and has the amino acid sequence: AASN<u>R</u>GS ((SEQ ID NO:158), the substituted arginine is shown underlined). It is contemplated that a similar substitution may be incorporated into any of the PD-1 mAb 7 CDR$_L$2 Domains described above.

H. Murine Anti-Human PD-1 Antibody PD-1 mAb 8

The amino acid sequence of the VH Domain of PD-1 mAb 8 (SEQ ID NO:159) is shown below (CDR$_H$ residues are shown underlined).

```
EGQLQQSGPE LVKPGASVKI SCKASGYTFT DYYMNWVKQN

HGKSLEWIGD INPKNGDTHY NQKFKGEATL TVDKSSTTAY

MELRSLTSED SAVYYCASDF DYWGQGTTLT VSS

CDR_H1 of PD-1 mAb 8 (SEQ ID NO: 161):
DYYMN

CDR_H2 of PD-1 mAb 8 (SEQ ID NO: 162):
DINPKNGDTHYNQKFKG

CDR_H3 of PD-1 mAb 8 (SEQ ID NO: 163):
DFDY
```

An exemplary polynucleotide that encodes the VH Domain of PD-1 mAb 8 is SEQ ID NO:160 (nucleotides encoding the CDR$_H$ residues are shown underlined):

```
gagggccagc tgcaacaatc tggacctgag ctggtgaagc ctggggcttc agtgaagata tcctgtaagg cttctggata cacgttcact gactactaca tgaactgggt gaagcagaac catggaaaga gccttgagtg gattggagat attaatccta aaaatggtga cactcactac aaccagaagt caagggcga ggccacattg actgtagaca agtcctccac cacagcctac atggagctcc gcagcctgac atctgaggac tctgcagtct attactgtgc gagcgatttt gactactggg gccaaggcac cactctcaca gtctcctcc
```

The amino acid sequence of the VL Domain of PD-1 mAb 8 (SEQ ID NO:164) is shown below (CDR$_L$ residues are shown underlined):

```
DVVMTQTPLS LPVGLGDQAS ISCRSSQTLV YSNGNTYLNW

FLQKPGQSPK LLIYKVSNRF SGVPDRFSGS GSGTDFTLKI

SRVEAEDLGV YFCSQSTHVP FTFGSGTKLE IK

CDR_L1 of PD-1 mAb 8 (SEQ ID NO: 166):
RSSQTLVYSNGNTYLN

CDR_L2 of PD-1 mAb 8 (SEQ ID NO: 167):
KVSNRFS

CDR_L3 of PD-1 mAb 8 (SEQ ID NO: 168):
SQSTHVPFT
```

An exemplary polynucleotide that encodes the VL Domain of PD-1 mAb 8 is SEQ ID NO:165 (nucleotides encoding the CDR$_L$ residues are shown underlined):

```
gatgttgtga tgacccaaac tccactctcc ctgcctgtcg gtcttggaga tcaagcctcc atctcttgca gatctagtca gacccttgta tatagtaatg gaaacaccta tttaaattgg ttcctgcaga agccaggcca gtctccaaag ctcctgatct acaaagtttc caaccgattt tctggggtcc cagacaggtt cagtggcagt ggatcaggga cagatttcac actcaagatc agcagagtgg aggctgagga tctgggagtt tatttctgct ctcaaagtac acatgttcca ttcacgttcg gctcggggac aaagttggaa ataaaa
```

I. The Anti-Human PD-1 Antibody PD-1 mAb 9
1. Murine Anti-Human PD-1 Antibody PD-1 mAb 9

The amino acid sequence of the VH Domain of PD-1 mAb 9 (SEQ ID NO:169) is shown below (CDR$_H$ residues are shown underlined).

```
EVMLVESGGG LVKPGGSLKL SCAASGFTFS SYLVSWVRQT

PEKRLEWVAT ISGGGGNTYY SDSVKGRFTI SRDNAKNTLY

LQISSLRSED TALYYCARYG FDGAWFAYWG QGTLVTVSS

CDR_H1 of PD-1 mAb 9 (SEQ ID NO: 171):
SYLVS

CDR_H2 of PD-1 mAb 9 (SEQ ID NO: 172):
TISGGGGNTYYSDSVKG

CDR_H3 of PD-1 mAb 9 (SEQ ID NO: 173):
YGFDGAWFAY
```

An exemplary polynucleotide that encodes the VH Domain of PD-1 mAb 9 is SEQ ID NO:170 (nucleotides encoding the CDR$_H$ residues are shown underlined):

```
gaagtgatgc tggtggagtc tgggggaggc ttagtgaagc ctggagggtc cctgaaactc tcctgtgcag cctctggatt cactttcagt agttatcttg tgtcttgggt tcgccagact ccggagaaga ggctggagtg ggtcgcaacc attagtggtg gtggtggtaa cacctactat tcagacagtg tgaagggtcg attcaccatc tccagagaca atgccaagaa cacctgtac ctgcaaatca gcagtctgag gtctgaggac acggccttgt attactgtgc aaggtatggt ttcgacggcg cctggtttgc ttactgggc caagggactc tggtcactgt ctcttcc
```

The amino acid sequence of the VL Domain of PD-1 mAb 9 (SEQ ID NO:174) is shown below (CDR$_L$ residues are shown underlined):

```
DIQMTQSPAS LSASVGDIVT ITCRASENIY SYLAWYQQKQ

EKSPQLLVYN AKTLAAGVPS RFSGSGSGTQ FSLTINSLQP
```

```
EDFGNYYCQH HYAVPWTFGG GTRLEIT

CDR_L1 of PD-1 mAb 9 (SEQ ID NO: 176):
RASENIYSYLA

CDR_L2 of PD-1 mAb 9 (SEQ ID NO: 177):
NAKTLAA

CDR_L3 of PD-1 mAb 9 (SEQ ID NO: 178):
QHHYAVPWT
```

An exemplary polynucleotide that encodes the VL Domain of PD-1 mAb 9 is SEQ ID NO:175 (nucleotides encoding the CDR_L residues are shown underlined):

```
gacatccaga tgactcagtc tccagcctcc ctatctgcat ctgtgggaga tattgtcacc atcacatgtc gagcaagtga gaatatttac agttatttag catggtatca gcagaaacag gaaaaatctc ctcagctcct ggtctataat gcaaaaacct tggcagcagg tgtgccatca aggttcagtg gcagtggatc aggcacacag tttctctga ccatcaacag cctgcagcct gaagattttg ggaattatta ctgtcagcat cattatgctg ttccgtggac gttcggtgga ggcaccagac tggaaatcac a
```

2. Humanization of the Anti-Human PD-1 Antibody PD-1 mAb 9 to Form "hPD-1 mAb 9"

The above-described murine anti-human PD-1 antibody PD-1 mAb 9 was humanized and further deimmunized when antigenic epitopes were identified in order to demonstrate the capability of humanizing an anti-human PD-1 antibody so as to decrease its antigenicity upon administration to a human recipient. The humanization yielded two humanized VH Domains, designated herein as "hPD-1 mAb 9 VH1," and "hPD-1 mAb 9 VH2," and two humanized VL Domains designated herein as "hPD-1 mAb 9 VL1," and "hPD-1 mAb 9 VL2." Any of the humanized VL Domains may be paired with the humanized VH Domains. Accordingly, any antibody comprising one of the humanized VL Domains paired with the humanized VH Domain is referred to generically as "hPD-1 mAb 9," and particular combinations of humanized VH/VL Domains are referred to by reference to the specific VH/VL Domains, for example a humanized antibody comprising hPD-1 mAb 9 VH1 and hPD-1 mAb 9 VL2 is specifically referred to as "hPD-1 mAb 9(1.2)."

The amino acid sequence of the VH Domain of hPD-1 mAb 9 VH1 (SEQ ID NO:179) is shown below (CDR_H residues are shown underlined):

```
EVQLVESGGG LVRPGGSLKL SCAASGFTFS SYLVSWVRQA

PGKGLEWVAT ISGGGGNTYY SDSVKGRFTI SRDNAKNSLY

LQMNSLRAED TATYYCARYG FDGAWFAYWG QGTLVTVSS
```

An exemplary polynucleotide that encodes hPD-1 mAb 9 VH1 is SEQ ID NO:180 (nucleotides encoding the CDR_H residues are shown underlined):

```
gaggtgcagc tggtggaaag tggggggcgg ctggtgcgac ccggggggaag tctgaaactg tcctgtgcag catcaggatt tacttttttca tcttatctcg tgtcttgggt aagacaagca cccggaaaag gcttggaatg ggtggccact atctccggtg gaggtggcaa cactactat agcgacagtg tcaagggaag atttaccatc agtcgcgaca acgctaagaa tagcctgtac ctccagatga actccctgcg cgccgaggac accgccacct attactgtgc acgctatgga tttgacggcg catggtttgc ctactgggga cagggcacat tggtaaccgt tagctcc
```

The amino acid sequence of the VH Domain of hPD-1 mAb 9 VH2 (SEQ ID NO:181) is shown below (CDR_H residues are shown underlined):

```
EVQLVESGGG LARPGGSLKL SCAASGFTFS SYLVGWVRQA

PGKGLEWTAT ISGGGGNTYY SDSVKGRFTI SRDNAKNSLY

LQMNSARAED TATYYCARYG FDGAWFAYWG QGTLVTVSS
```

An exemplary polynucleotide that encodes hPD-1 mAb 9 VH2 is SEQ ID NO:182 (nucleotides encoding the CDR_H residues are shown underlined):

```
gaggtgcagc tggtggaaag tggggggcgg ctggcgcgac ccggggggaag tctgaaactg tcctgtgcag catcaggatt tacttttttca tcttatctcg tgggctgggt aagacaagca cccggaaaag gcttggaatg gacggccact atctccggtg gaggtggcaa cactactat agcgacagtg tcaagggaag atttaccatc agtcgcgaca acgctaagaa tagcctgtac ctccagatga actccgcacg cgccgaggac accgccacct attactgtgc acgctatgga tttgacggcg catggtttgc ctactgggga cagggcacat tggtaaccgt tagctcc
```

The CDR_H1 of the VH Domain of hPD-1 mAb 9 VH2 comprises a serine to glycine amino acid substitution and has the amino acid sequence: SYLVG ((SEQ ID NO:183), the substituted glycine is shown underlined). It is contemplated that a similar substitution may be incorporated into any of the PD-1 mAb 9 CDR_H1 Domains described above.

The amino acid sequence of the VL Domain of hPD-1 mAb 9 VL1 (SEQ ID NO:184) is shown below (CDR_H residues are shown underlined):

```
DIQMTQSPSS LSASVGDRVT ITCRASENIY SYLAWYQQKP

GKAPKLLIYN AKTLAAGVPS RFSGSGSGTD FTLTISSLQP

EDFATYYCQH HYAVPWTFGQ GTKLEIK
```

An exemplary polynucleotide that encodes hPD-1 mAb 9 VL1 is SEQ ID NO:185 (nucleotides encoding the CDR_H residues are shown underlined):

```
gacattcaga tgactcagtc tccagcagt ctgtccgcat ccgtggggga tcgggtcacc atcacctgcc gtgcctcaga aaacatctat tcatacctcg cctggtatca acagaaacct
```

```
ggtaaagccc caaaattgct catttacaac gccaagaccc tcgcagctgg cgtgccaagt aggttctcag gcagcggctc agggacagat tcaccctca ccatatcctc actgcagccc gaggattttg ccacttacta ctgccagcat cattacgcag tgccctggac cttcggacaa ggcactaagc tcgagatcaa a
```

The amino acid sequence of the VL Domain of hPD-1 mAb 9 VL2 (SEQ ID NO:186) is shown below (CDR$_H$ residues are shown underlined):

```
DIQMTQSPSS LSASVGDRVT ITCRASENIY NYLAWYQQKP

GKAPKLLIYD AKTLAAGVPS RFSGSGSGTD FTLTISSLQP

EDFATYYCQH HYAVPWTFGQ GTKLEIK
```

An exemplary polynucleotide that encodes hPD-1 mAb 9 VL2 is SEQ ID NO:187 (nucleotides encoding the CDR$_H$ residues are shown underlined):

```
gacattcaga tgactcagtc tcccagcagt ctgtccgcat ccgtggggga tcgggtcacc atcacctgcc gtgcctcaga aaacatctat aactacctcg cctggtatca acagaaacct ggtaaagccc caaaattgct catttacgac gccaagaccc tcgcagctgg cgtgccaagt aggttctcag gcagcggctc agggacagat tcaccctca ccatatcctc actgcagccc gaggattttg ccacttacta ctgccagcat cattacgcag tgccctggac cttcggacaa ggcactaagc tcgagatcaa a
```

The CDR$_L$1 of the VL Domain of hPD-1 mAb 9 VL2 comprises a serine to asparagine amino acid substitution and has the amino acid sequence: RASENIYNYLA (SEQ ID NO:188), the substituted asparagine is shown underlined). It is contemplated that a similar substitution may be incorporated into any of the PD-1 mAb 9 CDR$_L$1 Domains described above.

The CDR$_L$2 of the VL Domain of hPD-1 mAb 9 VL2 comprises an asparagine to aspartate amino acid substitution and has the amino acid sequence: DAKTLAA ((SEQ ID NO:189), the substituted aspartate is shown underlined). It is contemplated that a similar substitution may be incorporated into any of the PD-1 mAb 7 CDR$_L$2 Domains described above.

J. Murine Anti-Human PD-1 Antibody PD-1 mAb 10

The amino acid sequence of the VH Domain of PD-1 mAb 10 (SEQ ID NO:190) is shown below (CDR$_H$ residues are shown underlined).

```
EVILVESGGG LVKPGGSLKL SCAASGFTFS NYLMSWVRQT

PEKRLEWVAS ISGGGSNIYY PDSVKGRFTI SRDNAKNTLY

LQMNSLRSED TALYYCARQE LAFDYWGQGT TLTVSS

CDR$_H$1 of PD-1 mAb 10 (SEQ ID NO: 192):
NYLMS

CDR$_H$2 of PD-1 mAb 10 (SEQ ID NO: 193):
SISGGGSNIYYPDSVKG

CDR$_H$3 of PD-1 mAb 10 (SEQ ID NO: 194):
QELAFDY
```

An exemplary polynucleotide that encodes the VH Domain of PD-1 mAb 10 is SEQ ID NO:191 (nucleotides encoding the CDR$_H$ residues are shown underlined):

```
gaagtgatac tggtggagtc tgggggaggc ttagtgaagc ctggagggtc cctgaaactc tcctgtgcag cctctggatt cactttcagt aactatctca tgtcttgggt tcgccagact ccggagaaga ggctggagtg ggtcgcaagt attagtggtg gtggtagtaa tatctactat ccagacagtg tgaagggtcg attcaccata tccagggaca atgccaagaa caccctgtac ctgcaaatga acagtctgag gtctgaggac acggccttgt attactgtgc aagacaagaa ctggctttg actactgggg ccaaggcacc actctcacag tctcctcc
```

The amino acid sequence of the VL Domain of PD-1 mAb 10 (SEQ ID NO:195) is shown below (CDR$_L$ residues are shown underlined):

```
DIQMTQTTSS LSASLGDRVT ISCRTSQDIS NFLNWYQQKP

DGTIKLLIYY TSRLHSGVPS RFSGSGSGTD YSLTISNLEQ

EDIATYFCQQ GSTLPWTFGG GTKLEII

CDR$_L$1 of PD-1 mAb 10 (SEQ ID NO: 197):
RTSQDISNFLN

CDR$_L$2 of PD-1 mAb 10 (SEQ ID NO: 198):
YTSRLHS

CDR$_L$3 of PD-1 mAb 10 (SEQ ID NO: 199):
QQGSTLPWT
```

An exemplary polynucleotide that encodes the VL Domain of PD-1 mAb 10 is SEQ ID NO:196 (nucleotides encoding the CDR$_L$ residues are shown underlined):

```
gatatccaga tgacacagac tacatcctcc ctgtctgcct ctctgggaga cagagtcacc atcagttgca ggacaagtca ggacattagc aattttttaa actggtatca gcagaaacca gatggaacta ttaaactcct gatctactac acatcaagat tacactcagg agtcccatca aggttcagtg gcagtgggtc tggaacagat tattctctca ccattagcaa cctggagcaa gaagatattg ccacttactt ttgccaacag ggtagtacgc ttccgtggac gttcggtgga ggcaccaagc tggaaatcat a
```

K. Murine Anti-Human PD-1 Antibody PD-1 mAb 11

The amino acid sequence of the VH Domain of PD-1 mAb 11 (SEQ ID NO:200) is shown below (CDR$_H$ residues are shown underlined).

```
EVQLQQSGTV LARPGASVKM SCKTSGYTFT GYWMHWVKQR

PGQGLKWMGA IYPGNSDTHY NQKFKGKAKL TAVTSASTAY

MELSSLTNED SAIYYCTTGT YSYFDVWGTG TTVTVSS

CDR_H1 of PD-1 mAb 11 (SEQ ID NO: 202):
GYWMH

CDR_H2 of PD-1 mAb 11 (SEQ ID NO: 203):
AIYPGNSDTHYNQKFKG

CDR_H3 of PD-1 mAb 11 (SEQ ID NO: 204):
GTYSYFDV
```

An exemplary polynucleotide that encodes the VH Domain of PD-1 mAb 11 is SEQ ID NO:201 (nucleotides encoding the CDR$_H$ residues are shown underlined):

```
gaggttcagc tccagcagtc tgggactgtg ctggcaaggc ctggggcttc agtgaagatg tcctgcaaga cttctggcta cacatttacc ggctactgga tgcactgggt aaaacagagg cctggacagg gtctgaaatg gatggggct atttatcctg gaaatagtga tactcactac aaccagaagt tcaagggcaa ggccaaactg actgcagtca catccgccag cactgcctac atggagctca gcagcctgac aaatgaggac tctgcgatct attactgtac tactgggacc tactcgtact tcgatgtctg gggcacaggg accacggtca ccgtctcctc a
```

The amino acid sequence of the VL Domain of PD-1 mAb 11 (SEQ ID NO:205) is shown below (CDR$_L$ residues are shown underlined):

```
DILLTQSPAI LSVSPGERVS FSCRASQSIG TSIHWYQHRT

NGSPRLLIKY ASESISGIPS RFSGSGSGTD FTLSINSVES

EDIADYYCQQ SNSWLTFGAG TKLELK

CDR_L1 of PD-1 mAb 11 (SEQ ID NO: 207):
RASQSIGTSIH

CDR_L2 of PD-1 mAb 11 (SEQ ID NO: 208):
YASESIS

CDR_L3 of PD-1 mAb 11 (SEQ ID NO: 209):
QQSNSWLT
```

An exemplary polynucleotide that encodes the VL Domain of PD-1 mAb 11 is SEQ ID NO:206 (nucleotides encoding the CDR$_L$ residues are shown underlined):

```
gacatcttgc tgactcagtc tccagccatc ctgtctgtga gtccaggaga aagagtcagt ttctcctgca gggccagtca gagcattggc acaagcatac actggtatca gcacagaaca aatggttctc caaggcttct cataaagtat gcttctgagt ctatctctgg gatccttcc aggtttagtg gcagtggatc agggactgat tttactctta gcatcaacag tgtggagtct gaagatattg cagattatta ctgtcaacaa agtaatagct ggctcacgtt cggtgctggg accaagctgg agctgaaa
```

L. Murine Anti-Human PD-1 Antibody PD-1 mAb 12

The amino acid sequence of the VH Domain of PD-1 mAb 12 (SEQ ID NO:210) is shown below (CDR$_H$ residues are shown underlined).

```
QGHLQQSGAE LVRPGASVTL SCKASGFTFT DYEMHWVKQT

PVHGLEWIGT IDPETGGTAY NQKFKGKAIL TVDKSSTTTY

MELRSLTSED SAVFYCSRER ITTVVEGAYW YFDVWGTGTT

VTVSS

CDR_H1 of PD-1 mAb 12 (SEQ ID NO: 212):
DYEMH

CDR_H2 of PD-1 mAb 12 (SEQ ID NO: 213):
TIDPETGGTAYNQKFKG

CDR_H3 of PD-1 mAb 12 (SEQ ID NO: 214):
ERITTVVEGAYWYFDV
```

An exemplary polynucleotide that encodes the VH Domain of PD-1 mAb 12 is SEQ ID NO:211 (nucleotides encoding the CDR$_H$ residues are shown underlined):

```
cagggtcacc tgcagcagtc tggggctgag ctggtgaggc ctggggcttc agtgacgctg tcctgcaagg cttcgggctt cacatttact gactatgaga tgcactgggt gaaacagaca cctgtgcatg gcctggaatg gattgggact attgatcctg aaactggtgg tactgcctac aatcagaagt tcaagggcaa ggccatactg acagtagaca atcttccac tacaacctac atggagctcc gcagcctgac atctgaggac tctgccgtct tttattgttc aagagagagg attactacgg ttgttgaggg ggcatactgg tacttcgatg tctggggcac agggaccacg gtcaccgtct cctca
```

The amino acid sequence of the VL Domain of PD-1 mAb 12 (SEQ ID NO:215) is shown below (CDR$_L$ residues are shown underlined):

```
DVLMTQTPLS LPVSLGDQAS ISCRSSQNIV HSNGNTYLEW

YLQKPGQSPK LLICKVSTRF SGVPDRFSGS GSGTDFTLKI

SRVEAEDLGV YYCFQGSHVP YTFGGGTKLE IK

CDR_L1 of PD-1 mAb 12 (SEQ ID NO: 217):
RSSQNIVHSNGNTYLE

CDR_L2 of PD-1 mAb 12 (SEQ ID NO: 218):
KVSTRFS

CDR_L3 of PD-1 mAb 12 (SEQ ID NO: 219):
FQGSHVPYT
```

An exemplary polynucleotide that encodes the VL Domain of PD-1 mAb 12 is SEQ ID NO:216 (nucleotides encoding the CDR$_L$ residues are shown underlined):

```
gatgtttga tgacccagac tccactctcc ctgcctgtca gtcttggaga tcaagcctcc atctcttgca gatctagtca gaacattgta catagtaatg gaaacaccta tttagaatgg tacctgcaga aaccaggcca gtctccaaag ctcctgatct gcaaagtttc cacccgattt tctggggtcc cagacaggtt cagtggcagt ggatcaggga cagatttcac actcaagatc agcagagtgg aggctgagga tctgggagtt tattattgct ttcaaggttc acatgttccg tacacgttcg gagggggac caagctggaa ataaaa
```

M. Murine Anti-Human PD-1 Antibody PD-1 mAb 13

The amino acid sequence of the VH Domain of PD-1 mAb 13 (SEQ ID NO:220) is shown below (CDR$_H$ residues are shown underlined).

```
EVMLVESGGG LVKPGGSLKL SCAASGFTFS SHTMSWVRQT

PEKRLEWVAT ISGGGSNIYY PDSVKGRFTI SRDNAKNTLY

LQMSSLRSED TALYYCARQA YYGNYWYFDV WGTGTTVTVS

S

CDR$_H$1 of PD-1 mAb 13 (SEQ ID NO: 222):
SHTMS

CDR$_H$2 of PD-1 mAb 13 (SEQ ID NO: 223):
TISGGGSNIYYPDSVKG

CDR$_H$3 of PD-1 mAb 13 (SEQ ID NO: 224):
QAYYGNYWYFDV
```

An exemplary polynucleotide that encodes the VH Domain of PD-1 mAb 13 is SEQ ID NO:221 (nucleotides encoding the CDR$_H$ residues are shown underlined):

```
gaagtgatgc tggtggagtc tgggggaggc ttagtgaagc ctggagggtc cctgaaactc tcctgtgcag cctctggatt cactttcagt agccatacca tgtcttgggt tcgccagact ccggagaaga ggctggagtg ggtcgcaacc attagtggtg gtggttctaa tatctactat ccagacagtg tgaagggtcg attcaccatc tccagagaca atgccaagaa caccctgtac ctgcaaatga gcagtctgag gtctgaggac acggccttgt attactgtgc aagacaagct tactacggta attactggta cttcgatgtc tggggcacag ggaccacggt caccgtctcc tcc
```

The amino acid sequence of the VL Domain of PD-1 mAb 13 (SEQ ID NO:225) is shown below (CDR$_L$ residues are shown underlined):

```
DIQMTQSPAT QSASLGESVT ITCLASQTIG TWLAWYQQKP

GKSPQLLIYA ATSLADGVPS RFSGSGSGTK FSFKISSLQA

EDFVSYYCQQ LDSIPWTFGG GTKLEIK

CDR$_L$1 of PD-1 mAb 13 (SEQ ID NO: 227):
LASQTIGTWLA

CDR$_L$2 of PD-1 mAb 13 (SEQ ID NO: 228):
AATSLAD

CDR$_L$3 of PD-1 mAb 13 (SEQ ID NO: 229):
QQLDSIPWT
```

An exemplary polynucleotide that encodes the VL Domain of PD-1 mAb 13 is SEQ ID NO:226 (nucleotides encoding the CDR$_L$ residues are shown underlined):

```
gacattcaga tgacccagtc tcctgccacc cagtctgcat ctctgggaga aagtgtcacc atcacgtgcc tggcaagtca gaccattggt acatggttag catggtatca gcagaaacca gggaaatctc ctcagctcct gatttatgct gcaaccagct tggcagatgg ggtcccatca aggttcagtg gtagtggatc tggcacaaaa ttttctttca agatcagcag cctacaggct gaagattttg taagttatta ctgtcaacaa cttgacagta ttccgtggac gttcggtgga ggcaccaagc tggaaatcaa a
```

N. Murine Anti-Human PD-1 Antibody PD-1 mAb 14

The amino acid sequence of the VH Domain of PD-1 mAb 14 (SEQ ID NO:230) is shown below (CDR$_H$ residues are shown underlined).

```
QVQLQQPGAE LVKPGASVKM SCKASGYNFI SYWITWVKQR

PGQGLQWIGN IYPGTDGTTY NEKFKSKATL TVDTSSSTAY

MHLSRLTSED SAVYYCATGL HWYFDVWGTG TTVTVSS

CDR$_H$1 of PD-1 mAb 14 (SEQ ID NO: 232):
SYWIT

CDR$_H$2 of PD-1 mAb 14 (SEQ ID NO: 233):
NIYPGTDGTTYNEKFKS

CDR$_H$3 of PD-1 mAb 14 (SEQ ID NO: 234):
GLHWYFDV
```

An exemplary polynucleotide that encodes the VH Domain of PD-1 mAb 14 is SEQ ID NO:231 (nucleotides encoding the CDR$_H$ residues are shown underlined):

```
caggtccaac tgcagcagcc tggggctgag cttgtgaagc ctggggcttc agtgaagatg tcctgcaagg cttctggcta caacttcatc agctactgga taactgggt gaaacagagg cctggacaag gccttcagtg gattggaaat atttatcctg gtactgatgg tactacctac aatgagaagt tcaagagcaa
```

```
ggccacactg actgtagaca catcctccag cacagcctac atgcacctca gtcgcctgac atctgaggac tctgcggtct attactgtgc aactgggcta cactggtact tcgatgtctg gggcacaggg accacggtca ccgtctcctc c
```

The amino acid sequence of the VL Domain of PD-1 mAb 14 (SEQ ID NO:235) is shown below (CDR$_L$ residues are shown underlined):

```
DIVMTQSQKF MSTSVGDRVS VTCKASQSVG TNVAWYQQKP

GQSPKALIYS ASSRFSGVPD RFTGSGSGTD FTLTISNVQS

EDLAEYFCQQ YNSYPYTFGG GTKLEIK

CDR_L1 of PD-1 mAb 14 (SEQ ID NO: 237):
KASQSVGTNVA

CDR_L2 of PD-1 mAb 14 (SEQ ID NO: 238):
SASSRFS

CDR_L3 of PD-1 mAb 14 (SEQ ID NO: 239):
QQYNSYPYT
```

An exemplary polynucleotide that encodes the VL Domain of PD-1 mAb 14 is SEQ ID NO:236 (nucleotides encoding the CDR$_L$ residues are shown underlined):

```
gacattgtga tgacccagtc tcaaaaattc atgtccacat cagtaggaga cagggtcagt gtcacctgca aggccagtca gagtgtgggt actaatgtag cctggtatca acagaagccc ggtcaatctc ctaaagcact gatttactcg gcatcctcc gattcagtgg cgtccctgat cgcttcacag gcagtggatc tgggacagat ttcactctca ccatcagtaa tgtgcagtct gaagacttgg cagagtattt ctgtcagcaa tataacagct atccgtacac gttcggaggg gggaccaagc tggaaataaa a
```

O. The Anti-Human PD-1 Antibody PD-1 mAb 15

1. Murine Anti-Human PD-1 Antibody PD-1 mAb 15

The amino acid sequence of the VH Domain of PD-1 mAb 15 (SEQ ID NO:240) is shown below (CDR$_H$ residues are shown underlined).

```
EVMLVESGGG LVKPGGSLKL SCAASGFIFS SYLISWVRQT

PEKRLEWVAA ISGGGADTYY ADSVKGRFTI SRDNAKNTLY

LQMSSLRSED TALYYCTRRG TYAMDYWGQG TSVTVSS

CDR_H1 of PD-1 mAb 15 (SEQ ID NO: 242):
SYLIS

CDR_H2 of PD-1 mAb 15 (SEQ ID NO: 243):
AISGGGADTYYADSVKG

CDR_H3 of PD-1 mAb 15 (SEQ ID NO: 244):
RGTYAMDY
```

An exemplary polynucleotide that encodes the VH Domain of PD-1 mAb 15 is SEQ ID NO:241 (nucleotides encoding the CDR$_H$ residues are shown underlined):

```
gaagtgatgc tggtggagtc tgggggaggc ttagtgaagc ctggagggtc cctgaaactc tcctgtgcag cctctggatt cattttcagt agctatctca tctcttgggt tcgccagact ccggagaaga ggctggagtg ggtcgctgcc attagtggtg gtggtgctga cacctactat gccgacagtg tgaagggtcg attcaccatc tccagagaca atgccaagaa caccctgtat ctgcaaatga gcagtctgag gtctgaggac acggccttat attactgtac aagacgaggg acctatgcta tggactactg gggtcaagga acctcagtca ccgtctcctc c
```

The amino acid sequence of the VL Domain of PD-1 mAb 15 (SEQ ID NO:245) is shown below (CDR$_L$ residues are shown underlined):

```
DIQMTQSPAS QSASLGESVT ITCLASQTIG TWLAWYQQKP

GKSPQLLIYA ATSLADGVPS RFSGSGSGTK FSFKISSLQA

EDFVNYYCQQ LYSIPWTFGG GTKLEIK

CDR_L1 of PD-1 mAb 15 (SEQ ID NO: 247):
LASQTIGTWLA

CDR_L2 of PD-1 mAb 15 (SEQ ID NO: 248):
AATSLAD

CDR_L3 of PD-1 mAb 15 (SEQ ID NO: 249):
QQLYSIPWT
```

An exemplary polynucleotide that encodes the VL Domain of PD-1 mAb 15 is SEQ ID NO:246 (nucleotides encoding the CDR$_L$ residues are shown underlined):

```
gacattcaga tgacccagtc tcccgcctcc cagtctgcat ctctgggaga aagtgtcacc atcacatgcc tggcaagtca gaccattggt acatggttag catggtatca gcagaaacca gggaaatctc ctcagctcct gatttatgct gcaaccagct tggcagatgg ggtcccatca aggttcagtg gtagtggatc tggcacaaaa ttttctttca agatcagcag cctacaggct gaagattttg taaattatta ctgtcaacaa ctttacagta ttccgtggac gttcggtgga ggcaccaagc tggaaatcaa a
```

2. Humanization of the Anti-Human PD-1 Antibody PD-1 mAb 15 to Form "hPD-1 mAb 15"

The above-described murine anti-human PD-1 antibody PD-1 mAb 15 was humanized and further deimmunized when antigenic epitopes were identified in order to demonstrate the capability of humanizing an anti-human PD-1 antibody so as to decrease its antigenicity upon administration to a human recipient. The humanization yielded one humanized VH Domain, designated herein as "hPD-1 mAb 2 VH1," and one humanized VL Domains designated herein as "hPD-1 mAb 1 VL1." An antibody comprising the humanized VL Domain paired with the humanized VH Domain is referred to as "hPD-1 mAb 15."

The amino acid sequence of the VH Domain of hPD-1 mAb 15 VH1 (SEQ ID NO:250) is shown below (CDR$_H$ residues are shown underlined):

```
EVQLVESGGG LVRPGGSLRL SCAASGFTFS SYLISWVRQA

PGKGLEWVAA ISGGGADTYY ADSVKGRFTI SRDNAKNSLY

LQMNSLRAED TATYYCARRG TYAMDYWGQG TLVTVSS
```

An exemplary polynucleotide that encodes hPD-1 mAb 15 VH1 is SEQ ID NO:251 (nucleotides encoding the CDR$_H$ residues are shown underlined):

```
gaagtgcaac tggttgaaag tggcggcggg ctggtgcggc caggtggttc actcagactg tcttgtgcag cttcaggctt tacattctcc tcttatctta tctcttgggt gcgccaagcc ccaggtaagg gccttgaatg ggtcgccgcc attagtgggg gtggtgccga tacatattat gccgacagcg tcaagggacg tttcaccatc agcagggaca acgccaagaa tagcctttac ctgcagatga actcacttag agctgaagac accgctactt attactgtgc ccggcgcggg acttacgcta tggactattg gggccagggc accttggtca ctgtctcatc c
```

The amino acid sequence of the VH Domain of hPD-1 mAb 15 VL1 (SEQ ID NO:252) is shown below (CDR$_H$ residues are shown underlined):

```
DIQMTQSPSS LSASVGDRVT ITCLASQTIG TWLAWYQQKP

GKAPKLLIYA ATSLADGVPS RFSGSGSGTD FTFTISSLQP

EDFATYYCQQ LYSIPWTFGQ GTKLEIK
```

An exemplary polynucleotide that encodes hPD-1 mAb 15 VL1 is SEQ ID NO:253 (nucleotides encoding the CDR$_H$ residues are shown underlined):

```
gatatccaga tgacccagtc tcccagctct ctcagtgcaa gcgtaggcga ccgtgtgacc atcacctgtc tggccagtca gaccattgga acctggctcg cctggtatca gcagaaacct ggcaaggccc ctaagctgct gatttacgcc gccacctcca tcgcagatgg agtgccctcc cgatttagcg ggtccgggtc cggcaccgac ttcacattca caatcagcag cctccagccc gaggatttcg ctacatacta ctgtcaacag ctctactcca ttccatggac ctttggtcag ggtactaaac tggagatcaa a
```

V. Anti-Human PD-1 Antibodies PD-1 mAb 1-15, and Their Derivatives Having an Engineered Fc Region In traditional immune function, the interaction of antibody-antigen complexes with cells of the immune system results in a wide array of responses, ranging from effector functions such as antibody dependent cytotoxicity, mast cell degranulation, and phagocytosis to immunomodulatory signals such as regulating lymphocyte proliferation and antibody secretion. All of these interactions are initiated through the binding of the Fc Region of antibodies or immune complexes to specialized cell surface receptors on hematopoietic cells. The diversity of cellular responses triggered by antibodies and immune complexes results from the structural heterogeneity of the three Fc receptors: FcγRI (CD64), FcγRII (CD32), and FcγRIII (CD16). FcγRI (CD64), FcγRIIA (CD32A) and FcγRIII (CD16) are activating (i.e., immune system enhancing) receptors; FcγRIIB (CD32B) is an inhibiting (i.e., immune system dampening) receptor. In addition, interaction with the neonatal Fc Receptor (FcRn) mediates the recycling of IgG molecules from the endosome to the cell surface and release into the blood. The amino acid sequence of exemplary wild-type IgG1 (SEQ ID NO:1), IgG2 (SEQ ID NO:2), IgG3 (SEQ ID NO:3), and IgG4 (SEQ ID NO:4) are presented above.

Modification of the Fc Region normally leads to an altered phenotype, for example altered serum half-life, altered stability, altered susceptibility to cellular enzymes or altered effector function. It may be desirable to modify an antibody or other binding molecule of the present invention with respect to effector function, for example, so as to enhance the effectiveness of such molecule in treating cancer. Reduction or elimination of effector function is desirable in certain cases, for example in the case of antibodies whose mechanism of action involves blocking or antagonism, but not killing of the cells bearing a target antigen. Increased effector function is generally desirable when directed to undesirable cells, such as tumor and foreign cells, where the FcγRs are expressed at low levels, for example, tumor-specific B cells with low levels of FcγRIIB (e.g., non-Hodgkins lymphoma, CLL, and Burkitt's lymphoma). In said embodiments, molecules of the invention with conferred or altered effector function activity are useful for the treatment and/or prevention of a disease, disorder or infection where an enhanced efficacy of effector function activity is desired.

In certain embodiments, the PD-1-binding molecules of the present invention comprise an Fc Region that possesses one or more modifications (e.g., substitutions, deletions, or insertions) to the sequence of amino acids of a wild-type Fc Region (e.g., SEQ ID NO:1), which reduce the affinity and avidity of the Fc Region and, thus, the molecule of the invention, for one or more FcγR receptors. In other embodiments, the molecules of the invention comprise an Fc Region that possesses one or more modifications to the amino acids of the wild-type Fc Region, which increase the affinity and avidity of the Fc Region and, thus, the molecule of the invention, for one or more FcγR receptors. In other embodiments, the molecules comprise a variant Fc Region wherein said variant confers or mediates increased antibody dependent cell mediated cytotoxicity (ADCC) activity and/or an increased binding to FcγRIIA, relative to a molecule comprising no Fc Region or comprising a wild-type Fc Region. In alternate embodiments, the molecules comprise a variant Fc Region wherein said variant confers or mediates decreased ADCC activity (or other effector function) and/or an increased binding to FcγRIIB, relative to a molecule comprising no Fc Region or comprising a wild-type Fc Region. In some embodiments, the invention encompasses PD-1-binding molecules comprising a variant Fc Region, which variant Fc Region does not show a detectable binding to any FcγR, relative to a comparable molecule comprising the wild-type Fc Region. In other embodiments, the invention encompasses PD-1-binding molecules comprising a variant Fc Region, which variant Fc Region only binds a single FcγR, preferably one of FcγRIIA, FcγRIIB, or FcγRIIIA Any such increased affinity and/or avidity is preferably assessed by measuring in vitro the extent of detectable binding to the FcγR or FcγR-related activity in cells that express low levels of the FcγR when binding activity of the parent molecule (without the modified Fc Region) cannot be detected in the cells, or in cells which express non-FcγR receptor target antigens at a density of 30,000 to 20,000 molecules/cell, at a density of 20,000 to 10,000 molecules/cell, at a density of 10,000 to 5,000 molecules/cell, at a density of 5,000 to 1,000 molecules/cell, at a density of 1,000 to 200 molecules/cell or at a density of 200 molecules/cell or less (but at least 10, 50, 100 or 150 molecules/cell).

The PD-1-binding molecules of the present invention may comprise a variant Fc Region having altered affinities for an activating and/or inhibitory Fcγ receptor. In one embodiment, the PD-1-binding molecule comprises a variant Fc Region that has increased affinity for FcγRIIB and decreased affinity for FcγRIIIA and/or FcγRIIA, relative to a comparable molecule with a wild-type Fc Region. In another embodiment, the PD-1-binding molecule of the present invention comprise a variant Fc Region, which has decreased affinity for FcγRIIB and increased affinity for FcγRIIIA and/or FcγRIIA, relative to a comparable molecule with a wild-type Fc Region. In yet another embodiment, the PD-1-binding molecules of the present invention comprise a variant Fc Region that has decreased affinity for FcγRIIB and decreased affinity for FcγRIIIA and/or FcγRIIA, relative to a comparable molecule with a wild-type Fc Region. In still another embodiment, the PD-1-binding molecules of the present invention comprise a variant Fc Region, which has unchanged affinity for FcγRIIB and decreased (or increased) affinity for FcγRIIIA and/or FcγRIIA, relative to a comparable molecule with a wild-type Fc Region.

In certain embodiments, the PD-1-binding molecules of the present invention comprise a variant Fc Region having an altered affinity for FcγRIIIA and/or FcγRIIA such that the immunoglobulin has an enhanced effector function. Non-limiting examples of effector cell functions include antibody dependent cell mediated cytotoxicity, antibody dependent phagocytosis, phagocytosis, opsonization, opsonophagocytosis, cell binding, rosetting, C1q binding, and complement dependent cell mediated cytotoxicity.

In a preferred embodiment, the alteration in affinity or effector function is at least 2-fold, preferably at least 4-fold, at least 5-fold, at least 6-fold, at least 7-fold, at least 8-fold, at least 9-fold, at least 10-fold, at least 50-fold, or at least 100-fold, relative to a comparable molecule comprising a wild-type Fc Region. In other embodiments of the invention, the variant Fc Region immunospecifically binds one or more FcRs with at least 65%, preferably at least 70%, 75%, 80%, 85%, 90%, 95%, 100%, 125%, 150%, 175%, 200%, 225%, or 250% greater affinity relative to a molecule comprising a wild-type Fc Region. Such measurements can be in vivo or in vitro assays, and in a preferred embodiment are in vitro assays such as ELISA or surface plasmon resonance assays.

In different embodiments, the PD-1-binding molecules of the present invention comprise a variant Fc Region wherein said variant agonizes at least one activity of an FcγR receptor, or antagonizes at least one activity of an FcγR receptor. In a preferred embodiment, the molecules comprise a variant that antagonizes one or more activities of FcγRIIB, for example, B-cell receptor-mediated signaling, activation of B-cells, B-cell proliferation, antibody production, intracellular calcium influx of B cells, cell cycle progression, FcγRIIB-mediated inhibition of FcεRI signaling, phosphorylation of FcγRIIB, SHIP recruitment, SHIP phosphorylation and association with Shc, or activity of one or more downstream molecules (e.g., MAP kinase, JNK, p38, or Akt) in the FcγRIIB signal transduction pathway. In another embodiment, the PD-1-binding molecules of the present invention comprise a variant that agonizes one or more activities of FcεRI, for example, mast cell activation, calcium mobilization, degranulation, cytokine production, or serotonin release.

In certain embodiments, the molecules comprise an Fc Region comprising regions from two or more IgG isotypes (e.g., IgG1, IgG2, IgG3 and IgG4). As used herein, an Fc Region is said to be of a particular IgG isotype if its amino acid sequence is most homologous to that isotype relative to other IgG isotypes. The various IgG isotypes exhibit differing physical and functional properties including serum half-life, complement fixation, FcγR binding affinities and effector function activities (e.g., ADCC, CDC, etc.) due to differences in the amino acid sequences of their hinge and/or Fc Regions, for example as described in Flesch and Neppert (1999) J. Clin. Lab. Anal. 14:141-156; Chappel et al. (1993) J. Biol. Chem. 33:25124-25131; Chappel et al. (1991) Proc. Natl. Acad. Sci. (U.S.A.) 88:9036-9040; or Bruggemann et al. (1987) J. Exp. Med 166:1351-1361. This type of variant Fc Region may be used alone, or in combination with an amino acid modification, to affect Fc-mediated effector function and/or binding activity. In combination, the amino acid modification and IgG hinge/Fc Region may display similar functionality (e.g., increased affinity for FcγRIIA) and may act additively or, more preferably, synergistically to modify the effector functionality in the molecule of the invention, relative to a molecule of the invention comprising a wild-type Fc Region. In other embodiments, the amino acid modification and IgG Fc Region may display opposite functionality (e.g., increased and decreased affinity for FcγRIIA, respectively) and may act to selectively temper or reduce a specific functionality in the molecule of the invention, relative to a molecule of the invention not comprising an Fc Region or comprising a wild-type Fc Region of the same isotype.

In a preferred specific embodiment, the PD-1-binding molecules of the present invention comprise a variant Fc Region, wherein said variant Fc Region comprises at least one amino acid modification relative to a wild-type Fc Region, such that said molecule has an altered affinity for an FcR, provided that said variant Fc Region does not have a substitution at positions that make a direct contact with FcγR based on crystallographic and structural analysis of Fc-FcR interactions such as those disclosed by Sondermann et al. (2000) Nature 406:267-73. Examples of positions within the Fc Region that make a direct contact with FcγR are amino acid residues 234-239, amino acid residues 265-269 (B/C loop), amino acid residues 297-299 (C'/E loop), and amino acid residues 327-332 (F/G loop). In some embodiments, the molecules of the invention comprise variant Fc Regions comprise modification of at least one residue that does not make a direct contact with an FcγR based on structural and crystallographic analysis, e.g., is not within the Fc-FcγR binding site.

Variant Fc Regions are well known in the art, and any known variant Fc Region may be used in the present invention to confer or modify the effector function exhibited by a molecule of the invention comprising an Fc Region (or portion thereof) as functionally assayed, e.g., in an NK dependent or macrophage dependent assay. For example, Fc Region variants identified as altering effector function are disclosed in PCT Publications No. WO 04/063351; WO 06/088494; WO 07/024249; WO 06/113665; WO 07/021841; WO 07/106707; and WO 2008/140603, and any suitable variant disclosed therein may be used in the present molecules.

In certain embodiments, the PD-1-binding molecules of the present invention comprise a variant Fc Region, having one or more amino acid modifications in one or more regions, which modification(s) alter (relative to a wild-type Fc Region) the Ratio of Affinities of the variant Fc Region to an activating FcγR (such as FcγRIIA or FcγRIIIA) relative to an inhibiting FcγR (such as FcγRIIB).

Ratio of Affinities =

$$\frac{\text{Wild-Type to Variant Change in Affinity to } FcγR_{Activating}}{\text{Wild-Type to Variant Change in Affinity to } FcγR_{Inhibiting}}$$

Particularly preferred are PD-1-binding molecules of the present invention that possess a variant Fc Region (relative to the wild-type Fc Region) in which the variant Fc Region has a Ratio of Affinities greater than 1. Such molecules have particular use in providing a therapeutic or prophylactic treatment of a disease, disorder, or infection, or the amelioration of a symptom thereof, where an enhanced efficacy of effector cell function (e.g., ADCC) mediated by FcγR is desired, e.g., cancer or infectious disease. In contrast, a variant Fc Region having a Ratio of Affinities less than 1 mediates decreased efficacy of effector cell function. Table 1 lists exemplary single, double, triple, quadruple and quintuple mutations by whether their Ratio of Affinities is greater than or less than 1.

TABLE 1

Exemplary Single and Multiple Mutations Listed by Ratio of Affinities

| Single | Double | Triple | Quadruple | Quintuple |
|---|---|---|---|---|
| Ratio of Affinities > 1 | | | | |
| F243L | F243L & R292P | F243L, P247L & N421K | L234F, F243L, R292P & Y300L | L235V, F243L, R292P, Y300L & P396L |
| D270E | F243L & Y300L | F243L, R292P & Y300L | L235I, F243L, R292P & Y300L | L235P, F243L, R292P, Y300L & P396L |
| R292G | F243L & P396L | F243L, R292P & V305I | L235Q, F243L, R292P & Y300L | F243L, R292P, V305I, Y300L & P396L |
| R292P | D270E & P396L | F243L, R292P & P396L | F243L, P247L, D270E & N421K | |
| | R292P & Y300L | F243L, Y300L & P396L | F243L, R255L, D270E & P396L | |
| | R292P & V305I | P247L, D270E & N421K | F243L, D270E, G316D & R416G | |
| | R292P & P396L | R255L, D270E & P396L | F243L, D270E, K392T & P396L | |
| | Y300L & P396L | D270E, G316D & R416G | F243L, D270E, P396L & Q419H | |
| | P396L & Q419H | D270E, K392T & P396L | F243L, R292P, Y300L, & P396L | |
| | | D270E, P396L & Q419H | F243L, R292P, V305I & P396L | |
| | | V284M, R292L & K370N | P247L, D270E, Y300L & N421K | |
| | | R292P, Y300L & P396L | R255L, D270E, R292G & P396L | |
| | | | R255L, D270E, Y300L & P396L | |
| | | | D270E, G316D, P396L & R416G | |
| Ratio of Affinities < 1 | | | | |
| Y300L | F243L & P396L | F243L, R292P & V305I | | |
| P396L | P247L & N421K | | | |
| | R255L & P396L | | | |
| | R292P & V305I | | | |
| | K392T & P396L | | | |
| | P396L & Q419H | | | |

In a specific embodiment, in variant Fc Regions, any amino acid modifications (e.g., substitutions) at any of positions 235, 240, 241, 243, 244, 247, 262, 263, 269, 298, 328, or 330 and preferably one or more of the following residues: A240, I240, L241, L243, H244, N298, I328 or V330. In a different specific embodiment, in variant Fc Regions, any amino acid modifications (e.g., substitutions) at any of positions 268, 269, 270, 272, 276, 278, 283, 285, 286, 289, 292, 293, 301, 303, 305, 307, 309, 331, 333, 334, 335, 337, 338, 340, 360, 373, 376, 416, 419, 430, 434, 435, 437, 438 or 439 and preferably one or more of the following residues: H280, Q280, Y280, G290, S290, T290, Y290, N294, K295, P296, D298, N298, P298, V298, I300 or L300.

In a preferred embodiment, in variant Fc Regions that bind an FcγR with an altered affinity, any amino acid modifications (e.g., substitutions) at any of positions 255, 256, 258, 267, 268, 269, 270, 272, 276, 278, 280, 283, 285, 286, 289, 290, 292, 293, 294, 295, 296, 298, 300, 301, 303, 305, 307, 309, 312, 320, 322, 326, 329, 330, 332, 331, 333, 334, 335, 337, 338, 339, 340, 359, 360, 373, 376, 416, 419, 430, 434, 435, 437, 438 or 439. Preferably, the variant Fc Region has any of the following residues: A256, N268, Q272, D286, Q286, S286, A290, S290, A298, M301, A312, E320, M320, Q320, R320, E322, A326, D326, E326, N326, S326, K330, T339, A333, A334, E334, H334, L334, M334, Q334, V334, K335, Q335, A359, A360 or A430.

In a different embodiment, in variant Fc Regions that bind an FcγR (via its Fc Region) with a reduced affinity, any amino acid modifications (e.g., substitutions) at any of positions 252, 254, 265, 268, 269, 270, 278, 289, 292, 293, 294, 295, 296, 298, 300, 301, 303, 322, 324, 327, 329, 333, 335, 338, 340, 373, 376, 382, 388, 389, 414, 416, 419, 434, 435, 437, 438 or 439.

In a different embodiment, in variant Fc Regions that bind an FcγR (via its Fc Region) with an enhanced affinity, any amino acid modifications (e.g., substitutions) at any of positions 280, 283, 285, 286, 290, 294, 295, 298, 300, 301, 305, 307, 309, 312, 315, 331, 333, 334, 337, 340, 360, 378, 398 or 430. In a different embodiment, in variant Fc Regions that binds FcγRIIA with an enhanced affinity, any of the following residues: A255, A256, A258, A267, A268, N268, A272, Q272, A276, A280, A283, A285, A286, D286, Q286, S286, A290, S290, M301, E320, M320, Q320, R320, E322, A326, D326, E326, S326, K330, A331, Q335, A337 or A430.

Preferred variants include one or more modifications at any of positions: 228, 230, 231, 232, 233, 234, 235, 239, 240, 241, 243, 244, 245, 247, 262, 263, 264, 265, 266, 271, 273, 275, 281, 284, 291, 296, 297, 298, 299, 302, 304, 305, 313, 323, 325, 326, 328, 330 or 332.

Particularly preferred variants include one or more modifications selected from groups A-AI:

| | |
|---|---|
| A | 228E, 228K, 228Y or 228G; |
| B | 230A, 230E, 230Y or 230G; |
| C | 231E, 231K, 231Y, 231P or 231G; |
| D | 232E, 232K, 232Y, 232G; |
| E | 233D; |
| F | 234I or 234F; |
| G | 235D, 235Q, 235P, 235I or 235V; |
| H | 239D, 239E, 239N or 239Q; |
| I | 240A, 240I, 240M or 240T; |
| J | 243R, 243, 243Y, 243L, 243Q, 243W, 243H or 243I; |
| K | 244H; |
| L | 245A; |
| M | 247G, 247V or 247L; |
| N | 262A, 262E, 262I, 262T, 262E or 262F; |
| O | 263A, 263I, 263M or 263T; |
| P | 264F, 264E, 264R, 264I, 264A, 264T or 264W; |
| Q | 265F, 265Y, 265H, 265I, 265L, 265T, 265V, 265N or 265Q; |
| R | 266A, 266I, 266M or 266T; |
| S | 271D, 271E, 271N, 271Q, 271K, 271R, 271S, 271T, 271H, 271A, 271V, 271L, 271I, 271F, 271M, 271Y, 271W or 271G; |
| T | 273I; |
| U | 275L or 275W; |
| V | 281D, 281K, 281Y or 281P; |
| W | 284E, 284N, 284T, 284L, 284Y or 284M; |
| X | 291D, 291E, 291Q, 291T, 291H, 291I or 291G; |
| Y | 299A, 299D, 299E, 299F, 299G, 299H, 299I, 299K, 299L, 299M, 299N, 299P, 299Q, 299R, 299S, 299V, 299W or 299Y; |
| Z | 302I; |
| AA | 304D, 304N, 304T, 304H or 304L |
| AB | 305I; |
| AC | 313F; |
| AD | 323I; |
| AE | 325A, 325D, 325E, 325G, 325H, 325I, 325L, 325K, 325R, 325S, 325F, 325M, 325T, 325V, 325Y, 325W or 325P; |
| AF | 328D, 328Q, 328K, 328R, 328S, 328T, 328V, 328I, 328Y, 328W, 328P, 328G, 328A, 328E, 328F, 328H, 328M or 328N; |
| AG | 330L, 330Y, 330I or 330V; |
| AH | 332A, 332D, 332E, 332H, 332N, 332Q, 332T, 332K, 332R, 332S, 332V, 332L, 332F, 332M, 332W, 332P, 332G or 332Y; and |
| AI | 336E, 336K or 336Y |

Still more particularly preferred variants include one or more modifications selected from Groups 1-105:

| Group | Variant |
|---|---|
| 1 | A330L/I332E |
| 2 | D265F/N297E/I332E |
| 3 | D265Y/N297D/I332E |
| 4 | D265Y/N297D/T299L/I332E |
| 5 | F241E/F243Q/V262T/V264F |
| 6 | F241E/F243Q/V262T/V264E/I332E |
| 7 | F241E/F243R/V262E/V264R |
| 8 | F241E/F243R/V262E/V264R/I332E |
| 9 | F241E/F243Y/V262T/V264R |
| 10 | F241E/F243Y/V262T/V264R/I332E |
| 11 | F241L/F243L/V262I/V264I |
| 12 | F241L/V262I |
| 13 | F241R/F243Q/V262T/V264R |
| 14 | F241R/F243Q/V262T/V264R/I332E |
| 15 | F241W/F243W/V262A/V264A |
| 16 | F241Y/F243Y/V262T/V264T |
| 17 | F241Y/F243Y/V262T/V264T/N297D/I332E |
| 18 | F243L/V262I/V264W |
| 19 | P243L/V264I |
| 20 | L328D/I332E |
| 21 | L328E/I332E |
| 22 | L328H/I332E |
| 23 | L328I/I332E |
| 24 | L328M/I332E |
| 25 | L328N/I332E |
| 26 | L328Q/I332E |
| 27 | L328T/I332E |
| 28 | L328V/I332E |
| 29 | N297D/A330Y/I332E |
| 30 | N297D/I332E |
| 31 | N297D/I332E/S239D/A330L |
| 32 | N297D/S298A/A330Y/I332E |
| 33 | N297D/T299L/I332E |
| 34 | N297D/T299F/I332E/N297D/T299H/I332E |
| 35 | N297D/T299I/I332E |
| 36 | N297D/T299L/I332E |
| 37 | N297D/T299V/I332E |
| 38 | N297E/I332E |
| 39 | N297S/I332E |

| Group | Variant |
|---|---|
| 40 | P230A/E233D/I332E |
| 41 | P244H/P245A/P247V |
| 42 | S239D/A330L/I332E |
| 43 | S239D/A330Y/I332E |
| 44 | S239D/A330Y/I332E/K326E |
| 45 | S239D/A330Y/I332E/K326T |
| 46 | S239D/A330Y/I332E/L234I |
| 47 | S239D/A330Y/I332E/L235D |
| 48 | S239D/A330Y/I332E/V240I |
| 49 | S239D/A330Y/I332E/V264T |
| 50 | S239D/A330Y/I332E/V266I |
| 51 | S239D/D265F/N297D/I332E |
| 52 | S239D/D265H/N297D/I332E |
| 53 | S239D/D265I/N297D/I332E |
| 54 | S239D/D265L/N297D/I332E |
| 55 | S239D/D265T/N297D/I332E |
| 56 | S239D/D265V/N297D/I332E |
| 57 | S239D/D265Y/N297D/I332E |
| 58 | S239D/I332D |
| 59 | S239D/I332E |
| 60 | S239D/I332E/A330I |
| 61 | S239D/I332N |
| 62 | S239D/I332Q |
| 63 | S239D/N297D/I332E |
| 64 | S239D/N297D/I332E/A330Y |
| 65 | S239D/N297D/I332E/A330Y/F241S/F243H/V262T/V264T |
| 66 | S239D/N297D/I332E/K326E |
| 67 | S239D/N297D/I332E/L235D |
| 68 | S239D/S298A/I332E |
| 69 | S239D/V264I/A330L/I332E |
| 70 | S239D/V264I/I332E |
| 71 | S239D/V264I/S298A/I332E |
| 72 | S239E/D265N |
| 73 | S239E/D265Q |
| 74 | S239E/I332D |
| 75 | S239E/I332E |
| 76 | S239E/I332N |
| 77 | S239E/I332Q |
| 78 | S239E/N297D/I332E |
| 79 | S239E/V264I/A330Y/I332E |
| 80 | S239E/V264I/I332E |
| 81 | S239E/V264I/S298A/A330Y/I332E |
| 82 | S239N/A330L/I332E |
| 83 | S239N/A330Y/I332E |
| 84 | S239N/I332D |
| 85 | S239N/I332E |
| 86 | S239N/I332N |
| 87 | S239N/I332Q |
| 88 | S239N1S298A/I332E |
| 89 | S239Q/I332D |
| 90 | S239Q/I332E |
| 91 | S239Q/I332N |
| 92 | S239Q/I332Q |
| 93 | S239Q/V264I/I332E |
| 94 | S298A/I332E |
| 95 | V264E/N297D/I332E |
| 96 | V264I/A330L/I332E |
| 97 | V264I/A330Y/I332E |
| 98 | V264I/I332E |
| 99 | V264I/S298A/I332E |
| 100 | Y296D/N297D/I332E |
| 101 | Y296E/N297D/I332E |
| 102 | Y296H/N297D/I332E |
| 103 | Y296N/N297D/I332E |
| 104 | Y296Q/N297I/I332E |
| 105 | Y296T/N297D/I332E |

In one embodiment, a PD-1-binding molecule of the invention will comprise a variant Fc Region having at least one modification in the Fc Region. In certain embodiments, the variant Fc Region comprises at least one substitution selected from the group consisting of L235V, F243L, R292P, Y300L, V305I, and P396L.

In a specific embodiment, the variant Fc Region comprises:
(A) at least one substitution selected from the group consisting of F243L, R292P, Y300L, V305I, and P396L;
(B) at least two substitutions selected from the group consisting of:
(1) F243L and P396L;
(2) F243L and R292P; and
(3) R292P and V305I;
(C) at least three substitutions selected from the group consisting of:
(1) F243L, R292P and Y300L;
(2) F243L, R292P and V305I;
(3) F243L, R292P and P396L; and
(4) R292P, V305I and P396L;
(D) at least four substitutions selected from the group consisting of:
(1) F243L, R292P, Y300L and P396L; and
(2) F243L, R292P, V305I and P396L; or
(E) at least the five substitutions selected from the group consisting of:
(1) F243L, R292P, Y300L, V305I and P396L; and
(2) L235V, F243L, R292P, Y300L and P396L.

In another specific embodiment, the variant Fc Region comprises substitutions of:
(A) F243L, R292P, and Y300L;
(B) L235V, F243L, R292P, Y300L, and P396L; or
(C) F243L, R292P, Y300L, V305I, and P396L.

In one embodiment, a PD-1-binding molecule of the invention comprises a variant Fc Region that exhibits decreased (or substantially no) binding to FcγRIA (CD64), FcγRIIA (CD32A), FcγRIIB (CD32B), FcγRIIIA (CD16a) or FcγRIIIB (CD16b) (relative to the binding exhibited by the wild-type IgG1 Fc Region (SEQ ID NO:1)). In one embodiment, a PD-1-binding molecule of the invention will comprise a variant Fc Region that exhibits reduced (or substantially no) binding to an FcγR (e.g., FcγRIIIA) and reduced (or substantially no) ADCC effector function. In certain embodiments, the variant Fc Region comprises at least one substitution selected from the group consisting of L234A, L235A, D265A,N297Q, and N297G. In a specific embodiment, the variant Fc Region comprises the substitution of L234A; L235A; L234A and L235A; D265A; N297Q, or N297G.

A preferred IgG1 sequence for the CH2 and CH3 Domains of the PD-1-binding molecules of the invention will have the L234A/L235A substitutions (SEQ ID NO:5):

```
APEAAGGPSV FLFPPKPKDT LMISRTPEVT CVVVDVSHED

PEVKFNWYVD GVEVHNAKTK PREEQYNSTY RVVSVLTVLH

QDWLNGKEYK CKVSNKALPA PIEKTISKAK GQPREPQVYT

LPPSREEMTK NQVSLTCLVK GFYPSDIAVE WESNGQPENN

YKTTPPVLDS DGSFFLYSKL TVDKSRWQQG NVFSCSVMHE

ALHNHYTQKS LSLSPGX
``` wherein, X is a lysine (K) or is absent.

In a different embodiment, a PD-1-binding molecule of the invention comprises an Fc Region which inherently exhibits decreased (or substantially no) binding to FcγRIIIA (CD16a) and/or reduced effector function (relative to the binding exhibited by the wild-type IgG1 Fc Region (SEQ ID NO:1)). In a specific embodiment, a PD-1-binding molecule of the present invention comprises an IgG2 Fc Region (SEQ ID NO:2) or an IgG4 Fc Region (SEQ ID:NO:4). When an IgG4 Fc Region in utilized, the instant invention also encompasses the introduction of a stabilizing mutation, such the IgG4 hinge region S228P substitution (see, e.g., SEQ ID NO:13: ESKYGPPCPPCP, (Lu et al., (2008) "*The Effect Of A Point Mutation On The Stability Of Igg4 As Monitored By Analytical Ultracentrifugation*," J. Pharmaceutical Sciences 97:960-969) to reduce the incidence of strand exchange. Other stabilizing mutations known in the art may be introduced into an IgG4 Fc Region (Peters, P et al., (2012) "*Engineering an Improved IgG4 Molecule with Reduced Disulfide Bond Heterogeneity and Increased Fab Domain Thermal Stability*," J. Biol. Chem., 287:24525-24533; PCT Patent Publication No: WO 2008/145142).

In other embodiments, the invention encompasses the use of any variant Fc Region known in the art, such as those disclosed in Jefferis, B. J. et al. (2002) "*Interaction Sites On Human IgG-Fc For FcgammaR: Current Models*," Immunol. Lett. 82:57-65; Presta, L. G. et al. (2002) "*Engineering Therapeutic Antibodies For Improved Function*," Biochem. Soc. Trans. 30:487-90; Idusogie, E. E. et al. (2001) "*Engineered Antibodies With Increased Activity To Recruit Complement*," J. Immunol. 166:2571-75; Shields, R. L. et al. (2001) "*High Resolution Mapping Of The Binding Site On Human IgG1 For Fc Gamma RI, Fc Gamma RII, Fc Gamma NIL And FcRn And Design Of IgG1 Variants With Improved Binding To The Fc gamma R*," J. Biol. Chem. 276:6591-6604; Idusogie, E. E. et al. (2000) "*Mapping Of The C1q Binding Site On Rituxan, A Chimeric Antibody With A Human IgG Fc*," J. Immunol. 164:4178-84; Reddy, M. P. et al. (2000) "*Elimination Of Fc Receptor-Dependent Effector Functions Of A Modified IgG4 Monoclonal Antibody To Human CD4*," J. Immunol. 164:1925-1933; Xu, D. et al. (2000) "*In Vitro Characterization of Five Humanized OKT3 Effector Function Variant Antibodies*," Cell. Immunol. 200: 16-26; Armour, K. L. et al. (1999) "*Recombinant human IgG Molecules Lacking Fcgamma Receptor I Binding And Monocyte Triggering Activities*," Eur. J. Immunol. 29:2613-24; Jefferis, R. et al. (1996) "*Modulation Of Fc(Gamma)R And Human Complement Activation By IgG3-Core Oligosaccharide Interactions*," Immunol. Lett. 54:101-04; Lund, J. et al. (1996) "*Multiple Interactions Of IgG With Its Core Oligosaccharide Can Modulate Recognition By Complement And Human Fc Gamma Receptor I And Influence The Synthesis Of Its Oligosaccharide Chains*," J. Immunol. 157:4963-4969; Hutchins et al. (1995) "*Improved Biodistribution, Tumor Targeting, And Reduced Immunogenicity In Mice With A Gamma 4 Variant Of Campath-1H*," Proc. Natl. Acad. Sci. (U.S.A.) 92:11980-84; Jefferis, R. et al. (1995) "*Recognition Sites On Human IgG For Fc Gamma Receptors: The Role Of Glycosylation*," Immunol. Lett. 44:111-17; Lund, J. et al. (1995) "*Oligosaccharide-Protein Interactions In IgG Can Modulate Recognition By Fc Gamma Receptors*," FASEB J. 9:115-19; Alegre, M. L. et al. (1994) "*A Non Activating "Humanized" Anti-CD3 Monoclonal Antibody Retains Immunosuppressive Properties In Vivo*," Transplantation 57:1537-1543; Lund et al. (1992) "*Multiple Binding Sites On The CH2 Domain Of IgG For Mouse Fc Gamma R11*," Mol. Immunol. 29:53-59; Lund et al. (1991) "*Human Fc Gamma RI And Fc Gamma RH Interact With Distinct But Overlapping Sites On Human IgG*," J. Immunol. 147:2657-2662; Duncan, A. R. et al. (1988) "*Localization Of The Binding Site For The Human High-Affinity Fc Receptor On IgG*," Nature 332:563-564; U.S. Pat. Nos. 5,624,821; 5,885,573; 6,194,551; 7,276,586; and 7,317,091; and PCT Publications WO 00/42072 and PCT WO 99/58572.

In some embodiments, the molecules of the invention further comprise one or more glycosylation sites, so that one or more carbohydrate moieties are covalently attached to the molecule. Preferably, the molecules of the invention with one or more glycosylation sites and/or one or more modifications in the Fc Region confer or have an enhanced antibody mediated effector function, e.g., enhanced ADCC activity, compared to the unmodified antibody. In some embodiments, the invention further comprises molecules comprising one or more modifications of amino acids that are directly or indirectly known to interact with a carbohydrate moiety of the Fc Region, including but not limited to amino acids at positions 241, 243, 244, 245, 245, 249, 256, 258, 260, 262, 264, 265, 296, 299, and 301. Amino acids that directly or indirectly interact with a carbohydrate moiety of an Fc Region are known in the art, see, e.g., Jefferis et al., 1995 *Immunology Letters,* 44: 111-7, which is incorporated herein by reference in its entirety.

In another embodiment, the invention encompasses molecules that have been modified by introducing one or more glycosylation sites into one or more sites of the molecules, preferably without altering the functionality of the molecules, e.g., binding activity to target antigen or FcγR. Glycosylation sites may be introduced into the variable and/or constant region of the molecules of the invention. As used herein, "glycosylation sites" include any specific amino acid sequence in an antibody to which an oligosaccharide (i.e., carbohydrates containing two or more simple sugars linked together) will specifically and covalently attach. Oligosaccharide side chains are typically linked to the backbone of an antibody via either N- or O-linkages. N-linked glycosylation refers to the attachment of an oligosaccharide moiety to the side chain of an asparagine residue. O-linked glycosylation refers to the attachment of an oligosaccharide moiety to a hydroxyamino acid, e.g., serine, threonine. The molecules of the invention may comprise one or more glycosylation sites, including N-linked and O-linked glycosylation sites. Any glycosylation site for N-linked or O-linked glycosylation known in the art may be used in accordance with the instant invention. An exemplary N-linked glycosylation site that is useful in accordance with the methods of the present invention is the amino acid sequence: Asn-X-Thr/Ser, wherein X may be any amino acid and Thr/Ser indicates a threonine or a serine. Such a site or sites may be introduced into a molecule of the invention using methods well known in the art to which this invention pertains (see for example, IN VITRO MUTAGENESIS, RECOMBINANT DNA: A SHORT COURSE, J. D. Watson, et al. W. H. Freeman and Company, New York, 1983, chapter 8, pp. 106-116, which is incorporated herein by reference in its entirety. An exemplary method for introducing a glycosylation site into a molecule of the invention may comprise: modifying or mutating an amino acid sequence of the molecule so that the desired Asn-X-Thr/Ser sequence is obtained.

In some embodiments, the invention encompasses methods of modifying the carbohydrate content of a molecule of the invention by adding or deleting a glycosylation site. Methods for modifying the carbohydrate content of antibodies (and molecules comprising antibody domains, e.g., Fc Region) are well known in the art and encompassed within the invention, see, e.g., U.S. Pat. No. 6,218,149; EP 0 359 096 B1; U.S. Publication No. US 2002/0028486; WO 03/035835; U.S. Publication No. 2003/0115614; U.S. Pat. Nos. 6,218,149; 6,472,511; all of which are incorporated herein by reference in their entirety. In other embodiments, the invention encompasses methods of modifying the carbohydrate content of a molecule of the invention by deleting one or more endogenous carbohydrate moieties of the molecule. In a specific embodiment, the invention encompasses shifting the glycosylation site of the Fc Region of an antibody, by modifying positions adjacent to 297. In a specific embodiment, the invention encompasses modifying position 296 so that position 296 and not position 297 is glycosylated.

Effector function can also be modified by techniques such as by introducing one or more cysteine residues into the Fc Region, thereby allowing interchain disulfide bond formation in this region to occur, resulting in the generation of a homodimeric antibody that may have improved internalization capability and/or increased complement-mediated cell killing and ADCC (Caron, P. C. et al. (1992) "*Engineered Humanized Dimeric Forms Of IgG Are More Effective Antibodies*," J. Exp. Med. 176:1191-1195; Shopes, B. (1992) "*A Genetically Engineered Human IgG Mutant With Enhanced Cytolytic Activity*," J. Immunol. 148(9):2918-2922. Homodimeric antibodies with enhanced antitumor activity may also be prepared using heterobifunctional cross-linkers as described in Wolff, E. A. et al. (1993) "*Monoclonal Antibody Homodimers: Enhanced Antitumor Activity In Nude Mice*," Cancer Research 53:2560-2565. Alternatively, an antibody can be engineered which has dual Fc Regions and may thereby have enhanced complement lysis and ADCC capabilities (Stevenson, G. T. et al. (1989) "*A Chimeric Antibody With Dual Fc Regions (bisFabFc) Prepared By Manipulations At The IgG Hinge*," Anti-Cancer Drug Design 3:219-230).

The serum half-life of the molecules of the present invention comprising Fc Regions may be increased by increasing the binding affinity of the Fc Region for FcRn. The term "half-life" as used herein means a pharmacokinetic property of a molecule that is a measure of the mean survival time of the molecules following their administration. Half-life can be expressed as the time required to eliminate fifty percent (50%) of a known quantity of the molecule from a subject's body (e.g., human patient or other mammal) or a specific compartment thereof, for example, as measured in serum, i.e., circulating half-life, or in other tissues. In general, an increase in half-life results in an increase in mean residence time (MRT) in circulation for the molecule administered.

In some embodiments, the PD-1-binding molecules of the present invention comprise a variant Fc Region, wherein said variant Fc Region comprises at least one amino acid modification relative to a wild-type Fc Region, such that said molecule has an increased half-life (relative to a wild-type Fc Region).

In some embodiments, the PD-1-binding molecules of the present invention comprise a variant Fc Region, wherein said variant Fc Region comprises a half-live extending amino acid substitution at one or more positions selected from the group consisting of 238, 250, 252, 254, 256, 257, 256, 265, 272, 286, 288, 303, 305, 307, 308, 309, 311, 312, 317, 340, 356, 360, 362, 376, 378, 380, 382, 413, 424, 428, 433, 434, 435, and 436. Numerous specific mutations capable of increasing the half-life of an Fc Region-containing molecule are known in the art and include, for example M252Y, S254T, T256E, and combinations thereof. For example, see the mutations described in U.S. Pat. Nos. 6,277,375, 7,083,784; 7,217,797, 8,088,376; U.S. Publication Nos. 2002/0147311; 2007/0148164; and International Publication Nos. WO 98/23289; WO 2009/058492; and WO 2010/033279, which are herein incorporated by reference in their entireties. Fc Region-containing molecules with enhanced half-life also include those with substitutions at two or more of Fc Region residues 250, 252, 254, 256, 257, 288, 307, 308, 309, 311, 378, 428, 433, 434, 435 and 436. In particular, two or more substitutions selected from: T250Q, M252Y, S254T, T256E, K288D, T307Q, V308P, A378V, M428L, N434A, H435K, and Y436I.

In a specific embodiment, the variant Fc Region comprises substitutions of:
  (A) M252Y, S254T and T256E;
  (B) M252Y and S254T;
  (C) M252Y and T256E;
  (D) T250Q and M428L;
  (E) T307Q and N434A;
  (F) A378V and N434A;
  (G) N434A and Y436I;
  (H) V308P and N434A; or
  (I) K288D and H435K.

The instant invention further encompasses variant Fc Regions comprising:
  (A) one or more mutations which alter effector function and/or FcγR; and
  (B) one or more mutations which extend serum half-life.

VI. Bispecific Anti-Human PD-1-Binding Molecules

One embodiment of the present invention relates to bispecific binding molecules that are capable of binding to a "first epitope" and a "second epitope," wherein the first epitope is an epitope of human PD-1 and the second epitope is the same or a different epitope of PD-1, or is an epitope of another molecule that is present on the surface of an immune cell (such as a T lymphocyte) and is involved in regulating an immune checkpoint. In one embodiment, the second epitope is an epitope of B7-H3, B7-H4, BTLA, CD3, CD8, CD16, CD27, CD32, CD40, CD40L, CD47, CD64, CD70, CD80, CD86, CD94, CD137, CD137L, CD226, CTLA-4, Galectin-9, GITR, GITRL, HHLA2, ICOS, ICOSL, KIR, LAG-3, LIGHT, MHC class I or II, NKG2a, NKG2d, OX40, OX40L, PD1H, PD-1, PD-L1, PD-L2, PVR, SIRPa, TCR, TIGIT, TIM-3 or VISTA. In one embodiment, the second epitope not an epitope of PD-1. In a specific embodiment, the second epitope is CD137, CTLA-4, LAG-3, OX40, TIGIT, or TIM-3. In certain embodiments, a bispecific molecule comprises more than two epitope binding sites. Such bispecific molecules may bind two or more different epitopes of LAG-3 and at least one epitope of a molecule that is not LAG-3.

The instant invention encompasses bispecific antibodies capable of simultaneously binding to PD-1 and the second epitope (e.g. B7-H3, B7-H4, BTLA, CD40, CD80, CD86, CD137, CTLA-4, ICOS, KIR, LAG-3, MHC class I or II, OX40, PD-L1, TCR, TIM-3, etc.). In some embodiments, the bispecific antibody capable of simultaneously binding to PD-1 and the second epitope is produced using any of the methods described in PCT Publication Nos. WO 1998/002463, WO 2005/070966, WO 2006/107786 WO 2007/024715, WO 2007/075270, WO 2006/107617, WO 2007/046893, WO 2007/146968, WO 2008/003103, WO 2008/003116, WO 2008/027236, WO 2008/024188, WO 2009/132876, WO 2009/018386, WO 2010/028797, WO2010028796, WO 2010/028795, WO 2010/108127, WO 2010/136172, WO 2011/086091, WO 2011/133886, WO 2012/009544, WO 2013/003652, WO 2013/070565, WO 2012/162583, WO 2012/156430, WO 2013/174873, and WO 2014/022540, each of which is hereby incorporated herein by reference in its entirety.

A. Bispecific Diabodies Lacking Fc Regions

One embodiment of the present invention relates to bispecific diabodies that comprise, and most preferably are composed of, a first polypeptide chain and a second polypeptide chain, whose sequences permit the polypeptide chains to covalently bind to each other to form a covalently associated diabody that is capable of simultaneously binding to a first epitope and a second epitope, such epitopes not being identical to one another. Such bispecific diabodies thus comprise "VL1"/"VH1" domains that are capable of binding to the first epitope and "VL2"/"VH2" domains that are capable of binding to the second epitope. The notation "VL1" and "VH1" denote respectively, the Variable Light Chain Domain and Variable Heavy Chain Domain that bind the "first" epitope of such bispecific diabody. Similarly, the notation "VL2" and "VH2" denote respectively, the Variable Light Chain Domain and Variable Heavy Chain Domain that bind the "second" epitope of such bispecific diabody. It is irrelevant whether a particular epitope is designated as the first vs. the second epitope; such notation having relevance only with respect to the presence and orientation of domains of the polypeptide chains of the binding molecules of the present invention. In one embodiment, one of such epitopes is an epitope of PD-1 and the other of such epitopes is not an epitope of PD-1 (for example, an epitope of B7-H3, B7-H4, BTLA, CD40, CD80, CD86, CD137, CTLA-4, ICOS, KIR, LAG-3, MEW class I or II, OX40, PD-L1, TCR, TIM-3, etc.).

The VL Domain of the first polypeptide chain interacts with the VH Domain of the second polypeptide chain to form a first functional antigen-binding site that is specific for a first antigen (i.e., either PD-1 or an antigen that contains the second epitope). Likewise, the VL Domain of the second polypeptide chain interacts with the VH Domain of the first polypeptide chain in order to form a second functional antigen-binding site that is specific for a second antigen (i.e., either an antigen that contains the second epitope or PD-1). Thus, the selection of the VL and VH Domains of the first and second polypeptide chains is coordinated, such that the two polypeptide chains of the diabody collectively comprise VL and VH Domains capable of binding to both an epitope of PD-1 and to the second epitope (i.e., they comprise $VL_{PD-1}/VH_{PD-1}$ and VL2/VH2, wherein PD-1 is the "first" epitope, or VL1/VH1 and $VL_{PD-1}/VH_{PD-1}$, wherein PD-1 is the "second" epitope).

The first polypeptide chain of an embodiment of such bispecific diabodies comprises, in the N-terminal to C-terminal direction, an N-terminus, the VL1 Domain of a monoclonal antibody capable of binding to either the first or second epitope (i.e., either $VL_{PD-1}$ or $VL_{Epitope\ 2}$), a first intervening spacer peptide (Linker 1), a VH2 Domain of a monoclonal antibody capable of binding to either the second epitope (if such first polypeptide chain contains $VL_{PD-1}$) or the first epitope (if such first polypeptide chain contains $VL_{Epitope\ 2}$), a second intervening spacer peptide (Linker 2) optionally containing a cysteine residue, a Heterodimer-Promoting Domain and a C-terminus (FIG. 1).

The second polypeptide chain of this embodiment of bispecific diabodies comprises, in the N-terminal to C-terminal direction, an N-terminus, a VL2 Domain of a monoclonal antibody capable of binding to either PD-1 or the second epitope (i.e., either $VL_{PD-1}$ or $VL_{Epitope\ 2}$, and being the VL Domain not selected for inclusion in the first polypeptide chain of the diabody), an intervening linker peptide (Linker 1), a VH1 Domain of a monoclonal antibody capable of binding to either the second epitope (if such second polypeptide chain contains $VL_{PD-1}$) or to PD-1 (if such second polypeptide chain contains $VL_{Epitope\ 2}$), a second intervening spacer peptide (Linker 2) optionally containing a cysteine residue, a Heterodimer-Promoting Domain, and a C-terminus (FIG. 1).

Most preferably, the length of the intervening linker peptide (e.g., Linker 1) that separates such VL and VH Domains is selected to substantially or completely prevent the VL and VH Domains of the polypeptide chain from binding to one another. Thus the VL and VH Domains of the first polypeptide chain are substantially or completely incapable of binding to one another. Likewise, the VL and VH Domains of the second polypeptide chain are substantially or completely incapable of binding to one another. A preferred intervening spacer peptide (Linker 1) has the sequence (SEQ ID NO:14): GGGSGGGG.

The length and composition of the second intervening linker peptide (Linker 2) is selected based on the choice of heterodimer-promoting domains. Typically, the second intervening linker peptide (Linker 2) will comprise 3-20 amino acid residues. In particular, where the heterodimer-promoting domains do not comprise a cysteine residue a cysteine-containing second intervening linker peptide (Linker 2) is utilized. A cysteine-containing second intervening spacer peptide (Linker 2) will contain 1, 2, 3 or more cysteines. A preferred cysteine-containing spacer peptide (Linker 2) has the sequence is SEQ ID NO:15: GGCGGG. Alternatively, Linker 2 does not comprise a cysteine (e.g., GGG, GGGS (SEQ ID NO:29), LGGGSG (SEQ ID NO:261), GGGSGGGSGGG (SEQ ID NO:262), ASTKG (SEQ ID NO:30), LEPKSS (SEQ ID NO:33), APSSS (SEQ ID NO:34), etc.) and a Cysteine-Containing Heterodimer-Promoting Domain, as described below is used. Optionally, both a cysteine-containing Linker 2 and a cysteine-containing Heterodimer-Promoting Domain are used.

The Heterodimer-Promoting Domains may be GVEPKSC (SEQ ID NO:16) or VEPKSC (SEQ ID NO:17) or AEPKSC (SEQ ID NO:18) on one polypeptide chain and GFNRGEC (SEQ ID NO:19) or FNRGEC (SEQ ID NO:20) on the other polypeptide chain (US2007/0004909).

More preferably, however, the Heterodimer-Promoting Domains of such diabodies are formed from one, two, three or four tandemly repeated coil domains of opposing charge that comprise a sequence of at least six, at least seven or at least eight amino acid residues such that the Heterodimer-Promoting Domain possesses a net charge (Apostolovic, B. et al. (2008) "*pH-Sensitivity of the E3/K3 Heterodimeric Coiled Coil,*" Biomacromolecules 9:3173-3180; Arndt, K. M. et al. (2001) "*Helix-stabilized Fv (hsFv) Antibody Fragments: Substituting the Constant Domains of a Fab Fragment for a Heterodimeric Coiled-coil Domain,*" J. Molec. Biol. 312:221-228; Arndt, K. M. et al. (2002) "*Comparison of In Vivo Selection and Rational Design of Heterodimeric Coiled Coils,*" Structure 10:1235-1248; Boucher, C. et al. (2010) "*Protein Detection By Western Blot Via Coiled-Coil Interactions,*" Analytical Biochemistry 399:138-140; Cachia, P. J. et al. (2004) "*Synthetic Peptide Vaccine Development: Measurement Of Polyclonal Antibody Affinity And Cross Reactivity Using A New Peptide Capture And Release System For Surface Plasmon Resonance Spectroscopy,*" J. Mol. Recognit. 17:540-557; De Crescenzo, G. D. et al. (2003) "*Real-Time Monitoring of the Interactions of Two-Stranded de novo Designed Coiled-Coils: Effect of Chain Length on the Kinetic and Thermodynamic Constants of Binding,*" Biochemistry 42:1754-1763; Fernandez-Rodriquez, J. et al. (2012) "*Induced Heterodimerization And Purification Of Two Target Proteins By A Synthetic Coiled-Coil Tag,*" Protein Science 21:511-519; Ghosh, T. S. et al. (2009) "*End-To-End And End-To-Middle Interhelical Interactions: New Classes Of Interacting Helix Pairs In Protein Structures,*" Acta Crystallographica D65:1032-1041; Grigoryan, G. et al. (2008) "*Structural Specificity In Coiled-Coil*

Interactions," Curr. Opin. Struc. Biol. 18:477-483; Litowski, J. R. et al. (2002) "*Designing Heterodimeric Two-Stranded a-Helical Coiled-Coils: The Effects Of Hydrophobicity And a-Helical Propensity On Protein Folding, Stability, And Specificity*," J. Biol. Chem. 277:37272-37279; Steinkruger, J. D. et al. (2012) "*The d'-d-d' Vertical Triad is Less Discriminating Than the a'-a-a' Vertical Triad in the Antiparallel Coiled-coil Dimer Motif*," J. Amer. Chem. Soc. 134(5):2626-2633; Straussman, R. et al. (2007) "*Kinking the Coiled Coil—Negatively Charged Residues at the Coiled-coil Interface*," J. Molec. Biol. 366:1232-1242; Tripet, B. et al. (2002) "*Kinetic Analysis of the Interactions between Troponin C and the C-terminal Troponin I Regulatory Region and Validation of a New Peptide Delivery/Capture System used for Surface Plasmon Resonance*," J. Molec. Biol. 323:345-362; Woolfson, D. N. (2005) "*The Design Of Coiled-Coil Structures And Assemblies*," Adv. Prot. Chem. 70:79-112; Zeng, Y. et al. (2008) "*A Ligand-Pseudoreceptor System Based On de novo Designed Peptides For The Generation Of Adenoviral Vectors With Altered Tropism*," J. Gene Med. 10:355-367).

Such repeated coil domains may be exact repeats or may have substitutions. For example, the coil domain of the Heterodimer-Promoting Domain of the first polypeptide chain may comprise a sequence of eight amino acid residues selected to confer a negative charge to such Heterodimer-Promoting Domain, and the coil domain of the Heterodimer-Promoting Domain of the second polypeptide chain may comprise a sequence of eight amino acid residues selected to confer a positive charge to such Heterodimer-Promoting Domain. It is immaterial which coil is provided to the first or second polypeptide chains, provided that a coil of opposite charge is used for the other polypeptide chain. The positively charged amino acid may be lysine, arginine, histidine, etc. and/or the negatively charged amino acid may be glutamic acid, aspartic acid, etc. The positively charged amino acid is preferably lysine and/or the negatively charged amino acid is preferably glutamic acid. It is possible for only a single Heterodimer-Promoting Domain to be employed (since such domain will inhibit homodimerization and thereby promote heterodimerization), however, it is preferred for both the first and second polypeptide chains of the diabodies of the present invention to contain Heterodimer-Promoting Domains.

In a preferred embodiment, one of the Heterodimer-Promoting Domains will comprise four tandem "E-coil" helical domains (SEQ ID NO:21: EVAALEK-EVAALEK-EVAALEK-EVAALEK), whose glutamate residues will form a negative charge at pH 7, while the other of the Heterodimer-Promoting Domains will comprise four tandem "K-coil" domains (SEQ ID NO:22: KVAALKE-KVAALKE-KVAALKE-KVAALKE), whose lysine residues will form a positive charge at pH 7. The presence of such charged domains promotes association between the first and second polypeptides, and thus fosters heterodimer formation. Especially preferred is a Heterodimer-Promoting Domain in which one of the four tandem "E-coil" helical domains of SEQ ID NO:21 has been modified to contain a cysteine residue: EVAACEK-EVAALEK-EVAALEK-EVAALEK (SEQ ID NO:23). Likewise, especially preferred is a Heterodimer-Promoting Domain in which one of the four tandem "K-coil" helical domains of SEQ ID NO:22 has been modified to contain a cysteine residue: KVAACKE-KVAALKE-KVAALKE-KVAALKE (SEQ ID NO:24).

As disclosed in WO 2012/018687, in order to improve the in vivo pharmacokinetic properties of diabodies, a diabody may be modified to contain a polypeptide portion of a serum-binding protein at one or more of the termini of the diabody. Most preferably, such polypeptide portion of a serum-binding protein will be installed at the C-terminus of the diabody. Albumin is the most abundant protein in plasma and has a half-life of 19 days in humans. Albumin possesses several small molecule binding sites that permit it to non-covalently bind to other proteins and thereby extend their serum half-lives. The Albumin-Binding Domain 3 (ABD3) of protein G of *Streptococcus* strain G148 consists of 46 amino acid residues forming a stable three-helix bundle and has broad albumin-binding specificity (Johansson, M. U. et al. (2002) "*Structure, Specificity, And Mode Of Interaction For Bacterial Albumin-Binding Modules*," J. Biol. Chem. 277(10):8114-8120. Thus, a particularly preferred polypeptide portion of a serum-binding protein for improving the in vivo pharmacokinetic properties of a diabody is the Albumin-Binding Domain (ABD) from streptococcal protein G, and more preferably, the Albumin-Binding Domain 3 (ABD3) of protein G of *Streptococcus dysgalactiae* strain G148 (SEQ ID NO:25): LAEAKVLANR ELDKYGVSDY YKNLIDNAKS AEGVKALIDE ILAALP.

As disclosed in WO 2012/162068 (herein incorporated by reference), "deimmunized" variants of SEQ ID NO:25 have the ability to attenuate or eliminate MHC class II binding. Based on combinational mutation results, the following combinations of substitutions are considered to be preferred substitutions for forming such a deimmunized ABD: 66D/70S+71A; 66S/70S+71A; 66S/70S+79A; 64A/65A/71A; 64A/65A/71A+66S; 64A/65A/71A+66D; 64A/65A/71A+66E; 64A/65A/79A+66S; 64A/65A/79A+66D; 64A/65A/79A+66E. Variant ABDs having the modifications L64A, I65A and D79A or the modifications N66S, T70S and D79A. Variant deimmunized ABD having the amino acid sequence:

```
                                       (SEQ ID NO: 26)
LAEAKVLANR ELDKYGVSDY YKNLID₆₆NAKS₇₀ A₇₁EGVKALIDE

ILAALP, or the amino acid sequence:
                                       (SEQ ID NO: 27)
LAEAKVLANR ELDKYGVSDY YKNA₆₄A₆₅NNAKT VEGVKALIA₇₉E

ILAALP, or the amino acid sequence:
                                       (SEQ ID NO: 28)
LAEAKVLANR ELDKYGVSDY YKNLIS₆₆NAKS₇₀ VEGVKALIA₇₉E

ILAALP,
``` are particularly preferred as such deimmunized ABD exhibit substantially wild-type binding while providing attenuated MHC class II binding. Thus, the first polypeptide chain of such a diabody having an ABD contains a peptide linker preferably positioned C-terminally to the E-coil (or K-coil) Domain of such polypeptide chain so as to intervene between the E-coil (or K-coil) Domain and the ABD (which is preferably a deimmunized ABD). A preferred sequence for such a peptide linker is SEQ ID NO:29: GGGS.

B. Bispecific Diabodies Containing Fc Regions

Figure 2:
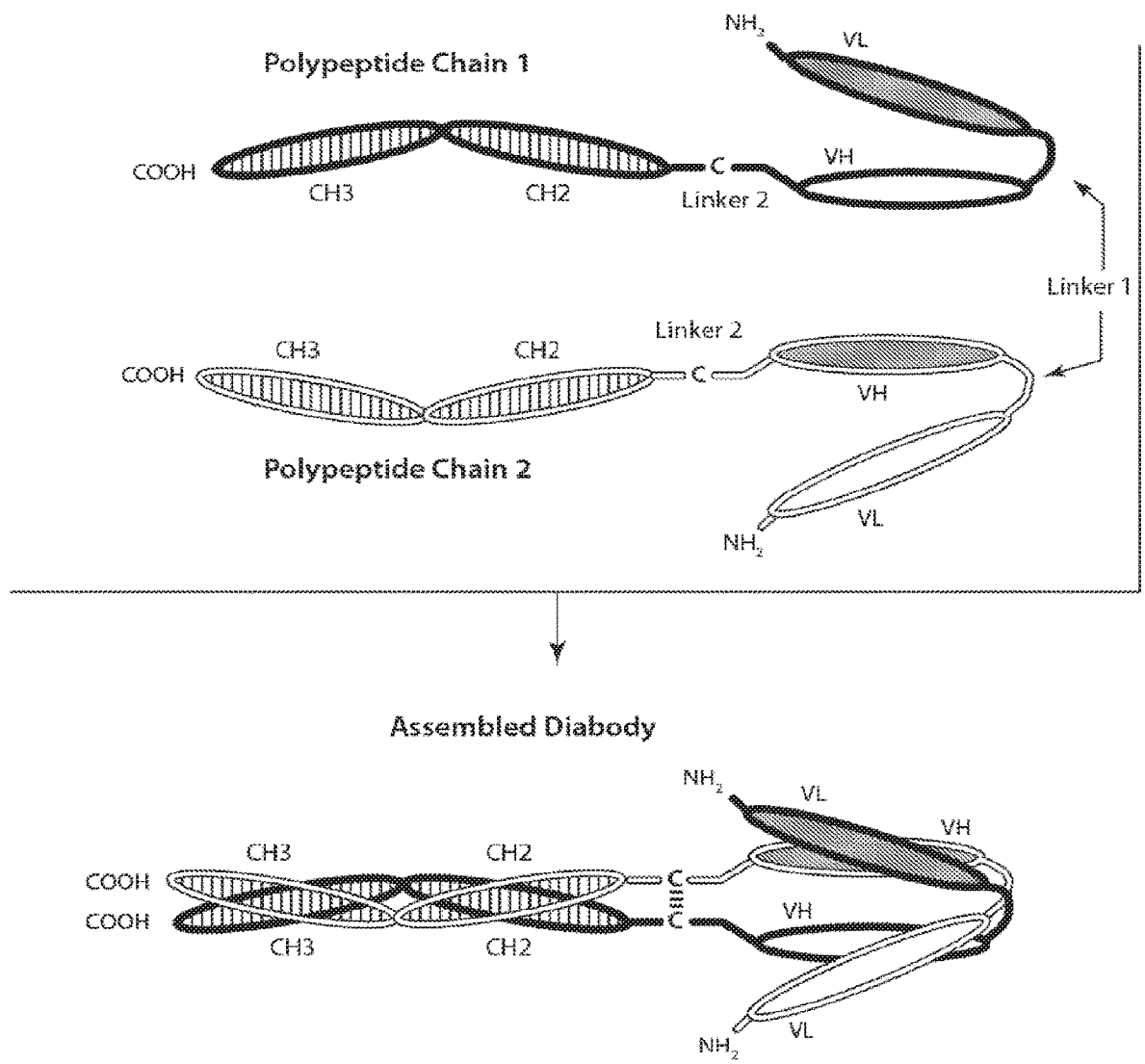
FIG. 2 provides a schematic of a representative covalently bonded diabody molecule having two epitope-binding sites composed of two polypeptide chains, each having a CH2 and CH3 Domain, such that the associated chains form all or part of an Fc Region. VL and VH Domains that recognize the same epitope are shown using the same shading or fill pattern.

One embodiment of the present invention relates to bispecific diabodies comprising an Fc Region capable of simultaneously binding to PD-1 and a second epitope (e.g. B7-H3, B7-H4, BTLA, CD40, CD80, CD86, CD137, CTLA-4, ICOS, KIR, LAG-3, MEW class I or II, OX40, PD-1, PD-L1, TCR, TIM-3, etc.). The addition of an IgG CH2-CH3 Domain to one or both of the diabody polypeptide chains, such that the complexing of the diabody chains results in the formation of an Fc Region, increases the biological half-life and/or alters the valency of the diabody. Incorporating an IgG CH2-CH3 Domains onto both of the diabody polypeptides will permit a two-chain bispecific Fc-Region-containing diabody to form (FIG. 2).

Alternatively, incorporating an IgG CH2-CH3 Domains onto only one of the diabody polypeptides will permit a more complex four-chain bispecific Fc Region-containing diabody to form (FIGS. 3A-3C). FIG. 3C shows a representative four-chain diabody possessing the Constant Light (CL) Domain and the Constant Heavy CH1 Domain, however fragments of such domains as well as other polypeptides may alternatively be employed (see, e.g., FIGS. 3A and 3B, United States Patent Publications No. 2013-0295121; 2010-0174053 and 2009-0060910; European Patent Publication No. EP 2714079; EP 2601216; EP 2376109; EP 2158221 and PCT Publications No. WO 2012/162068; WO 2012/018687; WO 2010/080538). Thus, for example, in lieu of the CH1 Domain, one may employ a peptide having the amino acid sequence GVEPKSC (SEQ ID NO:16) VEPKSC (SEQ ID NO:17), or AEPKSC (SEQ ID NO:18), derived from the hinge domain of a human IgG, and in lieu of the CL Domain, one may employ the C-terminal 6 amino acids of the human kappa light chain, GFNRGEC (SEQ ID NO:19) or FNRGEC (SEQ ID NO:20). A representative peptide containing four-chain diabody is shown in FIG. 3A. Alternatively, or in addition, one may employ a peptide comprising tandem coil domains of opposing charge such as the "E-coil" helical domains (SEQ ID NO:21: EVAALEK-EVAALEK-EVAALEK-EVAALEK or SEQ ID NO:23: EVAACEK-EVAALEK-EVAALEK-EVAALEK); and the "K-coil" domains (SEQ ID NO:22: KVAALKE-KVAAL KE-KVAALKE-KVAALKE or SEQ ID NO:24: KVAACKE KVAALKE-KVAALKE-KVAALKE). A representative coil domain containing four-chain diabody is shown in FIG. 3B.

The Fc Region-containing diabody molecules of the present invention generally include additional intervening linker peptides (Linkers). Typically, the additional Linkers will comprise 3-20 amino acid residues. Additional or alternative linkers that may be employed in the Fc Region-containing diabody molecules of the present invention include: GGGS (SEQ ID NO:29), LGGGSG (SEQ ID NO:261), GGGSGGGSGGG (SEQ ID NO:262), ASTKG (SEQ ID NO:30), DKTHTCPPCP (SEQ ID NO:31), EPKSCDKTH-TCPPCP (SEQ ID NO:32), LEPKSS (SEQ ID NO:33), APSSS (SEQ ID NO:34), and APSSSPME (SEQ ID NO:35), LEPKSADKTHTCPPC (SEQ ID NO:36), GGC, and GGG. SEQ ID NO:33 may be used in lieu of GGG or GGC for ease of cloning. Additionally, the amino acids GGG, or SEQ ID NO:33 may be immediately followed by SEQ ID NO:31 to form the alternate linkers: GGGDKTH-TCPPCP (SEQ ID NO:263); and LEPKSSDKTHTCPPCP (SEQ ID NO:37). Fc Region-containing diabody molecule of the present invention may incorporate an IgG hinge region in addition to or in place of a linker. Exemplary hinge regions include: EPKSCDKTHTCPPCP (SEQ ID NO:32) from IgG1, ERKCCVECPPCP (SEQ ID NO:11) from IgG2, ESKYGPPCPSCP (SEQ ID NO:12) from IgG4, and ESKY-GPPCPPCP (SEQ ID NO:13) an IgG4 hinge variant comprising a stabilizing substitute to reduce strand exchange.

As provided in FIG. 3A-3C, diabodies of the invention may comprise four different chains. The first and third polypeptide chains of such a diabody contain three domains: (i) a VL1-containing Domain, (ii) a VH2-containing Domain, (iii) Heterodimer-Promoting Domain and (iv) a Domain containing a CH2-CH3 sequence. The second and fourth polypeptide chains contain: (i) a VL2-containing Domain, (ii) a VH1-containing Domain and (iii) a Heterodimer-Promoting Domain, where the Heterodimer-Promoting Domains promote the dimerization of the first/third polypeptide chains with the second/fourth polypeptide chains. The VL and/or VH Domains of the third and fourth polypeptide chains, and VL and/or VH Domains of the first and second polypeptide chains may be the same or different so as to permit tetravalent binding that is either monospecific, bispecific or tetraspecific. The notation "VL3" and "VH3" denote respectively, the Variable Light Chain Domain and Variable Heavy Chain Domain that bind the "third" epitope of such diabody. Similarly, the notation "VL4" and "VH4" denote respectively, the Variable Light Chain Domain and Variable Heavy Chain Domain that bind the "fourth" epitope of such diabody. The general structure of the polypeptide chains of a representative four-chain Fc Region-containing diabodies of invention is provided in Table 2:

TABLE 2

| | | |
|---|---|---|
| Bispecific | 2nd Chain | $NH_2$—VL2—VH1—HPD—COOH |
| | 1st Chain | $NH_2$—VL1—VH2—HPD—CH2—CH3—COOH |
| | 1st Chain | $NH_2$—VL1—VH2—HPD—CH2—CH3—COOH |
| | 2nd Chain | $NH_2$—VL2—VH1—HPD—COOH |
| Tetra-specific | 2nd Chain | $NH_2$—VL2—VH1—HPD—COOH |
| | 1st Chain | $NH_2$—VL1—VH2—HPD—CH2—CH3—COOH |
| | 3rd Chain | $NH_2$—VL3—VH4—HPD—CH2—CH3—COOH |
| | 4th Chain | $NH_2$—VL4—VH3—HPD—COOH |

HPD = Heterodimer-Promoting Domain

In a specific embodiment, diabodies of the present invention are bispecific, tetravalent (i.e., possess four epitope-binding sites), Fc-containing diabodies (FIGS. 3A-3C) that are composed of four total polypeptide chains. The bispecific, tetravalent, Fc-containing diabodies of the invention comprise two epitope-binding sites immunospecific for PD-1 (which may be capable of binding to the same epitope of PD-1 or to different epitopes of PD-1), and two epitope-binding sites specific for a second epitope (e.g., B7-H3, B7-H4, BTLA, CD40, CD80, CD86, CD137, CTLA-4, ICOS, KIR, LAG-3 MHC class I or II, OX40, PD-L1, TCR, TIM-3, etc.).

In a further embodiment, the bispecific Fc Region-containing diabodies may comprise three polypeptide chains. The first polypeptide of such a diabody contains three domains: (i) a VL1-containing Domain, (ii) a VH2-containing Domain and (iii) a Domain containing a CH2-CH3 sequence. The second polypeptide of such diabodies contains: (i) a VL2-containing Domain, (ii) a VH1-containing Domain and (iii) a Domain that promotes heterodimerization and covalent bonding with the diabody's first polypeptide chain. The third polypeptide of such diabodies comprises a CH2-CH3 sequence. Thus, the first and second polypeptide chains of such diabodies associate together to form a VL1/VH1 binding site that is capable of binding to the first epitope, as well as a VL2/VH2 binding site that is capable of binding to the second epitope. The first and second polypeptides are bonded to one another through a disulfide bond involving cysteine residues in their respective Third Domains. Notably, the first and third polypeptide chains complex with one another to form an Fc Region that is stabilized via a disulfide bond. Such diabodies have enhanced potency. FIGS. 4A and 4B illustrate the structures of such diabodies. Such Fc-Region-containing bispecific diabodies may have either of two orientations (Table 3):

TABLE 3

| | | |
|---|---|---|
| First Orientation | 3$^{rd}$ Chain | NH$_2$—CH2—CH3—COOH |
| | 1$^{st}$ Chain | NH$_2$—VL1—VH2—HPD—CH2—CH3—COOH |
| | 2$^{nd}$ Chain | NH$_2$—VL2—VH1—HPD-COOH |
| Second Orientation | 3$^{rd}$ Chain | NH$_2$—CH2—CH3—COOH |
| | 1$^{st}$ Chain | NH$_2$—CH2—CH3—VL1—VH2—HPD—COOH |
| | 2$^{nd}$ Chain | NH$_2$—VL2—VH1—HPD—COOH |

HPD = Heterodimer-Promoting Domain

In a specific embodiment, diabodies of the present invention are bispecific, bivalent (i.e., possess two epitope-binding sites), Fc-containing diabodies (FIGS. 4A-4B) that are composed of three total polypeptide chains. The bispecific, bivalent Fc-containing diabodies of the invention comprise one epitope-binding site immunospecific for PD-1, and one epitope-binding site specific for a second epitope (e.g., B7-H3, B7-H4, BTLA, CD40, CD80, CD86, CD137, CTLA-4, ICOS, KIR, LAG-3 MHC class I or II, OX40, PD-L1, TCR, TIM-3, etc.).

In a further embodiment, the bispecific Fc Region-containing diabodies may comprise a total of five polypeptide chains. In a particular embodiment, two of said five polypeptide chains have the same amino acid sequence. The first polypeptide chain of such diabodies contains: (i) a VH1-containing domain, (ii) a CH1-containing domain, and (iii) a Domain containing a CH2-CH3 sequence. The first polypeptide chain may be the heavy chain of an antibody that contains a VH1 and a heavy chain constant region. The second and fifth polypeptide chains of such diabodies contain: (i) a VL1-containing domain, and (ii) a CL-containing domain. The second and/or fifth polypeptide chains of such diabodies may be light chains of an antibody that contains a VL1 complementary to the VH1 of the first/third polypeptide chain. The first, second and/or fifth polypeptide chains may be isolated from naturally occurring antibodies. Alternatively, they may be constructed recombinantly. The third polypeptide chain of such diabodies contains: (i) a VH1-containing domain, (ii) a CH1-containing domain, (iii) a Domain containing a CH2-CH3 sequence, (iv) a VL2-containing Domain, (v) a VH3-containing Domain and (vi) a Heterodimer-Promoting Domain, where the Heterodimer-Promoting Domains promote the dimerization of the third chain with the fourth chain. The fourth polypeptide of such diabodies contains: (i) a VL3-containing Domain, (ii) a VH2-containing Domain and (iii) a Domain that promotes heterodimerization and covalent bonding with the diabody's third polypeptide chain.

Thus, the first and second, and the third and fifth, polypeptide chains of such diabodies associate together to form two VL1/VH1 binding sites capable of binding a first epitope. The third and fourth polypeptide chains of such diabodies associate together to form a VL2/VH2 binding site that is capable of binding to a second epitope, as well as a VL3/VH3 binding site that is capable of binding to a third epitope. The first and third polypeptides are bonded to one another through a disulfide bond involving cysteine residues in their respective constant regions. Notably, the first and third polypeptide chains complex with one another to form an Fc Region. Such diabodies have enhanced potency. FIG. 5 illustrates the structure of such diabodies. It will be understood that the VL1/VH1, VL2/VH2, and VL3/VH3 Domains may be the same or different so as to permit binding that is monospecific, bispecific or trispecific. However, as provided herein, these domains are preferably selected so as to bind PD-1 and a second epitope (e.g., B7-H3, B7-H4, BTLA, CD40, CD80, CD86, CD137, CTLA-4, ICOS, KIR, LAG-3 MEW class I or II, OX40, PD-L1, TCR, TIM-3, etc.).

The VL and VH Domains of the polypeptide chains are selected so as to form VL/VH binding sites specific for a desired epitope. The VL/VH binding sites formed by the association of the polypeptide chains may be the same or different so as to permit tetravalent binding that is monospecific, bispecific, trispecific or tetraspecific. In particular, the VL and VH Domains maybe selected such that a bispecific diabody may comprise two binding sites for a first epitope and two binding sites for a second epitope, or three binding sites for a first epitope and one binding site for a second epitope, or two binding sites for a first epitope, one binding site for a second epitope and one binding site for a third epitope (as depicted in FIG. 5). The general structure of the polypeptide chains of representative five-chain Fc Region-containing diabodies of invention is provided in Table 4:

TABLE 4

| | | |
|---|---|---|
| Bispecific (2 × 2) | 2$^{nd}$ Chain | NH$_2$—VL1—CL—COOH |
| | 1$^{st}$ Chain | NH$_2$—VH1—CH1—CH2—CH3—COOH |
| | 3$^{rd}$ Chain | NH$_2$—VH1—CH1—CH2—CH3—VL2—VH2—HPD—COOH |
| | 5$^{nd}$ Chain | NH$_2$—VL1—CL—COOH |
| | 4$^{th}$ Chain | NH$_2$—VL2—VH2—HPD—COOH |
| Bispecific (3 × 1) | 2$^{nd}$ Chain | NH$_2$—VL1—CL—COOH |
| | 1$^{st}$ Chain | NH$_2$—VH1—CH1—CH2—CH3—COOH |
| | 3$^{rd}$ Chain | NH$_2$—VH1—CH1—CH2—CH3—VL1—VH2—HPD—COOH |
| | 5$^{nd}$ Chain | NH$_2$—VL1—CL—COOH |
| | 4$^{th}$ Chain | NH$_2$—VL2—VH1—HPD—COOH |
| Trispecific (2 × 1 × 1) | 2$^{nd}$ Chain | NH$_2$—VL1—CL—COOH |
| | 1$^{st}$ Chain | NH$_2$—VH1—CH1—CH2—CH3—COOH |
| | 3$^{rd}$ Chain | NH$_2$—VH1—CH1—CH2—CH3—VL2—VH3—HPD—COOH |
| | 5$^{nd}$ Chain | NH$_2$—VL1—CL—COOH |
| | 4$^{th}$ Chain | NH$_2$—VL3—VH2—HPD—COOH |

HPD = Heterodimer-Promoting Domain

In a specific embodiment, diabodies of the present invention are bispecific, tetravalent (i.e., possess four epitope-binding sites), Fc-containing diabodies that are composed of five total polypeptide chains having two binding sites for a first epitope and two binding sites for a second epitope. In one embodiment, the bispecific, tetravalent, Fc-containing diabodies of the invention comprise two epitope-binding sites immunospecific for PD-1 (which may be capable of binding to the same epitope of PD-1 or to different epitopes of PD-1), and two epitope-binding sites specific for a second epitope (e.g., B7-H3, B7-H4, BTLA, CD40, CD80, CD86, CD137, CTLA-4, ICOS, KIR, LAG-3 MHC class I or II, OX40, PD-L1, TCR, TIM-3, etc.). In another embodiment, the bispecific, tetravalent, Fc-containing diabodies of the invention comprise three epitope-binding sites immunospecific for PD-1 which may be capable of binding to the same epitope of PD-1 or to different epitopes of PD-1), and one epitope-binding sites specific for a second epitope (e.g., B7-H3, B7-H4, BTLA, CD40, CD80, CD86, CD137, CTLA-4, ICOS, KIR, LAG-3 MHC class I or II, OX40, PD-L1, TCR, TIM-3, etc.). In another embodiment, the bispecific, tetravalent, Fc-containing diabodies of the invention comprise one epitope-binding sites immunospecific for PD-1, and three epitope-binding sites specific for a second epitope (e.g., B7-H3, B7-H4, BTLA, CD40, CD80, CD86, CD137, CTLA-4, ICOS, KIR, LAG-3 MHC class I or II, OX40, PD-L1, TCR, TIM-3, etc.).

C. Bispecific Trivalent Binding Molecules Containing Fc Regions

A further embodiment of the present invention relates to bispecific, trivalent binding molecules, comprising an Fc Region, and being capable of simultaneously binding to a first epitope, a second epitope and a third epitope, wherein at least one of such epitopes is not identical to another. Such bispecific diabodies thus comprise "VL1"/"VH1" domains that are capable of binding to the first epitope, "VL2"/"VH2" domains that are capable of binding to the second epitope and "VL3"/"VH3" domains that are capable of binding to the third epitope. In one embodiment, one or two of such epitopes is an epitope of PD-1 and another (or the other) of such epitopes is not an epitope of PD-1 (for example, an epitope of B7-H3, B7-H4, BTLA, CD40, CD80, CD86, CD137, CTLA-4, ICOS, KIR, LAG-3, MHC class I or II, OX40, PD-1, PD-L1, TCR, TIM-3, etc.). Such bispecific trivalent binding molecules comprise three epitope-binding sites, two of which are diabody-type binding domains, which provide binding Site A and binding Site B, and one of which is a non-diabody-type binding domain, which provides binding Site C (see, e.g., FIGS. 6A-6F, and PCT Application No: PCT/US15/33081; and PCT/US15/33076).

Typically, the trivalent binding molecules of the present invention will comprise four different polypeptide chains (see FIGS. 6A-6B), however, the molecules may comprise fewer or greater numbers of polypeptide chains, for example by fusing such polypeptide chains to one another (e.g., via a peptide bond) or by dividing such polypeptide chains to form additional polypeptide chains, or by associating fewer or additional polypeptide chains via disulfide bonds. FIGS. 6B-6F illustrate this aspect of the present invention by schematically depicting such molecules having three polypeptide chains. As provided in FIGS. 6A-6F, the trivalent binding molecules of the present invention may have alternative orientations in which the diabody-type binding domains are N-terminal (FIGS. 6A, 6C and 6D) or C-terminal (FIGS. 6B, 6E and 6F) to an Fc Region.

In certain embodiments, the first polypeptide chain of such trivalent binding molecules of the present invention contains: (i) a VL1-containing Domain, (ii) a VH2-containing Domain, (iii) a Heterodimer-Promoting Domain, and (iv) a Domain containing a CH2-CH3 sequence. The VIA and VL2 Domains are located N-terminal or C-terminal to the CH2-CH3-containing domain as presented in Table 5 (FIGS. 6A and 6B). The second polypeptide chain of such embodiments contains: (i) a VL2-containing Domain, (ii) a VH1-containing Domain, and (iii) a Heterodimer-Promoting Domain. The third polypeptide chain of such embodiments contains: (i) a VH3-containing Domain, (ii) a CH1-containing Domain and (iii) a Domain containing a CH2-CH3 sequence. The third polypeptide chain may be the heavy chain of an antibody that contains a VH3 and a heavy chain constant region. The fourth polypeptide of such embodiments contains: (i) a VL3-containing Domain and (ii) a CL-containing Domain. The fourth polypeptide chains may be a light chain of an antibody that contains a VL3 complementary to the VH3 of the third polypeptide chain. The third or fourth polypeptide chains may be isolated from naturally occurring antibodies. Alternatively, they may be constructed recombinantly, synthetically or by other means.

The Variable Light Chain Domain of the first and second polypeptide chains are separated from the Variable Heavy Chain Domains of such polypeptide chains by an intervening spacer linker having a length that is too short to permit their VL1/VH2 (or their VL2/VH1) domains to associate together to form epitope-binding site capable of binding to either the first or second epitope. A preferred intervening spacer peptide (Linker 1) for this purpose has the sequence (SEQ ID NO:14): GGGSGGGG. Other Domains of the trivalent binding molecules may be separated by one or more intervening spacer peptides, optionally comprising a cysteine residue. Exemplary linkers useful for the generation of trivalent binding molecules are provided herein and are also provided in PCT Application Nos: PCT/US15/33081; and PCT/US15/33076. Thus, the first and second polypeptide chains of such trivalent binding molecules associate together to form a VL1/VH1 binding site capable of binding a first epitope, as well as a VL2/VH2 binding site that is capable of binding to a second epitope. The third and fourth polypeptide chains of such trivalent binding molecules associate together to form a VL3/VH3 binding site that is capable of binding to a third epitope. It will be understood that the VL1/VH1, VL2/VH2, and VL3/VH3 Domains may be the same or different so as to permit binding that is monospecific, bispecific or trispecific.

As described above, the trivalent binding molecules of the present invention may comprise three polypeptides. Trivalent binding molecules comprising three polypeptide chains may be obtained by linking the domains of the fourth polypeptide N-terminal to the VH3-containing Domain of the third polypeptide. Alternatively, a third polypeptide chain of a trivalent binding molecule of the invention containing the following three domains is utilized: (i) a VL3-containing Domain, (ii) a VH3-containing Domain, and (iii) a Domain containing a CH2-CH3 sequence, wherein the VL3 and VH3 are spaced apart from one another by an intervening spacer peptide that is sufficiently long (at least 9 or more amino acid residues) so as to allow the association of these domains to form an epitope-binding site.

It will be understood that the VL1/VH1, VL2/VH2, and VL3/VH3 Domains may be the same or different so as to permit binding that is monospecific, bispecific or trispecific. However, as provided herein, these domains are preferably selected so as to bind PD-1 and a second epitope (or a second and third epitope) (preferably, such epitopes are epitopes of B7-H3, B7-H4, BTLA, CD40, CD80, CD86, CD137, CTLA-4, ICOS, KIR, LAG-3 MHC class I or II, OX40, PD-L1, TCR, TIM-3, etc.).

In particular, the VL and VH Domains may be selected such that a trivalent binding molecule comprises two binding sites for a first epitope and one binding sites for a second epitope, or one binding site for a first epitope and two binding sites for a second epitope, or one binding site for a first epitope, one binding site for a second epitope and one binding site for a third epitope. The general structure of the polypeptide chains of representative trivalent binding molecules of invention is provided in FIGS. 6A-6F and in Table 5:

TABLE 5

| Four Chain 1st Orientation | 2nd Chain | NH₂—VL2—VH1—HPD—COOH |
| --- | --- | --- |
| | 1st Chain | NH₂—VL1—VH2—HPD—CH2—CH3—COOH |
| | 3rd Chain | NH₂—VH3—CH1—CH2—CH3—COOH |
| | 4th Chain | NH₂—VL3—CL—COOH |
| Four Chain 2nd Orientation | 2nd Chain | NH₂—VL2—VH1—HPD—COOH |
| | 1st Chain | NH₂—CH2—CH3——VL1—VH2—HPD COOH |
| | 3rd Chain | NH₂—VH3—CH1—CH2—CH3—COOH |
| | 4th Chain | NH₂—VL3—CL—COOH |
| Three Chain 1st Orientation | 2nd Chain | NH₂—VL2—VH1—HPD—COOH |
| | 1st Chain | NH₂—VL1—VH2—HPD—CH2—CH3—COOH |
| | 3rd Chain | NH₂—VL3—VH3—HPD—CH2—CH3—COOH |
| Three Chain 2nd Orientation | 2nd Chain | NH₂—VL2—VH1—HPD—COOH |
| | 1st Chain | NH₂—CH2—CH3—VL1—VH2—HPD COOH |
| | 3rd Chain | NH₂—VL3—VH3—HPD—CH2—CH3—COOH |

HPD = Heterodimer-Promoting Domain

One embodiment of the present invention relates to bispecific trivalent binding molecules that comprise two epitope-binding sites for PD-1 and one epitope-binding site for the second epitope present on a molecule other than PD-1 (e.g. B7-H3, B7-H4, BTLA, CD40, CD80, CD86, CD137, CTLA-4, ICOS, KIR, LAG-3, MHC class I or II, OX40, PD-L1, TCR, TIM-3, etc.). The two epitope-binding sites for PD-1 may bind the same epitope or different epitopes. Another embodiment of the present invention relates to bispecific trivalent binding molecules that comprise, one epitope-binding site for PD-1 and two epitope-binding sites that bind a second antigen present on a molecule other than PD-1 (e.g. B7-H3, B7-H4, BTLA, CD40, CD80, CD86, CD137, CTLA-4, ICOS, KIR, LAG-3, MHC class I or II, OX40, PD-L1, TCR, TIM-3, etc.). The two epitope-binding sites for the second antigen may bind the same epitope or different epitopes of the antigen (e.g., the same or different epitopes of LAG-3). As provided above, such bispecific trivalent binding molecules may comprise three or four polypeptide chains.

VII. Constant Domains and Fc Regions

Provided herein are antibody Constant Domains useful in the generation of the PD-1-binding molecules (e.g., antibodies, diabodies, trivalent binding molecules, etc.) of the invention.

A preferred CL Domain is a human IgG CL Kappa Domain. The amino acid sequence of an exemplary human CL Kappa Domain is (SEQ ID NO:8):

RTVAAPSVFI FPPSDEQLKS GTASVVCLLN NFYPREAKVQ

WKVDNALQSG NSQESVTEQD SKDSTYSLSS TLTLSKADYE

KHKVYACEVT HQGLSSPVTK SFNRGEC

Alternatively, an exemplary CL Domain is a human IgG CL Lambda Domain. The amino acid sequence of an exemplary human CL Kappa Domain is (SEQ ID NO:9):

QPKAAPSVTL FPPSSEELQA NKATLVCLIS DFYPGAVTVA

WKADSSPVKA GVETTPSKQS NNKYAASSYL SLTPEQWKSH

RSYSCQVTHE GSTVEKTVAP TECS

As provided herein, the PD-1-binding molecules of the invention may comprise an Fc Region. The Fc Region of such molecules of the invention may be of any isotype (e.g., IgG1, IgG2, IgG3, or IgG4). The PD-1-binding molecules of the invention may further comprise a CH1 Domain and/or a hinge region. When present, the CH1 Domain and/or hinge region may be of any isotype (e.g., IgG1, IgG2, IgG3, or IgG4), and is preferably of the same isotype as the desired Fc Region.

An exemplary CH1 Domain is a human IgG1 CH1 Domain. The amino acid sequence of an exemplary human IgG1 CH1 Domain is (SEQ ID NO:10):

ASTKGPSVFP LAPSSKSTSG GTAALGCLVK DYFPEPVTVS

WNSGALTSGV HTFPAVLQSS GLYSLSSVVT VPSSSLGTQT

YICNVNHKPS NTKVDKRV

An exemplary CH1 Domain is a human IgG2 CH1 Domain. The amino acid sequence of an exemplary human IgG2 CH1 Domain is (SEQ ID NO:257):

ASTKGPSVFP LAPCSRSTSE STAALGCLVK DYFPEPVTVS

WNSGALTSGV HTFPAVLQSS GLYSLSSVVT VPSSNFGTQT

YTCNVDHKPS NTKVDKTV

An exemplary CH1 Domain is a human IgG4 CH1 Domain. The amino acid sequence of an exemplary human IgG4 CH1 Domain is (SEQ ID NO:254):

ASTKGPSVFP LAPCSRSTSE STAALGCLVK DYFPEPVTVS

WNSGALTSGV HTFPAVLQSS GLYSLSSVVT VPSSSLGTKT

YTCNVDHKPS NTKVDKRV

One exemplary hinge region is a human IgG1 hinge region. The amino acid sequence of an exemplary human IgG1 hinge region is (SEQ ID NO:32): EPKSCDKTH-TCPPCP.

Another exemplary hinge region is a human IgG2 hinge region. The amino acid sequence of an exemplary human IgG2 hinge region is (SEQ ID NO:11): ERKCCVECPPCP.

Another exemplary hinge region is a human IgG4 hinge region. The amino acid sequence of an exemplary human IgG4 hinge region is (SEQ ID NO:12): ESKYGPPCPSCP. As described herein, an IgG4 hinge region may comprise a stabilizing mutation such as the S228P substitution. The amino acid sequence of an exemplary stabilized IgG4 hinge region is (SEQ ID NO:13): ESKYGPPCPPCP.

The Fc Region of the Fc Region-containing molecules (e.g., antibodies, diabodies, and trivalent molecules) of the present invention may be either a complete Fc Region (e.g., a complete IgG Fc Region) or only a fragment of an Fc Region. Optionally, the Fc Region of the Fc Region-containing molecules of the present invention lacks the C-terminal lysine amino acid residue. In particular, the Fc Region of the Fc Region-containing molecules of the present invention may be an engineered variant Fc Region. Although the Fc Region of the bispecific Fc Region-containing molecules of the present invention may possess the ability to bind to one or more Fc receptors (e.g., FcγR(s)), more preferably such variant Fc Region have altered binding to FcγRIA (CD64), FcγRIIA (CD32A), FcγRIIB (CD32B), FcγRIIIA (CD16a) or FcγRIIIB (CD16b) (relative to the binding exhibited by a wild-type Fc Region) or will have substantially reduced or no ability to bind to inhibitory receptor(s). Thus, the Fc Region of the Fc Region-containing molecules of the present invention may include some or all of the CH2

Domain and/or some or all of the CH3 Domain of a complete Fc Region, or may comprise a variant CH2 and/or a variant CH3 sequence (that may include, for example, one or more insertions and/or one or more deletions with respect to the CH2 or CH3 domains of a complete Fc Region). Such Fc Regions may comprise non-Fc polypeptide portions, or may comprise portions of non-naturally complete Fc Regions, or may comprise non-naturally occurring orientations of CH2 and/or CH3 Domains (such as, for example, two CH2 domains or two CH3 domains, or in the N-terminal to C-terminal direction, a CH3 Domain linked to a CH2 Domain, etc.).

Fc Region modifications identified as altering effector function are known in the art, including modifications that increase binding to activating receptors (e.g., FcγRIIA (CD16A) and reduce binding to inhibitory receptors (e.g., FcγRIIB (CD32B) (see, e.g., Stavenhagen, J. B. et al. (2007) "Fc Optimization Of Therapeutic Antibodies Enhances Their Ability To Kill Tumor Cells In Vitro And Controls Tumor Expansion In Vivo Via Low Affinity Activating Fcgamma Receptors," Cancer Res. 57(18):8882-8890). Exemplary variants of human IgG1 Fc Regions with reduced binding to CD32B and/or increased binding to CD16A contain F243L, R292P, Y300L, V305I or P296L substitutions. These amino acid substitutions may be present in a human IgG1 Fc Region in any combination or sub-combination. In one embodiment, the human IgG1 Fc Region variant contains a F243L, R292P and Y300L substitution. In another embodiment, the human IgG1 Fc Region variant contains F243L, R292P, Y300L, V305I and P296L substitutions.

In particular, it is preferred for the Fc Regions of the polypeptide chains of the Fc Region-containing molecules of the present invention to exhibit decreased (or substantially no) binding to FcγRIA (CD64), FcγRIIA (CD32A), FcγRIIB (CD32B), FcγRIIIA (CD16a) or FcγRIIIB (CD16b) (relative to the binding exhibited by the wild-type IgG1 Fc Region (SEQ ID NO:1). Variant Fc Regions and mutant forms capable of mediating such altered binding are described above. In a specific embodiment, the Fc Region-containing molecules of the present invention comprise an IgG Fc Region that exhibits reduced ADCC effector function. In a preferred embodiment the CH2-CH3 Domain of the first and/or third polypeptide chains of such Fc Region-containing molecules include any 1, 2, or 3, of the substitutions: L234A, L235A, N297Q, and N297G. In another embodiment, the human IgG Fc Region variant contains an N297Q substitution, an N297G substitution, L234A and L235A substitutions or a D265A substitution, as these mutations abolish FcR binding. Alternatively, a CH2-CH3 Domain of an Fc region which inherently exhibits decreased (or substantially no) binding to FcγRIIIA (CD16a) and/or reduced effector function (relative to the binding exhibited by the wild-type IgG1 Fc Region (SEQ ID NO:1)) is utilized. In a specific embodiment, the Fc Region-containing molecules of the present invention comprise an IgG2 Fc Region (SEQ ID NO:2) or an IgG4 Fc Region (SEQ ID:NO:4). When an IgG4 Fc Region in utilized, the instant invention also encompasses the introduction of a stabilizing mutation, such as the hinge region S228P substitution described above (see, e.g., SEQ ID NO:13). Since the N297G, N297Q, L234A, L235A and D265A substitutions abolish effector function, in circumstances in which effector function is desired, these substitutions would preferably not be employed.

In particular, it is preferred for the Fc Regions of the polypeptide chains of the Fc Region-containing molecules of the present invention to exhibit increased serum half-life (relative to the half-life exhibited by the corresponding wild-type Fc). Variant Fc Regions and mutant forms exhibiting extended serum half-life are described above. In a preferred embodiment the CH2-CH3 Domain of the first and/or third polypeptide chains of such Fc Region-containing molecules include any 1, 2, or 3, of the substitutions: M252Y, S254T and T256E. The invention further encompasses Fc Region-containing molecules of the present invention comprising variant Fc Regions comprising:

(A) one or more mutations which alter effector function and/or FcγR; and (B) one or more mutations which extend serum half-life.

A preferred IgG1 sequence for the CH2 and CH3 Domains of the Fc Region-containing molecules of the present invention will comprise the substitutions L234A/L235A/M252Y/S254T/T256E (SEQ ID NO:258):

```
APEAAGGPSV FLFPPKPKDT LYITREPEVT CVVVDVSHED

PEVKFNWYVD GVEVHNAKTK PREEQYNSTY RVVSVLTVLH

QDWLNGKEYK CKVSNKALPA PIEKTISKAK GQPREPQVYT

LPPSREEMTK NQVSLTCLVK GFYPSDIAVE WESNGQPENN

YKTTPPVLDS DGSFFLYSKL TVDKSRWQQG NVFSCSVMHE

ALHNHYTQKS LSLSPGX
``` wherein, X is a lysine (K) or is absent.

A preferred IgG4 sequence for the CH2 and CH3 Domains of the Fc Region-containing molecules of the present invention will comprise the M252Y/S254T/T256E substitutions (SEQ ID NO:259):

```
APEFLGGPSV FLFPPKPKDT LYITREPEVT CVVVDVSQED

PEVQFNWYVD GVEVHNAKTK PREEQFNSTY RVVSVLTVLH

QDWLNGKEYK CKVSNKGLPS SIEKTISKAK GQPREPQVYT

LPPSQEEMTK NQVSLTCLVK GFYPSDIAVE WESNGQPENN

YKTTPPVLDS DGSFFLYSRL TVDKSRWQEG NVFSCSVMHE

ALHNHYTQKS LSLSLGX
``` wherein, X is a lysine (K) or is absent.

For diabodies and trivalent binding molecules whose first and third polypeptide chains are not identical), it is desirable to reduce or prevent homodimerization from occurring between the CH2-CH3 Domains of two first polypeptide chains or between the CH2-CH3 Domains of two third polypeptide chains. The CH2 and/or CH3 Domains of such polypeptide chains need not be identical in sequence, and advantageously are modified to foster complexing between the two polypeptide chains. For example, an amino acid substitution (preferably a substitution with an amino acid comprising a bulky side group forming a "knob", e.g., tryptophan) can be introduced into the CH2 or CH3 Domain such that steric interference will prevent interaction with a similarly mutated domain and will obligate the mutated domain to pair with a domain into which a complementary, or accommodating mutation has been engineered, i.e., "the hole" (e.g., a substitution with glycine). Such sets of mutations can be engineered into any pair of polypeptides comprising CH2-CH3 Domains that forms an Fc Region. Methods of protein engineering to favor heterodimerization over homodimerization are well known in the art, in particular with respect to the engineering of immunoglobulin-like molecules, and are encompassed herein (see e.g., Ridgway et al. (1996) "'*Knobs-Into-Holes' Engineering Of Antibody CH3 Domains For Heavy Chain Heterodimerization*," Protein Engr. 9:617-621, Atwell et al. (1997) "*Stable Heterodimers From Remodeling The Domain Interface Of A Homodimer Using A Phage Display Library*," J. Mol. Biol. 270: 26-35, and Xie et al. (2005) "*A New Format Of Bispecific Antibody: Highly Efficient Heterodimerization, Expression And Tumor Cell Lysis*," J. Immunol. Methods 296:95-101; each of which is hereby incorporated herein by reference in its entirety). Preferably the "knob" is engineered into the CH2-CH3 Domains of the first polypeptide chain and the "hole" is engineered into the CH2-CH3 Domains of the third polypeptide chain of diabodies comprising three polypeptide chains. Thus, the "knob" will help in preventing the first polypeptide chain from homodimerizing via its CH2 and/or CH3 Domains. As the third polypeptide chain preferably contains the "hole" substitution it will heterodimerize with the first polypeptide chain as well as homodimerize with itself. This strategy may be utilized for diabodies and trivalent binding molecules comprising three, four or five chains as detailed above, where the "knob" is engineered into the CH2-CH3 Domains of the first polypeptide chain and the "hole" is engineered into the CH2-CH3 Domains the third polypeptide chain.

A preferred knob is created by modifying an IgG Fc Region to contain the modification T366W. A preferred hole is created by modifying an IgG Fc Region to contain the modification T366S, L368A and Y407V. To aid in purifying the hole-bearing third polypeptide chain homodimer from the final bispecific heterodimeric Fc Region-containing molecule, the protein A binding site of the hole-bearing CH2 and CH3 Domains of the third polypeptide chain is preferably mutated by amino acid substitution at position 435 (H435R). Thus, the hole-bearing third polypeptide chain homodimer will not bind to protein A, whereas the bispecific heterodimer will retain its ability to bind protein A via the protein A binding site on the first polypeptide chain. In an alternative embodiment, the hole-bearing third polypeptide chain may incorporate amino acid substitutions at positions 434 and 435 (N434A/N435K).

A preferred IgG1 amino acid sequence for the CH2 and CH3 Domains of the first polypeptide chain of an Fc Region-containing molecule of the present invention will have the "knob-bearing" sequence (SEQ ID NO:6):

```
APEAAGGPSV FLFPPKPKDT LMISRTPEVT CVVVDVSHED

PEVKFNWYVD GVEVHNAKTK PREEQYNSTY RVVSVLTVLH

QDWLNGKEYK CKVSNKALPA PIEKTISKAK GQPREPQVYT

LPPSREEMTK NQVSLWCLVK GFYPSDIAVE WESNGQPENN

YKTTPPVLDS DGSFFLYSKL TVDKSRWQQG NVFSCSVMHE

ALHNHYTQKS LSLSPGX
``` wherein, X is a lysine (K) or is absent.

A preferred IgG1 amino acid sequence for the CH2 and CH3 Domains of the second polypeptide chain of an Fc Region-containing molecule of the present invention having two polypeptide chains (or the third polypeptide chain of an Fc Region-containing molecule having three, four, or five polypeptide chains) will have the "hole-bearing" sequence (SEQ ID NO:7):

```
APEAAGGPSV FLFPPKPKDT LMISRTPEVT CVVVDVSHED

PEVKFNWYVD GVEVHNAKTK PREEQYNSTY RVVSVLTVLH

QDWLNGKEYK CKVSNKALPA PIEKTISKAK GQPREPQVYT

LPPSREEMTK NQVSLSCAVK GFYPSDIAVE WESNGQPENN

YKTTPPVLDS DGSFFLVSKL TVDKSRWQQG NVFSCSVMHE

ALHNRYTQKS LSLSPGX
``` wherein, X is a lysine (K) or is absent.

As will be noted, the CH2-CH3 Domains of SEQ ID NO:6, and SEQ ID NO:7 include a substitution at position 234 with alanine and 235 with alanine, and thus form an Fc Region exhibit decreased (or substantially no) binding to FcγRIA (CD64), FcγRIIA (CD32A), FcγRIIB (CD32B), FcγRIIIA (CD16a) or FcγRIIIB (CD16b) (relative to the binding exhibited by the wild-type Fc Region (SEQ ID NO:1). The invention also encompasses such CH2-CH3 Domains, which comprise alternative and/or additional substitutions which modify effector function and/or FγR binding activity of the Fc region. The invention also encompasses such CH2-CH3 Domains, which further comprise one or more half-live extending amino acid substitutions. In particular, the invention encompasses such hole-bearing and such knob-bearing CH2-CH3 Domains which further comprise the M252Y/S254T/T256E.

It is preferred that the first polypeptide chain will have a "knob-bearing" CH2-CH3 sequence, such as that of SEQ ID NO:6. However, as will be recognized, a "hole-bearing" CH2-CH3 Domain (e.g., SEQ ID NO:7) could be employed in the first polypeptide chain, in which case, a "knob-bearing" CH2-CH3 Domain (e.g., SEQ ID NO:6) would be employed in the second polypeptide chain of an Fc Region-containing molecule of the present invention having two polypeptide chains (or in the third polypeptide chain of an Fc Region-containing molecule having three, four, or five polypeptide chains).

As detailed above the invention encompasses Fc Region-containing molecules (e.g., antibodies and Fc Region-containing diabodies) having wild type CH2 and CH3 Domains, or having CH2 and CH3 Domains comprising combinations of the substitutions described above. An exemplary amino acid sequence of an IgG1 CH2-CH3 Domain encompassing such variations is (SEQ ID NO:260):

```
APEX₁X₂GGPSV FLFPPKPKDT LX₃IX₄RX₅PEVT CVVVDVSHED

PEVKFNWYVD GVEVHNAKTK PREEQYNSTY RVVSVLTVLH

QDWLNGKEYK CKVSNKALPA PIEKTISKAK GQPREPQVYT

LPPSREEMTK NQVSLX₆CX₇VK GFYPSDIAVE WESNGQPENN

YKTTPPVLDS DGSFFLX₈SKL TVDKSRWQQG NVFSCSVMHE

ALHX₉X₁₀YTQKS LSLSPGX₁₁
``` wherein:
(a) $X_1$ and $X_2$ are both L (wild type), or are both A (decreased FcγR binding);
(b) $X_3$, $X_4$, and $X_5$ respectively are M, S and T (wild type), or are Y, T and E (extended half-life),
(c) $X_6$, $X_7$, and $X_8$ respectively are: T, L and Y (wild type), or are W, L and Y (knob), or S, A and V (hole);

(d) $x_9$ and $X_{10}$ respectively are N and H (wild type), or are N and R (no protein A binding), or A and K (no protein A binding); and (e) $X_{11}$ is K or is absent.

In other embodiments, the invention encompasses PD-1-binding molecules comprising CH2 and/or CH3 Domains that have been engineered to favor heterodimerization over homodimerization using mutations known in the art, such as those disclosed in PCT Publication No. WO 2007/110205; WO 2011/143545; WO 2012/058768; WO 2013/06867, all of which are incorporated herein by reference in their entirety.

VIII. PD-1×LAG-3 Bispecific Binding Molecules

The present invention particularly relates to PD-1×LAG-3 bispecific binding molecules (e.g., bispecific antibodies, bispecific diabodies, etc.) comprising an epitope-binding fragment of an anti-PD-1 antibody, and preferably one of the novel anti-human PD-1 antibodies provided herein, and an epitope-binding fragment of an anti-human LAG-3 antibody, preferably one of the novel anti-human LAG-3 antibodies provided herein. The preferred PD-1×LAG-3 bispecific binding molecules of the present invention possess epitope-binding fragments of antibodies that enable them to be able to coordinately bind to two different epitopes: an epitope of PD-1 and an epitope of LAG-3, so as to attenuate the inhibitory activities of such molecules. As used herein, such attenuation refers to a decrease of at least 20%, a decrease of at least 50%, a decrease of at least 80%, or a decrease of at least 90% in detectable PD-1 and/or LAG-3 inhibitory activity, or the complete elimination of detectable PD-1 and/or LAG-3 inhibitory activity. Selection of the epitope-binding fragments (e.g., VL and VH Domains) of the anti-human PD-1 antibody and anti-LAG-3 antibody is coordinated such that the polypeptides chains that make up such PD-1×LAG-3 bispecific binding molecules assemble to form at least one functional antigen binding site that is specific for the first antigen (i.e., either PD-1 or LAG-3) and at least one functional antigen binding site that is specific for the second antigen (i.e., either PD-1 or LAG-3, depending upon the identity of the first antigen).

In a particular embodiment, a PD-1×LAG-3 bispecific binding molecule of the instant invention is a bispecific diabody, which preferably comprises two, three, four, or five polypeptide chains as described herein. In another particular embodiment, a PD-1×LAG-3 bispecific binding molecule of the instant invention is a bispecific antibody, which preferably comprises two, three, or four polypeptide chains as described herein (also see, e.g., WO 2007/024715; WO2007/110205; WO 2009/080251; WO 2009/080254; WO 2009/089004; WO 2011/069104; WO 2011/117329; WO 2011/131746; WO 2011/133886; WO 2011/143545; WO 2012/023053; WO 2013/060867, all of which descriptions are incorporated herein by reference in their entirety).

A. Anti-Human LAG-3 Antibodies

Exemplary antibodies that are immunospecific for human LAG-3 are provided below. Additional desired antibodies may be made by isolating antibody-secreting hybridomas elicited using LAG-3 or a peptide fragment thereof, or by screening recombinant antibody libraries for binding to LAG-3 or a peptide fragment thereof. Human LAG-3 (including a 28 amino acid residue signal sequence (shown underlined) and the 497 amino acid residue mature protein) has the amino acid sequence (SEQ ID NO:38):

```
MWEAQFLGLL FLQPLWVAPV KPLQPGAEVP VVWAQEGAPA
QLPCSPTIPL QDLSLLRRAG VTWQHQPDSG PPAAAPGHPL
APGPHPAAPS SWGPRPRRYT VLSVGPGGLR SGRLPLQPRV
QLDERGRQRG DFSLWLRPAR RADAGEYRAA VHLRDRALSC
RLRLRLGQAS MTASPPGSLR ASDWVILNCS FSRPDRPASV
HWFRNRGQGR VPVRESPHHH LAESFLFLPQ VSPMDSGPWG
CILTYRDGFN VSIMYNLTVL GLEPPTPLTV YAGAGSRVGL
PCRLPAGVGT RSFLTAKWTP PGGGPDLLVT GDNGDFTLRL
EDVSQAQAGT YTCHIHLQEQ QLNATVTLAI ITVTPKSFGS
PGSLGKLLCE VTPVSGQERF VWSSLDTPSQ RSFSGPWLEA
QEAQLLSQPW QCQLYQGERL LGAAVYFTEL SSPGAQRSGR
APGALPAGHL LLFLILGVLS LLLLVTGAFG FHLWRRQWRP
RRFSALEQGI HPPQAQSKIE ELEQEPEPEP EPEPEPEPEP
EPEQL
```

1. LAG-3 mAb A

The anti-human LAG-3 antibody BMS-986016 (25F7; Medarex/BMS), designated herein as "LAG-3 mAb A," and variants thereof have been described (see, e.g., WO 2014/008218). The amino acid sequence of the Heavy Chain Variable Domain of LAG-3 mAb A has the amino acid sequence (SEQ ID NO:39) (CDRs are shown underlined):

```
QVQLQQWGAG LLKPSETLSL TCAVYGGSFS DYYWNWIRQP
PGKGLEWIGE INHNGNTNSN PSLKSRVTLS LDTSKNQFSL
KLRSVTAADT AVYYCAFGYS DYEYNWFDPW GQGTLVTVSS
```

The amino acid sequence of the Light Chain Variable Domain of LAG-3 mAb A has the amino acid sequence (SEQ ID NO:40) (CDRs are shown underlined):

```
EIVLTQSPAT LSLSPGERAT LSCRASQSIS SYLAWYQQKP
GQAPRLLIYD ASNRATGIPA RFSGSGSGTD FTLTISSLEP
EDFAVYYCQQ RSNWPLTFGQ GTNLEIK
```

Additional murine anti-human LAG-3 antibodies possessing unique binding characteristics have recently been identified (see, U.S. Patent Application No. 62/172,277). Preferred PD-1×LAG-3 bispecific binding molecules of the present invention comprise the epitope-binding fragments of the anti-human LAG-3 antibody LAG-3 mAb 1 or LAG-3 mAb 6, antibodies, which bind a novel epitope and do not compete with BMS-986016 for LAG-3 binding. Particularly preferred, are PD-1×LAG-3 bispecific binding molecules of the present invention which possess a humanized VH and/or VL Domains of LAG-3 mAb 1 or LAG-3 mAb 6.

2. LAG-1 mAb 1

The amino acid sequence of the VH Domain of LAG-3 mAb 1 (SEQ ID NO:41) is shown below (CDR$_H$ residues are shown underlined).

```
QIQLVQSGPE LKKPGETVKI SCKASGYTFR NYGMNWVKQA
PGKVLKWMGW INTYTGESTY ADDFEGRFAF SLGTSASTAY
```

LQINILKNED TATYFCARES LYDYYSMDYW GQGTSVTVSS

CDR$_H$1 of LAG-3 mAb 1 (SEQ ID NO: 42):
RNYGMN

CDR$_H$2 of LAG-3 mAb 1 (SEQ ID NO: 43):
WINTYTGESTYADDFEG

CDR$_H$3 of LAG-3 mAb 1 (SEQ ID NO: 44):
ESLYDYYSMDY

The amino acid sequence of the VL Domain of LAG-3 mAb 1 (SEQ ID NO:45) is shown below (CDR$_L$ residues are shown underlined):

DVVVTQTPLT LSVTIGQPAS ISCKSSQSLL HSDGKTYLNW

LLQRPGQSPE RLIYLVSELD SGVPDRFTGS GSGTDFTLKI

SRVEAEDLGV YYCWQGTHFP YTFGGGTKLE IK

CDR$_L$1 of LAG-3 mAb 1 (SEQ ID NO: 46):
KSSQSLLHSDGKTYLN

CDR$_L$2 of LAG-3 mAb 1 (SEQ ID NO: 47):
LVSELDS

CDR$_L$3 of LAG-3 mAb 1 (SEQ ID NO: 48):
WQGTHFPYT

Two exemplary humanized VH Domains of LAG-3 mAb 1 designated herein as "hLAG-3 mAb 1 VH1," and "hLAG-3 mAb 1 VH2," and four exemplary humanized VL Domains of LAG-3 mAb 1 "hLAG-3 mAb 1 VL1," "hLAG-3 mAb 1 VL2," "hLAG-3 mAb 1 VL3," and "hLAG-3 mAb 1 VL4," are provided below. Any of the humanized VL Domains may be paired with any of the humanized VH Domains to generate a LAG-3 binding domain. Accordingly, any antibody comprising one of the humanized VL Domains paired with the humanized VH Domain is referred to generically as "hLAG-3 mAb 1," and particular combinations of humanized VH/VL Domains are referred to by reference to the specific VH/VL Domains, for example a humanized antibody comprising hLAG-3 mAb 1 VH1 and hLAG-3 mAb 1 VL2 is specifically referred to as "hLAG-3 mAb 1(1.2)."

The amino acid sequence of the VH Domain of hLAG-3 mAb 1 VH1 (SEQ ID NO:49) is shown below (CDR$_H$ residues are shown underlined):

QVQLVQSGAE VKKPGASVKV SCKASGYTFT NYGMNWVRQA

PGQGLEWMGW INTYTGESTY ADDFEGRFVF SMDTSASTAY

LQISSLKAED TAVYYCARES LYDYYSMDYW GQGTTVTSS

The amino acid sequence of the VH Domain of hLAG-3 mAb 1 VH2 (SEQ ID NO:50) is shown below (CDR$_H$ residues are shown underlined):

QVQLVQSGAE VKKPGASVKV SCKASGYTFT NYGMNWVRQA

PGQGLEWMGW INTYTGESTY ADDFEGRFVF SMDTSASTAY

LQISSLKAED TAVYFCARES LYDYYSMDYW GQGTTVTSS

The amino acid sequence of the VL Domain of hLAG-3 mAb 1 VL1 (SEQ ID NO:51) is shown below (CDR$_L$ residues are shown underlined):

DIVMTQTPLS LSVTPGQPAS ISCKSSQSLL HSDGKTYLNW

LLQKPGQSPE RLIYLVSELD SGVPDRFSGS GSGTDFTLKI

SRVEAEDVGV YYCWQGTHFP YTFGGGTKVE IK

The amino acid sequence of the VL Domain of hLAG-3 mAb 1 VL2 (SEQ ID NO:52) is shown below (CDR$_L$ residues are shown underlined):

DIVMTQTPLS LSVTPGQPAS ISCKSSQSLL HSDGKTYLNW

LLQRPGQSPE RLIYLVSELD SGVPDRFSGS GSGTDFTLKI

SRVEAEDVGV YYCWQGTHFP YTFGGGTKVE IK

The amino acid sequence of the VL Domain of hLAG-3 mAb 1 VL3 (SEQ ID NO:53) is shown below (CDR$_L$ residues are shown underlined):

DIVMTQTPLS LSVTPGQPAS ISCKSSQSLL HSDGKTYLNW

LLQKPGQPPE RLIYLVSELD SGVPDRFSGS GSGTDFTLKI

SRVEAEDVGV YYCWQGTHFP YTFGGGTKVE IK

The amino acid sequence of the VL Domain of hLAG-3 mAb 1 VL4 (SEQ ID NO:54) is shown below (CDR$_L$ residues are shown underlined):

DIVMTQTPLS LSVTPGQPAS ISCKSSQSLL HSDAKTYLNW

LLQKPGQPPE RLIYLVSELD SGVPDRFSGS GSGTDFTLKI

SRVEAEDVGV YYCWQGTHFP YTFGGGTKVE IK

The CDR$_L$1 of the VL Domain of hLAG-3 mAb 1 VL4 comprises an glycine to alanine amino acid substitution and has the amino acid sequence: KSSQSLLHSDAKTYLN (SEQ ID NO:55), the substituted alanine is shown underlined). It is contemplated that a similar substitution may be incorporated into any of the LAG-3 mAb 1 CDR$_L$1 Domains described above.

3. LAG-3 mAb 6

The amino acid sequence of the VH Domain of LAG-3 mAb 6 (SEQ ID NO:56) is shown below (CDR$_H$ residues are shown underlined):

EVLLQQSGPE LVKPGASVKI PCKASGYTFT DYNMDWVKQS

HGESLEWIGD INPDNGVTIY NQKFEGKATL TVDKSSSTAY

MELRSLTSED TAVYYCAREA DYFYFDYWGQ GTTLTVSS

CDR$_H$1 of LAG-3 mAb 6 (SEQ ID NO: 57):
DYNMD

CDR$_H$2 of LAG-3 mAb 6 (SEQ ID NO: 58):
DINPDNGVTIYNQKFEG

CDR$_H$3 of LAG-3 mAb 6 (SEQ ID NO: 59):
EADYFYFDY

The amino acid sequence of the VL Domain of LAG-3 mAb 6 (SEQ ID NO:60) is shown below (CDR residues are shown underlined):

```
DIVMTQSHRF MSTSVGDRVS ITCKASQDVS SVVAWYQQKP

GQSPKLLIFS ASYRYTGVPD RFTGSGSGTD FTFTISSVQA

ADLAVYYCQQ HYSTPWTFGG GTKLEIK

CDR_L1 of LAG-3 mAb 6 (SEQ ID NO: 61):
KASQDVSSVVA

CDR_L2 of LAG-3 mAb 6 (SEQ ID NO: 62):
SASYRYT

CDR_L3 of LAG-3 mAb 6 (SEQ ID NO: 63):
HYSTPWT
```

Two exemplary humanized VH Domains of LAG-3 mAb 6 designated herein as "hLAG-3 mAb 6 VH1," and "hLAG-3 mAb 6 VH2," and two exemplary humanized VL Domains of LAG-3 mAb 6 "hLAG-3 mAb 1 VL1," and "hLAG-3 mAb 1 VL2," are provided below. Any of the humanized VL Domains may be paired with any of the humanized VH Domains to generate a LAG-3 binding domain. Accordingly, any antibody comprising one of the humanized VL Domains paired with the humanized VH Domain is referred to generically as "hLAG-3 mAb 6," and particular combinations of humanized VH/VL Domains are referred to by reference to the specific VH/VL Domains, for example a humanized antibody comprising hLAG-3 mAb 6 VH1 and hLAG-3 mAb 6 VL2 is specifically referred to as "hLAG-3 mAb 6(1.2)."

The amino acid sequence of the VH Domain of hLAG-3 mAb 6 VH1 (SEQ ID NO:294) is shown below (CDR$_H$ residues are shown underlined):

```
QVQLVQSGAE VKKPGASVKV SCKASGYTFT DYNMDWVRQA

PGQGLEWMGD INPDNGVTIY NQKFEGRVTM TTDTSTSTAY

MELRSLRSDD TAVYYCAREA DYFYFDYWGQ GTTLTVSS
```

An amino acid sequence of the VH Domain of hLAG-3 mAb 6 VH2 (SEQ ID NO:295) is shown below (CDR$_H$ residues are shown underlined):

```
EVQLVESGGG LVKPGGSLRL SCAASGFTFS DYNMDWVRQA

PGKGLEWVSD INPDNGVTIY NQKFEGRFTI SRDNAKNSLY

LQMNSLRAED TAVYYCAREA DYFYFDYWGQ GTTLTVSS
```

The amino acid sequence of the VL Domain of hLAG-3 mAb 6 VL1 (SEQ ID NO:296) is shown below (CDR$_L$ residues are shown underlined):

```
DIQMTQSPSS LSASVGDRVT ITCRASQDVS SVVAWYQQKP

GKAPKLLIYS ASYRYTGVPS RFSGSGSGTD FTLTISSLQP

EDFATYYCQQ HYSTPWTFGG GTKLEIK
```

The amino acid sequence of the VL Domain of hLAG-3 mAb 6 VL2 (SEQ ID NO:297) is shown below (CDR$_L$ residues are shown underlined):

```
DIVMTQSPSS LSASVGDRVT ITCRASQDVS SVVAWYQQKP

GKAPKLLIYS ASYRYTGVPD RFSGSGSGTD FTFTISSLQP

EDIAVYYCQQ HYSTPWTFGG GTKLEIK
```

The CDR$_L$1 of the VL Domain of hLAG-3 mAb 6 VL1 and VL2 comprises a lysine to arginine amino acid substitution and has the amino acid sequence: RASQDVSSVVA (SEQ ID NO:298), the substituted arginine is shown underlined). It is contemplated that a similar substitution may be incorporated into any of the LAG-3 mAb 6 CDR$_L$1 Domains described above.

B. Exemplary Four Chain Fc Region-Containing Diabodies Having E/K-Coils

Four exemplary PD-1×LAG-3 bispecific, four chain Fc Region-containing diabodies comprising E/K-coil Heterodimer-Promoting Domains (designated "DART A," "DART B," "DART C," and "DART I") were generated. The structure of these Fc Region-containing diabodies is detailed below. These exemplary PD-1×LAG-3 diabodies are intended to illustrate, but in no way limit, the scope of the invention.

1. DART A

DART A is a bispecific, four chain, Fc Region-containing diabody having two binding sites specific for PD-1, two binding sites specific for LAG-3, a variant IgG4 Fc Region engineered for extended half-life, and cysteine-containing E/K-coil Heterodimer-Promoting Domains. The first and third polypeptide chains of DART A comprise, in the N-terminal to C-terminal direction: an N-terminus, a VL Domain of a monoclonal antibody capable of binding to LAG-3 (VL$_{LAG-3}$ hLAG-3 mAb 1 VL4) (SEQ ID NO:54); an intervening linker peptide (Linker 1: GGGSGGGG (SEQ ID NO:14)); a VH Domain of a monoclonal antibody capable of binding to PD-1 (VH$_{PD-1}$ hPD-1 mAb 7 VH1) (SEQ ID NO:147); a cysteine-containing intervening linker peptide (Linker 2: GGCGGG (SEQ ID NO:15)); a cysteine-containing Heterodimer-Promoting (E-coil) Domain (EVAACEK-EVAALEK-EVAALEK-EVAALEK (SEQ ID NO:23)); a stabilized IgG4 hinge region (SEQ ID NO:13); a variant IgG4 CH2-CH3 Domain comprising substitutions M252Y/S254T/T256E and lacking the C-terminal residue (SEQ ID NO:259); and a C-terminus.

The amino acid sequence of the first and third polypeptide chains of DART A is a variant of SEQ ID NO:267:

```
DIVMTQTPLS LSVTPGQPAS ISCKSSQSLL HSDX₁KTYLNW

LLQKPGQPPE RLIYLVSELD SGVPDRFSGS GSGTDFTLKI

SRVEAEDVGV YYCWQGTHFP YTFGGGTKVE IKGGGSGGGG

QVQLVQSGAE VKKPGASVKV SCKASGYSFT SYWMNWVRQA

PGQGLEWIGV IHPSDSETWL DQKFKDRVTI TVDKSTSTAY

MELSSLRSED TAVYYCAREH YGTSPFAYWG QGTLVTVSSG

GCGGGEVAAC EKEVAALEKE VAALEKEVAA LEKESKYGPP

CPPCPAPEFL GGPSVFLFPP KPKDTLX₂IX₃R X₄PEVTCVVVD

VSQEDPEVQF NWYVDGVEVH NAKTKPREEQ FNSTYRVVSV
```

-continued
```
LTVLHQDWLN GKEYKCKVSN KGLPSSIEKT ISKAKGQPRE

PQVYTLPPSQ EEMTKNQVSL TCLVKGFYPS DIAVEWESNG

QPENNYKTTP PVLDSDGSFF LYSRLTVDKS RWQEGNVFSC

SVMHEALHNH YTQKSLSLSL G
``` wherein $X_1$, $X_2$, $X_3$ and $X_4$ are independently selected, and wherein $X_1$ is A or G; $X_2$ is Y or M; $X_3$ is T or S; and $X_4$ is E or T.

The amino acid sequences of the first and third polypeptide chains of DART A is SEQ ID NO:267, wherein $X_1$ is A; $X_2$ is Y; $X_3$ is T; and $X_4$ is E.

The second and fourth polypeptide chains of DART A comprise, in the N-terminal to C-terminal direction: an N-terminus, a VL Domain of a monoclonal antibody capable of binding to PD-1 ($VL_{PD-1}$ hPD-1 mAb 7 VL2) (SEQ ID NO:153); an intervening linker peptide (Linker 1: GGGSGGGG (SEQ ID NO:14)); a VH Domain of a monoclonal antibody capable of binding LAG-3 ($VH_{LAG-3}$ hLAG-3 mAb 1 VH1) (SEQ ID NO:49); a cysteine-containing intervening linker peptide (Linker 2: GGCGGG (SEQ ID NO:15)); a cysteine-containing Heterodimer-Promoting (K-coil) Domain (KVAACKE-KVAALKE-KVAALKE-KVAALKE (SEQ ID NO:24); and a C-terminus.

The amino acid sequence of the second and fourth polypeptide chains of DART A is (SEQ ID NO:268):

```
EIVLTQSPAT LSLSPGERAT LSCRASESVD NYGMSFMNWF

QQKPGQPPKL LIHAASNQGS GVPSRFSGSG SGTDFTLTIS

SLEPEDFAVY FCQQSKEVPY TFGGGTKVEI KGGGSGGGGQ

VQLVQSGAEV KKPGASVKVS CKASGYTFTN YGMNWVRQAP

GQGLEWMGWI NTYTGESTYA DDFEGRFVFS MDTSASTAYL

QISSLKAEDT AVYYCARESL YDYYSMDYWG QGTTVTVSSG

GCGGGKVAAC KEKVAALKEK VAALKEKVAA LKE
```

2. DART B

DART B is identical to DART A, except that the first and third polypeptide chains of DART B comprise the VL Domain of hLAG-3 mAb 1 VL3 (SEQ ID NO:53), which comprises an amino acid substitution in $CDR_L1$. Thus, the first and third polypeptide chains of DART B comprise, in the N-terminal to C-terminal direction: an N-terminus; a VL Domain of a monoclonal antibody capable of binding to LAG-3 ($VL_{LAG-3}$ hLAG-3 mAb 1 VL3) (SEQ ID NO:53); an intervening linker peptide (Linker 1: GGGSGGGG (SEQ ID NO:14)); a VH Domain of a monoclonal antibody capable of binding to PD-1 ($VH_{PD-1}$ hPD-1 mAb 7 VH1) (SEQ ID NO:147); an intervening linker peptide (Linker 2: GGCGGG (SEQ ID NO:15)); a cysteine-containing Heterodimer-Promoting (E-coil) Domain (EVAACEK-EVAALEK-EVAALEK-EVAALEK (SEQ ID NO:23)); a stabilized IgG4 hinge region (SEQ ID NO:13); a variant of IgG4 CH2-CH3 Domain comprising substitutions M252Y/S254T/T256E and lacking the C-terminal residue (SEQ ID NO:259); and a C-terminus.

The amino acid sequence of the first and third polypeptide chains of DART B is SEQ ID NO:267, wherein $X_1$ is G; $X_2$ is Y; $X_3$ is T; and $X_4$ is E.

The amino acid sequence of the second and fourth polypeptide chains of DART B is SEQ ID NO:268.

3. DART C

DART C is identical to DART B, except that the first and third polypeptide chains of DART B comprise a wild type IgG4 CH2-CH3 Domain lacking the C-terminal residue (SEQ ID NO:4). Thus, the first and third polypeptide chains of DART C comprise, in the N-terminal to C-terminal direction: an N-terminus, a VL Domain of a monoclonal antibody capable of binding to LAG-3 ($VL_{LAG-3}$ hLAG-3 mAb 1 VL3) (SEQ ID NO:53); an intervening linker peptide (Linker 1: GGGSGGGG (SEQ ID NO:14)); a VH Domain of a monoclonal antibody capable of binding to PD-1 ($VH_{PD-1}$ hPD-1 mAb 7 VH1) (SEQ ID NO:147); an intervening linker peptide (Linker 2: GGCGGG (SEQ ID NO:15)); a cysteine-containing Heterodimer-Promoting (E-coil) Domain (EVAACEK-EVAALEK-EVAALEK-EVAALEK (SEQ ID NO:23)); a stabilized IgG4 hinge region (SEQ ID NO:13); an IgG4 CH2-CH3 Domain lacking the C-terminal residue (SEQ ID NO:4); and a C-terminus.

The amino acid sequence of the first and third polypeptide chains of DART C is SEQ ID NO:267, wherein $X_1$ is G; $X_2$ is M; $X_3$ is S; and $X_4$ is T.

The amino acid sequence of the second and fourth polypeptide chains of DART C is SEQ ID NO:268.

4. DART I

DART I is a bispecific, four chain, Fc Region-containing diabody having two binding sites specific for PD-1, two binding sites specific for LAG-3, a variant IgG4 Fc Region engineered for extended half-life, and cysteine-containing E/K-coil Heterodimer-Promoting Domains. The first and third polypeptide chains of DART I comprise, in the N-terminal to C-terminal direction: an N-terminus, a VL Domain of a monoclonal antibody capable of binding to LAG-3 ($VL_{LAG-3}$ hLAG-3 mAb 6 VL1) (SEQ ID NO:296); an intervening linker peptide (Linker 1: GGGSGGGG (SEQ ID NO:14)); a VH Domain of a monoclonal antibody capable of binding to PD-1 ($VH_{PD-1}$ hPD-1 mAb 7 VH1) (SEQ ID NO:147); a cysteine-containing intervening linker peptide (Linker 2: GGCGGG (SEQ ID NO:15)); a cysteine-containing Heterodimer-Promoting (E-coil) Domain (EVAACEK-EVAALEK-EVAALEK-EVAALEK (SEQ ID NO:23)); a stabilized IgG4 hinge region (SEQ ID NO:13); a variant IgG4 CH2-CH3 Domain comprising substitutions M252Y/S254T/T256E and lacking the C-terminal residue (SEQ ID NO:259); and a C-terminus.

The amino acid sequence of the first and third polypeptide chains of DART I is (SEQ ID NO:290):

```
DIQMTQSPSS LSASVGDRVT ITCRASQDVS SVVAWYQQKP

GKAPKLLIYS ASYRYTGVPS RFSGSGSGTD FTLTISSLQP

EDFATYYCQQ HYSTPWTFGG GTKLEIKGGG SGGGGQVQLV

QSGAEVKKPG ASVKVSCKAS GYSFTSYWMN WVRQAPGQGL

EWIGVIHPSD SETWLDQKFK DRVTITVDKS TSTAYMELSS

LRSEDTAVYY CAREHYGTSP FAYWGQGTLV TVSSGGCGGG

EVAACEKEVA ALEKEVAALE KEVAALEKES KYGPPCPPCP

APEFLGGPSV FLFPPKPKDT LYITREPEVT CVVVDVSQED

PEVQFNWYVD GVEVHNAKTK PREEQFNSTY RVVSVLTVLH

QDWLNGKEYK CKVSNKGLPS SIEKTISKAK GQPREPQVYT

LPPSQEEMTK NQVSLTCLVK GFYPSDIAVE WESNGQPENN
```

```
YKTTPPVLDS DGSFFLYSRL TVDKSRWQEG NVFSCSVMHE

ALHNHYTQKS LSLSLG
```

The second and fourth polypeptide chains of DART I comprise, in the N-terminal to C-terminal direction: an N-terminus, a VL Domain of a monoclonal antibody capable of binding to PD-1 (VL$_{PD-1}$ hPD-1 mAb 7 VL2) (SEQ ID NO:153); an intervening linker peptide (Linker 1: GGGSGGGG (SEQ ID NO:14)); a VH Domain of a monoclonal antibody capable of binding LAG-3 (VH$_{LAG-3}$ hLAG-3 mAb 6 VH1) (SEQ ID NO:294); a cysteine-containing intervening linker peptide (Linker 2: GGCGGG (SEQ ID NO:15)); a cysteine-containing Heterodimer-Promoting (K-coil) Domain (KVAACKE-KVAALKE-KVAALKE-KVAALKE (SEQ ID NO:24); and a C-terminus.

The amino acid sequence of the second and fourth polypeptide chains of DART I is (SEQ ID NO:291):

```
EIVLTQSPAT LSLSPGERAT LSCRASESVD NYGMSFMNWF

QQKPGQPPKL LIHAASNQGS GVPSRFSGSG SGTDFTLTIS

SLEPEDFAVY FCQQSKEVPY TFGGGTKVEI KGGGSGGGGQ

VQLVQSGAEV KKPGASVKVS CKASGYTFTD YNMDWVRQAP

GQGLEWMGDI NPDNGVTIYN QKFEGRVTMT TDTSTSTAYM

ELRSLRSDDT AVYYCAREAD YFYFDYWGQG TTLTVSSGGC

GGGKVAACKE KVAALKEKVA ALKEKVAALK E
```

C. Exemplary Four Chain Fc Region-Containing Diabodies Having CL/CH1 Domains

Four exemplary PD-1×LAG-3 bispecific, four chain Fc Region-containing diabodies comprising CL/CH1 Domains designated "DART D," "DART E," "DART J" and "DART 1" were generated. The structure of these Fc Region-containing diabodies is detailed below. These exemplary PD-1× LAG-3 diabodies are intended to illustrate, but in no way limit, the scope of the invention.

1. DART D

DART D is a bispecific, four chain, Fc Region-containing diabody having two binding sites specific for PD-1, two binding sites specific for LAG-3, CL/CH1 Domains, and a variant IgG4 Fc Region engineered for extended half-life. The first and third polypeptide chains of DART D comprise, in the N-terminal to C-terminal direction: an N-terminus; a VL Domain of a monoclonal antibody capable of binding to PD-1 (VL$_{PD-1}$ hPD-1 mAb 7 VL2) (SEQ ID NO:153); an intervening linker peptide (Linker 1: GGGSGGGG (SEQ ID NO:14)); a VH Domain of a monoclonal antibody capable of binding to LAG-3 (VH$_{LAG-3}$ hLAG-3 mAb 1 VH1) (SEQ ID NO:49); an intervening linker peptide (Linker 2: LGGGSG (SEQ ID NO:261)); an IgG4 CH1 Domain (SEQ ID NO:254); a stabilized IgG4 hinge region (SEQ ID NO: 13); a variant of an IgG4 CH2-CH3 Domain comprising substitutions M252Y/S254T/T256E and lacking the C-terminal residue (SEQ ID NO:259); and a C-terminus.

The amino acid sequence of the first and third polypeptide chains of DART D is (SEQ ID NO:269):

```
EIVLTQSPAT LSLSPGERAT LSCRASESVD NYGMSFMNWF

QQKPGQPPKL LIHAASNQGS GVPSRFSGSG SGTDFTLTIS

SLEPEDFAVY FCQQSKEVPY TFGGGTKVEI KGGGSGGGGQ

VQLVQSGAEV KKPGASVKVS CKASGYTFTN YGMNWVRQAP

GQGLEWMGWI NTYTGESTYA DDFEGRFVFS MDTSASTAYL

QISSLKAEDT AVYYCARESL YDYYSMDYWG QGTTVTVSSL

GGGSGASTKG PSVFPLAPCS RSTSESTAAL GCLVKDYFPE

PVTVSWNSGA LTSGVHTFPA VLQSSGLYSL SSVVTVPSSS

LGTKTYTCNV DHKPSNTKVD KRVESKYGPP CPPCPAPEFL

GGPSVFLFPP KPKDTLYITR EPEVTCVVVD VSQEDPEVQF

NWYVDGVEVH NAKTKPREEQ FNSTYRVVSV LTVLHQDWLN

GKEYKCKVSN KGLPSSIEKT ISKAKGQPRE PQVYTLPPSQ

EEMTKNQVSL TCLVKGFYPS DIAVEWESNG QPENNYKTTP

PVLDSDGSFF LYSRLTVDKS RWQEGNVFSC SVMHEALHNH

YTQKSLSLSL G
```

The second and fourth polypeptide chains of DART D comprise, in the N-terminal to C-terminal direction: an N-terminus; a VL Domain of a monoclonal antibody capable of binding to LAG-3 (VL$_{LAG-3}$ hLAG-3 mAb 1 VL4) (SEQ ID NO:54); an intervening linker peptide (Linker 1: GGGSGGGG (SEQ ID NO:14)); a VH Domain of a monoclonal antibody capable of binding PD-1 (VH$_{PD-1}$ hPD-1 mAb 7 VH1) (SEQ ID NO:147); an intervening linker peptide (Linker 2: LGGGSG (SEQ ID NO:261)); a Kappa CL Domain (SEQ ID NO:8); and a C-terminus.

The amino acid sequence of the second and fourth polypeptide chains of DART D is (SEQ ID NO:270):

```
DIVMTQTPLS LSVTPGQPAS ISCKSSQSLL HSDAKTYLNW

LLQKPGQPPE RLIYLVSELD SGVPDRFSGS GSGTDFTLKI

SRVEAEDVGV YYCWQGTHFP YTFGGGTKVE IKGGGSGGGG

QVQLVQSGAE VKKPGASVKV SCKASGYSFT SYWMNWVRQA

PGQGLEWIGV IHPSDSETWL DQKFKDRVTI TVDKSTSTAY

MELSSLRSED TAVYYCAREH YGTSPFAYWG QGTLVTVSSL

GGGSGRTVAA PSVFIFPPSD EQLKSGTASV VCLLNNFYPR

EAKVQWKVDN ALQSGNSQES VTEQDSKDST YSLSSTLTLS

KADYEKHKVY ACEVTHQGLS SPVTKSFNRG EC
```

2. DART E

DART E is another bispecific, four chain, Fc Region-containing diabody having two binding sites specific for PD-1, two binding sites specific for LAG-3, CL/CH1 Domains, and a variant IgG4 Fc Region engineered for extended half-life. The position of the PD-1 and LAG-3 binding sites of DART E is reversed as compared to DART D.

The first and third polypeptide chains of DART E comprise, in the N-terminal to C-terminal direction: an N-terminus, a VL Domain of a monoclonal antibody capable of binding to LAG-3 (VL$_{LAG-3}$ hLAG-3 mAb 1 VL4) (SEQ ID NO:54); an intervening linker peptide (Linker 1: GGGSGGGG (SEQ ID NO:14)); a VH Domain of a monoclonal antibody capable of binding PD-1 (VH$_{PD-1}$ hPD-1 mAb 7 VH1) (SEQ ID NO:147); an intervening linker peptide (Linker 2: LGGGSG (SEQ ID NO:261)); an IgG4 CH1 Domain (SEQ ID NO:254); a stabilized IgG4 hinge region (SEQ ID NO: 13); a variant of an IgG4 CH2-CH3 Domain comprising substitutions M252Y/S254T/T256E and lacking the C-terminal residue (SEQ ID NO:259); and a C-terminus.

The amino acid sequence of the first and third polypeptide chains of DART E is (SEQ ID NO:271):

```
DIVMTQTPLS LSVTPGQPAS ISCKSSQSLL HSDAKTYLNW

LLQKPGQPPE RLIYLVSELD SGVPDRFSGS GSGTDFTLKI

SRVEAEDVGV YYCWQGTHFP YTFGGGTKVE IKGGGSGGGG

QVQLVQSGAE VKKPGASVKV SCKASGYSFT SYWMNWVRQA

PGQGLEWIGV IHPSDSETWL DQKFKDRVTI TVDKSTSTAY

MELSSLRSED TAVYYCAREH YGTSPFAYWG QGTLVTVSSL

GGGSGASTKG PSVFPLAPCS RSTSESTAAL GCLVKDYFPE

PVTVSWNSGA LTSGVHTFPA VLQSSGLYSL SSVVTVPSSS

LGTKTYTCNV DHKPSNTKVD KRVESKYGPP CPPCPAPEFL

GGPSVFLFPP KPKDTLYITR EPEVTCVVVD VSQEDPEVQF

NWYVDGVEVH NAKTKPREEQ FNSTYRVVSV LTVLHQDWLN

GKEYKCKVSN KGLPSSIEKT ISKAKGQPRE PQVYTLPPSQ

EEMTKNQVSL TCLVKGFYPS DIAVEWESNG QPENNYKTTP

PVLDSDGSFF LYSRLTVDKS RWQEGNVFSC SVMHEALHNH

YTQKSLSLSL G
```

The second and fourth polypeptide chains of DART E comprise, in the N-terminal to C-terminal direction: an N-terminus; a VL Domain of a monoclonal antibody capable of binding to PD-1 (VL$_{PD-1}$ hPD-1 mAb 7 VL2) (SEQ ID NO:153); an intervening linker peptide (Linker 1: GGGSGGGG (SEQ ID NO:14)); a VH Domain of a monoclonal antibody capable of binding to LAG-3 (VH$_{LAG-3}$ hLAG-3 mAb 1 VH1) (SEQ ID NO:49); an intervening linker peptide (Linker 2: LGGGSG (SEQ ID NO:261)); a Kappa CL Domain (SEQ ID NO:8), and a C-terminus.

The amino acid sequence of the second and fourth polypeptide chains of DART E is (SEQ ID NO:272):

```
EIVLTQSPAT LSLSPGERAT LSCRASESVD NYGMSFMNWF

QQKPGQPPKL LIHAASNQGS GVPSRFSGSG SGTDFTLTIS

SLEPEDFAVY FCQQSKEVPY TFGGGTKVEI KGGGSGGGGQ

VQLVQSGAEV KKPGASVKVS CKASGYTFTN YGMNWVRQAP

GQGLEWMGWI NTYTGESTYA DDFEGRFVFS MDTSASTAYL

QISSLKAEDT AVYYCARESL YDYYSMDYWG QGTTVTVSSL

GGGSGRTVAA PSVFIFPPSD EQLKSGTASV VCLLNNFYPR
```

```
EAKVQWKVDN ALQSGNSQES VTEQDSKDST YSLSSTLTLS

KADYEKHKVY ACEVTHQGLS SPVTKSFNRG EC
```

3. DART J

DART J is a bispecific, four chain, Fc Region-containing diabody having two binding sites specific for PD-1, two binding sites specific for LAG-3, CL/CH1 Domains, and a variant IgG4 Fc Region engineered for extended half-life. The first and third polypeptide chains of DART J comprise, in the N-terminal to C-terminal direction: an N-terminus; a VL Domain of a monoclonal antibody capable of binding to LAG-3 (VL$_{LAG-3}$ hLAG-3 mAb 6 VL1) (SEQ ID NO:296); an intervening linker peptide (Linker 1: GGGSGGGG (SEQ ID NO:14)); a VH Domain of a monoclonal antibody capable of binding PD-1 (VH$_{PD-1}$ hPD-1 mAb 7 VH1) (SEQ ID NO:147); an intervening linker peptide (Linker 2: LGGGSG (SEQ ID NO:261)); an IgG4 CH1 Domain (SEQ ID NO:254); a stabilized IgG4 hinge region (SEQ ID NO: 13); a variant of an IgG4 CH2-CH3 Domain comprising substitutions M252Y/S254T/T256E and lacking the C-terminal residue (SEQ ID NO:259); and a C-terminus.

The amino acid sequence of the first and third polypeptide chains of DART J is (SEQ ID NO:292):

```
DIQMTQSPSS LSASVGDRVT ITCRASQDVS SVVAWYQQKP

GKAPKLLIYS ASYRYTGVPS RFSGSGSGTD FTLTISSLQP

EDFATYYCQQ HYSTPWTFGG GTKLEIKGGG SGGGGQVQLV

QSGAEVKKPG ASVKVSCKAS GYSFTSYWMN WVRQAPGQGL

EWIGVIHPSD SETWLDQKFK DRVTITVDKS TSTAYMELSS

LRSEDTAVYY CAREHYGTSP FAYWGQGTLV TVSSLGGGSG

ASTKGPSVFP LAPCSRSTSE STAALGCLVK DYFPEPVTVS

WNSGALTSGV HTFPAVLQSS GLYSLSSVVT VPSSSLGTKT

YTCNVDHKPS NTKVDKRVES KYGPPCPPCP APEFLGGPSV

FLFPPKPKDT LYITREPEVT CVVVDVSQED PEVQFNWYVD

GVEVHNAKTK PREEQFNSTY RVVSVLTVLH QDWLNGKEYK

CKVSNKGLPS SIEKTISKAK GQPREPQVYT LPPSQEEMTK

NQVSLTCLVK GFYPSDIAVE WESNGQPENN YKTTPPVLDS

DGSFFLYSRL TVDKSRWQEG NVFSCSVMHE ALHNHYTQKS

LSLSLG
```

The second and fourth polypeptide chains of DART J comprise, in the N-terminal to C-terminal direction: an N-terminus; a VL Domain of a monoclonal antibody capable of binding to PD-1 (VL$_{PD-1}$ hPD-1 mAb 7 VL2) (SEQ ID NO:153); an intervening linker peptide (Linker 1: GGGSGGGG (SEQ ID NO:14)); a VH Domain of a monoclonal antibody capable of binding to LAG-3 (VH$_{LAG-3}$ hLAG-3 mAb 6 VH1) (SEQ ID NO:294); an intervening linker peptide (Linker 2: LGGGSG (SEQ ID NO:261)); a Kappa CL Domain (SEQ ID NO:8); and a C-terminus.

The amino acid sequence of the second and fourth polypeptide chains of DART J is (SEQ ID NO:293):

```
EIVLTQSPAT LSLSPGERAT LSCRASESVD NYGMSFMNWF

QQKPGQPPKL LIHAASNQGS GVPSRFSGSG SGTDFTLTIS
```

```
SLEPEDFAVY FCQQSKEVPY TFGGGTKVEI KGGGSGGGGQ

VQLVQSGAEV KKPGASVKVS CKASGYTFTD YNMDWVRQAP

GQGLEWMGDI NPDNGVTIYN QKFEGRVTMT TDTSTSTAYM

ELRSLRSDDT AVYYCAREAD YFYFDYWGQG TTLTVSSLGG

GSGRTVAAPS VFIFPPSDEQ LKSGTASVVC LLNNFYPREA

KVQWKVDNAL QSGNSQESVT EQDSKDSTYS LSSTLTLSKA

DYEKHKVYAC EVTHQGLSSP VTKSFNRGEC
```

4. DART 1

DART 1 is a bispecific, four chain, Fc Region-containing diabody having two binding sites specific for PD-1, two binding sites specific for LAG-3, CL/CH1 Domains, and a variant IgG1 Fc Region engineered for reduced FcγR binding. The first and third polypeptide chains of DART 1 comprise, in the N-terminal to C-terminal direction: an N-terminus; a VL Domain of a monoclonal antibody capable of binding to PD-1 ($VL_{PD-1}$ PD-1 mAb A VL) (SEQ ID NO:65); an intervening linker peptide (Linker 1: GGGSGGGG (SEQ ID NO:14)); a VH Domain of a monoclonal antibody capable of binding to LAG-3 ($VH_{LAG-3}$ LAG-3 mAb A VH1) (SEQ ID NO:39); an intervening linker peptide (Linker 2: LGGGSG (SEQ ID NO:261)); an IgG1 CH1 Domain (SEQ ID NO:10); an IgG1 hinge region (SEQ ID NO: 32); a variant of an IgG1 CH2-CH3 Domain comprising substitutions L234A/L235A and lacking the C-terminal residue (SEQ ID NO:5); and a C-terminus.

The amino acid sequence of the first and third polypeptide chains of DART 1 is (SEQ ID NO:284):

```
EIVLTQSPAT LSLSPGERAT LSCRASQSIS SYLAWYQQKP

GQAPRLLIYD ASNRATGIPA RFSGSGSGTD FTLTISSLEP

EDFAVYYCQQ RSNWPLTFGQ GTNLEIKGGG SGGGGQVQLV

ESGGGVVQPG RSLRLDCKAS GITFSNSGMH WVRQAPGKGL

EWVAVIWYDG SKRYYADSVK GRFTISRDNS KNTLFLQMNS

LRAEDTAVYY CATNDDYWGQ GTLVTVSSLG GGSGASTKGP

SVFPLAPSSK STSGGTAALG CLVKDYFPEP VTVSWNSGAL

TSGVHTFPAV LQSSGLYSLS SVVTVPSSSL GTQTYICNVN

HKPSNTKVDK RVEPKSCDKT HTCPPCPAPE AAGGPSVFLF

PPKPKDTLYI TREPEVTCVV VDVSHEDPEV KFNWYVDGVE

VHNAKTKPRE EQYNSTYRVV SVLTVLHQDW LNGKEYKCKV

SNKALPAPIE KTISKAKGQP REPQVYTLPP SREEMTKNQV

SLTCLVKGFY PSDIAVEWES NGQPENNYKT TPPVLDSGS

FFLYSKLTVD KSRWQQGNVF SCSVMHEALH NHYTQKSLSL

SPG
```

The second and fourth polypeptide chains of DART 1 comprise, in the N-terminal to C-terminal direction: an N-terminus; a VL Domain of a monoclonal antibody capable of binding to LAG-3 ($VL_{LAG-3}$ LAG-3 mAb A VL) (SEQ ID NO:40); an intervening linker peptide (Linker 1: GGGSGGGG (SEQ ID NO:14)); a VH Domain of a monoclonal antibody capable of binding PD-1 ($VH_{PD-1}$ PD-1 mAb A VH) (SEQ ID NO:64); an intervening linker peptide (Linker 2: LGGGSG (SEQ ID NO:261)); a Kappa CL Domain (SEQ ID NO:8); and a C-terminus.

The amino acid sequence of the second and fourth polypeptide chains of DART 1 is (SEQ ID NO:285):

```
EIVLTQSPAT LSLSPGERAT LSCRASQSVS SYLAWYQQKP

GQAPRLLIYD ASNRATGIPA RFSGSGSGTD FTLTISSLEP

EDFAVYYCQQ SSNWPRTFGQ GTKVEIKGGG SGGGGQVQLQ

QWGAGLLKPS ETLSLTCAVY GGSFSDYYWN WIRQPPGKGL

EWIGEINHNG NTNSNPSLKS RVTLSLDTSK NQFSLKLRSV

TAADTAVYYC AFGYSDYEYN WFDPWGQGTL VTVSSLGGGS

GRTVAAPSVF IFPPSDEQLK SGTASVVCLL NNFYPREAKV

QWKVDNALQS GNSQESVTEQ DSKDSTYSLS STLTLSKADY

EKHKVYACEV THQGLSSPVT KSFNRGEC
```

D. Exemplary Five Chain Fc Region-Containing Diabodies

Two exemplary PD-1×LAG-3 bispecific, five chain Fc Region-containing diabodies comprising CL/CH1 Domains and E/K-coil Heterodimer-Promoting Domains designated "DART F," and "DART G" were generated. The structure of these Fc Region-containing diabodies is detailed below. These exemplary PD-1×LAG-3 diabodies are intended to illustrate, but in no way limit, the scope of the invention.

1. DART F

DART F is a bispecific, five chain, Fc Region-containing diabody having three binding sites specific for PD-1, one binding site specific for LAG-3, CL/CH1 Domains, a variant knob/hole-bearing IgG1 Fc Region engineered for reduced FcγR binding and extended half-life, and E/K-coil Heterodimer-Promoting Domains. The first polypeptide chain of DART F comprises, in the N-terminal to C-terminal direction: an N-terminus; a VH Domain of a monoclonal antibody capable of binding PD-1 ($VH_{PD-1}$ hPD-1 mAb 7 VH1) (SEQ ID NO:147); an IgG1 CH1 Domain (SEQ ID NO:10); an IgG1 hinge region (SEQ ID NO:32); a hole-bearing IgG1 CH2-CH3 Domain comprising substitutions L234A/L235A/M252Y/S254T/T256E/N434A/H435K and lacking the C-terminal residue (SEQ ID NO:260, wherein $X_1$ is A, $X_2$ is A; $X_3$ is Y, $X_4$ is T, $X_5$ is E, $X_6$ is S, $X_7$ is A, $X_8$ is V, $X_9$ is A, $X_{10}$ is K, and $X_{11}$ is absent); and a C-terminus.

The amino acid sequence of the first polypeptide chain of DART F is (SEQ ID NO:273):

```
QVQLVQSGAE VKKPGASVKV SCKASGYSFT SYWMNWVRQA

PGQGLEWIGV IHPSDSETWL DQKFKDRVTI TVDKSTSTAY

MELSSLRSED TAVYYCAREH YGTSPFAYWG QGTLVTVSSA

STKGPSVFPL APSSKSTSGG TAALGCLVKD YFPEPVTVSW

NSGALTSGVH TFPAVLQSSG LYSLSSVVTV PSSSLGTQTY

ICNVNHKPSN TKVDKRVEPK SCDKTHTCPP CPAPEAAGGP

SVFLFPPKPK DTLYITREPE VTCVVVDVSH EDPEVKFNWY

VDGVEVHNAK TKPREEQYNS TYRVVSVLTV LHQDWLNGKE

YKCKVSNKAL PAPIEKTISK AKGQPREPQV YTLPPSREEM

TKNQVSLSCA VKGFYPSDIA VEWESNGQPE NNYKTTPPVL
```

```
DSDGSFFLVS KLTVDKSRWQ QGNVFSCSVM HEALHAKYTQ

KSLSLSPG
```

The second and fifth polypeptide chains of DART F comprise, in the N-terminal to C-terminal direction: an N-terminus; a VL Domain of a monoclonal antibody capable of binding to PD-1 (VL$_{PD-1}$ hPD-1 mAb 7 VL2) (SEQ ID NO:153), a Kappa CL Domain (SEQ ID NO:8), and a C-terminus.

The amino acid sequence of the second and fifth polypeptide chain of DART F is (SEQ ID NO:274):

```
EIVLTQSPAT LSLSPGERAT LSCRASESVD NYGMSFMNWF

QQKPGQPPKL LIHAASNQGS GVPSRFSGSG SGTDFTLTIS

SLEPEDFAVY FCQQSKEVPY TFGGGTKVEI KRTVAAPSVF

IFPPSDEQLK SGTASVVCLL NNFYPREAKV QWKVDNALQS

GNSQESVTEQ DSKDSTYSLS STLTLSKADY EKHKVYACEV

THQGLSSPVT KSFNRGEC
```

The third polypeptide chain of DART F comprises, in the N-terminal to C-terminal direction: an N-terminus; a VH Domain of a monoclonal antibody capable of binding PD-1 (VH$_{PD-1}$ hPD-1 mAb 7 VH1) (SEQ ID NO:147); an IgG1 CH1 Domain (SEQ ID NO:10); an IgG1 hinge region (SEQ ID NO:32); a knob-bearing IgG1 CH2-CH3 Domain comprising substitutions L234A/L235A/M252Y/S254T/T256E and lacking the C-terminal residue (SEQ ID NO:260, wherein $X_1$ is A, $X_2$ is A; $X_3$ is Y, $X_4$ is T, $X_5$ is E, $X_6$ is W, $X_7$ is L, $X_8$ is Y, $X_9$ is N, $X_{10}$ is H, and $X_{11}$ is absent); an intervening linker peptide (GGGSGGGSGGG (SEQ ID NO:262)); a VL Domain of a monoclonal antibody capable of binding to LAG-3 (VL$_{LAG-3}$ hLAG-3 mAb 1 VL4) (SEQ ID NO:54); an intervening linker peptide (Linker 1: GGGSGGGG (SEQ ID NO:14)); a VH Domain of a monoclonal antibody capable of binding PD-1 (VH$_{PD-1}$ hPD-1 mAb 7 VH1) (SEQ ID NO:147); a cysteine-containing intervening linker peptide (Linker 2: GGCGGG (SEQ ID NO:15)); a Heterodimer-Promoting (E-coil) Domain (EVAALEK-EVAALEK-EVAALEK-EVAALEK (SEQ ID NO:21)); and a C-terminus.

The amino acid sequence of the third polypeptide chain of DART F is (SEQ ID NO:275):

```
QVQLVQSGAE VKKPGASVKV SCKASGYSFT SYWMNWVRQA

PGQGLEWIGV IHPSDSETWL DQKFKDRVTI TVDKSTSTAY

MELSSLRSED TAVYYCAREH YGTSPFAYWG QGTLVTVSSA

STKGPSVFPL APSSKSTSGG TAALGCLVKD YFPEPVTVSW

NSGALTSGVH TFPAVLQSSG LYSLSSVVTV PSSSLGTQTY

ICNVNHKPSN TKVDKRVEPK SCDKTHTCPP CPAPEAAGGP

SVFLFPPKPK DTLYITREPE VTCVVVDVSH EDPEVKFNWY

VDGVEVHNAK TKPREEQYNS TYRVVSVLTV LHQDWLNGKE

YKCKVSNKAL PAPIEKTISK AKGQPREPQV YTLPPSREEM

TKNQVSLWCL VKGFYPSDIA VEWESNGQPE NNYKTTPPVL

DSDGSFFLYS KLTVDKSRWQ QGNVFSCSVM HEALHNHYTQ

KSLSLSPGGG GSGGGSGGGD IVMTQTPLSL SVTPGQPASI

SCKSSQSLLH SDAKTYLNWL LQKPGQPPER LIYLVSELDS

GVPDRFSGSG SGTDFTLKIS RVEAEDVGVY YCWQGTHFPY

TFGGGTKVEI KGGGSGGGGQ VQLVQSGAEV KKPGASVKVS

CKASGYSFTS YWMNWVRQAP GQGLEWIGVI HPSDSETWLD

QKFKDRVTIT VDKSTSTAYM ELSSLRSEDT AVYYCAREHY

GTSPFAYWGQ GTLVTVSSGG CGGGEVAALE KEVAALEKEV

AALEKEVAAL EK
```

The fourth polypeptide chain of DART F comprises, in the N-terminal to C-terminal direction: an N-terminus; a VL Domain of a monoclonal antibody capable of binding to PD-1 (VL$_{PD-1}$ hPD-1 mAb 7 VL2) (SEQ ID NO:153); an intervening linker peptide (Linker 1: GGGSGGGG (SEQ ID NO:14)); a VH Domain of a monoclonal antibody capable of binding to LAG-3 (VH$_{LAG-3}$ hLAG-3 mAb 1 VH1) (SEQ ID NO:49); a cysteine-containing intervening linker peptide (Linker 2: GGCGGG (SEQ ID NO:15)); a Heterodimer-Promoting (K-coil) Domain (KVAALKE-KVAALKE-KVAALKE-KVAALKE (SEQ ID NO:22)); and a C-terminus.

The amino acid sequence of the fourth polypeptide chains of DART F is (SEQ ID NO:276):

```
EIVLTQSPAT LSLSPGERAT LSCRASESVD NYGMSFMNWF

QQKPGQPPKL LIHAASNQGS GVPSRFSGSG SGTDFTLTIS

SLEPEDFAVY FCQQSKEVPY TFGGGTKVEI KGGGSGGGGQ

VQLVQSGAEV KKPGASVKVS CKASGYTFTN YGMNWVRQAP

GQGLEWMGWI NTYTGESTYA DDFEGRFVFS MDTSASTAYL

QISSLKAEDT AVYYCARESL YDYYSMDYWG QGTTVTVSSG

GCGGGKVAAL KEKVAALKEK VAALKEKVAA LKE
```

2. DART G

DART G is a bispecific, five chain, Fc Region-containing diabody having two binding sites specific for PD-1, two binding sites specific for LAG-3, CL/CH1 Domains, a variant knob/hole-bearing IgG1 Fc Region engineered for reduced FcγR binding and extended half-life, and E/K-coil Heterodimer-Promoting Domains. The first polypeptide chain of DART G comprises, in the N-terminal to C-terminal direction: an N-terminus; a VH Domain of a monoclonal antibody capable of binding to LAG-3 (VH$_{LAG-3}$ hLAG-3 mAb 1 VH1) (SEQ ID NO:49); an IgG1 CH1 Domain (SEQ ID NO:10); an IgG1 hinge region (SEQ ID NO:32); a hole-bearing IgG1 CH2-CH3 Domain comprising substitutions L234A/L235A/M252Y/S254T/T256E/N434A/H435K and lacking the C-terminal residue (SEQ ID NO:260, wherein $X_1$ is A, $X_2$ is A; $X_3$ is Y, $X_4$ is T, $X_5$ is E, $X_6$ is S, $X_7$ is A, $X_8$ is V, $X_9$ is A, $X_{10}$ is K, and $X_{11}$ is absent); and a C-terminus.

The amino acid sequence of the first polypeptide chain of DART G is (SEQ ID NO:277):

```
QVQLVQSGAE VKKPGASVKV SCKASGYTFT NYGMNWVRQA
PGQGLEWMGW INTYTGESTY ADDFEGRFVF SMDTSASTAY
LQISSLKAED TAVYYCARES LYDYYSMDYW GQGTTVTVSS
ASTKGPSVFP LAPSSKSTSG GTAALGCLVK DYFPEPVTVS
WNSGALTSGV HTFPAVLQSS GLYSLSSVVT VPSSSLGTQT
YICNVNHKPS NTKVDKRVEP KSCDKTHTCP PCPAPEAAGG
PSVFLFPPKP KDTLYITREP EVTCVVVDVS HEDPEVKFNW
YVDGVEVHNA KTKPREEQYN STYRVVSVLT VLHQDWLNGK
EYKCKVSNKA LPAPIEKTIS KAKGQPREPQ VYTLPPSREE
MTKNQVSLSC AVKGFYPSDI AVEWESNGQP ENNYKTTPPV
LDSDGSFFLV SKLTVDKSRW QQGNVFSCSV MHEALHAKYT
QKSLSLSPG
```

The second and fifth polypeptide chains of DART G comprise, in the N-terminal to C-terminal direction: an N-terminus; a VL Domain of a monoclonal antibody capable of binding to LAG-3 (VL$_{LAG-3}$ hLAG-3 mAb 1 VL4) (SEQ ID NO:54), a Kappa CL Domain (SEQ ID NO:8), and a C-terminus.

The amino acid sequence of the second and fifth polypeptide chain of DART G is (SEQ ID NO:278):

```
DIVMTQTPLS LSVTPGQPAS ISCKSSQSLL HSDAKTYLNW
LLQKPGQPPE RLIYLVSELD SGVPDRFSGS GSGTDFTLKI
SRVEAEDVGV YYCWQGTHFP YTFGGGTKVE IKRTVAAPSV
FIFPPSDEQL KSGTASVVCL LNNFYPREAK VQWKVDNALQ
SGNSQESVTE QDSKDSTYSL SSTLTLSKAD YEKHKVYACE
VTHQGLSSPV TKSFNRGEC
```

The third polypeptide chain of DART G comprises, in the N-terminal to C-terminal direction: an N-terminus; a VH Domain of a monoclonal antibody capable of binding to LAG-3 (VH$_{LAG-3}$ hLAG-3 mAb 1 VH1) (SEQ ID NO:49); an IgG1 CH1 Domain (SEQ ID NO:10); an IgG1 hinge region (SEQ ID NO:32); a knob-bearing IgG1 CH2-CH3 Domain comprising substitutions L234A/L235A/M252Y/S254T/T256E and lacking the C-terminal residue (SEQ ID NO:260, wherein $X_1$ is A, $X_2$ is A; $X_3$ is Y, $X_4$ is T, $X_5$ is E, $X_6$ is W, $X_7$ is L, $X_8$ is Y, $X_9$ is N, $X_{10}$ is H, and $X_{11}$ is absent); an intervening linker peptide (GGGSGGGSGGG (SEQ ID NO:262)); a VL Domain of a monoclonal antibody capable of binding to PD-1 (VL$_{PD-1}$ hPD-1 mAb 7 VL2) (SEQ ID NO:153); an intervening linker peptide (Linker 1: GGGSGGGG (SEQ ID NO:14)); a VH Domain of a monoclonal antibody capable of binding PD-1 (VH$_{PD-1}$ hPD-1 mAb 7 VH1) (SEQ ID NO:147); a cysteine-containing intervening linker peptide (Linker 2: GGCGGG (SEQ ID NO:15)); a Heterodimer-Promoting (E-coil) Domain (EVAALEK-EVAALEK-EVAALEK-EVAALEK (SEQ ID NO:21)); and a C-terminus.

The amino acid sequence of the third polypeptide chain of DART G is (SEQ ID NO:279):

```
QVQLVQSGAE VKKPGASVKV SCKASGYTFT NYGMNWVRQA
PGQGLEWMGW INTYTGESTY ADDFEGRFVF SMDTSASTAY
LQISSLKAED TAVYYCARES LYDYYSMDYW GQGTTVTVSS
ASTKGPSVFP LAPSSKSTSG GTAALGCLVK DYFPEPVTVS
WNSGALTSGV HTFPAVLQSS GLYSLSSVVT VPSSSLGTQT
YICNVNHKPS NTKVDKRVEP KSCDKTHTCP PCPAPEAAGG
PSVFLFPPKP KDTLYITREP EVTCVVVDVS HEDPEVKFNW
YVDGVEVHNA KTKPREEQYN STYRVVSVLT VLHQDWLNGK
EYKCKVSNKA LPAPIEKTIS KAKGQPREPQ VYTLPPSREE
MTKNQVSLWC LVKGFYPSDI AVEWESNGQP ENNYKTTPPV
LDSDGSFFLY SKLTVDKSRW QQGNVFSCSV MHEALHNHYT
QKSLSLSPGG GGSGGGSGGG EIVLTQSPAT LSLSPGERAT
LSCRASESVD NYGMSFMNWF QQKPGQPPKL LIHAASNQGS
GVPSRFSGSG SGTDFTLTIS SLEPEDFAVY FCQQSKEVPY
TFGGGTKVEI KGGGSGGGGQ VQLVQSGAEV KKPGASVKVS
CKASGYSFTS YWMNWVRQAP GQGLEWIGVI HPSDSETWLD
QKFKDRVTIT VDKSTSTAYM ELSSLRSEDT AVYYCAREHY
GTSPFAYWGQ GTLVTVSSGG CGGGEVAALE KEVAALEKEV
AALEKEVAAL EK
```

The fourth polypeptide chain of DART G comprises, in the N-terminal to C-terminal direction: an N-terminus; a VL Domain of a monoclonal antibody capable of binding to PD-1 (VL$_{PD-1}$ hPD-1 mAb 7 VL2) (SEQ ID NO:153); an intervening linker peptide (Linker 1: GGGSGGGG (SEQ ID NO:14)); a VH Domain of a monoclonal antibody capable of binding PD-1 (VH$_{PD-1}$ hPD-1 mAb 7 VH1) (SEQ ID NO:147); a cysteine-containing intervening linker peptide (Linker 2: GGCGGG (SEQ ID NO:15)); a Heterodimer-Promoting (K-coil) Domain (KVAALKE-KVAALKE-KVAALKE-KVAALKE (SEQ ID NO:22); and a C-terminus.

The amino acid sequence of the fourth polypeptide chains of DART G is (SEQ ID NO:280):

```
EIVLTQSPAT LSLSPGERAT LSCRASESVD NYGMSFMNWF
QQKPGQPPKL LIHAASNQGS GVPSRFSGSG SGTDFTLTIS
SLEPEDFAVY FCQQSKEVPY TFGGGTKVEI KGGGSGGGGQ
VQLVQSGAEV KKPGASVKVS CKASGYSFTS YWMNWVRQAP
GQGLEWIGVI HPSDSETWLD QKFKDRVTIT VDKSTSTAYM
ELSSLRSEDT AVYYCAREHY GTSPFAYWGQ GTLVTVSSGG
CGGGKVAALK EKVAALKEKV AALKEKVAAL KE
```

E. Exemplary Three Chain Fc Region-Containing Diabody Having E/K-Coils

The present invention additionally provides PD-1×LAG-3 bispecific, three chain Fc Region-containing diabodiesy comprising E/K-coil Heterodimer-Promoting Domains. An exemplary PD-1×LAG-3 bispecific, three chain Fc Region-containing diabody comprising E/K-coil Heterodimer-Promoting Domains designated "DART H" was generated. The structure of this Fc Region-containing diabodies is detailed below. This exemplary PD-1×LAG-3 diabody is intended to illustrate, but in no way limit, the scope of the invention.

DART H is a bispecific, three chain, Fc Region-containing diabody having one binding site specific for PD-1, one binding site specific for LAG-3, a variant knob/hole-bearing IgG1 Fc Region engineered for reduced FcγR binding, and E/K-coil Heterodimer-Promoting Domains.

The first polypeptide chain of DART H comprises, in the N-terminal to C-terminal direction: an N-terminus; a VL Domain of a monoclonal antibody capable of binding to PD-1 (VL$_{PD-1}$ hPD-1 mAb 7 VL2) (SEQ ID NO:153); an intervening linker peptide (Linker 1: GGGSGGGG (SEQ ID NO:14)); a VH Domain of a monoclonal antibody capable of binding to LAG-3 (VH$_{LAG-3}$ hLAG-3 mAb 1 VH1) (SEQ ID NO:49); a cysteine-containing intervening linker peptide (Linker 2: GGCGGG (SEQ ID NO:15)); a Heterodimer-Promoting (E-coil) Domain (EVAALEK-EVAALEK-EVAALEK-EVAALEK (SEQ ID NO:21)); an intervening linker (Spacer-Linker 3: GGGDKTHTCPPCP (SEQ ID NO:263)); a knob-bearing IgG1 CH2-CH3 Domain comprising substitutions L234A/L235A and having the C-terminal lysine residue (SEQ ID NO:6); and a C-terminus.

The amino acid sequence of the first polypeptide chain of DART H is (SEQ ID NO:281):

```
EIVLTQSPAT LSLSPGERAT LSCRASESVD NYGMSFMNWF
QQKPGQPPKL LIHAASNQGS GVPSRFSGSG SGTDFTLTIS
SLEPEDFAVY FCQQSKEVPY TFGGGTKVEI KGGGSGGGGQ
VQLVQSGAEV KKPGASVKVS CKASGYTFTN YGMNWVRQAP
GQGLEWMGWI NTYTGESTYA DDFEGRFVFS MDTSASTAYL
QISSLKAEDT AVYYCARESL YDYYSMDYWG QGTTVTVSSG
GCGGGEVAAL EKEVAALEKE VAALEKEVAA LEKGGGDKTH
TCPPCPAPEA AGGPSVFLFP PKPKDTLMIS RTPEVTCVVV
DVSHEDPEVK FNWYVDGVEV HNAKTKPREE QYNSTYRVVS
VLTVLHQDWL NGKEYKCKVS NKALPAPIEK TISKAKGQPR
EPQVYTLPPS REEMTKNQVS LWCLVKGFYP SDIAVEWESN
GQPENNYKTT PPVLDSDGSF FLYSKLTVDK SRWQQGNVFS
CSVMHEALHN HYTQKSLSLS PGK
```

The second polypeptide chain of DART H comprises, in the N-terminal to C-terminal direction: an N-terminus; a VL Domain of a monoclonal antibody capable of binding to LAG-3 (VL$_{LAG-3}$ hLAG-3 mAb 1 VL4) (SEQ ID NO:54); an intervening linker peptide (Linker 1: GGGSGGGG (SEQ ID NO:14)); a VH Domain of a monoclonal antibody capable of binding to PD-1 (VH$_{PD-1}$ hPD-1 mAb 7 VH1) (SEQ ID NO:147); a cysteine-containing intervening linker peptide (Linker 2: GGCGGG (SEQ ID NO:15)); a Heterodimer-Promoting (K-coil) Domain (EVAAL<u>KE</u>-<u>K</u>VAAL<u>KE</u>-<u>K</u>VAAL<u>KE</u>-<u>K</u>VAAL<u>KE</u> (SEQ ID NO:22)); and a C-terminus.

The amino acid sequence of the second polypeptide chain of DART H is (SEQ ID NO:282):

```
DIVMTQTPLS LSVTPGQPAS ISCKSSQSLL HSDAKTYLNW
LLQKPGQPPE RLIYLVSELD SGVPDRFSGS GSGTDFTLKI
SRVEAEDVGV YYCWQGTHFP YTFGGGTKVE IKGGGSGGGG
QVQLVQSGAE VKKPGASVKV SCKASGYSFT SYWMNWVRQA
PGQGLEWIGV IHPSDSETWL DQKFKDRVTI TVDKSTSTAY
MELSSLRSED TAVYYCAREH YGTSPFAYWG QGTLVTVSSG
GCGGGKVAAL KEKVAALKEK VAALKEKVAA LKE
```

The third polypeptide chain of DART H comprises, in the N-terminal to C-terminal direction: an N-terminus; a hinge region (DKTHTCPPCP (SEQ ID NO:31); a hole-bearing IgG1 CH2-CH3 Domain comprising substitutions L234A/L235A and having the C-terminal lysine residue (SEQ ID NO:7); and a C-terminus.

The amino acid sequence of the third polypeptide chain of DART H is (SEQ ID NO:283):

```
DKTHTCPPCP APEAAGGPSV FLFPPKPKDT LMISRTPEVT
CVVVDVSHED PEVKFNWYVD GVEVHNAKTK PREEQYNSTY
RVVSVLTVLH QDWLNGKEYK CKVSNKALPA PIEKTISKAK
GQPREPQVYT LPPSREEMTK NQVSLSCAVK GFYPSDIAVE
WESNGQPENN YKTTPPVLDS DGSFFLVSKL TVDKSRWQQG
NVFSCSVMHE ALHNRYTQKS LSLSPGK
```

F. Exemplary Bispecific Antibody

An exemplary PD-1×LAG-3 four chain bispecific antibody designated "BSAB A" was generated. The structure of this bispecific antibody is detailed below. This exemplary PD-1×LAG-3 bispecific antibody is intended to illustrate, but in no way limit, the scope of the invention.

BSAB A is a bispecific antibody having one binding site specific for PD-1, one binding site specific for LAG-3, a variant IgG1 Fc Region engineered to reduce FcγR binding and to foster complexing between the two different heavy chain polypeptides (see, e.g., WO 2011/143545).

The first polypeptide chain of BSAB A comprises, in the N-terminal to C-terminal direction: an N-terminus; a VH Domain of a monoclonal antibody capable of binding to PD-1 (VH$_{PD-1}$ hPD-1 mAb 7 VH1) (SEQ ID NO:147); an IgG1 CH1 Domain (SEQ ID NO:10); a variant IgG1 hinge region comprising substitutions D221E/P228E (numbered by the EU index as in Kabat and underlined in SEQ ID NO:286, below); a variant IgG1 CH2-CH3 Domain comprising substitutions L234A/L235A/L368E (underlined in SEQ ID NO:286, below) and lacking the C-terminal residue; and a C-terminus.

The amino acid sequence of the first polypeptide chain of BSAB A is (SEQ ID NO:286):

```
QVQLVQSGAE VKKPGASVKV SCKASGYSFT SYWMNWVRQA
PGQGLEWIGV IHPSDSETWL DQKFKDRVTI TVDKSTSTAY
MELSSLRSED TAVYYCAREH YGTSPFAYWG QGTLVTVSSA
STKGPSVFPL APSSKSTSGG TAALGCLVKD YFPEPVTVSW
```

```
NSGALTSGVH TFPAVLQSSG LYSLSSVVTV PSSSLGTQTY

ICNVNHKPSN TKVDKRVEPK SCEKTHTCPE CPAPEAAGGP

SVFLFPPKPK DTLMISRTPE VTCVVVDVSH EDPEVKFNWY

VDGVEVHNAK TKPREEQYNS TYRVVSVLTV LHQDWLNGKE

YKCKVSNKAL PAPIEKTISK AKGQPREPQV YTLPPSREEM

TKNQVSLTCE VKGFYPSDIA VEWESNGQPE NNYKTTPPVL

DSDGSFFLYS KLTVDKSRWQ QGNVFSCSVM HEALHNHYTQ

KSLSLSPG
```

The second polypeptide chain of BSAB comprises, in the N-terminal to C-terminal direction: an N-terminus; a VL Domain of a monoclonal antibody capable of binding to PD-1 ($VL_{PD-1}$ hPD-1 mAb 7 VL2) (SEQ ID NO:153); a Kappa CL Domain (SEQ ID NO:8), and a C-terminus.

The amino acid sequence of the second polypeptide chain of BSAB is (SEQ ID NO:287):

```
EIVLTQSPAT LSLSPGERAT LSCRASESVD NYGMSFMNWF

QQKPGQPPKL LIHAASNQGS GVPSRFSGSG SGTDFTLTIS

SLEPEDFAVY FCQQSKEVPY TFGGGTKVEI KRTVAAPSVF

IFPPSDEQLK SGTASVVCLL NNFYPREAKV QWKVDNALQS

GNSQESVTEQ DSKDSTYSLS STLTLSKADY EKHKVYACEV

THQGLSSPVT KSFNRGEC
```

The third polypeptide chain of BSAB A comprises, in the N-terminal to C-terminal direction: an N-terminus; a VH Domain of a monoclonal antibody capable of binding to LAG-3 ($VH_{LAG-3}$ hLAG-3 mAb 1 VH1) (SEQ ID NO:49); an IgG1 CH1 Domain (SEQ ID NO:10); a variant IgG1 hinge region comprising substitutions D221R/P228R (underlined in SEQ ID NO:288, below); a variant IgG1 CH2-CH3 Domain comprising substitutions L234A/L235A/L409R (underlined in SEQ ID NO:288, below) and lacking the C-terminal residue; and a C-terminus.

The amino acid sequence of the third polypeptide chain of BSAB A is (SEQ ID NO:288):

```
QVQLVQSGAE VKKPGASVKV SCKASGYTFT NYGMNWVRQA

PGQGLEWMGW INTYTGESTY ADDFEGRFVF SMDTSASTAY

LQISSLKAED TAVYYCARES LYDYYSMDYW GQGTTVTVSS

ASTKGPSVFP LAPSSKSTSG GTAALGCLVK DYFPEPVTVS

WNSGALTSGV HTFPAVLQSS GLYSLSSVVT VPSSSLGTQT

YICNVNHKPS NTKVDKRVEP KSCRKTHTCP RCPAPEAAGG

PSVFLFPPKP KDTLMISRTP EVTCVVVDVS HEDPEVKFNW

YVDGVEVHNA KTKPREEQYN STYRVVSVLT VLHQDWLNGK

EYKCKVSNKA LPAPIEKTIS KAKGQPREPQ VYTLPPSREE

MTKNQVSLTC LVKGFYPSDI AVEWESNGQP ENNYKTTPPV

LDSDGSFFLY SRLTVDKSRW QQGNVFSCSV MHEALHNHYT

QKSLSLSPG
```

The fourth polypeptide chain of BSAB A comprises, in the N-terminal to C-terminal direction: an N-terminus; a VL Domain of a monoclonal antibody capable of binding to LAG-3 ($VL_{LAG-3}$ hLAG-3 mAb 1 VL4) (SEQ ID NO:54); a Kappa CL Domain (SEQ ID NO:8), and a C-terminus.

The amino acid sequence of the fourth polypeptide chain of BSAB A is (SEQ ID NO:289):

```
DIVMTQTPLS LSVTPGQPAS ISCKSSQSLL HSDAKTYLNW

LLQKPGQPPE RLIYLVSELD SGVPDRFSGS GSGTDFTLKI

SRVEAEDVGV YYCWQGTHFP YTFGGGTKVE IKRTVAAPSV

FIFPPSDEQL KSGTASVVCL LNNFYPREAK VQWKVDNALQ

SGNSQESVTE QDSKDSTYSL SSTLTLSKAD YEKHKVYACE

VTHQGLSSPV TKSFNRGEC
```

IX. Reference Antibodies

A. Reference Anti-Human PD-1 Antibodies

In order to assess and characterize the novel anti-human PD-1-binding molecules of the present invention, the following reference antibodies were employed: nivolumab (also known as 5C4, BMS-936558, ONO-4538, MDX-1106, and marketed as OPDIVO® by Bristol-Myers Squibb), a human IgG4 antibody designated herein as "PD-1 mAb A;" and pembrolizumab (formerly known as lambrolizumab, also known as MK-3475, SCH-900475, and marketed as KEYTRUDA® by Merck) a humanized IgG4 antibody designated herein as "PD-1 mAb B."

1. Nivolumab ("PD-1 mAb A")

The amino acid sequence of the Heavy Chain Variable Domain of PD-1 mAb A has the amino acid sequence (SEQ ID NO:64) ($CDR_H$ residues are shown underlined):

```
QVQLVESGGG VVQPGRSLRL DCKASGITFS NSGMHWVRQA

PGKGLEWVAV IWYDGSKRYY ADSVKGRFTI SRDNSKNTLF

LQMNSLRAED TAVYYCATND DYWGQGTLVT VSS
```

The amino acid sequence of the Light Chain Variable Domain of PD-1 mAb A has the amino acid sequence (SEQ ID NO:65) ($CDR_L$ residues are shown underlined):

```
EIVLTQSPAT LSLSPGERAT LSCRASQSVS SYLAWYQQKP

GQAPRLLIYD ASNRATGIPA RFSGSGSGTD FTLTISSLEP

EDFAVYYCQQ SSNWPRTFGQ GTKVEIK
```

2. Pembrolizumab ("PD-1 mAb B")

The amino acid sequence of the Heavy Chain Variable Domain of PD-1 mAb B has the amino acid sequence (SEQ ID NO:66) ($CDR_H$ residues are shown underlined):

```
QVQLVQSGVE VKKPGASVKV SCKASGYTFT NYYMYWVRQA

PGQGLEWMGG INPSNGGTNF NEKFKNRVTL TTDSSTTTAY

MELKSLQFDD TAVYYCARRD YRFDMGFDYW GQGTTVTVSS
```

The amino acid sequence of the Light Chain Variable Domain of PD-1 mAb B has the amino acid sequence (SEQ ID NO:67) (CDR$_L$ residues are shown underlined):

```
EIVLTQSPAT LSLSPGERAT LSCRASKGVS TSGYSYLHWY

QQKPGQAPRL LIYLASYLES GVPARFSGSG SGTDFTLTIS

SLEPEDFAVY YCQHSRDLPL TFGGGTKVEIK
```

X. Methods of Production

An anti-human PD-1 polypeptide, and other PD-1 agonists, antagonists and modulators can be created from the polynucleotides and/or sequences of the anti-PD-1 antibodies PD-1 mAb 1-15 by methods known in the art, for example, synthetically or recombinantly. One method of producing such peptide agonists, antagonists and modulators involves chemical synthesis of the polypeptide, followed by treatment under oxidizing conditions appropriate to obtain the native conformation, that is, the correct disulfide bond linkages. This can be accomplished using methodologies well known to those skilled in the art (see, e.g., Kelley, R. F. et al. (1990) In: GENETIC ENGINEERING PRINCIPLES AND METHODS, Setlow, J. K. Ed., Plenum Press, N.Y., vol. 12, pp 1-19; Stewart, J. M et al. (1984) SOLID PHASE PEPTIDE SYNTHESIS, Pierce Chemical Co., Rockford, Ill.; see also U.S. Pat. Nos. 4,105,603; 3,972,859; 3,842,067; and 3,862,925).

Polypeptides of the invention may be conveniently prepared using solid phase peptide synthesis (Merrifield, B. (1986) "*Solid Phase Synthesis,*" Science 232(4748):341-347; Houghten, R. A. (1985) "*General Method For The Rapid Solid-Phase Synthesis Of Large Numbers Of Peptides: Specificity Of Antigen-Antibody Interaction At The Level Of Individual Amino Acids,*" Proc. Natl. Acad. Sci. (U.S.A.) 82(15):5131-5135; Ganesan, A. (2006) "*Solid-Phase Synthesis In The Twenty First Century,*" Mini Rev. Med. Chem. 6(1):3-10).

In yet another alternative, fully human antibodies having one or more of the CDRs of PD-1 mAb 1, PD-1 mAb 2, PD-1 mAb 3, PD-1 mAb 4, PD-1 mAb 5, PD-1 mAb 6, PD-1 mAb 7, PD-1 mAb 8, PD-1 mAb 9, PD-1 mAb 10, PD-1 mAb 11, PD-1 mAb 12, PD-1 mAb 13, PD-1 mAb 14, or PD-1 mAb 15, or which compete with PD-1 mAb 1, PD-1 mAb 2, PD-1 mAb 3, PD-1 mAb 4, PD-1 mAb 5, PD-1 mAb 6, PD-1 mAb 7, PD-1 mAb 8, PD-1 mAb 9, PD-1 mAb 10, PD-1 mAb 11, PD-1 mAb 12, PD-1 mAb 13, PD-1 mAb 14, or PD-1 mAb 15, for binding to human PD-1 or a soluble form thereof may be obtained through the use of commercially available mice that have been engineered to express specific human immunoglobulin proteins. Transgenic animals that are designed to produce a more desirable (e.g., fully human antibodies) or more robust immune response may also be used for generation of humanized or human antibodies. Examples of such technology are XENOMOUSE™ (Abgenix, Inc., Fremont, Calif.) and HUMAB-MOUSE® and TC MOUSE™ (both from Medarex, Inc., Princeton, N.J.).

In an alternative, antibodies may be made recombinantly and expressed using any method known in the art. Antibodies may be made recombinantly by first isolating the antibodies made from host animals, obtaining the gene sequence, and using the gene sequence to express the antibody recombinantly in host cells (e.g., CHO cells). Another method that may be employed is to express the antibody sequence in plants {e.g., tobacco) or transgenic milk. Suitable methods for expressing antibodies recombinantly in plants or milk have been disclosed (see, for example, Peeters et al. (2001) "*Production Of Antibodies And Antibody Fragments In Plants,*" Vaccine 19:2756; Lonberg, N. et al. (1995) "*Human Antibodies From Transgenic Mice,*" Int. Rev. Immunol 13:65-93; and Pollock et al. (1999) "*Transgenic Milk As A Method For The Production Of Recombinant Antibodies,*" J. Immunol Methods 231:147-157). Suitable methods for making derivatives of antibodies, e.g., humanized, single-chain, etc. are known in the art. In another alternative, antibodies may be made recombinantly by phage display technology (see, for example, U.S. Pat. Nos. 5,565,332; 5,580,717; 5,733,743; 6,265,150; and Winter, G. et al. (1994) "*Making Antibodies By Phage Display Technology,*" Annu. Rev. Immunol. 12.433-455).

The antibodies or protein of interest may be subjected to sequencing by Edman degradation, which is well known to those of skill in the art. The peptide information generated from mass spectrometry or Edman degradation can be used to design probes or primers that are used to clone the protein of interest.

An alternative method of cloning the protein of interest is by "panning" using purified PD-1 or portions thereof for cells expressing an antibody or protein of interest that possesses one or more of the CDRs of PD-1 mAb 1, PD-1 mAb 2, PD-1 mAb 3, PD-1 mAb 4, PD-1 mAb 5, PD-1 mAb 6, PD-1 mAb 7, PD-1 mAb 8, PD-1 mAb 9, PD-1 mAb 10, PD-1 mAb 11, PD-1 mAb 12, PD-1 mAb 13, PD-1 mAb 14, or PD-1 mAb 15, or of an antibody that competes with PD-1 mAb 1, PD-1 mAb 2, PD-1 mAb 3, PD-1 mAb 4, PD-1 mAb 5, PD-1 mAb 6, PD-1 mAb 7, PD-1 mAb 8, PD-1 mAb 9, PD-1 mAb 10, PD-1 mAb 11, PD-1 mAb 12, PD-1 mAb 13, PD-1 mAb 14, or PD-1 mAb 15, for binding to human PD-1. The "panning" procedure may be conducted by obtaining a cDNA library from tissues or cells that express PD-1, overexpressing the cDNAs in a second cell type, and screening the transfected cells of the second cell type for a specific binding to PD-1 in the presence or absence of PD-1 mAb 1, PD-1 mAb 2, PD-1 mAb 3, PD-1 mAb 4, PD-1 mAb 5, PD-1 mAb 6, PD-1 mAb 7, PD-1 mAb 8, PD-1 mAb 9, PD-1 mAb 10, PD-1 mAb 11, PD-1 mAb 12, PD-1 mAb 13, PD-1 mAb 14, or PD-1 mAb 15. Detailed descriptions of the methods used in cloning mammalian genes coding for cell surface proteins by "panning" can be found in the art (see, for example, Aruffo, A. et al. (1987) "*Molecular Cloning Of A CD28 cDNA By A High-Efficiency COS Cell Expression System,*" Proc. Natl. Acad. Sci. (U.S.A.) 84:8573-8577 and Stephan, J. et al. (1999) "*Selective Cloning Of Cell Surface Proteins Involved In Organ Development: Epithelial Glycoprotein Is Involved In Normal Epithelial Differentiation,*" Endocrinol. 140:5841-5854).

Vectors containing polynucleotides of interest can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell.

Any host cell capable of overexpressing heterologous DNAs can be used for the purpose of isolating the genes encoding the antibody, polypeptide or protein of interest. Non-limiting examples of suitable mammalian host cells include but are not limited to COS, HeLa, and CHO cells. Preferably, the host cells express the cDNAs at a level of about 5-fold higher, more preferably 10-fold higher, even more preferably 20-fold higher than that of the corresponding endogenous antibody or protein of interest, if present, in the host cells. Screening the host cells for a specific binding to PD-1 is effected by an immunoassay or FACS. A cell overexpressing the antibody or protein of interest can be identified.

The invention includes polypeptides comprising an amino acid sequence of the antibodies of this invention. The polypeptides of this invention can be made by procedures known in the art. The polypeptides can be produced by proteolytic or other degradation of the antibodies, by recombinant methods (i.e., single or fusion polypeptides) as described above or by chemical synthesis. Polypeptides of the antibodies, especially shorter polypeptides up to about 50 amino acids, are conveniently made by chemical synthesis. Methods of chemical synthesis are known in the art and are commercially available. For example, an anti-human PD-1 polypeptide could be produced by an automated polypeptide synthesizer employing the solid phase method.

The invention includes variants of PD-1 mAb 1, PD-1 mAb 2, PD-1 mAb 3, PD-1 mAb 4, PD-1 mAb 5, PD-1 mAb 6, PD-1 mAb 7, PD-1 mAb 8, PD-1 mAb 9, PD-1 mAb 10, PD-1 mAb 11, PD-1 mAb 12, PD-1 mAb 13, PD-1 mAb 14, or PD-1 mAb 15 antibodies and their polypeptide fragments that bind to PD-1, including functionally equivalent antibodies and fusion polypeptides that do not significantly affect the properties of such molecules as well as variants that have enhanced or decreased activity. Modification of polypeptides is routine practice in the art and need not be described in detail herein. Examples of modified polypeptides include polypeptides with conservative substitutions of amino acid residues, one or more deletions or additions of amino acids which do not significantly deleteriously change the functional activity, or use of chemical analogs. Amino acid residues that can be conservatively substituted for one another include but are not limited to: glycine/alanine; serine/threonine; valine/isoleucine/leucine; asparagine/glutamine; aspartic acid/glutamic acid; lysine/arginine; and phenylalanine/tyrosine. These polypeptides also include glycosylated and non-glycosylated polypeptides, as well as polypeptides with other post-translational modifications, such as, for example, glycosylation with different sugars, acetylation, and phosphorylation. Preferably, the amino acid substitutions would be conservative, i.e., the substituted amino acid would possess similar chemical properties as that of the original amino acid. Such conservative substitutions are known in the art, and examples have been provided above. Amino acid modifications can range from changing or modifying one or more amino acids to complete redesign of a region, such as the Variable Domain. Changes in the Variable Domain can alter binding affinity and/or specificity. Other methods of modification include using coupling techniques known in the art, including, but not limited to, enzymatic means, oxidative substitution and chelation. Modifications can be used, for example, for attachment of labels for immunoassay, such as the attachment of radioactive moieties for radioimmunoassay. Modified polypeptides are made using established procedures in the art and can be screened using standard assays known in the art.

The invention encompasses fusion proteins comprising one or more of the polypeptides or PD-1 mAb 1, PD-1 mAb 2, PD-1 mAb 3, PD-1 mAb 4, PD-1 mAb 5, PD-1 mAb 6, PD-1 mAb 7, PD-1 mAb 8, PD-1 mAb 9, PD-1 mAb 10, PD-1 mAb 11, PD-1 mAb 12, PD-1 mAb 13, PD-1 mAb 14, or PD-1 mAb 15 antibodies of this invention. In one embodiment, a fusion polypeptide is provided that comprises a light chain, a heavy chain or both a light and heavy chain. In another embodiment, the fusion polypeptide contains a heterologous immunoglobulin constant region. In another embodiment, the fusion polypeptide contains a Light Chain Variable Domain and a Heavy Chain Variable Domain of an antibody produced from a publicly-deposited hybridoma. For purposes of this invention, an antibody fusion protein contains one or more polypeptide domains that specifically bind to PD-1 and another amino acid sequence to which it is not attached in the native molecule, for example, a heterologous sequence or a homologous sequence from another region.

XI. Uses of the PD-1-Binding Molecules of the Present Invention

The present invention encompasses compositions, including pharmaceutical compositions, comprising the PD-1-binding molecules of the present invention (e.g., anti-PD-1 antibodies, anti-PD-1 bispecific diabodies, etc.), polypeptides derived from such molecules, polynucleotides comprising sequences encoding such molecules or polypeptides, and other agents as described herein.

A. Therapeutic Uses

As discussed above, PD-1 plays an important role in negatively regulating T-cell proliferation, function and homeostasis. Certain of the PD-1-binding molecules of the present invention have the ability to inhibit PD-1 function, and thus reverse the PD-1-mediated immune system inhibition. As such, PD-1 mAb 1, PD-1 mAb 3, PD-1 mAb 5, PD-1 mAb 6, PD-1 mAb 7, PD-1 mAb 8, PD-1 mAb 9, PD-1 mAb 10, PD-1 mAb 11, PD-1 mAb 12, PD-1 mAb 13, PD-1 mAb 14, and PD-1 mAb 15, their humanized derivatives, and molecules comprising their PD-1-binding fragments (e.g., bispecific antibodies, bispecific diabodies (including, but not limited to, DART-A, DART-B, DART-C, DART-D, DART-E, DART-F, DART-G, DART-H, DART-I, and DART-J), etc.), or that compete for binding with such antibodies, may be used to block PD-1-mediated immune system inhibition, and thereby promote the activation of the immune system.

Such bispecific PD-1-binding molecules of the present invention that bind to PD-1 and another molecule involved in regulating an immune check point present on the cell surface (e.g., LAG-3) augment the immune system by blocking immune system inhibition mediated by PD-1 and such immune check point molecules. Thus, such PD-1-binding molecules of the invention are useful for augmenting an immune response (e.g., the T-cell mediated immune response) of a subject. In particular, such PD-1-binding molecules of the invention and may be used to treat any disease or condition associated with an undesirably suppressed immune system, including cancer and diseases that are associated with the presence of a pathogen (e.g., a bacterial, fungal, viral or protozoan infection).

The cancers that may be treated by such PD-1-binding molecules of the present invention include cancers characterized by the presence of a cancer cell selected from the group consisting of a cell of: an adrenal gland tumor, an AIDS-associated cancer, an alveolar soft part sarcoma, an astrocytic tumor, bladder cancer, bone cancer, a brain and spinal cord cancer, a metastatic brain tumor, a breast cancer, a carotid body tumors, a cervical cancer, a chondrosarcoma, a chordoma, a chromophobe renal cell carcinoma, a clear cell carcinoma, a colon cancer, a colorectal cancer, a cutaneous benign fibrous histiocytoma, a desmoplastic small round cell tumor, an ependymoma, a Ewing's tumor, an extraskeletal myxoid chondrosarcoma, a fibrogenesis imperfecta ossium, a fibrous dysplasia of the bone, a gallbladder or bile duct cancer, gastric cancer, a gestational trophoblastic disease, a germ cell tumor, a head and neck cancer, hepatocellular carcinoma, an islet cell tumor, a Kaposi's Sarcoma, a kidney cancer, a leukemia, a lipoma/benign lipomatous tumor, a liposarcoma/malignant lipomatous tumor, a liver cancer, a lymphoma, a lung cancer, a medulloblastoma, a melanoma, a meningioma, a multiple endocrine neoplasia, a multiple myeloma, a myelodysplastic syndrome, a neuroblastoma, a neuroendocrine tumors, an ovarian cancer, a pancreatic cancer, a papillary thyroid carcinoma, a parathyroid tumor, a pediatric cancer, a peripheral nerve sheath tumor, a phaeochromocytoma, a pituitary tumor, a prostate cancer, a posterious uveal melanoma, a rare hematologic disorder, a renal metastatic cancer, a rhabdoid tumor, a rhabdomysarcoma, a sarcoma, a skin cancer, a soft-tissue sarcoma, a squamous cell cancer, a stomach cancer, a synovial sarcoma, a testicular cancer, a thymic carcinoma, a thymoma, a thyroid metastatic cancer, and a uterine cancer.

In particular, such PD-1-binding molecules of the present invention may be used in the treatment of colorectal cancer, hepatocellular carcinoma, glioma, kidney cancer, breast cancer, multiple myeloma, bladder cancer, neuroblastoma; sarcoma, non-Hodgkin's lymphoma, non-small cell lung cancer, ovarian cancer, pancreatic cancer and rectal cancer.

Pathogen-associated diseases that may be treated by such PD-1-binding molecules of the present invention include chronic viral, bacterial, fungal and parasitic infections. Chronic infections that may be treated by the PD-1-binding molecules of the present invention include Epstein Barr virus, Hepatitis A Virus (HAV); Hepatitis B Virus (HBV); Hepatitis C Virus (HCV); herpes viruses (e.g. HSV-1, HSV-2, CMV), Human Immunodeficiency Virus (HIV), Vesicular Stomatitis Virus (VSV), *Bacilli, Citrobacter, Cholera, Diphtheria, Enterobacter, Gonococci, Helicobacter pylori, Klebsiella, Legionella, Meningococci, mycobacteria, Pseudomonas, Pneumonococci, rickettsia* bacteria, *Salmonella, Serratia, Staphylococci, Streptococci, Tetanus, Aspergillus (fumigatus, niger*, etc.), *Blastomyces dermatitidis, Candida (albicans, krusei, glabrata, tropicalis*, etc.), *Cryptococcus neoformans*, Genus *Mucorales (mucor, absidia, rhizopus), Sporothrix schenkii, Paracoccidioides brasiliensis, Coccidioides immitis, Histoplasma capsulatum, Leptospirosis, Borrelia burgdorferi*, helminth parasite (hookworm, tapeworms, flukes, flatworms (e.g. *Schistosomia), Giardia Zambia, trichinella, Dientamoeba Fragilis, Trypanosoma brucei, Trypanosoma cruzi*, and *Leishmania donovani*.

Such PD-1-binding molecules of the invention can be combined with other anti-cancer agents, in particular, molecules that specifically bind a cancer antigen (e.g., antibodies, diabodies). Anti-cancer therapies that may be combined with the PD-1-binding molecules of the invention include molecules which specifically bind one more cancer antigens including: 19.9 as found in colon cancer, gastric cancer mucins; 4.2; A33 (a colorectal carcinoma antigen; Almqvist, Y. 2006, *Nucl Med Biol.* November; 33(8):991-998); ADAM-9 (United States Patent Publication No. 2006/0172350; PCT Publication No. WO 06/084075); AH6 as found in gastric cancer; ALCAM (PCT Publication No. WO 03/093443); APO-1 (malignant human lymphocyte antigen) (Trauth et al. (1989) "*Monoclonal Antibody-Mediated Tumor Regression By Induction Of Apoptosis*," Science 245:301-304); B1 (Egloff, A. M. et al. 2006, Cancer Res. 66(1):6-9); B7-H3 (Collins, M. et al. (2005) "*The B7 Family Of Immune-Regulatory Ligands*," Genome Biol. 6:223.1-223.7). Chapoval, A. et al. (2001) "*B7-H3: A Costimulatory Molecule For T Cell Activation and IFN-γ Production*," Nature Immunol. 2:269-274; Sun, M. et al. (2002) "*Characterization of Mouse and Human B7-H3 Genes*," J. Immunol. 168:6294-6297); BAGE (Bodey, B. 2002 Expert Opin Biol Ther. 2(6):577-84); beta-catenin (Prange W. et al. 2003 *J Pathol*. 201(2):250-9); blood group ALe$^b$/Le$^y$ as found in colonic adenocarcinoma; Burkitt's lymphoma antigen-38.13, C14 as found in colonic adenocarcinoma; CA125 (ovarian carcinoma antigen) (Bast, R. C. Jr. et al. 2005 *Int J Gynecol Cancer* 15 Suppl 3:274-81; Yu et al. (1991) "*Coexpression Of Different Antigenic Markers On Moieties That Bear CA 125 Determinants*," Cancer Res. 51(2):468-475); Carboxypeptidase M (United States Patent Publication No. 2006/0166291); CD5 (Calin, G. A. et al. 2006 *Semin Oncol.* 33(2): 167-73; CD19 (Ghetie et al. (1994) "*Anti-CD19 Inhibits The Growth Of Human B-Cell Tumor Lines In Vitro And Of Daudi Cells In SCID Mice By Inducing Cell Cycle Arrest*," Blood 83:1329-1336; Troussard, X. et al. 1998 *Hematol Cell Ther.* 40(4): 139-48); CD20 (Reff et al. (1994) "*Depletion Of B Cells In Vivo By A Chimeric Mouse Human Monoclonal Antibody To CD20*," Blood 83:435-445; Thomas, D. A. et al. 2006 Hematol Oncol Clin North Am. 20(5):1125-36); CD22 (Kreitman, R. J. 2006 AAPS J. 18; 8(3):E532-51); CD23 (Rosati, S. et al. 2005 *Curr Top Microbiol Immunol.* 5; 294:91-107); CD25 (Troussard, X. et al. 1998 *Hematol Cell Ther.* 40(4):139-48); CD27 (Bataille, R. 2006 *Haematologica* 91(9):1234-40); CD28 (Bataille, R. 2006 *Haematologica* 91(9):1234-40); CD33 (Sgouros et al. (1993) "*Modeling And Dosimetry Of Monoclonal Antibody M195 (Anti-CD33) In Acute Myelogenous Leukemia*," J. Nucl. Med. 34:422-430); CD36 (Ge, Y. 2005 *Lab Hematol.* 11(1):31-7); CD40/CD154 (Messmer, D. et al. 2005 *Ann NY Acad Sci.* 1062:51-60); CD45 (Jurcic, J. G. 2005 *Curr Oncol Rep.* 7(5):339-46); CD56 (Bataille, R. 2006 *Haematologica* 91(9):1234-40); CD46 (U.S. Pat. No. 7,148,038; PCT Publication No. WO 03/032814); CD52 (Eketorp, S. S. et al. (2014) "*Alemtuzumab (Anti-CD52 Monoclonal Antibody) As Single-Agent Therapy In Patients With Relapsed/Refractory Chronic Lymphocytic Leukaemia (CLL)-A Single Region Experience On Consecutive Patients*," Ann Hematol. 93(10):1725-1733; Suresh, T. et al. (2014) "*New Antibody Approaches To Lymphoma Therapy*," J. Hematol. Oncol. 7:58; Hoelzer, D. (2013) "*Targeted Therapy With Monoclonal Antibodies In Acute Lymphoblastic Leukemia*," Curr. Opin. Oncol. 25(6):701-706); CD56 (Bataille, R. 2006 *Haematologica* 91(9):1234-40); CD79a/CD79b (Troussard, X. et al. 1998 *Hematol Cell Ther.* 40(4):139-48; Chu, P. G. et al. 2001 Appl Immunohistochem Mol Morphol. 9(2):97-106); CD103 (Troussard, X. et al. 1998 *Hematol Cell Ther.* 40(4):139-48); CD317 (Kawai, S. et al. (2008) "*Interferon-A Enhances CD317 Expression And The Antitumor Activity Of Anti-CD317 Monoclonal Antibody In Renal Cell Carcinoma Xenograft Models*," Cancer Science 99(12):2461-2466; Wang, W. et al. (2009) HM1.24 (CD317) *Is A Novel Target Against Lung Cancer For Immunotherapy Using Anti-HM1.24 Antibody*," Cancer Immunology, Immunotherapy 58(6):967-976; Wang, W. et al. (2009) "*Chimeric And Humanized Anti-HM1.24 Antibodies Mediate Antibody-Dependent Cellular Cytotoxicity Against Lung Cancer Cells. Lung Cancer*," 63(1):23-31; Sayeed, A. et al. (2013) "*Aberrant Regulation Of The BST2 (Tetherin) Promoter Enhances Cell Proliferation And Apoptosis Evasion In High Grade Breast Cancer Cells*," PLoS ONE 8(6)e67191, pp. 1-10); CDK4 (Lee, Y. M. et al. 2006 Cell Cycle 5(18):2110-4); CEA (carcinoembryonic antigen; Foon et al. (1995) "*Immune Response To The Carcinoembryonic Antigen In Patients Treated With An Anti-Idiotype Antibody Vaccine*," J. Clin. Invest. 96(1):334-42); Mathelin, C. 2006 *Gynecol Obstet Fertil.* 34(7-8):638-46; Tellez-Avila, F. I. et al. 2005 *Rev Invest Clin.* 57(6):814-9); CEACAM9/CEACAM6 (Zheng, C. et al. (2011) "*A Novel Anti-CEACAM5 Monoclonal Antibody, CC4, Suppresses Colorectal Tumor Growth and Enhances NK Cells-Mediated*

Tumor Immunity," PLoS One 6(6):e21146, pp. 1-11); C017-1A (Ragnhammar et al. (1993) "Effect Of Monoclonal Antibody 17-1A And GM-CSF In Patients With Advanced Colorectal Carcinoma—Long-Lasting, Complete Remissions Can Be Induced," Int. J. Cancer 53:751-758); CO-43 (blood group Le$^b$); CO-514 (blood group Le$^a$) as found in adenocarcinoma; CTA-1; CTLA-4 (Peggs, K. S. et al. 2006 Curr Opin Immunol. 18(2):206-13); Cytokeratin 8 (PCT Publication No. WO 03/024191); D1.1; D$_1$56-22; DR5 (Abdulghani, J. et al. (2010) "TRAIL Receptor Signaling And Therapeutics," Expert Opin. Ther. Targets 14(10):1091-1108; Andera, L. (2009) "Signaling Activated By The Death Receptors Of The TNFR Family," Biomed. Pap. Med. Fac. Univ. Palacky Olomouc Czech. Repub. 153(3):173-180; Carlo-Stella, C. et al. (2007) "Targeting TRAIL Agonistic Receptors for Cancer Therapy," Clin, Cancer 13(8):2313-2317; Chaudhari, B. R. et al. (2006) "Following the TRAIL to Apoptosis," Immunologic Res. 35(3):249-262); E$_1$ series (blood group B) as found in pancreatic cancer; EGFR (Epidermal Growth Factor Receptor; Adenis, A. et al. 2003 Bull Cancer. 90 Spec No:5228-32); Ephrin receptors (and in particular EphA2 (U.S. Pat. No. 7,569,672; PCT Publication No. WO 06/084226); Erb (ErbB1; ErbB3; ErbB4; Zhou, H. et al. 2002 Oncogene 21(57):8732-8740; Rimon, E. et al. 2004 Int J Oncol. 24(5):1325-1338); GAGE (GAGE-1; GAGE-2; Akcakanat, A. et al. 2006 Int J Cancer. 118(1):123-128); GD2/GD3/GM2 (Livingston, P. O. et al. 2005 Cancer Immunol Immunother. 54(10):1018-1025); ganglioside GD2 (G$_{D2}$; Saleh et al. (1993) "Generation Of A Human Anti-Idiotypic Antibody That Mimics The GD2 Antigen," J. Immunol., 151, 3390-3398); ganglioside GD3 (GD3; Shitara et al. (1993) "A Mouse/Human Chimeric Anti-(Ganglioside GD3) Antibody With Enhanced Antitumor Activities," Cancer Immunol. Immunother. 36:373-380); ganglioside GM2 (G$_{M2}$; Livingston et al. (1994) "Improved Survival In Stage III Melanoma Patients With GM2 Antibodies: A Randomized Trial Of Adjuvant Vaccination With GM2 Ganglioside," J. Clin. Oncol. 12:1036-1044); ganglioside GM3 (GM3; Hoon et al. (1993) "Molecular Cloning Of A Human Monoclonal Antibody Reactive To Ganglioside GM3 Antigen On Human Cancers," Cancer Res. 53:5244-5250); GICA 19-9 (Herlyn et al. (1982) "Monoclonal Antibody Detection Of A Circulating Tumor-Associated Antigen. I. Presence Of Antigen In Sera Of Patients With Colorectal, Gastric, And Pancreatic Carcinoma," J. Clin. Immunol. 2:135-140); gp100 (Lotem, M. et al. 2006 J Immunother. 29(6):616-27); Gp37 (human leukemia T cell antigen; Bhattacharya-Chatterjee et al. (1988) "Idiotype Vaccines Against Human T Cell Leukemia. II. Generation And Characterization Of A Monoclonal Idiotype Cascade (Ab1, Ab2, and Ab3)," J. Immunol. 141:1398-1403); gp75 (melanoma antigen; Vijayasardahl et al. (1990) "The Melanoma Antigen Gp75 Is The Human Homologue Of The Mouse B (Brown) Locus Gene Product," J. Exp. Med. 171(4):1375-1380); gpA33 (Heath, J. K. et al. (1997) "The Human A33 Antigen Is A Transmembrane Glycoprotein And A Novel Member Of The Immunoglobulin Superfamily," Proc. Natl. Acad. Sci. (U.S.A.) 94(2):469-474; Ritter, G. et al. (1997) "Characterization Of Posttranslational Modifications Of Human A33 Antigen, A Novel Palmitoylated Surface Glycoprotein Of Human Gastrointestinal Epithelium," Biochem. Biophys. Res. Commun. 236(3):682-686; Wong, N. A. et al. (2006) "EpCAM and gpA33 Are Markers Of Barrett's Metaplasia," J. Clin. Pathol. 59(3):260-263); HER2 antigen (HER2/neu, p185$^{HER2}$; Kumar, Pal S et al. 2006 Semin Oncol. 33(4):386-91); HMFG (human milk fat globule antigen; WO1995015171); human papillomavirus-E6/human papillomavirus-E7 (DiMaio, D. et al. 2006 Adv Virus Res. 66:125-59; HMW-MAA (high molecular weight melanoma antigen; Natali et al. (1987) "Immunohistochemical Detection Of Antigen In Human Primary And Metastatic Melanomas By The Monoclonal Antibody 140.240 And Its Possible Prognostic Significance," Cancer 59:55-63; Mittelman et al. (1990) "Active Specific Immunotherapy In Patients With Melanoma. A Clinical Trial With Mouse Antiidiotypic Monoclonal Antibodies Elicited With Syngeneic Anti-High-Molecular-Weight-Melanoma-Associated Antigen Monoclonal Antibodies," J. Clin. Invest. 86:2136-2144); I antigen (differentiation antigen; Feizi (1985) "Demonstration By Monoclonal Antibodies That Carbohydrate Structures Of Glycoproteins And Glycolipids Are Onco-Developmental Antigens," Nature 314:53-57); IL13Rα2 (PCT Publication No. WO 2008/146911; Brown, C. E. et al. (2013) "Glioma IL13Rα2 Is Associated With Mesenchymal Signature Gene Expression And Poor Patient Prognosis," PLoS One. 18; 8(10):e77769; Barderas, R. et al. (2012) "High Expression Of IL-13 Receptor A2 In Colorectal Cancer Is Associated With Invasion, Liver Metastasis, And Poor Prognosis," Cancer Res. 72(11):2780-2790; Kasaian, M. T. et al. (2011) "IL-13 Antibodies Influence IL-13 Clearance In Humans By Modulating Scavenger Activity Of IL-13Rα2," J. Immunol. 187(1):561-569; Bozinov, O. et al. (2010) "Decreasing Expression Of The Interleukin-13 Receptor IL-13Ralpha2 In Treated Recurrent Malignant Gliomas," Neurol. Med. Chir. (Tokyo) 50(8):617-621; Fujisawa, T. et al. (2009) "A novel role of interleukin-13 receptor alpha2 in pancreatic cancer invasion and metastasis," Cancer Res. 69(22):8678-8685); Integrin D6 (PCT Publication No. WO 03/087340); JAM-3 (PCT Publication No. WO 06/084078); KID3 (PCT Publication No. WO 05/028498); KID31 (PCT Publication No. WO 06/076584); KS 1/4 pan-carcinoma antigen (Perez et al. (1989) "Isolation And Characterization Of A cDNA Encoding The Ks1/4 Epithelial Carcinoma Marker," J. Immunol. 142:3662-3667; Möller et al. (1991) "Bi-specific-Monoclonal-Antibody-Directed Lysis Of Ovarian Carcinoma Cells By Activated Human T Lymphocytes," Cancer Immunol. Immunother. 33(4):210-216; Ragupathi, G. 2005 Cancer Treat Res. 123:157-80); L6 and L20 (human lung carcinoma antigens; Hellstrom et al. (1986) "Monoclonal Mouse Antibodies Raised Against Human Lung Carcinoma," Cancer Res. 46:3917-3923); LEA; LUCA-2 (United States Patent Publication No. 2006/0172349; PCT Publication No. WO 06/083852); M1:22:25:8; M18; M39; MAGE (MAGE-1; MAGE-3; (Bodey, B. 2002 Expert Opin Biol Ther. 2(6):577-84); MART (Kounalakis, N. et al. 2005 Curr Oncol Rep. 7(5):377-82; mesothelin (Chang K, and Pastan I. 1996 "Molecular cloning of mesothelin, a differentiation antigen present on mesothelium, mesotheliomas, and ovarian cancers," Proc Natl Acad Sci USA 93:136-40), MUC-1 (Mathelin, C. 2006 Gynecol Obstet Fertil. 34(7-8):638-46); MUM-(Castelli, C. et al. 2000 J Cell Physiol. 182(3):323-31); Myl; N-acetylglucosaminyltransferase (Dennis, J. W. 1999 Biochim Biophys Acta. 6; 1473(1): 21-34); neoglycoprotein; NS-10 as found in adenocarcinomas; OFA-1; OFA-2; Oncostatin M (Oncostatin Receptor Beta; U.S. Pat. No. 7,572,896; PCT Publication No. WO 06/084092); p15 (Gil, J. et al. 2006 Nat Rev Mol Cell Biol. 7(9):667-77); p97 (melanoma-associated antigen; Estin et al. (1989) "Transfected Mouse Melanoma Lines That Express Various Levels Of Human Melanoma-Associated Antigen p97," J. Natl. Cancer Instit. 81(6):445-454); PEM (polymorphic epithelial mucin; Hilkens et al. (1992) "Cell Membrane-Associated Mucins And Their Adhesion-Modulating Property," Trends in Biochem. Sci. 17:359-363); PEMA (polymorphic epithelial mucin antigen); PIPA (U.S. Pat. No. 7,405,061; PCT Publication No. WO 04/043239); PSA (prostate-specific antigen; Henttu et al. (1989) "*cDNA Coding For The Entire Human Prostate Specific Antigen Shows High Homologies To The Human Tissue Kallikrein Genes*," Biochem. Biophys. Res. Comm. 10(2):903-910; Israeli et al. (1993) "*Molecular Cloning Of A Complementary DNA Encoding A Prostate-Specific Membrane Antigen*," Cancer Res. 53:227-230; Cracco, C. M. et al. 2005 *Minerva Urol Nefrol.* 57(4):301-11); PSMA (prostate-specific membrane antigen; Ragupathi, G. 2005 *Cancer Treat Res.* 123:157-180); prostatic acid phosphate (Tailor et al. (1990) "*Nucleotide Sequence Of Human Prostatic Acid Phosphatase Determined From A Full-Length cDNA Clone*," Nucl. Acids Res. 18(16):4928); R24 as found in melanoma; ROR1 (U.S. Pat. No. 5,843,749); sphingolipids; SSEA-1; SSEA-3; SSEA-4; sTn (Holmberg, L. A. 2001 *Expert Opin Biol Ther.* 1(5):881-91); T cell receptor derived peptide from a cutaneous T cell lymphoma (see Edelson (1998) "*Cutaneous T-Cell Lymphoma: A Model For Selective Immunotherapy*," Cancer J Sci Am. 4:62-71); $T_5A_7$ found in myeloid cells; TAG-72 (Yokota et al. (1992) "*Rapid Tumor Penetration Of A Single-Chain Fv And Comparison With Other Immunoglobulin Forms*," Cancer Res. 52:3402-3408); TL5 (blood group A); TNF-receptor (TNF-α receptor, TNF-β receptor; TNF-γ receptor (van Horssen, R. et al. 2006 *Oncologist.* 11(4):397-408; Gardnerova, M. et al. 2000 *Curr Drug Targets.* 1(4):327-64); TRA-1-85 (blood group H); Transferrin Receptor (U.S. Pat. No. 7,572,895; PCT Publication No. WO 05/121179); 5T4 (TPBG, trophoblast glycoprotein; Boghaert, E. R. et al. (2008) "*The Oncofetal Protein, 5T4, Is A Suitable Target For Antibody-Guided Anti-Cancer Chemotherapy With Calicheamicin*," Int. J. Oncol. 32(1):221-234; Eisen, T. et al. (2014) "*Naptumomab Estafenatox: Targeted Immunotherapy with a Novel Immunotoxin*," Curr. Oncol. Rep. 16:370, pp. 1-6); TSTA (tumor-specific transplantation antigen) such as virally-induced tumor antigens including T-antigen DNA tumor viruses and envelope antigens of RNA tumor viruses, oncofetal antigen-alpha-fetoprotein such as CEA of colon, bladder tumor oncofetal antigen (Hellstrom et al. (1985) "*Monoclonal Antibodies To Cell Surface Antigens Shared By Chemically Induced Mouse Bladder Carcinomas*," Cancer. Res. 45:2210-2188); VEGF (Pietrantonio, F. et al. (2015) "*Bevacizumab-Based Neoadjuvant Chemotherapy For Colorectal Cancer Liver Metastases: Pitfalls And Helpful Tricks In A Review For Clinicians*," Crit. Rev. Oncol. Hematol. 95(3): 272-281; Grabowski, J. P. (2015) "*Current Management Of Ovarian Cancer*," Minerva Med. 106(3):151-156; Field, K. M. (2015) "*Bevacizumab And Glioblastoma: Scientific Review, Newly Reported Updates, And Ongoing Controversies*," Cancer 121(7):997-1007; Suh, D. H. et al. (2015) "*Major Clinical Research Advances In Gynecologic Cancer In 2014*," J. Gynecol. Oncol. 26(2):156-167; Liu, K. J. et al. (2015) "*Bevacizumab In Combination With Anticancer Drugs For Previously Treated Advanced Non-Small Cell Lung Cancer*," Tumour Biol. 36(3):1323-1327; Di Bartolomeo, M. et al. (2015) "*Bevacizumab treatment in the elderly patient with metastatic colorectal cancer*," Clin. Interv. Aging 10:127-133); VEGF Receptor (O'Dwyer. P. J. 2006 *Oncologist.* 11(9):992-998); VEP8; VEP9; VIM-D5; and $Y$ hapten, $Le^y$ as found in embryonal carcinoma cells.

In certain embodiments, such anti-PD-1-binding molecules of the invention are used in combination with one or more molecules that specifically bind 5T4, B7H3, CD19, CD20, CD51, CD123, DR5, EGFR, EpCam, GD2, gpA33, HER2, ROR-1, TAG-72, VEGF-A antibody, and/or VEGFR2.

Such PD-1-binding molecules of the invention can be combined with an immunogenic agent such as a tumor vaccine. Such vaccines may comprise purified tumor antigens (including recombinant proteins, peptides, and carbohydrate molecules), autologous or allogeneic tumor cells. A number of tumor vaccine strategies have been described (see for example, Palena, C., et al., (2006) "*Cancer vaccines: preclinical studies and novel strategies*," Adv. Cancer Res. 95, 115-145; Mellman, I., et al. (2011) "*Cancer immunotherapy comes of age*," Nature 480, 480-489; Zhang, X. M. et al. (2008) "*The anti-tumor immune response induced by a combination of MAGE-3/MAGE-n-derived peptides*," Oncol. Rep. 20, 245-252; Disis, M. L. et al. (2002) "*Generation of T-cell immunity to the HER-2/neu protein after active immunization with HER-2/neu peptide-based vaccines*," J. Clin. Oncol. 20, 2624-2632; Vermeij, R. et al. (2012) "*Potentiation of a p53-SLP vaccine by cyclophosphamide in ovarian cancer: a single-arm phase II study*." Int. J. Cancer 131, E670-E680). Such PD-1-binding molecules of the invention can be combined with chemotherapeutic regimes. In these instances, it may be possible to reduce the dose of chemotherapeutic reagent administered (Mokyr et al. (1998) Cancer Research 58: 5301-5304).

Such PD-1-binding molecules of the invention can be combined with other immunostimulatory molecules such as antibodies which activate host immune responsiveness to provide for increased levels of T-cell activation. In particular, anti-PD-1 antibodies, anti-PD-L1 antibodies and/or an anti-CTLA-4 antibodies have been demonstrated to active the immune system (see, e.g., del Rio, M-L. et al. (2005) "*Antibody-Mediated Signaling Through PD-*1 *Costimulates T Cells And Enhances CD28-Dependent Proliferation*," Eur. J. Immunol 35:3545-3560; Barber, D. L. et al. (2006) "*Restoring function in exhausted CD8 T cells during chronic viral infection*," Nature 439, 682-687; Iwai, Y. et al. (2002) "*Involvement Of PD-L*1 *On Tumor Cells In The Escape From Host Immune System And Tumor Immunotherapy By PD-L*1 *Blockade*," Proc. Natl Acad. Sci. USA 99, 12293-12297; Leach, D. R., et al., (1996) "*Enhancement Of Anti-tumor Immunity By CTLA-*4 *Blockade*," Science 271, 1734-1736). Additional immunostimulatory molecules that may be combined with the PD-1-binding molecules of the invention include antibodies to molecules on the surface of dendritic cells that activate dendritic cell (DC) function and antigen presentation, anti-CD40 antibodies able to substitute for T-cell helper activity, and activating antibodies to T-cell costimulatory molecules such as PD-L1, CTLA-4, OX-40 4-1BB, and ICOS (see, for example, Ito et al. (2000) "*Effective Priming Of Cytotoxic T Lymphocyte Precursors By Subcutaneous Administration Of Peptide Antigens In Liposomes Accompanied By Anti-CD*40 *And Anti-CTLA-*4 *Antibodies*," Immunobiology 201:527-40; U.S. Pat. No. 5,811,097; Weinberg et al. (2000) "*Engagement of the OX-*40 *Receptor In Vivo Enhances Antitumor Immunity*," Immunol 164:2160-2169; Melero et al. (1997) "*Monoclonal Antibodies Against The* 4-1*BB T-Cell Activation Molecule Eradicate Established Tumors*," Nature Medicine 3: 682-685; Hutloff et al. (1999) "*ICOS Is An Inducible T-Cell Co-Stimulator Structurally And Functionally Related To CD*28," Nature 397: 263-266; and Moran, A. E. et al. (2013) "*The TNFRs OX*40, 4-1*BB, and CD*40 *As Targets For Cancer Immunotherapy*," Curr Opin Immunol. 2013 April; 25(2): 10.1016/j.coi.2013.01.004), and/or stimulatory Chimeric Antigen Receptors (CARs) comprising an antigen binding domain directed against a disease antigen fused to one or more intracellular signaling domains from various costimulatory protein receptors (e.g., CD28, 4-1BB, ICOS, OX40, etc.) which serve to stimulate T-cells upon antigen binding (see, for example, Tettamanti, S. et al. (2013) *"Targeting Of Acute Myeloid Leukaemia By Cytokine-Induced Killer Cells Redirected With A Novel CD123-Specific Chimeric Antigen Receptor,"* Br. J. Haematol. 161:389-401; Gill, S. et al. (2014) *"Efficacy Against Human Acute Myeloid Leukemia And Myeloablation Of Normal Hematopoiesis In A Mouse Model Using Chimeric Antigen Receptor Modified T Cells,"* Blood 123(15): 2343-2354; Mardiros, A. et al. (2013) *"T Cells Expressing CD123-Specific Chimeric Antigen Receptors Exhibit Specific Cytolytic Effector Functions And Antitumor Effects Against Human Acute Myeloid Leukemia,"* Blood 122:3138-3148; Pizzitola, I. et al. (2014) *"Chimeric Antigen Receptors Against CD33/CD123 Antigens Efficiently Target Primary Acute Myeloid Leukemia Cells in vivo,"* Leukemia doi:10.1038/1eu.2014.62).

Such PD-1-binding molecules of the invention can be combined with inhibitory Chimeric Antigen Receptors (iCARs) to divert off target immunotherapy responses. iCARs an antigen binding domain directed against a disease antigen fused to one or more intracellular signaling domains from various inhibitory protein receptors (e.g., CTLA-4, PD-1, etc.) which serve to constrain T-cell responses upon antigen binding (see, for example, Fedorov V. D. (2013) *"PD-1- and CTLA-4-Based Inhibitory Chimeric Antigen Receptors (iCARs) Divert Off-Target Immunotherapy Responses,"* Sci. Tranl. Med. 5: 215ra172 doi:10.1126/scitranslmed.3006597.

In particular, such anti-PD-1-binding molecules of the invention are used in combination with an anti-CD137 antibody, an anti-CTLA-4 antibody, an anti-OX40 antibody, an anti-LAG-3 antibody, an anti-PD-L1 antibody, an anti-TIGIT antibody, an anti TIM-3 antibody and/or a cancer vaccine.

B. Diagnostic and Theranostic Utility

Certain of the PD-1-binding molecules of the present invention exhibit little of no ability to block binding between PD-1 and the PD-1L ligand. As such, antibodies PD-1 mAb 2 and PD-1 mAb 4, their humanized derivatives, and molecules comprising their PD-1-binding fragments (e.g., bispecific diabodies, etc.) or that compete for binding with such antibodies may be detectably labeled (e.g., with radioactive, enzymatic, fluorescent, chemiluminescent, paramagnetic, diamagnetic, or other labelling moieties) and used in the detection of PD-1 in samples or in the imaging of PD-1 on cells. Since such molecules do not affect the biological activity of PD-1, they are particularly useful in methods of determining the extent, location and change in PD-1 expression in subjects (e.g., subjects being treated for cancer associated with the expression or targeting of PD-1).

XII. Pharmaceutical Compositions

The compositions of the invention include bulk drug compositions useful in the manufacture of pharmaceutical compositions (e.g., impure or non-sterile compositions) and pharmaceutical compositions (i.e., compositions that are suitable for administration to a subject or patient) that can be used in the preparation of unit dosage forms. Such compositions comprise a prophylactically or therapeutically effective amount of the PD-1-binding molecules of the present invention, or a combination of such agents and a pharmaceutically acceptable carrier. Preferably, compositions of the invention comprise a prophylactically or therapeutically effective amount of the PD-1-binding molecules of the present invention and a pharmaceutically acceptable carrier. The invention particularly encompasses such pharmaceutical compositions in which the PD-1-binding molecule is: a PD-1 mAb 1, PD-1 mAb 2, PD-1 mAb 3, PD-1 mAb 4, PD-1 mAb 5, PD-1 mAb 6, PD-1 mAb 7, PD-1 mAb 8, PD-1 mAb 9, PD-1 mAb 10, PD-1 mAb 11, PD-1 mAb 12, PD-1 mAb 13, PD-1 mAb 14, or PD-1 mAb 15; a humanized PD-1 mAb 1; PD-1 mAb 2, PD-1 mAb 3, PD-1 mAb 4, PD-1 mAb 5, PD-1 mAb 6, PD-1 mAb 7, PD-1 mAb 8, PD-1 mAb 9, PD-1 mAb 10, PD-1 mAb 11, PD-1 mAb 12, PD-1 mAb 13, PD-1 mAb 14, or PD-1 mAb 15; a PD-1-binding fragment of any such antibody; or in which the PD-1-binding molecule is a bispecific PD-1 diabody (e.g., a PD-1×LAG-3 bispecific diabody). Especially encompassed are such molecules that comprise the 3 $CDR_L$s and the 3 $CDR_H$s of PD-1 mAb 1, PD-1 mAb 2, PD-1 mAb 3, PD-1 mAb 4, PD-1 mAb 5, PD-1 mAb 6, PD-1 mAb 7, PD-1 mAb 8, PD-1 mAb 9, PD-1 mAb 10, PD-1 mAb 11, PD-1 mAb 12, PD-1 mAb 13, PD-1 mAb 14, or PD-1 mAb 15 antibody; a humanized PD-1 mAb 1; PD-1 mAb 2, PD-1 mAb 3, PD-1 mAb 4, PD-1 mAb 5, PD-1 mAb 6, PD-1 mAb 7, PD-1 mAb 8, PD-1 mAb 9, PD-1 mAb 10, PD-1 mAb 11, PD-1 mAb 12, PD-1 mAb 13, PD-1 mAb 14, or PD-1 mAb 15.

The invention also encompasses such pharmaceutical compositions that additionally include a second therapeutic antibody (e.g., tumor-specific monoclonal antibody) that is specific for a particular cancer antigen, and a pharmaceutically acceptable carrier.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like.

Generally, the ingredients of compositions of the invention are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the invention can be formulated as neutral or salt forms. Pharmaceutically acceptable salts include, but are not limited to those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The invention also provides a pharmaceutical pack or kit comprising one or more containers filled with a PD-1-binding molecule of the present invention (and more preferably, a PD-1 mAb 1, PD-1 mAb 2, PD-1 mAb 3, PD-1 mAb 4, PD-1 mAb 5, PD-1 mAb 6, PD-1 mAb 7, PD-1 mAb 8, PD-1 mAb 9, PD-1 mAb 10, PD-1 mAb 11, PD-1 mAb 12, PD-1 mAb 13, PD-1 mAb 14, or PD-1 mAb 15; a humanized PD-1 mAb 1, PD-1 mAb 2, PD-1 mAb 3, PD-1 mAb 4, PD-1 mAb 5, PD-1 mAb 6, PD-1 mAb 7, PD-1 mAb 8, PD-1 mAb 9, PD-1 mAb 10, PD-1 mAb 11, PD-1 mAb 12, PD-1 mAb 13, PD-1 mAb 14, or PD-1 mAb 15 antibody; a PD-1-binding fragment of any such antibody; or in which the PD-1-binding molecule is a bispecific PD-1 diabody (e.g., a PD-1×LAG-3 bispecific diabody)). Especially encompassed are such molecules that comprise the 3 $CDR_L$s and the 3 $CDR_H$s of PD-1 mAb 1, PD-1 mAb 2, PD-1 mAb 3, PD-1 mAb 4, PD-1 mAb 5, PD-1 mAb 6, PD-1 mAb 7, PD-1 mAb 8, PD-1 mAb 9, PD-1 mAb 10, PD-1 mAb 11, PD-1 mAb 12, PD-1 mAb 13, PD-1 mAb 14, or PD-1 mAb 15, alone or with such pharmaceutically acceptable carrier. Additionally, one or more other prophylactic or therapeutic agents useful for the treatment of a disease can also be included in the pharmaceutical pack or kit. The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

The present invention provides kits that can be used in the above methods. A kit can comprise any of the PD-1-binding molecules of the present invention. The kit can further comprise one or more other prophylactic and/or therapeutic agents useful for the treatment of cancer, in one or more containers; and/or the kit can further comprise one or more cytotoxic antibodies that bind one or more cancer antigens associated with cancer. In certain embodiments, the other prophylactic or therapeutic agent is a chemotherapeutic. In other embodiments, the prophylactic or therapeutic agent is a biological or hormonal therapeutic.

XIII. Methods of Administration

The compositions of the present invention may be provided for the treatment, prophylaxis, and amelioration of one or more symptoms associated with a disease, disorder or infection by administering to a subject an effective amount of a fusion protein or a conjugated molecule of the invention, or a pharmaceutical composition comprising a fusion protein or a conjugated molecule of the invention. In a preferred aspect, such compositions are substantially purified (i.e., substantially free from substances that limit its effect or produce undesired side effects). In a specific embodiment, the subject is an animal, preferably a mammal such as non-primate (e.g., bovine, equine, feline, canine, rodent, etc.) or a primate (e.g., monkey such as, a cynomolgus monkey, human, etc.). In a preferred embodiment, the subject is a human.

Various delivery systems are known and can be used to administer the compositions of the invention, e.g., encapsulation in liposomes, microparticles, microcapsules, recombinant cells capable of expressing the antibody or fusion protein, receptor-mediated endocytosis (See, e.g., Wu et al. (1987) "*Receptor Mediated In Vitro Gene Transformation By A Soluble DNA Carrier System,*" J. Biol. Chem. 262: 4429-4432), construction of a nucleic acid as part of a retroviral or other vector, etc.

Methods of administering a molecule of the invention include, but are not limited to, parenteral administration (e.g., intradermal, intramuscular, intraperitoneal, intravenous and subcutaneous), epidural, and mucosal (e.g., intranasal and oral routes). In a specific embodiment, the PD-1-binding molecules of the present invention are administered intramuscularly, intravenously, or subcutaneously. The compositions may be administered by any convenient route, for example, by infusion or bolus injection, by absorption through epithelial or mucocutaneous linings (e.g., oral mucosa, rectal and intestinal mucosa, etc.) and may be administered together with other biologically active agents. Administration can be systemic or local. In addition, pulmonary administration can also be employed, e.g., by use of an inhaler or nebulizer, and formulation with an aerosolizing agent. See, e.g., U.S. Pat. Nos. 6,019,968; 5,985,320; 5,985,309; 5,934,272; 5,874,064; 5,855,913; 5,290,540; and 4,880,078; and PCT Publication Nos. WO 92/19244; WO 97/32572; WO 97/44013; WO 98/31346; and WO 99/66903, each of which is incorporated herein by reference in its entirety.

The invention also provides that the PD-1-binding molecules of the present invention are packaged in a hermetically sealed container such as an ampoule or sachette indicating the quantity of the molecule. In one embodiment, such molecules are supplied as a dry sterilized lyophilized powder or water free concentrate in a hermetically sealed container and can be reconstituted, e.g., with water or saline to the appropriate concentration for administration to a subject. Preferably, the PD-1-binding molecules of the present invention are supplied as a dry sterile lyophilized powder in a hermetically sealed container.

The lyophilized PD-1-binding molecules of the present invention should be stored at between 2° C. and 8° C. in their original container and the molecules should be administered within 12 hours, preferably within 6 hours, within 5 hours, within 3 hours, or within 1 hour after being reconstituted. In an alternative embodiment, such molecules are supplied in liquid form in a hermetically sealed container indicating the quantity and concentration of the molecule, fusion protein, or conjugated molecule. Preferably, such PD-1-binding molecules when provided in liquid form are supplied in a hermetically sealed container.

The amount of the composition of the invention which will be effective in the treatment, prevention or amelioration of one or more symptoms associated with a disorder can be determined by standard clinical techniques. The precise dose to be employed in the formulation will also depend on the route of administration, and the seriousness of the condition, and should be decided according to the judgment of the practitioner and each patient's circumstances. Effective doses may be extrapolated from dose-response curves derived from in vitro or animal model test systems.

As used herein, an "effective amount" of a pharmaceutical composition, in one embodiment, is an amount sufficient to effect beneficial or desired results including, without limitation, clinical results such as decreasing symptoms resulting from the disease, attenuating a symptom of infection (e.g., viral load, fever, pain, sepsis, etc.) or a symptom of cancer (e.g., the proliferation, of cancer cells, tumor presence, tumor metastases, etc.), thereby increasing the quality of life of those suffering from the disease, decreasing the dose of other medications required to treat the disease, enhancing the effect of another medication such as via targeting and/or internalization, delaying the progression of the disease, and/or prolonging survival of individuals.

An effective amount can be administered in one or more administrations. For purposes of this invention, an effective amount of drug, compound, or pharmaceutical composition is an amount sufficient to reduce the proliferation of (or the effect of) viral presence and to reduce and/or delay the development of the viral disease, either directly or indirectly. In some embodiments, an effective amount of a drug, compound, or pharmaceutical composition may or may not be achieved in conjunction with another drug, compound, or pharmaceutical composition. Thus, an "effective amount" may be considered in the context of administering one or more chemotherapeutic agents, and a single agent may be considered to be given in an effective amount if, in conjunction with one or more other agents, a desirable result may be or is achieved. While individual needs vary, determination of optimal ranges of effective amounts of each component is within the skill of the art.

For the PD-1-binding molecules encompassed by the invention, the dosage administered to a patient is preferably determined based upon the body weight (kg) of the recipient subject. For the PD-1-binding molecules encompassed by the invention, the dosage administered to a patient is typically at least about 0.01 µg/kg, at least about 0.05 µg/kg, at least about 0.1 µg/kg, at least about 0.2 µg/kg, at least about 0.5 µg/kg, at least about 1 µg/kg, at least about 2 µg/kg, at least about 5 µg/kg, at least about 10 µg/kg, at least about 20 µg/kg, at least about 50 µg/kg, at least about 0.1 mg/kg, at least about 1 mg/kg, at least about 3 mg/kg, at least about 5 mg/kg, at least about 10 mg/kg, at least about 30 mg/kg, at least about 50 mg/kg, at least about 75 mg/kg, at least about 100 mg/kg, at least about 125 mg/kg, at least about 150 mg/kg or more of the subject's body weight.

The dosage and frequency of administration of a PD-1-binding molecule of the present invention may be reduced or altered by enhancing uptake and tissue penetration of the molecule by modifications such as, for example, lipidation.

The dosage of a PD-1-binding molecule of the invention administered to a patient may be calculated for use as a single agent therapy. Alternatively, the molecule may be used in combination with other therapeutic compositions and the dosage administered to a patient are lower than when said molecules are used as a single agent therapy.

The pharmaceutical compositions of the invention may be administered locally to the area in need of treatment; this may be achieved by, for example, and not by way of limitation, local infusion, by injection, or by means of an implant, said implant being of a porous, non-porous, or gelatinous material, including membranes, such as sialastic membranes, or fibers. Preferably, when administering a molecule of the invention, care must be taken to use materials to which the molecule does not absorb.

The compositions of the invention can be delivered in a vesicle, in particular a liposome (See Langer (1990) "*New Methods Of Drug Delivery*," Science 249:1527-1533); Treat et al., in LIPOSOMES IN THE THERAPY OF INFECTIOUS DISEASE AND CANCER, Lopez-Berestein and Fidler (eds.), Liss, New York, pp. 353-365 (1989); Lopez-Berestein, ibid., pp. 3 17-327).

The compositions of the invention can be delivered in a controlled-release or sustained-release system. Any technique known to one of skill in the art can be used to produce sustained-release formulations comprising one or more of the PD-1-binding molecule(s) of the invention. See, e.g., U.S. Pat. No. 4,526,938; PCT publication WO 91/05548; PCT publication WO 96/20698; Ning et al. (1996) "*Intratumoral Radioimmunotheraphy Of A Human Colon Cancer Xenograft Using A Sustained-Release Gel*," Radiotherapy & Oncology 39:179-189, Song et al. (1995) "*Antibody Mediated Lung Targeting Of Long-Circulating Emulsions*," PDA Journal of Pharmaceutical Science & Technology 50:372-397; Cleek et al. (1997) "*Biodegradable Polymeric Carriers For A bFGF Antibody For Cardiovascular Application*," Pro. Int'l. Symp. Control. Rel. Bioact. Mater. 24:853-854; and Lam et al. (1997) "*Microencapsulation Of Recombinant Humanized Monoclonal Antibody For Local Delivery*," Proc. Int'l. Symp. Control Rel. Bioact. Mater. 24:759-760, each of which is incorporated herein by reference in its entirety. In one embodiment, a pump may be used in a controlled-release system (See Langer, supra; Sefton, (1987) "*Implantable Pumps*," CRC Crit. Rev. Biomed. Eng. 14:201-240; Buchwald et al. (1980) "*Long-Term, Continuous Intravenous Heparin Administration By An Implantable Infusion Pump In Ambulatory Patients With Recurrent Venous Thrombosis*," Surgery 88:507-516; and Saudek et al. (1989) "*A Preliminary Trial Of The Programmable Implantable Medication System For Insulin Delivery*," N. Engl. J. Med. 321:574-579). In another embodiment, polymeric materials can be used to achieve controlled-release of the molecules (see e.g., MEDICAL APPLICATIONS OF CONTROLLED RELEASE, Langer and Wise (eds.), CRC Pres., Boca Raton, Fla. (1974); CONTROLLED DRUG BIOAVAILABILITY, DRUG PRODUCT DESIGN AND PERFORMANCE, Smolen and Ball (eds.), Wiley, New York (1984); Levy et al. (1985) "*Inhibition Of Calcification Of Bioprosthetic Heart Valves By Local Controlled-Release Diphosphonate*," Science 228:190-192; During et al. (1989) "*Controlled Release Of Dopamine From A Polymeric Brain Implant: In Vivo Characterization*," Ann. Neurol. 25:351-356; Howard et al. (1989) "*Intracerebral Drug Delivery In Rats With Lesion Induced Memory Deficits*," J. Neurosurg. 7(1):105-112); U.S. Pat. Nos. 5,679,377; 5,916,597; 5,912,015; 5,989,463; 5,128,326; PCT Publication No. WO 99/15154; and PCT Publication No. WO 99/20253). Examples of polymers used in sustained-release formulations include, but are not limited to, poly(-hydroxy ethyl methacrylate), poly(methyl methacrylate), poly (acrylic acid), poly(ethylene-co-vinyl acetate), poly(methacrylic acid), polyglycolides (PLG), polyanhydrides, poly (N-vinyl pyrrolidone), poly(vinyl alcohol), polyacrylamide, poly(ethylene glycol), polylactides (PLA), poly(lactide-co-glycolides) (PLGA), and polyorthoesters. A controlled-release system can be placed in proximity of the therapeutic target (e.g., the lungs), thus requiring only a fraction of the systemic dose (see, e.g., Goodson, in MEDICAL APPLICATIONS OF CONTROLLED RELEASE, supra, vol. 2, pp. 115-138 (1984)). Polymeric compositions useful as controlled-release implants can be used according to Dunn et al. (See U.S. Pat. No. 5,945,155). This particular method is based upon the therapeutic effect of the in situ controlled-release of the bioactive material from the polymer system. The implantation can generally occur anywhere within the body of the patient in need of therapeutic treatment. A non-polymeric sustained delivery system can be used, whereby a non-polymeric implant in the body of the subject is used as a drug delivery system. Upon implantation in the body, the organic solvent of the implant will dissipate, disperse, or leach from the composition into surrounding tissue fluid, and the non-polymeric material will gradually coagulate or precipitate to form a solid, microporous matrix (See U.S. Pat. No. 5,888, 533).

Controlled-release systems are discussed in the review by Langer (1990, "New Methods Of Drug Delivery," Science 249:1527-1533). Any technique known to one of skill in the art can be used to produce sustained-release formulations comprising one or more therapeutic agents of the invention. See, e.g., U.S. Pat. No. 4,526,938; International Publication Nos. WO 91/05548 and WO 96/20698; Ning et al. (1996) "*Intratumoral Radioimmunotheraphy Of A Human Colon Cancer Xenograft Using A Sustained-Release Gel*," Radiotherapy & Oncology 39:179-189, Song et al. (1995) "*Antibody Mediated Lung Targeting Of Long-Circulating Emulsions*," PDA Journal of Pharmaceutical Science & Technology 50:372-397; Cleek et al. (1997) "*Biodegradable Polymeric Carriers For A bFGF Antibody For Cardiovascular Application*," Pro. Int'l. Symp. Control. Rel. Bioact. Mater. 24:853-854; and Lam et al. (1997) "*Microencapsulation Of Recombinant Humanized Monoclonal Antibody For Local Delivery*," Proc. Int'l. Symp. Control Rel. Bioact. Mater. 24:759-760, each of which is incorporated herein by reference in its entirety.

Where the composition of the invention is a nucleic acid encoding a PD-1-binding molecule of the present invention, the nucleic acid can be administered in vivo to promote expression of its encoded PD-1-binding molecule by constructing it as part of an appropriate nucleic acid expression vector and administering it so that it becomes intracellular, e.g., by use of a retroviral vector (See U.S. Pat. No. 4,980,286), or by direct injection, or by use of microparticle bombardment (e.g., a gene gun; Biolistic, Dupont), or coating with lipids or cell surface receptors or transfecting agents, or by administering it in linkage to a homeobox-like peptide which is known to enter the nucleus (See e.g., Joliot et al. (1991) "*Antennapedia Homeobox Peptide Regulates Neural Morphogenesis*," Proc. Natl. Acad. Sci. (U.S.A.) 88:1864-1868), etc. Alternatively, a nucleic acid can be introduced intracellularly and incorporated within host cell DNA for expression by homologous recombination.

Treatment of a subject with a therapeutically or prophylactically effective amount of a PD-1-binding molecule of the present invention can include a single treatment or, preferably, can include a series of treatments. In a preferred example, a subject is treated with such a diabody one time per week for between about 1 to 10 weeks, preferably between 2 to 8 weeks, more preferably between about 3 to 7 weeks, and even more preferably for about 4, 5, or 6 weeks. The pharmaceutical compositions of the invention can be administered once a day, twice a day, or three times a day. Alternatively, the pharmaceutical compositions can be administered once a week, twice a week, once every two weeks, once a month, once every six weeks, once every two months, twice a year or once per year. It will also be appreciated that the effective dosage of the molecules used for treatment may increase or decrease over the course of a particular treatment.

EXAMPLES

The following examples illustrate various methods for compositions in the diagnostic or treatment methods of the invention. The examples are intended to illustrate, but in no way limit, the scope of the invention.

Example 1

Characterization of Anti-Human PD-1 Monoclonal Antibodies

Fifteen murine monoclonal antibodies were isolated as being capable specifically binding to both human and cynomolgus monkey PD-1, and accorded the designations "PD-1 mAb 1," "PD-1 mAb 2," "PD-1 mAb 3," "PD-1 mAb 4," "PD-1 mAb 5," "PD-1 mAb 6," "PD-1 mAb 7," "PD-1 mAb 8," "PD-1 mAb 9," "PD-1 mAb 10," "PD-1 mAb 11," "PD-1 mAb 12," "PD-1 mAb 13," "PD-1 mAb 14," and "PD-1 mAb 15." The CDRs of these antibodies were found to differ and are provided above. Binding to the extracellular domain of human and cynomologus monkey PD-1 was evaluated as follows, flat bottom maxisorb 96-well plates were coated with soluble human or cynomolgus monkey PD-1 (the extracellular domain of human PD-1 fused to a His tag (shPD-1 His) or to a human Fc Region (shPD-1 hFc), or the extracellular domain of cynomolgus monkey PD-1 fused to a human Fc Region (scyno-PD1 Fc)) each at 0.5 or 1 µg/mL, the plates were washed and incubated with one of the isolated anti-PD-1 antibodies PD-1 mAb 1-15. For these studies the anti-PD-1 antibodies were utilized at 3, 1.0, 0.3333, 0.1111, 0.0370, 0.0123, or 0.0041 µg/mL (three fold serial dilutions). The amount of antibody binding to the immobilized PD-1 (human or cynomolgus monkey) was assessed using a goat anti-mouse IgG-HRP secondary antibody. All samples were analyzed on a plate reader (Victor 2 Wallac, Perkin Elmers). Representative binding curves for soluble human and soluble cynomolgus PD-1 are shown in FIGS. 7A-7D and FIGS. 8A-8C, respectively.

The results of these binding assays (FIGS. 7A-7D and FIGS. 8A-8C) show that all the anti-PD-1 antibodies PD-1 mAb 1-15 bind to both soluble human and soluble cynomolgus monkey PD-1.

In order to further characterize the murine anti-PD-1 antibodies their ability to block binding of soluble human PD-L1 to soluble human PD-1 was assessed in two different assays. In one assay the ability of the antibodies to block the binding of human PD-1 to PD-L1 immobilized on a surface was examined. For this assay each of the anti-PD-1 antibodies PD-1 mAb 1-15, or a reference anti-PD-1 antibody (PD-1 mAb A) was mixed with shPD-1 His fusion protein, (at 2.5 µg/mL) and was separately incubated with biotin labeled soluble human PD-L1 (the extracellular domain of PD-L1 fused to human Fc (sPD-L1)) at 1 µg/mL immobilized on a streptavidin coated plate. For these studies the anti-PD-1 antibodies were utilized at 10, 5.0, 2.5, 1.25, 0.625, 0.3125, or 0.1563 µg/mL (two fold serial dilutions). The amount of shPD-1 His binding to the immobilized sPD-L1 was assessed via the His-Tag using an anti-His-Tag-HRP secondary antibody. All samples were analyzed on a plate reader (Victor 2 Wallac, Perkin Elmers). The results of this experiment are shown in FIGS. 9A-9D.

The results of these inhibition assays (FIGS. 9A-9D) show that the anti-PD-antibodies PD-1 mAb 1, PD-1 mAb 3, PD-1 mAb 5, PD-1 mAb 6, PD-1 mAb 7, PD-1 mAb 8, PD-1 mAb 9, PD-1 mAb 10, PD-1 mAb 11, PD-1 mAb 12, PD-1 mAb 13, PD-1 mAb 14, and PD-1 mAb 15, were able to block the binding of soluble human PD-L1 to soluble human PD-1 to varying degrees while PD-1 mAb 2 and PD-1 mAb 4 exhibited little to no blocking activity in this assay format.

In the second assay the ability of the murine anti-PD-1 antibodies PD-1 mAb 1-15 to block binding of PD-1 ligand (i.e., human PD-L1 or human PD-L2) to PD-1 expressed on the surface of NSO cells was examined. For this assay each of the anti-PD-1 antibodies PD-1 mAb 1-15, or a reference anti-PD-1 antibody (PD-1 mAb A or PD-1 mAb B) was separately mixed with a biotinylated-soluble human PD-L1 (shPD-L1 fusion protein) or biotinylated-soluble human PD-L2-muIgFc fusion protein (shPD-L2; Ancell Cat #573-030), each at 0.1 µg/test, and incubated with NSO cells expressing human PD-1 (~250,000 cells/well) in blocking buffer (FACS+10% human serum albumin). For these studies the anti-PD-1 antibodies were utilized at 4.0, 1.0, 2.5×10$^{-1}$, 6.25×10$^{-2}$, 1.56×10$^{-2}$, 3.90×10$^{-3}$, 9.76×10$^{-4}$, 2.4×10$^{-4}$, 0.6×10$^{-4}$ µg/test (four fold serial dilutions). The amount of shPD-L1 (or shPD-L2) binding to the surface of the NSO cells was determined using a PE-conjugated Streptavidin secondary antibody by FACS analysis. The IC50 values for inhibition of PD-1/PD-L1 binding were determined and the sample mean ($\bar{x}$) of at least two experiments are provided (except where indicated) in Table 6.

TABLE 6

| Anti-PD-1 Antibody | IC50 (µg/test) |
|---|---|
| PD-1 mAb A | 0.0044 |
| PD-1 mAb B | 0.0064 |
| PD-1 mAb 1 | 0.0048 |
| PD-1 mAb 2 | 0.0110 |
| PD-1 mAb 3 | 0.0361 ‡ |
| PD-1 mAb 4 | 0.0156 ‡ |
| PD-1 mAb 5 | 0.0039 |
| PD-1 mAb 6 | 0.0051 |
| PD-1 mAb 7 | 0.0024 |
| PD-1 mAb 8 | 0.6611 |
| PD-1 mAb 9 | 0.0154 |
| PD-1 mAb 10 | 0.0057 |
| PD-1 mAb 11 | 0.0259 ‡ |
| PD-1 mAb 12 | 0.0238 ‡ |
| PD-1 mAb 13 | 0.0117 |
| PD-1 mAb 14 | 0.0149 ‡ |
| PD-1 mAb 15 | 0.0060 |

‡ Results from a single experiment

The results of the shPD-L1 inhibition assays (Table 6) show that the anti-PD-1 antibodies PD-1 mAb 1, PD-1 mAb 2, PD-1 mAb 3, PD-1 mAb 4, PD-1 mAb 5, PD-1 mAb 6, PD-1 mAb 7, PD-1 mAb 9, PD-1 mAb 10, PD-1 mAb 11, PD-1 mAb 12, PD-1 mAb 13, PD-1 mAb 14, and PD-1 mAb 15, were able to block the binding of human PD-L1 to human PD-1 expressed on the surface of NSO cells. In particular, PD-1 mAb 1, PD-1 mAb 5, PD-1 mAb 6, PD-1 mAb 7, PD-1 mAb 10, and PD-1 mAb 15 blocked shPD-L1 binding as well as or better than the reference PD-1 antibodies (PD-1 mAb A, PD-1 mAb B), while PD-1 mAb 8 was essentially non-blocking in this assay format. Both PD-1 mAb 2 and PD-1 mAb 4 were able to block PD-1/PD-L1 binding in this assay format.

Similarly, the anti-PD-1 antibodies PD-1 mAb 1, PD-1 mAb 2, and PD-1 mAb 3, PD-1 mAb 4, PD-1 mAb 5, PD-1 mAb 6, PD-1 mAb 7, PD-1 mAb 9, PD-1 mAb 10, PD-1 mAb 12, PD-1 mAb 13, PD-1 mAb 14, were able to block the binding of human PD-L2 to human PD-1 expressed on the surface of NSO cells, while PD-1 mAb 8 was essentially non-blocking in this assay format. In particular, PD-1 mAb 1, PD-1 mAb 5, PD-1 mAb 6, PD-1 mAb 7, and PD-1 mAb 10 blocked shPD-L2 binding as well as, or better than the reference PD-1 antibodies (PD-1 mAb A, PD-1 mAb B). The PD-1 antibodies PD-1 mAb 11 and PD-1 mAb 15 were not tested in this assay. The results for several humanized anti-PD-1 antibodies including hPD-1 mAb 15 are provided below.

Example 2

Humanization and Further Characterization

The Variable Domains of the anti-PD-1 antibodies PD-1 mAb 1, PD-1 mAb 2, PD-1 mAb 7, PD-1 mAb 9, and PD-1 mAb 15 were humanized, where antigenic epitopes were identified the antibodies were further deimmunized to generate the final humanized Variable Domains. Humanization of PD-1 mAb 1, PD-1 mAb 2, and PD-1 mAb 15 yielded one humanized VH Domain and one humanized VL Domain for each antibody designated herein as "hPD-1 mAb 1 VH1," and "hPD-1 mAb 1 VL1;" "hPD-1 mAb 2 VH1," and "hPD-1 mAb 2 VL1;" and "hPD-1 mAb 15 VH1," and "hPD-1 mAb 15 VL1." Humanization of PD-1 mAb 7 yielded two humanized VH Domains, designated herein as "hPD-1 mAb 7 VH1," and "hPD-1 mAb 7 VH2," and three humanized VL Domains designated herein as "hPD-1 mAb 1 VL1," "hPD-1 mAb 7 VL2," and "hPD-1 mAb 7 VL3." Humanization of PD-1 mAb 9 yielded two humanized VH Domains, designated herein as "hPD-1 mAb 9 VH1," and "hPD-1 mAb 9 VH2," and two humanized VL Domains designated herein as "hPD-1 mAb 9 VL1," and "hPD-1 mAb 1 VL2." Where multiple humanized Variable Domains were generated the humanized heavy and light chain Variable Domains of a particular anti-PD-1 antibody (e.g., PD-1 mAb 7) may be used in any combination and particular combinations of humanized chains are referred to by reference to the specific VH/VL Domains, for example a humanized antibody comprising hPD-1 mAb 7 VH1 and hPD-1 mAb 7 VL2 is specifically referred to as "hPD-1 mAb 7(1.2)." Full length humanized antibodies were generated with either a human IgG1 constant region comprising the L234A/L235A substitutions (IgG1 (AA)) or a human IgG4 constant region comprising the S228P substitution (IgG4 (P)).

Full length IgG1 humanized antibody heavy chains were constructed as follows: the C-terminus of the humanized VH Domain was fused to the N-terminus of a human IgG1 Constant Region having a variant CH2-CH3 Domain (comprising the L234A/L235A (AA) substitutions) and lacking the C-terminal lysine residue (SEQ ID NO:255):

```
ASTKGPSVFP LAPSSKSTSG GTAALGCLVK DYFPEPVTVS

WNSGALTSGV HTFPAVLQSS GLYSLSSVVT VPSSSLGTQT

YICNVNHKPS NTKVDKRVEP KSCDKTHTCP PCPAPEAAGG

PSVFLFPPKP KDTLMISRTP EVTCVVVDVS HEDPEVKFNW

YVDGVEVHNA KTKPREEQYN STYRVVSVLT VLHQDWLNGK

EYKCKVSNKA LPAPIEKTIS KAKGQPREPQ VYTLPPSREE

MTKNQVSLTC LVKGFYPSDI AVEWESNGQP ENNYKTTPPV

LDSDGSFFLY SKLTVDKSRW QQGNVFSCSV MHEALHNHYT

QKSLSLSPG
```

In SEQ ID NO:255, amino acid residues 1-98 correspond to the IgG1 CH1 Domain (SEQ ID NO: 10), amino acid residues 99-113 correspond to the IgG1 hinge region (SEQ ID NO: 32) and amino acid residues 114-329 correspond to the IgG1 CH2-CH3 Domain comprising the L234A/L235A substitutions (underlined) (SEQ ID NO:5) but lacking the C-terminal lysine residue.

The amino acid sequence of a heavy chain of an exemplary humanized antibody ((hPD-1 mAb 7(1.2)) having an IgG1 heavy chain constant region comprising the L234A/L235A mutation and lacking the C-terminal lysine residue is (SEQ ID NO:265):

```
QVQLVQSGAE VKKPGASVKV SCKASGYSFT SYWMNWVRQA

PGQGLEWIGV IHPSDSETWL DQKFKDRVTI TVDKSTSTAY
```

```
MELSSLRSED TAVYYCAREH YGTSPFAYWG QGTLVTVSSA

STKGPSVFPL APSSKSTSGG TAALGCLVKD YFPEPVTVSW

NSGALTSGVH TFPAVLQSSG LYSLSSVVTV PSSSLGTQTY

ICNVNHKPSN TKVDKRVEPK SCDKTHTCPP CPAPEAAGGP

SVFLFPPKPK DTLMISRTPE VTCVVVDVSH EDPEVKFNWY

VDGVEVHNAK TKPREEQYNS TYRVVSVLTV LHQDWLNGKE

YKCKVSNKAL PAPIEKTISK AKGQPREPQV YTLPPSREEM

TKNQVSLTCL VKGFYPSDIA VEWESNGQPE NNYKTTPPVL

DSDGSFFLYS KLTVDKSRWQ QGNVFSCSVM HEALHNHYTQ

KSLSLSPG
```

In SEQ ID NO: 265, amino acid residues 1-119 correspond to the VH Domain of hPD-1 mAb 7 VH1 (SEQ ID NO: 147), amino acid residues 120-217 correspond to the IgG1 CH1 Domain (SEQ ID NO: 10), residues 218-232 correspond to the IgG1 hinge region (SEQ ID NO: 32) and residues 233-448 correspond to the IgG1 CH2-CH3 Domain comprising the L234A/L235A substitutions (underlined) (SEQ ID NO:5) but lacking the C-terminal lysine residue.

Full length IgG4 humanized antibody heavy chains were constructed as follows: the C-terminus of the humanized VH Domain was fused to the N-terminus of a human IgG4 Constant Region having a stabilized hinge region (comprising the S228P substitution) and lacking the C-terminal lysine residue (SEQ ID NO:256):

```
ASTKGPSVFP LAPCSRSTSE STAALGCLVK DYFPEPVTVS

WNSGALTSGV HTFPAVLQSS GLYSLSSVVT VPSSSLGTKT

YTCNVDHKPS NTKVDKRVES KYGPPCPPCP APEFLGGPSV

FLFPPKPKDT LMISRTPEVT CVVVDVSQED PEVQFNWYVD

GVEVHNAKTK PREEQFNSTY RVVSVLTVLH QDWLNGKEYK

CKVSNKGLPS SIEKTISKAK GQPREPQVYT LPPSQEEMTK

NQVSLTCLVK GFYPSDIAVE WESNGQPENN YKTTPPVLDS

DGSFFLYSRL TVDKSRWQEG NVFSCSVMHE ALHNHYTQKS

LSLSLG
```

In SEQ ID NO:256, amino acid residues 1-98 correspond to the IgG4 CH1 Domain (SEQ ID NO:254), amino acid residues 99-110 correspond to the stabilized IgG4 hinge region comprising the S228P substitutions (underlined) (SEQ ID NO: 13) and amino acid residues 111-326 correspond to the IgG4 CH2-CH3 Domain (SEQ ID NO:4) but lacking the C-terminal lysine residue.

The amino acid sequence of a heavy chain of an exemplary humanized antibody ((hPD-1 mAb 7(1.2)) having an IgG4 heavy chain constant region comprising a stabilized hinge region having the S228P mutation and lacking the C-terminal lysine residue is (SEQ ID NO:266):

```
QVQLVQSGAE VKKPGASVKV SCKASGYSFT SYWMNWVRQA

PGQGLEWIGV IHPSDSETWL DQKFKDRVTI TVDKSTSTAY

MELSSLRSED TAVYYCAREH YGTSPFAYWG QGTLVTVSSA

STKGPSVFPL APCSRSTSES TAALGCLVKD YFPEPVTVSW

NSGALTSGVH TFPAVLQSSG LYSLSSVVTV PSSSLGTKTY

TCNVDHKPSN TKVDKRVESK YGPPCPPCPA PEFLGGPSVF

LFPPKPKDTL MISRTPEVTC VVVDVSQEDP EVQFNWYVDG

VEVHNAKTKP REEQFNSTYR VVSVLTVLHQ DWLNGKEYKC

KVSNKGLPSS IEKTISKAKG QPREPQVYTL PPSQEEMTKN

QVSLTCLVKG FYPSDIAVEW ESNGQPENNY KTTPPVLDSD

GSFFLYSRLT VDKSRWQEGN VFSCSVMHEA LHNHYTQKSL

SLSLG
```

In SEQ ID NO:266, amino acid residues 1-119 correspond to the VH Domain of hPD-1 mAb 7 VH1 (SEQ ID NO:147), amino acid residues 120-217 correspond to the IgG4 CH1 Domain (SEQ ID NO:254), amino acid residues 218-229 correspond to the stabilized IgG4 hinge region comprising the S228P substitutions (underlined) (SEQ ID NO:13) and amino acid residues 230-445 correspond to the IgG4 CH2-CH3 Domain (SEQ ID NO:4) but lacking the C-terminal lysine residue.

Full length humanized antibody light chains were constructed as follows: the C-terminus of the humanized VL Domain was fused to the N-terminus of a human light chain kappa region (SEQ ID NO:8). The same light chain is paired with the IgG1 (AA) and the IgG4 (P) heavy chains.

The amino acid sequence of a light chain of an exemplary humanized PD-1 antibody (hPD-1 mAb 7(1.2)) having a kappa constant region is (SEQ ID NO:264):

```
EIVLTQSPAT LSLSPGERAT LSCRASESVD NYGMSFMNWF

QQKPGQPPKL LIHAASNQGS GVPSRFSGSG SGTDFTLTIS

SLEPEDFAVY FCQQSKEVPY TFGGGTKVEI KRTVAAPSVF

IFPPSDEQLK SGTASVVCLL NNFYPREAKV QWKVDNALQS

GNSQESVTEQ DSKDSTYSLS STLTLSKADY EKHKVYACEV

THQGLSSPVT KSFNRGEC
```

In SEQ ID NO:264, amino acid residues 1-111 correspond to the VL Domain of hPD-1 mAb 7 VL2 (SEQ ID NO:151), and amino acid residues 112-218 correspond to the light chain kappa constant region (SEQ ID NO: 8).

Anti-PD-1 antibodies having alternative Constant Regions, for example Engineered Fc Regions, are readily generated by incorporating different Constant Regions and/or by introducing one or more amino acid substitutions, additions or deletions. For example, where a bispecific antibody is desired knob-bearing and hole-bearing CH2-CH3 domains are used to facilitate heterodimerization. Chimeric anti-PD-1 antibodies comprising the murine Variable Domains and human Constant Regions are generated as described above.

The humanized antibodies (IgG1 (AA) and/or IgG4 (P)) were tested for binding and blocking activity as described in above. The binding to human PD-1 (shPD-1 His, and shPD-1 hFc) and cynomolgus monkey PD-1 (shPD-L1 hFc) of the humanized antibodies was comparable to that of the corresponding murine antibody. In addition, the humanized antibodies retained the ability to block the binding of human PD-L1 to human PD-1 in an ELISA assay.

The binding kinetics of the murine antibodies PD-1 mAb 2, PD-1 mAb 7, PD-1 mAb 9, PD-1 mAb 15, the humanized antibodies hPD-1 mAb 2, hPD-1 mAb 7(1.2), hPD-1 mAb 9(1.1), hPD-1 mAb 15, and the reference anti-PD-1 antibodies PD-1 mAb A and PD-1 mAb B was investigated using Biacore analysis. The anti-PD-1 antibodies were captured on immobilized Protein A and were incubated with His-tagged soluble human PD-1 (shPD-1-His) or soluble human cynomolgus monkey PD-1 Fc fusion (scyno PD-1 hFc) cleaved to remove Fc portion, and the kinetics of binding was determined via Biacore analysis. In additional studies the anti-PD-1 antibodies hPD-1 mAb 7(1.2) IgG1 (AA), hPD-1 mAb 7(1.2) IgG4 (P), hPD-1 mAb 9(1.1) IgG1 (AA), hPD-1 mAb 9(1.1) IgG4 (P), PD-1 mAb A IgG1 (AA), PD-1 mAb A IgG4 (P), PD-1 mAb B IgG1 (AA), and PD-1 mAb B IgG4 (P), were captured on immobilized F(ab)$_2$ goat anti-human Fc and the binding kinetics were determined by Biacore analysis as described above. The calculated ka, kd and KD from these studies are presented in Table 7.

TABLE 7

| Anti-PD-1 Antibody | Human[a] | | | Cynomolgus Monkey[b] | | |
|---|---|---|---|---|---|---|
| | $k_a$ ($\times 10^4$) | $k_d$ ($\times 10^{-4}$) | KD (nM) | $k_a$ ($\times 10^4$) | $k_d$ ($\times 10^{-4}$) | KD (nM) |
| Protein A Capture | | | | | | |
| PD-1 mAb A | 60 | 18 | 3 | 14 | 9.6 | 6.9 |
| PD-1 mAb B | 140 | 35 | 2.5 | 37 | 12 | 3.2 |
| PD-1 mAb 7 | 21 | 2.8 | 1.3 | 17 | 6 | 3.5 |
| hPD-1 mAb 7(1.2) | 110 | 4.3 | 0.39 | 37 | 6.4 | 1.7 |
| PD-1 mAb 9 | 4.3 | 4.2 | 9.8 | 2.2 | 16 | 72.7 |
| hPD-1 mAb 9(1.1) | 1.8 | 6.5 | 36.1 | 1.5 | 11 | 73.3 |
| PD-1 mAb 15 | 4.5 | 1.3 | 2.9 | 2.7 | 11 | 40.7 |
| hPD-1 mAb 15 | 2.4 | 3.2 | 13.3 | 2.3 | 18 | 78.3 |
| PD-1 mAb 2 | 5.5 | 5.6 | 10.2 | 4.2 | 6.0 | 14.3 |
| hPD-1 mAb 2 | 3.2 | 1.6 | 5.0 | 2.3 | 3.9 | 17 |
| F(ab)$_2$ goat anti-human Fc Capture | | | | | | |
| PD-1 mAb A IgG1 (AA) | 13 | 8.4 | 6.5 | 8.1 | 4.5 | 5.6 |
| PD-1 mAb A IgG4 (P) | 13 | 7.9 | 6.1 | 8.4 | 5.0 | 6.0 |
| PD-1 mAb B IgG1 (AA) | 25 | 28 | 11.2 | 20 | 6.4 | 3.2 |
| PD-1 mAb B IgG4 (P) | 26 | 25 | 9.6 | 20 | 7.9 | 4.0 |
| hPD-1 mAb 7(1.2) IgG1 (AA) | 25 | 3.8 | 1.5 | 16 | 7.8 | 4.9 |
| hPD-1 mAb 7(1.2) IgG4 (P) | 27 | 4.1 | 1.5 | 17 | 7.8 | 4.6 |
| hPD-1 mAb 9(1.1) IgG1 (AA) | 5.6 | 6.1 | 10.9 | 5.6 | 5.2 | 9.3 |
| hPD-1 mAb 9(1.1) IgG4 (P) | 6.1 | 5.8 | 9.5 | 4.9 | 7.4 | 15.1 |

[a]His tagged soluble human PD-1 (shPD-1 His)
[b]soluble cynomolgus monkey PD-1 (scyno PD-1 hFc) cleaved The results demonstrate that PD-1 mAb 7 and the humanized hPD-1 mAb 7(1.2) exhibit better binding kinetics relative to the reference anti-PD-1 antibodies PD-1 mAb A and PD-1 mAb B. PD-1 mAb 2, and hPD-1 mAb 2 exhibit binding kinetics within about two fold of the reference anti-PD-1 antibodies while PD-1 mAb 9, hPD-1 mAb 9(1.1), PD-1 mAb 15, and hPD-1 mAb 15 exhibit binding kinetics within about 2-6 fold of the reference anti-PD-1 antibodies.

The tissue specificity of the anti-human PD-1 antibody PD-1 mAb 7 was investigated. Normal tissue was contacted with PD-1 mAb 7 or with an isotype control (0.313 µg/mL) and the extent of staining was visualized. Bloxall used for endogenous enzyme block to reduce non-specific mucin staining in the colon tissue. As shown in FIG. 10A, Panels i-xii, PD-1 mAb 7 and the isotype control both failed to label cells of normal colon, liver, lung, pancreas, kidney and heart tissue. In addition, PD-1 mAb 7 and the isotype control failed to stain normal skin (FIG. 10B, Panels i-ii). In contrast, PD-1 mAb 7 was found to strongly label lymphocytes present in normal tonsil tissue and PDCD1 transfected NS0 cells expressing PD-1 (FIG. 10B, Panels iii and v), while the isotype control failed to label either (FIG. 10B, Panels iv and vi). The results presented in FIGS. 10A-10B thus indicate that PD-1 mAb 7 was capable of specifically binding to lymphocytes and cells expressing PD-1.

The binding saturation profiles of hPD-1 mAb 2 IgG1 (AA), hPD-1 mAb 7(1.1) IgG1 (AA), hPD-1 mAb 7(1.2) IgG1, (AA), hPD-1 mAb 7(1.2) IgG4 (P), hPD-1 mAb 9(1.1) IgG1 (AA), hPD-1 mAb 9(1.1) IgG4 (P), hPD-1 mAb 15 IgG1 (AA), and the reference anti-PD-1 antibodies PD-1 mAb A and PD-1 mAb B was examined. Briefly, each of the anti-PD-1 antibodies, PD-1 mAb 1-15, or the reference anti-PD-1 antibodies (PD-1 mAb A and PD-1 mAb B) was mixed with NS0 cells expressing human PD-1 (~250,000 cells/well) in blocking buffer (FACS+10% human serum albumin). For these studies the anti-PD-1 antibodies were utilized at 50, 12.5, 3.13, $2.0\times10^{-1}$, $4.9\times10^{-2}$, $1.2\times10^{-2}$, $3.0\times10^{-3}$, $1.9\times10^{-4}$, $7.6\times10^{-4}$, $4.75\times10^{-5}$, or $1.19\times10^{-5}$ m/test (four fold serial dilutions). The amount of antibody binding to the surface of the NS0 cells was determined using goat anti-human-APC secondary antibody by FACS analysis. Representative saturation curves are shown in FIG. 11. The EC50 and EC90 values were determined and the sample mean (SM) and standard deviation (SD a) from four separate experiments are provided in Table 8.

TABLE 8

| | Saturation Binding | | | |
|---|---|---|---|---|
| | EC50 (µg/test) | | EC90 (µg/test) | |
| Anti-PD-1 Antibody | SM | SD σ | SM | SD σ |
| PD-1 mAb A IgG1 (AA) | 0.1991 | 0.1309 | 1.4528 | 0.8040 |
| PD-1 mAb A IgG4 (P) | 0.1581 | 0.1161 | 1.5464 | 1.7690 |
| PD-1 mAb B IgG1 (AA) | 0.1347 | 0.0681 | 1.3917 | 0.9573 |
| PD-1 mAb B IgG4 (P) | 0.1398 | 0.0951 | 1.1619 | 1.2681 |
| hPD-1 mAb 2 IgG1 (AA) | 0.4431 | 0.1997 | 2.4374 | 1.2637 |
| hPD-1 mAb 7(1.1) IgG1 (AA) | 0.1069 | 0.0500 | 0.9102 | 0.5476 |
| hPD-1 mAb 7(1.2) IgG1 (AA) | 0.1872 | 0.1553 | 0.6810 | 0.3226 |
| hPD-1 mAb 7(1.2) IgG4 (P) | 0.1376 | 0.0926 | 0.6609 | 0.3437 |
| hPD-1 mAb 9(1.1) IgG1 (AA) | 0.3123 | 0.2291 | 1.6486 | 0.9117 |
| hPD-1 mAb 9(1.1) IgG4 (P) | 0.5128 | 0.2228 | 3.0563 | 0.9437 |
| hPD-1 mAb 15 IgG1 (AA) | 0.2927 | 0.1333 | 2.0640 | 0.6096 |

The binding saturation studies demonstrate that the humanized versions of PD-1 mAb 2, PD-1 mAb 7, PD-1 mAb 9, and PD-1 mAb 15 have favorable profile for binding to cell surface PD-1. In particular, humanized PD-1 mAb 7 (hPD-1 mAb 7(1.1), and hPD-1 mAb 7(1.2) having either an IgG1 (AA) or an IgG4 (P) Fc Region) have the lowest EC90 values of all the antibodies examined.

In order to further characterize the humanized anti-PD-1 antibodies hPD-1 mAb 2 IgG1 (AA), hPD-1 mAb 7(1.1) IgG1 (AA), hPD-1 mAb 7(1.2) IgG1, (AA), hPD-1 mAb 7(1.2) IgG4 (P), hPD-1 mAb 9(1.1) IgG1 (AA), hPD-1 mAb 9(1.1) IgG4 (P), and hPD-1 mAb 15 IgG1 (AA), their ability to block binding of human PD-L1 (shPD-L1) and human PD-L2 (shPD-L2) to PD-1 expressed on the surface of NS0 cells was examined. These assays were performed essentially as described above. Representative curves for inhibition of sPD-L1 and sPD-L2 binding to PD-1 expressed on NSO cells are shown in FIGS. 12A and 12B, respectively. The IC50 and IC90 values were determined and the sample mean (SM) and standard deviation (SD a) from three separate experiments are provided in Table 9.

strate (Promega) was then added to each well and the plate was incubated for an additional 5-10 minutes at ambient temperature, the luminescence was measured in a Victor Plate Reader. Representative saturation curves are shown in FIG. 13. The EC50 and EC90 values were determined and the sample mean (SM) and standard deviation (SD a) from four separate experiments are provided in Table 10.

TABLE 9

| Anti-PD-1 Antibody | sPD-L1 | | | | sPD-L2 | | | |
|---|---|---|---|---|---|---|---|---|
| | IC50 (µg/test) | | IC90 (µg/test) | | IC50 (µg/test) | | IC90 (µg/test) | |
| | SM | SD σ | SM | SD σ | SM | SD σ | SM | SD σ |
| PD-1 mAb A IgG1 (AA) | 0.0203 | 0.0089 | 0.2985 | 0.3279 | 0.0414 | 0.0124 | 0.1601 | 0.066 |
| PD-1 mAb A IgG4 (P) | 0.0156 | 0.0096 | 0.0776 | 0.0208 | 0.0280 | 0.0070 | 0.1594 | 0.1153 |
| PD-1 mAb B IgG1 (AA) | 0.0148 | 0.0008 | 0.1034 | 0.0100 | 0.0280 | 0.0059 | 0.1190 | 0.060 |
| PD-1 mAb B IgG4 (P) | 0.0143 | 0.0013 | 0.0798 | 0.0239 | 0.0280 | 0.0055 | 0.0924 | 0.0065 |
| hPD-1 mAb 2 IgG1 (AA) | 0.0578 | 0.0124 | 0.2480 | 0.050 | 0.1294 | 0.0143 | 0.3813 | 0.0656 |
| hPD-1 mAb 7(1.1) IgG1 (AA) | 0.0166 | 0.0032 | 0.0674 | 0.0041 | 0.0283 | 0.0147 | 0.0886 | 0.0166 |
| hPD-1 mAb 7(1.2) IgG1 (AA) | 0.0118 | 0.0027 | 0.0678 | 0.0031 | 0.0212 | 0.0031 | 0.0672 | 0.0043 |
| hPD-1 mAb 7(1.2) IgG4 (P) | 0.0103 | 0.0023 | 0.0520 | 0.0033 | 0.0213 | 0.0019 | 0.0616 | 0.0063 |
| hPD-1 mAb 9(1.1) IgG1 (AA) | 0.0593 | 0.0036 | 0.3238 | 0.0508 | 0.4002 | 0.5000 | 0.4573 | 0.1805 |
| hPD-1 mAb 9(1.1) IgG4 (P) | 0.0460 | 0.0118 | 0.2461 | 0.0513 | 0.1105 | 0.0146 | 0.2914 | 0.0526 |
| hPD-1 mAb 15 IgG1 (AA) | 0.0440 | 0.0092 | 0.2068 | 0.035 | 0.0945 | 0.0022 | 0.3093 | 0.0588 |

The ligand binding inhibition studies demonstrate that the humanized versions of PD-1 mAb 2, PD-1 mAb 7, PD-1 mAb 9, and PD-1 mAb 15 are able to inhibit the binding of sPD-L1 and sPD-L2 to PD-1 on the cell surface. In particular, humanized PD-1 mAb 7 (hPD-1 mAb 7(1.1), and hPD-1 mAb 7(1.2)) have the lowest IC90 values of all the antibodies examined.

Example 3

Blockade of the PD-1/PD-L1 Checkpoint by Humanized Anti-Human PD-1 Antibodies

The ability of hPD-1 mAb 2 IgG1 (AA), hPD-1 mAb 7(1.1) IgG1 (AA), hPD-1 mAb 7(1.2) IgG1, (AA), hPD-1 mAb 7(1.2) IgG4 (P), hPD-1 mAb 9(1.1) IgG1 (AA), hPD-1 mAb 9(1.1) IgG4 (P), hPD-1 mAb 15 IgG1 (AA), and the reference anti-PD-1 antibodies PD-1 mAb A and PD-1 mAb B to antagonize the PD-1/PD-L1 axis (i.e., block the PD-1/PD-L1 interaction and prevent down-regulation of T-cell responses) was examined in a Jurkat-luc-NFAT/CHO-PD-L1 luciferase reporter assay. Briefly, CHO cells expressing PD-L1 (CHO/PD-L1) were plated at 40,000/well in 100 µL of culture medium (RPMI+10% FBS+100 µg/mL Hygromycine B+100 µg/mL G418) and incubated overnight. The next day the media was removed and MNFAT-luc2/PD-1 Jurkat cells (Promega) at 50,000 cells/well in 40 µL in assay buffer (RPMI+2% FBS), and the anti-PD-1 antibodies PD-1 mAb 1-15, or a reference anti-PD-1 antibodies (PD-1 mAb A and PD-1 mAb B) (0-25 µg/mL; eight 2.5 fold serial dilutions in assay buffer) were added to each well and incubated for 6 hours at 37° C. followed by a 5-10 minutes incubated at ambient temperature. 80 µL of BioGlo Sub-

TABLE 10

| | Reporter Signaling | | | |
|---|---|---|---|---|
| | EC50 (µg/test) | | EC90 (µg/test) | |
| Anti-PD-1 Antibody | SM | SD σ | SM | SD σ |
| PD-1 mAb A IgG1 (AA) | 0.2549 | 0.0480 | 2.4474 | 1.2228 |
| PD-1 mAb A IgG4 (P) | 0.2049 | 0.0719 | 2.5535 | 1.2139 |
| PD-1 mAb B IgG1 (AA) | 0.2119 | 0.1781 | 2.2036 | 2.0118 |
| PD-1 mAb B IgG4 (P) | 0.1142 | 0.0323 | 0.9418 | 0.2863 |
| hPD-1 mAb 2 IgG1 (AA) | 0.3539 | 0.0983 | 3.8975 | 2.0054 |
| hPD-1 mAb 7(1.1) IgG1 (AA) | 0.1080 | 0.0386 | 1.1992 | 0.5103 |
| hPD-1 mAb 7(1.2) IgG1 (AA) | 0.0944 | 0.0153 | 0.6452 | 0.2615 |
| hPD-1 mAb 7(1.2) IgG4 (P) | 0.0965 | 0.0169 | 0.6885 | .01858 |
| hPD-1 mAb 9 IgG1 (AA) | 0.2835 | 0.0530 | 2.9968 | 0.8866 |
| hPD-1 mAb 9 IgG4 (P) | 0.3154 | 0.0872 | 5.0940 | 4.0496 |
| hPD-1 mAb 15 IgG1 (AA) | 0.2585 | 0.0592 | 3.3138 | 1.0532 |

The reporter signaling studies demonstrate that the humanized versions of PD-1 mAb 2, PD-1 mAb 7, PD-1 mAb 9, and PD-1 mAb 15 can block the PD-1/PD-L1 axis and will prevent down-regulation of T-cell responses. In particular, humanized PD-1 mAb 7 (hPD-1 mAb 7(1.1), and hPD-1 mAb 7(1.2) having either an IgG1 (AA) or an IgG4 (P) Fc Region) have the lowest EC50/EC90 values.

Example 4

Functional Activity of Anti-Human PD-1 Antibodies

*Staphylococcus aureus* enterotoxin type B (SEB) is a microbial superantigen capable of activating a large proportion of T-cells (5-30%) in SEB-responsive donors. SEB binds to MHC II outside the peptide binding grove and thus is MHC II dependent, but unrestricted and TCR mediated. SEB-stimulation of T-cells results in oligoclonal T-cell proliferation and cytokine production (although donor variability may be observed and some donors will not respond). Within 48 hours of SEB-stimulation PMBCs upregulate PD-1 and LAG-3 with a further enhancement see at day 5, post-secondary culture in 96-well plate with SEB-stimulation. Upregulation of the immune check point proteins PD-1 and LAG-3 following SEB-stimulation of PBMCs limits cytokine release upon restimulation. The ability of anti-PD-1 antibodies alone and in combination with anti-LAG-3 antibodies to enhance cytokine release through checkpoint inhibition was examined.

Briefly, PBMCs were purified using the Ficoll-Paque Plus (GE Healthcare) density gradient centrifugation method according to manufacturer's instructions from whole blood obtained under informed consent from healthy donors (Biological Specialty Corporation) and T cells were then purified using the Dynabeads® Untouched Human T Cells Kit (Life Technologies) according to manufacturer's instructions. Purified PBMCs were cultured in RPMI-media+10% heat inactivated FBS+1% Penicillin/Streptomycin in T-25 bulk flasks for 2-3 days alone or with SEB (Sigma-Aldrich) at 0.1 ng/mL (primary stimulation). At the end of the first round of SEB-stimulation, PBMCs were washed twice with PBS and immediately plated in 96-well tissue culture plates at a concentration of $1-5\times10^5$ cells/well in media alone, media with a control or an anti-PD-1 antibody, media with SEB at 0.1 ng/mL (secondary stimulation) and no antibody, or media with SEB and a control IgG or an anti-PD-1 antibody +/− an anti-LAG-3 mAb, and cultured for an additional 2-3 days. At the end of the second stimulation, supernatants were harvested to measure cytokine secretion using human DuoSet ELISA Kits for IFNγ, TNFα, IL-10, and IL-4 (R&D Systems) according to the manufacturer's instructions.

The ability of PD-1 mAb 2, PD-1 mAb 7, PD-1 mAb 9, and PD-1 mAb 15 alone, or in combination with the unique anti-LAG-3 antibody LAG-3 mAb 1 to enhance cytokine release through checkpoint inhibition was examined. These studies also included one or more of the following reference anti-PD-1 antibodies: PD-1 mAb A; PD-1 mAb B; and LAG-3 mAb A, alone or in combination. FIG. 14 shows the IFNγ secretion profiles from SEB-stimulated (0.1 ng/mL) PBMCs from a representative responding donor (D:38941), treated with: no antibody; isotype control antibody; PD-1 mAb 7 and/or LAG-3 mAb 7; PD-1 mAb 9 and/or LAG-3 mAb 1; PD-1 mAb 15 and/or LAG-3 mAb 1; PD-1 mAb 2 and/or LAG-3 mAb 1; or the reference anti-PD-1 antibodies PD-1 mAb B and/or LAG-3 mAb A (antibodies were used at 10 μg/mL).

In additional studies the ability of the humanized versions of PD-1 mAb 2, PD-1 mAb 7, PD-1 mAb 9, and PD-1 mAb 15 (comprising a human IgG1 (AA) or a human IgG4 (P) Fc Region) as well as the reference anti-PD-1 antibodies PD-1 mAb A and PD-1 mAb B to enhance cytokine release through checkpoint inhibition was examined. For these studies the antibodies were utilized at 0.625, 2.5, and 10 μg/mL. FIGS. 15A-15B shows the IFNγ (FIG. 15A) and TNFα (FIG. 15B), secretion profiles from SEB-stimulated (0.2 ng/mL) PBMCs from a representative responding donor (D:57709), treated with no antibody or one of the following antibodies: isotype control; hPD-1 mAb 2 IgG1 (AA); hPD-1 mAb 7(1.2) IgG1 (AA); hPD-1 mAb 7(1.2) IgG4 (P); hPD-1 mAb 9(1.1) IgG1 (AA); hPD-1 mAb 9(1.1) IgG4 (P); hPD-1 mAb 15 IgG1 (AA); or the reference anti-PD-1 antibodies PD-1 mAb A IgG1 (AA), PD-1 mAb A IgG4 (P), PD-1 mAb B IgG1 (AA), PD-1 mAb B IgG4 (P). The total pg/mg of IFNγ in samples treated with SEB+Ab were determined for the samples treated with the anti-PD-1 antibodies at 0.625, 2.5 and 10 μg/mL and the sample mean (SM) and standard deviation (SD a) from 3 different responding donors (except where noted) are provided in Table 11. The ratio of IFNγ secreted in sample treated with the humanized versions of PD-1 mAb 2, PD-1 mAb 7, PD-1 mAb 9, and PD-1 mAb 15 (comprising a human IgG1 (AA) or a human IgG4 (P) Fc Region) over the reference anti-PD-1 antibodies PD-1 mAb A and PD-1 mAb B (i.e., humanized anti-PD-1/PD-1 mAb A, and humanized anti-PD-1/PD-1 mAb B) is presented in Table 12 and Table 13, respectively.

TABLE 11

| | IFNγ Secretion (pg/mL) μg/mL anti-PD1 antibody | | | | | |
|---|---|---|---|---|---|---|
| | 0.625 μg/mL | | 2.5 μg/mL | | 10 μg/mL | |
| anti-PD-1 Antibody | SM | SD σ | SM | SD σ | SM | SD σ |
| PD-1 mAb A IgG1 (AA) | 221.18 | 110.89 | 341.13 | 247.93 | 347.46 | 144.72 |
| PD-1 mAb A IgG4 (P) | 281.36 | 132.65 | 495.15 | 190.57 | 399.41 | 117.56 |
| PD-1 mAb B IgG1 (AA) | 366.69 | 196.64 | 387.682 | 215.51 | 387.32 | 282.81 |
| PD-1 mAb B IgG4 (P) | 348.40 | 185.96 | 433.382 | 163.23 | 551.68 | 125.08 |
| hPD-1 mAb 7(1.2) IgG1 (AA) | 302.05 | 185.71 | 610.70 | 209.77 | 414.63 | 272.65 |
| hPD-1 mAb 7(1.2) IgG4 (P) | 384.57‡ | 323.79‡ | 411.40 | 398.59 | 370.06 | 108.12 |
| hPD-1 mAb 9(1.1) IgG1 (AA) | 340.81 | 207.76 | 442.598 | 303.70 | 655.29 | 567.91 |
| hPD-1 mAb 9(1.1) IgG4 (P) | 309.82 | 130.30 | 468.62 | 350.15 | 424.35 | 288.95 |
| hPD-1 mAb 15 IgG1 (AA) | 360.00 | 274.28 | 373.32 | 160.25 | 541.83 | 444.22 |
| hPD-1 mAb 2 IgG1 (AA) | 275.88 | 135.23 | 372.73 | 53.53 | 496.70 | 235.37 |
| Control IgG | 137.14 | 76.61 | 100.65 | 48.67 | 138.10 | 120.81 |
| No Antibody | 120.05 | 73.90 | 120.05 | 73.90 | 109.46 | 85.18 |

‡Results from two responding donors

TABLE 12

Ratio IFNγ Secretion (New Anti-PD-1/PD-1 mAb A) μg/mL anti-PD1 antibody

| anti-PD-1 Antibody | 0.625 μg/mL | | 2.5 μg/mL | | 10 μg/mL | |
|---|---|---|---|---|---|---|
| | SM | SD σ | SM | SD σ | SM | SD σ |
| PD-1 mAb A IgG1 (AA) | 1.00 | 0.00 | 1.00 | 0.00 | 1.00 | 0.00 |
| PD-1 mAb A IgG4 (P) | 1.00 | 0.00 | 1.00 | 0.00 | 1.00 | 0.00 |
| PD-1 mAb B IgG1 (AA) | 1.77 | 0.92 | 1.28 | 0.36 | 1.07 | 0.42 |
| PD-1 mAb B IgG4 (P) | 1.23 | 0.16 | 0.92 | 0.27 | 1.40 | 0.12 |
| hPD-1 mAb 7(1.2) IgG1 (AA) | 1.36 | 0.37 | 2.46 | 1.85 | 1.17 | 0.41 |
| hPD-1 mAb 7(1.2) IgG4 (P) | 1.20‡ | 0.35‡ | 0.79 | 0.54 | 0.95 | 0.22 |
| hPD-1 mAb 9(1.1) IgG1 (AA) | 1.48 | 0.19 | 1.46 | 0.71 | 1.70 | 0.84 |
| hPD-1 mAb 9(1.1) IgG4 (P) | 1.13 | 0.13 | 0.91 | 0.42 | 1.02 | 0.46 |
| hPD-1 mAb 15 IgG1 (AA) | 1.50 | 0.39 | 1.51 | 1.23 | 1.48 | 0.71 |
| hPD-1 mAb 2 IgG1 (AA) | 1.32 | 0.53 | 1.48 | 0.86 | 1.42 | 0.12 |
| Control IgG | 0.63 | 0.2 | 0.33 | 0.08 | 0.39 | 0.24 |
| No Antibody | 0.54 | 0.12 | 0.39 | 0.14 | 0.31 | 0.17 |

‡Results from two responding donors

TABLE 13

Ratio IFNγ Secretion (New Anti-PD-1/PD-1 mAb B) μg/mL anti-PD1 antibody

| anti-PD-1 Antibody | 0.625 μg/mL | | 2.5 μg/mL | | 10 μg/mL | |
|---|---|---|---|---|---|---|
| | SM | SD σ | SM | SD σ | SM | SD σ |
| PD-1 mAb A IgG1 (AA) | 0.37 | 0.37 | 0.82 | 0.20 | 1.06 | 0.48 |
| PD-1 mAb A IgG4 (P) | 0.82 | 0.12 | 1.16 | 0.38 | 0.72 | 0.07 |
| PD-1 mAb B IgG1 (AA) | 1.0 | 0.00 | 1.0 | 0.00 | 1.0 | 0.00 |
| PD-1 mAb B IgG4 (P) | 1.0 | 0.00 | 1.0 | 0.00 | 1.0 | 0.00 |
| hPD-1 mAb 7(1.2) IgG1 (AA) | 0.84 | 0.22 | 1.77 | 0.81 | 1.11 | 0.07 |
| hPD-1 mAb 7(1.2) IgG4 (P) | 0.91‡ | 0.26‡ | 0.83 | 0.50 | 0.68 | 0.17 |
| hPD-1 mAb 9(1.1) IgG1 (AA) | 1.04 | 0.59 | 1.12 | 0.29 | 1.60 | 0.42 |
| hPD-1 mAb 9(1.1) IgG4 (P) | 0.92 | 0.09 | 0.99 | 0.36 | 0.75 | 0.39 |
| hPD-1 mAb 15 IgG1 (AA) | 1.01 | 0.48 | 1.07 | 0.57 | 1.34 | 0.15 |
| hPD-1 mAb 2 IgG1 (AA) | 0.78 | 0.12 | 1.10 | 0.38 | 1.46 | 0.53 |
| Control IgG | 0.39 | 0.08 | 0.27 | 0.08 | 0.34 | 0.13 |
| No Antibody | 0.34 | 0.11 | 0.31 | 0.03 | 0.28 | 0.08 |

‡Results from two responding donors

The results of these studies demonstrate that the PD-1 antibodies PD-1 mAb 2, PD-1 mAb 7, PD-1 mAb 9, and PD-1 mAb 15 dramatically enhanced IFNγ (FIGS. 14 and 15A, and Tables 11-13), and TNFα (FIG. 15B) production from SEB-stimulated PBMCs upon restimulation. In addition, the combination of anti-PD-1 antibodies with anti-LAG-3 antibodies resulted in a further enhancement of cytokine release (FIG. 14) from SEB-stimulated PBMCs upon restimulation. In particular, the combination of PD-1 mAb 2, PD-1 mAb 7, PD-1 mAb 9, or PD-1 mAb 15 with the unique anti-LAG-3 antibody LAG-3 mAb 1 provided the largest enhancement.

Example 5

PD-1×LAG-3 Bispecific Molecules Binding Studies

A number of PD-1×LAG-3 bispecific molecules were generated, including Fc Region-containing diabodies comprising three, four, and five chains and a bispecific antibody. Four diabodies having four chains and comprising E/K-coil Heterodimer-Promoting Domains were generated and accorded the designations "DART A," "DART B," "DART C, and "DART I." Four diabodies having four chains and comprising CH1/CL Domains were generated and accorded the designations "DART D," "DART E," "DART J," and "DART 1." Two diabodies having five chains and comprising E/K-coil Heterodimer-Promoting Domains and CH1/CL Domains were generated and accorded the designations "DART F," and "DART G." One diabody having three chains and comprising E/K-coil Heterodimer-Promoting Domains was generated and accorded the designation "DART H." One bispecific antibody having four chains was generated and accorded the designation "BSAB A." The structure and amino acid sequences of these PD-1×LAG-3 bispecific molecules are provided above and are summarized in Table 14 below.

TABLE 14

| Name | Parental mAbs | Fc‡ | Chains | SEQ ID NOs: | Other Components |
|---|---|---|---|---|---|
| DART A | hPD-1 mAb 7(1.2) hLAG-3 mAb 1(1.4) | IgG4 (YTE) | 4 | 267 ($X_1$ = A; $X_2$ = Y; $X_3$ = T; $X_4$ = E) and 268 | E/K-Coils; see FIG. 3B |
| DART B | hPD-1 mAb 7(1.2) hLAG-3mAb 1(1.3) | IgG4 (YTE) | 4 | 267 ($X_1$ = G; $X_2$ = Y; $X_3$ = T; $X_4$ = E) and 268 | E/K-Coils; see FIG. 3B |
| DART C | hPD-1 mAb 7(1.2) hLAG-3 mAb 1(1.3) | IgG4 | 4 | 267 ($X_1$ = G; $X_2$ = M; $X_3$ = S; $X_4$ = T) and 268 | E/K-Coils; see FIG. 3B |
| DART D | hPD-1 mAb 7(1.2) hLAG-3 mAb 1(1.4) | IgG4 (YTE) | 4 | 269 and 270 | CL/CH1; see FIG. 3C |
| DART E | hPD-1 mAb 7(1.2) hLAG-3 mAb 1(1.4) | IgG4 (YTE) | 4 | 271 and 272 | CL/CH1; see FIG. 3C |
| DART F | hPD-1 mAb 7(1.2) hLAG-3 mAb 1(1.4) | IgG1 (AA/YTE) | 5 | 273, 274, 275, and 276 | CL/CH1 and E/K-Coils; see FIG. 5 |
| DART G | hPD-1 mAb 7(1.2) hLAG-3 mAb 1(1.4) | IgG1 (AA/YTE) | 5 | 277, 278, 279, and 280 | CL/CH1 and E/K-Coils; see FIG. 5 |
| DART H | hPD-1 mAb 7(1.2) hLAG-3 mAb 1(1.4) | IgG1 (AA) | 3 | 281, 282, and 283 | E/K Coils; See FIG. 4A |
| DART I | hPD-1 mAb 7(1.2) hLAG-3 mAb 6(1.1) | IgG4 (YTE) | 4 | 290 and 291 | E/K-Coils; see FIG. 3B |

TABLE 14-continued

| Name | Parental mAbs | Fc‡ | Chains | SEQ ID NOs: | Other Components |
|---|---|---|---|---|---|
| DART J | hPD-1 mAb 7(1.2) hLAG-3 mAb 6(1.1) | IgG4 (YTE) | 4 | 292 and 293 | CL/CH1; see FIG. 3C |
| DART 1 | PD-1 mAb A LAG-3 mAb A | IgG1 (AA) | 4 | 284 and 285 | CL/CH1; see FIG. 3C |
| BSAB A | hPD-1 mAb 7(1.2) hLAG-3 mAb 1(1.4) | IgG1 (AA) | 4 | 286, 287, 288, and 289 | mAb with charge engineered Fc Region |

‡Molecules incorporating IgG4 Fc regions also incorporate a stabilized IgG4 hinge region.

Additional PD-1×LAG-3 bispecific molecules comprising alternative PD-1 and/or LAG-3 epitope-binding sites may be readily generated by incorporating different VH and VL Domains. Similarly, molecules binding an antigen other than LAG-3 may be generated by incorporating the VH and VL having the desired specificity.

The binding saturation profiles of the PD-1×LAG-3 bispecific diabody constructs: DART A, DART B, DART D, DART E, DART F, DART G, DART H, DART I, and DART 1; the anti-PD-1 antibodies: hPD-1 mAb 7(1.2) IgG4 (P), hPD-1 mAb 7(1.2) IgG1 (AA), PD-1 mAb A IgG1 (AA) and PD-1 mAb A IgG4 (P); and the anti-LAG-3 antibodies: hLAG-3 mAb 1(1.4) IgG4 (P), LAG-3 mAb A IgG4 (P), hLAG-3 mAb 1(1.4) IgG1 (AA), and LAG-3 mAb A IgG1 (AA) were examined essentially as described above. The PD-1×LAG-3 bispecific diabody constructs were tested for both PD-1 and LAG-3 binding, while the anti-PD-1 and anti-LAG-3 antibodies were only tested for binding to their respective antigens. For these studies NSO cells expressing PD-1 or LAG-3 were utilized. The diabodies and antibodies were utilized (170.0-0.013 µM or 85.0-0.0021 µM (four fold serial dilutions). The EC50 and EC90 values were determined and are presented in Tables 15-16. The sample mean (SM) and standard deviation (SD σ) are provided where 2 or more separate experiments were performed.

TABLE 15

| | Saturation Binding PD-1 | | | |
|---|---|---|---|---|
| | EC50 (µM) | | EC90 (µM) | |
| Molecule | SM | SD σ | SM | SD σ |
| DART A | 1.9297 | 0.4324 | 9.6027 | 0.4801 |
| DART B | 1.764§ | | 12.2700§ | |
| DART D | 2.2267 | 0.4140 | 10.9313 | 2.6351 |
| DART E | 3.2180 | 0.5742 | 23.840 | 3.2385 |
| DART F | 1.4320§ | | 14.5800§ | |
| DART G | 1.1488 | 0.6227 | 3.4220 | 2.4600 |
| DART H | 4.5310§ | | 22.6600§ | |
| DART I | 1.3232 | 0.4890 | 7.8135 | 4.0821 |
| DART 1 | 2.1329 | 1.4850 | 13.8113 | 9.0256 |
| hPD-1 mAb 7(1.2) IgG4 (P) | 1.2083 | 0.8112 | 3.9340 | 1.8746 |
| PD-1 mAb A IgG4 (P) | 2.3470 | 1.2362 | 22.7770 | 15.0690 |
| h1PD-1 mAb 7(1.2) IgG1 (AA) | 1.0879 | 0.3958 | 7.4153 | 3.0794 |
| PD-1 mAb A IgG1 (AA) | 1.6733 | 0.5464 | 9.9543 | 6.6569 |

§results from a single experiment

TABLE 16

| | Saturation Binding LAG-3 | | | |
|---|---|---|---|---|
| | EC50 (µM) | | EC90 (µM) | |
| Molecule | SM | SD σ | SM | SD σ |
| DART A | 0.8402 | 0.2231 | 4.4448 | 2.4770 |
| DART B | 1.075§ | | 9.858§ | |
| DART D | 0.8985 | 0.5326 | 5.7967 | 4.7329 |
| DART E | 0.9250 | 0.8075 | 5.6450 | 5.6809 |
| DART F | 5.0090 | 0.5770 | 19.3350 | 4.7447 |
| DART G | 0.9396 | 0.3045 | 8.5507 | 4.7448 |
| DART H | 2.384§ | | 9.7810 | 4.2412 |
| DART I | 0.5321 | 0.0547 | 4.198 | 3.2188 |
| DART 1 | 20.0233 | 2.1454 | 115.97 | 15.2425 |
| hLAG-3 mAb 1(1.4) IgG4 (P) | 1.0057 | 0.1969 | 5.1360 | 4.7904 |
| LAG-3 mAb A IgG4 (P) | 0.5968 | 0.1376 | 2.0833 | 0.3244 |
| hLAG-3 mAb 1(1.4) IgG1 (AA) | 0.6069 | 0.3430 | 3.6373 | 2.4762 |
| LAG-3 mAb A IgG1 (AA) | 0.4523 | 0.1660 | 2.0187 | 0.7035 |

§results from a single experiment

The binding saturation studies demonstrate that the PD-1×LAG-3 bispecific diabody constructs retain binding to PD-1 and have binding profiles that are similar to the binding profiles of the parental anti-PD-1 antibodies. Similarly, the PD-1×LAG-3 bispecific diabody constructs retain binding to LAG-3 and, with the exception of DART 1, have binding profiles that are similar to the binding profiles of the parental anti-LAG-3 antibodies.

Example 6

PD-1×LAG-3 Bispecific Molecules Inhibition Studies

The ability of the PD-1×LAG-3 bispecific molecules: DART A, DART B, DART D, DART E, DART F, DART G, DART H, DART I, DART 1 and BSAB A; and the anti-PD-1 antibodies: hPD-1 mAb 7(1.2) IgG4 (P), hPD-1 mAb 7(1.2) IgG1 (AA), PD-1 mAb A IgG1 (AA) and PD-1 mAb A IgG4 (P), to block binding of human PD-L1 (shPD-L1) and human PD-L2 (shPD-L2) to PD-1 expressed on the surface of NSO cells was examined essentially as described above. The diabodies and antibodies were utilized at 33.75-0.002 µM or 107.5-0.0001 µM (four fold serial dilutions).

The IC50 and IC90 values were determined and are presented in Table 17. The sample mean (SM) and standard deviation (SD σ) are provided where 2 or more separate experiments were performed.

TABLE 17

| Molecule | block sPD-L1/PD-1 binding | | | | block sPD-L2/PD-1 binding | | | |
|---|---|---|---|---|---|---|---|---|
| | IC50 (µM) | | IC90 (µM) | | IC50 (µM) | | IC90 (µM) | |
| | SM | SD σ | SM | SD σ | SM | SD σ | SM | SD σ |
| DART A | 0.9645 | 0.1485 | 5.6312 | 1.5247 | 1.6273 | 0.4285 | 6.9335 | 3.9849 |
| DART B | 1.1515 | 0.0007 | 4.8615 | 0.2199 | 2.1150 | 0.3154 | 7.9550 | 0.0933 |
| DART D | 1.5548 | 0.1692 | 7.8950 | 2.5135 | 3.1255 | 0.5869 | 9.2973 | 5.5426 |
| DART E | 1.6533 | 0.3307 | 7.8470 | 1.1642 | 2.9460 | 0.7736 | 6.6135 | 0.0177 |
| DART F | 0.5697 | 0.1729 | 2.0360 | 0.1174 | 0.8389 | 0.0846 | 1.7995 | 0.2171 |
| DART G | 1.6013 | 0.3581 | 8.1953 | 1.5708 | 2.5540 | 0.7891 | 7.4810 | 0.2333 |
| DART H | 3.3950 | 0.1018 | 18.640 | 9.5742 | 6.2065 | 3.6847 | 29.395 | 3.8679 |
| DART I | 0.8363 | 0.1302 | 5.3115 | 0.3125 | 1.286 | 0.3125 | 6.2485 | 1.3951 |
| DART 1 | 1.7467 | 0.3097 | 5.4533 | 1.0214 | 2.8355 | 1.8250 | 7.2735 | 3.9831 |
| BSAB A | 2.1590 | 0.3097 | 11.075 | 0.8132 | 4.8775 | 0.5438 | 15.580 | 1.3294 |
| hPD-1 mAb 7(1.2) IgG4 (P) | 0.5186 | 0.1668 | 3.8050 | 1.2227 | 1.0425 | 0.2563 | 3.4880 | 0.5459 |
| PD-1 mAb A IgG4 (P) | 0.9209 | 0.3256 | 4.3023 | 0.7069 | 1.3859 | 0.3882 | 5.1675 | 0.2943 |
| hPD-1 mAb 7(1.2) IgG1(AA) | 0.7320 | 0.2337 | 3.2048 | 1.1479 | 0.9769 | 0.2893 | 2.8437 | 1.4801 |
| PD-1 mAb A IgG1 (AA) | 1.0765 | 0.2393 | 5.2775 | 0.9933 | 1.9510 | 0.8814 | 5.0880 | 1.3831 |

The ligand binding inhibition studies demonstrate that the PD-1×LAG-3 bispecific diabody constructs retain the ability to inhibit the binding of sPD-L1 and sPD-L2 to PD-1 on the cell surface.

In addition, the ability of the PD-1×LAG-3 bispecific molecules: DART A, DART B, DART D, DART E, DART F, DART G, DART H, DART I, DART 1 and BSAB A; and the anti-LAG-3 antibodies: hLAG-3 mAb 1(1.4) IgG4 (P), LAG-3 mAb A IgG4 (P), hLAG-3 mAb 1(1.4) IgG1 (AA), and LAG-3 mAb A IgG1 (AA), to block binding of human LAG-3 to native MHC class II on the surface of Daudi cells was examined. Briefly, each PD-1×LAG-3 bispecific molecule and control anti-LAG-3 antibody was mixed with a biotinylated-soluble human LAG-3-Fc fusion protein (sh-LAG-3), (at 0.5 µg/ml) and were separately incubated with MHC II-positive Daudi cells ($2.5 \times 10^6$ cells). The amount of LAG-3 binding to the surface of the Daudi cells was determined using a PE-conjugated Streptavidin secondary antibody by FACS analysis. The diabodies and antibodies were utilized at 27.5-0.026 µM (two fold serial dilutions) or 107.5-0.0001 µM (four fold serial dilutions), or 35-0.002 µM (four fold serial dilutions).

The IC50 and IC90 values were determined and are presented in Table 18. The sample mean (SM) and standard deviation (SD a) are provided where 2 or more separate experiments were performed.

TABLE 18

| Molecule | Block shLAG-3/MHC Class II Binding | | | |
|---|---|---|---|---|
| | EC50 (µM) | | EC90 (µM) | |
| | SM | SD σ | SM | SD σ |
| DART A | 1.3835 | 1.6465 | 8.396102 | 8.3962 |
| DART B | 0.4081 | 0.1104 | 3.0645 | 0.3924 |
| DART D | 1.1843 | 1.1398 | 8.0041 | 7.3317 |
| DART E | 3.2706 | 2.9177 | 28.9683 | 24.1694 |
| DART F | 1.5347 | 1.2674 | 10.3920 | 11.2555 |
| DART G | 2.0618 | 3.3552 | 11.4422 | 12.4964 |
| DART H | 2.8967 | 4.9817 | 17.2533 | 21.1420 |
| DART I | 0.4864 | 0.1549 | 2.339 | 1.1780 |
| DART 1 | 15.9610 | 14.0883 | 87.1486 | 109.533 |
| BSAB A | 0.7101 | 0.0571 | 7.2470 | 1.0706 |
| hLAG-3 mAb 1(1.4) IgG4 (P) | 0.4815 | 0.2176 | 3.4837 | 1.7564 |
| LAG-3 mAb A IgG4 (P) | 0.7011 | 0.1900 | 2.4232 | 0.3481 |
| hLAG-3 mAb 1(1.4) IgG1 (AA) | 0.3637 | 0.1409 | 9.4422 | 7.9319 |
| LAG-3 mAb A IgG1 (AA) | 0.5923 | 0.3407 | 2.1451 | 1.1139 |

The ligand binding inhibition studies demonstrate that the PD-1×LAG-3 bispecific diabody constructs retain the ability to inhibit the binding of a shLAG-3-Fc fusion protein to MHC class II on the cell surface. With the exception of DART 1 the PD-1×LAG-3 bispecific molecules have similar inhibition profiles as the parental anti-LAG-3 antibodies.

Example 7

Blockade of the PD-1/PD-L1 Checkpoint by PD-1×LAG-3 Bispecific Molecules

The ability of the PD-1×LAG-3 bispecific molecules: DART A, DART B, DART D, DART E, DART F, DART G, DART H, DART I, DART 1 and BSAB A; and the anti-PD-1 antibodies: hPD-1 mAb 7(1.2) IgG4 (P), hPD-1 mAb 7(1.2) IgG1 (AA), PD-1 mAb A IgG1 (AA) and PD-1 mAb A IgG4 (P), to antagonize the PD-1/PD-L1 axis (i.e., block the PD-1/PD-L 1 interaction and prevent down-regulation of T-cell responses) was examined in a Jurkat-luc2-NFAT/ CHO-PD-L1 luciferase reporter assay (using CHO/PD-L1 cells and MNFAT-luc2/PD-1 Jurkat cells) essentially as described above. The diabodies and antibodies were utilized at 100-0.0065 µM (four fold serial dilutions) or 100-0.0013 µM (five fold serial dilutions).

The IC50 and IC90 values were determined and are presented in Table 19. The sample mean (SM) and standard deviation (SD a) are provided where 2 or more separate experiments were performed.

TABLE 19

| Molecule | Reporter Signaling | | | |
|---|---|---|---|---|
| | IC50 (μM) | | IC90 (μM) | |
| | SM | SD σ | SM | SD σ |
| DART A | 0.8804 | 0.1949 | 7.9115 | 1.3232 |
| DART B | 1.079 | 0.1535 | 7.5413 | 3.1483 |
| DART D | 1.4044 | 0.2584 | 12.0786 | 3.6616 |
| DART E | 1.4060 | 0.1222 | 13.7867 | 1.4981 |
| DART F | 0.3404 | 0.0103 | 1.8710 | 0.481 |
| DART G | 0.6914 | 0.0206 | 4.2090 | 0.7331 |
| DART H | 36.6167 | 20.8078 | 968.300 | 811.8471 |
| DART I | 1.3335 | 0.3641 | 12.146 | 6.8787 |
| DART 1 | 11.8807 | 3.4905 | 1048.2000 | 1508.9992 |
| BSAB A | 9.7825 | 1.0288 | 113.3350 | 22.2951 |
| hPD-1 mAb 7(1.2) IgG4 (P) | 0.6460 | 0.3035 | 6.0736 | 2.5513 |
| PD-1 mAb A IgG4 (P) | 1.328 | 0.7439 | 16.5138 | 9.7149 |
| h1PD-1 mAb 7(1.2) IgG1(AA) | 0.5214 | 0.1541 | 4.7592 | 2.1044 |
| PD-1 mAb A IgG1 (AA) | 1.4514 | 1.0049 | 35.7382 | 40.9858 |

The reporter signaling studies demonstrate that the majority of the PD-1×LAG-3 bispecific diabody constructs retain the ability to inhibit the binding of sPD-L1 to PD-1 on the cell surface. The tetravalent PD-1×LAG-3 bispecific diabody constructs, DART A, DART B, DART D, DART-E, DART F, DART G and DART I were the strongest inhibitors in this assay. Similar results were obtained for several of these bispecific constructs examined in a PD-L2 reporter assay.

Example 8

Functional Activity of PD-1×LAG-3 Bispecific Molecules

The ability of PD-1×LAG-3 bispecific molecules to enhance cytokine release through checkpoint inhibition was examined in SEB-stimulated PBMCs upon restimulation essentially as described above except where noted.

In initial studies the ability of the PD-1×LAG-3 bispecific molecules: DART A, DART D, DART E, DART F, DART G, DART H; and the anti-PD-1 and anti-LAG antibodies: PD-1 mAb A IgG4 (P) and LAG-3 mAb A IgG4 (P), alone or in combination to enhance cytokine release through checkpoint inhibition was examined. In these assays the PD-1×LAG-3 bispecific molecules and antibodies were used at a total concentration of 3.125, 12.5, or 50 nM, and the PBMCs were stimulated with 0.2 ng/mL of SEB (previous studies used 0.1 ng/mL). For these studies, where a combination of antibodies is used each antibody is provided at one half of the total concentration, (i.e., 1.563, 6.25, or 25 nM). FIGS. 16A and 16B shows the IFNγ secretion profiles from SEB-stimulated PBMCs from two representative responding donors, D: 35644 and D: 59697, respectively.

As noted, not all donors respond to SEB at 0.1 or 0.2 ng/mL. To enhance SEB stimulation of PBMCs from a wider number of donors SEB was used at a high concentration of 85 ng/mL, or a middle concentration of 0.5 ng/mL in additional studies. At these concentrations SEB stimulation is more robust across more donors, although donor to donor variability may still be seen.

In one such study the ability of the PD-1×LAG-3 bispecific molecules: DART A, DART B; the anti-PD-1 antibody: hPD-1 mAb 7(1.2) IgG4(P); the anti-LAG-3 antibody: LAG-3 mAb 1(1.4) IgG4(P); and the combination of: PD-1 mAb A IgG4 (P) and LAG-3 mAb A IgG4 (P), to enhance cytokine release through checkpoint inhibition was examined. In these assays the PD-1×LAG-3 bispecific molecules and antibodies were used at a concentration of 0.019, 0.078, 0.3125, 1.25, 5, or 20 nM and the PBMCs were stimulated with 85 ng/mL of SEB. For this assay where a combination of antibodies is used each antibody was provided at the indicated concentration and thus the total antibody concentration is twice the concentration used for each antibody (i.e., 0.038, 0.156, 0.625, 2.5, 10, or 40 nM). FIGS. 17A and 17B show the IFNγ secretion profiles from SEB-stimulated PBMCs from two representative donors, D: 55515 and D: 54024, respectively.

In another study the PD-1×LAG-3 bispecific molecules: DART A, DART B, DART C; the anti-PD-1 antibody: hPD-1 mAb 7(1.2) IgG4(P); the anti-LAG-3 antibody: LAG-3 mAb 1(1.4) IgG4(P); and the combination of: PD-1 mAb A IgG4 (P) and LAG-3 mAb A IgG4 (P), to enhance cytokine release through checkpoint inhibition was examined. In these assays the PD-1×LAG-3 bispecific molecules and antibodies were used at a total concentration of 0.048, 0.195, 0.78, 3.125, 12.5, or 50 nM and the PBMCs were stimulated with 0.5 ng/mL of SEB. For these studies, where a combination of antibodies is used each antibody is provided at one half of the total concentration (i.e., 0.024, 0.098, 0.39, 1.563, 6.25, or 25 nM). FIGS. 18A and 18B show the IFNγ secretion profiles from SEB-stimulated PBMCs from two representative donors, D: 20990 and D: 54947, respectively).

In a further study, the release of the cytokine IL-2 was examined. Specifically, the PD-1×LAG-3 bispecific molecules: DART D, DART H; the anti-PD-1 antibodies: PD-1 mAb A IgG4 (P), hPD-1 mAb 7(1.2) IgG4(P); the anti-LAG-3 antibodies: LAG-3 mAb A IgG4 (P) and LAG-3 mAb 1(1.4) IgG4(P); and the combination of: PD-1 mAb A IgG4 (P) and LAG-3 mAb A IgG4 (P), and hPD-1 mAb 7(1.2) IgG4(P) and LAG-3 mAb 1(1.4) IgG4(P), to enhance IL-2 release through checkpoint inhibition was examined. In these assays the PD-1×LAG-3 bispecific molecules and antibodies were used at a total concentration of 3.125, 12.5, or 50 nM and the PBMCs were stimulated with the high 85 ng/mL concentration of SEB. For these studies, where a combination of antibodies is used each antibody is provided at one half of the total concentration (i.e., 1.563, 6.25, or 25 nM). FIG. 19 shows the IL-2 secretion profile from SEB-stimulated PBMCs from a representative donor (D: 54024).

In additional studies the PD-1×LAG-3 bispecific molecules: DART B, and DART I; the anti-PD-1 antibodies: PD-1 mAb A IgG4 (P), and hPD-1 mAb 7(1.2) IgG4(P); the anti-LAG-3 antibodies: LAG-3 mAb A IgG4 (P), hLAG-3 mAb 1(1.4) IgG4(P), and hLAG-3 mAb 6(1.1) IgG4 (P); and the combinations of: PD-1 mAb A IgG4 (P) and LAG-3 mAb A IgG4 (P), hPD-1 mAb 7(1.2) IgG4(P) and hLAG-3 mAb 1(1.4) IgG4(P), and hPD-1 mAb 7(1.2) IgG4(P) and hLAG-3 mAb 6(1.1) IgG4 (P) to enhance cytokine release through checkpoint inhibition was examined. In these assays the PD-1×LAG-3 bispecific molecules and antibodies were used at a concentration of 0.0061, 0.024, 0.09, 0.39, 1.56, 6.25 or 25 nM and the PBMCs were stimulated with 0.5 ng/mL of SEB. For these studies, where a combination of antibodies is used each antibody is provided at the indicated concentration and thus the total antibody concentration is twice the concentration used for each antibody (i.e., 0.0122, 0.048, 0.18, 0.78, 3.12, 12.5 or 50 nM). FIG. 20 shows the IFNγ secretion profiles from SEB-stimulated PBMCs from a representative donor D: 56041).

The ability of the PD-1×LAG-3 bispecific molecule DART I; the combination of the anti-PD-1 antibody PD-1 mAb A IgG4 and the anti-LAG-3 antibody LAG-3 mAb A IgG4 (P); and a negative control antibody to enhance antigen-specific T cell responses was examined using a Tetanus-Toxoid Recall Assay. In particular, the response of antigen-specific enhanced secretion of cytokines was measured using tetanus toxoid as a recall antigen in coculture assay system. Briefly, CD4 memory T cells ($0.5-1.0\times10^5$ cells/well) were isolated using negative selection isolation kits (Miltenyi Biotec, San Diego, Calif. and Invitrogen, Carlsbad, Calif.) from human peripheral blood and cultured for 5-7 days with irradiated monocytes ($0.01-0.05\times10^5$ cells/well, 3500 rads) from the same donor in the presence or absence of 5 µg/mL the recall antigen tetanus toxoid (TTd) and dilution (starting at 25 nM) of DART I, PD-1 mAb A IgG4+LAG-3 mAb A IgG4(P), or an isotype control. In parallel plates, proliferation was measured through the incorporation of tritiated thymidine and IL-2 and IFNγ was measured using ELISA (R&D systems, Minneapolis, Minn.) at days 5-7. FIGS. 21A-D show the IFNγ (FIG. 21A, 21C) and IL-2 (FIG. 21B, 21D) secretion profiles at day 7, from two representative donors (D50702 and D54267).

The results of these studies demonstrate that the PD-1×LAG-3 bispecific molecules dramatically enhanced IFNγ (FIGS. 16A-16B, 17A-17B, 18A-18B, 20), and IL-2 (FIG. 19) production from SEB-stimulated PBMCs upon restimulation. In addition, the PD-1×LAG-3 bispecific molecules dramatically enhanced IFNγ production (FIGS. 21A and 21C) from CD4 memory T cells stimulated with tetanus toxoid. In particular, the tetravalent PD-1×LAG-3 bispecific molecules provided a greater enhancement than the combination of anti-PD-1 antibodies with anti-LAG-3 antibodies.

Example 9

Pharmacokinetics of PD-1×LAG-3 Bispecific Molecules

The pharmacokinetics of a representative PD-1×LAG-3 bispecific molecule, DART I and a representative anti-PD-1 antibody, PD-1 mAb A were examined in Cynomolgus monkeys. Briefly, two cynomolgus monkeys (one male and one female) were infused with a single dose of DART I (5 mg/kg) or PD-1 mAb A (10 mg/kg) and the serum concentration of the molecules was monitored over time using a sandwich ELISA assay. Briefly, maxisorb 96-well assay plates were coated with soluble human PD-1 (shPD-1), blocked with bovine serum albumin, washed and incubated with calibration standards, quality control standards and diluted serum samples. The amount of captured DART I and PD-1 mAb A was assessed by the sequential addition of a goat anti-human IgG Fc-biotin secondary and streptavidin-horseradish peroxidase (SA-HRP). HRP activity was detected using TMB substrate. All samples were analyzed a microplate reader (SpectraMax M2e, Molecular Device, Sunnyvale, Calif.) and the OD signals produced by the standard calibrators were used in the four-parameter logistic model using SoftMax Pro software (Version 5.4, Molecular Devices). The concentrations of PD-1 mAb A, or DART I were determined from the interpolation of the samples' OD signal data with the equation describing the standard curve. The lower limit of quantitation (LLOQ) for this assay was estimated at 9.775 ng/mL.

FIG. 22 shows the serum concentration over time, the lines represents the mean of both male (filled symbols) and female (open symbols) monkeys infused with DART I (solid line, triangles) or PD-1 mAb A (dashed line, circles). These data demonstrate that the pharmacokinetics of a PD-1×LAG-3 bispecific molecule are comparable to those of an anti-PD-1 antibody in cynomolgus monkeys.

Example 10

Toxicology Study of PD-1 Antibodies and PD-1×LAG-3 Bispecific Molecules

The safety profile of a representative a representative anti-PD1 antibody, hPD-1 mAb 7 (1.2) IgG4 (P), and a representative PD1×LAG3 bispecific molecule, DART I, was assessed in a non-GLP (Good Laboratory Practice) dosing study in cynomolgus monkeys.

In this study the potential toxicity and toxicokinetics of the anti-PD-1 antibody (hPD-1 mAb 7 (1.2) IgG4 (P)), when administered by multiple intravenous infusions was evaluated. In addition, the potential toxicity and pharmacokinetics of the PD-1×LAG-3 DART molecule (DART I), when administered by single intravenous infusion was also evaluated. The study design is presented in Table 20.

TABLE 20

| Group No. | Test Material | Dose Level (mg/kg) | Dosing Days | Dose Volume (mL) | Dose (mg/mL) | No. of Animals Males | No. of Animals Females |
|---|---|---|---|---|---|---|---|
| 1 | Control | 0 | 1, 8, 15 | 5 | 0 | 1[a] | 1[a] |
| 2A | hPD-1 mAb 7 (1.2) IgG4 (P) | 1 | 1, 8, 15 | 5 | 0.2 | 1[a] | 1[a] |
| 2B | hPD-1 mAb 7 (1.2) IgG4 (P) | 1 | 1, 8, 15 | 5 | 0.2 | 1[b] | 1[b] |
| 3A | hPD-1 mAb 7 (1.2) IgG4 (P) | 100 | 1, 8, 15 | 5 | 20 | 1[a] | 1[a] |
| 3B | hPD-1 mAb 7 (1.2) IgG4 (P) | 100 | 1, 8, 15 | 5 | 20 | 1[b] | 1[b] |
| 4 | DART I | 5 | 1 | 5 | 1 | 1[c] | 1[c] |

[a]Groups 1, 2A, and 3A were dosed beginning on Day 1 and necropsied 72 hours following their last (third) dose on Day 18.
[b]Groups 2B and 3B were dosed beginning on Day 1 and necropsied 7 days following their last (third) dose on Day 22.
[c]Group 4 was dosed beginning on Day 1 and followed for 28 days post single dose administration (to Day 29); animals were then returned to colony.

The following parameters and endpoints were evaluated in this study: clinical signs, body weights, food consumption, body temperature, clinical pathology parameters (hematology, coagulation, and clinical chemistry), bioanalysis and toxicokinetic parameters, anti-drug antibody analysis, flow cytometry, cytokine, gross necropsy findings, organ weights, and histopathologic examinations.

All animals survived until scheduled euthanasia on Day 18 or 22 or release from study on Day 29. For hPD-1 mAb 7 (1.2) IgG4 (P) there were no test article-related changes in clinical signs, food consumption, body weights, body temperature, hematology, coagulation, or clinical chemistry parameters, or gross necropsy findings. At Days 18 and 22, increases in spleen weight and a dose-dependent mild to moderate lymphohistiocytic infiltrate of the red pulp were evident in animals receiving hPD-1 mAb 7 (1.2) IgG4 (P) at 1 or 100 mg/kg. As compared to surrounding lymphocytes, the lymphohistiocytic cells had pale cytoplasm and irregular nuclei. Rare mitotic figures were evident. The infiltrate was a microscopic correlate for the increased spleen weight.

The serum concentration-time profiles for animals given hPD-1 mAb 7 (1.2) IgG4 (P) show the profile expected for an antibody in this species, with a few exceptions. The slopes of the curves after the third dose dropped more sharply than after the first dose for two animals in the 1 mg/kg dose group and two animals in the 100 mg/kg dose group, indicating the possible emergence of anti-drug antibodies (ADA) at the later cycles. Analysis showed that 2/4 animals developed ADA in the 1 mg/kg group and 1/4 animals developed ADA in the 100 mg/kg group.

In conclusion, administration of hPD-1 mAb 7 (1.2) IgG4 (P) by intravenous infusion once weekly for 3 weeks (Days 1, 8, and 15) was well-tolerated in cynomolgus monkeys at levels of 1 and 100 mg/kg. A dose-dependent mild to moderate lymphohistiocytic cellular infiltrate of the splenic red pulp was present at 1 and 100 mg/kg hPD-1 mAb 7 (1.2) IgG4 (P).

For DART I, there were no test article-related changes in clinical signs, food consumption, body weights, body temperature, hematology, or coagulation parameters. DART I-related changes in clinical chemistry parameters included non-adverse, transient elevations in aspartate aminotransferase (AST) and lactate dehydrogenase (LDH) on Day 2. The average AST change was 3.2× vehicle-treated control animals and 7.8× prestudy levels, with levels above the control reference range2. The average LDH change was 2.5× vehicle-treated control animals and 6.9× prestudy levels. Both parameters returned to near baseline levels on Day 8. In conclusion, single administration of DART-I by intravenous infusion was well tolerated in cynomolgus monkeys at a level of 5 mg/kg.

Example 11

Single Dose PK Study with anti-PD-1 Antibodies

A single-dose PK study with selected toxicological endpoints was conducted in cynomolgus monkeys. In this study, hPD-1 mAb 7 (1.2) IgG4 (P) was compared to two other anti-PD1 IgG4 (P), κ mAbs: PD-1 mAb A IgG4 (P) and PD-1 mAb B IgG4 (P). Each antibody was administered at 10 mg/kg by 1-hour intravenous infusion to 2 monkeys (1M, 1F) and animals were monitored for 65 days.

There were no test article-related clinical signs, changes in body weight, food consumption, cytokine, or immunophenotyping associated with administration of hPD-1 mAb 7 (1.2) IgG4 (P) or PD-1 mAb A IgG4 (P). Data were similar for PD-1 mAb B IgG4 (P) with the exception that elevations in IL-5 were observed following PD-1 mAb B IgG4 (P) administration.

Anti-PD-1 antibody binding to PD-1 on the surface of T cells was determined by flow cytometry using a competition method in which the mean fluorescence intensity (MFI) of fluorescently labeled hPD-1 mAb 7 (1.2) IgG4 (P) binding to T cells in the absence (PBS control) or presence of excess competitor (unlabeled hPD-1 mAb 7 (1.2) IgG4 (P)) for the full time course of blood samples collected from the cynomolgus monkeys treated with hPD-1 mAb 7 (1.2) IgG4 (P), PD-1 mAb A IgG4 (P) or PD-1 mAb B IgG4 (P). As shown in FIGS. 23A-23C, hPD-1 mAb 7 (1.2) IgG4 (P) and PD-1 mAb B IgG4 (P) demonstrated prolonged binding to PD-1 on the surface of CD4+ and CD8+ T cells (PD-1 binding maintained at ≥80% for 28 days or more) (FIGS. 23A and 23C, respectively) compared to PD-1 mAb A IgG4 (P) (PD-1 binding maintained at ≥80% for 21 days or less) (FIG. 23B). For each of the anti-PD-1 antibodies, the T-cell PD-1 binding data correlated with their serum concentrations.

Example 12

Repeat Dose Toxicology Studies

To assess the safety, toxicokinetic, and pharmacodynamic profile of the therapeutic molecules of the present invention, an exemplary molecule (hPD-1 mAb 7 (1.2) IgG4 (P)) was administered to cynomolgus monkeys and a GLP (Good Laboratory Practice) dosing study was performed. In this study, four groups of animals (10 per group, 5 males, and 5 females) were treated with hPD-1 mAb 7 (1.2) IgG4 (P) or a control article, once weekly by infusion at 3 dose levels. The animals were evaluated for any potential toxicity during a 4-week drug dosing period followed by monitoring during an additional 10-week drug-free period. The experimental design of this study is presented in Table 21. Animals were dosed once weekly via a one-hour intravenous infusion using a calibrated infusion pump on Study Days 1, 8, 15, and 22. One male and one female from each group were sacrificed on Day 25, the remaining animals were sacrificed on Study Day 95. The effects of hPD-1 mAb 7 (1.2) IgG4 (P) administration on the leukocyte subpopulations in circulation, including the occupancy of PD-1 receptors on T-lymphocytes were assessed. In addition, the anti-drug antibody (ADA) profiles were determined.

TABLE 21

| Group No. | Test Material[a] | Dose Level (mg/kg) | Dose Volume (mL/kg) | Dose (mg/mL) | Main Study M | Main Study F | Recovery Study M | Recovery Study F |
|---|---|---|---|---|---|---|---|---|
| 1 | Control | 0 | 5.88 | 0 | 3 | 3 | 2 | 2 |
| 2 | hPD-1 mAb 7 (1.2) IgG4 (P) | 10 | 5.88 | 1.7 | 3 | 3 | 2 | 2 |
| 3 | hPD-1 mAb 7 (1.2) IgG4 (P) | 40 | 5.88 | 6.8 | 3 | 3 | 2 | 2 |
| 4 | hPD-1 mAb 7 (1.2) IgG4 (P) | 150 | 5.88 | 25.5 | 3 | 3 | 2 | 2 |

No. of Animals[b]

[a]Control and hPD-1 mAb 7 (1.2) IgG4 (P) were administered weekly via intravenous infusion
[b]Six monkeys (3M/3F) per group were necropsied on Day 25, while the remaining recovery group monkeys (2M/2F) were necropsied on Day 95

Once weekly intravenous (IV) infusions of hPD-1 mAb 7 (1.2) IgG4 (P) at 0, 10, 40, and 150 mg/kg in cynomolgus monkeys were well tolerated and all animals survived to their scheduled euthanasia on Days 25 or 95. There were no hPD-1 mAb 7 (1.2) IgG4 (P)-related changes in clinical signs, food consumption, body weights, physical, ophthalmic, and neurological examinations, electrocardiology, body temperatures, respiratory rates, blood pressure and heart rates, coagulation, clinical chemistry, and urinalysis parameters, organ weights, or gross necropsy findings.

hPD-1 mAb 7 (1.2) IgG4 (P)-related changes in hematology parameters included transient decreases in lymphocyte titers. Lymphocyte titers were moderately decreased compared to pre-study (Day 1 predose) on Day 2 (23 hours post infusion) in males and females at ≥10 mg/kg, statistically significant for males at 10 and 40 mg/kg and females at 40 and 150 mg/kg compared to controls. Lymphocyte titers returned to near prestudy levels on Day 8 predose but were mildly decreased for some individual males and females at all dose levels (0.47× to 0.68× prestudy) on Day 9 (23 hours post infusion). Lymphocyte titers increased prior to dosing on Days 15 and 22, but decreased for some individual males and females (0.36× to 0.54× prestudy) on Days 16 and 23 (23 hours post infusion).

A dose-independent, transient decline in circulating immune cell populations, including total leukocytes, T cells, B cells, and NK cells, was observed 23 hours following the end of infusion in hPD-1 mAb 7 (1.2) IgG4 (P)-treated animals compared with the control group. The largest magnitude in change was observed following the first dose administration on Day 1; smaller magnitude changes were transiently observed following subsequent doses on Days 8, 15, or 22. Immune cell populations generally recovered to at or near baseline values by 72 hours post-EOI and throughout the recovery phase. No changes in circulating monocytes were observed in hPD-1 mAb 7 (1.2) IgG4 (P)-treated animals compared with the control group.

Maximal hPD-1 mAb 7 (1.2) IgG4 (P) binding to PD-1+/CD4+ and PD-1+/CD8+ cells was observed during the hPD-1 mAb 7 (1.2) IgG4 (P) treatment phase of the study at all doses tested (10, 40 or 150 mg/kg). In recovery, animals that did not develop anti-drug antibody (ADA) responses, serum hPD-1 mAb 7 (1.2) IgG4 (P) concentrations remained above 29 µg/mL and maximal hPD-1 mAb 7 (1.2) IgG4 (P) binding to PD-1+/CD4+ and PD-1+/CD8+ T cells was maintained during the entire 10-week recovery period. In these animals, there was no evidence of PD-1 modulation on the T cells. In recovery animals that developed ADA responses, the frequency of MGD012-bound PD-1+ T cells declined to baseline levels. The declines from maximal hPD-1 mAb 7 (1.2) IgG4 (P) binding on PD-1+/CD4+ and PD-1+/CD8+ cells of ADA-positive animals generally occurred when the apparent serum hPD-1 mAb 7 (1.2) IgG4 (P) concentrations dropped below approximately 25 µg/mL. However, it is not known if this apparent threshold relationship applies to ADA-negative animals, since the presence of ADA in ADA-positive animals may contribute to blocking the binding of PD-1 antibodies to PD-1.

There were minimal sex-associated differences in the pharmacokinetic responses of hPD-1 mAb 7 (1.2) IgG4 (P), which were linear across the dose range evaluated (10 to 150 mg/kg). For hPD-1 mAb 7 (1.2) IgG4 (P) at 10, 40, and 150 mg/kg, the gender combined mean $C_{max}$ was 240 µg/mL (0.240 mg/mL), 1078 µg/mL (1.08 mg/mL), and 3938 µg/mL (3.94 mg/mL) and the AUC was 47310 h·µg/mL (47.3 h·mg/mL), 205723 h·µg/mL (206 h·mg/mL), and 745681 h·µg/mL (746 h·mg/mL), respectively. Mean clearance by non-compartmental analysis (NCA) of the first cycle of hPD-1 mAb 7 (1.2) IgG4 (P) before the emergence of ADA, was 0.21 mL/h/kg, substantially lower than the glomerular filtration rate of cynomolgus monkeys, as would be expected for a large molecular weight protein. Mean steady-state volume of distribution by NCA of the first cycle of hPD-1 mAb 7 (1.2) IgG4 (P) was 68 mL/kg, approximately 1.5 times the serum volume, but less than the extracellular water space. This suggests that hPD-1 mAb 7 (1.2) IgG4 (P) extravasates from the vascular compartment into the tissue extracellular space, but that not all of the extracellular space was accessible to this molecule. The average value of the mean residence time (MRT) by NCA of the first cycle of hPD-1 mAb 7 (1.2) IgG4 (P) was 335 hours or approximately 14 days. Emergence of ADA decreased the concentrations of hPD-1 mAb 7 (1.2) IgG4 (P) in Cycles 2 to 4. Evidence of decreased hPD-1 mAb 7 (1.2) IgG4 (P) serum concentrations following repeated doses of hPD-1 mAb 7 (1.2) IgG4 (P) were observed in 7/10, 4/10, and 3/10 animals in the 10, 40, and 150 mg/kg dose groups, respectively. The presence of ADA against hPD-1 mAb 7 (1.2) IgG4 (P) was confirmed in 4, 2, and 1 of these animals in the 10, 40, and 150 mg/kg dose groups, respectively; all the animals in which ADA was not confirmed were in the terminal necropsy group during which hPD-1 mAb 7 (1.2) IgG4 (P) serum concentrations likely interfered with the ability to detect ADA. Accordingly, in subsequent TK analysis, when a trough concentration was lower than the preceding trough concentration, data from this time forward were censored. From two-compartment modeling of data across all cycles for the 3 dose groups, excluding points that were affected by ADA, mean values for the primary TK parameters for a 2-compartment model were 0.22 mL/h/kg for clearance, 38.5 mL/kg for initial volume of distribution ($V_1$), and 33.8 mL/kg for $V_2$, which yielded a mean steady-state volume of distribution ($V_{ss}$) of 72.3 mL/kg, and an MRT of 329 hours. These values were consistent with parameters obtained from NCA of the first dose. In the absence of ADA, simulations predict that with weekly dosing, steady state would be achieved in cynomolgus monkeys after the 5th dose and the accumulation index would be 2.4.

On Day 25, hPD-1 mAb 7 (1.2) IgG4 (P)-related minimal multifocal perivascular mononuclear cell infiltrates were present in the superficial dermis of the IV injection site in males at ≥40 mg/kg and in females at ≥10 mg/kg and were an expected reaction to repeated injection of a foreign protein (monoclonal antibody). On Day 95, there were no hPD-1 mAb 7 (1.2) IgG4 (P)-related microscopic changes noted, indicating recovery of the test article-related change present on Day 25.

In summary, the results of this study indicate that administration of hPD-1 mAb 7 (1.2) IgG4 (P) via intravenous infusion once weekly (Days 1, 8, 15, and 22) was clinically well tolerated in cynomolgus monkeys at levels of 10, 40, or 150 mg/kg. Effects observed were limited to transient decreases in circulating lymphocytes and minimal injection-site changes related to injection of a foreign protein. Based on these results, the no-observed-adverse-effect level (NO-AEL) was considered to be 150 mg/kg (gender combined mean $C_{max}$ of 3.94 mg/mL and AUC of 746 h·mg/mL).

All publications and patents mentioned in this specification are herein incorporated by reference to the same extent as if each individual publication or patent application was specifically and individually indicated to be incorporated by reference in its entirety. While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. A bispecific binding molecule capable of binding to PD-1 and LAG-3, wherein the bispecific binding molecule comprises:
   (I) a PD-1-binding domain comprising a Variable Heavy Chain Domain and a Variable Light Chain Domain, wherein the Variable Heavy Chain Domain of the PD-1-binding domain comprises a $CDR_H1$ Domain, a $CDR_H2$ Domain and a $CDR_H3$ Domain, and the Variable Light Chain Domain of the PD-1-binding domain comprises a $CDR_L1$ Domain, a $CDR_L2$ Domain, and a $CDR_L3$ Domain, wherein:
      (A) the $CDR_H1$ Domain, $CDR_H2$ Domain, and $CDR_H3$ Domain of the PD-1-binding domain are the Heavy Chain CDRs of hPD-1 mAb 7(1.2), and have the amino acid sequences SEQ ID NO:139, SEQ ID NO:140, and SEQ ID NO:141, respectively; and
      (B) the $CDR_L1$ Domain, $CDR_L2$ Domain, and $CDR_L3$ Domain of the PD-1-binding domain are the Light Chain CDRs of hPD-1 mAb 7(1.2), and, respectively have the amino acid sequences SEQ ID NO:157, SEQ ID NO:145, and SEQ ID NO:146, respectively; and
   (II) a LAG-3 binding domain comprising a Variable Heavy Chain Domain and a Variable Light Chain Domain, wherein the Variable Heavy Chain Domain of the LAG-3-binding domain comprises a $CDR_H1$ Domain, a $CDR_H2$ Domain, and a $CDR_H3$ Domain, and the Variable Light Chain Domain of the LAG-3-binding domain comprises a $CDR_L1$ Domain, a $CDR_L2$ Domain, and a $CDR_L3$ Domain.

2. The bispecific binding molecule of claim 1, wherein the Variable Heavy Chain Domain of the PD-1-binding domain comprises the amino acid sequence set forth in SEQ ID NO:147.

3. The bispecific binding molecule of claim 1, wherein the Light Chain Variable Domain of the PD-1-binding domain comprises the amino acid sequence set forth in SEQ ID NO:153.

4. The bispecific binding molecule of claim 1, wherein the Heavy Chain Variable Domain of the PD-1-binding domain comprises the amino acid sequence set forth in SEQ ID NO:147, and the Light Chain Variable Domain of the PD-1-binding domain comprises the amino acid sequence set forth in SEQ ID NO:153.

5. The bispecific binding molecule of claim 1, wherein:
   (A) the $CDR_H1$ Domain, $CDR_H2$ Domain, and $CDR_H3$ Domain of the Variable Heavy Chain of the LAG-3-binding domain are the Heavy Chain CDRs of hLAG-3 mAb 6 VH1, and have the amino acid sequences SEQ ID NO:57, SEQ ID NO:58, and SEQ ID NO:59, respectively; and
   (B) the $CDR_L1$ Domain, $CDR_L2$ Domain, and $CDR_L3$ Domain of the Variable Light Chain of the LAG-3-binding domain are the Light Chain CDRs of hLAG-3 mAb 6 VL1, having the amino acid sequences SEQ ID NO:298, SEQ ID NO:62, and SEQ ID NO:63, respectively.

6. The bispecific binding molecule of claim 5, wherein the Variable Heavy Chain Domain of the LAG-3-binding domain comprises the amino acid sequence set forth in SEQ ID NO:294.

7. The bispecific binding molecule of claim 5, wherein the Variable Light Chain Domain of the LAG-3-binding domain comprises the amino acid sequence set forth in SEQ ID NO:296.

8. The bispecific binding molecule of claim 5, wherein the Variable Heavy Chain Domain of the LAG-3-binding domain comprises the amino acid sequence set forth in SEQ ID NO:294, and the Variable Light Chain Domain of the LAG-3-binding domain comprises the amino acid sequence set forth in SEQ ID NO:296.

9. The bispecific binding molecule of claim 1, wherein the molecule is:
(A) a diabody, the diabody being a covalently bonded complex that comprises four or five polypeptide chains; or
(B) a bispecific antibody.

10. The bispecific binding molecule of claim 5, wherein the molecule is:
(A) a diabody, the diabody being a covalently bonded complex that comprises four or five polypeptide chains; or
(B) a bispecific antibody.

11. The bispecific binding molecule of claim 1, wherein the molecule comprises an Fc Region that is of the IgG1, IgG2, IgG3, or IgG4 isotype; wherein when the Fc Region is of the IgG4 isotype, the bispecific binding molecule comprises a Hinge Domain of the IgG4 isotype that comprises a stabilizing mutation.

12. The bispecific binding molecule of claim 5, wherein the molecule comprises an Fc Region that is of the IgG1, IgG2, IgG3, or IgG4 isotype; wherein when the Fc Region is of the IgG4 isotype, the bispecific binding molecule comprises a Hinge Domain of the IgG4 isotype that comprises a stabilizing mutation.

13. The bispecific binding molecule of claim 1, wherein the molecule comprises a variant Fc Region that comprises:
(a) one or more amino acid modifications that reduces the affinity of the variant Fc Region for an FcγR, wherein the one or more modifications that reduces the affinity of the variant Fc Region for an FcγR comprise the substitution of L234A; L235A; or L234A and L235A, wherein the numbering is that of the EU index as in Kabat; and/or
(b) one or more amino acid modifications that enhances the serum half-life of the variant Fc Region, wherein the one or more modifications that enhances the serum half-life of the variant Fc Region comprise the substitution of M252Y; M252Y and S254T; M252Y and T256E; M252Y, S254T and T256E; or K288D and H435K, wherein the numbering is that of the EU index as in Kabat.

14. The bispecific binding molecule of claim 5, wherein the molecule comprises a variant Fc Region that comprises:
(a) one or more amino acid modifications that reduces the affinity of the variant Fc Region for an FcγR, wherein the one or more modifications that reduces the affinity of the variant Fc Region for an FcγR comprise the substitution of L234A; L235A; or L234A and L235A, wherein the numbering is that of the EU index as in Kabat; and/or
(b) one or more amino acid modifications that enhances the serum half-life of the variant Fc Region, wherein the one or more modifications that enhances the serum half-life of the variant Fc Region comprise the substitution of M252Y; M252Y and S254T; M252Y and T256E; M252Y, S254T and T256E; or K288D and H435K, wherein the numbering is that of the EU index as in Kabat.

15. The bispecific binding molecule of claim 14, wherein the molecule comprises a variant IgG1 Fc Region that comprises the substitution of L234A and L235A, and wherein the variant optionally further comprises the substitution of M252Y, S254T and T256E, wherein the numbering is that of the EU index as in Kabat.

16. The bispecific binding molecule of claim 15, wherein the molecule comprises a variant IgG1 Fc Region that comprises the substitution of L234A and L235A, and wherein the variant optionally further comprises the substitution of M252Y, S254T and T256E, wherein the numbering is that of the EU index as in Kabat.

17. The bispecific binding molecule of claim 14, wherein the molecule comprises:
(A) a variant IgG4 Fc Region that comprises the substitution of M252Y, S254T and T256E; and
(B) a Hinge Domain of the IgG4 isotype that comprises the substitution S228P, wherein the numbering is that of the EU index as in Kabat.

18. The bispecific binding molecule of claim 15, wherein the molecule comprises:
(A) a variant IgG4 Fc Region that comprises the substitution of M252Y, S254T and T256E; and
(B) a Hinge Domain of the IgG4 isotype that comprises the substitution S228P, wherein the numbering is that of the EU index as in Kabat.

19. The bispecific binding molecule of claim 1, wherein the bispecific binding molecule is a diabody comprising SEQ ID NO:290 and SEQ ID NO:291.

20. A bispecific diabody capable of binding to PD-1 and LAG-3, wherein the bispecific diabody is a covalently bonded complex that comprises four polypeptide chains, wherein two of the polypeptide chains comprise SEQ ID NO:290, and two of the polypeptide chains comprise SEQ ID NO:291.

21. A pharmaceutical composition comprising the bispecific binding molecule of claim 1 and a pharmaceutically acceptable carrier.

22. A pharmaceutical composition comprising the bispecific binding molecule of claim 5 and a pharmaceutically acceptable carrier.

23. A pharmaceutical composition comprising the bispecific binding molecule of claim 20 and a pharmaceutically acceptable carrier.

* * * * *

SEQUENCE LISTING

<160> NUMBER OF SEQ ID NOS: 298

<210> SEQ ID NO 1
<211> LENGTH: 217
<212> TYPE: PRT
<213> ORGANISM: Homo sapiens
<220> FEATURE:
<221> NAME/KEY: MISC_FEATURE

```
<222> LOCATION: (1)..(217)
<223> OTHER INFORMATION: Human IgG1 CH2-CH3 Domain
<220> FEATURE:
<221> NAME/KEY: MISC_FEATURE
<222> LOCATION: (217)..(217)
<223> OTHER INFORMATION: Xaa is a lysine (K) or is absent

<400> SEQUENCE: 1

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Xaa
    210                 215

<210> SEQ ID NO 2
<211> LENGTH: 216
<212> TYPE: PRT
<213> ORGANISM: Homo sapiens
<220> FEATURE:
<221> NAME/KEY: MISC_FEATURE
<222> LOCATION: (1)..(216)
<223> OTHER INFORMATION: Human IgG2 CH2-CH3 Domain
<220> FEATURE:
<221> NAME/KEY: MISC_FEATURE
<222> LOCATION: (216)..(216)
<223> OTHER INFORMATION: Xaa is a lysine (K) or is absent

<400> SEQUENCE: 2

Ala Pro Pro Val Ala Gly Pro Ser Val Phe Leu Phe Pro Pro Lys Pro
1               5                   10                  15

Lys Asp Thr Leu Met Ile Ser Arg Thr Pro Glu Val Thr Cys Val Val
            20                  25                  30

Val Asp Val Ser His Glu Asp Pro Glu Val Gln Phe Asn Trp Tyr Val
        35                  40                  45

Asp Gly Val Glu Val His Asn Ala Lys Thr Lys Pro Arg Glu Glu Gln
    50                  55                  60
```

```
Phe Asn Ser Thr Phe Arg Val Val Ser Val Leu Thr Val Val His Gln
 65                  70                  75                  80

Asp Trp Leu Asn Gly Lys Glu Tyr Lys Cys Lys Val Ser Asn Lys Gly
                 85                  90                  95

Leu Pro Ala Pro Ile Glu Lys Thr Ile Ser Lys Thr Lys Gly Gln Pro
            100                 105                 110

Arg Glu Pro Gln Val Tyr Thr Leu Pro Pro Ser Arg Glu Glu Met Thr
        115                 120                 125

Lys Asn Gln Val Ser Leu Thr Cys Leu Val Lys Gly Phe Tyr Pro Ser
    130                 135                 140

Asp Ile Ser Val Glu Trp Glu Ser Asn Gly Gln Pro Glu Asn Asn Tyr
145                 150                 155                 160

Lys Thr Thr Pro Pro Met Leu Asp Ser Asp Gly Ser Phe Phe Leu Tyr
                165                 170                 175

Ser Lys Leu Thr Val Asp Lys Ser Arg Trp Gln Gln Gly Asn Val Phe
                180                 185                 190

Ser Cys Ser Val Met His Glu Ala Leu His Asn His Tyr Thr Gln Lys
                195                 200                 205

Ser Leu Ser Leu Ser Pro Gly Xaa
    210                 215

<210> SEQ ID NO 3
<211> LENGTH: 217
<212> TYPE: PRT
<213> ORGANISM: Homo sapiens
<220> FEATURE:
<221> NAME/KEY: MISC_FEATURE
<222> LOCATION: (1)..(217)
<223> OTHER INFORMATION: Human IgG3 CH2-CH3 Domain
<220> FEATURE:
<221> NAME/KEY: MISC_FEATURE
<222> LOCATION: (217)..(217)
<223> OTHER INFORMATION: Xaa is a lysine (K) or is absent

<400> SEQUENCE: 3

Ala Pro Glu Leu Leu Gly Gly Pro Ser Val Phe Leu Phe Pro Pro Lys
  1               5                  10                  15

Pro Lys Asp Thr Leu Met Ile Ser Arg Thr Pro Glu Val Thr Cys Val
             20                  25                  30

Val Val Asp Val Ser His Glu Asp Pro Glu Val Gln Phe Lys Trp Tyr
         35                  40                  45

Val Asp Gly Val Glu Val His Asn Ala Lys Thr Lys Pro Arg Glu Glu
     50                  55                  60

Gln Tyr Asn Ser Thr Phe Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Thr Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Ser Gly Gln Pro Glu Asn Asn
145                 150                 155                 160

Tyr Asn Thr Thr Pro Pro Met Leu Asp Ser Asp Gly Ser Phe Phe Leu
                165                 170                 175
```

```
Tyr Ser Lys Leu Thr Val Asp Lys Ser Arg Trp Gln Gln Gly Asn Ile
            180                 185                 190

Phe Ser Cys Ser Val Met His Glu Ala Leu His Asn Arg Phe Thr Gln
        195                 200                 205

Lys Ser Leu Ser Leu Ser Pro Gly Xaa
        210                 215

<210> SEQ ID NO 4
<211> LENGTH: 217
<212> TYPE: PRT
<213> ORGANISM: Homo sapiens
<220> FEATURE:
<221> NAME/KEY: MISC_FEATURE
<222> LOCATION: (1)..(217)
<223> OTHER INFORMATION: Human IgG4 CH2-CH3 Domain
<220> FEATURE:
<221> NAME/KEY: MISC_FEATURE
<222> LOCATION: (217)..(217)
<223> OTHER INFORMATION: Xaa is a lysine (K) or is absent

<400> SEQUENCE: 4

Ala Pro Glu Phe Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys Gly Gln
            100                 105                 110

Pro Arg Glu Pro Gln Val Tyr Thr Leu Pro Pro Ser Gln Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Arg Leu Thr Val Asp Lys Ser Arg Trp Gln Glu Gly Asn Val
            180                 185                 190

Phe Ser Cys Ser Val Met His Glu Ala Leu His Asn His Tyr Thr Gln
        195                 200                 205

Lys Ser Leu Ser Leu Ser Leu Gly Xaa
        210                 215

<210> SEQ ID NO 5
<211> LENGTH: 217
<212> TYPE: PRT
<213> ORGANISM: Artificial Sequence
<220> FEATURE:
<223> OTHER INFORMATION: Human IgG1 CH2-CH3 Domain Having L234A/L235A
      Substitutions
<220> FEATURE:
<221> NAME/KEY: MISC_FEATURE
<222> LOCATION: (217)..(217)
<223> OTHER INFORMATION: Xaa is a lysine (K) or is absent
```

<400> SEQUENCE: 5

```
Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Xaa
    210                 215
```

<210> SEQ ID NO 6
<211> LENGTH: 217
<212> TYPE: PRT
<213> ORGANISM: Artificial Sequence
<220> FEATURE:
<223> OTHER INFORMATION: "Knob-Bearing" Human IgG1 CH2-CH3 Domain
<220> FEATURE:
<221> NAME/KEY: MISC_FEATURE
<222> LOCATION: (217)..(217)
<223> OTHER INFORMATION: Xaa is a lysine (K) or is absent

<400> SEQUENCE: 6

```
Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110
```

```
Pro Arg Glu Pro Gln Val Tyr Thr Leu Pro Pro Ser Arg Glu Glu Met
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
            165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
            195                 200                 205

Lys Ser Leu Ser Leu Ser Pro Gly Xaa
    210                 215

<210> SEQ ID NO 7
<211> LENGTH: 217
<212> TYPE: PRT
<213> ORGANISM: Artificial Sequence
<220> FEATURE:
<223> OTHER INFORMATION: "Hole-Bearing" Human IgG1 CH2-CH3 Domain
<220> FEATURE:
<221> NAME/KEY: MISC_FEATURE
<222> LOCATION: (217)..(217)
<223> OTHER INFORMATION: Xaa is a lysine (K) or is absent

<400> SEQUENCE: 7

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
            85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Ser Cys Ala Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
            165                 170                 175

Val Ser Lys Leu Thr Val Asp Lys Ser Arg Trp Gln Gln Gly Asn Val
            180                 185                 190

Phe Ser Cys Ser Val Met His Glu Ala Leu His Asn Arg Tyr Thr Gln
            195                 200                 205

Lys Ser Leu Ser Leu Ser Pro Gly Xaa
    210                 215
```

```
<210> SEQ ID NO 8
<211> LENGTH: 107
<212> TYPE: PRT
<213> ORGANISM: Homo sapiens
<220> FEATURE:
<221> NAME/KEY: MISC_FEATURE
<222> LOCATION: (1)..(107)
<223> OTHER INFORMATION: Human IgG CL Kappa Domain

<400> SEQUENCE: 8

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 9
<211> LENGTH: 104
<212> TYPE: PRT
<213> ORGANISM: Homo sapiens
<220> FEATURE:
<221> NAME/KEY: MISC_FEATURE
<222> LOCATION: (1)..(104)
<223> OTHER INFORMATION: Human IgG CL Lambda Domain

<400> SEQUENCE: 9

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Pro Ser Lys Gln Ser Asn Asn Lys Tyr
    50                  55                  60

Ala Ala Ser Ser Tyr Leu Ser Leu Thr Pro Glu Gln Trp Lys Ser His
65                  70                  75                  80

Arg Ser Tyr Ser Cys Gln Val Thr His Glu Gly Ser Thr Val Glu Lys
                85                  90                  95

Thr Val Ala Pro Thr Glu Cys Ser
            100

<210> SEQ ID NO 10
<211> LENGTH: 98
<212> TYPE: PRT
<213> ORGANISM: Homo sapiens
<220> FEATURE:
<221> NAME/KEY: MISC_FEATURE
<222> LOCATION: (1)..(98)
<223> OTHER INFORMATION: Human IgG1 CH1 Domain

<400> SEQUENCE: 10

Ala Ser Thr Lys Gly Pro Ser Val Phe Pro Leu Ala Pro Ser Ser Lys
1               5                   10                  15
```

```
Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val

<210> SEQ ID NO 11
<211> LENGTH: 12
<212> TYPE: PRT
<213> ORGANISM: Homo sapiens
<220> FEATURE:
<221> NAME/KEY: MISC_FEATURE
<222> LOCATION: (1)..(12)
<223> OTHER INFORMATION: Human IgG2 Hinge Region

<400> SEQUENCE: 11

Glu Arg Lys Cys Cys Val Glu Cys Pro Pro Cys Pro
1               5                   10

<210> SEQ ID NO 12
<211> LENGTH: 12
<212> TYPE: PRT
<213> ORGANISM: Homo sapiens
<220> FEATURE:
<221> NAME/KEY: MISC_FEATURE
<222> LOCATION: (1)..(12)
<223> OTHER INFORMATION: Human IgG4 Hinge Region

<400> SEQUENCE: 12

Glu Ser Lys Tyr Gly Pro Pro Cys Pro Ser Cys Pro
1               5                   10

<210> SEQ ID NO 13
<211> LENGTH: 12
<212> TYPE: PRT
<213> ORGANISM: Artificial Sequence
<220> FEATURE:
<223> OTHER INFORMATION: Stabilized IgG4 Hinge Region

<400> SEQUENCE: 13

Glu Ser Lys Tyr Gly Pro Pro Cys Pro Pro Cys Pro
1               5                   10

<210> SEQ ID NO 14
<211> LENGTH: 8
<212> TYPE: PRT
<213> ORGANISM: Artificial Sequence
<220> FEATURE:
<223> OTHER INFORMATION: Linker 1

<400> SEQUENCE: 14

Gly Gly Gly Ser Gly Gly Gly Gly
1               5

<210> SEQ ID NO 15
<211> LENGTH: 6
<212> TYPE: PRT
<213> ORGANISM: Artificial Sequence
```

```
<220> FEATURE:
<223> OTHER INFORMATION: Cysteine-containing Linker 2

<400> SEQUENCE: 15

Gly Gly Cys Gly Gly Gly
1               5

<210> SEQ ID NO 16
<211> LENGTH: 7
<212> TYPE: PRT
<213> ORGANISM: Artificial Sequence
<220> FEATURE:
<223> OTHER INFORMATION: Heterodimer-Promoting Domain

<400> SEQUENCE: 16

Gly Val Glu Pro Lys Ser Cys
1               5

<210> SEQ ID NO 17
<211> LENGTH: 6
<212> TYPE: PRT
<213> ORGANISM: Artificial Sequence
<220> FEATURE:
<223> OTHER INFORMATION: Heterodimer-Promoting Domain

<400> SEQUENCE: 17

Val Glu Pro Lys Ser Cys
1               5

<210> SEQ ID NO 18
<211> LENGTH: 6
<212> TYPE: PRT
<213> ORGANISM: Artificial Sequence
<220> FEATURE:
<223> OTHER INFORMATION: Heterodimer-Promoting Domain

<400> SEQUENCE: 18

Ala Glu Pro Lys Ser Cys
1               5

<210> SEQ ID NO 19
<211> LENGTH: 7
<212> TYPE: PRT
<213> ORGANISM: Artificial Sequence
<220> FEATURE:
<223> OTHER INFORMATION: Heterodimer-Promoting Domain

<400> SEQUENCE: 19

Gly Phe Asn Arg Gly Glu Cys
1               5

<210> SEQ ID NO 20
<211> LENGTH: 6
<212> TYPE: PRT
<213> ORGANISM: Artificial Sequence
<220> FEATURE:
<223> OTHER INFORMATION: Heterodimer-Promoting Domain

<400> SEQUENCE: 20

Phe Asn Arg Gly Glu Cys
1               5

<210> SEQ ID NO 21
<211> LENGTH: 28
<212> TYPE: PRT
<213> ORGANISM: Artificial Sequence
<220> FEATURE:
```

```
<223> OTHER INFORMATION: Heterodimer-Promoting (E-coil) Domain

<400> SEQUENCE: 21

Glu Val Ala Ala Leu Glu Lys Glu Val Ala Ala Leu Glu Lys Glu Val
1               5                   10                  15

Ala Ala Leu Glu Lys Glu Val Ala Ala Leu Glu Lys
            20                  25

<210> SEQ ID NO 22
<211> LENGTH: 28
<212> TYPE: PRT
<213> ORGANISM: Artificial Sequence
<220> FEATURE:
<223> OTHER INFORMATION: Heterodimer-Promoting "K-coil" Domain

<400> SEQUENCE: 22

Lys Val Ala Ala Leu Lys Glu Lys Val Ala Ala Leu Lys Glu Lys Val
1               5                   10                  15

Ala Ala Leu Lys Glu Lys Val Ala Ala Leu Lys Glu
            20                  25

<210> SEQ ID NO 23
<211> LENGTH: 28
<212> TYPE: PRT
<213> ORGANISM: Artificial Sequence
<220> FEATURE:
<223> OTHER INFORMATION: Cysteine-Containing Heterodimer-Promoting
      "E-coil" Domain

<400> SEQUENCE: 23

Glu Val Ala Ala Cys Glu Lys Glu Val Ala Ala Leu Glu Lys Glu Val
1               5                   10                  15

Ala Ala Leu Glu Lys Glu Val Ala Ala Leu Glu Lys
            20                  25

<210> SEQ ID NO 24
<211> LENGTH: 28
<212> TYPE: PRT
<213> ORGANISM: Artificial Sequence
<220> FEATURE:
<223> OTHER INFORMATION: Cysteine-Containing Heterodimer-Promoting
      "K-coil" Domain

<400> SEQUENCE: 24

Lys Val Ala Ala Cys Lys Glu Lys Val Ala Ala Leu Lys Glu Lys Val
1               5                   10                  15

Ala Ala Leu Lys Glu Lys Val Ala Ala Leu Lys Glu
            20                  25

<210> SEQ ID NO 25
<211> LENGTH: 46
<212> TYPE: PRT
<213> ORGANISM: Streptococcus dysgalactiae
<220> FEATURE:
<221> NAME/KEY: MISC_FEATURE
<222> LOCATION: (1)..(46)
<223> OTHER INFORMATION: Albumin-Binding Domain 3 of Protein G of
      Streptococcus Strain G148

<400> SEQUENCE: 25

Leu Ala Glu Ala Lys Val Leu Ala Asn Arg Glu Leu Asp Lys Tyr Gly
1               5                   10                  15

Val Ser Asp Tyr Tyr Lys Asn Leu Ile Asp Asn Ala Lys Ser Ala Glu
            20                  25                  30
```

-continued

Gly Val Lys Ala Leu Ile Asp Glu Ile Leu Ala Ala Leu Pro
        35                  40                  45

<210> SEQ ID NO 26
<211> LENGTH: 46
<212> TYPE: PRT
<213> ORGANISM: Artificial Sequence
<220> FEATURE:
<223> OTHER INFORMATION: Variant deimmunized Albumin Binding Domain

<400> SEQUENCE: 26

Leu Ala Glu Ala Lys Val Leu Ala Asn Arg Glu Leu Asp Lys Tyr Gly
1               5                   10                  15

Val Ser Asp Tyr Tyr Lys Asn Leu Ile Asp Asn Ala Lys Ser Ala Glu
            20                  25                  30

Gly Val Lys Ala Leu Ile Asp Glu Ile Leu Ala Ala Leu Pro
        35                  40                  45

<210> SEQ ID NO 27
<211> LENGTH: 46
<212> TYPE: PRT
<213> ORGANISM: Artificial Sequence
<220> FEATURE:
<223> OTHER INFORMATION: Variant Deimmunized Albumin Binding Domain

<400> SEQUENCE: 27

Leu Ala Glu Ala Lys Val Leu Ala Asn Arg Glu Leu Asp Lys Tyr Gly
1               5                   10                  15

Val Ser Asp Tyr Tyr Lys Asn Ala Ala Asn Asn Ala Lys Thr Val Glu
            20                  25                  30

Gly Val Lys Ala Leu Ile Ala Glu Ile Leu Ala Ala Leu Pro
        35                  40                  45

<210> SEQ ID NO 28
<211> LENGTH: 46
<212> TYPE: PRT
<213> ORGANISM: Artificial Sequence
<220> FEATURE:
<223> OTHER INFORMATION: Variant deimmunized Albumin Binding Domain

<400> SEQUENCE: 28

Leu Ala Glu Ala Lys Val Leu Ala Asn Arg Glu Leu Asp Lys Tyr Gly
1               5                   10                  15

Val Ser Asp Tyr Tyr Lys Asn Leu Ile Ser Asn Ala Lys Ser Val Glu
            20                  25                  30

Gly Val Lys Ala Leu Ile Ala Glu Ile Leu Ala Ala Leu Pro
        35                  40                  45

<210> SEQ ID NO 29
<211> LENGTH: 4
<212> TYPE: PRT
<213> ORGANISM: Artificial Sequence
<220> FEATURE:
<223> OTHER INFORMATION: Alternative Linker 2

<400> SEQUENCE: 29

Gly Gly Gly Ser
1

<210> SEQ ID NO 30
<211> LENGTH: 5
<212> TYPE: PRT
<213> ORGANISM: Artificial Sequence
<220> FEATURE:

```
<223> OTHER INFORMATION: Alternative Linker 2

<400> SEQUENCE: 30

Ala Ser Thr Lys Gly
1               5

<210> SEQ ID NO 31
<211> LENGTH: 10
<212> TYPE: PRT
<213> ORGANISM: Artificial Sequence
<220> FEATURE:
<223> OTHER INFORMATION: Linker

<400> SEQUENCE: 31

Asp Lys Thr His Thr Cys Pro Pro Cys Pro
1               5                   10

<210> SEQ ID NO 32
<211> LENGTH: 15
<212> TYPE: PRT
<213> ORGANISM: Artificial Sequence
<220> FEATURE:
<223> OTHER INFORMATION: Linker

<400> SEQUENCE: 32

Glu Pro Lys Ser Cys Asp Lys Thr His Thr Cys Pro Pro Cys Pro
1               5                   10                  15

<210> SEQ ID NO 33
<211> LENGTH: 6
<212> TYPE: PRT
<213> ORGANISM: Artificial Sequence
<220> FEATURE:
<223> OTHER INFORMATION: Alternative Linker 2

<400> SEQUENCE: 33

Leu Glu Pro Lys Ser Ser
1               5

<210> SEQ ID NO 34
<211> LENGTH: 5
<212> TYPE: PRT
<213> ORGANISM: Artificial Sequence
<220> FEATURE:
<223> OTHER INFORMATION: Alternative Linker 2

<400> SEQUENCE: 34

Ala Pro Ser Ser Ser
1               5

<210> SEQ ID NO 35
<211> LENGTH: 8
<212> TYPE: PRT
<213> ORGANISM: Artificial Sequence
<220> FEATURE:
<223> OTHER INFORMATION: Linker

<400> SEQUENCE: 35

Ala Pro Ser Ser Ser Pro Met Glu
1               5

<210> SEQ ID NO 36
<211> LENGTH: 15
<212> TYPE: PRT
<213> ORGANISM: Artificial Sequence
<220> FEATURE:
<223> OTHER INFORMATION: Linker
```

<400> SEQUENCE: 36

```
Leu Glu Pro Lys Ser Ala Asp Lys Thr His Thr Cys Pro Pro Cys
1               5                   10                  15
```

<210> SEQ ID NO 37
<211> LENGTH: 16
<212> TYPE: PRT
<213> ORGANISM: Artificial Sequence
<220> FEATURE:
<223> OTHER INFORMATION: Linker

<400> SEQUENCE: 37

```
Leu Glu Pro Lys Ser Ser Asp Lys Thr His Thr Cys Pro Pro Cys Pro
1               5                   10                  15
```

<210> SEQ ID NO 38
<211> LENGTH: 525
<212> TYPE: PRT
<213> ORGANISM: Homo sapiens
<220> FEATURE:
<221> NAME/KEY: MISC_FEATURE
<222> LOCATION: (1)..(525)
<223> OTHER INFORMATION: Human LAG-3 (Signaling Sequence and Mature
      Protein)
<220> FEATURE:
<221> NAME/KEY: MISC_FEATURE
<222> LOCATION: (1)..(28)
<223> OTHER INFORMATION: Signaling Sequence
<220> FEATURE:
<221> NAME/KEY: MISC_FEATURE
<222> LOCATION: (29)..(525)
<223> OTHER INFORMATION: Mature Protein

<400> SEQUENCE: 38

```
Met Trp Glu Ala Gln Phe Leu Gly Leu Leu Phe Leu Gln Pro Leu Trp
1               5                   10                  15

Val Ala Pro Val Lys Pro Leu Gln Pro Gly Ala Glu Val Pro Val Val
                20                  25                  30

Trp Ala Gln Glu Gly Ala Pro Ala Gln Leu Pro Cys Ser Pro Thr Ile
            35                  40                  45

Pro Leu Gln Asp Leu Ser Leu Leu Arg Arg Ala Gly Val Thr Trp Gln
        50                  55                  60

His Gln Pro Asp Ser Gly Pro Pro Ala Ala Pro Gly His Pro Leu
65                  70                  75                  80

Ala Pro Gly Pro His Pro Ala Ala Pro Ser Ser Trp Gly Pro Arg Pro
                85                  90                  95

Arg Arg Tyr Thr Val Leu Ser Val Gly Pro Gly Gly Leu Arg Ser Gly
            100                 105                 110

Arg Leu Pro Leu Gln Pro Arg Val Gln Leu Asp Glu Arg Gly Arg Gln
        115                 120                 125

Arg Gly Asp Phe Ser Leu Trp Leu Arg Pro Ala Arg Arg Ala Asp Ala
    130                 135                 140

Gly Glu Tyr Arg Ala Ala Val His Leu Arg Asp Arg Ala Leu Ser Cys
145                 150                 155                 160

Arg Leu Arg Leu Arg Leu Gly Gln Ala Ser Met Thr Ala Ser Pro Pro
                165                 170                 175

Gly Ser Leu Arg Ala Ser Asp Trp Val Ile Leu Asn Cys Ser Phe Ser
            180                 185                 190

Arg Pro Asp Arg Pro Ala Ser Val His Trp Phe Arg Asn Arg Gly Gln
        195                 200                 205
```

```
Gly Arg Val Pro Val Arg Glu Ser Pro His His Leu Ala Glu Ser
            210                 215                 220

Phe Leu Phe Leu Pro Gln Val Ser Pro Met Asp Ser Gly Pro Trp Gly
225                 230                 235                 240

Cys Ile Leu Thr Tyr Arg Asp Gly Phe Asn Val Ser Ile Met Tyr Asn
                245                 250                 255

Leu Thr Val Leu Gly Leu Glu Pro Pro Thr Pro Leu Thr Val Tyr Ala
            260                 265                 270

Gly Ala Gly Ser Arg Val Gly Leu Pro Cys Arg Leu Pro Ala Gly Val
        275                 280                 285

Gly Thr Arg Ser Phe Leu Thr Ala Lys Trp Thr Pro Pro Gly Gly Gly
    290                 295                 300

Pro Asp Leu Leu Val Thr Gly Asp Asn Gly Asp Phe Thr Leu Arg Leu
305                 310                 315                 320

Glu Asp Val Ser Gln Ala Gln Ala Gly Thr Tyr Thr Cys His Ile His
                325                 330                 335

Leu Gln Glu Gln Gln Leu Asn Ala Thr Val Thr Leu Ala Ile Ile Thr
            340                 345                 350

Val Thr Pro Lys Ser Phe Gly Ser Pro Gly Ser Leu Gly Lys Leu Leu
        355                 360                 365

Cys Glu Val Thr Pro Val Ser Gly Gln Glu Arg Phe Val Trp Ser Ser
    370                 375                 380

Leu Asp Thr Pro Ser Gln Arg Ser Phe Ser Gly Pro Trp Leu Glu Ala
385                 390                 395                 400

Gln Glu Ala Gln Leu Leu Ser Gln Pro Trp Gln Cys Gln Leu Tyr Gln
                405                 410                 415

Gly Glu Arg Leu Leu Gly Ala Ala Val Tyr Phe Thr Glu Leu Ser Ser
            420                 425                 430

Pro Gly Ala Gln Arg Ser Gly Arg Ala Pro Gly Ala Leu Pro Ala Gly
        435                 440                 445

His Leu Leu Leu Phe Leu Ile Leu Gly Val Leu Ser Leu Leu Leu Leu
    450                 455                 460

Val Thr Gly Ala Phe Gly Phe His Leu Trp Arg Arg Gln Trp Arg Pro
465                 470                 475                 480

Arg Arg Phe Ser Ala Leu Glu Gln Gly Ile His Pro Pro Gln Ala Gln
                485                 490                 495

Ser Lys Ile Glu Glu Leu Glu Gln Glu Pro Glu Pro Glu Pro Glu Pro
            500                 505                 510

Glu Pro Glu Pro Glu Pro Glu Pro Glu Pro Gln Leu
        515                 520                 525

<210> SEQ ID NO 39
<211> LENGTH: 120
<212> TYPE: PRT
<213> ORGANISM: Mus musculus
<220> FEATURE:
<221> NAME/KEY: MISC_FEATURE
<222> LOCATION: (1)..(120)
<223> OTHER INFORMATION: Heavy Chain Variable Domain of LAG-3 mAb A

<400> SEQUENCE: 39

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Asp Tyr
            20                  25                  30

Tyr Trp Asn Trp Ile Arg Gln Pro Pro Gly Lys Gly Leu Glu Trp Ile
```

```
                35                  40                  45
Gly Glu Ile Asn His Asn Gly Asn Thr Asn Ser Asn Pro Ser Leu Lys
         50                  55                  60
Ser Arg Val Thr Leu Ser Leu Asp Thr Ser Lys Asn Gln Phe Ser Leu
 65                  70                  75                  80
Lys Leu Arg Ser Val Thr Ala Ala Asp Thr Ala Val Tyr Tyr Cys Ala
                 85                  90                  95
Phe Gly Tyr Ser Asp Tyr Glu Tyr Asn Trp Phe Asp Pro Trp Gly Gln
                100                 105                 110
Gly Thr Leu Val Thr Val Ser Ser
            115                 120

<210> SEQ ID NO 40
<211> LENGTH: 107
<212> TYPE: PRT
<213> ORGANISM: Mus musculus
<220> FEATURE:
<221> NAME/KEY: MISC_FEATURE
<222> LOCATION: (1)..(107)
<223> OTHER INFORMATION: Light Chain Variable Domain of LAG-3 mAb A

<400> SEQUENCE: 40

Glu Ile Val Leu Thr Gln Ser Pro Ala Thr Leu Ser Leu Ser Pro Gly
 1               5                  10                  15
Glu Arg Ala Thr Leu Ser Cys Arg Ala Ser Gln Ser Ile Ser Ser Tyr
            20                  25                  30
Leu Ala Trp Tyr Gln Gln Lys Pro Gly Gln Ala Pro Arg Leu Leu Ile
        35                  40                  45
Tyr Asp Ala Ser Asn Arg Ala Thr Gly Ile Pro Ala Arg Phe Ser Gly
    50                  55                  60
Ser Gly Ser Gly Thr Asp Phe Thr Leu Thr Ile Ser Ser Leu Glu Pro
 65                  70                  75                  80
Glu Asp Phe Ala Val Tyr Tyr Cys Gln Gln Arg Ser Asn Trp Pro Leu
                 85                  90                  95
Thr Phe Gly Gln Gly Thr Asn Leu Glu Ile Lys
            100                 105

<210> SEQ ID NO 41
<211> LENGTH: 120
<212> TYPE: PRT
<213> ORGANISM: Mus musculus
<220> FEATURE:
<221> NAME/KEY: MISC_FEATURE
<222> LOCATION: (1)..(107)
<223> OTHER INFORMATION: Heavy Chain Variable Domain of LAG-3 mAb 1

<400> SEQUENCE: 41

Gln Ile Gln Leu Val Gln Ser Gly Pro Glu Leu Lys Lys Pro Gly Glu
 1               5                  10                  15
Thr Val Lys Ile Ser Cys Lys Ala Ser Gly Tyr Thr Phe Arg Asn Tyr
            20                  25                  30
Gly Met Asn Trp Val Lys Gln Ala Pro Gly Lys Val Leu Lys Trp Met
        35                  40                  45
Gly Trp Ile Asn Thr Tyr Thr Gly Glu Ser Thr Tyr Ala Asp Asp Phe
    50                  55                  60
Glu Gly Arg Phe Ala Phe Ser Leu Gly Thr Ser Ala Ser Thr Ala Tyr
 65                  70                  75                  80
Leu Gln Ile Asn Ile Leu Lys Asn Glu Asp Thr Ala Thr Tyr Phe Cys
                 85                  90                  95
```

Ala Arg Glu Ser Leu Tyr Asp Tyr Tyr Ser Met Asp Tyr Trp Gly Gln
            100                 105                 110

Gly Thr Ser Val Thr Val Ser Ser
        115                 120

<210> SEQ ID NO 42
<211> LENGTH: 6
<212> TYPE: PRT
<213> ORGANISM: Mus musculus
<220> FEATURE:
<221> NAME/KEY: MISC_FEATURE
<222> LOCATION: (1)..(6)
<223> OTHER INFORMATION: CDRH1 of LAG-3 mAb 1

<400> SEQUENCE: 42

Arg Asn Tyr Gly Met Asn
1               5

<210> SEQ ID NO 43
<211> LENGTH: 17
<212> TYPE: PRT
<213> ORGANISM: Mus musculus
<220> FEATURE:
<221> NAME/KEY: MISC_FEATURE
<222> LOCATION: (1)..(17)
<223> OTHER INFORMATION: CDRH2 of LAG-3 mAb 1

<400> SEQUENCE: 43

Trp Ile Asn Thr Tyr Thr Gly Glu Ser Thr Tyr Ala Asp Asp Phe Glu
1               5                   10                  15

Gly

<210> SEQ ID NO 44
<211> LENGTH: 11
<212> TYPE: PRT
<213> ORGANISM: Mus musculus
<220> FEATURE:
<221> NAME/KEY: MISC_FEATURE
<222> LOCATION: (1)..(11)
<223> OTHER INFORMATION: CDRH3 of LAG-3 mAb 1

<400> SEQUENCE: 44

Glu Ser Leu Tyr Asp Tyr Tyr Ser Met Asp Tyr
1               5                   10

<210> SEQ ID NO 45
<211> LENGTH: 112
<212> TYPE: PRT
<213> ORGANISM: Mus musculus
<220> FEATURE:
<221> NAME/KEY: MISC_FEATURE
<222> LOCATION: (1)..(112)
<223> OTHER INFORMATION: VL Domain of LAG-3 mAb 1

<400> SEQUENCE: 45

Asp Val Val Val Thr Gln Thr Pro Leu Thr Leu Ser Val Thr Ile Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Asn Trp Leu Leu Gln Arg Pro Gly Gln Ser
        35                  40                  45

Pro Glu Arg Leu Ile Tyr Leu Val Ser Glu Leu Asp Ser Gly Val Pro
    50                  55                  60

Asp Arg Phe Thr Gly Ser Gly Ser Gly Thr Asp Phe Thr Leu Lys Ile

```
                65                  70                  75                  80
Ser Arg Val Glu Ala Glu Asp Leu Gly Val Tyr Tyr Cys Trp Gln Gly
                    85                  90                  95

Thr His Phe Pro Tyr Thr Phe Gly Gly Gly Thr Lys Leu Glu Ile Lys
                100                 105                 110

<210> SEQ ID NO 46
<211> LENGTH: 16
<212> TYPE: PRT
<213> ORGANISM: Mus musculus
<220> FEATURE:
<221> NAME/KEY: MISC_FEATURE
<222> LOCATION: (1)..(16)
<223> OTHER INFORMATION: CDRL1 of LAG-3 mAb 1

<400> SEQUENCE: 46

Lys Ser Ser Gln Ser Leu Leu His Ser Asp Gly Lys Thr Tyr Leu Asn
1               5                   10                  15

<210> SEQ ID NO 47
<211> LENGTH: 7
<212> TYPE: PRT
<213> ORGANISM: Mus musculus
<220> FEATURE:
<221> NAME/KEY: MISC_FEATURE
<222> LOCATION: (1)..(7)
<223> OTHER INFORMATION: CDRL2 of LAG-3 mAb 1

<400> SEQUENCE: 47

Leu Val Ser Glu Leu Asp Ser
1               5

<210> SEQ ID NO 48
<211> LENGTH: 9
<212> TYPE: PRT
<213> ORGANISM: Mus musculus
<220> FEATURE:
<221> NAME/KEY: MISC_FEATURE
<222> LOCATION: (1)..(9)
<223> OTHER INFORMATION: CDRL3 of LAG-3 mAb 1

<400> SEQUENCE: 48

Trp Gln Gly Thr His Phe Pro Tyr Thr
1               5

<210> SEQ ID NO 49
<211> LENGTH: 120
<212> TYPE: PRT
<213> ORGANISM: Artificial Sequence
<220> FEATURE:
<223> OTHER INFORMATION: VH Domain of hLAG-3 mAb 1 VH1

<400> SEQUENCE: 49

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Gly Met Asn Trp Val Arg Gln Ala Pro Gly Gln Gly Leu Glu Trp Met
            35                  40                  45

Gly Trp Ile Asn Thr Tyr Thr Gly Glu Ser Thr Tyr Ala Asp Asp Phe
        50                  55                  60

Glu Gly Arg Phe Val Phe Ser Met Asp Thr Ser Ala Ser Thr Ala Tyr
65                  70                  75                  80

Leu Gln Ile Ser Ser Leu Lys Ala Glu Asp Thr Ala Val Tyr Tyr Cys
```

85                  90                  95

Ala Arg Glu Ser Leu Tyr Asp Tyr Tyr Ser Met Asp Tyr Trp Gly Gln
                100                 105                 110

Gly Thr Thr Val Thr Val Ser Ser
        115                 120

<210> SEQ ID NO 50
<211> LENGTH: 120
<212> TYPE: PRT
<213> ORGANISM: Artificial Sequence
<220> FEATURE:
<223> OTHER INFORMATION: VH Domain of hLAG-3 mAb 1 VH2

<400> SEQUENCE: 50

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Gly Met Asn Trp Val Arg Gln Ala Pro Gly Gln Gly Leu Glu Trp Met
            35                  40                  45

Gly Trp Ile Asn Thr Tyr Thr Gly Glu Ser Thr Tyr Ala Asp Asp Phe
    50                  55                  60

Glu Gly Arg Phe Val Phe Ser Met Asp Thr Ser Ala Ser Thr Ala Tyr
65                  70                  75                  80

Leu Gln Ile Ser Ser Leu Lys Ala Glu Asp Thr Ala Val Tyr Phe Cys
                85                  90                  95

Ala Arg Glu Ser Leu Tyr Asp Tyr Tyr Ser Met Asp Tyr Trp Gly Gln
                100                 105                 110

Gly Thr Thr Val Thr Val Ser Ser
        115                 120

<210> SEQ ID NO 51
<211> LENGTH: 112
<212> TYPE: PRT
<213> ORGANISM: Artificial Sequence
<220> FEATURE:
<223> OTHER INFORMATION: VH Domain of hLAG-3 mAb 1 VL1

<400> SEQUENCE: 51

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
                20                  25                  30

Asp Gly Lys Thr Tyr Leu Asn Trp Leu Leu Gln Lys Pro Gly Gln Ser
            35                  40                  45

Pro Glu Arg Leu Ile Tyr Leu Val Ser Glu Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Tyr Thr Phe Gly Gly Gly Thr Lys Val Glu Ile Lys
                100                 105                 110

<210> SEQ ID NO 52
<211> LENGTH: 112
<212> TYPE: PRT
<213> ORGANISM: Artificial Sequence
<220> FEATURE:

<223> OTHER INFORMATION: VL Domain of hLAG-3 mAb 1 VL2

<400> SEQUENCE: 52

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Asn Trp Leu Leu Gln Arg Pro Gly Gln Ser
        35                  40                  45

Pro Glu Arg Leu Ile Tyr Leu Val Ser Glu Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Tyr Thr Phe Gly Gly Gly Thr Lys Val Glu Ile Lys
            100                 105                 110

<210> SEQ ID NO 53
<211> LENGTH: 112
<212> TYPE: PRT
<213> ORGANISM: Artificial Sequence
<220> FEATURE:
<223> OTHER INFORMATION: VL Domain of hLAG-3 mAb 1 VL3

<400> SEQUENCE: 53

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Asn Trp Leu Leu Gln Lys Pro Gly Gln Pro
        35                  40                  45

Pro Glu Arg Leu Ile Tyr Leu Val Ser Glu Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Tyr Thr Phe Gly Gly Gly Thr Lys Val Glu Ile Lys
            100                 105                 110

<210> SEQ ID NO 54
<211> LENGTH: 112
<212> TYPE: PRT
<213> ORGANISM: Artificial Sequence
<220> FEATURE:
<223> OTHER INFORMATION: VL Domain of hLAG-3 mAb 1 VL4

<400> SEQUENCE: 54

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Ala Lys Thr Tyr Leu Asn Trp Leu Leu Gln Lys Pro Gly Gln Pro
        35                  40                  45

Pro Glu Arg Leu Ile Tyr Leu Val Ser Glu Leu Asp Ser Gly Val Pro
    50                  55                  60

Asp Arg Phe Ser Gly Ser Gly Ser Gly Thr Asp Phe Thr Leu Lys Ile

```
                65                  70                  75                  80
Ser Arg Val Glu Ala Glu Asp Val Gly Val Tyr Tyr Cys Trp Gln Gly
                    85                  90                  95

Thr His Phe Pro Tyr Thr Phe Gly Gly Gly Thr Lys Val Glu Ile Lys
                100                 105                 110

<210> SEQ ID NO 55
<211> LENGTH: 16
<212> TYPE: PRT
<213> ORGANISM: Artificial Sequence
<220> FEATURE:
<223> OTHER INFORMATION: CDRL1 of the VL Domain of hLAG-3 mAb 1 VL4

<400> SEQUENCE: 55

Lys Ser Ser Gln Ser Leu Leu His Ser Asp Ala Lys Thr Tyr Leu Asn
1               5                   10                  15

<210> SEQ ID NO 56
<211> LENGTH: 118
<212> TYPE: PRT
<213> ORGANISM: Mus musculus
<220> FEATURE:
<221> NAME/KEY: MISC_FEATURE
<222> LOCATION: (1)..(118)
<223> OTHER INFORMATION: VH Domain of LAG-3 mAb 6

<400> SEQUENCE: 56

Glu Val Leu Leu Gln Gln Ser Gly Pro Glu Leu Val Lys Pro Gly Ala
1               5                   10                  15

Ser Val Lys Ile Pro Cys Lys Ala Ser Gly Tyr Thr Phe Thr Asp Tyr
                20                  25                  30

Asn Met Asp Trp Val Lys Gln Ser His Gly Glu Ser Leu Glu Trp Ile
            35                  40                  45

Gly Asp Ile Asn Pro Asp Asn Gly Val Thr Ile Tyr Asn Gln Lys Phe
        50                  55                  60

Glu Gly Lys Ala Thr Leu Thr Val Asp Lys Ser Ser Ser Thr Ala Tyr
65                  70                  75                  80

Met Glu Leu Arg Ser Leu Thr Ser Glu Asp Thr Ala Val Tyr Tyr Cys
                85                  90                  95

Ala Arg Glu Ala Asp Tyr Phe Tyr Phe Asp Tyr Trp Gly Gln Gly Thr
                100                 105                 110

Thr Leu Thr Val Ser Ser
            115

<210> SEQ ID NO 57
<211> LENGTH: 5
<212> TYPE: PRT
<213> ORGANISM: Mus musculus
<220> FEATURE:
<221> NAME/KEY: MISC_FEATURE
<222> LOCATION: (1)..(5)
<223> OTHER INFORMATION: CDRH1 of LAG-3 mAb 6

<400> SEQUENCE: 57

Asp Tyr Asn Met Asp
1               5

<210> SEQ ID NO 58
<211> LENGTH: 17
<212> TYPE: PRT
<213> ORGANISM: Mus musculus
<220> FEATURE:
<221> NAME/KEY: MISC_FEATURE
```

```
<222> LOCATION: (1)..(17)
<223> OTHER INFORMATION: CDRH2 of LAG-3 mAb 6

<400> SEQUENCE: 58

Asp Ile Asn Pro Asp Asn Gly Val Thr Ile Tyr Asn Gln Lys Phe Glu
1               5                   10                  15

Gly

<210> SEQ ID NO 59
<211> LENGTH: 9
<212> TYPE: PRT
<213> ORGANISM: Mus musculus
<220> FEATURE:
<221> NAME/KEY: MISC_FEATURE
<222> LOCATION: (1)..(9)
<223> OTHER INFORMATION: CDRH3 of LAG-3 mAb 6

<400> SEQUENCE: 59

Glu Ala Asp Tyr Phe Tyr Phe Asp Tyr
1               5

<210> SEQ ID NO 60
<211> LENGTH: 107
<212> TYPE: PRT
<213> ORGANISM: Mus musculus
<220> FEATURE:
<221> NAME/KEY: MISC_FEATURE
<222> LOCATION: (1)..(107)
<223> OTHER INFORMATION: VL Domain of LAG-3 mAb 6

<400> SEQUENCE: 60

Asp Ile Val Met Thr Gln Ser His Arg Phe Met Ser Thr Ser Val Gly
1               5                   10                  15

Asp Arg Val Ser Ile Thr Cys Lys Ala Ser Gln Asp Val Ser Ser Val
            20                  25                  30

Val Ala Trp Tyr Gln Gln Lys Pro Gly Gln Ser Pro Lys Leu Leu Ile
        35                  40                  45

Phe Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Ala Asp Leu Ala Val Tyr Tyr Cys Gln Gln His Tyr Ser Thr Pro Trp
                85                  90                  95

Thr Phe Gly Gly Gly Thr Lys Leu Glu Ile Lys
            100                 105

<210> SEQ ID NO 61
<211> LENGTH: 11
<212> TYPE: PRT
<213> ORGANISM: Mus musculus
<220> FEATURE:
<221> NAME/KEY: MISC_FEATURE
<222> LOCATION: (1)..(11)
<223> OTHER INFORMATION: CDRL1 of LAG-3 mAb 6

<400> SEQUENCE: 61

Lys Ala Ser Gln Asp Val Ser Ser Val Val Ala
1               5                   10

<210> SEQ ID NO 62
<211> LENGTH: 7
<212> TYPE: PRT
<213> ORGANISM: Mus musculus
<220> FEATURE:
```

```
<221> NAME/KEY: MISC_FEATURE
<222> LOCATION: (1)..(7)
<223> OTHER INFORMATION: CDRL2 of LAG-3 mAb 6

<400> SEQUENCE: 62

Ser Ala Ser Tyr Arg Tyr Thr
1               5

<210> SEQ ID NO 63
<211> LENGTH: 7
<212> TYPE: PRT
<213> ORGANISM: Mus musculus
<220> FEATURE:
<221> NAME/KEY: MISC_FEATURE
<222> LOCATION: (1)..(7)
<223> OTHER INFORMATION: CDRL3 of LAG-3 mAb 6

<400> SEQUENCE: 63

His Tyr Ser Thr Pro Trp Thr
1               5

<210> SEQ ID NO 64
<211> LENGTH: 113
<212> TYPE: PRT
<213> ORGANISM: Homo sapiens
<220> FEATURE:
<221> NAME/KEY: MISC_FEATURE
<222> LOCATION: (1)..(113)
<223> OTHER INFORMATION: Heavy Chain Variable Domain of PD-1 mAb A

<400> SEQUENCE: 64

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser

<210> SEQ ID NO 65
<211> LENGTH: 107
<212> TYPE: PRT
<213> ORGANISM: Homo sapiens
<220> FEATURE:
<221> NAME/KEY: MISC_FEATURE
<222> LOCATION: (1)..(107)
<223> OTHER INFORMATION: Light Chain Variable Domain of PD-1 mAb A

<400> SEQUENCE: 65

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45
```

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys
            100                 105

<210> SEQ ID NO 66
<211> LENGTH: 120
<212> TYPE: PRT
<213> ORGANISM: Homo sapiens
<220> FEATURE:
<221> NAME/KEY: MISC_FEATURE
<222> LOCATION: (1)..(120)
<223> OTHER INFORMATION: Heavy Chain Variable Domain of PD-1 mAb B

<400> SEQUENCE: 66

Gln Val Gln Leu Val Gln Ser Gly Val Glu Val Lys Lys Pro Gly Ala
 1               5                  10                  15

Ser Val Lys Val Ser Cys Lys Ala Ser Gly Tyr Thr Phe Thr Asn Tyr
                20                  25                  30

Tyr Met Tyr Trp Val Arg Gln Ala Pro Gly Gln Gly Leu Glu Trp Met
            35                  40                  45

Gly Gly Ile Asn Pro Ser Asn Gly Gly Thr Asn Phe Asn Glu Lys Phe
        50                  55                  60

Lys Asn Arg Val Thr Leu Thr Thr Asp Ser Ser Thr Thr Thr Ala Tyr
 65                  70                  75                  80

Met Glu Leu Lys Ser Leu Gln Phe Asp Asp Thr Ala Val Tyr Tyr Cys
                85                  90                  95

Ala Arg Arg Asp Tyr Arg Phe Asp Met Gly Phe Asp Tyr Trp Gly Gln
            100                 105                 110

Gly Thr Thr Val Thr Val Ser Ser
        115                 120

<210> SEQ ID NO 67
<211> LENGTH: 111
<212> TYPE: PRT
<213> ORGANISM: Homo sapiens
<220> FEATURE:
<221> NAME/KEY: MISC_FEATURE
<222> LOCATION: (1)..(111)
<223> OTHER INFORMATION: Light Chain Variable Domain of PD-1 mAb B

<400> SEQUENCE: 67

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Lys Gly Val Ser Thr Ser
                20                  25                  30

Gly Tyr Ser Tyr Leu His Trp Tyr Gln Gln Lys Pro Gly Gln Ala Pro
            35                  40                  45

Arg Leu Leu Ile Tyr Leu Ala Ser Tyr Leu Glu Ser Gly Val Pro Ala
        50                  55                  60

Arg Phe Ser Gly Ser Gly Ser Gly Thr Asp Phe Thr Leu Thr Ile Ser
 65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys
            100                 105                 110

<210> SEQ ID NO 68
<211> LENGTH: 288
<212> TYPE: PRT
<213> ORGANISM: Homo sapiens
<220> FEATURE:
<221> NAME/KEY: MISC_FEATURE
<222> LOCATION: (1)..(288)
<223> OTHER INFORMATION: Human PD-1 Polypeptide (NCI Sequence NP
      005009.2)
<220> FEATURE:
<221> NAME/KEY: MISC_FEATURE
<222> LOCATION: (1)..(20)
<223> OTHER INFORMATION: Human PD-1 Signal Sequence

<400> SEQUENCE: 68

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
            35                  40                  45

Asn Ala Thr Phe Thr Cys Ser Phe Ser Asn Thr Ser Glu Ser Phe Val
        50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
            115                 120                 125

Ala Pro Lys Ala Gln Ile Lys Glu Ser Leu Arg Ala Glu Leu Arg Val
        130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
            195                 200                 205

Leu Lys Glu Asp Pro Ser Ala Val Pro Val Phe Ser Val Asp Tyr Gly
        210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
            275                 280                 285

<210> SEQ ID NO 69
<211> LENGTH: 121
<212> TYPE: PRT
<213> ORGANISM: Mus musculus

```
<220> FEATURE:
<221> NAME/KEY: MISC_FEATURE
<222> LOCATION: (1)..(121)
<223> OTHER INFORMATION: VH Domain of PD-1 mAb 1

<400> SEQUENCE: 69

Asp Val Gln Leu Gln Glu Ser Gly Pro Gly Arg Val Lys Pro Ser Gln
1               5                   10                  15

Ser Leu Ser Leu Thr Cys Thr Val Thr Gly Phe Ser Ile Thr Asn Asp
            20                  25                  30

Tyr Ala Trp Asn Trp Ile Arg Gln Phe Pro Gly Asn Lys Leu Glu Trp
        35                  40                  45

Met Gly His Ile Thr Tyr Ser Gly Ser Thr Ser Tyr Asn Pro Ser Leu
50                  55                  60

Lys Ser Arg Ile Ser Ile Thr Arg Asp Thr Ser Lys Asn His Phe Phe
65                  70                  75                  80

Leu Gln Leu Ser Ser Val Thr Pro Glu Asp Thr Ala Thr Tyr Tyr Cys
            85                  90                  95

Ala Arg Asp Tyr Gly Ser Gly Tyr Pro Tyr Thr Leu Asp Tyr Trp Gly
            100                 105                 110

Gln Gly Thr Ser Val Thr Val Ser Ser
        115                 120

<210> SEQ ID NO 70
<211> LENGTH: 373
<212> TYPE: DNA
<213> ORGANISM: Mus musculus
<220> FEATURE:
<221> NAME/KEY: misc_feature
<222> LOCATION: (1)..(373)
<223> OTHER INFORMATION: Polynucleotide Encoding VH Domain of PD-1 mAb 1

<400> SEQUENCE: 70
cagatccagt gatgtgcagc ttcaggagtc gggacctggc cgggtgaaac cttctcagtc      60
tctgtccctc acctgcactg tcactggctt ctcaatcacc aatgattatg cctggaactg     120
gatccgacag tttccaggaa acaaactgga gtggatgggc cacataacct acagtggcag     180
cactagctac aacccatctc tcaaaagtcg aatctctatc actcgggaca catccaagaa     240
ccacttcttc ctgcagttga gttctgtgac tcctgaggac acagccacat attactgtgc     300
aagagattac ggtagtggct accctatac  tttggactac tggggtcaag gtacctcagt    360
caccgtctcc tcc                                                        373

<210> SEQ ID NO 71
<211> LENGTH: 6
<212> TYPE: PRT
<213> ORGANISM: Mus musculus
<220> FEATURE:
<221> NAME/KEY: MISC_FEATURE
<222> LOCATION: (1)..(6)

<400> SEQUENCE: 71

Asn Asp Tyr Ala Trp Asn
1               5

<210> SEQ ID NO 72
<211> LENGTH: 16
<212> TYPE: PRT
<213> ORGANISM: Mus musculus
<220> FEATURE:
<221> NAME/KEY: MISC_FEATURE
<222> LOCATION: (1)..(16)
```

<223> OTHER INFORMATION: CDRH2 of PD-1 mAb 1

<400> SEQUENCE: 72

His Ile Thr Tyr Ser Gly Ser Thr Ser Tyr Asn Pro Ser Leu Lys Ser
1               5                   10                  15

<210> SEQ ID NO 73
<211> LENGTH: 12
<212> TYPE: PRT
<213> ORGANISM: Mus musculus
<220> FEATURE:
<221> NAME/KEY: MISC_FEATURE
<222> LOCATION: (1)..(12)
<223> OTHER INFORMATION: CDRH3 of PD-1 mAb 1

<400> SEQUENCE: 73

Asp Tyr Gly Ser Gly Tyr Pro Tyr Thr Leu Asp Tyr
1               5                   10

<210> SEQ ID NO 74
<211> LENGTH: 106
<212> TYPE: PRT
<213> ORGANISM: Mus musculus
<220> FEATURE:
<221> NAME/KEY: MISC_FEATURE
<222> LOCATION: (1)..(106)
<223> OTHER INFORMATION: VL Domain of PD-1 mAb 1

<400> SEQUENCE: 74

Gln Ile Val Leu Thr Gln Ser Pro Ala Leu Met Ser Ala Ser Pro Gly
1               5                   10                  15

Glu Lys Val Thr Met Thr Cys Ser Ala Thr Ser Ile Val Ser Tyr Val
                20                  25                  30

Tyr Trp Tyr Gln Gln Lys Pro Gly Ser Ser Pro Gln Pro Trp Ile Tyr
            35                  40                  45

Leu Thr Ser Asn Leu Ala Ser Gly Val Pro Ala Arg Phe Ser Gly Ser
        50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Asp Asn Pro Tyr Thr
                85                  90                  95

Phe Gly Gly Gly Thr Lys Leu Glu Ile Lys
            100                 105

<210> SEQ ID NO 75
<211> LENGTH: 318
<212> TYPE: DNA
<213> ORGANISM: Mus musculus
<220> FEATURE:
<221> NAME/KEY: misc_feature
<222> LOCATION: (1)..(318)
<223> OTHER INFORMATION: Polynucleotide Encoding VL Domain of PD-1 mAb 1

<400> SEQUENCE: 75
caaattgttc tcacccagtc tccagcactc atgtctgcat ctccagggga gaaggtcacc      60
atgacctgca gtgccacctc aattgtaagt tacgtttact ggtaccagca gaagcctgga     120 tcctccccc  aaccctggat ttatctcaca tccaacctgg cttctggagt ccctgctcgc     180
ttcagtggca gtgggtctgg gacctcttac tctctcacaa tcagcagcat ggaggctgaa     240
gatgctgcca cttattactg ccagcagtgg agtgataacc cgtacacgtt cggagggggg     300
accaagctgg aaataaaa                                                   318

```
<210> SEQ ID NO 76
<211> LENGTH: 10
<212> TYPE: PRT
<213> ORGANISM: Mus musculus
<220> FEATURE:
<221> NAME/KEY: MISC_FEATURE
<222> LOCATION: (1)..(10)
<223> OTHER INFORMATION: CDRL1 of PD-1 mAb 1

<400> SEQUENCE: 76

Ser Ala Thr Ser Ile Val Ser Tyr Val Tyr
1               5                   10

<210> SEQ ID NO 77
<211> LENGTH: 7
<212> TYPE: PRT
<213> ORGANISM: Mus musculus
<220> FEATURE:
<221> NAME/KEY: MISC_FEATURE
<222> LOCATION: (1)..(7)
<223> OTHER INFORMATION: CDRL2 of PD-1 mAb 1

<400> SEQUENCE: 77

Leu Thr Ser Asn Leu Ala Ser
1               5

<210> SEQ ID NO 78
<211> LENGTH: 9
<212> TYPE: PRT
<213> ORGANISM: Mus musculus
<220> FEATURE:
<221> NAME/KEY: MISC_FEATURE
<222> LOCATION: (1)..(9)
<223> OTHER INFORMATION: CDRL3 of PD-1 mAb 1

<400> SEQUENCE: 78

Gln Gln Trp Ser Asp Asn Pro Tyr Thr
1               5

<210> SEQ ID NO 79
<211> LENGTH: 121
<212> TYPE: PRT
<213> ORGANISM: Artificial Sequence
<220> FEATURE:
<223> OTHER INFORMATION: VH Domain of hPD-1 mAb 1 VH1

<400> SEQUENCE: 79

Asp Val Gln Leu Gln Glu Ser Gly Pro Gly Leu Val Lys Pro Ser Gln
1               5                   10                  15

Thr Leu Ser Leu Thr Cys Thr Val Ser Gly Phe Ser Ile Ser Asn Asp
            20                  25                  30

Tyr Ala Trp Asn Trp Ile Arg Gln Pro Pro Gly Lys Gly Leu Glu Trp
        35                  40                  45

Ile Gly His Ile Thr Tyr Ser Gly Ser Thr Ser Tyr Asn Pro Ser Leu
    50                  55                  60

Lys Ser Arg Leu Thr Ile Thr Arg Asp Thr Ser Lys Asn Gln Phe Val
65                  70                  75                  80

Leu Thr Met Thr Asn Met Asp Pro Val Asp Thr Ala Thr Tyr Tyr Cys
                85                  90                  95

Ala Arg Asp Tyr Gly Ser Gly Tyr Pro Tyr Thr Leu Asp Tyr Trp Gly
            100                 105                 110

Gln Gly Thr Thr Val Thr Val Ser Ser
        115                 120
```

<210> SEQ ID NO 80
<211> LENGTH: 363
<212> TYPE: DNA
<213> ORGANISM: Artificial Sequence
<220> FEATURE:
<223> OTHER INFORMATION: Polynucleotide Encoding hPD-1 mAb 1 VH1

<400> SEQUENCE: 80

```
gacgtacagc tccaggaaag tggcccaggt ctggtgaagc catcccagac actgagcctg      60
acttgcaccg tgagtggctt ctccatctca aatgactacg cctggaattg gattaggcag     120
cctcccggta aagggctgga gtggatcggc cacatcacat acagcggctc cacatcatat     180
aatcccagtc tgaagagccg tcttaccatt actcgcgaca ctagtaagaa ccagtttgtt     240
ctgaccatga ccaacatgga ccctgtggat actgcaacat actattgtgc tcgagattat     300
ggttctggtt acccttatac actcgactac tggggacagg gaaccactgt gaccgtgagc     360
tcc                                                                    363
```

<210> SEQ ID NO 81
<211> LENGTH: 106
<212> TYPE: PRT
<213> ORGANISM: Artificial Sequence
<220> FEATURE:
<223> OTHER INFORMATION: VL Domain of hPD-1 mAb 1 VL1

<400> SEQUENCE: 81

Glu Ile Val Leu Thr Gln Ser Pro Ala Thr Leu Ser Val Ser Pro Gly
1               5                   10                  15

Glu Lys Val Thr Ile Thr Cys Ser Ala Thr Ser Ile Val Ser Tyr Val
            20                  25                  30

Tyr Trp Tyr Gln Gln Lys Pro Gly Gln Ala Pro Gln Pro Leu Ile Tyr
        35                  40                  45

Leu Thr Ser Asn Leu Ala Ser Gly Ile Pro Ala Arg Phe Ser Gly Ser
    50                  55                  60

Gly Ser Gly Thr Asp Phe Thr Leu Thr Ile Ser Ser Leu Glu Ala Glu
65                  70                  75                  80

Asp Ala Ala Thr Tyr Tyr Cys Gln Gln Trp Ser Asp Asn Pro Tyr Thr
                85                  90                  95

Phe Gly Gly Gly Thr Lys Val Glu Ile Lys
            100                 105

<210> SEQ ID NO 82
<211> LENGTH: 318
<212> TYPE: DNA
<213> ORGANISM: Artificial Sequence
<220> FEATURE:
<223> OTHER INFORMATION: Polynucleotide Encoding hPD-1 mAb 1 VL1

<400> SEQUENCE: 82

```
gaaatcgttc tgacccagag cccagcaacc ctgtctgtct ccccggaga aaaggtcacc       60 attacttgct ctgctacttc tatcgtgtcc tacgtgtact ggtatcagca gaagcccggt     120
caggctcccc agccattgat atatctgacc agcaacctgg cttctggtat cccagctcgt     180
ttttccggta gcgggtccgg gactgatttc actttgacta tcagctctct ggaggcagaa     240
gacgccgcca cctattattg tcaacagtgg tcagacaatc catacacttt tggcggtggc     300
accaaagtcg aaataaag                                                   318
```

<210> SEQ ID NO 83

```
<211> LENGTH: 116
<212> TYPE: PRT
<213> ORGANISM: Mus musculus
<220> FEATURE:
<221> NAME/KEY: MISC_FEATURE
<222> LOCATION: (1)..(116)
<223> OTHER INFORMATION: VH Domain of PD-1 mAb 2

<400> SEQUENCE: 83

Asp Val Gln Leu Val Glu Ser Gly Gly Gly Leu Val Gln Pro Gly Gly
1               5                  10                  15

Ser Arg Lys Leu Ser Cys Ala Ala Ser Gly Phe Val Phe Ser Ser Phe
            20                  25                  30

Gly Met His Trp Val Arg Gln Ala Pro Glu Lys Gly Leu Glu Trp Val
        35                  40                  45

Ala Tyr Ile Ser Ser Gly Ser Met Ser Ile Ser Tyr Ala Asp Thr Val
    50                  55                  60

Lys Gly Arg Phe Thr Val Thr Arg Asp Asn Ala Lys Asn Thr Leu Phe
65                  70                  75                  80

Leu Gln Met Thr Ser Leu Arg Ser Glu Asp Thr Ala Ile Tyr Tyr Cys
                85                  90                  95

Ala Ser Leu Ser Asp Tyr Phe Asp Tyr Trp Gly Gln Gly Thr Thr Leu
            100                 105                 110

Thr Val Ser Ser
        115

<210> SEQ ID NO 84
<211> LENGTH: 348
<212> TYPE: DNA
<213> ORGANISM: Mus musculus
<220> FEATURE:
<221> NAME/KEY: misc_feature
<222> LOCATION: (1)..(348)
<223> OTHER INFORMATION: Polynucleotide Encoding the VH Domain of PD-1
      mAb 2

<400> SEQUENCE: 84
gatgtgcagc tcgtggagtc tgggggaggc ttagtgcagc ctggagggtc ccggaaactc     60
tcctgtgcag cctctggatt cgttttcagt agctttggaa tgcactgggt tcgtcaggct    120
ccagagaagg ggctggagtg ggtcgcatac atcagtagtg gcagtatgag catttcctat    180
gcagacacag tgaagggccg attcaccgtc accagagaca tgccaagaa cacccctgttc    240 ctgcaaatga ccagtctaag gtctgaggac acggccattt attactgtgc atccctgagt    300
gactactttg actactgggg ccaaggcacc actctcacag tctcctcc               348

<210> SEQ ID NO 85
<211> LENGTH: 5
<212> TYPE: PRT
<213> ORGANISM: Mus musculus
<220> FEATURE:
<221> NAME/KEY: MISC_FEATURE
<222> LOCATION: (1)..(5)
<223> OTHER INFORMATION: CDRH1 of PD-1 mAb 2

<400> SEQUENCE: 85

Ser Phe Gly Met His
1               5

<210> SEQ ID NO 86
<211> LENGTH: 17
<212> TYPE: PRT
<213> ORGANISM: Mus musculus
```

```
<220> FEATURE:
<221> NAME/KEY: MISC_FEATURE
<222> LOCATION: (1)..(17)
<223> OTHER INFORMATION: CDRH2 of PD-1 mAb 2

<400> SEQUENCE: 86

Tyr Ile Ser Ser Gly Ser Met Ser Ile Ser Tyr Ala Asp Thr Val Lys
1               5                   10                  15

Gly

<210> SEQ ID NO 87
<211> LENGTH: 7
<212> TYPE: PRT
<213> ORGANISM: Mus musculus
<220> FEATURE:
<221> NAME/KEY: MISC_FEATURE
<222> LOCATION: (1)..(7)
<223> OTHER INFORMATION: CDRH3 of PD-1 mAb 2

<400> SEQUENCE: 87

Leu Ser Asp Tyr Phe Asp Tyr
1               5

<210> SEQ ID NO 88
<211> LENGTH: 112
<212> TYPE: PRT
<213> ORGANISM: Mus musculus
<220> FEATURE:
<221> NAME/KEY: MISC_FEATURE
<222> LOCATION: (1)..(112)
<223> OTHER INFORMATION: VL Domain of PD-1 mAb 2

<400> SEQUENCE: 88

Asp Val Val Met Ser Gln Thr Pro Leu Ser Leu Pro Val Ser Leu Gly
1               5                   10                  15

Asp Gln Ala Ser Ile Ser Cys Arg Ser Ser Gln Ser Leu Val His Ser
                20                  25                  30

Thr Gly Asn Thr Tyr Leu His Trp Tyr Leu Gln Lys Pro Gly Gln Ser
            35                  40                  45

Pro Lys Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Phe Phe Cys Ser Gln Thr
                85                  90                  95

Thr His Val Pro Trp Thr Phe Gly Gly Gly Thr Lys Leu Glu Ile Lys
            100                 105                 110

<210> SEQ ID NO 89
<211> LENGTH: 336
<212> TYPE: DNA
<213> ORGANISM: Mus musculus
<220> FEATURE:
<221> NAME/KEY: misc_feature
<222> LOCATION: (1)..(336)
<223> OTHER INFORMATION: Polynucleotide Encoding the VL Domain of PD-1
      mAb 2

<400> SEQUENCE: 89
gatgttgtga tgtcccaaac tccactctcc ctgcctgtca gtcttggaga tcaagcctcc      60
atctcttgca gatctagtca gagccttgtt cacagtactg gaaacaccta tttacattgg     120
tacctgcaga agccaggcca gtctccaaag ctcctgatct acagggtttc taaccgattt     180
```

-continued

```
tctggggtcc cgacaggtt cagtggcagt ggatcaggga cagatttcac actcaagatc    240
agtagagtgg aggctgagga tctgggagtt tttttctgct ctcaaactac acatgttccg    300
tggacgttcg gtggaggcac caagctggaa atcaaa                             336
```

<210> SEQ ID NO 90
<211> LENGTH: 16
<212> TYPE: PRT
<213> ORGANISM: Mus musculus
<220> FEATURE:
<221> NAME/KEY: MISC_FEATURE
<222> LOCATION: (1)..(16)
<223> OTHER INFORMATION: CDRL1 of PD-1 mAb 2

<400> SEQUENCE: 90

Arg Ser Ser Gln Ser Leu Val His Ser Thr Gly Asn Thr Tyr Leu His
1               5                   10                  15

<210> SEQ ID NO 91
<211> LENGTH: 7
<212> TYPE: PRT
<213> ORGANISM: Mus musculus
<220> FEATURE:
<221> NAME/KEY: MISC_FEATURE
<222> LOCATION: (1)..(7)
<223> OTHER INFORMATION: CDRL2 of PD-1 mAb 2

<400> SEQUENCE: 91

Arg Val Ser Asn Arg Phe Ser
1               5

<210> SEQ ID NO 92
<211> LENGTH: 9
<212> TYPE: PRT
<213> ORGANISM: Mus musculus
<220> FEATURE:
<221> NAME/KEY: MISC_FEATURE
<222> LOCATION: (1)..(9)
<223> OTHER INFORMATION: CDRL3 of PD-1 mAb 2

<400> SEQUENCE: 92

Ser Gln Thr Thr His Val Pro Trp Thr
1               5

<210> SEQ ID NO 93
<211> LENGTH: 116
<212> TYPE: PRT
<213> ORGANISM: Artificial Sequence
<220> FEATURE:
<223> OTHER INFORMATION: VH Domain of hPD-1 mAb 2 VH1

<400> SEQUENCE: 93

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Val Phe Ser Ser Phe
            20                  25                  30

Gly Met His Trp Val Arg Gln Ala Pro Gly Lys Gly Leu Glu Trp Val
        35                  40                  45

Ala Tyr Ile Ser Ser Gly Ser Met Ser Ile Ser Tyr Ala Asp Thr Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Thr Glu Asp Thr Ala Leu Tyr Tyr Cys
                85                  90                  95

Ala Ser Leu Ser Asp Tyr Phe Asp Tyr Trp Gly Gln Gly Thr Thr Val
            100                 105                 110

Thr Val Ser Ser
        115

<210> SEQ ID NO 94
<211> LENGTH: 348
<212> TYPE: DNA
<213> ORGANISM: Artificial Sequence
<220> FEATURE:
<223> OTHER INFORMATION: Polynucleotide Encoding hPD-1 mAb 2 VH1

<400> SEQUENCE: 94
gaagtgcaat tggttgagag tggtggtggc ctggtgcagc caggtggaag tctgcggttg      60
tcctgtgcag caagcggatt tgtgttcagc tcttttggga tgcattgggt gcgccaggct     120
cccggcaagg gtctcgagtg ggtagcatac atctccagcg ggtccatgtc tattagttat     180
gccgacacag tgaaaggcag gtttactatc tcccgtgaca atgcaaaaaa cacactgtac     240
ctgcaaatga atagcctgcg caccgaggac accgccttgt actactgcgc ttccctgtct     300
gattacttcg actactgggg tcagggcaca actgtgacag tttcttcc                 348

<210> SEQ ID NO 95
<211> LENGTH: 112
<212> TYPE: PRT
<213> ORGANISM: Artificial Sequence
<220> FEATURE:
<223> OTHER INFORMATION: VL Domain of hPD-1 mAb 2 VL1

<400> SEQUENCE: 95

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Thr Gly Asn Thr Tyr Leu His Trp Tyr Leu Gln Lys Pro Gly Gln Ser
        35                  40                  45

Pro Gln Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Thr
                85                  90                  95

Thr His Val Pro Trp Thr Phe Gly Gln Gly Thr Lys Leu Glu Ile Lys
            100                 105                 110

<210> SEQ ID NO 96
<211> LENGTH: 336
<212> TYPE: DNA
<213> ORGANISM: Artificial Sequence
<220> FEATURE:
<223> OTHER INFORMATION: Polynucleotide Encoding hPD-1 mAb 2 VL1

<400> SEQUENCE: 96
gacgttgtga tgacacagtc accactgagt ctgccagtta ccctgggcca gccagccagt      60
atttcttgtc ggagttcaca gagtctggta cattccacag gaaatacata tctccattgg     120
tacctgcaaa aaccagggca gagcccccag ctgctgattt atagagtgtc taatcgattt     180
tctggcgtgc cagatcggtt cagcggcagc gggtctggca ctgatttcac actgaaaatc     240
tctagggtgg aggcagagga cgtaggcgtt tactactgta gtcagaccac ccatgtaccc     300 tggactttg gccaaggtac taagctggaa atcaag    336

<210> SEQ ID NO 97
<211> LENGTH: 125
<212> TYPE: PRT
<213> ORGANISM: Mus musculus
<220> FEATURE:
<221> NAME/KEY: MISC_FEATURE
<222> LOCATION: (1)..(125)
<223> OTHER INFORMATION: VH Domain of PD-1 mAb 3

<400> SEQUENCE: 97

Gln Val Gln Leu Gln Gln Ser Gly Ala Glu Leu Val Arg Pro Gly Ala
1               5                   10                  15

Ser Val Thr Leu Ser Cys Lys Ala Ser Gly Tyr Thr Phe Thr Asp Tyr
            20                  25                  30

Val Met His Trp Val Lys Gln Thr Pro Val His Gly Leu Glu Trp Ile
        35                  40                  45

Gly Thr Ile Asp Pro Glu Thr Gly Gly Thr Ala Tyr Asn Gln Lys Phe
    50                  55                  60

Lys Gly Lys Ala Ile Leu Thr Ala Asp Lys Ser Ser Asn Thr Ala Tyr
65                  70                  75                  80

Met Glu Leu Arg Ser Leu Thr Ser Glu Asp Ser Ala Val Tyr Tyr Phe
                85                  90                  95

Thr Arg Glu Lys Ile Thr Thr Ile Val Glu Gly Thr Tyr Trp Tyr Phe
            100                 105                 110

Asp Val Trp Gly Thr Gly Thr Thr Val Thr Val Ser Ser
        115                 120                 125

<210> SEQ ID NO 98
<211> LENGTH: 375
<212> TYPE: DNA
<213> ORGANISM: Mus musculus
<220> FEATURE:
<221> NAME/KEY: misc_feature
<222> LOCATION: (1)..(375)
<223> OTHER INFORMATION: Polynucleotide Encoding the VH Domain of PD-1
      mAb 3

<400> SEQUENCE: 98
caggttcaac tgcaacagtc tggggctgag ctggtgaggc ctggggcttc agtgacgctg    60
tcctgcaagg cttcgggcta cacatttact gactatgtaa tgcactgggt gaagcagaca   120
cctgtgcatg gcctggaatg gattggaact attgatcctg aaactggtgg tactgcctac   180
aatcagaagt tcaagggcaa ggccatactg actgcagaca gtcctccaa cacagcctac    240 atggagctcc gcagcctgac atctgaggac tctgccgtct attactttac aagagagaag   300
attactacga tagtagaggg gacatactgg tacttcgatg tctggggcac agggaccacg   360
gtcaccgtct cctca                                                    375

<210> SEQ ID NO 99
<211> LENGTH: 5
<212> TYPE: PRT
<213> ORGANISM: Mus musculus
<220> FEATURE:
<221> NAME/KEY: MISC_FEATURE
<222> LOCATION: (1)..(5)
<223> OTHER INFORMATION: CDRH1 of PD-1 mAb 3

<400> SEQUENCE: 99

Asp Tyr Val Met His
1               5

<210> SEQ ID NO 100
<211> LENGTH: 17
<212> TYPE: PRT
<213> ORGANISM: Mus musculus
<220> FEATURE:
<221> NAME/KEY: MISC_FEATURE
<222> LOCATION: (1)..(17)
<223> OTHER INFORMATION: CDRH2 of PD-1 mAb 3

<400> SEQUENCE: 100

Thr Ile Asp Pro Glu Thr Gly Gly Thr Ala Tyr Asn Gln Lys Phe Lys
1               5                   10                  15

Gly

<210> SEQ ID NO 101
<211> LENGTH: 16
<212> TYPE: PRT
<213> ORGANISM: Mus musculus
<220> FEATURE:
<221> NAME/KEY: MISC_FEATURE
<222> LOCATION: (1)..(16)
<223> OTHER INFORMATION: CDRH3 of PD-1 mAb 3

<400> SEQUENCE: 101

Glu Lys Ile Thr Thr Ile Val Glu Gly Thr Tyr Trp Tyr Phe Asp Val
1               5                   10                  15

<210> SEQ ID NO 102
<211> LENGTH: 112
<212> TYPE: PRT
<213> ORGANISM: Mus musculus
<220> FEATURE:
<221> NAME/KEY: MISC_FEATURE
<222> LOCATION: (1)..(112)
<223> OTHER INFORMATION: VL Domain of PD-1 mAb 3

<400> SEQUENCE: 102

Asp Val Leu Leu Thr Gln Thr Pro Leu Ser Leu Pro Val Ser Leu Gly
1               5                   10                  15

Asp Gln Ala Ser Ile Ser Cys Arg Ser Ser Gln Asn Ile Val His Ser
                20                  25                  30

Asn Gly Asp Thr Tyr Leu Glu Trp Tyr Leu Gln Lys Pro Gly Gln Ser
            35                  40                  45

Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Leu Pro Tyr Thr Phe Gly Gly Gly Thr Lys Leu Glu Ile Lys
            100                 105                 110

<210> SEQ ID NO 103
<211> LENGTH: 336
<212> TYPE: DNA
<213> ORGANISM: Mus musculus
<220> FEATURE:
<221> NAME/KEY: misc_feature
<222> LOCATION: (1)..(336)
<223> OTHER INFORMATION: Polynucleotide Encoding the VL Domain of PD-1
      mAb 3

<400> SEQUENCE: 103

```
gatgttttgc tgacccaaac tccactctcc ctgcctgtca gtcttggaga tcaagcctcc    60
atctcttgca gatctagtca gaacattgta catagtaatg gagacaccta tttggaatgg   120
tacctgcaga aaccaggcca gtctccaaag ctcctgatct ataaagtttc caaccgattt   180
tctggggtcc cagacaggtt cagtggcagt gggtcaggga cagattttac actcaaaatc   240
agcagagtgg aggctgagga tctgggagtt tattactgct ttcaaggttc acatcttccg   300
tacacgttcg gaggggggac caagctggaa ataaaa                             336
```

<210> SEQ ID NO 104
<211> LENGTH: 16
<212> TYPE: PRT
<213> ORGANISM: Mus musculus
<220> FEATURE:
<221> NAME/KEY: MISC_FEATURE
<222> LOCATION: (1)..(16)
<223> OTHER INFORMATION: CDRL1 of PD-1 mAb 3

<400> SEQUENCE: 104

Arg Ser Ser Gln Asn Ile Val His Ser Asn Gly Asp Thr Tyr Leu Glu
 1               5                  10                  15

<210> SEQ ID NO 105
<211> LENGTH: 7
<212> TYPE: PRT
<213> ORGANISM: Mus musculus
<220> FEATURE:
<221> NAME/KEY: MISC_FEATURE
<222> LOCATION: (1)..(7)
<223> OTHER INFORMATION: CDRL2 of PD-1 mAb 3

<400> SEQUENCE: 105

Lys Val Ser Asn Arg Phe Ser
 1               5

<210> SEQ ID NO 106
<211> LENGTH: 9
<212> TYPE: PRT
<213> ORGANISM: Mus musculus
<220> FEATURE:
<221> NAME/KEY: MISC_FEATURE
<222> LOCATION: (1)..(9)
<223> OTHER INFORMATION: CDRL3 of PD-1 mAb 3

<400> SEQUENCE: 106

Phe Gln Gly Ser His Leu Pro Tyr Thr
 1               5

<210> SEQ ID NO 107
<211> LENGTH: 116
<212> TYPE: PRT
<213> ORGANISM: Mus musculus
<220> FEATURE:
<221> NAME/KEY: MISC_FEATURE
<222> LOCATION: (1)..(116)
<223> OTHER INFORMATION: VH Domain of PD-1 mAb 4

<400> SEQUENCE: 107

Asp Val Gln Leu Val Glu Ser Gly Gly Gly Leu Val Gln Pro Gly Gly
 1               5                  10                  15

Ser Arg Lys Leu Ser Cys Ala Ala Ser Gly Phe Val Phe Ser Ser Phe
                20                  25                  30

Gly Met His Trp Val Arg Gln Ala Pro Glu Lys Gly Leu Glu Trp Val
            35                  40                  45

Ala Tyr Ile Ser Ser Gly Ser Met Ser Ile Ser Tyr Ala Asp Thr Val

```
                50                  55                  60
Lys Gly Arg Phe Thr Val Thr Arg Asp Asn Ala Lys Asn Thr Leu Phe
65                  70                  75                  80

Leu Gln Met Thr Ser Leu Arg Ser Glu Asp Thr Ala Ile Tyr Tyr Cys
                85                  90                  95

Ala Ser Leu Thr Asp Tyr Phe Asp Tyr Trp Gly Gln Gly Thr Thr Leu
            100                 105                 110

Thr Val Ser Ser
        115

<210> SEQ ID NO 108
<211> LENGTH: 348
<212> TYPE: DNA
<213> ORGANISM: Mus musculus
<220> FEATURE:
<221> NAME/KEY: misc_feature
<222> LOCATION: (1)..(348)
<223> OTHER INFORMATION: Polynucleotide Encoding the VH Domain of PD-1
      mAb 4

<400> SEQUENCE: 108
gatgtgcagc tcgtggagtc tgggggaggc ttagtgcagc ctggagggtc ccggaaactc        60
tcctgtgcag cctctggatt cgttttcagt agctttggaa tgcactgggt tcgtcaggct       120
ccagagaagg ggctggagtg ggtcgcatat attagtagtg gcagtatgag tatttcctat       180
gcagacacag tgaagggccg attcaccgtc accagagaca atgccaagaa cacccttgttc      240 ctgcaaatga ccagtctaag gtctgaggac acggccattt attactgtgc atccctgact       300
gactactttg actactgggg ccaaggcacc actctcacag tctcctca                    348

<210> SEQ ID NO 109
<211> LENGTH: 5
<212> TYPE: PRT
<213> ORGANISM: Mus musculus
<220> FEATURE:
<221> NAME/KEY: MISC_FEATURE
<222> LOCATION: (1)..(5)
<223> OTHER INFORMATION: CDRH1 of PD-1 mAb 4

<400> SEQUENCE: 109

Ser Phe Gly Met His
1               5

<210> SEQ ID NO 110
<211> LENGTH: 17
<212> TYPE: PRT
<213> ORGANISM: Mus musculus
<220> FEATURE:
<221> NAME/KEY: MISC_FEATURE
<222> LOCATION: (1)..(17)
<223> OTHER INFORMATION: CDRH2 of PD-1 mAb 4

<400> SEQUENCE: 110

Tyr Ile Ser Ser Gly Ser Met Ser Ile Ser Tyr Ala Asp Thr Val Lys
1               5                   10                  15

Gly

<210> SEQ ID NO 111
<211> LENGTH: 7
<212> TYPE: PRT
<213> ORGANISM: Mus musculus
<220> FEATURE:
<221> NAME/KEY: MISC_FEATURE
<222> LOCATION: (1)..(7)
```

<223> OTHER INFORMATION: CDRH3 of PD-1 mAb 4

<400> SEQUENCE: 111

Leu Thr Asp Tyr Phe Asp Tyr
1               5

<210> SEQ ID NO 112
<211> LENGTH: 112
<212> TYPE: PRT
<213> ORGANISM: Mus musculus
<220> FEATURE:
<221> NAME/KEY: MISC_FEATURE
<222> LOCATION: (1)..(112)
<223> OTHER INFORMATION: VL Domain of PD-1 mAb 4

<400> SEQUENCE: 112

Asp Val Val Met Ser Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Thr Gly Asn Thr Tyr Phe His Trp Tyr Leu Gln Lys Pro Gly Gln Ser
        35                  40                  45

Pro Lys Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Thr
                85                  90                  95

Thr His Val Pro Trp Thr Phe Gly Gly Gly Thr Lys Leu Glu Ile Lys
            100                 105                 110

<210> SEQ ID NO 113
<211> LENGTH: 336
<212> TYPE: DNA
<213> ORGANISM: Mus musculus
<220> FEATURE:
<221> NAME/KEY: misc_feature
<222> LOCATION: (1)..(336)
<223> OTHER INFORMATION: Polynucleotide Encoding the VL Domain of PD-1
      mAb

<400> SEQUENCE: 113
gatgttgtga tgtcccaaac tccactctcc ctgcctgtca gtcttggaga tcaagcctcc    60
atctcctgca gatctagtca gagccttgtt cacagtactg gaaacaccta tttccattgg   120
tacctgcaga agccaggcca gtctccaaag ctcctgatct acagggtttc taaccgattt   180
tctggggtcc ccgacaggtt cagtggcagt ggatcaggga cagatttcac actcaagatc   240
agcagagtgg aggctgagga tctgggagtt tatttctgct ctcaaactac acatgttccg   300
tggacgttcg gtggaggcac caagctggaa atcaaa                             336

<210> SEQ ID NO 114
<211> LENGTH: 16
<212> TYPE: PRT
<213> ORGANISM: Mus musculus
<220> FEATURE:
<221> NAME/KEY: MISC_FEATURE
<222> LOCATION: (1)..(16)
<223> OTHER INFORMATION: CDRL1 of PD-1 mAb 4

<400> SEQUENCE: 114

Arg Ser Ser Gln Ser Leu Val His Ser Thr Gly Asn Thr Tyr Phe His
1               5                   10                  15

<210> SEQ ID NO 115
<211> LENGTH: 7
<212> TYPE: PRT
<213> ORGANISM: Mus musculus
<220> FEATURE:
<221> NAME/KEY: MISC_FEATURE
<222> LOCATION: (1)..(7)
<223> OTHER INFORMATION: CDRL2 of PD-1 mAb 4

<400> SEQUENCE: 115

Arg Val Ser Asn Arg Phe Ser
1               5

<210> SEQ ID NO 116
<211> LENGTH: 9
<212> TYPE: PRT
<213> ORGANISM: Mus musculus
<220> FEATURE:
<221> NAME/KEY: MISC_FEATURE
<222> LOCATION: (1)..(9)
<223> OTHER INFORMATION: CDRL3 of PD-1 mAb 4

<400> SEQUENCE: 116

Ser Gln Thr Thr His Val Pro Trp Thr
1               5

<210> SEQ ID NO 117
<211> LENGTH: 119
<212> TYPE: PRT
<213> ORGANISM: Mus musculus
<220> FEATURE:
<221> NAME/KEY: MISC_FEATURE
<222> LOCATION: (1)..(119)
<223> OTHER INFORMATION: VH Domain of PD-1 mAb 5

<400> SEQUENCE: 117

Gln Val Gln Leu Gln Gln Pro Gly Val Glu Leu Val Arg Pro Gly Ala
1               5                   10                  15

Ser Val Lys Leu Ser Cys Lys Ala Ser Gly Tyr Ser Phe Thr Ala Tyr
            20                  25                  30

Trp Met Asn Trp Met Lys Gln Arg Pro Gly Gln Gly Leu Glu Trp Ile
        35                  40                  45

Gly Val Ile His Pro Ser Asp Ser Glu Thr Trp Leu Asn Gln Lys Phe
    50                  55                  60

Lys Asp Lys Ala Thr Leu Thr Val Asp Lys Ser Ser Ser Thr Ala Tyr
65                  70                  75                  80

Met Gln Leu Ile Ser Pro Thr Ser Glu Asp Ser Ala Val Tyr Tyr Cys
                85                  90                  95

Ala Arg Glu His Tyr Gly Ser Ser Pro Phe Ala Tyr Trp Gly Gln Gly
            100                 105                 110

Thr Leu Val Thr Val Ser Ala
        115

<210> SEQ ID NO 118
<211> LENGTH: 357
<212> TYPE: DNA
<213> ORGANISM: Mus musculus
<220> FEATURE:
<221> NAME/KEY: misc_feature
<222> LOCATION: (1)..(357)
<223> OTHER INFORMATION: Polynucleotide Encoding the VH Domain of PD-1
      mAb 5

<400> SEQUENCE: 118

```
caggtccaac tgcagcagcc tggggttgaa ctggtgaggc ctggagcttc agtgaagctg      60
tcctgcaagg cttctggcta ctccttcacc gcctactgga tgaactggat gaaacagagg     120
cctggacaag gccttgagtg gattggcgtg attcatcctt ccgatagtga aacttggtta     180
aatcagaagt tcaaggacaa ggccacattg actgtagaca atcctccag cacagcctac      240 atgcaactca tcagcccgac atctgaggac tctgcggtct attactgtgc aagagagcac     300
tacggtagta gcccgtttgc ttactggggc caagggactc tggtcactgt ctctgca        357

<210> SEQ ID NO 119
<211> LENGTH: 5
<212> TYPE: PRT
<213> ORGANISM: Mus musculus
<220> FEATURE:
<221> NAME/KEY: MISC_FEATURE
<222> LOCATION: (1)..(5)
<223> OTHER INFORMATION: CDRH1 of PD-1 mAb 5

<400> SEQUENCE: 119

Ala Tyr Trp Met Asn
1               5

<210> SEQ ID NO 120
<211> LENGTH: 17
<212> TYPE: PRT
<213> ORGANISM: Mus musculus
<220> FEATURE:
<221> NAME/KEY: MISC_FEATURE
<222> LOCATION: (1)..(17)
<223> OTHER INFORMATION: CDRH2 of PD-1 mAb 5

<400> SEQUENCE: 120

Val Ile His Pro Ser Asp Ser Glu Thr Trp Leu Asn Gln Lys Phe Lys
1               5                   10                  15

Asp

<210> SEQ ID NO 121
<211> LENGTH: 10
<212> TYPE: PRT
<213> ORGANISM: Mus musculus
<220> FEATURE:
<221> NAME/KEY: MISC_FEATURE
<222> LOCATION: (1)..(10)
<223> OTHER INFORMATION: CDRH3 of PD-1 mAb 5

<400> SEQUENCE: 121

Glu His Tyr Gly Ser Ser Pro Phe Ala Tyr
1               5                   10

<210> SEQ ID NO 122
<211> LENGTH: 111
<212> TYPE: PRT
<213> ORGANISM: Mus musculus
<220> FEATURE:
<221> NAME/KEY: MISC_FEATURE
<222> LOCATION: (1)..(111)
<223> OTHER INFORMATION: VL Domain of PD-1 mAb 5

<400> SEQUENCE: 122

Asp Ile Val Leu Thr Gln Ser Pro Ala Ser Leu Ala Val Ser Leu Gly
1               5                   10                  15

Gln Arg Ala Thr Ile Ser Cys Arg Ala Asn Glu Ser Val Asp Asn Tyr
            20                  25                  30

Gly Met Ser Phe Met Asn Trp Phe Gln Gln Lys Pro Gly Gln Pro Pro
```

35                  40                  45
Lys Leu Leu Ile Tyr Ala Ala Ser Asn Gln Gly Ser Gly Val Pro Ala
 50                  55                  60

Arg Phe Ser Gly Ser Gly Ser Gly Thr Asp Phe Ser Leu Asn Ile His
 65                  70                  75                  80

Pro Met Glu Glu Asp Asp Thr Ala Met Tyr Phe Cys Gln Gln Ser Lys
                 85                  90                  95

Glu Val Pro Tyr Thr Phe Gly Gly Gly Thr Lys Leu Glu Ile Lys
                100                 105                 110

<210> SEQ ID NO 123
<211> LENGTH: 333
<212> TYPE: DNA
<213> ORGANISM: Mus musculus
<220> FEATURE:
<221> NAME/KEY: misc_feature
<222> LOCATION: (1)..(333)
<223> OTHER INFORMATION: Polynucleotide Encoding the VL Domain of PD-1
      mAb 5

<400> SEQUENCE: 123
gacattgtgc tgacccaatc tccagcttct ttggctgtgt ctctagggca gagggccacc      60
atctcctgca gagccaacga aagtgttgat aattatggca tgagttttat gaactggttc     120
caacagaaac caggacagcc acccaaactc ctcatctatg ctgcatccaa ccaaggatcc     180
ggggtccctg ccaggtttag tggcagtggg tctgggacag atttcagcct caacatccat     240
cctatggagg aggatgatac tgcaatgtat ttctgtcagc aaagtaagga ggttccgtac     300
acgttcggag gggggaccaa gctggaaata aaa                                  333

<210> SEQ ID NO 124
<211> LENGTH: 15
<212> TYPE: PRT
<213> ORGANISM: Mus musculus
<220> FEATURE:
<221> NAME/KEY: MISC_FEATURE
<222> LOCATION: (1)..(15)
<223> OTHER INFORMATION: CDRL1 of PD-1 mAb 5

<400> SEQUENCE: 124

Arg Ala Asn Glu Ser Val Asp Asn Tyr Gly Met Ser Phe Met Asn
 1               5                  10                  15

<210> SEQ ID NO 125
<211> LENGTH: 7
<212> TYPE: PRT
<213> ORGANISM: Mus musculus
<220> FEATURE:
<221> NAME/KEY: MISC_FEATURE
<222> LOCATION: (1)..(7)
<223> OTHER INFORMATION: CDRL2 of PD-1 mAb 5

<400> SEQUENCE: 125

Ala Ala Ser Asn Gln Gly Ser
 1               5

<210> SEQ ID NO 126
<211> LENGTH: 9
<212> TYPE: PRT
<213> ORGANISM: Mus musculus
<220> FEATURE:
<221> NAME/KEY: MISC_FEATURE
<222> LOCATION: (1)..(9)
<223> OTHER INFORMATION: CDRL3 of PD-1 mAb 5

<400> SEQUENCE: 126

Gln Gln Ser Lys Glu Val Pro Tyr Thr
1               5

<210> SEQ ID NO 127
<211> LENGTH: 118
<212> TYPE: PRT
<213> ORGANISM: Mus musculus
<220> FEATURE:
<221> NAME/KEY: MISC_FEATURE
<222> LOCATION: (1)..(118)
<223> OTHER INFORMATION: VH Domain of PD-1 mAb 6

<400> SEQUENCE: 127

Glu Val Lys Leu Val Glu Ser Gly Gly Gly Leu Val Asn Pro Gly Gly
1               5                   10                  15

Ser Leu Lys Leu Ser Cys Ala Ala Ser Gly Phe Thr Phe Ser Ser Tyr
            20                  25                  30

Gly Met Ser Trp Val Arg Gln Thr Pro Glu Lys Arg Leu Glu Trp Val
        35                  40                  45

Ala Thr Ile Ser Gly Gly Ser Asp Thr Tyr Tyr Pro Asp Ser Val
    50                  55                  60

Lys Gly Arg Phe Thr Ile Ser Arg Asp Asn Ala Lys Asn Asn Leu Tyr
65                  70                  75                  80

Leu Gln Met Ser Ser Leu Arg Ser Glu Asp Thr Ala Leu Tyr Tyr Cys
                85                  90                  95

Ala Arg Gln Lys Ala Thr Thr Trp Phe Ala Tyr Trp Gly Gln Gly Thr
            100                 105                 110

Leu Val Thr Val Ser Thr
        115

<210> SEQ ID NO 128
<211> LENGTH: 333
<212> TYPE: DNA
<213> ORGANISM: Mus musculus
<220> FEATURE:
<221> NAME/KEY: misc_feature
<222> LOCATION: (1)..(333)
<223> OTHER INFORMATION: Polynucleotide Encoding the VH Domain of PD-1
      mAb 6

<400> SEQUENCE: 128
gaaatcgtac tcacccagtc acctgcaacc ctttctctga gcccggtga  acgtgccact    60 ctcagctgca gagcaagtga gagtgtggac aattacggca tgtccttcat gaactggttt   120
cagcagaagc ctgggcagcc acctaagctg ctcatccacg ccgcctctaa ccgcggatct   180
ggggtgcctt cacgttttc tggatcagga agtggcactg acttcaccct tacaatcagc   240
tctctggagc cagaggactt tgccgtctat ttctgccagc aatctaaaga ggtgccctat   300
acttttggtg gcgggaccaa ggttgagatc aaa                                333

<210> SEQ ID NO 129
<211> LENGTH: 5
<212> TYPE: PRT
<213> ORGANISM: Mus musculus
<220> FEATURE:
<221> NAME/KEY: MISC_FEATURE
<222> LOCATION: (1)..(5)
<223> OTHER INFORMATION: CDRH1 of PD-1 mAb 6

<400> SEQUENCE: 129

Ser Tyr Gly Met Ser

<210> SEQ ID NO 130
<211> LENGTH: 17
<212> TYPE: PRT
<213> ORGANISM: Mus musculus
<220> FEATURE:
<221> NAME/KEY: MISC_FEATURE
<222> LOCATION: (1)..(17)
<223> OTHER INFORMATION: CDRH2 of PD-1 mAb 6

<400> SEQUENCE: 130

Thr Ile Ser Gly Gly Gly Ser Asp Thr Tyr Tyr Pro Asp Ser Val Lys
1               5                   10                  15

Gly

<210> SEQ ID NO 131
<211> LENGTH: 9
<212> TYPE: PRT
<213> ORGANISM: Mus musculus
<220> FEATURE:
<221> NAME/KEY: MISC_FEATURE
<222> LOCATION: (1)..(9)
<223> OTHER INFORMATION: CDRH3 of PD-1 mAb 6

<400> SEQUENCE: 131

Gln Lys Ala Thr Thr Trp Phe Ala Tyr
1               5

<210> SEQ ID NO 132
<211> LENGTH: 111
<212> TYPE: PRT
<213> ORGANISM: Mus musculus
<220> FEATURE:
<221> NAME/KEY: MISC_FEATURE
<222> LOCATION: (1)..(111)
<223> OTHER INFORMATION: VL Domain of PD-1 mAb 6

<400> SEQUENCE: 132

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
            20                  25                  30

Gly Ile Ser Phe Met Asn Trp Phe Gln Gln Lys Pro Gly Gln Pro Pro
        35                  40                  45

Lys Leu Leu Ile Tyr Pro Ala Ser Asn Gln Gly Ser Gly Val Pro Ala
    50                  55                  60

Arg Phe Ser Gly Ser Gly Ser Gly Thr Asp Phe Ser Leu Asn Ile His
65                  70                  75                  80

Pro Met Glu Glu Asp Asp Ala Ala Met Tyr Phe Cys Gln Gln Ser Lys
                85                  90                  95

Glu Val Pro Trp Thr Phe Gly Gly Gly Thr Lys Leu Glu Ile Lys
            100                 105                 110

<210> SEQ ID NO 133
<211> LENGTH: 333
<212> TYPE: DNA
<213> ORGANISM: Mus musculus
<220> FEATURE:
<221> NAME/KEY: misc_feature
<222> LOCATION: (1)..(333)
<223> OTHER INFORMATION: Polynucleotide Encoding the VL Domain of PD-1
      mAb 6

<400> SEQUENCE: 133

```
gacattgtgc tgacccaatc tccagcttct ttggctgtgt ctctagggca gagggccacc      60
atctcctgca gagccagcga aagtgttgat aattatggca ttagttttat gaactggttc     120
caacagaaac caggacagcc acccaaactc ctcatctatc ctgcatccaa ccaaggatcc     180
ggggtccctg ccaggtttag tggcagtggg tctgggacag acttcagcct caacatccat     240
cctatggagg aggatgatgc tgcaatgtat ttctgtcagc aaagtaagga ggttccgtgg     300
acgttcggtg aggcaccaa gctggaaatc aaa                                    333
```

<210> SEQ ID NO 134
<211> LENGTH: 15
<212> TYPE: PRT
<213> ORGANISM: Mus musculus
<220> FEATURE:
<221> NAME/KEY: MISC_FEATURE
<222> LOCATION: (1)..(15)
<223> OTHER INFORMATION: CDRL1 of PD-1 mAb 6

<400> SEQUENCE: 134

Arg Ala Ser Glu Ser Val Asp Asn Tyr Gly Ile Ser Phe Met Asn
1               5                   10                  15

<210> SEQ ID NO 135
<211> LENGTH: 7
<212> TYPE: PRT
<213> ORGANISM: Mus musculus
<220> FEATURE:
<221> NAME/KEY: MISC_FEATURE
<222> LOCATION: (1)..(7)
<223> OTHER INFORMATION: CDRL2 of PD-1 mAb 6

<400> SEQUENCE: 135

Pro Ala Ser Asn Gln Gly Ser
1               5

<210> SEQ ID NO 136
<211> LENGTH: 9
<212> TYPE: PRT
<213> ORGANISM: Mus musculus
<220> FEATURE:
<221> NAME/KEY: MISC_FEATURE
<222> LOCATION: (1)..(9)
<223> OTHER INFORMATION: CDRL3 of PD-1 mAb 6

<400> SEQUENCE: 136

Gln Gln Ser Lys Glu Val Pro Trp Thr
1               5

<210> SEQ ID NO 137
<211> LENGTH: 119
<212> TYPE: PRT
<213> ORGANISM: Mus musculus
<220> FEATURE:
<221> NAME/KEY: MISC_FEATURE
<222> LOCATION: (1)..(119)
<223> OTHER INFORMATION: VH Domain of PD-1 mAb 7

<400> SEQUENCE: 137

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Ser Phe Thr Ser Tyr
                20                  25                  30

Trp Met Asn Trp Val Lys Gln Arg Pro Gly Gln Gly Leu Glu Trp Ile
            35                  40                  45

Gly Val Ile His Pro Ser Asp Ser Glu Thr Trp Leu Asp Gln Lys Phe
    50                  55                  60

Lys Asp Lys Ala Thr Leu Thr Val Asp Lys Ser Ser Thr Thr Ala Tyr
65                  70                  75                  80

Met Gln Leu Ile Ser Pro Thr Ser Glu Asp Ser Ala Val Tyr Tyr Cys
                85                  90                  95

Ala Arg Glu His Tyr Gly Thr Ser Pro Phe Ala Tyr Trp Gly Gln Gly
            100                 105                 110

Thr Leu Val Thr Val Ser Ser
        115

<210> SEQ ID NO 138
<211> LENGTH: 357
<212> TYPE: DNA
<213> ORGANISM: Mus musculus
<220> FEATURE:
<221> NAME/KEY: misc_feature
<222> LOCATION: (1)..(357)
<223> OTHER INFORMATION: Polynucleotide Encoding the VH Domain of PD-1
      mAb 7

<400> SEQUENCE: 138
gaggtccaac tgcagcagcc tggggctgaa ctggtgaggc ctggagcttc agtgaagctg       60
tcctgcaagg cttctggcta ctccttcacc agctactgga tgaactgggt gaagcagagg      120
cctggacaag gccttgagtg gattggcgtg attcatcctt ccgatagtga aacttggtta      180
gatcagaagt tcaaggacaa ggccacattg actgtagaca atcctccac cacagcctac       240 atgcaactca tcagcccgac atctgaggac tctgcggtct attactgtgc aagggagcac      300
tacggtacta gcccgtttgc ttactggggc caagggactc tggtcactgt gtcttcc         357

<210> SEQ ID NO 139
<211> LENGTH: 5
<212> TYPE: PRT
<213> ORGANISM: Mus musculus
<220> FEATURE:
<221> NAME/KEY: MISC_FEATURE
<222> LOCATION: (1)..(5)
<223> OTHER INFORMATION: CDRH1 of PD-1 mAb 7

<400> SEQUENCE: 139

Ser Tyr Trp Met Asn
1               5

<210> SEQ ID NO 140
<211> LENGTH: 17
<212> TYPE: PRT
<213> ORGANISM: Mus musculus
<220> FEATURE:
<221> NAME/KEY: MISC_FEATURE
<222> LOCATION: (1)..(17)
<223> OTHER INFORMATION: CDRH2 of PD-1 mAb 7

<400> SEQUENCE: 140

Val Ile His Pro Ser Asp Ser Glu Thr Trp Leu Asp Gln Lys Phe Lys
1               5                   10                  15

Asp

<210> SEQ ID NO 141
<211> LENGTH: 10
<212> TYPE: PRT
<213> ORGANISM: Mus musculus
<220> FEATURE:
<221> NAME/KEY: MISC_FEATURE

```
<222> LOCATION: (1)..(10)
<223> OTHER INFORMATION: CDRH3 of PD-1 mAb 7

<400> SEQUENCE: 141

Glu His Tyr Gly Thr Ser Pro Phe Ala Tyr
1               5                   10

<210> SEQ ID NO 142
<211> LENGTH: 111
<212> TYPE: PRT
<213> ORGANISM: Mus musculus
<220> FEATURE:
<221> NAME/KEY: MISC_FEATURE
<222> LOCATION: (1)..(111)
<223> OTHER INFORMATION: VL Domain of PD-1 mAb 7

<400> SEQUENCE: 142

Asp Ile Val Leu Thr Gln Ser Pro Ala Ser Leu Ala Val Ser Leu Gly
1               5                   10                  15

Gln Arg Ala Thr Ile Ser Cys Arg Ala Asn Glu Ser Val Asp Asn Tyr
            20                  25                  30

Gly Met Ser Phe Met Asn Trp Phe Gln Gln Lys Pro Gly Gln Pro Pro
        35                  40                  45

Lys Leu Leu Ile His Ala Ala Ser Asn Gln Gly Ser Gly Val Pro Ala
    50                  55                  60

Arg Phe Ser Gly Ser Gly Phe Gly Thr Asp Phe Ser Leu Asn Ile His
65                  70                  75                  80

Pro Met Glu Glu Asp Asp Ala Ala Met Tyr Phe Cys Gln Gln Ser Lys
                85                  90                  95

Glu Val Pro Tyr Thr Phe Gly Gly Gly Thr Lys Leu Glu Ile Lys
            100                 105                 110

<210> SEQ ID NO 143
<211> LENGTH: 333
<212> TYPE: DNA
<213> ORGANISM: Mus musculus
<220> FEATURE:
<221> NAME/KEY: misc_feature
<222> LOCATION: (1)..(333)
<223> OTHER INFORMATION: Polynucleotide Encoding the VL Domain of PD-1
      mAb 7

<400> SEQUENCE: 143
gacattgtgc tgacccaatc tccagcttct ttggctgtgt ctctagggca gagggccacc        60
atctcctgca gagccaacga aagtgttgat aattatggca tgagttttat gaactggttc      120
caacagaaac caggacagcc acccaaactc ctcatccatg ctgcatccaa ccaaggatcc      180
ggggtccctg ccaggtttag tggcagtggg tttgggacag acttcagcct caacatccat      240
cctatggagg aggatgatgc tgcaatgtat ttctgtcagc aaagtaagga ggttccgtac      300
acgttcggag gggggaccaa gctggaaata aaa                                   333

<210> SEQ ID NO 144
<211> LENGTH: 15
<212> TYPE: PRT
<213> ORGANISM: Mus musculus
<220> FEATURE:
<221> NAME/KEY: MISC_FEATURE
<222> LOCATION: (1)..(15)
<223> OTHER INFORMATION: CDRL1 of PD-1 mAb 7

<400> SEQUENCE: 144

Arg Ala Asn Glu Ser Val Asp Asn Tyr Gly Met Ser Phe Met Asn
```

<210> SEQ ID NO 145
<211> LENGTH: 7
<212> TYPE: PRT
<213> ORGANISM: Mus musculus
<220> FEATURE:
<221> NAME/KEY: MISC_FEATURE
<222> LOCATION: (1)..(7)
<223> OTHER INFORMATION: CDRL2 of PD-1 mAb 7

<400> SEQUENCE: 145

Ala Ala Ser Asn Gln Gly Ser
1               5

<210> SEQ ID NO 146
<211> LENGTH: 9
<212> TYPE: PRT
<213> ORGANISM: Mus musculus
<220> FEATURE:
<221> NAME/KEY: MISC_FEATURE
<222> LOCATION: (1)..(9)
<223> OTHER INFORMATION: CDRL3 of PD-1 mAb 7

<400> SEQUENCE: 146

Gln Gln Ser Lys Glu Val Pro Tyr Thr
1               5

<210> SEQ ID NO 147
<211> LENGTH: 119
<212> TYPE: PRT
<213> ORGANISM: Artificial Sequence
<220> FEATURE:
<223> OTHER INFORMATION: VH Domain of hPD-1 mAb 7 VH1

<400> SEQUENCE: 147

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Tyr
            20                  25                  30

Trp Met Asn Trp Val Arg Gln Ala Pro Gly Gln Gly Leu Glu Trp Ile
        35                  40                  45

Gly Val Ile His Pro Ser Asp Ser Glu Thr Trp Leu Asp Gln Lys Phe
    50                  55                  60

Lys Asp Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu His Tyr Gly Thr Ser Pro Phe Ala Tyr Trp Gly Gln Gly
            100                 105                 110

Thr Leu Val Thr Val Ser Ser
        115

<210> SEQ ID NO 148
<211> LENGTH: 357
<212> TYPE: DNA
<213> ORGANISM: Artificial Sequence
<220> FEATURE:
<223> OTHER INFORMATION: Polynucleotide Encoding hPD-1 mAb 7 VH1

<400> SEQUENCE: 148
caagttcaat tggtacagag cggggcagag gtgaagaaac ccggcgccag tgttaaggtg      60
tcctgcaaag ccagcggtta cagctttaca agctattgga tgaattgggt gcgtcaagca     120

```
ccagggcagg gtctggaatg gattggggtg atacatcctt ctgacagcga aacatggttg      180
gaccagaaat ttaaagatcg tgtgacaatt acagtcgata agtccacaag cactgcttac      240
atggaactct ccagcttgcg gtccgaggac accgctgtgt attattgcgc cagagagcac      300
tacggcacat cacctttttgc atactggggc agggaactc tcgtaaccgt atcctcc        357
```

<210> SEQ ID NO 149
<211> LENGTH: 119
<212> TYPE: PRT
<213> ORGANISM: Artificial Sequence
<220> FEATURE:
<223> OTHER INFORMATION: VH Domain of hPD-1 mAb 7 VH2

<400> SEQUENCE: 149

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Ser Phe Thr Ser Tyr
            20                  25                  30

Trp Met Asn Trp Val Arg Gln Ala Pro Gly Gln Gly Leu Glu Trp Ala
        35                  40                  45

Gly Val Ile His Pro Ser Asp Ser Glu Thr Trp Leu Asp Gln Lys Phe
    50                  55                  60

Lys Asp Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu His Tyr Gly Thr Ser Pro Phe Ala Tyr Trp Gly Gln Gly
            100                 105                 110

Thr Leu Val Thr Val Ser Ser
        115
```

<210> SEQ ID NO 150
<211> LENGTH: 357
<212> TYPE: DNA
<213> ORGANISM: Artificial Sequence
<220> FEATURE:
<223> OTHER INFORMATION: Polynucleotide Encoding hPD-1 mAb 7 VH2

<400> SEQUENCE: 150

```
caagttcaat tggtacagag cgggggcagag gtgaagaaac ccggcgccag tgttaaggtg      60
tcctgcaaag ccagcggtta cagctttaca agctattgga tgaattgggt gcgtcaagca     120
ccagggcagg gtctggaatg ggctggggtg atacatcctt ctgacagcga aacatggttg     180
gaccagaaat ttaaagatcg tgtgacaatt acagtcgata agtccacaag cactgcttac     240
atggaactct ccagcttgcg gtccgaggac accgctgtgt attattgcgc cagagagcac     300
tacggcacat cacctttttgc atactggggc agggaactc tcgtaaccgt atcctcc        357
```

<210> SEQ ID NO 151
<211> LENGTH: 111
<212> TYPE: PRT
<213> ORGANISM: Artificial Sequence
<220> FEATURE:
<223> OTHER INFORMATION: VL Domain of hPD-1 mAb 7 VL1

<400> SEQUENCE: 151

```
Glu Ile Val Leu Thr Gln Ser Pro Ala Thr Leu Ser Leu Ser Pro Gly
 1               5                  10                  15

Glu Arg Ala Thr Leu Ser Cys Arg Ala Asn Glu Ser Val Asp Asn Tyr
```

```
            20                  25                  30
Gly Met Ser Phe Met Asn Trp Phe Gln Gln Lys Pro Gly Gln Pro Pro
            35                  40                  45

Lys Leu Leu Ile His Ala Ala Ser Asn Gln Gly Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Phe Cys Gln Gln Ser Lys
                85                  90                  95

Glu Val Pro Tyr Thr Phe Gly Gly Gly Thr Lys Val Glu Ile Lys
                100                 105                 110

<210> SEQ ID NO 152
<211> LENGTH: 333
<212> TYPE: DNA
<213> ORGANISM: Artificial Sequence
<220> FEATURE:
<223> OTHER INFORMATION: Polynucleotide Encoding hPD-1 mAb 7 VL1

<400> SEQUENCE: 152
gaaatcgtac tcacccagtc acctgcaacc ctttctctga gccccggtga acgtgccact      60
ctcagctgca gagcaaatga gagtgtggac aattacggca tgtccttcat gaactggttt     120
cagcagaagc ctgggcagcc acctaagctg ctcatccacg ccgcctctaa ccagggatct     180
ggggtgcctt cacgtttttc tggatcagga agtggcactg acttcaccct acaatcagc     240 tctctggagc cagaggactt tgccgtctat ttctgccagc aatctaaaga ggtgccctat     300
acttttggtg gcgggaccaa ggttgagatc aaa                                  333

<210> SEQ ID NO 153
<211> LENGTH: 111
<212> TYPE: PRT
<213> ORGANISM: Artificial Sequence
<220> FEATURE:
<223> OTHER INFORMATION: VL Domain of hPD-1 mAb 7 VL2

<400> SEQUENCE: 153

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Asp Asn Tyr
            20                  25                  30

Gly Met Ser Phe Met Asn Trp Phe Gln Gln Lys Pro Gly Gln Pro Pro
            35                  40                  45

Lys Leu Leu Ile His Ala Ala Ser Asn Gln Gly Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Phe Cys Gln Gln Ser Lys
                85                  90                  95

Glu Val Pro Tyr Thr Phe Gly Gly Gly Thr Lys Val Glu Ile Lys
                100                 105                 110

<210> SEQ ID NO 154
<211> LENGTH: 333
<212> TYPE: DNA
<213> ORGANISM: Artificial Sequence
<220> FEATURE:
<223> OTHER INFORMATION: Polynucleotide Encoding hPD-1 mAb 7 VL2

<400> SEQUENCE: 154
```

```
gaaatcgtac tcacccagtc acctgcaacc ctttctctga gccccggtga acgtgccact    60
ctcagctgca gagcaagtga gagtgtggac aattacggca tgtccttcat gaactggttt   120
cagcagaagc ctgggcagcc acctaagctg ctcatccacg ccgcctctaa ccagggatct   180
ggggtgcctt cacgttttc tggatcagga agtggcactg acttcaccct tacaatcagc    240
tctctggagc cagaggactt tgccgtctat ttctgccagc aatctaaaga ggtgccctat   300
acttttggtg gcgggaccaa ggttgagatc aaa                                333
```

```
<210> SEQ ID NO 155
<211> LENGTH: 111
<212> TYPE: PRT
<213> ORGANISM: Artificial Sequence
<220> FEATURE:
<223> OTHER INFORMATION: VL Domain of hPD-1 mAb 7 VL3

<400> SEQUENCE: 155
```

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Asp Asn Tyr
            20                  25                  30

Gly Met Ser Phe Met Asn Trp Phe Gln Gln Lys Pro Gly Gln Pro Pro
        35                  40                  45

Lys Leu Leu Ile His Ala Ala Ser Asn Arg Gly Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Phe Cys Gln Gln Ser Lys
                85                  90                  95

Glu Val Pro Tyr Thr Phe Gly Gly Gly Thr Lys Val Glu Ile Lys
            100                 105                 110
```

```
<210> SEQ ID NO 156
<211> LENGTH: 333
<212> TYPE: DNA
<213> ORGANISM: Artificial Sequence
<220> FEATURE:
<223> OTHER INFORMATION: Polynucleotide Encoding hPD-1 mAb 7 VL3

<400> SEQUENCE: 156
```

```
gaaatcgtac tcacccagtc acctgcaacc ctttctctga gccccggtga acgtgccact    60
ctcagctgca gagcaagtga gagtgtggac aattacggca tgtccttcat gaactggttt   120
cagcagaagc ctgggcagcc acctaagctg ctcatccacg ccgcctctaa ccgcggatct   180
ggggtgcctt cacgttttc tggatcagga agtggcactg acttcaccct tacaatcagc    240
tctctggagc cagaggactt tgccgtctat ttctgccagc aatctaaaga ggtgccctat   300
acttttggtg gcgggaccaa ggttgagatc aaa                                333
```

```
<210> SEQ ID NO 157
<211> LENGTH: 15
<212> TYPE: PRT
<213> ORGANISM: Artificial Sequence
<220> FEATURE:
<223> OTHER INFORMATION: CDRL1 of the VL Domain of hPD-1 mAb 7 VL2 and
      hPD-1 mAb 7 VL3

<400> SEQUENCE: 157
```

```
Arg Ala Ser Glu Ser Val Asp Asn Tyr Gly Met Ser Phe Met Asn
1               5                   10                  15
```

<210> SEQ ID NO 158
<211> LENGTH: 7
<212> TYPE: PRT
<213> ORGANISM: Artificial Sequence
<220> FEATURE:
<223> OTHER INFORMATION: CDRL2 of the VL Domain of hPD-1 mAb 7 VL3

<400> SEQUENCE: 158

Ala Ala Ser Asn Arg Gly Ser
1               5

<210> SEQ ID NO 159
<211> LENGTH: 113
<212> TYPE: PRT
<213> ORGANISM: Mus musculus
<220> FEATURE:
<221> NAME/KEY: MISC_FEATURE
<222> LOCATION: (1)..(113)
<223> OTHER INFORMATION: VH Domain of PD-1 mAb 8

<400> SEQUENCE: 159

Glu Gly Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Tyr Met Asn Trp Val Lys Gln Asn His Gly Lys Ser Leu Glu Trp Ile
        35                  40                  45

Gly Asp Ile Asn Pro Lys Asn Gly Asp Thr His Tyr Asn Gln Lys Phe
    50                  55                  60

Lys Gly Glu Ala Thr Leu Thr Val Asp Lys Ser Ser Thr Thr Ala Tyr
65                  70                  75                  80

Met Glu Leu Arg Ser Leu Thr Ser Glu Asp Ser Ala Val Tyr Tyr Cys
                85                  90                  95

Ala Ser Asp Phe Asp Tyr Trp Gly Gln Gly Thr Thr Leu Thr Val Ser
            100                 105                 110

Ser

<210> SEQ ID NO 160
<211> LENGTH: 339
<212> TYPE: DNA
<213> ORGANISM: Mus musculus
<220> FEATURE:
<221> NAME/KEY: misc_feature
<222> LOCATION: (1)..(339)
<223> OTHER INFORMATION: Polynucleotide Encoding the VH Domain of PD-1
      mAb 8

<400> SEQUENCE: 160
gagggccagc tgcaacaatc tggacctgag ctggtgaagc ctggggcttc agtgaagata      60
tcctgtaagg cttctggata cacgttcact gactactaca tgaactgggt gaagcagaac     120
catggaaaga gccttgagtg gattggagat attaatccta aaaatggtga cactcactac     180
aaccagaagt tcaagggcga ggccacattg actgtagaca gtcctccac cacagcctac      240 atggagctcc gcagcctgac atctgaggac tctgcagtct attactgtgc gagcgatttt     300
gactactggg gccaaggcac cactctcaca gtctcctcc                            339

<210> SEQ ID NO 161
<211> LENGTH: 5
<212> TYPE: PRT
<213> ORGANISM: Mus musculus

```
<220> FEATURE:
<221> NAME/KEY: MISC_FEATURE
<222> LOCATION: (1)..(5)
<223> OTHER INFORMATION: CDRH1 of PD-1 mAb 8

<400> SEQUENCE: 161

Asp Tyr Tyr Met Asn
1               5

<210> SEQ ID NO 162
<211> LENGTH: 17
<212> TYPE: PRT
<213> ORGANISM: Mus musculus
<220> FEATURE:
<221> NAME/KEY: MISC_FEATURE
<222> LOCATION: (1)..(17)
<223> OTHER INFORMATION: CDRH2 of PD-1 mAb 8

<400> SEQUENCE: 162

Asp Ile Asn Pro Lys Asn Gly Asp Thr His Tyr Asn Gln Lys Phe Lys
1               5                   10                  15

Gly

<210> SEQ ID NO 163
<211> LENGTH: 4
<212> TYPE: PRT
<213> ORGANISM: Mus musculus
<220> FEATURE:
<221> NAME/KEY: MISC_FEATURE
<222> LOCATION: (1)..(4)
<223> OTHER INFORMATION: CDRH3 of PD-1 mAb 8

<400> SEQUENCE: 163

Asp Phe Asp Tyr
1

<210> SEQ ID NO 164
<211> LENGTH: 112
<212> TYPE: PRT
<213> ORGANISM: Mus musculus
<220> FEATURE:
<221> NAME/KEY: MISC_FEATURE
<222> LOCATION: (1)..(112)
<223> OTHER INFORMATION: VL Domain of PD-1 mAb 8

<400> SEQUENCE: 164

Asp Val Val Met Thr Gln Thr Pro Leu Ser Leu Pro Val Gly Leu Gly
1               5                   10                  15

Asp Gln Ala Ser Ile Ser Cys Arg Ser Ser Gln Thr Leu Val Tyr Ser
            20                  25                  30

Asn Gly Asn Thr Tyr Leu Asn Trp Phe Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Phe Thr Phe Gly Ser Gly Thr Lys Leu Glu Ile Lys
            100                 105                 110

<210> SEQ ID NO 165
<211> LENGTH: 336
<212> TYPE: DNA
```

-continued

```
<213> ORGANISM: Mus musculus
<220> FEATURE:
<221> NAME/KEY: misc_feature
<222> LOCATION: (1)..(336)
<223> OTHER INFORMATION: Polynucleotide Encoding the VL Domain of PD-1
      mAb 8

<400> SEQUENCE: 165
gatgttgtga tgacccaaac tccactctcc ctgcctgtcg gtcttggaga tcaagcctcc      60
atctcttgca gatctagtca gacccttgta tatagtaatg gaaacaccta tttaaattgg    120
ttcctgcaga agccaggcca gtctccaaag ctcctgatct acaaagtttc caaccgattt    180
tctggggtcc cagacaggtt cagtggcagt ggatcaggga cagatttcac actcaagatc    240
agcagagtgg aggctgagga tctgggagtt tatttctgct ctcaaagtac acatgttcca    300
ttcacgttcg gctcggggac aaagttggaa ataaaa                              336

<210> SEQ ID NO 166
<211> LENGTH: 16
<212> TYPE: PRT
<213> ORGANISM: Mus musculus
<220> FEATURE:
<221> NAME/KEY: MISC_FEATURE
<222> LOCATION: (1)..(16)
<223> OTHER INFORMATION: CDRL1 of PD-1 mAb 8

<400> SEQUENCE: 166

Arg Ser Ser Gln Thr Leu Val Tyr Ser Asn Gly Asn Thr Tyr Leu Asn
1               5                   10                  15

<210> SEQ ID NO 167
<211> LENGTH: 7
<212> TYPE: PRT
<213> ORGANISM: Mus musculus
<220> FEATURE:
<221> NAME/KEY: MISC_FEATURE
<222> LOCATION: (1)..(7)
<223> OTHER INFORMATION: CDRL2 of PD-1 mAb 8

<400> SEQUENCE: 167

Lys Val Ser Asn Arg Phe Ser
1               5

<210> SEQ ID NO 168
<211> LENGTH: 9
<212> TYPE: PRT
<213> ORGANISM: Mus musculus
<220> FEATURE:
<221> NAME/KEY: MISC_FEATURE
<222> LOCATION: (1)..(9)
<223> OTHER INFORMATION: CDRL3 of PD-1 mAb 8

<400> SEQUENCE: 168

Ser Gln Ser Thr His Val Pro Phe Thr
1               5

<210> SEQ ID NO 169
<211> LENGTH: 119
<212> TYPE: PRT
<213> ORGANISM: Mus musculus
<220> FEATURE:
<221> NAME/KEY: MISC_FEATURE
<222> LOCATION: (1)..(119)
<223> OTHER INFORMATION: VH Domain of PD-1 mAb 9

<400> SEQUENCE: 169

Glu Val Met Leu Val Glu Ser Gly Gly Gly Leu Val Lys Pro Gly Gly
```

```
  1               5                  10                 15
Ser Leu Lys Leu Ser Cys Ala Ala Ser Gly Phe Thr Phe Ser Ser Tyr
            20                  25                  30

Leu Val Ser Trp Val Arg Gln Thr Pro Glu Lys Arg Leu Glu Trp Val
            35                  40                  45

Ala Thr Ile Ser Gly Gly Gly Asn Thr Tyr Tyr Ser Asp Ser Val
        50                  55                  60

Lys Gly Arg Phe Thr Ile Ser Arg Asp Asn Ala Lys Asn Thr Leu Tyr
 65                  70                  75                  80

Leu Gln Ile Ser Ser Leu Arg Ser Glu Asp Thr Ala Leu Tyr Tyr Cys
                 85                  90                  95

Ala Arg Tyr Gly Phe Asp Gly Ala Trp Phe Ala Tyr Trp Gly Gln Gly
            100                 105                 110

Thr Leu Val Thr Val Ser Ser
        115
```

```
<210> SEQ ID NO 170
<211> LENGTH: 357
<212> TYPE: DNA
<213> ORGANISM: Mus musculus
<220> FEATURE:
<221> NAME/KEY: misc_feature
<222> LOCATION: (1)..(357)
<223> OTHER INFORMATION: Polynucleotide Encoding the VH Domain of PD-1
      mAb 9

<400> SEQUENCE: 170
gaagtgatgc tggtggagtc tgggggaggc ttagtgaagc ctggagggtc cctgaaactc     60
tcctgtgcag cctctggatt cactttcagt agttatcttg tgtcttgggt tcgccagact    120
ccggagaaga ggctggagtg ggtcgcaacc attagtggtg gtggtggtaa cacctactat    180
tcagacagtg tgaagggtcg attcaccatc tccagagaca atgccaagaa caccctgtac    240
ctgcaaatca gcagtctgag gtctgaggac acggccttgt attactgtgc aaggtatggt    300
ttcgacggcg cctggtttgc ttactggggc caagggactc tggtcactgt ctcttcc      357
```

```
<210> SEQ ID NO 171
<211> LENGTH: 5
<212> TYPE: PRT
<213> ORGANISM: Mus musculus
<220> FEATURE:
<221> NAME/KEY: MISC_FEATURE
<222> LOCATION: (1)..(5)
<223> OTHER INFORMATION: CDRH1 of PD-1 mAb 9

<400> SEQUENCE: 171

Ser Tyr Leu Val Ser
 1               5
```

```
<210> SEQ ID NO 172
<211> LENGTH: 17
<212> TYPE: PRT
<213> ORGANISM: Mus musculus
<220> FEATURE:
<221> NAME/KEY: MISC_FEATURE
<222> LOCATION: (1)..(17)
<223> OTHER INFORMATION: CDRH2 of PD-1 mAb 9

<400> SEQUENCE: 172

Thr Ile Ser Gly Gly Gly Gly Asn Thr Tyr Tyr Ser Asp Ser Val Lys
 1               5                  10                  15

Gly
```

```
<210> SEQ ID NO 173
<211> LENGTH: 10
<212> TYPE: PRT
<213> ORGANISM: Mus musculus
<220> FEATURE:
<221> NAME/KEY: MISC_FEATURE
<222> LOCATION: (1)..(10)
<223> OTHER INFORMATION: CDRH3 of PD-1 mAb 9

<400> SEQUENCE: 173

Tyr Gly Phe Asp Gly Ala Trp Phe Ala Tyr
1               5                   10

<210> SEQ ID NO 174
<211> LENGTH: 107
<212> TYPE: PRT
<213> ORGANISM: Mus musculus
<220> FEATURE:
<221> NAME/KEY: MISC_FEATURE
<222> LOCATION: (1)..(107)
<223> OTHER INFORMATION: VL Domain of PD-1 mAb 9

<400> SEQUENCE: 174

Asp Ile Gln Met Thr Gln Ser Pro Ala Ser Leu Ser Ala Ser Val Gly
1               5                   10                  15

Asp Ile Val Thr Ile Thr Cys Arg Ala Ser Glu Asn Ile Tyr Ser Tyr
            20                  25                  30

Leu Ala Trp Tyr Gln Gln Lys Gln Glu Lys Ser Pro Gln Leu Leu Val
        35                  40                  45

Tyr Asn Ala Lys Thr Leu Ala Ala Gly Val Pro Ser Arg Phe Ser Gly
    50                  55                  60

Ser Gly Ser Gly Thr Gln Phe Ser Leu Thr Ile Asn Ser Leu Gln Pro
65                  70                  75                  80

Glu Asp Phe Gly Asn Tyr Tyr Cys Gln His His Tyr Ala Val Pro Trp
                85                  90                  95

Thr Phe Gly Gly Gly Thr Arg Leu Glu Ile Thr
            100                 105

<210> SEQ ID NO 175
<211> LENGTH: 321
<212> TYPE: DNA
<213> ORGANISM: Mus musculus
<220> FEATURE:
<221> NAME/KEY: misc_feature
<222> LOCATION: (1)..(321)
<223> OTHER INFORMATION: Polynucleotide Encoding the VL Domain of PD-1
      mAb 9

<400> SEQUENCE: 175
gacatccaga tgactcagtc tccagcctcc ctatctgcat ctgtgggaga tattgtcacc      60
atcacatgtc gagcaagtga gaatatttac agttatttag catggtatca gcagaaacag     120
gaaaaatctc ctcagctcct ggtctataat gcaaaaacct ggcagcagg tgtgccatca      180 aggttcagtg gcagtggatc aggcacacag ttttctctga ccatcaacag cctgcagcct     240
gaagattttg gaattatta ctgtcagcat cattatgctg ttccgtggac gttcggtgga      300
ggcaccagac tggaaatcac a                                               321

<210> SEQ ID NO 176
<211> LENGTH: 11
<212> TYPE: PRT
<213> ORGANISM: Mus musculus
```

```
<220> FEATURE:
<221> NAME/KEY: MISC_FEATURE
<222> LOCATION: (1)..(11)
<223> OTHER INFORMATION: CDRL1 of PD-1 mAb 9

<400> SEQUENCE: 176

Arg Ala Ser Glu Asn Ile Tyr Ser Tyr Leu Ala
1               5                   10

<210> SEQ ID NO 177
<211> LENGTH: 7
<212> TYPE: PRT
<213> ORGANISM: Mus musculus
<220> FEATURE:
<221> NAME/KEY: MISC_FEATURE
<222> LOCATION: (1)..(7)
<223> OTHER INFORMATION: CDRL2 of PD-1 mAb 9

<400> SEQUENCE: 177

Asn Ala Lys Thr Leu Ala Ala
1               5

<210> SEQ ID NO 178
<211> LENGTH: 9
<212> TYPE: PRT
<213> ORGANISM: Mus musculus
<220> FEATURE:
<221> NAME/KEY: MISC_FEATURE
<222> LOCATION: (1)..(9)
<223> OTHER INFORMATION: CDRL3 of PD-1 mAb 9

<400> SEQUENCE: 178

Gln His His Tyr Ala Val Pro Trp Thr
1               5

<210> SEQ ID NO 179
<211> LENGTH: 119
<212> TYPE: PRT
<213> ORGANISM: Artificial Sequence
<220> FEATURE:
<223> OTHER INFORMATION: VH Domain of hPD-1 mAb 9 VH1

<400> SEQUENCE: 179

Glu Val Gln Leu Val Glu Ser Gly Gly Gly Leu Val Arg Pro Gly Gly
1               5                   10                  15

Ser Leu Lys Leu Ser Cys Ala Ala Ser Gly Phe Thr Phe Ser Ser Tyr
            20                  25                  30

Leu Val Ser Trp Val Arg Gln Ala Pro Gly Lys Gly Leu Glu Trp Val
        35                  40                  45

Ala Thr Ile Ser Gly Gly Gly Asn Thr Tyr Tyr Ser Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Thr Tyr Tyr Cys
                85                  90                  95

Ala Arg Tyr Gly Phe Asp Gly Ala Trp Phe Ala Tyr Trp Gly Gln Gly
            100                 105                 110

Thr Leu Val Thr Val Ser Ser
        115

<210> SEQ ID NO 180
<211> LENGTH: 357
<212> TYPE: DNA
<213> ORGANISM: Artificial Sequence
```

<220> FEATURE:
<223> OTHER INFORMATION: Polynucleotide Encoding hPD-1 mAb 9 VH1

<400> SEQUENCE: 180

| | |
|---|---|
| gaggtgcagc tggtggaaag tgggggcggc ctggtgcgac ccggggggaag tctgaaactg | 60 |
| tcctgtgcag catcaggatt tacttttca tcttatctcg tgtcttgggt aagacaagca | 120 |
| cccggaaaag gcttggaatg ggtggccact atctccggtg gaggtggcaa cacctactat | 180 |
| agcgacagtg tcaagggaag atttaccatc agtcgcgaca acgctaagaa tagcctgtac | 240 |
| ctccagatga actccctgcg cgccgaggac accgccacct attactgtgc acgctatgga | 300 |
| tttgacggcg catggtttgc ctactgggga cagggcacat ggtaaccgt tagctcc | 357 |

<210> SEQ ID NO 181
<211> LENGTH: 119
<212> TYPE: PRT
<213> ORGANISM: Artificial Sequence
<220> FEATURE:
<223> OTHER INFORMATION: VH Domain of hPD-1 mAb 9 VH2

<400> SEQUENCE: 181

```
Glu Val Gln Leu Val Glu Ser Gly Gly Gly Leu Ala Arg Pro Gly Gly
1               5                  10                  15

Ser Leu Lys Leu Ser Cys Ala Ala Ser Gly Phe Thr Phe Ser Ser Tyr
            20                  25                  30

Leu Val Gly Trp Val Arg Gln Ala Pro Gly Lys Gly Leu Glu Trp Thr
        35                  40                  45

Ala Thr Ile Ser Gly Gly Gly Asn Thr Tyr Tyr Ser Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Ala Arg Ala Glu Asp Thr Ala Thr Tyr Tyr Cys
                85                  90                  95

Ala Arg Tyr Gly Phe Asp Gly Ala Trp Phe Ala Tyr Trp Gly Gln Gly
            100                 105                 110

Thr Leu Val Thr Val Ser Ser
        115
```

<210> SEQ ID NO 182
<211> LENGTH: 357
<212> TYPE: DNA
<213> ORGANISM: Artificial Sequence
<220> FEATURE:
<223> OTHER INFORMATION: Polynucleotide Encoding hPD-1 mAb 9 VH2

<400> SEQUENCE: 182

| | |
|---|---|
| gaggtgcagc tggtggaaag tgggggcggc ctggcgcgac ccggggggaag tctgaaactg | 60 |
| tcctgtgcag catcaggatt tacttttca tcttatctcg tgggctgggt aagacaagca | 120 |
| cccggaaaag gcttggaatg gacgccact atctccggtg gaggtggcaa cacctactat | 180 |
| agcgacagtg tcaagggaag atttaccatc agtcgcgaca acgctaagaa tagcctgtac | 240 |
| ctccagatga actccgcacg cgccgaggac accgccacct attactgtgc acgctatgga | 300 |
| tttgacggcg catggtttgc ctactgggga cagggcacat ggtaaccgt tagctcc | 357 |

<210> SEQ ID NO 183
<211> LENGTH: 5
<212> TYPE: PRT
<213> ORGANISM: Artificial Sequence
<220> FEATURE:

<223> OTHER INFORMATION: CDRH1 of the VH Domain of hPD-1 mAb 9 VH2
      Having a Serine to Glycine Amino Acid Substitution

<400> SEQUENCE: 183

Ser Tyr Leu Val Gly
1               5

<210> SEQ ID NO 184
<211> LENGTH: 107
<212> TYPE: PRT
<213> ORGANISM: Artificial Sequence
<220> FEATURE:
<223> OTHER INFORMATION: VL Domain of hPD-1 mAb 9 VL1

<400> SEQUENCE: 184

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Tyr
                20                  25                  30

Leu Ala Trp Tyr Gln Gln Lys Pro Gly Lys Ala Pro Lys Leu Leu Ile
            35                  40                  45

Tyr Asn Ala Lys Thr Leu Ala Ala Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Ala Val Pro Trp
                85                  90                  95

Thr Phe Gly Gln Gly Thr Lys Leu Glu Ile Lys
            100                 105

<210> SEQ ID NO 185
<211> LENGTH: 321
<212> TYPE: DNA
<213> ORGANISM: Artificial Sequence
<220> FEATURE:
<223> OTHER INFORMATION: Polynucleotide Encoding hPD-1 mAb 9 VL1

<400> SEQUENCE: 185
gacattcaga tgactcagtc tcccagcagt ctgtccgcat ccgtggggga tcgggtcacc        60
atcacctgcc gtgcctcaga aaacatctat tcatacctcg cctggtatca acagaaacct       120
ggtaaagccc caaaattgct catttacaac gccaagaccc tcgcagctgg cgtgccaagt       180
aggttctcag gcagcggctc agggacagat ttcaccctca ccatatcctc actgcagccc       240
gaggattttg ccacttacta ctgccagcat cattacgcag tgccctggac cttcggacaa       300
ggcactaagc tcgagatcaa a                                                 321

<210> SEQ ID NO 186
<211> LENGTH: 107
<212> TYPE: PRT
<213> ORGANISM: Artificial Sequence
<220> FEATURE:
<223> OTHER INFORMATION: VL Domain of hPD-1 mAb 9 VL2

<400> SEQUENCE: 186

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Asn Tyr
                20                  25                  30

Leu Ala Trp Tyr Gln Gln Lys Pro Gly Lys Ala Pro Lys Leu Leu Ile
            35                  40                  45

Tyr Asp Ala Lys Thr Leu Ala Ala Gly Val Pro Ser Arg Phe Ser Gly
            50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln His His Tyr Ala Val Pro Trp
                85                  90                  95

Thr Phe Gly Gln Gly Thr Lys Leu Glu Ile Lys
            100                 105

<210> SEQ ID NO 187
<211> LENGTH: 321
<212> TYPE: DNA
<213> ORGANISM: Artificial Sequence
<220> FEATURE:
<223> OTHER INFORMATION: Polynucleotide Encoding hPD-1 mAb 9 VL2

<400> SEQUENCE: 187

```
gacattcaga tgactcagtc tcccagcagt ctgtccgcat ccgtggggga tcgggtcacc      60
atcacctgcc gtgcctcaga aaacatctat aactacctcg cctggtatca acagaaacct    120
ggtaaagccc caaaattgct catttacgac gccaagaccc tcgcagctgg cgtgccaagt    180
aggttctcag gcagcggctc agggacagat ttcaccctca ccatatcctc actgcagccc    240
gaggattttg ccacttacta ctgccagcat cattacgcag tgccctggac cttcggacaa    300
ggcactaagc tcgagatcaa a                                              321
```

<210> SEQ ID NO 188
<211> LENGTH: 11
<212> TYPE: PRT
<213> ORGANISM: Artificial Sequence
<220> FEATURE:
<223> OTHER INFORMATION: CDRL1 of the VL Domain of hPD-1 mAb 9 VL2

<400> SEQUENCE: 188

Arg Ala Ser Glu Asn Ile Tyr Asn Tyr Leu Ala
 1               5                  10

<210> SEQ ID NO 189
<211> LENGTH: 7
<212> TYPE: PRT
<213> ORGANISM: Artificial Sequence
<220> FEATURE:
<223> OTHER INFORMATION: CDRL2 of the VL Domain of hPD-1 mAb 9 VL2

<400> SEQUENCE: 189

Asp Ala Lys Thr Leu Ala Ala
 1               5

<210> SEQ ID NO 190
<211> LENGTH: 116
<212> TYPE: PRT
<213> ORGANISM: Mus musculus
<220> FEATURE:
<221> NAME/KEY: MISC_FEATURE
<222> LOCATION: (1)..(116)
<223> OTHER INFORMATION: VH Domain of PD-1 mAb 10

<400> SEQUENCE: 190

Glu Val Ile Leu Val Glu Ser Gly Gly Gly Leu Val Lys Pro Gly Gly
 1               5                  10                  15

Ser Leu Lys Leu Ser Cys Ala Ser Gly Phe Thr Phe Ser Asn Tyr
            20                  25                  30

```
Leu Met Ser Trp Val Arg Gln Thr Pro Glu Lys Arg Leu Glu Trp Val
            35                  40                  45

Ala Ser Ile Ser Gly Gly Gly Ser Asn Ile Tyr Tyr Pro Asp Ser Val
 50                  55                  60

Lys Gly Arg Phe Thr Ile Ser Arg Asp Asn Ala Lys Asn Thr Leu Tyr
 65                  70                  75                  80

Leu Gln Met Asn Ser Leu Arg Ser Glu Asp Thr Ala Leu Tyr Tyr Cys
                 85                  90                  95

Ala Arg Gln Glu Leu Ala Phe Asp Tyr Trp Gly Gln Gly Thr Thr Leu
            100                 105                 110

Thr Val Ser Ser
            115

<210> SEQ ID NO 191
<211> LENGTH: 348
<212> TYPE: DNA
<213> ORGANISM: Mus musculus
<220> FEATURE:
<221> NAME/KEY: misc_feature
<222> LOCATION: (1)..(348)
<223> OTHER INFORMATION: Polynucleotide Encoding the VH Domain of PD-1
      mAb 10

<400> SEQUENCE: 191
gaagtgatac tggtggagtc tgggggaggc ttagtgaagc ctggagggtc cctgaaactc      60
tcctgtgcag cctctggatt cactttcagt aactatctca tgtcttgggt tcgccagact     120
ccggagaaga ggctggagtg ggtcgcaagt attagtggtg gtggtagtaa tatctactat     180
ccagacagtg tgaagggtcg attcaccata tccagggaca atgccaagaa caccctgtac     240
ctgcaaatga acagtctgag gtctgaggac acggccttgt attactgtgc aagacaagaa     300
ctggcttttg actactgggg ccaaggcacc actctcacag tctcctcc                  348

<210> SEQ ID NO 192
<211> LENGTH: 5
<212> TYPE: PRT
<213> ORGANISM: Mus musculus
<220> FEATURE:
<221> NAME/KEY: MISC_FEATURE
<222> LOCATION: (1)..(5)
<223> OTHER INFORMATION: CDRH1 of PD-1 mAb 10

<400> SEQUENCE: 192

Asn Tyr Leu Met Ser
 1               5

<210> SEQ ID NO 193
<211> LENGTH: 17
<212> TYPE: PRT
<213> ORGANISM: Mus musculus
<220> FEATURE:
<221> NAME/KEY: MISC_FEATURE
<222> LOCATION: (1)..(17)
<223> OTHER INFORMATION: CDRH2 of PD-1 mAb 10

<400> SEQUENCE: 193

Ser Ile Ser Gly Gly Gly Ser Asn Ile Tyr Tyr Pro Asp Ser Val Lys
 1               5                  10                  15

Gly

<210> SEQ ID NO 194
<211> LENGTH: 7
<212> TYPE: PRT
```

```
<213> ORGANISM: Mus musculus
<220> FEATURE:
<221> NAME/KEY: MISC_FEATURE
<222> LOCATION: (1)..(7)
<223> OTHER INFORMATION: CDRH3 of PD-1 mAb 10

<400> SEQUENCE: 194

Gln Glu Leu Ala Phe Asp Tyr
1               5

<210> SEQ ID NO 195
<211> LENGTH: 107
<212> TYPE: PRT
<213> ORGANISM: Mus musculus
<220> FEATURE:
<221> NAME/KEY: MISC_FEATURE
<222> LOCATION: (1)..(107)
<223> OTHER INFORMATION: VL Domain of PD-1 mAb 10

<400> SEQUENCE: 195

Asp Ile Gln Met Thr Gln Thr Thr Ser Ser Leu Ser Ala Ser Leu Gly
1               5                   10                  15

Asp Arg Val Thr Ile Ser Cys Arg Thr Ser Gln Asp Ile Ser Asn Phe
            20                  25                  30

Leu Asn Trp Tyr Gln Gln Lys Pro Asp Gly Thr Ile Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Ser Thr Leu Pro Trp
                85                  90                  95

Thr Phe Gly Gly Gly Thr Lys Leu Glu Ile Ile
            100                 105

<210> SEQ ID NO 196
<211> LENGTH: 321
<212> TYPE: DNA
<213> ORGANISM: Mus musculus
<220> FEATURE:
<221> NAME/KEY: misc_feature
<222> LOCATION: (1)..(321)
<223> OTHER INFORMATION: Polynucleotide Encoding the VL Domain of PD-1
      mAb 10

<400> SEQUENCE: 196
gatatccaga tgacacagac tacatcctcc ctgtctgcct ctctgggaga cagagtcacc      60
atcagttgca ggacaagtca ggacattagc aattttttaa actggtatca gcagaaacca     120
gatggaacta ttaaactcct gatctactac acatcaagat tacactcagg agtcccatca     180
aggttcagtg gcagtgggtc tggaacagat tattctctca ccattagcaa cctggagcaa     240
gaagatattg ccacttactt ttgccaacag ggtagtacgc ttccgtggac gttcggtgga     300
ggcaccaagc tggaaatcat a                                               321

<210> SEQ ID NO 197
<211> LENGTH: 11
<212> TYPE: PRT
<213> ORGANISM: Mus musculus
<220> FEATURE:
<221> NAME/KEY: MISC_FEATURE
<222> LOCATION: (1)..(11)
<223> OTHER INFORMATION: CDRL1 of PD-1 mAb 10
```

<400> SEQUENCE: 197

Arg Thr Ser Gln Asp Ile Ser Asn Phe Leu Asn
1               5                   10

<210> SEQ ID NO 198
<211> LENGTH: 7
<212> TYPE: PRT
<213> ORGANISM: Mus musculus
<220> FEATURE:
<221> NAME/KEY: MISC_FEATURE
<222> LOCATION: (1)..(7)
<223> OTHER INFORMATION: CDRL2 of PD-1 mAb 10

<400> SEQUENCE: 198

Tyr Thr Ser Arg Leu His Ser
1               5

<210> SEQ ID NO 199
<211> LENGTH: 9
<212> TYPE: PRT
<213> ORGANISM: Mus musculus
<220> FEATURE:
<221> NAME/KEY: MISC_FEATURE
<222> LOCATION: (19)..()
<223> OTHER INFORMATION: CDRL3 of PD-1 mAb 10

<400> SEQUENCE: 199

Gln Gln Gly Ser Thr Leu Pro Trp Thr
1               5

<210> SEQ ID NO 200
<211> LENGTH: 117
<212> TYPE: PRT
<213> ORGANISM: Mus musculus
<220> FEATURE:
<221> NAME/KEY: MISC_FEATURE
<222> LOCATION: (1)..(117)
<223> OTHER INFORMATION: VH Domain of PD-1 mAb 11

<400> SEQUENCE: 200

Glu Val Gln Leu Gln Gln Ser Gly Thr Val Leu Ala Arg Pro Gly Ala
1               5                   10                  15

Ser Val Lys Met Ser Cys Lys Thr Ser Gly Tyr Thr Phe Thr Gly Tyr
                20                  25                  30

Trp Met His Trp Val Lys Gln Arg Pro Gly Gln Gly Leu Lys Trp Met
            35                  40                  45

Gly Ala Ile Tyr Pro Gly Asn Ser Asp Thr His Tyr Asn Gln Lys Phe
        50                  55                  60

Lys Gly Lys Ala Lys Leu Thr Ala Val Thr Ser Ala Ser Thr Ala Tyr
65                  70                  75                  80

Met Glu Leu Ser Ser Leu Thr Asn Glu Asp Ser Ala Ile Tyr Tyr Cys
                85                  90                  95

Thr Thr Gly Thr Tyr Ser Tyr Phe Asp Val Trp Gly Thr Gly Thr Thr
                100                 105                 110

Val Thr Val Ser Ser
            115

<210> SEQ ID NO 201
<211> LENGTH: 351
<212> TYPE: DNA
<213> ORGANISM: Mus musculus
<220> FEATURE:
<221> NAME/KEY: misc_feature
<222> LOCATION: (1)..(351)

```
<223> OTHER INFORMATION: Polynucleotide Encoding the VH Domain of PD-1
      mAb 11

<400> SEQUENCE: 201
gaggttcagc tccagcagtc tgggactgtg ctggcaaggc ctggggcttc agtgaagatg      60
tcctgcaaga cttctggcta cacatttacc ggctactgga tgcactgggt aaaacagagg     120
cctggacagg gtctgaaatg gatgggggct atttatcctg gaaatagtga tactcactac     180
aaccagaagt tcaagggcaa ggccaaactg actgcagtca catccgccag cactgcctac     240
atggagctca gcagcctgac aaatgaggac tctgcgatct attactgtac tactgggacc     300
tactcgtact tcgatgtctg gggcacaggg accacggtca ccgtctcctc a              351

<210> SEQ ID NO 202
<211> LENGTH: 5
<212> TYPE: PRT
<213> ORGANISM: Mus musculus
<220> FEATURE:
<221> NAME/KEY: MISC_FEATURE
<222> LOCATION: (1)..(5)
<223> OTHER INFORMATION: CDRH1 of PD-1 mAb 11

<400> SEQUENCE: 202

Gly Tyr Trp Met His
1               5

<210> SEQ ID NO 203
<211> LENGTH: 17
<212> TYPE: PRT
<213> ORGANISM: Mus musculus
<220> FEATURE:
<221> NAME/KEY: MISC_FEATURE
<222> LOCATION: (1)..(17)
<223> OTHER INFORMATION: CDRH2 of PD-1 mAb 11

<400> SEQUENCE: 203

Ala Ile Tyr Pro Gly Asn Ser Asp Thr His Tyr Asn Gln Lys Phe Lys
1               5                   10                  15

Gly

<210> SEQ ID NO 204
<211> LENGTH: 8
<212> TYPE: PRT
<213> ORGANISM: Mus musculus
<220> FEATURE:
<221> NAME/KEY: MISC_FEATURE
<222> LOCATION: (1)..(8)
<223> OTHER INFORMATION: CDRH3 of PD-1 mAb 11

<400> SEQUENCE: 204

Gly Thr Tyr Ser Tyr Phe Asp Val
1               5

<210> SEQ ID NO 205
<211> LENGTH: 106
<212> TYPE: PRT
<213> ORGANISM: Mus musculus
<220> FEATURE:
<221> NAME/KEY: MISC_FEATURE
<222> LOCATION: (1)..(106)
<223> OTHER INFORMATION: VL Domain of PD-1 mAb 11

<400> SEQUENCE: 205

Asp Ile Leu Leu Thr Gln Ser Pro Ala Ile Leu Ser Val Ser Pro Gly
1               5                   10                  15
```

```
Glu Arg Val Ser Phe Ser Cys Arg Ala Ser Gln Ser Ile Gly Thr Ser
            20                  25                  30

Ile His Trp Tyr Gln His Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Ser Asn Ser Trp Leu Thr
                85                  90                  95

Phe Gly Ala Gly Thr Lys Leu Glu Leu Lys
            100                 105

<210> SEQ ID NO 206
<211> LENGTH: 318
<212> TYPE: DNA
<213> ORGANISM: Mus musculus
<220> FEATURE:
<221> NAME/KEY: misc_feature
<222> LOCATION: (1)..(318)
<223> OTHER INFORMATION: Polynucleotide Encoding the VL Domain of PD-1
      mAb 11

<400> SEQUENCE: 206
gacatcttgc tgactcagtc tccagccatc ctgtctgtga gtccaggaga aagagtcagt      60
ttctcctgca gggccagtca gagcattggc acaagcatac actggtatca gcacagaaca     120
aatggttctc caaggcttct cataaagtat gcttctgagt ctatctctgg gatcccttcc     180
aggtttagtg gcagtggatc agggactgat tttactctta gcatcaacag tgtggagtct     240
gaagatattg cagattatta ctgtcaacaa agtaatagct ggctcacgtt cggtgctggg     300
accaagctgg agctgaaa                                                   318

<210> SEQ ID NO 207
<211> LENGTH: 11
<212> TYPE: PRT
<213> ORGANISM: Mus musculus
<220> FEATURE:
<221> NAME/KEY: MISC_FEATURE
<222> LOCATION: (1)..(11)
<223> OTHER INFORMATION: CDRL1 of PD-1 mAb 11

<400> SEQUENCE: 207

Arg Ala Ser Gln Ser Ile Gly Thr Ser Ile His
1               5                   10

<210> SEQ ID NO 208
<211> LENGTH: 7
<212> TYPE: PRT
<213> ORGANISM: Mus musculus
<220> FEATURE:
<221> NAME/KEY: MISC_FEATURE
<222> LOCATION: (1)..(7)
<223> OTHER INFORMATION: CDRL2 of PD-1 mAb 11

<400> SEQUENCE: 208

Tyr Ala Ser Glu Ser Ile Ser
1               5

<210> SEQ ID NO 209
<211> LENGTH: 8
<212> TYPE: PRT
<213> ORGANISM: Mus musculus
<220> FEATURE:
```

```
<221> NAME/KEY: MISC_FEATURE
<222> LOCATION: (1)..(8)
<223> OTHER INFORMATION: CDRL3 of PD-1 mAb 11

<400> SEQUENCE: 209

Gln Gln Ser Asn Ser Trp Leu Thr
1               5

<210> SEQ ID NO 210
<211> LENGTH: 125
<212> TYPE: PRT
<213> ORGANISM: Mus musculus
<220> FEATURE:
<221> NAME/KEY: MISC_FEATURE
<222> LOCATION: (1)..(125)
<223> OTHER INFORMATION: VH Domain of PD-1 mAb 12

<400> SEQUENCE: 210

Gln Gly His Leu Gln Gln Ser Gly Ala Glu Leu Val Arg Pro Gly Ala
1               5                   10                  15

Ser Val Thr Leu Ser Cys Lys Ala Ser Gly Phe Thr Phe Thr Asp Tyr
            20                  25                  30

Glu Met His Trp Val Lys Gln Thr Pro Val His Gly Leu Glu Trp Ile
        35                  40                  45

Gly Thr Ile Asp Pro Glu Thr Gly Gly Thr Ala Tyr Asn Gln Lys Phe
    50                  55                  60

Lys Gly Lys Ala Ile Leu Thr Val Asp Lys Ser Ser Thr Thr Thr Tyr
65                  70                  75                  80

Met Glu Leu Arg Ser Leu Thr Ser Glu Asp Ser Ala Val Phe Tyr Cys
                85                  90                  95

Ser Arg Glu Arg Ile Thr Thr Val Val Glu Gly Ala Tyr Trp Tyr Phe
            100                 105                 110

Asp Val Trp Gly Thr Gly Thr Thr Val Thr Val Ser Ser
        115                 120                 125

<210> SEQ ID NO 211
<211> LENGTH: 375
<212> TYPE: DNA
<213> ORGANISM: Mus musculus
<220> FEATURE:
<221> NAME/KEY: misc_feature
<222> LOCATION: (1)..(375)
<223> OTHER INFORMATION: Polynucleotide Encoding the VH Domain of PD-1
      mAb 12

<400> SEQUENCE: 211
cagggtcacc tgcagcagtc tggggctgag ctggtgaggc ctggggcttc agtgacgctg      60
tcctgcaagg cttcgggctt cacatttact gactatgaga tgcactgggt gaaacagaca     120
cctgtgcatg gcctggaatg gattgggact attgatcctg aaactggtgg tactgcctac     180
aatcagaagt tcaagggcaa ggccatactg acagtagaca atcttccac tacaacctac      240 atggagctcc gcagcctgac atctgaggac tctgccgtct ttattgttc aagagagagg      300 attactacgg ttgttgaggg ggcatactgg tacttcgatg tctggggcac agggaccacg     360
gtcaccgtct cctca                                                      375

<210> SEQ ID NO 212
<211> LENGTH: 5
<212> TYPE: PRT
<213> ORGANISM: Mus musculus
<220> FEATURE:
<221> NAME/KEY: MISC_FEATURE
```

```
<222> LOCATION: (1)..(5)
<223> OTHER INFORMATION: CDRH1 of PD-1 mAb 12

<400> SEQUENCE: 212

Asp Tyr Glu Met His
1               5

<210> SEQ ID NO 213
<211> LENGTH: 17
<212> TYPE: PRT
<213> ORGANISM: Mus musculus
<220> FEATURE:
<221> NAME/KEY: MISC_FEATURE
<222> LOCATION: (1)..(17)
<223> OTHER INFORMATION: CDRH2 of PD-1 mAb 12

<400> SEQUENCE: 213

Thr Ile Asp Pro Glu Thr Gly Gly Thr Ala Tyr Asn Gln Lys Phe Lys
1               5                   10                  15

Gly

<210> SEQ ID NO 214
<211> LENGTH: 16
<212> TYPE: PRT
<213> ORGANISM: Mus musculus
<220> FEATURE:
<221> NAME/KEY: MISC_FEATURE
<222> LOCATION: (1)..(16)
<223> OTHER INFORMATION: CDRH3 of PD-1 mAb 12

<400> SEQUENCE: 214

Glu Arg Ile Thr Thr Val Val Glu Gly Ala Tyr Trp Tyr Phe Asp Val
1               5                   10                  15

<210> SEQ ID NO 215
<211> LENGTH: 112
<212> TYPE: PRT
<213> ORGANISM: Mus musculus
<220> FEATURE:
<221> NAME/KEY: MISC_FEATURE
<222> LOCATION: (1)..(112)
<223> OTHER INFORMATION: VL Domain of PD-1 mAb 4

<400> SEQUENCE: 215

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Asn Ile Val His Ser
                20                  25                  30

Asn Gly Asn Thr Tyr Leu Glu Trp Tyr Leu Gln Lys Pro Gly Gln Ser
            35                  40                  45

Pro Lys Leu Leu Ile Cys Lys Val Ser Thr Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
            100                 105                 110

<210> SEQ ID NO 216
<211> LENGTH: 336
<212> TYPE: DNA
<213> ORGANISM: Mus musculus
<220> FEATURE:
```

-continued

```
<221> NAME/KEY: misc_feature
<222> LOCATION: (1)..(336)
<223> OTHER INFORMATION: Polynucleotide Encoding the VL Domain of PD-1
      mAb 12

<400> SEQUENCE: 216
gatgttttga tgacccagac tccactctcc ctgcctgtca gtcttggaga tcaagcctcc      60
atctcttgca gatctagtca gaacattgta catagtaatg aaacaccta tttagaatgg     120 tacctgcaga aaccaggcca gtctccaaag ctcctgatct gcaaagtttc cacccgattt     180
tctggggtcc cagacaggtt cagtggcagt ggatcaggga cagatttcac actcaagatc     240
agcagagtgg aggctgagga tctgggagtt tattattgct ttcaaggttc acatgttccg     300
tacacgttcg gagggggac caagctggaa ataaaa                                336

<210> SEQ ID NO 217
<211> LENGTH: 16
<212> TYPE: PRT
<213> ORGANISM: Mus musculus
<220> FEATURE:
<221> NAME/KEY: MISC_FEATURE
<222> LOCATION: (1)..(16)
<223> OTHER INFORMATION: CDRL1 of PD-1 mAb 12

<400> SEQUENCE: 217

Arg Ser Ser Gln Asn Ile Val His Ser Asn Gly Asn Thr Tyr Leu Glu
1               5                   10                  15

<210> SEQ ID NO 218
<211> LENGTH: 7
<212> TYPE: PRT
<213> ORGANISM: Mus musculus
<220> FEATURE:
<221> NAME/KEY: MISC_FEATURE
<222> LOCATION: (1)..(7)
<223> OTHER INFORMATION: CDRL2 of PD-1 mAb 12

<400> SEQUENCE: 218

Lys Val Ser Thr Arg Phe Ser
1               5

<210> SEQ ID NO 219
<211> LENGTH: 9
<212> TYPE: PRT
<213> ORGANISM: Mus musculus
<220> FEATURE:
<221> NAME/KEY: MISC_FEATURE
<222> LOCATION: (1)..(9)
<223> OTHER INFORMATION: CDRL3 of PD-1 mAb 12

<400> SEQUENCE: 219

Phe Gln Gly Ser His Val Pro Tyr Thr
1               5

<210> SEQ ID NO 220
<211> LENGTH: 121
<212> TYPE: PRT
<213> ORGANISM: Mus musculus
<220> FEATURE:
<221> NAME/KEY: MISC_FEATURE
<222> LOCATION: (1)..(121)
<223> OTHER INFORMATION: VH Domain of PD-1 mAb 13

<400> SEQUENCE: 220

Glu Val Met Leu Val Glu Ser Gly Gly Gly Leu Val Lys Pro Gly Gly
1               5                   10                  15
```

```
Ser Leu Lys Leu Ser Cys Ala Ala Ser Gly Phe Thr Phe Ser Ser His
        20                  25                  30

Thr Met Ser Trp Val Arg Gln Thr Pro Glu Lys Arg Leu Glu Trp Val
    35                  40                  45

Ala Thr Ile Ser Gly Gly Gly Ser Asn Ile Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ser Glu Asp Thr Ala Leu Tyr Tyr Cys
                85                  90                  95

Ala Arg Gln Ala Tyr Tyr Gly Asn Tyr Trp Tyr Phe Asp Val Trp Gly
            100                 105                 110

Thr Gly Thr Thr Val Thr Val Ser Ser
        115                 120

<210> SEQ ID NO 221
<211> LENGTH: 363
<212> TYPE: DNA
<213> ORGANISM: Mus musculus
<220> FEATURE:
<221> NAME/KEY: misc_feature
<222> LOCATION: (1)..(363)
<223> OTHER INFORMATION: Polynucleotide Encoding the VH Domain of PD-1
      mAb 13

<400> SEQUENCE: 221
gaagtgatgc tggtggagtc tgggggaggc ttagtgaagc ctggagggtc cctgaaactc      60
tcctgtgcag cctctggatt cactttcagt agccatacca tgtcttgggt tcgccagact     120
ccggagaaga ggctggagtg ggtcgcaacc attagtggtg gtggttctaa tatctactat     180
ccagacagtg tgaagggtcg attcaccatc tccagagaca atgccaagaa caccctgtac     240
ctgcaaatga gcagtctgag gtctgaggac acggccttgt attactgtgc aagacaagct     300
tactacggta attactggta cttcgatgtc tggggcacag gaccacggt caccgtctcc     360 tcc                                                                   363

<210> SEQ ID NO 222
<211> LENGTH: 5
<212> TYPE: PRT
<213> ORGANISM: Mus musculus
<220> FEATURE:
<221> NAME/KEY: MISC_FEATURE
<222> LOCATION: (1)..(5)
<223> OTHER INFORMATION: CDRH1 of PD-1 mAb 13

<400> SEQUENCE: 222

Ser His Thr Met Ser
1               5

<210> SEQ ID NO 223
<211> LENGTH: 17
<212> TYPE: PRT
<213> ORGANISM: Mus musculus
<220> FEATURE:
<221> NAME/KEY: MISC_FEATURE
<222> LOCATION: (1)..(17)
<223> OTHER INFORMATION: CDRH2 of PD-1 mAb 13

<400> SEQUENCE: 223

Thr Ile Ser Gly Gly Gly Ser Asn Ile Tyr Tyr Pro Asp Ser Val Lys
1               5                   10                  15

Gly
```

<210> SEQ ID NO 224
<211> LENGTH: 12
<212> TYPE: PRT
<213> ORGANISM: Mus musculus
<220> FEATURE:
<221> NAME/KEY: MISC_FEATURE
<222> LOCATION: (1)..(12)
<223> OTHER INFORMATION: CDRH3 of PD-1 mAb 13

<400> SEQUENCE: 224

Gln Ala Tyr Tyr Gly Asn Tyr Trp Tyr Phe Asp Val
1               5                   10

<210> SEQ ID NO 225
<211> LENGTH: 107
<212> TYPE: PRT
<213> ORGANISM: Mus musculus
<220> FEATURE:
<221> NAME/KEY: MISC_FEATURE
<222> LOCATION: (1)..(107)
<223> OTHER INFORMATION: VL Domain of PD-1 mAb 13

<400> SEQUENCE: 225

Asp Ile Gln Met Thr Gln Ser Pro Ala Thr Gln Ser Ala Ser Leu Gly
1               5                   10                  15

Glu Ser Val Thr Ile Thr Cys Leu Ala Ser Gln Thr Ile Gly Thr Trp
            20                  25                  30

Leu Ala Trp Tyr Gln Gln Lys Pro Gly Lys Ser Pro Gln Leu Leu Ile
        35                  40                  45

Tyr Ala Ala Thr Ser Leu Ala Asp Gly Val Pro Ser Arg Phe Ser Gly
    50                  55                  60

Ser Gly Ser Gly Thr Lys Phe Ser Phe Lys Ile Ser Ser Leu Gln Ala
65                  70                  75                  80

Glu Asp Phe Val Ser Tyr Tyr Cys Gln Gln Leu Asp Ser Ile Pro Trp
                85                  90                  95

Thr Phe Gly Gly Gly Thr Lys Leu Glu Ile Lys
            100                 105

<210> SEQ ID NO 226
<211> LENGTH: 321
<212> TYPE: DNA
<213> ORGANISM: Mus musculus
<220> FEATURE:
<221> NAME/KEY: misc_feature
<222> LOCATION: (1)..(321)
<223> OTHER INFORMATION: Polynucleotide Encoding the VL Domain of PD-1
      mAb 13

<400> SEQUENCE: 226
gacattcaga tgacccagtc tcctgccacc cagtctgcat ctctgggaga aagtgtcacc      60
atcacgtgcc tggcaagtca gaccattggt acatggttag catggtatca gcagaaacca     120
gggaaatctc ctcagctcct gatttatgct gcaaccagct ggcagatgg ggtcccatca      180 aggttcagtg gtagtggatc tggcacaaaa ttttctttca agatcagcag cctacaggct     240
gaagattttg taagttatta ctgtcaacaa cttgacagta ttccgtggac gttcggtgga     300
ggcaccaagc tggaaatcaa a                                               321

<210> SEQ ID NO 227
<211> LENGTH: 11
<212> TYPE: PRT
<213> ORGANISM: Mus musculus -continued

```
<220> FEATURE:
<221> NAME/KEY: MISC_FEATURE
<222> LOCATION: (1)..(11)
<223> OTHER INFORMATION: CDRL1 of PD-1 mAb 13

<400> SEQUENCE: 227

Leu Ala Ser Gln Thr Ile Gly Thr Trp Leu Ala
1               5                   10

<210> SEQ ID NO 228
<211> LENGTH: 7
<212> TYPE: PRT
<213> ORGANISM: Mus musculus
<220> FEATURE:
<221> NAME/KEY: MISC_FEATURE
<222> LOCATION: (1)..(7)
<223> OTHER INFORMATION: CDRL2 of PD-1 mAb 13

<400> SEQUENCE: 228

Ala Ala Thr Ser Leu Ala Asp
1               5

<210> SEQ ID NO 229
<211> LENGTH: 9
<212> TYPE: PRT
<213> ORGANISM: Mus musculus
<220> FEATURE:
<221> NAME/KEY: MISC_FEATURE
<222> LOCATION: (1)..(9)
<223> OTHER INFORMATION: CDRL3 of PD-1 mAb 13

<400> SEQUENCE: 229

Gln Gln Leu Asp Ser Ile Pro Trp Thr
1               5

<210> SEQ ID NO 230
<211> LENGTH: 117
<212> TYPE: PRT
<213> ORGANISM: Mus musculus
<220> FEATURE:
<221> NAME/KEY: MISC_FEATURE
<222> LOCATION: (1)..(117)
<223> OTHER INFORMATION: VH Domain of PD-1 mAb 14

<400> SEQUENCE: 230

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Asn Phe Ile Ser Tyr
            20                  25                  30

Trp Ile Thr Trp Val Lys Gln Arg Pro Gly Gln Gly Leu Gln Trp Ile
        35                  40                  45

Gly Asn Ile Tyr Pro Gly Thr Asp Gly Thr Tyr Asn Glu Lys Phe
    50                  55                  60

Lys Ser Lys Ala Thr Leu Thr Val Asp Thr Ser Ser Ser Thr Ala Tyr
65                  70                  75                  80

Met His Leu Ser Arg Leu Thr Ser Glu Asp Ser Ala Val Tyr Tyr Cys
                85                  90                  95

Ala Thr Gly Leu His Trp Tyr Phe Asp Val Trp Gly Thr Gly Thr Thr
            100                 105                 110

Val Thr Val Ser Ser
        115

<210> SEQ ID NO 231
<211> LENGTH: 351
```

<212> TYPE: DNA
<213> ORGANISM: Mus musculus
<220> FEATURE:
<221> NAME/KEY: misc_feature
<222> LOCATION: (1)..(351)
<223> OTHER INFORMATION: Polynucleotide Encoding the VH Domain of PD-1
      mAb 14

<400> SEQUENCE: 231

```
caggtccaac tgcagcagcc tggggctgag cttgtgaagc ctggggcttc agtgaagatg      60
tcctgcaagg cttctggcta caacttcatc agctactgga taacctgggt gaaacagagg     120
cctggacaag gccttcagtg gattggaaat atttatcctg gtactgatgg tactacctac     180
aatgagaagt tcaagagcaa ggccacactg actgtagaca tcctccag cacagcctac       240 atgcacctca gtcgcctgac atctgaggac tctgcggtct attactgtgc aactgggcta    300
cactggtact cgatgtctg gggcacaggg accacggtca ccgtctcctc c              351
```

<210> SEQ ID NO 232
<211> LENGTH: 5
<212> TYPE: PRT
<213> ORGANISM: Mus musculus
<220> FEATURE:
<221> NAME/KEY: MISC_FEATURE
<222> LOCATION: (1)..(5)
<223> OTHER INFORMATION: CDRH1 of PD-1 mAb 14

<400> SEQUENCE: 232

Ser Tyr Trp Ile Thr
1               5

<210> SEQ ID NO 233
<211> LENGTH: 17
<212> TYPE: PRT
<213> ORGANISM: Mus musculus
<220> FEATURE:
<221> NAME/KEY: MISC_FEATURE
<222> LOCATION: (1)..(17)
<223> OTHER INFORMATION: CDRH2 of PD-1 mAb 14

<400> SEQUENCE: 233

Asn Ile Tyr Pro Gly Thr Asp Gly Thr Thr Tyr Asn Glu Lys Phe Lys
1               5                   10                  15

Ser

<210> SEQ ID NO 234
<211> LENGTH: 8
<212> TYPE: PRT
<213> ORGANISM: Mus musculus
<220> FEATURE:
<221> NAME/KEY: MISC_FEATURE
<222> LOCATION: (1)..(8)
<223> OTHER INFORMATION: CDRH3 of PD-1 mAb 14

<400> SEQUENCE: 234

Gly Leu His Trp Tyr Phe Asp Val
1               5

<210> SEQ ID NO 235
<211> LENGTH: 107
<212> TYPE: PRT
<213> ORGANISM: Mus musculus
<220> FEATURE:
<221> NAME/KEY: MISC_FEATURE
<222> LOCATION: (1)..(107)
<223> OTHER INFORMATION: VL Domain of PD-1 mAb 14

<400> SEQUENCE: 235

Asp Ile Val Met Thr Gln Ser Gln Lys Phe Met Ser Thr Ser Val Gly
1               5                   10                  15

Asp Arg Val Ser Val Thr Cys Lys Ala Ser Gln Ser Val Gly Thr Asn
            20                  25                  30

Val Ala Trp Tyr Gln Gln Lys Pro Gly Gln Ser Pro Lys Ala Leu Ile
        35                  40                  45

Tyr Ser Ala Ser Ser Arg Phe Ser Gly Val Pro Asp Arg Phe Thr Gly
50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Tyr Pro Tyr
                85                  90                  95

Thr Phe Gly Gly Gly Thr Lys Leu Glu Ile Lys
            100                 105

<210> SEQ ID NO 236
<211> LENGTH: 321
<212> TYPE: DNA
<213> ORGANISM: Mus musculus
<220> FEATURE:
<221> NAME/KEY: misc_feature
<222> LOCATION: (1)..(321)
<223> OTHER INFORMATION: Polynucleotide Encoding the VL Domain of PD-1
      mAb 14

<400> SEQUENCE: 236
gacattgtga tgacccagtc tcaaaaattc atgtccacat cagtaggaga cagggtcagt    60
gtcacctgca aggccagtca gagtgtgggt actaatgtag cctggtatca acagaagccc   120
ggtcaatctc ctaaagcact gatttactcg gcatcctccc gattcagtgg cgtccctgat   180
cgcttcacag gcagtggatc tgggacagat ttcactctca ccatcagtaa tgtgcagtct   240
gaagacttgg cagagtattt ctgtcagcaa tataacagct atccgtacac gttcggaggg   300
gggaccaagc tggaaataaa a                                              321

<210> SEQ ID NO 237
<211> LENGTH: 11
<212> TYPE: PRT
<213> ORGANISM: Mus musculus
<220> FEATURE:
<221> NAME/KEY: MISC_FEATURE
<222> LOCATION: (1)..(11)
<223> OTHER INFORMATION: CDRL1 of PD-1 mAb 14

<400> SEQUENCE: 237

Lys Ala Ser Gln Ser Val Gly Thr Asn Val Ala
1               5                   10

<210> SEQ ID NO 238
<211> LENGTH: 7
<212> TYPE: PRT
<213> ORGANISM: Mus musculus
<220> FEATURE:
<221> NAME/KEY: MISC_FEATURE
<222> LOCATION: (1)..(7)
<223> OTHER INFORMATION: CDRL2 of PD-1 mAb 14

<400> SEQUENCE: 238

Ser Ala Ser Ser Arg Phe Ser
1               5

```
<210> SEQ ID NO 239
<211> LENGTH: 9
<212> TYPE: PRT
<213> ORGANISM: Mus musculus
<220> FEATURE:
<221> NAME/KEY: MISC_FEATURE
<222> LOCATION: (1)..(9)
<223> OTHER INFORMATION: CDRL3 of PD-1 mAb 14

<400> SEQUENCE: 239

Gln Gln Tyr Asn Ser Tyr Pro Tyr Thr
1               5

<210> SEQ ID NO 240
<211> LENGTH: 117
<212> TYPE: PRT
<213> ORGANISM: Mus musculus
<220> FEATURE:
<221> NAME/KEY: MISC_FEATURE
<222> LOCATION: (1)..(117)
<223> OTHER INFORMATION: VH Domain of PD-1 mAb 15

<400> SEQUENCE: 240

Glu Val Met Leu Val Glu Ser Gly Gly Gly Leu Val Lys Pro Gly Gly
1               5                   10                  15

Ser Leu Lys Leu Ser Cys Ala Ala Ser Gly Phe Ile Phe Ser Ser Tyr
            20                  25                  30

Leu Ile Ser Trp Val Arg Gln Thr Pro Glu Lys Arg Leu Glu Trp Val
        35                  40                  45

Ala Ala Ile Ser Gly Gly Gly Ala Asp Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ser Glu Asp Thr Ala Leu Tyr Tyr Cys
                85                  90                  95

Thr Arg Arg Gly Thr Tyr Ala Met Asp Tyr Trp Gly Gln Gly Thr Ser
            100                 105                 110

Val Thr Val Ser Ser
        115

<210> SEQ ID NO 241
<211> LENGTH: 351
<212> TYPE: DNA
<213> ORGANISM: Mus musculus
<220> FEATURE:
<221> NAME/KEY: misc_feature
<222> LOCATION: (1)..(351)
<223> OTHER INFORMATION: Polynucleotide Encoding the VH Domain of PD-1
      mAb 15

<400> SEQUENCE: 241
gaagtgatgc tggtggagtc tgggggaggc ttagtgaagc ctggagggtc cctgaaactc      60
tcctgtgcag cctctggatt cattttcagt agctatctca tctcttgggt tcgccagact     120
ccggagaaga ggctggagtg ggtcgctgcc attagtggtg gtggtgctga cacctactat     180
gccgacagtg tgaagggtcg attcaccatc tccagagaca atgccaagaa caccctgtat     240
ctgcaaatga gcagtctgag gtctgaggac acggccttat attactgtac aagacgaggg     300
acctatgcta tggactactg gggtcaagga acctcagtca ccgtctcctc c              351

<210> SEQ ID NO 242
<211> LENGTH: 5
<212> TYPE: PRT
```

```
<213> ORGANISM: Mus musculus
<220> FEATURE:
<221> NAME/KEY: MISC_FEATURE
<222> LOCATION: (1)..(5)
<223> OTHER INFORMATION: CDRH1 of PD-1 mAb 15

<400> SEQUENCE: 242

Ser Tyr Leu Ile Ser
1               5

<210> SEQ ID NO 243
<211> LENGTH: 17
<212> TYPE: PRT
<213> ORGANISM: Mus musculus
<220> FEATURE:
<221> NAME/KEY: MISC_FEATURE
<222> LOCATION: (1)..(17)
<223> OTHER INFORMATION: CDRH2 of PD-1 mAb 15

<400> SEQUENCE: 243

Ala Ile Ser Gly Gly Gly Ala Asp Thr Tyr Tyr Ala Asp Ser Val Lys
1               5                   10                  15

Gly

<210> SEQ ID NO 244
<211> LENGTH: 8
<212> TYPE: PRT
<213> ORGANISM: Mus musculus
<220> FEATURE:
<221> NAME/KEY: MISC_FEATURE
<222> LOCATION: (1)..(8)
<223> OTHER INFORMATION: CDRH3 of PD-1 mAb 15

<400> SEQUENCE: 244

Arg Gly Thr Tyr Ala Met Asp Tyr
1               5

<210> SEQ ID NO 245
<211> LENGTH: 107
<212> TYPE: PRT
<213> ORGANISM: Mus musculus
<220> FEATURE:
<221> NAME/KEY: MISC_FEATURE
<222> LOCATION: (1)..(107)
<223> OTHER INFORMATION: VL Domain of PD-1 mAb 15

<400> SEQUENCE: 245

Asp Ile Gln Met Thr Gln Ser Pro Ala Ser Gln Ser Ala Ser Leu Gly
1               5                   10                  15

Glu Ser Val Thr Ile Thr Cys Leu Ala Ser Gln Thr Ile Gly Thr Trp
            20                  25                  30

Leu Ala Trp Tyr Gln Gln Lys Pro Gly Lys Ser Pro Gln Leu Leu Ile
        35                  40                  45

Tyr Ala Ala Thr Ser Leu Ala Asp Gly Val Pro Ser Arg Phe Ser Gly
    50                  55                  60

Ser Gly Ser Gly Thr Lys Phe Ser Phe Lys Ile Ser Ser Leu Gln Ala
65                  70                  75                  80

Glu Asp Phe Val Asn Tyr Tyr Cys Gln Gln Leu Tyr Ser Ile Pro Trp
                85                  90                  95

Thr Phe Gly Gly Gly Thr Lys Leu Glu Ile Lys
            100                 105

<210> SEQ ID NO 246
<211> LENGTH: 321
```

```
<212> TYPE: DNA
<213> ORGANISM: Mus musculus
<220> FEATURE:
<221> NAME/KEY: misc_feature
<222> LOCATION: (1)..(321)
<223> OTHER INFORMATION: Polynucleotide Encoding the VL Domain of PD-1
      mAb 15

<400> SEQUENCE: 246
gacattcaga tgacccagtc tcccgcctcc cagtctgcat ctctgggaga aagtgtcacc      60
atcacatgcc tggcaagtca gaccattggt acatggttag catggtatca gcagaaacca     120
gggaaatctc ctcagctcct gatttatgct gcaaccagct ggcagatggg gtcccatca     180 aggttcagtg gtagtggatc tggcacaaaa ttttctttca agatcagcag cctacaggct    240
gaagattttg taaattatta ctgtcaacaa ctttacagta ttccgtggac gttcggtgga    300
ggcaccaagc tggaaatcaa a                                              321

<210> SEQ ID NO 247
<211> LENGTH: 11
<212> TYPE: PRT
<213> ORGANISM: Mus musculus
<220> FEATURE:
<221> NAME/KEY: MISC_FEATURE
<222> LOCATION: (1)..(11)
<223> OTHER INFORMATION: CDRL1 of PD-1 mAb 15

<400> SEQUENCE: 247

Leu Ala Ser Gln Thr Ile Gly Thr Trp Leu Ala
1               5                   10

<210> SEQ ID NO 248
<211> LENGTH: 7
<212> TYPE: PRT
<213> ORGANISM: Mus musculus
<220> FEATURE:
<221> NAME/KEY: MISC_FEATURE
<222> LOCATION: (1)..(7)
<223> OTHER INFORMATION: CDRL2 of PD-1 mAb 15

<400> SEQUENCE: 248

Ala Ala Thr Ser Leu Ala Asp
1               5

<210> SEQ ID NO 249
<211> LENGTH: 9
<212> TYPE: PRT
<213> ORGANISM: Mus musculus
<220> FEATURE:
<221> NAME/KEY: MISC_FEATURE
<222> LOCATION: (1)..(9)
<223> OTHER INFORMATION: CDRL3 of PD-1 mAb 15

<400> SEQUENCE: 249

Gln Gln Leu Tyr Ser Ile Pro Trp Thr
1               5

<210> SEQ ID NO 250
<211> LENGTH: 117
<212> TYPE: PRT
<213> ORGANISM: Artificial Sequence
<220> FEATURE:
<223> OTHER INFORMATION: VH Domain of hPD-1 mAb 15 VH1

<400> SEQUENCE: 250

Glu Val Gln Leu Val Glu Ser Gly Gly Gly Leu Val Arg Pro Gly Gly
1               5                   10                  15
```

Ser Leu Arg Leu Ser Cys Ala Ala Ser Gly Phe Thr Phe Ser Ser Tyr
            20                  25                  30

Leu Ile Ser Trp Val Arg Gln Ala Pro Gly Lys Gly Leu Glu Trp Val
        35                  40                  45

Ala Ala Ile Ser Gly Gly Gly Ala Asp Thr Tyr Tyr Ala Asp Ser Val
 50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Thr Tyr Tyr Cys
                85                  90                  95

Ala Arg Arg Gly Thr Tyr Ala Met Asp Tyr Trp Gly Gln Gly Thr Leu
            100                 105                 110

Val Thr Val Ser Ser
            115

<210> SEQ ID NO 251
<211> LENGTH: 351
<212> TYPE: DNA
<213> ORGANISM: Artificial Sequence
<220> FEATURE:
<223> OTHER INFORMATION: Polynucleotide Encoding hPD-1 mAb 15 VH1

<400> SEQUENCE: 251
gaagtgcaac tggttgaaag tggcggcggg ctggtgcggc aggtggttc actcagactg      60 tcttgtgcag cttcaggctt tacattctcc tcttatctta tctcttgggt gcgccaagcc   120
ccaggtaagg gccttgaatg ggtcgccgcc attagtgggg gtggtgccga tacatattat   180
gccgacagcg tcaagggacg tttcaccatc agcagggaca acgccaagaa tagcctttac   240
ctgcagatga actcacttag agctgaagac accgctactt attactgtgc ccggcgcggg   300
acttacgcta tggactattg gggccagggc accttggtca ctgtctcatc c            351

<210> SEQ ID NO 252
<211> LENGTH: 107
<212> TYPE: PRT
<213> ORGANISM: Artificial Sequence
<220> FEATURE:
<223> OTHER INFORMATION: VH Domain of hPD-1 mAb 15 VL1

<400> SEQUENCE: 252

Asp Ile Gln Met Thr Gln Ser Pro Ser Ser Leu Ser Ala Ser Val Gly
1               5                   10                  15

Asp Arg Val Thr Ile Thr Cys Leu Ala Ser Gln Thr Ile Gly Thr Trp
            20                  25                  30

Leu Ala Trp Tyr Gln Gln Lys Pro Gly Lys Ala Pro Lys Leu Leu Ile
        35                  40                  45

Tyr Ala Ala Thr Ser Leu Ala Asp Gly Val Pro Ser Arg Phe Ser Gly
 50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Gln Gln Leu Tyr Ser Ile Pro Trp
                85                  90                  95

Thr Phe Gly Gln Gly Thr Lys Leu Glu Ile Lys
            100                 105

<210> SEQ ID NO 253
<211> LENGTH: 321
<212> TYPE: DNA

```
<213> ORGANISM: Artificial Sequence
<220> FEATURE:
<223> OTHER INFORMATION: Polynucleotide encoding hPD-1 mAb 15 VL1

<400> SEQUENCE: 253
gatatccaga tgacccagtc tcccagctct ctcagtgcaa gcgtaggcga ccgtgtgacc    60
atcacctgtc tggccagtca gaccattgga acctggctcg cctggtatca gcagaaacct   120
ggcaaggccc ctaagctgct gatttacgcc gccacctccc tcgcagatgg agtgccctcc   180
cgatttagcg gtccgggtc cggcaccgac ttcacattca caatcagcag cctccagccc    240
gaggatttcg ctacatacta ctgtcaacag ctctactcca ttccatggac ctttggtcag   300
ggtactaaac tggagatcaa a                                             321

<210> SEQ ID NO 254
<211> LENGTH: 98
<212> TYPE: PRT
<213> ORGANISM: Homo sapiens
<220> FEATURE:
<221> NAME/KEY: MISC_FEATURE
<222> LOCATION: (1)..(98)
<223> OTHER INFORMATION: Human IgG4 CH1 Domain

<400> SEQUENCE: 254

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val

<210> SEQ ID NO 255
<211> LENGTH: 329
<212> TYPE: PRT
<213> ORGANISM: Artificial Sequence
<220> FEATURE:
<223> OTHER INFORMATION: IgG1 Humanized Antibody Heavy Chain

<400> SEQUENCE: 255

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
```

```
                100              105              110
Pro Ala Pro Glu Ala Ala Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 256
<211> LENGTH: 326
<212> TYPE: PRT
<213> ORGANISM: Artificial Sequence
<220> FEATURE:
<223> OTHER INFORMATION: IgG4 Humanized Antibody Heavy Chain with
      Stabilized Hinge Region

<400> SEQUENCE: 256

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125
```

```
Asp Thr Leu Met Ile Ser Arg Thr Pro Glu Val Thr Cys Val Val Val
            130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly
                325

<210> SEQ ID NO 257
<211> LENGTH: 98
<212> TYPE: PRT
<213> ORGANISM: Homo sapiens
<220> FEATURE:
<221> NAME/KEY: MISC_FEATURE
<222> LOCATION: (1)..(98)
<223> OTHER INFORMATION: Human IgG2 CH1 Domain

<400> SEQUENCE: 257

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val

<210> SEQ ID NO 258
<211> LENGTH: 217
<212> TYPE: PRT
<213> ORGANISM: Artificial Sequence
<220> FEATURE:
<223> OTHER INFORMATION: IgG1 Sequence for the CH2 and CH3 Domains
<220> FEATURE:
```

<221> NAME/KEY: MISC_FEATURE
<222> LOCATION: (217)..(217)
<223> OTHER INFORMATION: Xaa is a lysine (K) or is absent

<400> SEQUENCE: 258

Ala Pro Glu Ala Ala Gly Gly Pro Ser Val Phe Leu Phe Pro Pro Lys
1               5                   10                  15

Pro Lys Asp Thr Leu Tyr Ile Thr Arg Glu Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Xaa
210                 215

<210> SEQ ID NO 259
<211> LENGTH: 217
<212> TYPE: PRT
<213> ORGANISM: Artificial Sequence
<220> FEATURE:
<223> OTHER INFORMATION: IgG4 Sequence for the CH2 and CH3 Domains
<220> FEATURE:
<221> NAME/KEY: MISC_FEATURE
<222> LOCATION: (217)..(217)
<223> OTHER INFORMATION: Xaa is a lysine (K) or is absent

<400> SEQUENCE: 259

Ala Pro Glu Phe Leu Gly Gly Pro Ser Val Phe Leu Phe Pro Pro Lys
1               5                   10                  15

Pro Lys Asp Thr Leu Tyr Ile Thr Arg Glu Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

```
Gly Leu Pro Ser Ser Ile Glu Lys Thr Ile Ser Lys Ala Lys Gly Gln
                100                 105                 110

Pro Arg Glu Pro Gln Val Tyr Thr Leu Pro Pro Ser Gln Glu Glu Met
            115                 120                 125

Thr Lys Asn Gln Val Ser Leu Thr Cys Leu Val Lys Gly Phe Tyr Pro
        130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Arg Leu Thr Val Asp Lys Ser Arg Trp Gln Glu Gly Asn Val
                180                 185                 190

Phe Ser Cys Ser Val Met His Glu Ala Leu His Asn His Tyr Thr Gln
            195                 200                 205

Lys Ser Leu Ser Leu Ser Leu Gly Xaa
    210                 215
```

<210> SEQ ID NO 260
<211> LENGTH: 217
<212> TYPE: PRT
<213> ORGANISM: Artificial Sequence
<220> FEATURE:
<223> OTHER INFORMATION: Wild-type and Variant Human IgG1 CH2 and CH3
      Domains
<220> FEATURE:
<221> NAME/KEY: MISC_FEATURE
<222> LOCATION: (4)..(5)
<223> OTHER INFORMATION: Xaa4 and Xaa5 are both L (wild type), or are
      both A (decreased FcgammaR binding)
<220> FEATURE:
<221> NAME/KEY: MISC_FEATURE
<222> LOCATION: (22)..(26)
<223> OTHER INFORMATION: Xaa22, Xaa24 and Xaa26 respectively are M, S
      and T (wild type), or are Y, T and E (extended half-life)
<220> FEATURE:
<221> NAME/KEY: MISC_FEATURE
<222> LOCATION: (136)..(177)
<223> OTHER INFORMATION: Xaa136, Xaa138, and Xaa177 respectively are: T,
      L and Y (wild type), or are W, L and Y (knob), or S, A and V
      (hole)
<220> FEATURE:
<221> NAME/KEY: MISC_FEATURE
<222> LOCATION: (204)..(205)
<223> OTHER INFORMATION: Xaa204 and Xaa205 respectively are N and H
      (wild type), or are N and R (no protein A binding), or A and K (no
      protein A binding)
<220> FEATURE:
<221> NAME/KEY: MISC_FEATURE
<222> LOCATION: (217)..(217)
<223> OTHER INFORMATION: Xaa217 is K or is absent

<400> SEQUENCE: 260

```
Ala Pro Glu Xaa Xaa Gly Gly Pro Ser Val Phe Leu Phe Pro Pro Lys
1               5                   10                  15

Pro Lys Asp Thr Leu Xaa Ile Xaa Arg Xaa Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95
```

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Xaa Cys Xaa Val Lys Gly Phe Tyr Pro
130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
            165                 170                 175

Xaa Ser Lys Leu Thr Val Asp Lys Ser Arg Trp Gln Gln Gly Asn Val
        180                 185                 190

Phe Ser Cys Ser Val Met His Glu Ala Leu His Xaa Xaa Tyr Thr Gln
            195                 200                 205

Lys Ser Leu Ser Leu Ser Pro Gly Xaa
        210                 215

<210> SEQ ID NO 261
<211> LENGTH: 6
<212> TYPE: PRT
<213> ORGANISM: Artificial Sequence
<220> FEATURE:
<223> OTHER INFORMATION: Alternative Linker 2

<400> SEQUENCE: 261

Leu Gly Gly Gly Ser Gly
1               5

<210> SEQ ID NO 262
<211> LENGTH: 11
<212> TYPE: PRT
<213> ORGANISM: Artificial Sequence
<220> FEATURE:
<223> OTHER INFORMATION: Linker 3

<400> SEQUENCE: 262

Gly Gly Gly Ser Gly Gly Gly Ser Gly Gly Gly
1               5                   10

<210> SEQ ID NO 263
<211> LENGTH: 13
<212> TYPE: PRT
<213> ORGANISM: Artificial Sequence
<220> FEATURE:
<223> OTHER INFORMATION: Linker 3

<400> SEQUENCE: 263

Gly Gly Gly Asp Lys Thr His Thr Cys Pro Pro Cys Pro
1               5                   10

<210> SEQ ID NO 264
<211> LENGTH: 218
<212> TYPE: PRT
<213> ORGANISM: Artificial Sequence
<220> FEATURE:
<223> OTHER INFORMATION: Light Chain of a Humanized PD-1 Antibody (hPD-1
      mAb 7(1.2))

<400> SEQUENCE: 264

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Asp Asn Tyr

```
                    20                  25                  30
Gly Met Ser Phe Met Asn Trp Phe Gln Gln Lys Pro Gly Gln Pro Pro
                35                  40                  45

Lys Leu Leu Ile His Ala Ala Ser Asn Gln Gly Ser Gly Val Pro Ser
 50                  55                  60

Arg Phe Ser Gly Ser Gly Ser Gly Thr Asp Phe Thr Leu Thr Ile Ser
 65                  70                  75                  80

Ser Leu Glu Pro Glu Asp Phe Ala Val Tyr Phe Cys Gln Gln Ser Lys
                 85                  90                  95

Glu Val Pro Tyr Thr Phe Gly Gly Gly Thr Lys Val Glu Ile Lys Arg
                100                 105                 110

Thr Val Ala Ala Pro Ser Val Phe Ile Phe Pro Pro Ser Asp Glu Gln
                115                 120                 125

Leu Lys Ser Gly Thr Ala Ser Val Val Cys Leu Leu Asn Asn Phe Tyr
            130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
                180                 185                 190

His Lys Val Tyr Ala Cys Glu Val Thr His Gln Gly Leu Ser Ser Pro
                195                 200                 205

Val Thr Lys Ser Phe Asn Arg Gly Glu Cys
                210                 215

<210> SEQ ID NO 265
<211> LENGTH: 448
<212> TYPE: PRT
<213> ORGANISM: Artificial Sequence
<220> FEATURE:
<223> OTHER INFORMATION: Heavy Chain of a Humanized Antibody ((hPD-1 mAb
      7(1.2))

<400> SEQUENCE: 265

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Ser Phe Thr Ser Tyr
                20                  25                  30

Trp Met Asn Trp Val Arg Gln Ala Pro Gly Gln Gly Leu Glu Trp Ile
                35                  40                  45

Gly Val Ile His Pro Ser Asp Ser Glu Thr Trp Leu Asp Gln Lys Phe
 50                  55                  60

Lys Asp Arg Val Thr Ile Thr Val Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Glu His Tyr Gly Thr Ser Pro Phe Ala Tyr Trp Gly Gln Gly
                100                 105                 110

Thr Leu Val Thr Val Ser Ser Ala Ser Thr Lys Gly Pro Ser Val Phe
                115                 120                 125

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160
```

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
        180                 185                 190

Ser Ser Leu Gly Thr Gln Thr Tyr Ile Cys Asn Val Asn His Lys Pro
    195                 200                 205

Ser Asn Thr Lys Val Asp Lys Arg Val Glu Pro Lys Ser Cys Asp Lys
210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
        260                 265                 270

Pro Glu Val Lys Phe Asn Trp Tyr Val Asp Gly Val Glu Val His Asn
    275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
        340                 345                 350

Leu Pro Pro Ser Arg Glu Glu Met Thr Lys Asn Gln Val Ser Leu Thr
    355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
        420                 425                 430

Ala Leu His Asn His Tyr Thr Gln Lys Ser Leu Ser Leu Ser Pro Gly
    435                 440                 445

<210> SEQ ID NO 266
<211> LENGTH: 445
<212> TYPE: PRT
<213> ORGANISM: Artificial Sequence
<220> FEATURE:
<223> OTHER INFORMATION: Heavy Chain of a Humanized Antibody ((hPD-1 mAb
      7(1.2))

<400> SEQUENCE: 266

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Tyr
            20                  25                  30

Trp Met Asn Trp Val Arg Gln Ala Pro Gly Gln Gly Leu Glu Trp Ile
        35                  40                  45

Gly Val Ile His Pro Ser Asp Ser Glu Thr Trp Leu Asp Gln Lys Phe
    50                  55                  60

Lys Asp Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu His Tyr Gly Thr Ser Pro Phe Ala Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly
        435                 440                 445

<210> SEQ ID NO 267
<211> LENGTH: 501
<212> TYPE: PRT
<213> ORGANISM: Artificial Sequence
<220> FEATURE:
<223> OTHER INFORMATION: First and Third Polypeptide Chains of DART A
<220> FEATURE:
<221> NAME/KEY: MISC_FEATURE -continued

```
<222> LOCATION: (34)..(34)
<223> OTHER INFORMATION: Xaa34 is A or G
<220> FEATURE:
<221> NAME/KEY: MISC_FEATURE
<222> LOCATION: (307)..(307)
<223> OTHER INFORMATION: Xaa307 is Y or M
<220> FEATURE:
<221> NAME/KEY: MISC_FEATURE
<222> LOCATION: (309)..(309)
<223> OTHER INFORMATION: Xaa309 is T or S
<220> FEATURE:
<221> NAME/KEY: MISC_FEATURE
<222> LOCATION: (311)..(311)
<223> OTHER INFORMATION: Xaa311 is E or T

<400> SEQUENCE: 267

Asp Ile Val Met Thr Gln Thr Pro Leu Ser Leu Ser Val Thr Pro Gly
1               5                   10                  15

Gln Pro Ala Ser Ile Ser Cys Lys Ser Gln Ser Leu Leu His Ser
            20                  25                  30

Asp Xaa Lys Thr Tyr Leu Asn Trp Leu Leu Gln Lys Pro Gly Gln Pro
        35                  40                  45

Pro Glu Arg Leu Ile Tyr Leu Val Ser Glu Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Tyr Thr Phe Gly Gly Gly Thr Lys Val Glu Ile Lys
            100                 105                 110

Gly Gly Gly Ser Gly Gly Gly Gln Val Gln Leu Val Gln Ser Gly
        115                 120                 125

Ala Glu Val Lys Lys Pro Gly Ala Ser Val Lys Val Ser Cys Lys Ala
    130                 135                 140

Ser Gly Tyr Ser Phe Thr Ser Tyr Trp Met Asn Trp Val Arg Gln Ala
145                 150                 155                 160

Pro Gly Gln Gly Leu Glu Trp Ile Gly Val Ile His Pro Ser Asp Ser
                165                 170                 175

Glu Thr Trp Leu Asp Gln Lys Phe Lys Asp Arg Val Thr Ile Thr Val
            180                 185                 190

Asp Lys Ser Thr Ser Thr Ala Tyr Met Glu Leu Ser Ser Leu Arg Ser
        195                 200                 205

Glu Asp Thr Ala Val Tyr Tyr Cys Ala Arg Glu His Tyr Gly Thr Ser
    210                 215                 220

Pro Phe Ala Tyr Trp Gly Gln Gly Thr Leu Val Thr Val Ser Ser Gly
225                 230                 235                 240

Gly Cys Gly Gly Gly Glu Val Ala Ala Cys Glu Lys Glu Val Ala Ala
                245                 250                 255

Leu Glu Lys Glu Val Ala Ala Leu Glu Lys Glu Val Ala Ala Leu Glu
            260                 265                 270

Lys Glu Ser Lys Tyr Gly Pro Pro Cys Pro Pro Cys Pro Ala Pro Glu
        275                 280                 285

Phe Leu Gly Gly Pro Ser Val Phe Leu Phe Pro Pro Lys Pro Lys Asp
    290                 295                 300

Thr Leu Xaa Ile Xaa Arg Xaa Pro Glu Val Thr Cys Val Val Val Asp
305                 310                 315                 320

Val Ser Gln Glu Asp Pro Glu Val Gln Phe Asn Trp Tyr Val Asp Gly
                325                 330                 335
```

Val Glu Val His Asn Ala Lys Thr Lys Pro Arg Glu Gln Phe Asn
            340                 345                 350

Ser Thr Tyr Arg Val Val Ser Val Leu Thr Val Leu His Gln Asp Trp
            355                 360                 365

Leu Asn Gly Lys Glu Tyr Lys Cys Lys Val Ser Asn Lys Gly Leu Pro
370                 375                 380

Ser Ser Ile Glu Lys Thr Ile Ser Lys Ala Lys Gly Gln Pro Arg Glu
385                 390                 395                 400

Pro Gln Val Tyr Thr Leu Pro Pro Ser Gln Glu Met Thr Lys Asn
            405                 410                 415

Gln Val Ser Leu Thr Cys Leu Val Lys Gly Phe Tyr Pro Ser Asp Ile
            420                 425                 430

Ala Val Glu Trp Glu Ser Asn Gly Gln Pro Glu Asn Asn Tyr Lys Thr
            435                 440                 445

Thr Pro Pro Val Leu Asp Ser Asp Gly Ser Phe Phe Leu Tyr Ser Arg
450                 455                 460

Leu Thr Val Asp Lys Ser Arg Trp Gln Glu Gly Asn Val Phe Ser Cys
465                 470                 475                 480

Ser Val Met His Glu Ala Leu His Asn His Tyr Thr Gln Lys Ser Leu
            485                 490                 495

Ser Leu Ser Leu Gly
            500

<210> SEQ ID NO 268
<211> LENGTH: 273
<212> TYPE: PRT
<213> ORGANISM: Artificial Sequence
<220> FEATURE:
<223> OTHER INFORMATION: Second and Fourth Polypeptide Chains of DART A

<400> SEQUENCE: 268

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Asp Asn Tyr
            20                  25                  30

Gly Met Ser Phe Met Asn Trp Phe Gln Gln Lys Pro Gly Gln Pro Pro
        35                  40                  45

Lys Leu Leu Ile His Ala Ala Ser Asn Gln Gly Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Phe Cys Gln Gln Ser Lys
                85                  90                  95

Glu Val Pro Tyr Thr Phe Gly Gly Gly Thr Lys Val Glu Ile Lys Gly
            100                 105                 110

Gly Gly Ser Gly Gly Gly Gln Val Gln Leu Val Gln Ser Gly Ala
        115                 120                 125

Glu Val Lys Lys Pro Gly Ala Ser Val Lys Val Ser Cys Lys Ala Ser
    130                 135                 140

Gly Tyr Thr Phe Thr Asn Tyr Gly Met Asn Trp Val Arg Gln Ala Pro
145                 150                 155                 160

Gly Gln Gly Leu Glu Trp Met Gly Trp Ile Asn Thr Tyr Thr Gly Glu
                165                 170                 175

Ser Thr Tyr Ala Asp Asp Phe Glu Gly Arg Phe Val Phe Ser Met Asp
            180                 185                 190

```
Thr Ser Ala Ser Thr Ala Tyr Leu Gln Ile Ser Ser Leu Lys Ala Glu
            195                 200                 205

Asp Thr Ala Val Tyr Tyr Cys Ala Arg Glu Ser Leu Tyr Asp Tyr Tyr
            210                 215                 220

Ser Met Asp Tyr Trp Gly Gln Gly Thr Thr Val Thr Val Ser Ser Gly
225                 230                 235                 240

Gly Cys Gly Gly Gly Lys Val Ala Ala Cys Lys Glu Lys Val Ala Ala
                245                 250                 255

Leu Lys Glu Lys Val Ala Ala Leu Lys Glu Lys Val Ala Ala Leu Lys
                260                 265                 270

Glu

<210> SEQ ID NO 269
<211> LENGTH: 571
<212> TYPE: PRT
<213> ORGANISM: Artificial Sequence
<220> FEATURE:
<223> OTHER INFORMATION: First and Third Polypeptide Chains of DART D

<400> SEQUENCE: 269

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Asp Asn Tyr
            20                  25                  30

Gly Met Ser Phe Met Asn Trp Phe Gln Gln Lys Pro Gly Gln Pro Pro
        35                  40                  45

Lys Leu Leu Ile His Ala Ala Ser Asn Gln Gly Ser Gly Val Pro Ser
50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Phe Cys Gln Gln Ser Lys
                85                  90                  95

Glu Val Pro Tyr Thr Phe Gly Gly Gly Thr Lys Val Glu Ile Lys Gly
            100                 105                 110

Gly Gly Ser Gly Gly Gly Gln Val Gln Leu Val Gln Ser Gly Ala
        115                 120                 125

Glu Val Lys Lys Pro Gly Ala Ser Val Lys Val Ser Cys Lys Ala Ser
130                 135                 140

Gly Tyr Thr Phe Thr Asn Tyr Gly Met Asn Trp Val Arg Gln Ala Pro
145                 150                 155                 160

Gly Gln Gly Leu Glu Trp Met Gly Trp Ile Asn Thr Tyr Thr Gly Glu
                165                 170                 175

Ser Thr Tyr Ala Asp Asp Phe Lys Gly Arg Phe Val Phe Ser Met Asp
            180                 185                 190

Thr Ser Ala Ser Thr Ala Tyr Leu Gln Ile Ser Ser Leu Lys Ala Glu
            195                 200                 205

Asp Thr Ala Val Tyr Tyr Cys Ala Arg Glu Ser Leu Tyr Asp Tyr Tyr
            210                 215                 220

Ser Met Asp Tyr Trp Gly Gln Gly Thr Thr Val Thr Val Ser Ser Leu
225                 230                 235                 240

Gly Gly Gly Ser Gly Ala Ser Thr Lys Gly Pro Ser Val Phe Pro Leu
                245                 250                 255

Ala Pro Cys Ser Arg Ser Thr Ser Glu Ser Thr Ala Ala Leu Gly Cys
            260                 265                 270
```

Leu Val Lys Asp Tyr Phe Pro Glu Pro Val Thr Val Ser Trp Asn Ser
            275                 280                 285

Gly Ala Leu Thr Ser Gly Val His Thr Phe Pro Ala Val Leu Gln Ser
        290                 295                 300

Ser Gly Leu Tyr Ser Leu Ser Ser Val Val Thr Val Pro Ser Ser Ser
305                 310                 315                 320

Leu Gly Thr Lys Thr Tyr Thr Cys Asn Val Asp His Lys Pro Ser Asn
                325                 330                 335

Thr Lys Val Asp Lys Arg Val Glu Ser Lys Tyr Gly Pro Pro Cys Pro
            340                 345                 350

Pro Cys Pro Ala Pro Glu Phe Leu Gly Gly Pro Ser Val Phe Leu Phe
        355                 360                 365

Pro Pro Lys Pro Lys Asp Thr Leu Tyr Ile Thr Arg Glu Pro Glu Val
370                 375                 380

Thr Cys Val Val Val Asp Val Ser Gln Glu Asp Pro Glu Val Gln Phe
385                 390                 395                 400

Asn Trp Tyr Val Asp Gly Val Glu Val His Asn Ala Lys Thr Lys Pro
                405                 410                 415

Arg Glu Glu Gln Phe Asn Ser Thr Tyr Arg Val Val Ser Val Leu Thr
            420                 425                 430

Val Leu His Gln Asp Trp Leu Asn Gly Lys Glu Tyr Lys Cys Lys Val
        435                 440                 445

Ser Asn Lys Gly Leu Pro Ser Ser Ile Glu Lys Thr Ile Ser Lys Ala
    450                 455                 460

Lys Gly Gln Pro Arg Glu Pro Gln Val Tyr Thr Leu Pro Pro Ser Gln
465                 470                 475                 480

Glu Glu Met Thr Lys Asn Gln Val Ser Leu Thr Cys Leu Val Lys Gly
                485                 490                 495

Phe Tyr Pro Ser Asp Ile Ala Val Glu Trp Glu Ser Asn Gly Gln Pro
            500                 505                 510

Glu Asn Asn Tyr Lys Thr Thr Pro Pro Val Leu Asp Ser Asp Gly Ser
        515                 520                 525

Phe Phe Leu Tyr Ser Arg Leu Thr Val Asp Lys Ser Arg Trp Gln Glu
530                 535                 540

Gly Asn Val Phe Ser Cys Ser Val Met His Glu Ala Leu His Asn His
545                 550                 555                 560

Tyr Thr Gln Lys Ser Leu Ser Leu Ser Leu Gly
                565                 570

<210> SEQ ID NO 270
<211> LENGTH: 352
<212> TYPE: PRT
<213> ORGANISM: Artificial Sequence
<220> FEATURE:
<223> OTHER INFORMATION: Second and Fourth Polypeptide Chains of DART D

<400> SEQUENCE: 270

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Ala Lys Thr Tyr Leu Asn Trp Leu Leu Gln Lys Pro Gly Gln Pro
        35                  40                  45

Pro Glu Arg Leu Ile Tyr Leu Val Ser Glu Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Tyr Thr Phe Gly Gly Gly Thr Lys Val Glu Ile Lys
            100                 105                 110

Gly Gly Gly Ser Gly Gly Gly Gly Gln Val Gln Leu Val Gln Ser Gly
            115                 120                 125

Ala Glu Val Lys Lys Pro Gly Ala Ser Val Lys Val Ser Cys Lys Ala
        130                 135                 140

Ser Gly Tyr Ser Phe Thr Ser Tyr Trp Met Asn Trp Val Arg Gln Ala
145                 150                 155                 160

Pro Gly Gln Gly Leu Glu Trp Ile Gly Val Ile His Pro Ser Asp Ser
                165                 170                 175

Glu Thr Trp Leu Asp Gln Lys Phe Lys Asp Arg Val Thr Ile Thr Val
            180                 185                 190

Asp Lys Ser Thr Ser Thr Ala Tyr Met Glu Leu Ser Ser Leu Arg Ser
        195                 200                 205

Glu Asp Thr Ala Val Tyr Tyr Cys Ala Arg Glu His Tyr Gly Thr Ser
210                 215                 220

Pro Phe Ala Tyr Trp Gly Gln Gly Thr Leu Val Thr Val Ser Ser Leu
225                 230                 235                 240

Gly Gly Gly Ser Gly Arg Thr Val Ala Ala Pro Ser Val Phe Ile Phe
                245                 250                 255

Pro Pro Ser Asp Glu Gln Leu Lys Ser Gly Thr Ala Ser Val Val Cys
            260                 265                 270

Leu Leu Asn Asn Phe Tyr Pro Arg Glu Ala Lys Val Gln Trp Lys Val
        275                 280                 285

Asp Asn Ala Leu Gln Ser Gly Asn Ser Gln Glu Ser Val Thr Glu Gln
        290                 295                 300

Asp Ser Lys Asp Ser Thr Tyr Ser Leu Ser Ser Thr Leu Thr Leu Ser
305                 310                 315                 320

Lys Ala Asp Tyr Glu Lys His Lys Val Tyr Ala Cys Glu Val Thr His
                325                 330                 335

Gln Gly Leu Ser Ser Pro Val Thr Lys Ser Phe Asn Arg Gly Glu Cys
            340                 345                 350

<210> SEQ ID NO 271
<211> LENGTH: 571
<212> TYPE: PRT
<213> ORGANISM: Artificial Sequence
<220> FEATURE:
<223> OTHER INFORMATION: First and Third Polypeptide Chains of DART E

<400> SEQUENCE: 271

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
                20                  25                  30

Asp Ala Lys Thr Tyr Leu Asn Trp Leu Leu Gln Lys Pro Gly Gln Pro
            35                  40                  45

Pro Glu Arg Leu Ile Tyr Leu Val Ser Glu Leu Asp Ser Gly Val Pro
        50                  55                  60

Asp Arg Phe Ser Gly Ser Gly Ser Gly Thr Asp Phe Thr Leu Lys Ile
65                  70                  75                  80

-continued

```
Ser Arg Val Glu Ala Glu Asp Val Gly Val Tyr Tyr Cys Trp Gln Gly
                85                  90                  95
Thr His Phe Pro Tyr Thr Phe Gly Gly Gly Thr Lys Val Glu Ile Lys
            100                 105                 110
Gly Gly Gly Ser Gly Gly Gly Gly Gln Val Gln Leu Val Gln Ser Gly
        115                 120                 125
Ala Glu Val Lys Lys Pro Gly Ala Ser Val Lys Val Ser Cys Lys Ala
    130                 135                 140
Ser Gly Tyr Ser Phe Thr Ser Tyr Trp Met Asn Trp Val Arg Gln Ala
145                 150                 155                 160
Pro Gly Gln Gly Leu Glu Trp Ile Gly Val Ile His Pro Ser Asp Ser
                165                 170                 175
Glu Thr Trp Leu Asp Gln Lys Phe Lys Asp Arg Val Thr Ile Thr Val
            180                 185                 190
Asp Lys Ser Thr Ser Thr Ala Tyr Met Glu Leu Ser Ser Leu Arg Ser
        195                 200                 205
Glu Asp Thr Ala Val Tyr Tyr Cys Ala Arg Glu His Tyr Gly Thr Ser
    210                 215                 220
Pro Phe Ala Tyr Trp Gly Gln Gly Thr Leu Val Thr Val Ser Ser Leu
225                 230                 235                 240
Gly Gly Gly Ser Gly Ala Ser Thr Lys Gly Pro Ser Val Phe Pro Leu
                245                 250                 255
Ala Pro Cys Ser Arg Ser Thr Ser Glu Ser Thr Ala Ala Leu Gly Cys
            260                 265                 270
Leu Val Lys Asp Tyr Phe Pro Glu Pro Val Thr Val Ser Trp Asn Ser
        275                 280                 285
Gly Ala Leu Thr Ser Gly Val His Thr Phe Pro Ala Val Leu Gln Ser
    290                 295                 300
Ser Gly Leu Tyr Ser Leu Ser Ser Val Val Thr Val Pro Ser Ser Ser
305                 310                 315                 320
Leu Gly Thr Lys Thr Tyr Thr Cys Asn Val Asp His Lys Pro Ser Asn
                325                 330                 335
Thr Lys Val Asp Lys Arg Val Glu Ser Lys Tyr Gly Pro Pro Cys Pro
            340                 345                 350
Pro Cys Pro Ala Pro Glu Phe Leu Gly Gly Pro Ser Val Phe Leu Phe
        355                 360                 365
Pro Pro Lys Pro Lys Asp Thr Leu Tyr Ile Thr Arg Glu Pro Glu Val
    370                 375                 380
Thr Cys Val Val Val Asp Val Ser Gln Glu Asp Pro Glu Val Gln Phe
385                 390                 395                 400
Asn Trp Tyr Val Asp Gly Val Glu Val His Asn Ala Lys Thr Lys Pro
                405                 410                 415
Arg Glu Glu Gln Phe Asn Ser Thr Tyr Arg Val Val Ser Val Leu Thr
            420                 425                 430
Val Leu His Gln Asp Trp Leu Asn Gly Lys Glu Tyr Lys Cys Lys Val
        435                 440                 445
Ser Asn Lys Gly Leu Pro Ser Ser Ile Glu Lys Thr Ile Ser Lys Ala
    450                 455                 460
Lys Gly Gln Pro Arg Glu Pro Gln Val Tyr Thr Leu Pro Pro Ser Gln
465                 470                 475                 480
Glu Glu Met Thr Lys Asn Gln Val Ser Leu Thr Cys Leu Val Lys Gly
                485                 490                 495
Phe Tyr Pro Ser Asp Ile Ala Val Glu Trp Glu Ser Asn Gly Gln Pro
```

```
                500               505                    510
Glu Asn Asn Tyr Lys Thr Thr Pro Pro Val Leu Asp Ser Asp Gly Ser
            515                 520                 525

Phe Phe Leu Tyr Ser Arg Leu Thr Val Asp Lys Ser Arg Trp Gln Glu
        530                 535                 540

Gly Asn Val Phe Ser Cys Ser Val Met His Glu Ala Leu His Asn His
545                 550                 555                 560

Tyr Thr Gln Lys Ser Leu Ser Leu Ser Leu Gly
                565                 570

<210> SEQ ID NO 272
<211> LENGTH: 352
<212> TYPE: PRT
<213> ORGANISM: Artificial Sequence
<220> FEATURE:
<223> OTHER INFORMATION: Second and Fourth Polypeptide Chains of DART E

<400> SEQUENCE: 272

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Asp Asn Tyr
            20                  25                  30

Gly Met Ser Phe Met Asn Trp Phe Gln Gln Lys Pro Gly Gln Pro Pro
        35                  40                  45

Lys Leu Leu Ile His Ala Ala Ser Asn Gln Gly Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Phe Cys Gln Gln Ser Lys
                85                  90                  95

Glu Val Pro Tyr Thr Phe Gly Gly Gly Thr Lys Val Glu Ile Lys Gly
            100                 105                 110

Gly Gly Ser Gly Gly Gly Gly Gln Val Gln Leu Val Gln Ser Gly Ala
        115                 120                 125

Glu Val Lys Lys Pro Gly Ala Ser Val Lys Val Ser Cys Lys Ala Ser
    130                 135                 140

Gly Tyr Thr Phe Thr Asn Tyr Gly Met Asn Trp Val Arg Gln Ala Pro
145                 150                 155                 160

Gly Gln Gly Leu Glu Trp Met Gly Trp Ile Asn Thr Tyr Thr Gly Glu
                165                 170                 175

Ser Thr Tyr Ala Asp Asp Phe Glu Gly Arg Phe Val Phe Ser Met Asp
            180                 185                 190

Thr Ser Ala Ser Thr Ala Tyr Leu Gln Ile Ser Ser Leu Lys Ala Glu
        195                 200                 205

Asp Thr Ala Val Tyr Tyr Cys Ala Arg Glu Ser Leu Tyr Asp Tyr Tyr
    210                 215                 220

Ser Met Asp Tyr Trp Gly Gln Gly Thr Thr Val Thr Val Ser Ser Leu
225                 230                 235                 240

Gly Gly Gly Ser Gly Arg Thr Val Ala Ala Pro Ser Val Phe Ile Phe
                245                 250                 255

Pro Pro Ser Asp Glu Gln Leu Lys Ser Gly Thr Ala Ser Val Val Cys
            260                 265                 270

Leu Leu Asn Asn Phe Tyr Pro Arg Glu Ala Lys Val Gln Trp Lys Val
        275                 280                 285

Asp Asn Ala Leu Gln Ser Gly Asn Ser Gln Glu Ser Val Thr Glu Gln
```

```
                290                 295                 300
Asp Ser Lys Asp Ser Thr Tyr Ser Leu Ser Thr Leu Thr Leu Ser
305                 310                 315                 320

Lys Ala Asp Tyr Glu Lys His Lys Val Tyr Ala Cys Glu Val Thr His
                325                 330                 335

Gln Gly Leu Ser Ser Pro Val Thr Lys Ser Phe Asn Arg Gly Glu Cys
                340                 345                 350
```

<210> SEQ ID NO 273
<211> LENGTH: 448
<212> TYPE: PRT
<213> ORGANISM: Artificial Sequence
<220> FEATURE:
<223> OTHER INFORMATION: First Polypeptide Chain of DART F

<400> SEQUENCE: 273

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Tyr
                20                  25                  30

Trp Met Asn Trp Val Arg Gln Ala Pro Gly Gln Gly Leu Glu Trp Ile
                35                  40                  45

Gly Val Ile His Pro Ser Asp Ser Glu Thr Trp Leu Asp Gln Lys Phe
        50                  55                  60

Lys Asp Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu His Tyr Gly Thr Ser Pro Phe Ala Tyr Trp Gly Gln Gly
                100                 105                 110

Thr Leu Val Thr Val Ser Ser Ala Ser Thr Lys Gly Pro Ser Val Phe
                115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Tyr Ile Thr
                245                 250                 255

Arg Glu Pro Glu Val Thr Cys Val Val Val Asp Val Ser His Glu Asp
                260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
```

```
                305                 310                 315                 320
        Tyr Lys Cys Lys Val Ser Asn Lys Ala Leu Pro Ala Pro Ile Glu Lys
                        325                 330                 335

Thr Ile Ser Lys Ala Lys Gly Gln Pro Arg Glu Pro Gln Val Tyr Thr
                        340                 345                 350

Leu Pro Pro Ser Arg Glu Glu Met Thr Lys Asn Gln Val Ser Leu Ser
                        355                 360                 365

Cys Ala Val Lys Gly Phe Tyr Pro Ser Asp Ile Ala Val Glu Trp Glu
                        370                 375                 380

Ser Asn Gly Gln Pro Glu Asn Asn Tyr Lys Thr Thr Pro Pro Val Leu
        385                 390                 395                 400

Asp Ser Asp Gly Ser Phe Phe Leu Val Ser Lys Leu Thr Val Asp Lys
                        405                 410                 415

Ser Arg Trp Gln Gln Gly Asn Val Phe Ser Cys Ser Val Met His Glu
                        420                 425                 430

Ala Leu His Ala Lys Tyr Thr Gln Lys Ser Leu Ser Leu Ser Pro Gly
                        435                 440                 445

<210> SEQ ID NO 274
<211> LENGTH: 218
<212> TYPE: PRT
<213> ORGANISM: Artificial Sequence
<220> FEATURE:
<223> OTHER INFORMATION: Second and Fifth Polypeptide Chains of DART F

<400> SEQUENCE: 274

Glu Ile Val Leu Thr Gln Ser Pro Ala Thr Leu Ser Leu Ser Pro Gly
        1               5                   10                  15

Glu Arg Ala Thr Leu Ser Cys Arg Ala Ser Glu Ser Val Asp Asn Tyr
                        20                  25                  30

Gly Met Ser Phe Met Asn Trp Phe Gln Gln Lys Pro Gly Gln Pro Pro
                    35                  40                  45

Lys Leu Leu Ile His Ala Ala Ser Asn Gln Gly Ser Gly Val Pro Ser
                    50                  55                  60

Arg Phe Ser Gly Ser Gly Ser Gly Thr Asp Phe Thr Leu Thr Ile Ser
        65                  70                  75                  80

Ser Leu Glu Pro Glu Asp Phe Ala Val Tyr Phe Cys Gln Gln Ser Lys
                        85                  90                  95

Glu Val Pro Tyr Thr Phe Gly Gly Gly Thr Lys Val Glu Ile Lys Arg
                        100                 105                 110

Thr Val Ala Ala Pro Ser Val Phe Ile Phe Pro Pro Ser Asp Glu Gln
                        115                 120                 125

Leu Lys Ser Gly Thr Ala Ser Val Val Cys Leu Leu Asn Asn Phe Tyr
                    130                 135                 140

Pro Arg Glu Ala Lys Val Gln Trp Lys Val Asp Asn Ala Leu Gln Ser
        145                 150                 155                 160

Gly Asn Ser Gln Glu Ser Val Thr Glu Gln Asp Ser Lys Asp Ser Thr
                        165                 170                 175

Tyr Ser Leu Ser Ser Thr Leu Thr Leu Ser Lys Ala Asp Tyr Glu Lys
                        180                 185                 190

His Lys Val Tyr Ala Cys Glu Val Thr His Gln Gly Leu Ser Ser Pro
                        195                 200                 205

Val Thr Lys Ser Phe Asn Arg Gly Glu Cys
                    210                 215
```

<210> SEQ ID NO 275
<211> LENGTH: 732
<212> TYPE: PRT
<213> ORGANISM: Artificial Sequence
<220> FEATURE:
<223> OTHER INFORMATION: Third Polypeptide Chain of DART F

<400> SEQUENCE: 275

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Tyr
                20                  25                  30

Trp Met Asn Trp Val Arg Gln Ala Pro Gly Gln Gly Leu Glu Trp Ile
            35                  40                  45

Gly Val Ile His Pro Ser Asp Ser Glu Thr Trp Leu Asp Gln Lys Phe
    50                  55                  60

Lys Asp Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu His Tyr Gly Thr Ser Pro Phe Ala Tyr Trp Gly Gln Gly
                100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Tyr Ile Thr
                245                 250                 255

Arg Glu Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Trp
        355                 360                 365

Cys Leu Val Lys Gly Phe Tyr Pro Ser Asp Ile Ala Val Glu Trp Glu
```

```
                    370                 375                 380
Ser Asn Gly Gln Pro Glu Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

Gly Gly Gly Ser Gly Gly Gly Ser Gly Gly Gly Asp Ile Val Met Thr
450                 455                 460

Gln Thr Pro Leu Ser Leu Ser Val Thr Pro Gly Gln Pro Ala Ser Ile
465                 470                 475                 480

Ser Cys Lys Ser Ser Gln Ser Leu Leu His Ser Asp Ala Lys Thr Tyr
                485                 490                 495

Leu Asn Trp Leu Leu Gln Lys Pro Gly Gln Pro Pro Glu Arg Leu Ile
                500                 505                 510

Tyr Leu Val Ser Glu Leu Asp Ser Gly Val Pro Asp Arg Phe Ser Gly
                515                 520                 525

Ser Gly Ser Gly Thr Asp Phe Thr Leu Lys Ile Ser Arg Val Glu Ala
530                 535                 540

Glu Asp Val Gly Val Tyr Tyr Cys Trp Gln Gly Thr His Phe Pro Tyr
545                 550                 555                 560

Thr Phe Gly Gly Gly Thr Lys Val Glu Ile Lys Gly Gly Gly Ser Gly
                565                 570                 575

Gly Gly Gly Gln Val Gln Leu Val Gln Ser Gly Ala Glu Val Lys Lys
                580                 585                 590

Pro Gly Ala Ser Val Lys Val Ser Cys Lys Ala Ser Gly Tyr Ser Phe
                595                 600                 605

Thr Ser Tyr Trp Met Asn Trp Val Arg Gln Ala Pro Gly Gln Gly Leu
                610                 615                 620

Glu Trp Ile Gly Val Ile His Pro Ser Asp Ser Glu Thr Trp Leu Asp
625                 630                 635                 640

Gln Lys Phe Lys Asp Arg Val Thr Ile Thr Val Asp Lys Ser Thr Ser
                645                 650                 655

Thr Ala Tyr Met Glu Leu Ser Ser Leu Arg Ser Glu Asp Thr Ala Val
                660                 665                 670

Tyr Tyr Cys Ala Arg Glu His Tyr Gly Thr Ser Pro Phe Ala Tyr Trp
                675                 680                 685

Gly Gln Gly Thr Leu Val Thr Val Ser Ser Gly Gly Cys Gly Gly Gly
                690                 695                 700

Glu Val Ala Ala Leu Glu Lys Glu Val Ala Ala Leu Glu Lys Glu Val
705                 710                 715                 720

Ala Ala Leu Glu Lys Glu Val Ala Ala Leu Glu Lys
                725                 730

<210> SEQ ID NO 276
<211> LENGTH: 273
<212> TYPE: PRT
<213> ORGANISM: Artificial Sequence
<220> FEATURE:
<223> OTHER INFORMATION: Fourth Polypeptide Chain of DART F

<400> SEQUENCE: 276

Glu Ile Val Leu Thr Gln Ser Pro Ala Thr Leu Ser Leu Ser Pro Gly
```

```
                1               5                  10                 15
        Glu Arg Ala Thr Leu Ser Cys Arg Ala Ser Glu Ser Val Asp Asn Tyr
                        20                  25                 30
        Gly Met Ser Phe Met Asn Trp Phe Gln Gln Lys Pro Gly Gln Pro Pro
                        35                  40                 45
        Lys Leu Leu Ile His Ala Ala Ser Asn Gln Gly Ser Gly Val Pro Ser
                        50                  55                 60
        Arg Phe Ser Gly Ser Gly Ser Gly Thr Asp Phe Thr Leu Thr Ile Ser
        65                      70                  75                 80
        Ser Leu Glu Pro Glu Asp Phe Ala Val Tyr Phe Cys Gln Gln Ser Lys
                        85                  90                 95
        Glu Val Pro Tyr Thr Phe Gly Gly Gly Thr Lys Val Glu Ile Lys Gly
                        100                 105                110
        Gly Gly Ser Gly Gly Gly Gly Gln Val Gln Leu Val Gln Ser Gly Ala
                        115                 120                125
        Glu Val Lys Lys Pro Gly Ala Ser Val Lys Val Ser Cys Lys Ala Ser
                        130                 135                140
        Gly Tyr Thr Phe Thr Asn Tyr Gly Met Asn Trp Val Arg Gln Ala Pro
        145                     150                 155                160
        Gly Gln Gly Leu Glu Trp Met Gly Trp Ile Asn Thr Tyr Thr Gly Glu
                        165                 170                175
        Ser Thr Tyr Ala Asp Asp Phe Glu Gly Arg Phe Val Phe Ser Met Asp
                        180                 185                190
        Thr Ser Ala Ser Thr Ala Tyr Leu Gln Ile Ser Ser Leu Lys Ala Glu
                        195                 200                205
        Asp Thr Ala Val Tyr Tyr Cys Ala Arg Glu Ser Leu Tyr Asp Tyr Tyr
                        210                 215                220
        Ser Met Asp Tyr Trp Gly Gln Gly Thr Thr Val Thr Val Ser Ser Gly
        225                     230                 235                240
        Gly Cys Gly Gly Gly Lys Val Ala Ala Leu Lys Glu Lys Val Ala Ala
                        245                 250                255
        Leu Lys Glu Lys Val Ala Ala Leu Lys Glu Lys Val Ala Ala Leu Lys
                        260                 265                270
        Glu

<210> SEQ ID NO 277
<211> LENGTH: 449
<212> TYPE: PRT
<213> ORGANISM: Artificial Sequence
<220> FEATURE:
<223> OTHER INFORMATION: First Polypeptide Chain of DART G

<400> SEQUENCE: 277

Gln Val Gln Leu Val Gln Ser Gly Ala Glu Val Lys Lys Pro Gly Ala
        1               5                   10                 15
        Ser Val Lys Val Ser Cys Lys Ala Ser Gly Tyr Thr Phe Thr Asn Tyr
                        20                  25                 30
        Gly Met Asn Trp Val Arg Gln Ala Pro Gly Gln Gly Leu Glu Trp Met
                        35                  40                 45
        Gly Trp Ile Asn Thr Tyr Thr Gly Glu Ser Thr Tyr Ala Asp Asp Phe
                        50                  55                 60
        Glu Gly Arg Phe Val Phe Ser Met Asp Thr Ser Ala Ser Thr Ala Tyr
        65                      70                  75                 80
        Leu Gln Ile Ser Ser Leu Lys Ala Glu Asp Thr Ala Val Tyr Tyr Cys
                        85                  90                 95
```

Ala Arg Glu Ser Leu Tyr Asp Tyr Tyr Ser Met Asp Tyr Trp Gly Gln
            100                 105                 110

Gly Thr Thr Val Thr Val Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Tyr Ile
                245                 250                 255

Thr Arg Glu Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Ser Cys Ala Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Val Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Ala Lys Tyr Thr Gln Lys Ser Leu Ser Leu Ser Pro
        435                 440                 445

Gly

<210> SEQ ID NO 278
<211> LENGTH: 219
<212> TYPE: PRT
<213> ORGANISM: Artificial Sequence
<220> FEATURE:
<223> OTHER INFORMATION: Second and Fifth Polypeptide Chain of DART G

<400> SEQUENCE: 278

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Ala Lys Thr Tyr Leu Asn Trp Leu Leu Gln Lys Pro Gly Gln Pro
        35                  40                  45

Pro Glu Arg Leu Ile Tyr Leu Val Ser Glu Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Tyr Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 279
<211> LENGTH: 732
<212> TYPE: PRT
<213> ORGANISM: Artificial Sequence
<220> FEATURE:
<223> OTHER INFORMATION: Third Polypeptide Chain of DART G

<400> SEQUENCE: 279

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Ser Thr Tyr Ala Asp Asp Phe
    50                  55                  60

Glu Gly Arg Phe Val Phe Ser Met Asp Thr Ser Ala Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Glu Ser Leu Tyr Asp Tyr Tyr Ser Met Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

```
Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Tyr Ile
                245                 250                 255

Thr Arg Glu Pro Glu Val Thr Cys Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Trp Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Gly Gly Gly Ser Gly Gly Gly Ser Gly Gly Gly Glu Ile Val Leu
    450                 455                 460

Thr Gln Ser Pro Ala Thr Leu Ser Leu Ser Pro Gly Glu Arg Ala Thr
465                 470                 475                 480

Leu Ser Cys Arg Ala Ser Glu Ser Val Asp Asn Tyr Gly Met Ser Phe
                485                 490                 495

Met Asn Trp Phe Gln Gln Lys Pro Gly Gln Pro Pro Lys Leu Leu Ile
            500                 505                 510

His Ala Ala Ser Asn Gln Gly Ser Gly Val Pro Ser Arg Phe Ser Gly
        515                 520                 525

Ser Gly Ser Gly Thr Asp Phe Thr Leu Thr Ile Ser Ser Leu Glu Pro
    530                 535                 540

Glu Asp Phe Ala Val Tyr Phe Cys Gln Gln Ser Lys Glu Val Pro Tyr
545                 550                 555                 560

Thr Phe Gly Gly Gly Thr Lys Val Glu Ile Lys Gly Gly Gly Ser Gly
```

Gly Gly Gly Gln Val Gln Leu Val Gln Ser Gly Ala Glu Val Lys Lys
            580                 585                 590

Pro Gly Ala Ser Val Lys Val Ser Cys Lys Ala Ser Gly Tyr Ser Phe
        595                 600                 605

Thr Ser Tyr Trp Met Asn Trp Val Arg Gln Ala Pro Gly Gln Gly Leu
    610                 615                 620

Glu Trp Ile Gly Val Ile His Pro Ser Asp Ser Glu Thr Trp Leu Asp
625                 630                 635                 640

Gln Lys Phe Lys Asp Arg Val Thr Ile Thr Val Asp Lys Ser Thr Ser
                645                 650                 655

Thr Ala Tyr Met Glu Leu Ser Ser Leu Arg Ser Glu Asp Thr Ala Val
                660                 665                 670

Tyr Tyr Cys Ala Arg Glu His Tyr Gly Thr Ser Pro Phe Ala Tyr Trp
                675                 680                 685

Gly Gln Gly Thr Leu Val Thr Val Ser Ser Gly Gly Cys Gly Gly Gly
            690                 695                 700

Glu Val Ala Ala Leu Glu Lys Glu Val Ala Ala Leu Glu Lys Glu Val
705                 710                 715                 720

Ala Ala Leu Glu Lys Glu Val Ala Ala Leu Glu Lys
                725                 730

<210> SEQ ID NO 280
<211> LENGTH: 272
<212> TYPE: PRT
<213> ORGANISM: Artificial Sequence
<220> FEATURE:
<223> OTHER INFORMATION: Fourth Polypeptide Chain of DART G

<400> SEQUENCE: 280

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Asp Asn Tyr
            20                  25                  30

Gly Met Ser Phe Met Asn Trp Phe Gln Gln Lys Pro Gly Gln Pro Pro
        35                  40                  45

Lys Leu Leu Ile His Ala Ala Ser Asn Gln Gly Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Phe Cys Gln Gln Ser Lys
                85                  90                  95

Glu Val Pro Tyr Thr Phe Gly Gly Gly Thr Lys Val Glu Ile Lys Gly
                100                 105                 110

Gly Gly Ser Gly Gly Gly Gly Gln Val Gln Leu Val Gln Ser Gly Ala
            115                 120                 125

Glu Val Lys Lys Pro Gly Ala Ser Val Lys Val Ser Cys Lys Ala Ser
        130                 135                 140

Gly Tyr Ser Phe Thr Ser Tyr Trp Met Asn Trp Val Arg Gln Ala Pro
145                 150                 155                 160

Gly Gln Gly Leu Glu Trp Ile Gly Val Ile His Pro Ser Asp Ser Glu
                165                 170                 175

Thr Trp Leu Asp Gln Lys Phe Lys Asp Arg Val Thr Ile Thr Val Asp
            180                 185                 190

Lys Ser Thr Ser Thr Ala Tyr Met Glu Leu Ser Ser Leu Arg Ser Glu

|  |  | 195 |  |  | 200 |  |  | 205 |  |  |  |
|--|--|--|--|--|--|--|--|--|--|--|--|

Asp Thr Ala Val Tyr Tyr Cys Ala Arg Glu His Tyr Gly Thr Ser Pro
210 215 220

Phe Ala Tyr Trp Gly Gln Gly Thr Leu Val Thr Val Ser Ser Gly Gly
225 230 235 240

Cys Gly Gly Gly Lys Val Ala Ala Leu Lys Glu Lys Val Ala Ala Leu
245 250 255

Lys Glu Lys Val Ala Ala Leu Lys Glu Lys Val Ala Ala Leu Lys Glu
260 265 270

<210> SEQ ID NO 281
<211> LENGTH: 503
<212> TYPE: PRT
<213> ORGANISM: Artificial Sequence
<220> FEATURE:
<223> OTHER INFORMATION: First Polypeptide Chain of DART H

<400> SEQUENCE: 281

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Asp Asn Tyr
                20                  25                  30

Gly Met Ser Phe Met Asn Trp Phe Gln Gln Lys Pro Gly Gln Pro Pro
            35                  40                  45

Lys Leu Leu Ile His Ala Ala Ser Asn Gln Gly Ser Gly Val Pro Ser
        50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Phe Cys Gln Gln Ser Lys
                85                  90                  95

Glu Val Pro Tyr Thr Phe Gly Gly Gly Thr Lys Val Glu Ile Lys Gly
                100                 105                 110

Gly Gly Ser Gly Gly Gly Gly Gln Val Gln Leu Val Gln Ser Gly Ala
            115                 120                 125

Glu Val Lys Lys Pro Gly Ala Ser Val Lys Val Ser Cys Lys Ala Ser
130                 135                 140

Gly Tyr Thr Phe Thr Asn Tyr Gly Met Asn Trp Val Arg Gln Ala Pro
145                 150                 155                 160

Gly Gln Gly Leu Glu Trp Met Gly Trp Ile Asn Thr Tyr Thr Gly Glu
                165                 170                 175

Ser Thr Tyr Ala Asp Asp Phe Glu Gly Arg Phe Val Phe Ser Met Asp
            180                 185                 190

Thr Ser Ala Ser Thr Ala Tyr Leu Gln Ile Ser Ser Leu Lys Ala Glu
        195                 200                 205

Asp Thr Ala Val Tyr Tyr Cys Ala Arg Glu Ser Leu Tyr Asp Tyr Tyr
210                 215                 220

Ser Met Asp Tyr Trp Gly Gln Gly Thr Thr Val Thr Val Ser Ser Gly
225                 230                 235                 240

Gly Cys Gly Gly Gly Glu Val Ala Ala Leu Glu Lys Glu Val Ala Ala
                245                 250                 255

Leu Glu Lys Glu Val Ala Ala Leu Glu Lys Glu Val Ala Ala Leu Glu
            260                 265                 270

Lys Gly Gly Gly Asp Lys Thr His Thr Cys Pro Pro Cys Pro Ala Pro
        275                 280                 285

Glu Ala Ala Gly Gly Pro Ser Val Phe Leu Phe Pro Pro Lys Pro Lys

```
                290                 295                 300
Asp Thr Leu Met Ile Ser Arg Thr Pro Glu Val Thr Cys Val Val Val
305                 310                 315                 320

Asp Val Ser His Glu Asp Pro Glu Val Lys Phe Asn Trp Tyr Val Asp
                325                 330                 335

Gly Val Glu Val His Asn Ala Lys Thr Lys Pro Arg Glu Glu Gln Tyr
                340                 345                 350

Asn Ser Thr Tyr Arg Val Val Ser Val Leu Thr Val Leu His Gln Asp
                355                 360                 365

Trp Leu Asn Gly Lys Glu Tyr Lys Cys Lys Val Ser Asn Lys Ala Leu
                370                 375                 380

Pro Ala Pro Ile Glu Lys Thr Ile Ser Lys Ala Lys Gly Gln Pro Arg
385                 390                 395                 400

Glu Pro Gln Val Tyr Thr Leu Pro Pro Ser Arg Glu Glu Met Thr Lys
                405                 410                 415

Asn Gln Val Ser Leu Trp Cys Leu Val Lys Gly Phe Tyr Pro Ser Asp
                420                 425                 430

Ile Ala Val Glu Trp Glu Ser Asn Gly Gln Pro Glu Asn Asn Tyr Lys
                435                 440                 445

Thr Thr Pro Pro Val Leu Asp Ser Asp Gly Ser Phe Phe Leu Tyr Ser
                450                 455                 460

Lys Leu Thr Val Asp Lys Ser Arg Trp Gln Gln Gly Asn Val Phe Ser
465                 470                 475                 480

Cys Ser Val Met His Glu Ala Leu His Asn His Tyr Thr Gln Lys Ser
                485                 490                 495

Leu Ser Leu Ser Pro Gly Lys
                500

<210> SEQ ID NO 282
<211> LENGTH: 273
<212> TYPE: PRT
<213> ORGANISM: Artificial Sequence
<220> FEATURE:
<223> OTHER INFORMATION: Second Polypeptide Chain of DART H

<400> SEQUENCE: 282

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
                20                  25                  30

Asp Ala Lys Thr Tyr Leu Asn Trp Leu Leu Gln Lys Pro Gly Gln Pro
                35                  40                  45

Pro Glu Arg Leu Ile Tyr Leu Val Ser Glu Leu Asp Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Tyr Thr Phe Gly Gly Gly Thr Lys Val Glu Ile Lys
                100                 105                 110

Gly Gly Gly Ser Gly Gly Gly Gly Gln Val Gln Leu Val Gln Ser Gly
                115                 120                 125

Ala Glu Val Lys Lys Pro Gly Ala Ser Val Lys Val Ser Cys Lys Ala
                130                 135                 140

Ser Gly Tyr Ser Phe Thr Ser Tyr Trp Met Asn Trp Val Arg Gln Ala
```

```
145                 150                 155                 160
Pro Gly Gln Gly Leu Glu Trp Ile Gly Val Ile His Pro Ser Asp Ser
                165                 170                 175

Glu Thr Trp Leu Asp Gln Lys Phe Lys Asp Arg Val Thr Ile Thr Val
            180                 185                 190

Asp Lys Ser Thr Ser Thr Ala Tyr Met Glu Leu Ser Ser Leu Arg Ser
            195                 200                 205

Glu Asp Thr Ala Val Tyr Tyr Cys Ala Arg Glu His Tyr Gly Thr Ser
        210                 215                 220

Pro Phe Ala Tyr Trp Gly Gln Gly Thr Leu Val Thr Val Ser Ser Gly
225                 230                 235                 240

Gly Cys Gly Gly Gly Lys Val Ala Ala Leu Lys Glu Lys Val Ala Ala
                245                 250                 255

Leu Lys Glu Lys Val Ala Ala Leu Lys Glu Lys Val Ala Ala Leu Lys
            260                 265                 270

Glu
```

<210> SEQ ID NO 283
<211> LENGTH: 227
<212> TYPE: PRT
<213> ORGANISM: Artificial Sequence
<220> FEATURE:
<223> OTHER INFORMATION: Third Polypeptide Chain of DART H

<400> SEQUENCE: 283

```
Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
        50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn Arg Tyr Thr Gln Lys Ser Leu Ser Leu Ser
    210                 215                 220

Pro Gly Lys
225
```

<210> SEQ ID NO 284
<211> LENGTH: 563
<212> TYPE: PRT
<213> ORGANISM: Artificial Sequence
<220> FEATURE:
<223> OTHER INFORMATION: First and Third Polypeptide Chains of DART 1

<400> SEQUENCE: 284

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gln Gly Thr Asn Leu Glu Ile Lys Gly Gly Gly Ser Gly
            100                 105                 110

Gly Gly Gly Gln Val Gln Leu Val Glu Ser Gly Gly Val Val Gln
        115                 120                 125

Pro Gly Arg Ser Leu Arg Leu Asp Cys Lys Ala Ser Gly Ile Thr Phe
    130                 135                 140

Ser Asn Ser Gly Met His Trp Val Arg Gln Ala Pro Gly Lys Gly Leu
145                 150                 155                 160

Glu Trp Val Ala Val Ile Trp Tyr Asp Gly Ser Lys Arg Tyr Tyr Ala
                165                 170                 175

Asp Ser Val Lys Gly Arg Phe Thr Ile Ser Arg Asp Asn Ser Lys Asn
            180                 185                 190

Thr Leu Phe Leu Gln Met Asn Ser Leu Arg Ala Glu Asp Thr Ala Val
        195                 200                 205

Tyr Tyr Cys Ala Thr Asn Asp Asp Tyr Trp Gly Gln Gly Thr Leu Val
    210                 215                 220

Thr Val Ser Ser Leu Gly Gly Gly Ser Gly Ala Ser Thr Lys Gly Pro
225                 230                 235                 240

Ser Val Phe Pro Leu Ala Pro Ser Ser Lys Ser Thr Ser Gly Gly Thr
                245                 250                 255

Ala Ala Leu Gly Cys Leu Val Lys Asp Tyr Phe Pro Glu Pro Val Thr
            260                 265                 270

Val Ser Trp Asn Ser Gly Ala Leu Thr Ser Gly Val His Thr Phe Pro
        275                 280                 285

Ala Val Leu Gln Ser Ser Gly Leu Tyr Ser Leu Ser Ser Val Val Thr
    290                 295                 300

Val Pro Ser Ser Ser Leu Gly Thr Gln Thr Tyr Ile Cys Asn Val Asn
305                 310                 315                 320

His Lys Pro Ser Asn Thr Lys Val Asp Lys Arg Val Glu Pro Lys Ser
                325                 330                 335

Cys Asp Lys Thr His Thr Cys Pro Pro Cys Pro Ala Pro Glu Ala Ala
            340                 345                 350

Gly Gly Pro Ser Val Phe Leu Phe Pro Pro Lys Pro Lys Asp Thr Leu
        355                 360                 365
```

```
Tyr Ile Thr Arg Glu Pro Glu Val Thr Cys Val Val Asp Val Ser
            370                 375                 380

His Glu Asp Pro Glu Val Lys Phe Asn Trp Tyr Val Asp Gly Val Glu
385                 390                 395                 400

Val His Asn Ala Lys Thr Lys Pro Arg Glu Glu Gln Tyr Asn Ser Thr
                405                 410                 415

Tyr Arg Val Val Ser Val Leu Thr Val Leu His Gln Asp Trp Leu Asn
            420                 425                 430

Gly Lys Glu Tyr Lys Cys Lys Val Ser Asn Lys Ala Leu Pro Ala Pro
        435                 440                 445

Ile Glu Lys Thr Ile Ser Lys Ala Lys Gly Gln Pro Arg Glu Pro Gln
    450                 455                 460

Val Tyr Thr Leu Pro Pro Ser Arg Glu Glu Met Thr Lys Asn Gln Val
465                 470                 475                 480

Ser Leu Thr Cys Leu Val Lys Gly Phe Tyr Pro Ser Asp Ile Ala Val
                485                 490                 495

Glu Trp Glu Ser Asn Gly Gln Pro Glu Asn Asn Tyr Lys Thr Thr Pro
            500                 505                 510

Pro Val Leu Asp Ser Asp Gly Ser Phe Phe Leu Tyr Ser Lys Leu Thr
        515                 520                 525

Val Asp Lys Ser Arg Trp Gln Gln Gly Asn Val Phe Ser Cys Ser Val
530                 535                 540

Met His Glu Ala Leu His Asn His Tyr Thr Gln Lys Ser Leu Ser Leu
545                 550                 555                 560

Ser Pro Gly

<210> SEQ ID NO 285
<211> LENGTH: 348
<212> TYPE: PRT
<213> ORGANISM: Artificial Sequence
<220> FEATURE:
<223> OTHER INFORMATION: Second and Fourth Polypeptide Chains of DART 1

<400> SEQUENCE: 285

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Gly Gly Gly Ser Gly
            100                 105                 110

Gly Gly Gly Gln Val Gln Leu Gln Gln Trp Gly Ala Gly Leu Leu Lys
        115                 120                 125

Pro Ser Glu Thr Leu Ser Leu Thr Cys Ala Val Tyr Gly Gly Ser Phe
    130                 135                 140

Ser Asp Tyr Tyr Trp Asn Trp Ile Arg Gln Pro Pro Gly Lys Gly Leu
145                 150                 155                 160
```

Glu Trp Ile Gly Glu Ile Asn His Asn Gly Asn Thr Asn Ser Asn Pro
                165                 170                 175

Ser Leu Lys Ser Arg Val Thr Leu Ser Leu Asp Thr Ser Lys Asn Gln
            180                 185                 190

Phe Ser Leu Lys Leu Arg Ser Val Thr Ala Ala Asp Thr Ala Val Tyr
        195                 200                 205

Tyr Cys Ala Phe Gly Tyr Ser Asp Tyr Glu Tyr Asn Trp Phe Asp Pro
    210                 215                 220

Trp Gly Gln Gly Thr Leu Val Thr Val Ser Ser Leu Gly Gly Gly Ser
225                 230                 235                 240

Gly Arg Thr Val Ala Ala Pro Ser Val Phe Ile Phe Pro Pro Ser Asp
                245                 250                 255

Glu Gln Leu Lys Ser Gly Thr Ala Ser Val Val Cys Leu Leu Asn Asn
            260                 265                 270

Phe Tyr Pro Arg Glu Ala Lys Val Gln Trp Lys Val Asp Asn Ala Leu
        275                 280                 285

Gln Ser Gly Asn Ser Gln Glu Ser Val Thr Glu Gln Asp Ser Lys Asp
    290                 295                 300

Ser Thr Tyr Ser Leu Ser Ser Thr Leu Thr Leu Ser Lys Ala Asp Tyr
305                 310                 315                 320

Glu Lys His Lys Val Tyr Ala Cys Glu Val Thr His Gln Gly Leu Ser
                325                 330                 335

Ser Pro Val Thr Lys Ser Phe Asn Arg Gly Glu Cys
            340                 345

<210> SEQ ID NO 286
<211> LENGTH: 448
<212> TYPE: PRT
<213> ORGANISM: Artificial Sequence
<220> FEATURE:
<223> OTHER INFORMATION: First Polypeptide Chain of BSAB A

<400> SEQUENCE: 286

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Tyr
            20                  25                  30

Trp Met Asn Trp Val Arg Gln Ala Pro Gly Gln Gly Leu Glu Trp Ile
        35                  40                  45

Gly Val Ile His Pro Ser Asp Ser Glu Thr Trp Leu Asp Gln Lys Phe
    50                  55                  60

Lys Asp Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu His Tyr Gly Thr Ser Pro Phe Ala Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
              180                 185                 190

Ser Ser Leu Gly Thr Gln Thr Tyr Ile Cys Asn Val Asn His Lys Pro
          195                 200                 205

Ser Asn Thr Lys Val Asp Lys Arg Val Glu Pro Lys Ser Cys Glu Lys
      210                 215                 220

Thr His Thr Cys Pro Glu Cys Pro Ala Pro Glu Ala Ala Gly Gly Pro
225                 230                 235                 240

Ser Val Phe Leu Phe Pro Pro Lys Pro Lys Asp Thr Leu Met Ile Ser
              245                 250                 255

Arg Thr Pro Glu Val Thr Cys Val Val Val Asp Val Ser His Glu Asp
          260                 265                 270

Pro Glu Val Lys Phe Asn Trp Tyr Val Asp Gly Val Glu Val His Asn
      275                 280                 285

Ala Lys Thr Lys Pro Arg Glu Glu Gln Tyr Asn Ser Thr Tyr Arg Val
  290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
              325                 330                 335

Thr Ile Ser Lys Ala Lys Gly Gln Pro Arg Glu Pro Gln Val Tyr Thr
          340                 345                 350

Leu Pro Pro Ser Arg Glu Glu Met Thr Lys Asn Gln Val Ser Leu Thr
      355                 360                 365

Cys Glu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
              405                 410                 415

Ser Arg Trp Gln Gln Gly Asn Val Phe Ser Cys Ser Val Met His Glu
          420                 425                 430

Ala Leu His Asn His Tyr Thr Gln Lys Ser Leu Ser Leu Ser Pro Gly
      435                 440                 445

<210> SEQ ID NO 287
<211> LENGTH: 218
<212> TYPE: PRT
<213> ORGANISM: Artificial Sequence
<220> FEATURE:
<223> OTHER INFORMATION: Second Polypeptide Chain of BSAB A

<400> SEQUENCE: 287

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Asp Asn Tyr
            20                  25                  30

Gly Met Ser Phe Met Asn Trp Phe Gln Gln Lys Pro Gly Gln Pro Pro
        35                  40                  45

Lys Leu Leu Ile His Ala Ala Ser Asn Gln Gly Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Phe Cys Gln Gln Ser Lys
                85                  90                  95

```
Glu Val Pro Tyr Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 288
<211> LENGTH: 449
<212> TYPE: PRT
<213> ORGANISM: Artificial Sequence
<220> FEATURE:
<223> OTHER INFORMATION: Third Polypeptide Chain of BSAB A

<400> SEQUENCE: 288

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Ser Tyr Ala Asp Asp Phe
    50                  55                  60

Glu Gly Arg Phe Val Phe Ser Met Asp Thr Ser Ala Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Glu Ser Leu Tyr Asp Tyr Tyr Ser Met Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Arg
    210                 215                 220

Lys Thr His Thr Cys Pro Arg Cys Pro Ala Pro Glu Ala Ala Gly Gly
225                 230                 235                 240
```

```
Pro Ser Val Phe Leu Phe Pro Pro Lys Pro Lys Asp Thr Leu Met Ile
                245                 250                 255

Ser Arg Thr Pro Glu Val Thr Cys Val Val Asp Val Ser His Glu
        260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Glu Glu Met Thr Lys Asn Gln Val Ser Leu
                355                 360                 365

Thr Cys Leu Val Lys Gly Phe Tyr Pro Ser Asp Ile Ala Val Glu Trp
                370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly

<210> SEQ ID NO 289
<211> LENGTH: 219
<212> TYPE: PRT
<213> ORGANISM: Artificial Sequence
<220> FEATURE:
<223> OTHER INFORMATION: Fourth Polypeptide Chain of BSAB A

<400> SEQUENCE: 289

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
                20                  25                  30

Asp Ala Lys Thr Tyr Leu Asn Trp Leu Leu Gln Lys Pro Gly Gln Pro
            35                  40                  45

Pro Glu Arg Leu Ile Tyr Leu Val Ser Glu Leu Asp Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Tyr Thr Phe Gly Gly Gly Thr Lys Val Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
```

```
145                 150                 155                 160
Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
                195                 200                 205

Pro Val Thr Lys Ser Phe Asn Arg Gly Glu Cys
                210                 215

<210> SEQ ID NO 290
<211> LENGTH: 496
<212> TYPE: PRT
<213> ORGANISM: Artificial Sequence
<220> FEATURE:
<223> OTHER INFORMATION: First and Third Polypeptide Chains of DART I

<400> SEQUENCE: 290

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Ser Val
                20                  25                  30

Val Ala Trp Tyr Gln Gln Lys Pro Gly Lys Ala Pro Lys Leu Leu Ile
            35                  40                  45

Tyr Ser Ala Ser Tyr Arg Tyr Thr Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Thr Pro Trp
                85                  90                  95

Thr Phe Gly Gly Gly Thr Lys Leu Glu Ile Lys Gly Gly Gly Ser Gly
                100                 105                 110

Gly Gly Gly Gln Val Gln Leu Val Gln Ser Gly Ala Glu Val Lys Lys
            115                 120                 125

Pro Gly Ala Ser Val Lys Val Ser Cys Lys Ala Ser Gly Tyr Ser Phe
        130                 135                 140

Thr Ser Tyr Trp Met Asn Trp Val Arg Gln Ala Pro Gly Gln Gly Leu
145                 150                 155                 160

Glu Trp Ile Gly Val Ile His Pro Ser Asp Ser Glu Thr Trp Leu Asp
                165                 170                 175

Gln Lys Phe Lys Asp Arg Val Thr Ile Thr Val Asp Lys Ser Thr Ser
                180                 185                 190

Thr Ala Tyr Met Glu Leu Ser Ser Leu Arg Ser Glu Asp Thr Ala Val
                195                 200                 205

Tyr Tyr Cys Ala Arg Glu His Tyr Gly Thr Ser Pro Phe Ala Tyr Trp
        210                 215                 220

Gly Gln Gly Thr Leu Val Thr Val Ser Ser Gly Gly Cys Gly Gly Gly
225                 230                 235                 240

Glu Val Ala Ala Cys Glu Lys Glu Val Ala Ala Leu Glu Lys Glu Val
                245                 250                 255

Ala Ala Leu Glu Lys Glu Val Ala Ala Leu Glu Lys Glu Ser Lys Tyr
                260                 265                 270

Gly Pro Pro Cys Pro Pro Cys Pro Ala Pro Glu Phe Leu Gly Gly Pro
                275                 280                 285

Ser Val Phe Leu Phe Pro Pro Lys Pro Lys Asp Thr Leu Tyr Ile Thr
```

```
                290                 295                 300
Arg Glu Pro Glu Val Thr Cys Val Val Asp Val Ser Gln Glu Asp
305                 310                 315                 320

Pro Glu Val Gln Phe Asn Trp Tyr Val Asp Gly Val Glu Val His Asn
                325                 330                 335

Ala Lys Thr Lys Pro Arg Glu Glu Gln Phe Asn Ser Thr Tyr Arg Val
            340                 345                 350

Val Ser Val Leu Thr Val Leu His Gln Asp Trp Leu Asn Gly Lys Glu
        355                 360                 365

Tyr Lys Cys Lys Val Ser Asn Lys Gly Leu Pro Ser Ser Ile Glu Lys
    370                 375                 380

Thr Ile Ser Lys Ala Lys Gly Gln Pro Arg Glu Pro Gln Val Tyr Thr
385                 390                 395                 400

Leu Pro Pro Ser Gln Glu Glu Met Thr Lys Asn Gln Val Ser Leu Thr
                405                 410                 415

Cys Leu Val Lys Gly Phe Tyr Pro Ser Asp Ile Ala Val Glu Trp Glu
            420                 425                 430

Ser Asn Gly Gln Pro Glu Asn Asn Tyr Lys Thr Thr Pro Pro Val Leu
        435                 440                 445

Asp Ser Asp Gly Ser Phe Phe Leu Tyr Ser Arg Leu Thr Val Asp Lys
    450                 455                 460

Ser Arg Trp Gln Glu Gly Asn Val Phe Ser Cys Ser Val Met His Glu
465                 470                 475                 480

Ala Leu His Asn His Tyr Thr Gln Lys Ser Leu Ser Leu Ser Leu Gly
                485                 490                 495

<210> SEQ ID NO 291
<211> LENGTH: 271
<212> TYPE: PRT
<213> ORGANISM: Artificial Sequence
<220> FEATURE:
<223> OTHER INFORMATION: Second and Fourth Polypeptide Chains of DART I

<400> SEQUENCE: 291

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Asp Asn Tyr
            20                  25                  30

Gly Met Ser Phe Met Asn Trp Phe Gln Gln Lys Pro Gly Gln Pro Pro
        35                  40                  45

Lys Leu Leu Ile His Ala Ala Ser Asn Gln Gly Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Phe Cys Gln Gln Ser Lys
                85                  90                  95

Glu Val Pro Tyr Thr Phe Gly Gly Gly Thr Lys Val Glu Ile Lys Gly
            100                 105                 110

Gly Gly Ser Gly Gly Gly Gly Gln Val Gln Leu Val Gln Ser Gly Ala
        115                 120                 125

Glu Val Lys Lys Pro Gly Ala Ser Val Lys Val Ser Cys Lys Ala Ser
    130                 135                 140

Gly Tyr Thr Phe Thr Asp Tyr Asn Met Asp Trp Val Arg Gln Ala Pro
145                 150                 155                 160

Gly Gln Gly Leu Glu Trp Met Gly Asp Ile Asn Pro Asp Asn Gly Val
```

165                 170                 175
Thr Ile Tyr Asn Gln Lys Phe Glu Gly Arg Val Thr Met Thr Thr Asp
                180                 185                 190

Thr Ser Thr Ser Thr Ala Tyr Met Glu Leu Arg Ser Leu Arg Ser Asp
            195                 200                 205

Asp Thr Ala Val Tyr Tyr Cys Ala Arg Glu Ala Asp Tyr Phe Tyr Phe
        210                 215                 220

Asp Tyr Trp Gly Gln Gly Thr Thr Leu Thr Val Ser Ser Gly Gly Cys
225                 230                 235                 240

Gly Gly Gly Lys Val Ala Ala Cys Lys Glu Lys Val Ala Ala Leu Lys
                245                 250                 255

Glu Lys Val Ala Ala Leu Lys Glu Lys Val Ala Ala Leu Lys Glu
            260                 265                 270

<210> SEQ ID NO 292
<211> LENGTH: 566
<212> TYPE: PRT
<213> ORGANISM: Artificial Sequence
<220> FEATURE:
<223> OTHER INFORMATION: First and Third Polypeptide Chains of DART J

<400> SEQUENCE: 292

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Ser Val
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Thr Pro Trp
                85                  90                  95

Thr Phe Gly Gly Gly Thr Lys Leu Glu Ile Lys Gly Gly Gly Ser Gly
            100                 105                 110

Gly Gly Gly Gln Val Gln Leu Val Gln Ser Gly Ala Glu Val Lys Lys
        115                 120                 125

Pro Gly Ala Ser Val Lys Val Ser Cys Lys Ala Ser Gly Tyr Ser Phe
    130                 135                 140

Thr Ser Tyr Trp Met Asn Trp Val Arg Gln Ala Pro Gly Gln Gly Leu
145                 150                 155                 160

Glu Trp Ile Gly Val Ile His Pro Ser Asp Ser Glu Thr Trp Leu Asp
                165                 170                 175

Gln Lys Phe Lys Asp Arg Val Thr Ile Thr Val Asp Lys Ser Thr Ser
            180                 185                 190

Thr Ala Tyr Met Glu Leu Ser Ser Leu Arg Ser Glu Asp Thr Ala Val
        195                 200                 205

Tyr Tyr Cys Ala Arg Glu His Tyr Gly Thr Ser Pro Phe Ala Tyr Trp
    210                 215                 220

Gly Gln Gly Thr Leu Val Thr Val Ser Ser Leu Gly Gly Gly Ser Gly
225                 230                 235                 240

Ala Ser Thr Lys Gly Pro Ser Val Phe Pro Leu Ala Pro Cys Ser Arg
                245                 250                 255

Ser Thr Ser Glu Ser Thr Ala Ala Leu Gly Cys Leu Val Lys Asp Tyr

```
                260                 265                 270
Phe Pro Glu Pro Val Thr Val Ser Trp Asn Ser Gly Ala Leu Thr Ser
            275                 280                 285
Gly Val His Thr Phe Pro Ala Val Leu Gln Ser Ser Gly Leu Tyr Ser
            290                 295                 300
Leu Ser Ser Val Val Thr Val Pro Ser Ser Ser Leu Gly Thr Lys Thr
305                 310                 315                 320
Tyr Thr Cys Asn Val Asp His Lys Pro Ser Asn Thr Lys Val Asp Lys
                325                 330                 335
Arg Val Glu Ser Lys Tyr Gly Pro Pro Cys Pro Pro Cys Pro Ala Pro
            340                 345                 350
Glu Phe Leu Gly Gly Pro Ser Val Phe Leu Phe Pro Pro Lys Pro Lys
            355                 360                 365
Asp Thr Leu Tyr Ile Thr Arg Glu Pro Glu Val Thr Cys Val Val Val
            370                 375                 380
Asp Val Ser Gln Glu Asp Pro Glu Val Gln Phe Asn Trp Tyr Val Asp
385                 390                 395                 400
Gly Val Glu Val His Asn Ala Lys Thr Lys Pro Arg Glu Glu Gln Phe
                405                 410                 415
Asn Ser Thr Tyr Arg Val Val Ser Val Leu Thr Val Leu His Gln Asp
            420                 425                 430
Trp Leu Asn Gly Lys Glu Tyr Lys Cys Lys Val Ser Asn Lys Gly Leu
            435                 440                 445
Pro Ser Ser Ile Glu Lys Thr Ile Ser Lys Ala Lys Gly Gln Pro Arg
            450                 455                 460
Glu Pro Gln Val Tyr Thr Leu Pro Pro Ser Gln Glu Glu Met Thr Lys
465                 470                 475                 480
Asn Gln Val Ser Leu Thr Cys Leu Val Lys Gly Phe Tyr Pro Ser Asp
                485                 490                 495
Ile Ala Val Glu Trp Glu Ser Asn Gly Gln Pro Glu Asn Asn Tyr Lys
            500                 505                 510
Thr Thr Pro Pro Val Leu Asp Ser Asp Gly Ser Phe Phe Leu Tyr Ser
            515                 520                 525
Arg Leu Thr Val Asp Lys Ser Arg Trp Gln Glu Gly Asn Val Phe Ser
            530                 535                 540
Cys Ser Val Met His Glu Ala Leu His Asn His Tyr Thr Gln Lys Ser
545                 550                 555                 560
Leu Ser Leu Ser Leu Gly
                565

<210> SEQ ID NO 293
<211> LENGTH: 350
<212> TYPE: PRT
<213> ORGANISM: Artificial Sequence
<220> FEATURE:
<223> OTHER INFORMATION: Second and Fourth Polypeptide Chains of DART J

<400> SEQUENCE: 293

Glu Ile Val Leu Thr Gln Ser Pro Ala Thr Leu Ser Leu Ser Pro Gly
1               5                   10                  15
Glu Arg Ala Thr Leu Ser Cys Arg Ala Ser Glu Ser Val Asp Asn Tyr
                20                  25                  30
Gly Met Ser Phe Met Asn Trp Phe Gln Gln Lys Pro Gly Gln Pro Pro
            35                  40                  45
Lys Leu Leu Ile His Ala Ala Ser Asn Gln Gly Ser Gly Val Pro Ser
```

```
            50                  55                  60
Arg Phe Ser Gly Ser Gly Ser Gly Thr Asp Phe Thr Leu Thr Ile Ser
 65                  70                  75                  80

Ser Leu Glu Pro Glu Asp Phe Ala Val Tyr Phe Cys Gln Gln Ser Lys
                 85                  90                  95

Glu Val Pro Tyr Thr Phe Gly Gly Gly Thr Lys Val Glu Ile Lys Gly
            100                 105                 110

Gly Gly Ser Gly Gly Gly Gln Val Gln Leu Val Gln Ser Gly Ala
        115                 120                 125

Glu Val Lys Lys Pro Gly Ala Ser Val Lys Val Ser Cys Lys Ala Ser
130                 135                 140

Gly Tyr Thr Phe Thr Asp Tyr Asn Met Asp Trp Val Arg Gln Ala Pro
145                 150                 155                 160

Gly Gln Gly Leu Glu Trp Met Gly Asp Ile Asn Pro Asp Asn Gly Val
                165                 170                 175

Thr Ile Tyr Asn Gln Lys Phe Glu Gly Arg Val Thr Met Thr Thr Asp
            180                 185                 190

Thr Ser Thr Ser Thr Ala Tyr Met Glu Leu Arg Ser Leu Arg Ser Asp
        195                 200                 205

Asp Thr Ala Val Tyr Tyr Cys Ala Arg Glu Ala Asp Tyr Phe Tyr Phe
    210                 215                 220

Asp Tyr Trp Gly Gln Gly Thr Thr Leu Thr Val Ser Ser Leu Gly Gly
225                 230                 235                 240

Gly Ser Gly Arg Thr Val Ala Ala Pro Ser Val Phe Ile Phe Pro Pro
                245                 250                 255

Ser Asp Glu Gln Leu Lys Ser Gly Thr Ala Ser Val Val Cys Leu Leu
            260                 265                 270

Asn Asn Phe Tyr Pro Arg Glu Ala Lys Val Gln Trp Lys Val Asp Asn
        275                 280                 285

Ala Leu Gln Ser Gly Asn Ser Gln Glu Ser Val Thr Glu Gln Asp Ser
    290                 295                 300

Lys Asp Ser Thr Tyr Ser Leu Ser Ser Thr Leu Thr Leu Ser Lys Ala
305                 310                 315                 320

Asp Tyr Glu Lys His Lys Val Tyr Ala Cys Glu Val Thr His Gln Gly
                325                 330                 335

Leu Ser Ser Pro Val Thr Lys Ser Phe Asn Arg Gly Glu Cys
            340                 345                 350

<210> SEQ ID NO 294
<211> LENGTH: 118
<212> TYPE: PRT
<213> ORGANISM: Artificial Sequence
<220> FEATURE:
<223> OTHER INFORMATION: VH Domain of hLAG-3 mAb 6 VH1

<400> SEQUENCE: 294

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asp Tyr
                20                  25                  30

Asn Met Asp Trp Val Arg Gln Ala Pro Gly Gln Gly Leu Glu Trp Met
            35                  40                  45

Gly Asp Ile Asn Pro Asp Asn Gly Val Thr Ile Tyr Asn Gln Lys Phe
    50                  55                  60

Glu Gly Arg Val Thr Met Thr Thr Asp Thr Ser Thr Ser Thr Ala Tyr
```

```
                65                  70                  75                  80
Met Glu Leu Arg Ser Leu Arg Ser Asp Asp Thr Ala Val Tyr Tyr Cys
                    85                  90                  95

Ala Arg Glu Ala Asp Tyr Phe Tyr Phe Asp Tyr Trp Gly Gln Gly Thr
                100                 105                 110

Thr Leu Thr Val Ser Ser
            115

<210> SEQ ID NO 295
<211> LENGTH: 118
<212> TYPE: PRT
<213> ORGANISM: Artificial Sequence
<220> FEATURE:
<223> OTHER INFORMATION: VH Domain of hLAG-3 mAb 6 VH2

<400> SEQUENCE: 295

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
                20                  25                  30

Asn Met Asp Trp Val Arg Gln Ala Pro Gly Lys Gly Leu Glu Trp Val
                35                  40                  45

Ser Asp Ile Asn Pro Asp Asn Gly Val Thr Ile Tyr Asn Gln Lys Phe
            50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                    85                  90                  95

Ala Arg Glu Ala Asp Tyr Phe Tyr Phe Asp Tyr Trp Gly Gln Gly Thr
                100                 105                 110

Thr Leu Thr Val Ser Ser
            115

<210> SEQ ID NO 296
<211> LENGTH: 107
<212> TYPE: PRT
<213> ORGANISM: Artificial Sequence
<220> FEATURE:
<223> OTHER INFORMATION: VL Domain of hLAG-3 mAb 6 VL1

<400> SEQUENCE: 296

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Ser Val
                20                  25                  30

Val Ala Trp Tyr Gln Gln Lys Pro Gly Lys Ala Pro Lys Leu Leu Ile
                35                  40                  45

Tyr Ser Ala Ser Tyr Arg Tyr Thr Gly Val Pro Ser Arg Phe Ser Gly
            50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Thr Pro Trp
                    85                  90                  95

Thr Phe Gly Gly Gly Thr Lys Leu Glu Ile Lys
            100                 105

<210> SEQ ID NO 297
<211> LENGTH: 107
```

```
<212> TYPE: PRT
<213> ORGANISM: Artificial Sequence
<220> FEATURE:
<223> OTHER INFORMATION: VL Domain of hLAG-3 mAb 6 VL2

<400> SEQUENCE: 297

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Asp Val Ser Ser Val
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Asp Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Val Tyr Tyr Cys Gln Gln His Tyr Ser Thr Pro Trp
                85                  90                  95

Thr Phe Gly Gly Gly Thr Lys Leu Glu Ile Lys
            100                 105

<210> SEQ ID NO 298
<211> LENGTH: 11
<212> TYPE: PRT
<213> ORGANISM: Artificial Sequence
<220> FEATURE:
<223> OTHER INFORMATION: CDRL1 of the VL Domain of hLAG-3 mAb 6 VL1 and
      VL2

<400> SEQUENCE: 298

Arg Ala Ser Gln Asp Val Ser Ser Val Val Ala
1               5                   10
```